United States Patent
Strohbach et al.

(10) Patent No.: US 10,494,374 B2
(45) Date of Patent: Dec. 3, 2019

(54) PYRROLOPYRIMIDINES AS CFTR POTENTIATORS

(71) Applicant: CYSTIC FIBROSIS FOUNDATION, Bethesda, MD (US)

(72) Inventors: Joseph Walter Strohbach, Wentzville, MO (US); David Christopher Limburg, Salem, CT (US); John Paul Mathias, Concord, MA (US); Atli Thorarensen, Stow, MA (US); Rajiah Aldrin Denny, Sharon, MA (US); Christoph Wolfgang Zapf, Oakland, CA (US); Daniel Elbaum, Newman, MA (US); Lori Krim Gavrin, Villanova, PA (US); Ivan Viktorovich Efremov, Chestnut, MA (US)

(73) Assignee: CYSTIC FIBROSIS FOUNDATION, Bethesda, MD (US)

( * ) Notice: Subject to any disclaimer, the term of this patent is extended or adjusted under 35 U.S.C. 154(b) by 0 days.

(21) Appl. No.: 16/377,005

(22) Filed: Apr. 5, 2019

(65) Prior Publication Data

US 2019/0225621 A1    Jul. 25, 2019

Related U.S. Application Data

(62) Division of application No. 15/815,809, filed on Nov. 17, 2017, now Pat. No. 10,301,315.

(60) Provisional application No. 62/423,919, filed on Nov. 18, 2016.

(51) Int. Cl.
| | |
|---|---|
| *A61K 31/519* | (2006.01) |
| *C07D 487/04* | (2006.01) |
| *A61K 45/06* | (2006.01) |
| *A61P 11/12* | (2006.01) |

(52) U.S. Cl.
CPC .......... *C07D 487/04* (2013.01); *A61K 31/519* (2013.01); *A61K 45/06* (2013.01); *A61P 11/12* (2018.01)

(58) Field of Classification Search
CPC ........................... A61K 31/519; C07D 487/04
USPC ........................... 514/265.1; 546/280
See application file for complete search history.

(56) References Cited

U.S. PATENT DOCUMENTS

| | | |
|---|---|---|
| 2007/0203143 A1 | 8/2007 | Sheppard et al. |
| 2007/0393516 | 12/2007 | Knight et al. |
| 2013/0344061 A1 | 12/2013 | Palombella et al. |

FOREIGN PATENT DOCUMENTS

WO    2004/100868 A2    11/2004

OTHER PUBLICATIONS

Spyryx, "Spyryx Biosciences to Present Safety, Stability & Effectiveness Data for SPX-101 at the North American Cystic Fibrosis Conference, Oct. 27-29, 2016 Orlando, FL," Spyryx Biosciences, Oct. 25, 2016, pp. 1-2, retrieved from https://www.prnewswire.com/news-releases/spyryx-biosciences-to-present-safety-stability-effectiveness-data-for-spx-101-at-the-north-american-cystic-fibrosis-conference-ctober-27-29-2016--orlando-fl-300350083.html.

Smart, "Proteostasis Therapeutics, Inc. Presents Preclinical Data for Its CFTR Amplifier Program at the 29th Annual North American Cystic Fibrosis Conference," Proteostasis, Oct. 8, 2015, pp. 1-2, retrieved from http://www.marketwired.com/press-release/proteostasis-therapeutics-inc-presents-preclinical-data-its-cflr-amplifier-program-29th-2062260.htm.

Kim, J., et al., "The Protein Kinase 2 Inhibitor CX-4945 Induces Autophagy in Human Cancer Cell Lines," Bull. Korean Chem. Soc. 2014;35(10):2985-2989.

(Continued)

*Primary Examiner* — Jeffrey H Murray
(74) *Attorney, Agent, or Firm* — Pillsbury Winthrop Shaw Pittman LLP

(57) ABSTRACT

The present invention relates to methods of using compounds of Formula I,

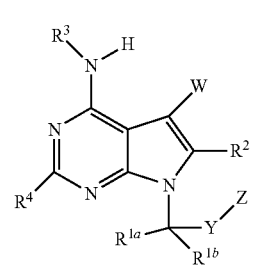

wherein $R^{1a}$, $R^{1b}$, $R^2$, $R^3$, $R^4$, W, Y, and Z are as described herein, and pharmaceutically acceptable salts thereof. The compounds are potentiators of Cystic Fibrosis Transmembrane conductance Regulator (CFTR). The invention also discloses pharmaceutical compositions comprising the compound, optionally in combination with additional therapeutic agents, and methods of potentiating, in mammals, including humans, CFTR by administration of the compounds. These compounds are useful for the treatment of cystic fibrosis (CF), asthma, bronchiectasis, chronic obstructive pulmonary disease (COPD), constipation, Diabetes mellitus, dry eye disease, pancreatitis, rhinosinusitis, Sjögren's Syndrome, and other CFTR associated disorders.

67 Claims, No Drawings

(56) References Cited

OTHER PUBLICATIONS

Graziano, "Nivalis Therapeutics Announces FDA Orphan Drug Designation for N91115 in Cystic Fibrosis," Globe News Wire, Jan. 15, 2016, pp. 1-3, retrieved from https://globenewswire.com/news-release/2016/01/15/802351/0/en/Nivalis-Therapeutics-Announces-FDA-Orphan-Drug-Designation-for-N91115-in-Cystic-Fibrosis.html.

Schweitzer, "ProQR Announces Enrollment Has Started in Global Phase 1b Study of QR-010 in Cystic Fibrosis Patie," MacDougall Biomedical Communication, Jun. 26, 2015, pp. 1-2, retrieved from http://ir.proqr.com/news-releases/news-release-details/proqr-announces-enrollment-has-started-global-phase-1-study-qr.

Patent Coopertation Treaty, International Search Report and Written Opinion for PCT/US2017/62148, dated Apr. 26, 2018, pp. 1-15.

PYRROLOPYRIMIDINES AS CFTR POTENTIATORS

CROSS REFERENCE TO RELATED APPLICATIONS

This application is a divisional of U.S. application Ser. No. 15/815,809 filed Nov. 17, 2017, which claims priority to U.S. Provisional Application 62/423,919 filed Nov. 18, 2016, the contents of which are incorporated herein by reference in their entirety.

FIELD OF THE INVENTION

The present invention relates to small molecule potentiators of Cystic Fibrosis Transmembrane conductance Regulator (CFTR). This invention also relates to pharmaceutical compositions comprising the potentiators, optionally in combination with additional therapeutic agents, and methods of potentiating, in mammals, including humans, CFTR by administration of the small molecule CFTR potentiators. The present invention also relates to the treatment of cystic fibrosis and other disorders in mammals, including humans, with the CFTR potentiators. More particularly, this invention relates to 2,5,6,7-tetrasubstituted-7H-pyrrolo[2,3-d]pyrimidin-4-amine derivatives useful for the treatment of cystic fibrosis (CF), asthma, bronchiectasis, chronic obstructive pulmonary disease (COPD), constipation, Diabetes mellitus, dry eye disease, pancreatitis, rhinosinusitis, Sjögren's Syndrome, and other CFTR associated disorders.

BACKGROUND OF THE INVENTION

Cystic fibrosis (CF) is the most common lethal genetic disease affecting Caucasians. CF is an autosomal recessive disease with an incidence of between 1 in 2000 and 1 in 3000 live births (Cutting, G. R., Accurso, F., Ramsey, B. W., and Welsh, M. J., Online Metabolic & Molecular Bases of Inherited Disease, McGraw-Hill, 2013). There are over 70,000 people affected worldwide, of which approximately 33,000 are in the United States (www.cff.org/What-is-CF/About-Cystic-Fibrosis/). The hallmarks of CF are excessive mucus secretion and defective mucus clearance resulting in obstruction, infection and inflammation in the airways; pancreatic insufficiency; and elevated sweat chloride concentration. CF is a multisystem disease affecting the lungs, pancreas, and gastrointestinal, hepatobiliary, and reproductive tracts (R. D. Coakley et al., in Cystic Fibrosis, Eds. Hodson, M., Geddes, D., and Bush, A., Edward Arnold, Third Ed., 2007, pp. 59-68).

For most patients, there is a high burden of care for supportive therapies that do not address the root cause of the disease. Supportive therapies include physical airway clearance techniques, inhaled medications (mucolytics, antibiotics, and hypertonic saline), oral anti-inflammatory drugs, pancreatic enzyme replacements, and nutritional supplements (Cystic Fibrosis Foundation Patient Registry 2011 Annual Data Report to the Center Directors, Cystic Fibrosis Foundation, Bethesda, Md., 2012). The median age of survival for patients with cystic fibrosis is into the fourth decade of life.

Cystic fibrosis is caused by mutations in the gene for CFTR (Cystic Fibrosis Transmembrane conductance Regulator), an ion channel found in epithelia as well as other tissues. CFTR is found at the apical membrane of epithelial cells in the airways, intestine, pancreas, and sweat glands (G. R. Cutting, Accurso, F., Ramsey, B. W., and Welsh, M. J., Online Metabolic & Molecular Bases of Inherited Disease, McGraw-Hill, 2013). Mutations in CFTR have been classified into six types (Welsh, M. J., and Smith, A. E., Cell, 1993, 73, 1251-1254 and Sloane, P. A., and Rowe, S. M., Curr. Opin. Pulm. Med., 2010, 16, 591-597): 1) premature termination due to deletion, nonsense, or frameshift mutations, 2) defective trafficking out of the endoplasmic reticulum due to improper folding, 3) improper gating, 4) reduced conductance due to changes in the channel pore, 5) reduced production of channel due to altered splicing, and 6) increased endocytosis from the plasma membrane.

Nearly 2,000 different mutations in CFTR are known to cause CF. Deletion of Phe508 of CFTR (F508del) occurs in approximately 70% of CFTR alleles (Bobadilla, J. L. et al., Human Mutation, 2002, 19, 575-606). Approximately 50% of patients are F508del homozygotes and ca. 40% are heterozygotes so that at least one copy of F508del is present in about 90% of patients. G551D is the third most common mutation and is present in about 4% of patients (Cystic Fibrosis Foundation Patient Registry 2011 Annual Data Report to the Center Directors, Cystic Fibrosis Foundation, Bethesda, Md., 2012).

The F508del mutation causes loss of CFTR function due to both reduced channel density and impaired channel gating. Channel density at the apical membrane is reduced due to protein misfolding. Misfolded CFTR is recognized by cellular quality control mechanisms and degraded (Ward, C. L. and Kopito, R. R., J. Biol. Chem., 1994, 269, 25710-25718). F508del function is further reduced because it has a significantly reduced channel open probability (gating defect) (Dalemans, W. et al., Nature, 1991, 354, 526-528). The G551D mutation results in a protein with normal folding but impaired gating (Illek, B. et al., Am. J. Physiol., 1999, 277, C833-C839).

Small molecules called 'correctors' have been shown to reverse the folding/trafficking defect of F508del CFTR and increase the density of CFTR channels at the plasma membrane (Pedemonte, N. et al., J. Clin. Invest., 2005, 115, 2564-2571, Van Goor, F. et al., Am. J. Physiol. Lung Cell. Mol. Physiol., 2006, 290, L1117-1130, Van Goor, F. et al., Proc. Nat. Acad. Sci. USA, 2011, 108, 18843-18848). 'Potentiators' are small molecules that increase the channel open probability of mutant CFTR, reversing the gating defect. Pharmacological repair of F508del is thought to require at least a corrector and a potentiator to address the folding and gating defects while G551D may see benefit from a potentiator only.

Kalydeco® (ivacaftor, VX-770) is a marketed potentiator that improves the gating characteristics of G551D. In G551D patients, it substantially improved lung function (percent predicted $FEV_1$ increased 10-13%), allowed weight gain, and reduced the frequency of pulmonary exacerbations (Ramsey, B. W. et al., New Eng. J. Med., 2011, 365, 1663-1672, Davies, J. C. et al., Am. J. Resp. Crit. Care Med., 2013, 187, 1219-1225). Kalydeco® is also approved for people with G1244E, G1349D, G178R, G551S, S1251N, 51255P, S549N, and S549R mutations and application to other mutations including those with partial function is being investigated.

While monotherapy with Kalydeco® did not lead to any appreciable improvement in F508del homozygote patients (Flume, P. A. et al., Chest, 2012, 142, 718-724), a combination of a corrector (VX-809, lumacaftor or VX-661, tezacaftor) with Kalydeco® resulted in a modest improvement in lung function (percent predicted $FEV_1$ increased 3-4%) (Wainwright, C. E. et al., N. Engl. J. Med., 2015, 373, 220-231, Pilewski, J. M. et al., J. Cystic Fibrosis, 2015, 14, Suppl. 1, S1). The VX-809 plus Kalydeco® combination (called Orkambi®) is a marketed therapy for F508del homozygote patients.

For both the G551D and the F508del patient populations, improved therapies are expected to provide further benefit to patients. Most G551D patients are G551D/F508del compound heterozygotes and treatment with the combination of the corrector VX-661 plus Kalydeco® resulted in a further increase in lung function over Kalydeco® alone (Pilewski, J. M. et al., J. Cystic Fibrosis, 2015, 14, Suppl. 1, S1).

Mutations in CFTR that are associated with moderate CFTR dysfunction are also evident in patients with conditions that share certain disease manifestations with cystic fibrosis but do not meet the diagnostic criteria for cystic fibrosis. In these patients, CFTR dysfunction at epithelial cell layers can occur and give rise to abnormal mucus and endocrine secretions that are similar to those that characterize cystic fibrosis. CFTR dysfunction may also be acquired. Chronic inhalation of particulate irritants, including cigarette smoke, pollution, and dust can result in reduced CFTR ion-channel activity.

Modulation of CFTR activity may also be beneficial for other diseases not directly caused by mutations in CFTR, such as secretory diseases and other protein folding diseases mediated by CFTR. CFTR regulates chloride and bicarbonate flux across the epithelia of many cells to control fluid movement, protein solubilization, mucus viscosity, and enzyme activity. Defects in CFTR can cause blockage of the airway or ducts in many organs, including the liver and pancreas. Potentiators are compounds that enhance the gating activity of CFTR present in the cell membrane. Any disease which involves thickening of the mucus, impaired fluid regulation, impaired mucus clearance, or blocked ducts leading to inflammation and tissue destruction could be a candidate for potentiators. Therefore, there exists a significant therapeutic need for novel small molecules that act as potentiators of CFTR.

In addition to cystic fibrosis, CFTR-related diseases or other diseases which may benefit from modulation of CFTR activity include, but are not limited to, asthma, bronchiectasis, chronic obstructive pulmonary disease (COPD), constipation, diabetes mellitus, dry eye disease, pancreatitis, rhinosinusitis, and Sjögren's Syndrome.

SUMMARY OF THE INVENTION

A first embodiment of a first aspect of the present invention is a compound of Formula I

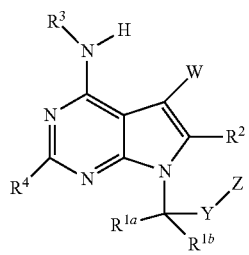

I or a pharmaceutically acceptable salt thereof, wherein

W is selected from the group consisting of phenyl, which is optionally fused with a five to six membered cycloalkyl or a five to six membered heterocycloalkyl comprising one, two, three, or four heteroatoms selected independently for each occurrence from the group consisting of N, O and $S(O)_n$;

a five to ten membered heteroaryl comprising one, two, three, or four heteroatoms selected independently for each occurrence from the group consisting of N, O and $S(O)_n$;

a four to seven membered heterocycloalkyl comprising one, two, three, or four heteroatoms selected independently for each occurrence from the group consisting of N, O, and $S(O)_n$; and $C_3$-$C_7$cycloalkyl;

wherein the phenyl, heteroaryl, heterocycloalkyl, and cycloalkyl are optionally substituted with one, two, three, four, or five $R^5$;

Y is a five membered heteroaryl comprising one, two, three, or four heteroatoms selected independently for each occurrence from the group consisting of N, O and $S(O)_n$; wherein the heteroaryl is optionally substituted with one, two, or three substituents independently selected from the group consisting of halo, $C_1$-$C_6$alkyl, and $C_1$-$C_6$haloalkyl;

Z is selected from the group consisting of phenyl, $C_1$-$C_6$alkyl, $C_3$-$C_7$cycloalkyl, a five or six membered heteroaryl comprising one, two or three heteroatoms selected independently for each occurrence from the group consisting of N, O and $S(O)_n$, and a four to seven membered heterocycloalkyl comprising one, two, or three heteroatoms selected independently for each occurrence from the group consisting of N, O and $S(O)_n$; wherein said phenyl, alkyl, cycloalkyl, heteroaryl, and heterocycloalkyl are each independently optionally substituted with one, two, three, four, or five $R^6$;

$R^{1a}$ and $R^{1b}$ are each independently selected from the group consisting of —H, —OH, halo, $C_1$-$C_6$alkyl, $C_3$-$C_7$cycloalkyl, and a four to seven membered heterocycloalkyl comprising one, two, or three heteroatoms each independently selected from the group consisting of N, O and $S(O)_n$; wherein the $C_1$-$C_6$alkyl group is optionally substituted with one, two, or three substituents each independently selected from the group consisting of halo, —OH, $C_1$-$C_3$alkyoxy, $C_3$-$C_7$cycloalkyl, and a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents independently selected for each occurrence from the group consisting of —OH, halo, and $C_1$-$C_6$alkyl;

or $R^{1a}$ and $R^{1b}$ taken together with the carbon to which they are attached form a $C_3$-$C_7$cycloalkyl or a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents each independently selected from the group consisting of —OH, halo, and $C_1$-$C_6$alkyl.

$R^2$ is selected from the group consisting of —H, halo, —CN, $C_1$-$C_6$alkyl and $C_1$-$C_6$haloalkyl;

$R^3$ and $R^4$ are independently selected for each occurrence from the group consisting of —H, $C_1$-$C_6$alkyl and $C_1$-$C_6$haloalkyl;

$R^5$ at each occurrence is independently selected from the group consisting of halo, —CN, $C_1$-$C_6$alkyl, $C_1$-$C_6$haloalkyl, —OR$^7$, —N(R$^7$)$_2$, —N(R$^7$)C(=O)R$^7$, —SR$^7$, oxo, $C_2$-$C_7$alkoxyalkyl, —S(=O)$_2$C$_1$-$C_6$alkyl, —C(=O)R$^7$, and a five membered heteroaryl comprising one, two, three, or four heteroatoms selected independently for each occurrence from the group consisting of N, O and S(O)$_n$, wherein the heteroaryl is optionally substituted with one, two, or three substituents independently selected for each occurrence from the group consisting of halo, —CN, $C_1$-$C_6$alkyl, $C_1$-$C_6$haloalkyl, —OR$^7$, —N(R$^7$)$_2$ and —SR$^7$;

R$^6$ at each occurrence is independently selected from the group consisting of halo, $C_1$-$C_6$alkyl and $C_1$-$C_6$haloalkyl, —OR$^7$, —N(R$^7$)$_2$, and —SR$^7$;

R$^7$ is independently selected for each occurrence from the group consisting of —H, $C_1$-$C_6$alkyl, $C_1$-$C_6$haloalkyl, $C_3$-$C_7$cycloalkyl, and $C_1$-$C_6$alkyl$C_3$-$C_7$cycloalkyl; and n at each occurrence is independently 0, 1, or 2.

A second embodiment of the first aspect of the present invention is the compound of the first embodiment, wherein R$^3$ and R$^4$ are both —H; or a pharmaceutically acceptable salt thereof.

A third embodiment of the first aspect of the present invention is the compound of the second embodiment, wherein Y is pyrazole, triazole, imidazole, or isoxazole, each optionally substituted with $C_1$-$C_6$alkyl; or a pharmaceutically acceptable salt thereof.

A fourth embodiment of the first aspect of the present invention is the compound of the second embodiment or a pharmaceutically acceptable salt thereof, wherein the moiety Y—Z is selected from the group consisting of:

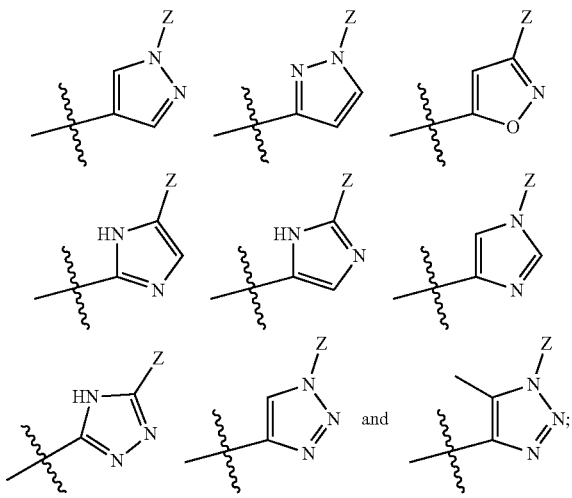

or a pharmaceutically acceptable salt thereof.

A fifth embodiment of the first aspect of the present invention is the compound of the third embodiment, wherein W is phenyl, optionally substituted with one, two, or three R$^5$; or a pharmaceutically acceptable salt thereof.

A sixth embodiment of the first aspect of the present invention is the compound of the third embodiment, wherein W is selected from the group consisting of pyrimidinyl, pyridinyl, pyrazinyl, and pyrazolyl each optionally substituted with one, two, or three R$^5$; or a pharmaceutically acceptable salt thereof.

A seventh embodiment of the first aspect of the present invention is the compound of the third embodiment, wherein W is $C_3$-$C_7$cycloalkyl, optionally substituted with one, two, or three R$^5$; or a pharmaceutically acceptable salt thereof.

An eighth embodiment of the first aspect of the present invention is the compound of the six embodiment wherein W is

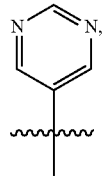 [SMILES: *c1cncnc1]

optionally substituted with one, two, or three R$^5$;

R$^5$ at each occurrence is independently selected from the group consisting of —OCH$_3$, —CHF$_2$, —CF$_3$, and —N(CH$_3$)$_2$; or a pharmaceutically acceptable salt thereof.

A ninth embodiment of the first aspect of the present invention is the compound of the third embodiment wherein Z is selected from the group consisting of phenyl, $C_3$-$C_7$cycloalkyl, and $C_1$-$C_6$alkyl, each optionally substituted with one, two, or three R$^6$; or a pharmaceutically acceptable salt thereof.

A tenth embodiment of the first aspect of the present invention is the compound of the ninth embodiment wherein Z is phenyl, optionally substituted with one or two fluoro or chloro; or a pharmaceutically acceptable salt thereof.

An eleventh embodiment of the first aspect of the present invention is the compound of the ninth embodiment or a pharmaceutically acceptable salt thereof, wherein Z is $C_1$-$C_6$alkyl or $C_3$-$C_7$cycloalkyl; or a pharmaceutically acceptable salt thereof.

A twelfth embodiment of the first aspect of the present invention is the compound of the second embodiment, wherein R$^2$ is selected from the group consisting of: —H, —CN, and —Br; or a pharmaceutically acceptable salt thereof.

A thirteenth embodiment of the first aspect of the present invention is a compound selected from the group consisting of 4-amino-5-[2-(difluoromethyl)pyrimidin-5-yl]-7-{(1S)-1-[1-(2-fluorophenyl)-1H-pyrazol-4-yl]ethyl}-7H-pyrrolo[2,3-d]pyrimidine-6-carbonitrile;

4-amino-5-[2-(difluoromethyl)pyrimidin-5-yl]-7-{(1R)-1-[1-(2-fluorophenyl)-1H-pyrazol-4-yl]ethyl}-7H-pyrrolo[2,3-d]pyrimidine-6-carbonitrile;

4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[3-(2-fluorophenyl)-1,2-oxazol-5-yl]ethyl}-5-(2-methoxypyrimidin-5-yl)-7H-pyrrolo[2,3-d]pyrimidine-6-carbonitrile;

4-amino-7-{(1S)-1-[3-(2-fluorophenyl)-1,2-oxazol-5-yl]ethyl}-5-(2-methoxypyrimidin-5-yl)-7H-pyrrolo[2,3-d]pyrimidine-6-carbonitrile;

4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;

4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;

4-amino-5-[2-(difluoromethyl)pyrimidin-5-yl]-7-{[1-(2-fluorophenyl)-1H-pyrazol-4-yl]methyl}-7H-pyrrolo[2,3-d]pyrimidine-6-carbonitrile;

4-amino-7-{[1-(2-fluorophenyl)-1H-1,2,3-triazol-4-yl]methyl}-5-[2-(trifluoromethyl)pyrimidin-5-yl]-7H-pyrrolo[2,3-d]pyrimidine-6-carbonitrile;

6-bromo-7-{[1-(2-fluorophenyl)-1H-pyrazol-4-yl]methyl}-5-[2-(trifluoromethyl)pyrimidin-5-yl]-7H-pyrrolo[2,3-d]pyrimidin-4-amine;

5-[4-(cyclopropyloxy)phenyl]-7-{[1-(2-fluorophenyl)-1H-1,2,3-triazol-4-yl]methyl}-7H-pyrrolo[2,3-d]pyrimidin-4-amine;

5-cyclobutyl-7-{(1S)-1-[1-(2-fluorophenyl)-1H-1,2,3-triazol-4-yl]ethyl}-7H-pyrrolo[2,3-d]pyrimidin-4-amine;

5-(4-chlorophenyl)-7-{(1S)-1-[1-(2-fluorophenyl)-1H-1,2,3-triazol-4-yl]ethyl}-7H-pyrrolo[2,3-d]pyrimidin-4-amine;

5-[6-(cyclopropyloxy)pyridin-3-yl]-7-{(1S)-1-[1-(2-fluorophenyl)-1H-1,2,3-triazol-4-yl]ethyl}-7H-pyrrolo[2,3-d]pyrimidin-4-amine;

5-(6-methoxypyridin-3-yl)-7-[(1S)-1-(1-phenyl-1H-1,2,3-triazol-4-yl)propyl]-7H-pyrrolo[2,3-d]pyrimidin-4-amine;

7-[(1S)-1-(1-phenyl-1H-1,2,3-triazol-4-yl)propyl]-5-[2-(trifluoromethyl)pyrimidin-5-yl]-7H-pyrrolo[2,3-d]pyrimidin-4-amine;

5-(4-chlorophenyl)-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(2-fluorophenyl)-1H-1,2,3-triazol-4-yl]propyl}-5-(3-methoxypyrazin-2-yl)-7H-pyrrolo[2,3-d]pyrimidin-4-amine;

7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine;

5-(5-fluoro-2-methoxypyridin-3-yl)-7-{(1S)-1-[1-(2-fluorophenyl)-1H-1,2,3-triazol-4-yl]propyl}-7H-pyrrolo[2,3-d]pyrimidin-4-amine;

5-[6-(difluoromethoxy)pyridin-3-yl]-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(3,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,5-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidin-4-amine;

7-{(1S)-1-[2-(2,4-difluorophenyl)-1H-imidazol-4-yl]propyl}-5-[2-(trifluoromethyl)pyrimidin-5-yl]-7H-pyrrolo[2,3-d]pyrimidin-4-amine;

7-{(1S)-1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,4-difluorophenyl)-5-methyl-1H-1,2,3-triazol-4-yl]propyl}-5-[2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-(2-methoxy-6-methylpyridin-3-yl)-7H-pyrrolo[2,3-d]pyrimidin-4-amine;

7-{[1-(2-fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine;

4-amino-7-{(1S)-1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-5-[2-(difluoromethoxy)pyrimidin-5-yl]-7-{(1S)-1-[1-(2-fluorophenyl)-1H-1,2,3-triazol-4-yl]propyl}-7H-pyrrolo[2,3-d]pyrimidine-6-carbonitrile;

4-amino-5-(4-chlorophenyl)-7-{[1-(propan-2-yl)-1H-pyrazol-4-yl]methyl}-7H-pyrrolo[2,3-d]pyrimidine-6-carbonitrile;

4-amino-5-(4-chlorophenyl)-7-{[1-(2-fluorophenyl)-1H-1,2,3-triazol-4-yl]methyl}-7H-pyrrolo[2,3-d]pyrimidine-6-carbonitrile;

5-(2-fluoro-4-methoxyphenyl)-7-{1-[2-(2-fluorophenyl)-1H-imidazol-5-yl]ethyl}-7H-pyrrolo[2,3-d]pyrimidin-4-amine;

5-(3-fluoro-4-methylphenyl)-7-{1-[2-(2-fluorophenyl)-1H-imidazol-5-yl]ethyl}-7H-pyrrolo[2,3-d]pyrimidin-4-amine;

7-{1-[2-(2-fluorophenyl)-1H-imidazol-5-yl]ethyl}-5-[4-(2H-1,2,3-triazol-2-yl)phenyl]-7H-pyrrolo[2,3-d]pyrimidin-4-amine;

5-(4-ethoxy-3-fluorophenyl)-7-{[1-(2-fluorophenyl)-1H-1,2,3-triazol-4-yl]methyl}-7H-pyrrolo[2,3-d]pyrimidin-4-amine;

5-(4-chloro-2-methoxyphenyl)-7-{[1-(2-fluorophenyl)-1H-1,2,3-triazol-4-yl]methyl}-7H-pyrrolo[2,3-d]pyrimidin-4-amine;

5-[4-(difluoromethoxy)phenyl]-7-{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[4-(methylsulfanyl)phenyl]-7H-pyrrolo[2,3-d]pyrimidin-4-amine;

5-[4-(difluoromethoxy)phenyl]-7-{1-[1-(2-fluorophenyl)-1H-1,2,3-triazol-4-yl]ethyl}-7H-pyrrolo[2,3-d]pyrimidin-4-amine;

5-[2-fluoro-4-(methylsulfanyl)phenyl]-7-{1-[1-(2-fluorophenyl)-1H-1,2,3-triazol-4-yl]ethyl}-7H-pyrrolo[2,3-d]pyrimidin-4-amine;

5-(4-chloro-3-fluorophenyl)-7-{1-[1-(2-fluorophenyl)-1H-1,2,3-triazol-4-yl]ethyl}-7H-pyrrolo[2,3-d]pyrimidin-4-amine;

5-(3-chloro-5-fluorophenyl)-7-{1-[1-(2-fluorophenyl)-1H-1,2,3-triazol-4-yl]ethyl}-7H-pyrrolo[2,3-d]pyrimidin-4-amine;

5-cyclopropyl-7-{(1S)-1-[1-(2-fluorophenyl)-1H-1,2,3-triazol-4-yl]ethyl}-7H-pyrrolo[2,3-d]pyrimidin-4-amine;

4-(4-amino-7-{(1S)-1-[1-(2-fluorophenyl)-1H-1,2,3-triazol-4-yl]ethyl}-7H-pyrrolo[2,3-d]pyrimidin-5-yl)-2-fluorobenzonitrile;

5-[4-(cyclopropyloxy)phenyl]-7-{(1S)-1-[1-(2-fluorophenyl)-1H-1,2,3-triazol-4-yl]ethyl}-7H-pyrrolo[2,3-d]pyrimidin-4-amine;

5-(4-methoxypyrimidin-5-yl)-7-[(1S)-1-(1-phenyl-1H-1,2,3-triazol-4-yl)propyl]-7H-pyrrolo[2,3-d]pyrimidin-4-amine;

7-{(1S)-1-[1-(2-fluorophenyl)-1H-1,2,3-triazol-4-yl]propyl}-5-(4-methoxypyrimidin-5-yl)-7H-pyrrolo[2,3-d]pyrimidin-4-amine;

5-[2-(difluoromethyl)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

5-[2-(dimethylamino)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

7-{(1R)-1-[1-(2-fluorophenyl)-1H-1,2,3-triazol-4-yl]propyl}-5-(1H-pyrazol-3-yl)-7H-pyrrolo[2,3-d]pyrimidin-4-amine;

7-{(1S)-1-[1-(4-fluorophenyl)-1H-1,2,3-triazol-4-yl]propyl}-5-(4-methoxypyrimidin-5-yl)-7H-pyrrolo[2,3-d]pyrimidin-4-amine;

7-{(1S)-1-[1-(3,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(3,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

5-cyclopropyl-7-{(1S)-1-[1-(2-fluorophenyl)-1H-1,2,3-triazol-4-yl]propyl}-7H-pyrrolo[2,3-d]pyrimidin-4-amine;

7-{(S)-cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine;

7-{(1S)-1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine;

5-(4-chlorophenyl)-7-{(1S)-1-[3-(2-fluorophenyl)-1,2-oxazol-5-yl]ethyl}-7H-pyrrolo[2,3-d]pyrimidin-4-amine;

7-{(1S)-1-[3-(2-fluorophenyl)-1,2-oxazol-5-yl]ethyl}-5-(2-methoxypyrimidin-5-yl)-7H-pyrrolo[2,3-d]pyrimidin-4-amine;

5-(5-fluoro-2-methoxypyridin-3-yl)-7-{[1-(2-fluorophenyl)-1H-1,2,3-triazol-4-yl]methyl}-7H-pyrrolo[2,3-d]pyrimidin-4-amine;

5-[2-(difluoromethoxy)pyridin-3-yl]-7-{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-4-amine;

7-{1-[1-(2-fluorophenyl)-1H-1,2,3-triazol-4-yl]ethyl}-5-[4-methoxy-2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-[4-methoxy-2-(trifluoromethyl)pyrimidin-5-yl]-7H-pyrrolo[2,3-d]pyrimidin-4-amine;

5-(4-chlorophenyl)-7-{2-[1-(2-fluorophenyl)-1H-1,2,3-triazol-4-yl]propan-2-yl}-7H-pyrrolo[2,3-d]pyrimidin-4-amine;

5-(4-chlorophenyl)-7-{1-[1-(2-fluorophenyl)-1H-1,2,3-triazol-4-yl]ethyl}-6-methyl-7H-pyrrolo[2,3-d]pyrimidin-4-amine;

5-(4-chlorophenyl)-7-{[2-(2-fluorophenyl)-1H-imidazol-5-yl]methyl}-7H-pyrrolo[2,3-d]pyrimidin-4-amine;

5-(4-chlorophenyl)-7-[(2-phenyl-1H-imidazol-5-yl)methyl]-7H-pyrrolo[2,3-d]pyrimidin-4-amine;

5-(4-chlorophenyl)-7-[(3-cyclohexyl-1,2-oxazol-5-yl)methyl]-7H-pyrrolo[2,3-d]pyrimidin-4-amine;

7-({1-[4-(difluoromethyl)phenyl]-1H-pyrazol-4-yl}methyl)-5-(2-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(4-methoxypyrimidin-5-yl)-7H-pyrrolo[2,3-d]pyrimidin-4-amine;

4-amino-5-[6-(cyclopropyloxy)pyridin-3-yl]-7-{(1S)-1-[1-(2,4-difluorophenyl)-1H-1,2,3-triazol-4-yl]ethyl}-7H-pyrrolo[2,3-d]pyrimidine-6-carbonitrile; and 4-amino-7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

or a pharmaceutically acceptable salt thereof.

A fourteenth embodiment of the first aspect of the present invention is a compound selected from the group consisting of 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile; and
4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;
or a pharmaceutically acceptable salt thereof.

A fifteenth embodiment of the first aspect of the present invention is the compound 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine or a pharmaceutically acceptable salt thereof.

A sixteenth embodiment of the first aspect of the present invention is the compound 4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile or a pharmaceutically acceptable salt thereof.

A seventeenth embodiment of the first aspect of the present invention is the compound 4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile or a pharmaceutically acceptable salt thereof.

An eighteenth embodiment of the first aspect of the present invention is the compound 4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

A nineteenth embodiment of the first aspect of the present invention is the compound 4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

A first embodiment of a second aspect of the present invention is a method of treating cystic fibrosis, asthma, bronchiectasis, chronic obstructive pulmonary disease (COPD), constipation, Diabetes mellitus, dry eye disease, pancreatitis, rhinosinusitis, or Sjögren's Syndrome in a patient in need of treatment thereof, the method comprising administering a therapeutically effective amount of a compound, or pharmaceutically acceptable salt of said compound, according to any one of the first through nineteenth embodiments of the first aspect, to a patient in need of treatment thereof.

A second embodiment of the second aspect of the present invention is a method for treating cystic fibrosis in a patient in need of treatment thereof, the method comprising administering a therapeutically effective amount of a compound, or pharmaceutically acceptable salt of said compound, according to any one of the first through nineteenth embodiments of the first aspect, to a patient in need of treatment thereof.

A first embodiment of a third aspect of the present invention is the compound or pharmaceutically acceptable salt thereof according to any one of the first through nineteenth embodiments of the first aspect for use in the treatment of cystic fibrosis.

A first embodiment of a fourth aspect of the present invention is a pharmaceutical composition comprising a therapeutically effective amount of a compound according to any one of the first through nineteenth embodiments of the first aspect, or a pharmaceutically acceptable salt thereof together with a pharmaceutically acceptable carrier.

A second embodiment of the fourth aspect of the present invention is the pharmaceutical composition of the first embodiment of the fourth aspect, further comprising one or more additional therapeutic agents.

A third embodiment of the fourth aspect of the present invention is the pharmaceutical composition of the second embodiment of the fourth aspect, wherein the one or more additional therapeutic agents are selected from the group consisting of a CFTR potentiator, a CFTR corrector, an epithelial sodium channel (ENaC) inhibitor, a CFTR amplifier, a CFTR stabilizer, a read-through agent, an oligonucleotide patch, an autophagy inducer, and a proteostasis modulator.

A fourth embodiment of the fourth aspect of the present invention is a pharmaceutical composition of the third embodiment of the fourth aspect, wherein the CFTR potentiator at each occurrence is selected from the group consisting of VX-770 (Ivacaftor), GLPG-1837, GLPG-2451, QBW-251, FDL-176, FDL-129, CTP-656, and PTI-P271.

A fifth embodiment of the fourth aspect of the present invention is a pharmaceutical composition of the third embodiment of the fourth aspect, wherein the CFTR corrector at each occurrence is selected from the group consisting of VX-809 (lumacaftor), VX-661 (tezacaftor), VX-983, VX-152, VX-440, VX-659, GLPG2737, P247-A, GLPG-2222, GLPG-2665, GLPG-2851, FDL-169, and PTI-C1811, A sixth embodiment of the fourth aspect of the present invention is a pharmaceutical composition of the third embodiment of the fourth aspect, wherein the epithelial sodium channel (ENaC) inhibitor at each occurrence is selected from the group consisting of SPX-101, QBW-276 and VX-371.

A seventh embodiment of the fourth aspect of the present invention is a pharmaceutical composition of the third embodiment of the fourth aspect, wherein the CFTR amplifier at each occurrence is selected from the group consisting of PTI-428 and PTI-130.

An eighth embodiment of the fourth aspect of the present invention is a pharmaceutical composition of the third embodiment of the fourth aspect, wherein the CFTR stabilizer is N-91115 (Cavosonstat).

A ninth embodiment of the fourth aspect of the present invention is a pharmaceutical composition of the third embodiment of the fourth aspect, wherein the read-through agent is ataluren (PTC124).

A tenth embodiment of the fourth aspect of the present invention is a pharmaceutical composition of the third embodiment of the fourth aspect, wherein the autophagy inducer at each occurrence is selected from the group consisting of CX-4945 and the combination of cysteamine and epigallocatechin gallate (EGCG).

A first embodiment of a fifth aspect of the present invention is a method for treating cystic fibrosis in a patient in need of treatment thereof, the method comprising administering the pharmaceutical composition according to any one of the first through tenth embodiments of the fourth aspect to the patient in need of treatment thereof.

A first embodiment of a sixth aspect of the present invention is the pharmaceutical composition according to any one of the first through tenth embodiments of the fourth aspect for use in the treatment of cystic fibrosis.

Definitions

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "haloalkyl" refers to an alkyl in which at least one hydrogen on the alkyl is replaced with a halogen atom. The term "$C_1$-$C_6$ haloalkyl" refers to a $C_1$-$C_6$ alkyl group, as defined herein, in which one, two, three, four, five, or six hydrogen atoms are replaced by halogen. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. Examples of haloakyls include: chloromethyl, fluoromethyl, difluoromethyl, trifluoromethyl, 1, 1-difluoroethyl, 2-fluoroethyl, 2,2-difluoroethyl, 2-chloro-3-fluoropentyl, and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen atom from a saturated carbocyclic molecule and having the specified number of carbon atoms. In one embodiment, a cycloalkyl substituent has three to seven carbon atoms (i.e., $C_3$-$C_7$cycloalkyl). Examples of cycloalkyl include cyclopropyl, cyclobutyl, cyclopentyl, cyclohexyl and cycloheptyl. The term "cycloalkyl" includes mono-, bi- and tricyclic saturated carbocycles, as well as bridged and fused ring carbocycles, as well as spiro-fused ring systems.

As used herein, the term "heterocycloalkyl" refers to a monocyclic ring system containing the heteroatoms N, O or $S(O)_n$ as specified. The term "heterocycloalkyl" refers to a substituent obtained by removing a hydrogen from a saturated or partially saturated ring structure containing the specified number of ring atoms, wherein at least one of the ring atoms is a heteroatom (i.e. oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. In some instances, the number of atoms in a cyclic substituent containing one or more heteroatoms (i.e., heteroaryl or heterocycloalkyl) is indicated by the prefix "x to y membered", wherein x is the minimum and y is the maximum number of atoms forming the cyclic moiety of the substituent. Thus, for example, "four to seven membered heterocycloalkyl" refers to a heterocycloalkyl containing from four to seven atoms, including one or more heteroatoms, in the cyclic moiety of the heterocycloalkyl. Examples of single-ring heterocycloalkyls include azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, and diazepinyl.

The term "heteroaryl" refers to an aromatic ring structure containing the specified number of ring atoms in which at least one of the ring atoms is a heteroatom (i.e. oxygen, nitrogen, or sulfur), with the remaining ring atoms being independently selected from the group consisting of carbon, oxygen, nitrogen, and sulfur. A five to six membered heteroaryl is an aromatic ring system which has five or six ring atoms with at least one of the ring atoms being N, O or $S(O)_n$. Similarly, a five to ten membered heteroaryl is an aromatic ring system which has five to ten ring atoms with at least one of the ring atoms being N, O or $S(O)_n$. A heteroaryl may be a single ring or 2 fused rings.

Examples of heteroaryl substituents include six membered ring substituents such as pyridinyl, pyrazinyl, pyrimidinyl, and pyridazinyl; five membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3, 4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridinyl N-oxides and groups containing a pyridine N-oxide ring. Examples of 2-fused-ring heteroaryls include indolizinyl, pyranopyrrolyl, 4H-quinolizinyl, purinyl, naphthyridinyl, pyridopyridinyl (including pyrido[3, 4-b]-pyridinyl, pyrido [3, 2-b]-pyridinyl, or pyrido[4, 3-5]-pyridinyl), pyrrolopyridinyl, pyrazolopyridinyl and imidazothiazolyl and pteridinyl.

Other examples of fused-ring heteroaryls include benzo-fused heteroaryls such as indolyl, isoindolyl, indoleninyl, isoindazolyl, benzazinyl (including quinolinyl or isoquinolinyl), phthalazinyl, quinoxalinyl, benzodiazinyl (including cinnolinyl or quinazolinyl), benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

The term "halo" or "halogen" refers to fluoro (which may be depicted as —F), chloro (which may be depicted as —Cl), bromo (which may be depicted as —Br), or iodo (which may be depicted as —I).

The term "hydrogen" refers to a hydrogen substituent, and may be depicted as —H.

The term "hydroxy" or "hydroxyl" refers to —OH. Compounds bearing a carbon to which one or more hydroxyl substituents are attached include, for example, alcohols, enols and phenol.

The term "phenyl" refers to an aromatic ring having the radical —$C_6H_5$, derived from benzene by removal of a hydrogen atom. Phenyl may be optionally fused with a five or six membered cycloalkyl or heterocycloalkyl ring to form bicyclic compounds. Examples of these bicyclic compounds include 1,2,3,4-tetrahydronaphthalene, 2,3-dihydrobenzo[1,4]oxazine, 2,3-dihydro-1H-indene, isoindoline, and 2,3-dihydrobenzo[1,4]dioxine.

If substituents are described as being "independently selected" from a group, each instance of a substituent is selected independent of the other. Each substituent therefore may be identical to or different from the other substituent(s).

As used herein, the term "formula I", "formula (I)", "Formula (I)", or "Formula I" may be referred to as a "compound(s) of the invention". Such terms are also defined to include all forms of the compound of formula I, including hydrates, solvates, isomers, crystalline and noncrystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288, Haleblian, J. K. (August 1975).

The compounds of the invention may have asymmetric carbon atoms. The carbon-carbon bonds of the compounds of the invention may be depicted herein using a solid line (———), a solid wedge (▬◀), or a dotted wedge (⋯⋯⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

Examples of types of potential tautomerisms shown by the compounds of the invention include hydroxypyridine⇔pyridone; amide⇔hydroxyl-imine and keto⇔enol tautomersims:

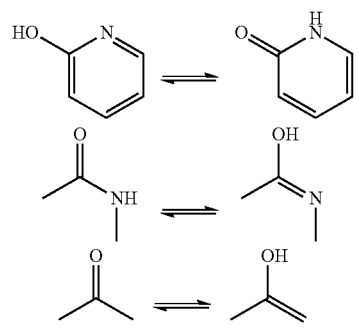

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound. Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts". Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, P-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N, N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g. methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs". Further information on the use of prodrugs may be found in "Pro-drugs as Novel Delivery Systems", Vol. 14, ACS Symposium Series (T. Higuchi and V. Stella, Eds.), American Chemical Society, 1975 Washington, D.C. and "Bioreversible Carriers in Drug Design", Pergamon Press, 1987 (E.B. Roche, Ed.) American Pharmaceutical Association. Prodrugs in accordance with the invention can, for example, be produced by replacing appropriate functionalities present in the compounds of any of formula I with certain moieties known to those skilled in the art as "pro-moieties" as described, for example, in Bundgaard, H. 1985. Design of Prodrugs. New York: Elsevier.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention.

In another embodiment, the oral administration may be in a powder or granule form. In another embodiment, the oral administration may be in a spray-dried dispersion. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing or wetting agents and suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety.

Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used.

Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and nonbiodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray, delivered from a pressurized container or a nebulizer with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Lieberman et al., Eds., Pharmaceutical Dosage Forms, Marcel Dekker, New York, N.Y., 1980; and Kibbe et al., Eds., Handbook of Pharmaceutical Excipients (3rd ed.), American Pharmaceutical Association, Washington, 2000.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration", "co-administration", "simultaneous administration," and "administered simultaneously" mean that the compounds are administered in combination.

The present invention includes the use of a combination of a CFTR potentiator compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; (c) optionally a third pharmaceutically active agent; and (d) a pharmaceutically acceptable carrier, vehicle or diluent.

Various pharmaceutically active agents may be selected for use in conjunction with the compounds of Formula I, depending on the disease, disorder, or condition to be treated. For example, a pharmaceutical composition for use in treating Cystic Fibrosis may comprise a compound of Formula I or a pharmaceutically acceptable salt thereof, together with one or more agents such as a CFTR modulator, for example another CFTR potentiator, a CFTR corrector, including a CAL (CFTR-associated ligand) inhibitor, a CFTR Production corrector or read-through agent, a CFTR stabilizer, including a CFTR-Dab2 (Disabled homolog 2) inhibitor, or a CFTR amplifier; an epithelial sodium channel (ENaC) inhibitor/blocker; an oligonucleotide patch; an autophagy inducer; a proteostasis modulator, including a histone deacetylase (HDAC) inhibitor; or supportive therapies such as a mucolytic agent, a bronchodilator, an antibiotic, an anti-infective agent, an anti-inflammatory agent, an anticholinergic, a mast cell stabilizer, a corticosteroid, a nutritional agent, or an enzyme replacement.

A combination can include more than one agent from a particular class of agents; for example, a combination of a compound of Formula I with two or more CFTR correctors. Pharmaceutically active agents that may be used in combination with the compounds of Formula I and compositions thereof include, without limitation:

(i) CFTR potentiators, such as VX-770 (ivacaftor), GLPG-1837, GLPG-2451, QBW-251, GLPG-3067, FDL-129, CTP-656, FDL-176, PTI-P271, and CTP-656;

(ii) CFTR correctors, such as VX-809 (lumacaftor), VX-661 (tezacaftor), VX-983 VX-152, VX-440, VX-659, GLPG-2737, P247-A, FDL-169, FDL-304, GLPG-2222, GLPG-2665, GLPG-2851, PTI-C1811, NU-001, and NU-002

(iii) CFTR amplifiers, such as PTI-428 and PTI-130

(iv) Read-through agents, such as ataluren (v) CFTR stabilizers, such as N91115 (cavosonstat, an S-nitrosoglutathione reductase "GSNOR" inhibitor)

(vi) Epithelial sodium channel (ENaC) inhibitors, such as SPX-101, QBW-276 and VX-371;

(vii) Oligonucleotide patches, such as QR-010

(viii) Autophagy inducers, such as CX-4945, the combination of cysteamine and epigallocatechin gallate (EGCG), cystamine, and rapamycin (ix) Proteostasis modulators, such as histone deacetylase (HDAC) inhibitors including 4-phenylbutyrate (4-PBA)

(x) Supportive therapies, such as albuterol, salmeterol, ciprofloxacin, fluticasone, prednisone, ipratropium bromide, lipase, protease, and amylase The present invention further comprises kits that are suitable for use in performing the methods of treatment described above. In one embodiment, the kit contains a first dosage form comprising one or more of the compounds of the present invention optionally in combination with one or more additional therapeutic agents and a container for the dosage, in quantities sufficient to carry out the methods of the present invention. In another embodiment, the kit of the present invention comprises one or more compounds of the invention optionally with one or more additional therapeutic agents.

General Synthetic Schemes

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I). It will be further appreciated that it may be necessary or desirable to carry out the transformations in a different order from that described in the schemes, or to modify one or more of the transformations, to provide the desired compound of the invention.

All of the derivatives of Formula I can be prepared by the procedures described in the general methods presented below or by routine modifications thereof. The present invention also encompasses any one or more of these processes for preparing the derivatives of Formula I, in addition to any novel intermediates used therein. The person skilled in the art will appreciate that the following reactions may be heated thermally or under microwave irradiation.

The routes below, including those mentioned in the Examples and Preparations, illustrate methods of synthesising compounds of Formula I. The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by RC Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by RK Mackie and DM Smith, Longman (1982); "Protective Groups in Organic Synthesis" by TW Greene and PGM Wuts, John Wiley and Sons, Inc. (1999); and "Protecting Groups" by PJ Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in a conventional manner. See, for example, those described in 'Greene's Protective Groups in Organic Synthesis' by Theodora W Greene and Peter G M Wuts, fifth edition, (John Wiley and Sons, 2014), incorporated herein by reference, which also describes methods for the removal of such groups.

In the general synthetic methods below, unless otherwise specified, the substituents are as defined above with reference to the compounds of Formula (I) above. Where ratios of solvents are given, the ratios are by volume unless otherwise specified.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula I.

According to a first process, compounds of Formula (IC) (where $R^2$=CN) may be prepared from compounds of Formulae (IA) and (IB) as illustrated by Scheme 1.

Scheme 1

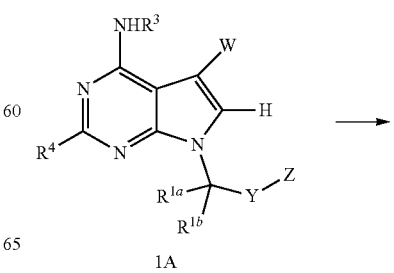

1A

Scheme 2

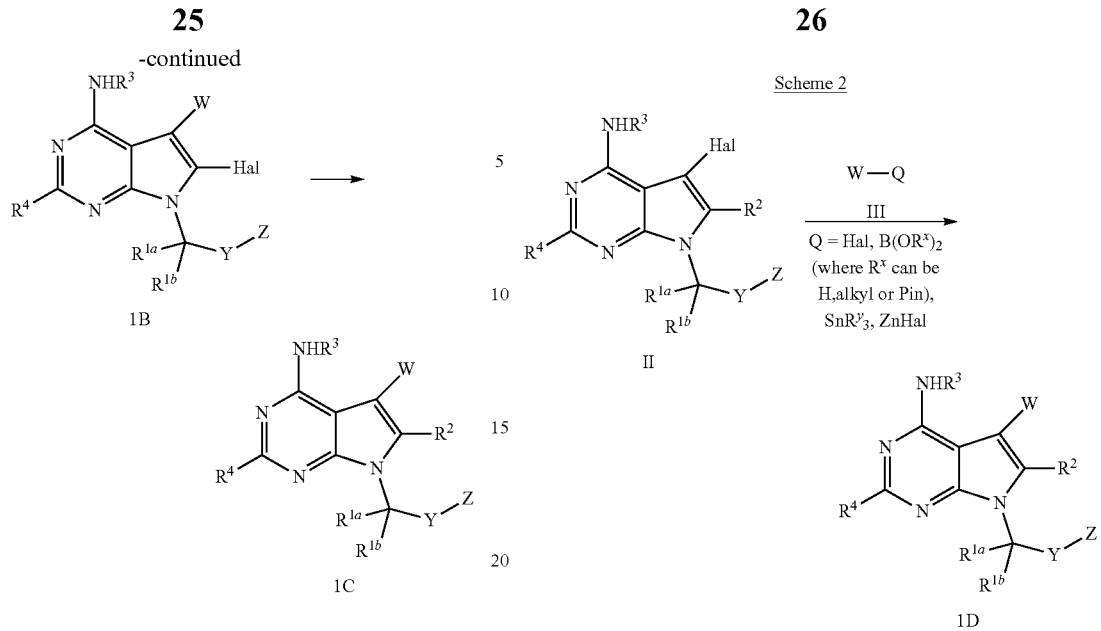

In Scheme 1, compound of the Formula (IA) is converted to a compound of Formula (IB) wherein Hal is chloro, bromo or iodo (preferably bromo) by treatment with a suitable halogenating agent such as N-(Hal)succinimide, preferably NBS, in a suitable solvent, such as DCM or DMF at an appropriate temperature such as 0° C. A skilled person also knows that alternative methods for specifically introducing a suitable halogen group such as Br are achievable using alternative reagents, solvents and temperatures. A compound of Formula (IB) is converted into a compound of Formula (IC) by treatment with a suitable organometallic source of cyanide such as $Zn(CN)_2$ or CuCN in the presence of a suitable catalyst, such as $Pd(dppf)Cl_2$ (or $Pd_2(dba)_3$ plus dppf) in a suitable solvent, such as DMF or NMP at a suitable temperature. A skilled person also knows that alternative organometallic coupling strategies can be used involving alternative coupling partners, metals and solvent combinations. It is well understood by a skilled person that a compound of the Formula (IB) is prepared and isolated as described above or prepared in situ without isolation in a sequential reaction strategy leading to a compound of Formula (IC). In the case of compounds of Formula (IA), (IB) or (IC) where $R^{1a}$ and $R^{1b}$ are different groups (for example where $R^{1a}$ is $(C_1-C_3)$alkyl and $R^{1b}$ is H) leading to the presence of a chiral center it is well understood by a skilled person that the individual enantiomers can be obtained using a suitable separation method such as SFC chromatography to afford both the (+) and (−)-enantiomers of compounds of Formula (IA), (IB) or (IC). It is well understood by a skilled person that an individual enantiomer of a compound of the Formula (IA), (IB) or (IC) is prepared and isolated as described above or isolated using an alternative separation technique such as HPLC using a suitable chiral stationary phase eluting with a suitable mobile phase as determined to be necessary to isolate the required enantiomers.

According to a second process, compounds of Formula (ID) (where $R^2$=H, CN, $(C_1-C_3)$alkyl) may be prepared from compounds of Formula (II) and (III) as illustrated by Scheme 2.

In Scheme 2, compounds of Formula (ID), wherein Hal is chloro, bromo or iodo, may be prepared from compounds of Formula (II) and (III) using a suitable organometallic cross-coupling reaction such as Suzuki cross-coupling reaction preceded if necessary by a boronic ester formation. Typical Suzuki cross-coupling conditions comprise a palladium catalyst containing suitable phosphine ligands, in the presence of an inorganic base, in aqueous dioxane or methanol, at elevated temperatures either thermally or under microwave irradiation. Preferred conditions comprise $Pd(OAc)_2$, $Pd(dppf)Cl_2$ or $Pd(PPh_3)_4$ with either sodium, cesium or potassium carbonate in aqueous dioxane or methanol at from room temperature to 120° C. Typical boronic ester formation conditions comprise $Pd(dppf)Cl_2$ and potassium acetate with bispinacolatodiboron with compounds of Formula W-Q (where Q=chloro, bromo or iodo) in dioxane at reflux. Alternatively, compounds of the Formula (ID) may be prepared by alternative cross-coupling strategies such as the Migita-Kosugi-Stille coupling using a compound of Formula (II) and Formula (III) (where Q=$SnRY_3$ and RY is alkyl (e.g., butyl)) preceded if necessary by an arylstannane formation reaction.

Compounds of Formula (ID) may also be prepared from compounds of Formula (II) using a suitable zinc reagent such as compounds of Formula (III) (where Q=ZnBr) with a palladium catalyst such as $Pd(OAc)_2$ in the presence of suitable phosphine ligands such as s-Phos, in a suitable solvent such as THF, at a suitable temperature such as room temperature.

Compounds of Formula (ID) may also be prepared by a suitable C—H activation strategy using a compound of Formula (II) and a compound of Formula (III) (where Q=H) in the presence of a palladium catalyst in the presence of an inorganic base, at a suitable temperature such as 50° C. Typical conditions comprise $Pd(OAc)_2$, with sodium acetate and $Bu_4NCl$. A skilled person will know that alternative conditions are available and can be selected depending on the reactivity of the substrates. Compounds of Formula (III) may be obtained commercially or by analogy with the methods described herein.

According to a third process, compounds of Formula (IE) may be prepared from compounds of Formula (IVa), (V), (VI) and (VII) as illustrated by Scheme 3.

Scheme 3

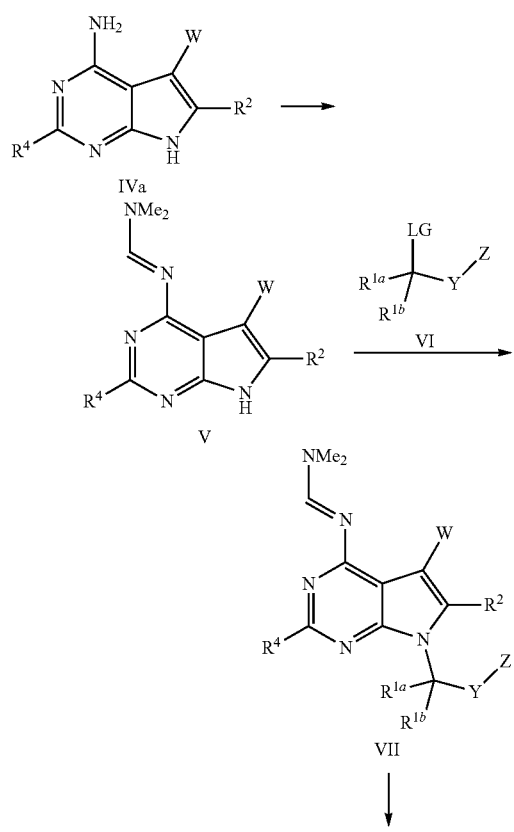

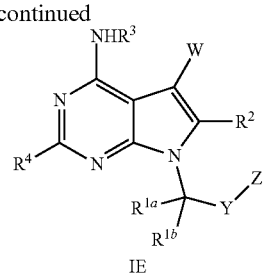

In Scheme 3, compounds of Formula (IE) (where $R^2$ and $R^3$=H) may be prepared from compounds of Formula (VII) by the reaction of aqueous ammonium hydroxide solution in a suitable solvent such as MeOH at a suitable temperature such as 70° C. for an appropriate time such as 18 hours in a sealed tube. Compounds of Formula (VII) may be prepared by a suitable alkylation reaction with compounds of Formula (V) and (VI) (LG is a suitable leaving group such as a halogen in particular a chlorine atom or a mesylate) in the presence of a suitable base such as $Cs_2CO_3$ in a suitable solvent such as DMF at a suitable temperature such as 80° C. Compounds of Formula (VI) may be obtained commercially or by analogy with the methods described herein. Compounds of Formula (V) may be prepared from compounds of Formula (IVa) by the reaction with DMF-DMA at a suitable temperature from room temperature to 100° C. preferably at 50° C.

Compounds of Formula (IV) may be prepared from compounds of Formulae (III), (VIII), (IX), (X), (XI) and (XII) as illustrated by Scheme 4.

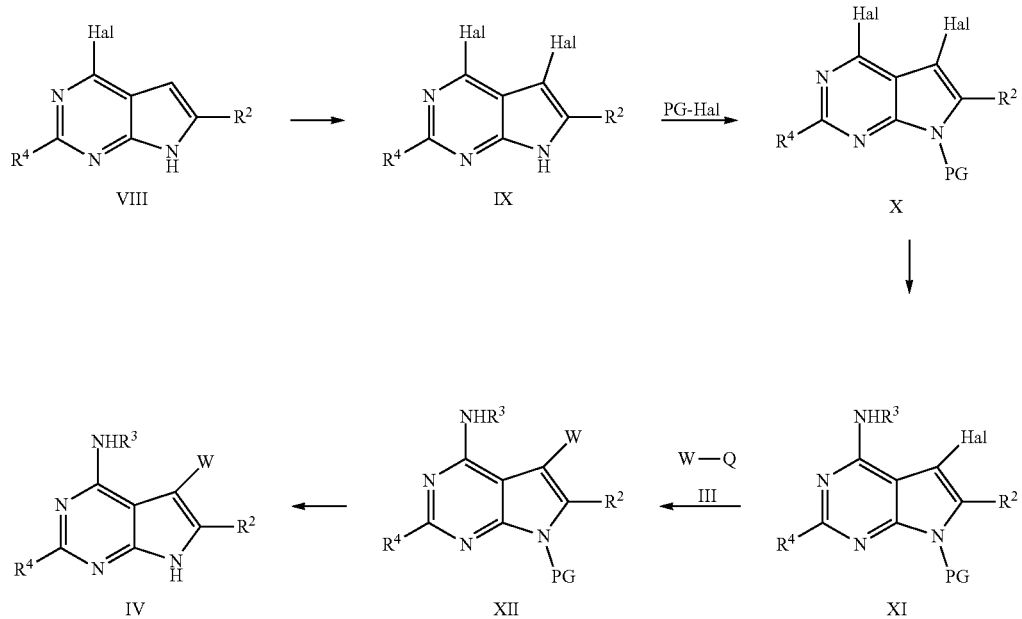

In Scheme 4 Hal is chloro, bromo or iodo; PG is a suitable protecting group understood by a skilled person; and the compound of Formula III (W-Q) is as defined in Scheme 2. Compounds of Formula (IX) may be prepared by halogenation of compounds of Formula (VIII). Compounds of Formula (IX) may be prepared by treatment of compounds of Formula (VIII) with a suitable halogenating agent such as N-(Hal)succinimide, preferably NIS, in a suitable solvent, such as DCM or DMF at an appropriate temperature such as 0° C. A skilled person also knows that alternative methods for specifically introducing a suitable halogen group such as iodo are achievable using alternative reagents, solvents and temperatures. A skilled person also knows that alternative halogenation strategies can be used involving alternative sources of halogen, solvent and temperature combinations. It is well understood by a skilled person that a compound of the Formula (IX) is prepared and isolated as described above or prepared in situ without isolation in a sequential reaction strategy leading to a compound of Formula (X). Compounds of the Formula (X) can be prepared from compounds of Formula (IX) using a suitable protecting group such as trimethylsilylethoxymethyl (SEM) by the reaction of SEMCl with compounds of Formula (IX) and a suitable base such as NaH in a suitable solvent such as THF and at a suitable temperature such as from 0° C. to room temperature. Compounds of the Formula (XI) (where $R^3$ is H) may be prepared from compounds of Formula (X) by the reaction of aqueous ammonium hydroxide solution in a suitable solvent such as MeOH at a suitable temperature such as 70° C. for an appropriate time such as 18 hours in a sealed tube. Additionally, compounds of the Formula (XI) (where $R^3$ is ($C_1$-$C_3$)alkyl) may be prepared from compounds of Formula (X) by the reaction with an appropriate primary amine such as methylamine in a suitable solvent such as THF at a suitable temperature such as 70° C. in a sealed tube. Compounds of the Formula (XII) may be prepared from compounds of Formulae (XI) and (III) using a suitable organometallic cross-coupling reaction such as Suzuki cross-coupling reaction preceded if necessary by a boronic ester formation reaction, as described in Scheme 2. Typical boronic ester formation conditions comprise Pd(dppf)Cl$_2$ and potassium acetate with bispinacolatodiboron with compounds of Formula (III) (where Q=Hal) in dioxane at reflux. Alternatively, compounds of the Formula (XII) may be prepared by alternative cross-coupling strategies such as the Migita-Kosugi-Stille coupling using a compound of Formula (XII) and Formula (III) (where Q=SnRY$_3$) preceded if necessary by an arylstannane formation reaction. Compounds of the Formula (IV) may be prepared from compounds of Formula (XII) (where PG=SEM) using a suitable deprotection method such as neat TFA or optionally in a suitable solvent such as DCM at a suitable temperature such as 0° C. to room temperature. It is well understood by a skilled person that alternative methods of deprotection may be used such as TBAF in a suitable solvent such as THF at a suitable temperature such as 0° C. to 70° C.

Compounds of Formula (II) may be prepared from compounds of Formula (VI), (IX) and (XIII) wherein Hal is chloro, bromo or iodo as illustrated by Scheme 5.

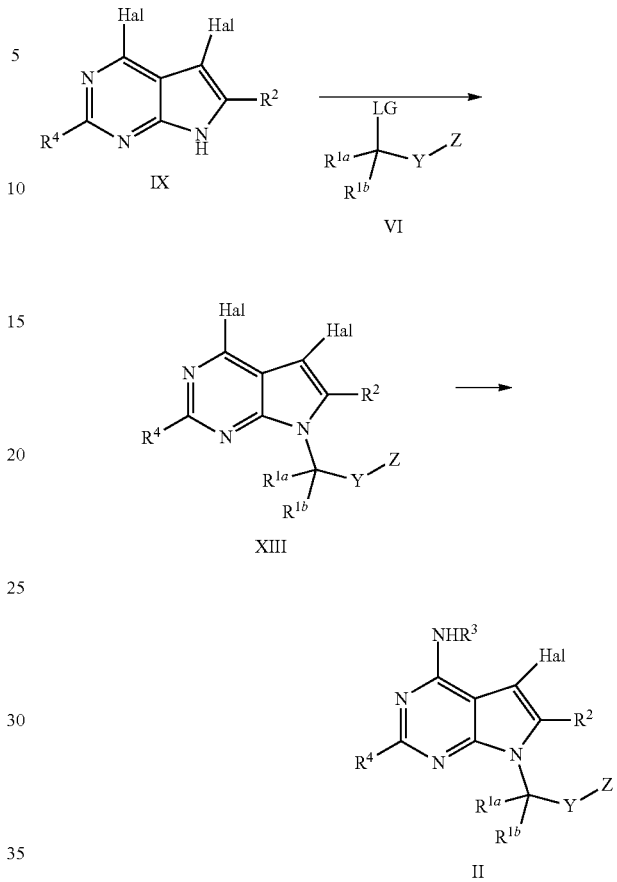

Scheme 5

Compounds of Formula (XIII) may be prepared from compounds of Formula (IX) and Formula (VI) (LG is a suitable leaving group such as a halogen in particular a chlorine atom or a mesylate) in the presence of a suitable base such as Cs$_2$CO$_3$ in a suitable solvent such as DMF at a suitable temperature such as 80° C. It is well understood by a skilled person that alternative methods to prepared compounds of Formula (XIII) are available such as a Mitsonobu reaction with compounds of Formulae (IX) and (VI) (where LG=OH) using a suitable alcohol activating reagent such as DIAD and PPh$_3$ in a suitable solvent such as THF at a suitable temperature such as 0° C. to room temperature. Compounds of the Formula (II) (where $R^3$ is H) may be prepared from compounds of Formula (XIII) by the reaction of aqueous ammonium hydroxide solution in a suitable solvent such as MeOH at a suitable temperature such as 70° C. for an appropriate time such as 18 hours in a sealed tube. Additionally, compounds of the Formula (II) (where $R^3$ is (C1-C3)alkyl) may be prepared from compounds of Formula (XIII) by the reaction with an appropriate primary amine such as methylamine in a suitable solvent such as THF at a suitable temperature such as 70° C. in a sealed tube.

Compounds of Formula (IIA) (where Y=1,2,3-triazole) may be prepared from compound of the Formula (IXa), (XIV), (XV), (XVI) and (XVII) wherein Hal is chloro, bromo or iodo as illustrated in Scheme 6.

Scheme 6

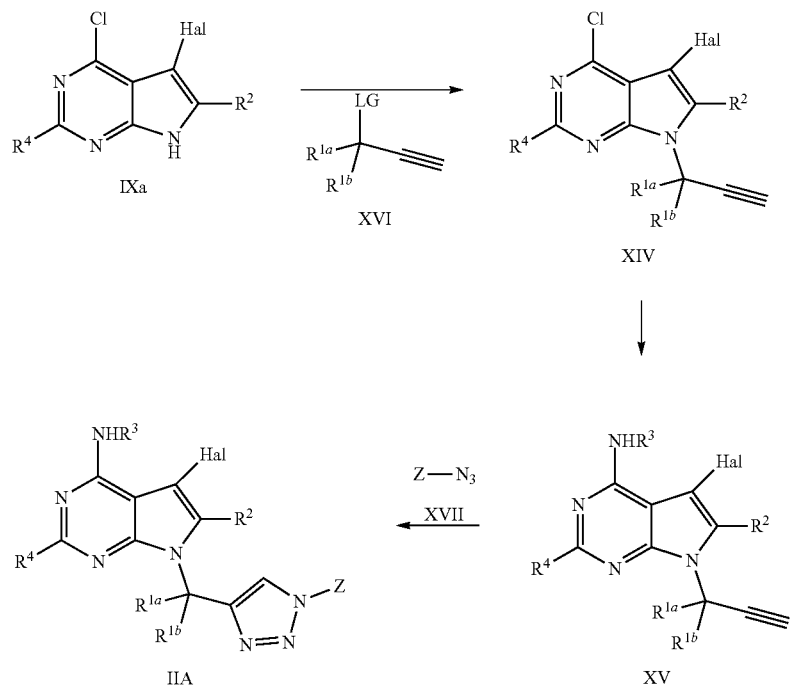

Compounds of Formula (IIA) may be prepared from compounds of Formula (XV) and (XVII) using a suitable 1,3-dipolar cycloaddition reaction such as a copper catalysed Click reaction using catalyst such as CuI in a suitable solvent such as toluene and tBuOH and a suitable base such as DIPEA and at a suitable temperature such as 0° C. to room temperature. It is well understood by a skilled person that alternative methods of heterocycle formation are also possible. Compounds of Formula (XV) (where $R^3$ is H) may be prepared from compounds of Formula (XIV) by the reaction of aqueous ammonium hydroxide solution in a suitable solvent such as MeOH at a suitable temperature such as 70° C. for an appropriate time such as 18 hours in a sealed tube. Additionally, compounds of the Formula (XV) (where $R^3$ is $(C_1-C_3)$alkyl) may be prepared from compounds of Formula (XIV) by the reaction with an appropriate primary amine such as methylamine in a suitable solvent such as THF at a suitable temperature such as 70° C. in a sealed tube. Compounds of Formula (XIV) may be prepared from compounds of Formula (IXa) and Formula (XVI) (LG is a suitable leaving group such as a halogen in particular a chlorine atom or a mesylate) in the presence of a suitable base such as $Cs_2CO_3$ in a suitable solvent such as DMF at a suitable temperature such as 80° C., preceded if necessary by a suitable functional group inter-conversion reaction such as conversion of an alcohol (LG=OH) to a chloride (LG=Cl) using methods known to a skilled person.

Compounds of Formula (Xi) (where $R^2=(C_1-C_3)$alkyl, PG=SEM and Hal is chloro, bromo or iodo) may be prepared from compounds of the Formula (X), (where $R^2=$H and Hal is chloro, bromo or iodo) as illustrated in Scheme 7.

Scheme 7

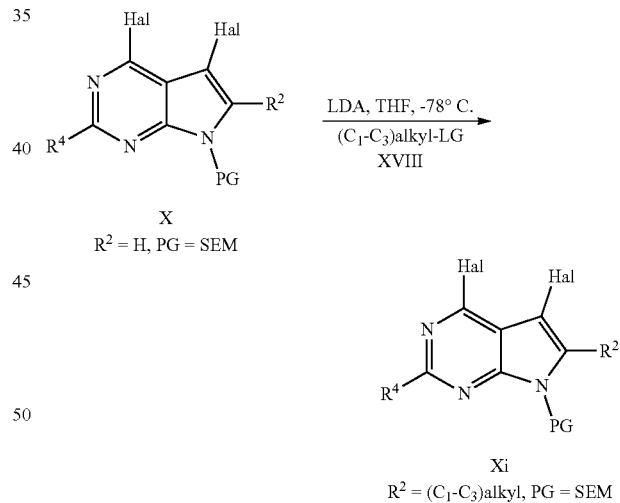

Compounds of Formula (Xi) (where $R^2=(C_1-C_3)$alkyl and PG=SEM) may be prepared from Compounds of Formula (X) (where $R^2=$H and PG=SEM) and compounds of Formula (XVIII) using a suitable aprotic base such as LDA at a suitable temperature such as −78° C. in a suitable solvent such as THF. It is well understood by a skilled person that alternative methods of selective ligand-directed deprotona-tion-alkylation may be used with alternative PG, base and alkylating group combinations in a suitable solvent and at a suitable temperature.

Compounds of Formula (IF) may be prepared from compounds of Formula (III), (XVII), (XIV), (XIX), (XX), (XXI), and (XXII), wherein Q is Hal and Hal is chloro, bromo or iodo, as illustrated in Scheme 8.

Scheme 8

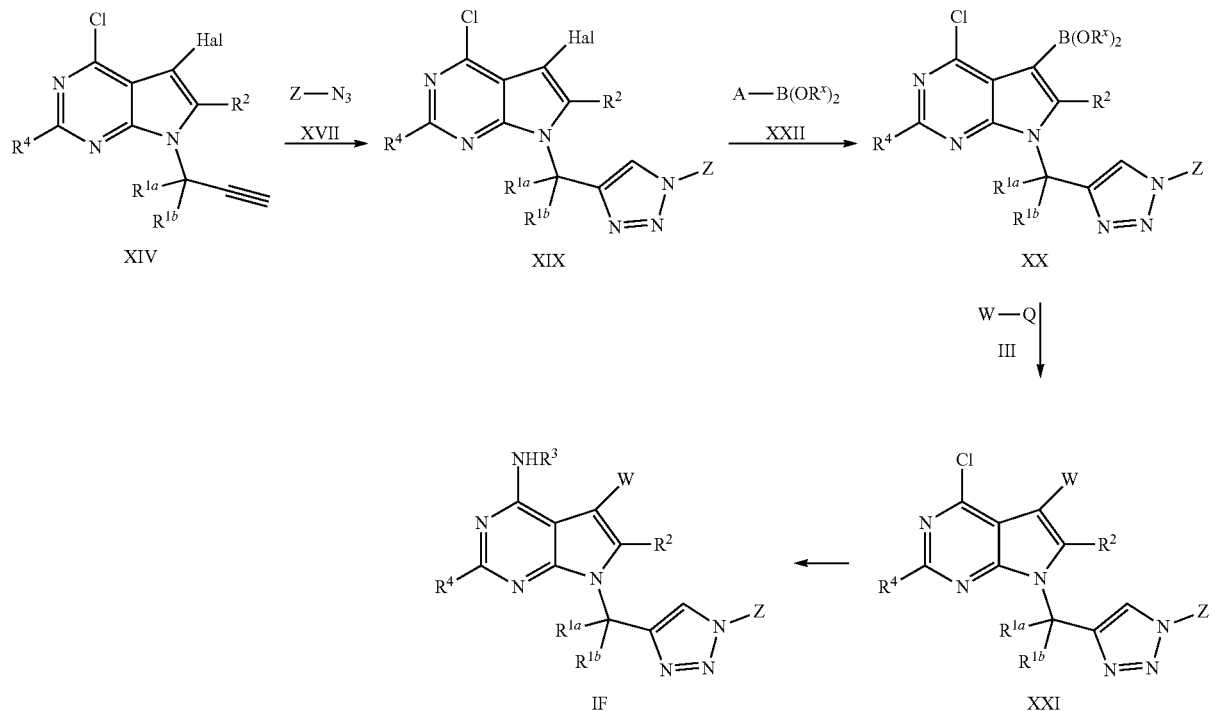

Compounds of Formula (IF) may be prepared from compounds of the Formula (XXI) by a suitable halogen displacement by analogy with Schemes 4, 5 and 6.

Compounds of the Formula (XXI) may be prepared from compounds of Formula (XX) and Formula (III) (where Q=Hal) by a suitable organometallic cross-coupling reaction such as a Suzuki cross-coupling reaction as described in Scheme 8. Typical Suzuki cross-coupling conditions comprise a palladium catalyst containing suitable phosphine ligands, in the presence of an inorganic base, in aqueous dioxane or methanol, at elevated temperatures either thermally or under microwave irradiation. Preferred conditions comprise Pd(OAc)$_2$, Pd(dppf)Cl$_2$ or Pd(PPh$_3$)$_4$ with either sodium, cesium or potassium carbonate in aqueous dioxane or methanol at room temperature to 120° C. Compounds of the Formula (XX) may be produced from compounds of Formula (XIX) and (XXII) by a boronic ester formation reaction. Typical boronic ester formation conditions comprise Pd(dppf)Cl$_2$ and potassium acetate with bispinacolatodiboron in dioxane at reflux. Compounds of Formula (XIX) may be prepared from compounds of Formula (XIV) and (XVII) using a suitable 1,3-dipolar cycloaddition reaction such as a copper catalysed Click reaction using catalyst such as CuI in a suitable solvent such as toluene and tBuOH and a suitable base such as DIPEA and at a suitable temperature such as 0° C. to room temperature. It is well understood by a skilled person that alternative methods of heterocycle formation are also possible.

Compounds of Formula (IIB) may be prepared from compounds of the Formulae (XV) and (XXIII) and wherein Hal is chloro, bromo or iodo as illustrated in Scheme 9.

Scheme 9

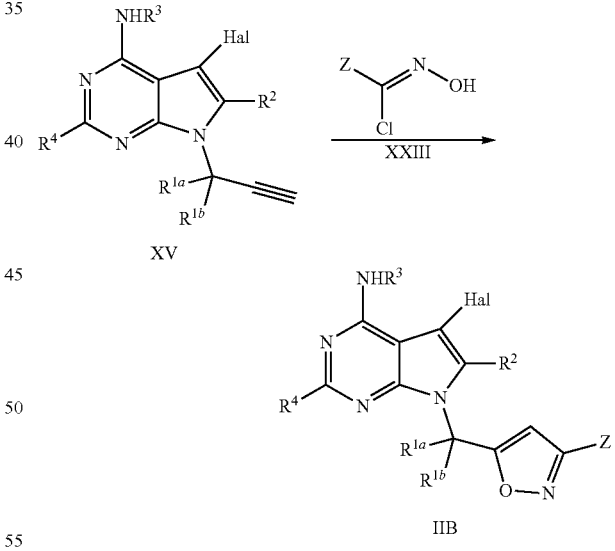

Compounds of Formula (IIB) may be prepared from compounds of the Formula (XV) and (XXIII) by a suitable 1,3-dipolar cycloaddition in a suitable solvent such as toluene in the presence of a suitable base such as Et$_3$N at a suitable temperature such a 0° C. to 60° C. for an appropriate time such as 16 hr.

Compounds of Formula (VI) may be prepared from compounds of Formula (XXXI), (XXIV), (XXV), and (XXVI), as illustrated in Scheme 10 wherein Hal is chloro, bromo or iodo; M is a suitable metal.

Scheme 10

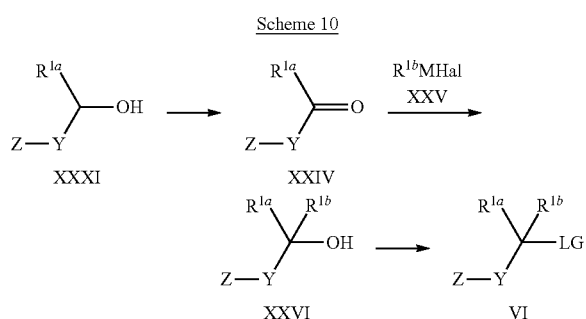

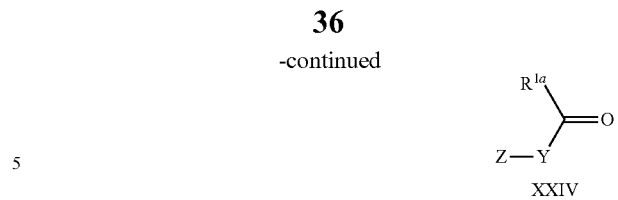

Compounds of Formula (VI) (wherein LG=Cl) may be prepared from compounds of Formulae (XXVI) by a suitable chlorination such as SOCl$_2$ either neat or in a suitable solvent at a suitable temperature. Compounds of Formula (XXVI) may be prepared from compounds of Formula (XXIV) and (XXV) by a suitable organometallic addition reaction using a suitable metal (M) such as Mg in a suitable solvent such as THF at a suitable temperature such a 0° C. to room temperature. Compounds of Formula (XXIV) may be prepared from a suitable oxidation of compounds of Formula (XXXI) using a suitable reagent such as MnO$_2$ in a suitable solvent. A skilled person also knows that alternative oxidation strategies can be used involving alternative oxidants and solvent combinations.

Compounds of Formula (XXXI) may alternatively be prepared from compounds of Formulae (XXVII) as illustrated in Scheme 11 wherein Hal is chloro, bromo or iodo; M is a suitable metal.

Scheme 11

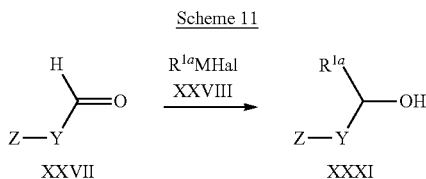

Compounds of Formula (XXXI) may be prepared from compounds of Formula (XXVII) and a suitable organometallic compound of Formula (XXVIII) in a suitable aprotic solvent such as THF at a suitable temperature such as 0° C. to reflux. A skilled person appreciates that alternative methods are available to add an alkyl group to an aldehyde using different organometallic nucleophiles.

Compounds of Formula (XXIV) may be alternatively prepared from compounds of Formulae (XXVII), (XXIX) and (XXX) as illustrated in Scheme 12 wherein Hal is chloro, bromo or iodo; M is a suitable metal.

Scheme 12

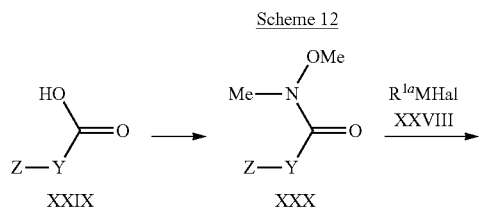

Compounds of Formula (XXIV) may be prepared from compounds of the Formula (XXX) and (XXVIII) using a suitable metal (M) such as Mg in a suitable solvent such as THF at a suitable temperature such as 0° C. to room temperature. Compounds of Formula (XXX) may be prepared from compounds of Formula (XXIX) and N,O-dimethylhydroxylamine in the presence of a suitable peptide coupling reagent such as HATU and in the presence of a suitable base such as DIPEA in a suitable solvent such as DCM at a suitable temperature such as 0° C. to room temperature.

In the case of compounds described in all of the preceding general method schemes where $R^{1a}$ and $R^{1b}$ are different groups (for example where $R^{1a}$ is (C1-C3)alkyl and $R^{1b}$ is H) leading to the presence of a chiral center it is well understood by a skilled person that the individual enantiomers can be obtained using a suitable separation method such as SFC chromatography to afford both the (+) and (−)-enantiomers of these compounds. It is well understood by a skilled person that an individual enantiomer of a compound described in the preceding general method schemes is prepared and isolated as described above or isolated using an alternative separation technique such as HPLC using a suitable chiral stationary phase eluting with a suitable mobile phase as determined to be necessary to isolate the required enantiomers.

The following non-limiting Preparations and Examples illustrate the preparation of compounds and salts of the present invention. In the Examples and Preparations that are set out below, and in the aforementioned Schemes, the following the abbreviations, definitions and analytical procedures may be referred to. Other abbreviations common in the art are also used. Standard IUPAC nomenclature has been used.

The following abbreviations may be used: AcOH is acetic acid; Ar is argon; aq is aqueous; Bn is benzyl; Boc is tert-butoxy carbonyl; Boc$_2$O is di-tert-butyl dicarbonate; br is broad; tBu is tert-butyl; tBuOH is tert-butanol; n-BuLi is n-butyl lithium; Bu$_4$NCl is tetrabutyl ammonium chloride; ° C. is degrees celcius; CDCl$_3$ is deutero-chloroform; Cs$_2$CO$_3$ is cesium carbonate; CsF is cesium fluoride; CuCN is copper cyanide; CuI is copper iodide; b is chemical shift; d is doublet; DCM is dichloromethane or methylene chloride; DIAD is diisopropyl azodicarboxylate; DIPEA is N-ethyl-diisopropylamine or N,N-diisopropylethylamine; DMA is N,N-dimethyl acetamide; DMAP is 4-dimethylaminopyridine; DMF is N,N-dimethylformamide; DMF-DMA is N,N-dimethylformamide dimethyl acetal; DMSO is dimethyl sulfoxide; DPPA is diphenyl phosphoryl azide; Dppf is 1,1'-bis(diphenylphosphino)ferrocene; EDA is ethylenediamine; Et$_2$O is diethyl ether; EtOAc is ethyl acetate; EtOH is ethanol; Et$_3$N is triethylamine; Et$_3$SiH is triethylsilane; g is gram; HATU is 1-[Bis(dimethylamino)methylene]-1H-1,2,3-triazolo[4,5-b]pyridinium 3-oxid hexaflurophosphate; HCl is hydrochloric acid; HCO$_2$H is formic acid; HPLC is high pressure liquid chromatography; H$_2$ is hydrogen; H$_2$O is water; Hr is hour, hrs are hours; K$_2$CO$_3$ is potassium carbonate; KHSO$_4$ is potassium hydrogen sulphate; KOAc is potassium acetate; K$_3$PO$_4$ is potassium phosphate; L is liter; LCMS is liquid chromatography mass spectrometry; LDA is lithium diisopropylamide LiAlH$_4$ or LAH is lithium aluminium hydride; LiCl is lithium chloride; LiHMDS is lithium bis(trimethylsilyl)amide; LiOH.H$_2$O is lithium hydroxide monohydrate; Li-Selectride® is lithium tri-sec-butylborohydride; m is multiplet; M is molar; MeCN is acetonitrile; MeMgBr is methyl magnesium bromide; MeOH is methanol; 2-MeTHF is 2-methyl tetrahydrofuran; mg is milligram; MgSO$_4$ is magnesium sulphate; MHz is mega Hertz; min is minutes; mL is milliliter; mmol is millimole; MnO$_2$ is manganese dioxide; mol is mole; MS m/z is mass spectrum peak; MTBE is tert-butyl methyl ether; MsCl is mesyl chloride; NaCN is sodium cyanide; NaBH$_4$ is sodium borohydride; Na$_2$CO$_3$ is sodium carbonate; NaH is sodium hydride; NaHCO$_3$ is sodium hydrogen carbonate; NaHSO$_4$ is sodium hydrogen sulfate; NaHMDS is sodium bis(trimethylsilyl)amide; NaOH is sodium hydroxide; NaOAc is sodium acetate; NaOMe is sodium methoxide; Na$_2$SO$_4$ is sodium sulphate; Na$_2$S$_2$O$_3$ is sodium thiosulfate; NBS is N-bromo succinimide; NCS is N-chlorosuccinimide; NH$_3$ is ammonia; NH$_4$Cl is ammonium chloride; NH$_4$HCO$_3$ is ammonium hydrogen carbonate; NH$_2$NH$_2$.H$_2$O is hydrazine hydrate; NH$_2$OH.HCl is hydroxylamine hydrochloride; NH$_4$OH is ammonium hydroxide; NH$_4$OAc is ammonium acetate; NiI is nickel iodide; NIS is N-iodosuccinimide; nM is nanomolar; NMP is 1-methyl-2-pyrrolidinone; NMR is nuclear magnetic resonance; Pd/C is palladium on carbon; Pd$_2$(dba)$_3$ is Tris(dibenzylideneacetone)dipalladium; Pd(dppf)Cl$_2$ is [1,1'-bis(diphenylphosphino) ferrocene]dichloropalladium(II); Pd(OH)$_2$ is palladium hydroxide; Pd(OAc)$_2$ is palladium acetate; PPh$_3$ is triphenylphosphine; Pd(PPh$_3$)$_4$ is tetrakis (triphenylphosphine)palladium (0); Pet. Ether is petroleum ether; pH is power of hydrogen; ppm is parts per million; PtO$_2$ is platinum (IV) oxide; q is quartet; rt is room temperature; RT is retention time; s is singlet; SCX is strong cation exchange; SEM-Cl is 2-(trimethylsilyl)ethoxymethyl chloride; SFC is supercritical fluid chromatography; S-Phos is 2-dicyclohexylphosphino-2',6'-dimethoxybiphenyl; SOCl$_2$ is thionyl chloride; t is triplet; T3P is propylphosphonic anhydride; TBAF is tert-butyl ammonium fluoride; TBD is 1,5,7-triazabicyclo[4.4.0]dec-5-ene; TBME is tert-butyl dimethyl ether; TFA is trifluoroacetic acid; TFP is tri(2-furyl)phosphine; THF is tetrahydrofuran; Ti(OiPr)$_4$ is titanium (IV) isopropoxide; TPTU is 2-(2-pyridon-1-yl)-1,1,3,3-tetramethyluronium tetrafluoroborate; µL is microliter; µmol is micromole; XPhos is 2-dicyclohexylphosphino-2',4',6'-trisopropylbiphenyl; and Zn(CN)$_2$ is Zinc cyanide.

$^1$H and $^{19}$F Nuclear magnetic resonance (NMR) spectra were in all cases consistent with the proposed structures. Characteristic chemical shifts (δ) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO-d$_6$, deuterodimethylsulphoxide; and MeOH-d$_4$, deuteromethanol. Where appropriate, tautomers may be recorded within the NMR data; and some exchangeable protons may not be visible.

Mass spectra, MS (m/z), were recorded using either electrospray ionisation (ESI) or atmospheric pressure chemical ionisation (APCI).

Where relevant and unless otherwise stated the m/z data provided are for isotopes $^{19}$F, $^{35}$Cl, $^{79}$Br and $^{127}$I.

Wherein preparative TLC or silica gel chromatography have been used, one skilled in the art may choose any combination of appropriate solvents to purify the desired compound.

The following are analytical and preparative chromatography methods used for the analysis and purification of compounds of the invention.

Preparative SFC Methods

SFC Method A1: Column: Lux Cellulose-3, 250 mm×21.2 mm 5u; Mobile Phase—Isocratic conditions: CO$_2$/MeOH, 80/20 (v/v); Flow rate: 80.0 mL/min.

SFC Method A3: Column: Lux Cellulose-3, 250 mm×21.2 mm 5u; Mobile Phase A: CO$_2$; Mobile Phase B: MeCN/MeOH, 50/50 (v/v); Isocratic conditions: 70% A/30% B; Flow rate: 80.0 mL/min.

SFC Method A4: Column: Lux Cellulose-1, 250 mm×21.2 mm 5u; Mobile Phase A: CO$_2$; Mobile Phase B: MeCN/MeOH, 50/50 (v/v); Isocratic conditions: 75% A/25% B; Flow rate: 80.0 mL/min.

SFC Method A6: Column: Lux Cellulose-1, 250 mm×21.2 mm 5u; Mobile Phase A: CO$_2$; Mobile Phase B: MeCN/MeOH, 50/50 (v/v); Isocratic conditions: 80% A/20% B; Flow rate: 80.0 mL/min.

SFC Method A7: Column: Lux Cellulose-3, 500 mm×21.2 mm 5u; Mobile Phase A: CO$_2$; Mobile Phase B: MeOH+0.2% NH$_4$OH; Isocratic conditions: 70% A/30% B; Flow rate: 80.0 mL/min.

SFC Method A9: Column: Lux Cellulose-3, 500 mm×21.2 mm 5u; Mobile Phase A: CO$_2$; Mobile Phase B: MeOH+0.2% NH$_4$OH; Isocratic conditions: 90% A/10% B; Flow rate: 80.0 mL/min.

SFC Method A10: Column: Lux Cellulose-3, 250 mm×21.2 mm 5u; Mobile Phase A: CO$_2$; Mobile Phase B: MeOH+0.2% NH$_4$OH; Isocratic conditions: 92.5% A/7.5% B; Flow rate: 80.0 mL/min.

SFC Method B1: Column: Chiral Tech OJ-H, 250 mm×21.2 mm 5u; Mobile Phase A: CO$_2$; Mobile Phase B: MeOH+0.2% NH$_4$OH; Isocratic conditions: 80% A/20% B; Flow rate: 80.0 mL/min.

SFC Method B3: Column: Chiral Tech OJ-H, 250 mm×50 mm 5u; Mobile Phase A: CO$_2$; Mobile Phase B: MeOH+0.2% NH$_4$OH; Isocratic conditions: 85% A/15% B; Flow rate: 250.0 mL/min.

SFC Method B4: Column: Chiral Tech OJ-H, 500 mm×21.2 mm 5u; Mobile Phase A: CO$_2$; Mobile Phase B: MeOH+0.2% NH$_4$OH; Isocratic conditions: 75% A/25% B; Flow rate: 80.0 mL/min.

SFC Method C1: Column: Chiral Tech AS-H, 250 mm×21.2 mm 5u; Mobile Phase A: CO$_2$; Mobile Phase B: MeOH+0.2% NH$_4$OH; Isocratic conditions: 75% A/25% B; Flow rate: 80.0 mL/min.

SFC Method C3: Column: Chiral Tech AS-H, 250 mm×21.2 mm 5u; Mobile Phase A: CO$_2$; Mobile Phase B: MeOH+0.2% NH$_4$OH; Isocratic conditions: 80% A/20% B; Flow rate: 80.0 mL/min.

SFC Method C4: Column: Chiral Tech AS-H, 250 mm×21.2 mm 5u; Mobile Phase A: CO$_2$; Mobile Phase B: MeOH+0.2% NH$_4$OH; Isocratic conditions: 85% A/15% B; Flow rate: 80.0 mL/min.

SFC Method C5: Column: Chiral Tech AS-H, 250 mm×21.2 mm 5u; Mobile Phase A: CO$_2$; Mobile Phase B: MeOH+0.2% NH$_4$OH; Isocratic conditions: 85% A/15% B; Flow rate: 80.0 mL/min.

SFC Method D1: Chiral Tech IA 250 mm×21.5 mm 5u; Mobile Phase A: CO$_2$; Mobile Phase B: IPA; Isocratic conditions: 60% A/40% B; Flow rate: 80.0 mL/min.

SFC Method D4: Chiral Tech IA 250 mm×21.5 mm 5u; Mobile Phase A: $CO_2$; Mobile Phase B: MeOH; Isocratic conditions: 60% A/40% B; Flow rate: 80.0 mL/min.

SFC Method F1: Chiral Tech OD-H 500 mm×21.5 mm 5u; Mobile Phase A: $CO_2$; Mobile Phase B: EtOH+0.2% $NH_4OH$; Isocratic conditions: 80% A/20% B; Flow rate: 80.0 mL/min.

Analytical SFC Methods

SFC Method A2: Column: Lux Cellulose-3, 250 mm×4.6 mm 5u; Mobile Phase A: $CO_2$; Mobile Phase B: MeOH; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method A5: Column: Lux Cellulose-1, 250 mm×4.6 mm 5u; Mobile Phase A: $CO_2$; Mobile Phase B: MeOH/MeCN, 50/50, (v/v); Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method A8: Column: Lux Cellulose-3, 250 mm×4.6 mm 5u; Mobile Phase A: $CO_2$; Mobile Phase B: MeOH+0.2% $NH_4OH$; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method B2: Column: Chiral Tech OJ-H, 250 mm×4.6 mm 5u; Mobile Phase A: $CO_2$; Mobile Phase B: MeOH+0.2% $NH_4OH$; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method C2: Column: Chiral Tech AS-H, 250 mm×4.6 mm 5u; Mobile Phase A: $CO_2$; Mobile Phase B: MeOH+0.2% $NH_4OH$; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method D2: Column: Chiral Tech IA 250 mm×4.6 mm 5u; Mobile Phase A: $CO_2$; Mobile Phase B: MeOH+0.2% $NH_4OH$; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method D3: Column: Chiral Tech IA 250 mm×4.6 mm 5u; Mobile Phase A: $CO_2$; Mobile Phase B: IPA; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

SFC Method F2: Column: Chiral Tech OD-H 250 mm×4.6 mm 5u; Mobile Phase A: $CO_2$; Mobile Phase B: EtOH+0.2% $NH_4OH$; Gradient Elution (time, % A, % B): (0.00 min, 95% A, 5% B), (1.00 min, 95% A, 5% B), (9.00 min, 40% A, 60% B), (9.50 min, 40% A, 60% B), (10.00 min, 95% A, 5% B); Flow rate: 3.0 mL/min.

Preparative HPLC Methods

HPLC Method C20A: Column: CHIRALPAK IC, 2.5 cm I.D.×25 cm long; Isocratic Mobile Phase: DCM/MeOH, 95/5 (v/v); Flow rate: 30 mL/min; Temperature: 35° C.

HPLC Method C20B: Column: CHIRALPAK IC, 5.0 cm I.D.×25 cm long; Isocratic Mobile Phase: DCM/MeOH, 95/5 (v/v); Flow rate: 60 mL/min; Temperature: 35° C.

HPLC Method C21: Column: CHIRALPAK IC, 5.0 cm I.D.×25 cm long; Isocratic Mobile Phase: DCM/MeOH, 90/10 (v/v); Flow rate: 60 mL/min.

HPLC Method C22A: Column: CHIRALPAK IC, 2.5 cm I.D.×25 cm long; Isocratic Mobile Phase: DCM/MeOH/DEA, 95/5/0.1 (v/v/v); Flow rate: 30 mL/min; Temperature: 35° C.

HPLC Method C22B: Column: CHIRALPAK IC, 5.0 cm I.D.×25 cm long; Isocratic Mobile Phase: DCM/MeOH/DEA, 95/5/0.1 (v/v/v); Flow rate: 30 mL/min; Temperature: 35° C.

HPLC Method C23A: Column: CHIRALPAK IC, 5.0 cm I.D.×25 cm long; Isocratic Mobile Phase: DCM/EtOH, 90/10 (v/v); Flow rate: 60 mL/min; Temperature: 35° C.

HPLC Method C23B: Column: CHIRALPAK IC, 2.5 cm I.D.×25 cm long; Isocratic Mobile Phase: DCM/EtOH, 90/10 (v/v); Flow rate: 60 mL/min; Temperature: 35° C.

HPLC Method C24A: Column: CHIRALPAK IC, 5.0 cm I.D.×25 cm long; Isocratic Mobile Phase: DCM/EtOH, 95/5 (v/v); Flow rate: 60 mL/min; Temperature: 35° C.

HPLC Method C24B: Column: CHIRALPAK IC, 2.5 cm I.D.×25 cm long; Isocratic Mobile Phase: DCM/EtOH, 95/5 (v/v); Flow rate: 60 mL/min; Temperature: 35° C.

HPLC Method C25A: Column: CHIRALPAK IC, 5.0 cm I.D.×25 cm long; Isocratic Mobile Phase: Hex/EtOH, 70/30 (v/v); Flow rate: 60 mL/min.

HPLC Method C25B: Column: CHIRALPAK IC, 2.0 cm I.D.×25 cm long; Isocratic Mobile Phase: Hex/EtOH, 70/30 (v/v); Flow rate: 9 mL/min.

HPLC Method C26: Column: CHIRALPAK IC, 5.0 cm I.D.×25 cm long; Isocratic Mobile Phase: Hexane/IPA, 70/30 (v/v); Flow rate: 60 mL/min.

HPLC Method C27: Column: CHIRALPAK IC, 5.0 cm I.D.×25 cm long; Isocratic Mobile Phase: Hexane/EtOAc/DEA, 60/40/0.1 (v/v/v); Flow rate: 60 mL/min; Temperature: 35° C.

HPLC Method C28: Column: CHIRALPAK IC, 2.5 cm I.D.×25 cm long; Isocratic Mobile Phase: Hexane/EtOH, 85/15 (v/v); Flow rate: 30 mL/min.

HPLC Method C29: Column: CHIRALPAK IC, 5.0 cm I.D.×25 cm long; Isocratic Mobile Phase: DCM/EtOH, 80/20 (v/v); Flow rate: 60 mL/min.

HPLC Method C30: Column: CHIRALPAK IC, 5.0 cm I.D.×25 cm long; Isocratic Mobile Phase: DCM/EtOH, 75/25 (v/v); Flow rate: 60 mL/min.

HPLC Method C31: Column: CHIRALPAK IC 5.0 cm I.D.×25 cm long; Isocratic Mobile Phase: DCM/EtOH/DEA, 90/10/0.1 (v/v/v); Flow rate: 60 mL/min.

HPLC Method C32: Column: CHIRALPAK IC, 5.0 cm I.D.×25 cm long; Isocratic Mobile Phase: DCM/EtOH/DEA, 85/15/0.1 (v/v/v); Flow rate: 60 mL/min.

HPLC Method C33: Column: CHIRALPAK IC, 5.0 cm I.D.×25 cm long; Isocratic Mobile Phase: Hexane/EtOH, 50/50 (v/v); Flow rate: 30 mL/min.

HPLC Method C34: Column: CHIRALPAK IC, 5.0 cm I.D.×25 cm long; Isocratic Mobile Phase: 100% MeOH; Flow rate: 60 mL/min.

HPLC Method B4: Column: CHIRALCEL OJ, 2.5 cm I.D.×25 cm long; Isocratic Mobile Phase: MeOH/DEA, 90/10 (v/v); Flow rate: 30 mL/min; Temperature: 35° C.

HPLC Method B5: Column: CHIRALCEL OJ, 2.5 cm I.D.×25 cm long; Isocratic Mobile Phase: MeOH/DEA, 100/0.1 (v/v); Flow rate: 30 mL/min; Temperature: 35° C.

HPLC Method B6: Column: CHIRALCEL OJ, 2.5 cm I.D.×25 cm long; Isocratic Mobile Phase: EtOH/DEA, 100/0.1 (v/v); Flow rate: 30 mL/min; Temperature: 35° C.

HPLC Method D4: Column: CHIRALPAK AD-H, 25 cm I.D.×250 cm long; Isocratic Mobile Phase: EtOH/MeCN, 80/20 (v/v); Flow rate: 20 mL/min; Temperature: 35° C.

HPLC Method D5: Column: CHIRALPAK AD-H, 2.5 cm I.D.×25 cm long; Isocratic Mobile Phase: Hexane/EtOH, 70/30 (v/v), Flow rate: 30 mL/min; Temperature: 35° C.
HPLC Method D6: Column: CHIRALPAK AD-H, 2.5 cm I.D.×25 cm long; Isocratic Mobile Phase: MeOH/MeCN, 90/10 (v/v); Flow rate: 30 mL/min.
HPLC Method D7: Column: CHIRALPAK AD-H, 5.0 cm I.D.×25 cm long; Isocratic Mobile Phase: Hexane/IPA, 70/30 (v/v); Flow rate: 60 mL/min.
HPLC Method E3: Column: CHIRALPAK IE, 2.5 cm I.D.×25 cm long; Isocratic Mobile Phase: Hexane/EtOH, 70/30 (v/v); Flow rate: 60 mL/min; Temperature: 35° C.
HPLC Method E4: Column: CHIRALPAK IE, 5.0 cm I.D.×25 cm long; Isocratic Mobile Phase: DCM/EtOH, 95/5 (v/v); Flow rate: 55 mL/min; Temperature: 35° C.
HPLC Method E5: Column: CHIRALPAK IE, 5.0 cm I.D.×25 cm long; Isocratic Mobile Phase: Hexane/EtOH, 80/20 (v/v); Flow rate: 60 mL/min; Temperature: 35° C.
HPLC Method E6: Column: CHIRALPAK IE, 2.5 cm I.D.×25 cm long; Isocratic Mobile Phase: Hexane/EtOH/DEA, 50/50/0.1 (v/v/v); Flow rate: 30 mL/min; Temperature: 35° C.
HPLC Method E8: Column: CHIRALPAK IE, 5.0 cm I.D.×25 cm long; Isocratic Mobile Phase: Hexane/EtOH, 50/50 (v/v); Flow rate: 60 mL/min; Temperature: 35° C.
HPLC Method F1: Column: CHIRALPAK AS-H, 5.0 cm I.D.×25 cm long; Isocratic Mobile Phase: Hexane/EtOH, 85/15 (v/v); Flow rate: 60 mL/min; Temperature: 35° C.
HPLC Method F2: Column: CHIRALPAK AS-H, 5.0 cm I.D.×25 cm long; Isocratic Mobile Phase: DCM/MeOH, 60/40 (v/v); Flow rate of 60 mL/min; Temperature: 35° C.
HPLC Method F4: Column: CHIRALPAK AS-H, 5.0 cm I.D.×25 cm long; Isocratic Mobile Phase: EtOH/DEA, 100/0.1 (v/v); Flow rate: 60 mL/min; Temperature: 35° C.
HPLC Method F7: Column: CHIRALPAK AS-H, 2.0 cm I.D.×25 cm long; Isocratic Mobile Phase: Hexane/EtOH/DEA, 50/50/0.2 (v/v/v); Flow rate: 14 mL/min; Temperature: 25° C.
HPLC Method F8: Column: CHIRALPAK AS-H, 2.5 cm I.D.×25 cm long; Isocratic Mobile Phase: DCM/MeOH, 95/5 (v/v); Flow rate: 30 mL/min; Temperature: 25° C.
HPLC Method F9: Column: CHIRALPAK AS-H, 5.0 cm I.D.×25 cm long; Isocratic Mobile Phase: DCM/EtOH/DEA, 90/10/0.1 (v/v/v); Flow rate: 60 mL/min; Temperature: 25° C.
HPLC Method G2: Column: CHIRALCEL OD-H, 2.5 cm I.D.×25 cm long; Isocratic Mobile Phase: Hexane/IPA, 60/40 (v/v); Flow rate: 30 mL/min; Temperature: 35° C.
HPLC Method G3: Column: CHIRALCEL OD-H, 2.0 cm I.D.×25 cm long; Isocratic Mobile Phase: IPA/TFA, 100/0.2 (v/v); Flow rate: 40 mL/min; Temperature: 40° C.
HPLC Method H1: Column: CHIRALCEL OZ-H, 5.0 cm I.D.×25 cm long; Isocratic Mobile Phase: Hexane/EtOH, 50/50 (v/v); Flow rate of 30 mL/min; Temperature: 35° C.
HPLC Method H3: Column: CHIRALCEL OZ-H, 2.5 cm I.D.×25 cm long; Isocratic Mobile Phase: Hexane/EtOH, 80/20 (v/v); Flow rate: 30 mL/min; Temperature: 35° C.
HPLC Method J1: Column: Xterra RP18 (19×250 mm, 10p); Mobile Phase A: 20 mM $(NH_4)_2CO_3$ in water; Mobile phase B: MeCN; Gradient Elution (time, % A, % B): (0 min, 90% A, 10% B), (3 min, 75% A, 25% B), (18 min, 40% A, 60% B), (19 min, 5% A, 95% B), (20 min, 5% A, 95% B); Flow rate: 16 mL/min;
HPLC Method K1: Column: YMC Triart C18 (20×250 mm, 5p); Mobile Phase A: 20 mM $(NH_4)_2CO_3$ in water; Mobile Phase B: MeCN; Gradient Elution (time, % A, % B): (0 min, 90% A, 10% B), (3 min, 75% A, 25% B), (18 min, 40% A, 60% B), (19 min, 5% A, 95% B), (20 min, 5% A, 95% B); Flow rate: 16 mL/min.
HPLC Method L1: Column: Reprosil Gold C18 (30×100 mm, 5p); Mobile Phase A: 10 mM $(NH_4)_2CO_3$ in water; Mobile Phase B: MeCN; Gradient Elution (time, % A, % B): (0 min, 90% A, 10% B), (2 min, 60% A, 40% B), (10 min, 30% A, 70% B), (11 min, 5% A, 95% B), (12 min, 5% A, 95% B); Flow rate: 30 mL/min.
HPLC Method L2: Column: Reprosil Gold C18 (250×20 mm, 5p); Mobile Phase A: 20 mM $NH_4HCO_3$ in water; Mobile Phase B: MeCN; Gradient Elution (time, % A, % B): (0 min, 90% A, 10% B), (3 min, 70% A, 30% B), (18 min, 40% A, 60% B), (19 min, 5% A, 95% B); Flow rate: 20 mL/min.
HPLC Method N1: Column: Hydrosphere C18 (250×20 mm, 5p); Mobile Phase A: 10 mM $NH_4OAc$ in water; Mobile phase B: MeCN; Gradient Elution (time, % A, % B): (0 min, 90% A, 10% B), (3 min, 70% A, 30% B), (18 min, 40% A, 60% B), (19 min, 5% A, 95% B); Flow rate: 20 mL/min.
HPLC Method N2: Column: Hydrosphere C18 (250×20 mm, 5p); Mobile Phase A: 0.1% Formic acid in water; Mobile Phase B: MeCN; Gradient Elution (time, % A, % B): (0 min, 90% A, 10% B), (3 min, 80% A, 20% B), (18 min, 40% A, 60% B), (19 min, 5% A, 95% B); Flow rate: 20 mL/min.
HPLC Method P1: Column: Gemini C18 (100×30 mm, 5p); Mobile Phase A: 20 mM $NH_4HCO_3$ in water; Mobile Phase B: MeCN; Flow rate: 30 mL/min; Gradient Elution (time, % A, % B): (0 min, 90% A, 10% B), (2 min, 70% A, 30% B), (10 min, 35% A, 65% B), (12 min, 5% A, 95% B).
HPLC Method Q1: Column: CHIRALPAK IB, 2.0 cm I.D.×25 cm long; Isocratic Mobile Phase: Hex/EtOH (50/50) (v/v); Flow rate: 14 mL/min; Temperature: 25° C.

Analytical HPLC Methods

HPLC Method A [Acidic]: Column: Acquity BEH C18, 50×2.1 mm, 1.7ρ; Mobile phase: MeCN (0.05% TFA)-Water (0.05% TFA); Gradient: 5%-95% MeCN over 2 min, hold at 95% MeCN for 0.5 min.; re-equilibrate back to 5% MeCN to 2.7 min.; Flow rate: 0.8 mL/min; Temperature: 45° C.
HPLC Method B1: Column: CHIRALCEL OJ-H, 0.46 cm I.D.×15 cm long; Injection: 20.0 ul; Mobile phase: MeOH/MeCN, 90/10 (v/v); Flow rate: 1.0 mL/min; Wave length: UV 254 nm; Temperature: 35° C.
HPLC Method B2: Column: CHIRALCEL OJ-H, 0.46 cm I.D.×15 cm long; Injection: 2.0 ul; Mobile phase: MeOH/DEA, 100/0.1 (v/v); Flow rate: 1.0 mL/min; Wave length: UV 214 nm; Temperature: 35° C.
HPLC Method B3: Column: CHIRALCEL OJ-H, 0.46 cm I.D.×15 cm long; Injection: 1.0 ul; Mobile phase: EtOH; Flow rate: 1.0 mL/min; Wave length: UV 214 nm; Temperature: 35° C.
HPLC Method C1: Column: CHIRALPAK IC, 0.46 cm I.D.×25 cm long; Mobile phase: DCM/EtOH, 95/5 (v/v); Flow rate: 1.0 mL/min; Wave length: UV 214 nm; Temperature: 25° C.
HPLC Method C2: Column: CHIRALPAK IC, 0.46 cm I.D.×15 cm long; Mobile phase: DCM/EtOH, 95/5 (v/v); Flow rate: 1.0 mL/min; Wave length: UV 214 nm; Temperature: 25° C.
HPLC Method C3: Column: CHIRALPAK IC, 0.46 cm I.D.×15 cm long, Mobile phase: DCM/EtOH, 98/2 (v/v); Flow rate: 1.0 mL/min; Wave length: UV 254 nm; Temperature: 25° C.

HPLC Method C4: Column: CHIRALPAK IC, 0.46 cm I.D.×25 cm long; Mobile phase: DCM/MeOH, 95/5 (v/v); Flow rate: 1.0 mL/min; Temperature: 25° C.
HPLC Method C5: Column: CHIRALPAK IC, 0.46 cm I.D.×15 cm long, 5p; Mobile phase: DCM/MeOH, 95/5 (v/v); Flow rate: 1.0 mL/min; Wave length: UV 254 nm; Temperature: 35° C.
HPLC Method C6: Column: CHIRALPAK IC, 0.46 cm I.D.×15 cm long; Mobile phase: DCM/EtOH, 90/10 (v/v); Flow rate: 1.0 mL/min; Wave length: UV 254 nm; Temperature: 25° C.
HPLC Method C7: Column: CHIRALPAK IC, 0.46 cm I.D.×15 cm long; Mobile phase: DCM/MeOH/DEA, 95/5/0.1 (v/v/v); Flow rate: 1.0 mL/min; Wave length: UV 214 nm; Temperature: 35° C.
HPLC Method C8: Column: CHIRALPAK IC, 0.46 cm I.D.×15 cm long; Mobile phase: MeOH; Flow rate: 1.0 mL/min; Wave length: UV 214 nm; Temperature: 35° C.
HPLC Method C9: Column: CHIRALPAK IC, 0.46 cm I.D.×15 cm long; Mobile phase: DCM/MeOH, 90/10 (v/v); Flow rate: 1.0 mL/min; Wave length: UV 254 nm; Temperature: 35° C.
HPLC Method C10: Column: CHIRALPAK IC, 0.46 cm I.D.×15 cm long; Mobile phase: DCM/EtOH/DEA, 90/10/0.1 (v/v); Flow rate: 1.0 mL/min; Wave length: UV 254 nm; Temperature: 25° C.
HPLC Method C11: Column: CHIRALPAK IC, 0.46 cm I.D.×25 cm long; Mobile phase: Hexane/EtOH, 70/30 (v/v); Flow rate: 1.0 mL/min; Wave length: UV 214 nm; Temperature: 35° C.
HPLC Method C12: Column: CHIRALPAK IC, 0.46 cm I.D.×15 cm long; Mobile phase: Hexane/EtOH, 85/15 (v/v); Flow rate: 1.0 mL/min; Wave length: UV 214 nm; Temperature: 35° C.
HPLC Method C13: Column: CHIRALPAK IC, 0.46 cm I.D.×15 cm long; Mobile phase: Hexane/EtOAC/DEA, 60/40/0.1 (v/v/v); Flow rate: 1.0 mL/min; Wave length: UV 214 nm; Temperature: 35° C.
HPLC Method C14: Column: CHIRALPAK IC, 0.46 cm I.D.×15 cm long; Mobile phase: Hexane/EtOH, 80/20 (v/v/v); Flow rate: 1.0 mL/min; Wave length: UV 214 nm; Temperature: 35° C.
HPLC Method C15: Column: CHIRALPAK IC, 0.46 cm I.D.×15 cm long; Mobile phase: Hexane/EtOH/DEA, 50/50/0.1 (v/v/v); Flow rate: 1.0 mL/min; Wave length: UV 214 nm; Temperature: 35° C.
HPLC Method C16: Column: CHIRALPAK IC, 0.46 cm I.D.×15 cm long; Mobile phase: MeOH/MeCN, 90/10 (v/v); Flow rate: 1.0 mL/min; Wave length: UV 214 nm; Temperature: 35° C.
HPLC Method C16A: Column: CHIRALPAK IC, 0.46 cm I.D.×25 cm long; Mobile phase: DCM/EtOAc/DEA, 85/15/0.1 (v/v/v); Flow rate: 1.0 mL/min; Wave length: UV 254 nm; Temperature: 35° C.
HPLC Method C17: Column: CHIRALPAK IC, 0.46 cm I.D.×25 cm long; Mobile phase: Hexane/EtOH, 50/50 (v/v); Flow rate: 1.0 mL/min; Wave length: UV 254 nm; Temperature: 35° C.
HPLC Method D1: Column: CHIRALPAK AD-H, 0.46 cm I.D.×15 cm long; Mobile phase EtOH/MeCN, 80/20 (v/v); Flow rate 1.0 mL/min; Wave length UV 214 nm; Temperature: 35° C.
HPLC Method D2: Column: CHIRALPAK AD-H, 0.46 cm ID×15 cm long; Mobile Phase: Hexane/EtOH, 70/30 (v/v); Flow rate: 1.0 mL/min; Wavelength: UV 214 nm; Temperature: 35° C.
HPLC Method D3: Column: CHIRALPAK AD-H, 0.46 cm ID×15 cm long; Mobile Phase: Hexane/EtOH, 60/40 (v/v); Flow rate: 1.0 mL/min; Wavelength: UV 214 nm; Temperature: 25° C.
HPLC Method E1: Column: CHIRALPAK IE, 0.46 cm I.D.×15 cm long; Mobile phase: Hexane/EtOH, 70/30 (v/v); Flow rate: 1.0 mL/min; Wave length: UV 214 nm; Temperature: 25° C.
HPLC Method E2: Column: CHIRALPAK IE, 0.46 cm I.D.×15 cm long; Mobile phase: Hexane/IPA, 70/30 (v/v); Flow rate: 1.0 mL/min; Wave length: UV 254 nm; Temperature: 35° C.
HPLC Method E7: Column: CHIRALPAK IE, 0.46 cm I.D.×25 cm long; Mobile phase: Hexane/EtOH/DEA, 50/50/0.1 (v/v/v); Flow rate: 1.0 mL/min; Wave length: UV 254 nm; Temperature: 35° C.
HPLC Method F3: Column: CHIRALPAK AS-H, 0.46 cm×15 cm long; Mobile Phase: Hexane/EtOH, 85/15 (v/v); Flow rate: 1.0 mL/min; Wavelength: 254 nm; Temperature: 35° C.
HPLC Method F5: Column: CHIRALPAK AS-H, 0.46 cm×15 cm long; Mobile Phase: MeOH; Flow rate: 1.0 mL/min; Wavelength: 254 nm; Temperature: 35° C.
HPLC Method G1: Column: CHIRALPAK OD-H, 0.46 cm×15 cm long; Mobile Phase: Hexane/IPA, 60/40 (v/v); Flow rate: 1.0 mL/min; Wavelength: 214 nm; Temperature: 25° C.
HPLC Method H2: Column: CHIRALCEL OZ-H, 0.46 cm×15 cm long; Mobile Phase: Hexane/EtOH, 50/50 (v/v); Flow rate: 1.0 mL/min; Wavelength: 214 nm; Temperature: 25° C.
HPLC Method M1: Column: RESTEK C18 (30×2.1) 3u; Temperature: 50° C.; Flow rate: 1.5 mL/min; Injection volume: 3 ul; Mobile Phase A: 0.05% HCOOH in water; Mobile Phase B: MeCN; Gradient Elution (time, % A, % B): (0 min, 98% A, 2% B), (0.75 min, 98% A, 2% B), (1.0 min, 90% A, 10% B), (2.0 min, 2% A, 98% B), (2.25 min, 2% A, 98% B).

Preparation of Intermediates

Preparation 1: N'-(7-{[1-(2,4-difluorophenyl)-1H-pyrazol-4-yl]methyl}-5-[2-(trifluoromethyl)pyrimidin-5-yl]-7H-pyrrolo[2,3-d]pyrimidin-4-yl)-N,N-dimethyl formimidamide

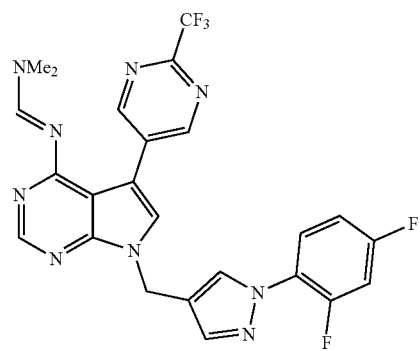 [SMILES: CN(C)/C=N/c1ncnc2c1c(-c1cnc(C(F)(F)F)nc1)cn2Cc1cnn(-c2ccc(F)cc2F)c1]

Step 1: To a solution of (1-(2,4-difluorophenyl)-1H-pyrazol-4-yl)methanol (Preparation 102, 0.698 g, 3.324 mmol) in DCM (15 mL) was added SOCl$_2$ (0.48 mL, 6.648 mmol) at 0° C. under N$_2$. The mixture was stirred at rt for 1 hr, evaporated to dryness in vacuo to afford 4-(chloromethyl)-1-(2,4-difluorophenyl)-1H-pyrazole as a brown oil (0.74 g, yield 93%). This material was used in the following reaction without further purification.

Step 2: To a solution of N,N-dimethyl-N'-{5-[2-(trifluoromethyl)pyrimidin-5-yl]-7H-pyrrolo[2,3-d]pyrimidin-4-yl}formimidamide (Preparation 17, 0.87 g, 2.591 mmol) in DMF (15 mL) was added $Cs_2CO_3$ (1.69 g, 5.182 mmol) and the mixture stirred at rt for 5 min. 4-(Chloromethyl)-1-(2, 4-difluorophenyl)-1H-pyrazole (Step 1, 0.74 g, 3.109 mmol) was added to the mixture drop wise at 0° C. and the mixture-stirred at 60° C. for 4 hr. The reaction was evaporated to dryness in vacuo and diluted with EtOAc (150 mL), washed with brine (2×100 mL) and dried ($Na_2SO_4$). The organics were evaporated to dryness in vacuo to give a residue which was purified by column chromatography on silica gel eluting with MeOH in DCM (0%-5%) to afford the title compound as a yellow solid (750 mg, 54%). $^1$HNMR (400 MHz, DMSO-$d_6$): 2.94 (s, 3H), 3.17 (s, 3H), 5.43 (s, 2H), 7.24 (t, 1H), 7.52 (t, 1H), 7.76 (t, 1H), 7.80 (s, 1H), 8.08 (s, 1H), 8.29 (s, 1H), 8.50 (s, 1H), 8.87 (s, 1H), 9.49 (s, 2H). LCMS m/z=528.1 [MH]$^+$ Preparation 2: N'-(7-{1-[1-(4-Fluorophenyl)-1H-pyrazol-4-yl]ethyl}-5-[2-(trifluoromethyl)pyrimidin-5-yl]-7H-pyrrolo[2,3-d]pyrimidin-4-yl)-N,N-dimethyl formimidamide

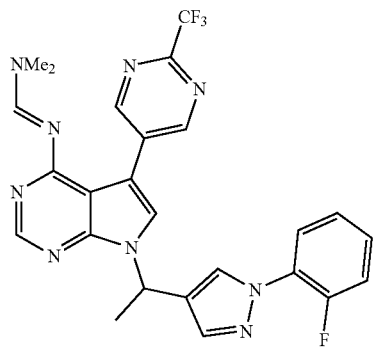 [SMILES: CC(c1cnn(-c2ccccc2F)c1)n1cc(-c2cnc(C(F)(F)F)nc2)c2c(/N=C/N(C)C)ncnc21]

To a solution of 1-[1-(2-fluorophenyl)-1H-pyrazol-4-yl]ethanol (869 mg, 4.2 mmol) in DCM (20 mL) was added $SOCl_2$ (613 µL) at 0° C. and the solution stirred at 40° C. for 2 hrs. The reaction mixture was evaporated to dryness, N,N-dimethyl-N'-[5-(2-(trifluoromethyl)pyrimidin-5-yl]-7H-pyrrolo[2,3-d]pyrimidin-4-yl)formimidamide (Preparation 17, 1.4 g, 4.2 mmol), $Cs_2CO_3$ (5.46 g, 16.8 mmol) and DMF (30 mL) added and the reaction stirred at 80° C. for 14 hr. The cooled mixture was poured into water (15 mL) and extracted with EtOAc (15 mL×3). The combined organic layers were washed by brine (20 mL), dried ($Na_2SO_4$) and concentrated in vacuo. The residue was purified by column chromatography on silica gel to provide the title compound as an off-white solid, (800 mg, 36%). LCMS m/z=524.1 [MH]$^+$ Preparation 3: N'-(7-(1-(1-(2,4-difluorophenyl)-1H-pyrazol-4-yl)ethyl)-5-(2-(trifluoromethyl)pyrimidin-5-yl)-7H-pyrrolo[2,3-d]pyrimidin-4-yl)-N,N-dimethylformimidamide

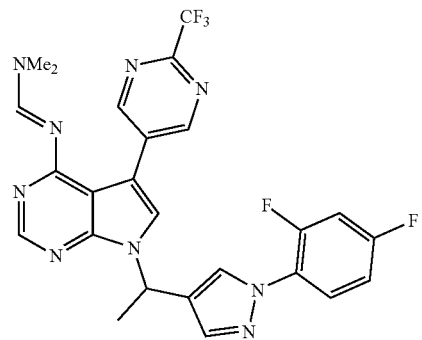 [SMILES: CC(c1cnn(-c2ccc(F)cc2F)c1)n1cc(-c2cnc(C(F)(F)F)nc2)c2c(/N=C/N(C)C)ncnc21]

To a solution of 4-(1-chloroethyl)-1-(2,4-difluorophenyl)-1H-pyrazole (Preparation 146, 1.08 g, 4.45 mmol) in DMF (30 mL) was added (E)-N-methyl-N'-(5-(2-(trifluoromethyl)pyrimidin-5-yl)-7H-pyrrolo[2,3-d]pyrimidin-4-yl)formimidamide (Preparation 17, 0.99 g, 52.97 mmol) and $Cs_2CO_3$ (4.84 g, 14.85 mmol) and the mixture stirred at 90° C. for 6 hr under $N_2$. The reaction mixture was diluted with water and extracted (EtOAc). The combined extracts were washed (brine), dried ($Na_2SO_4$) and evaporated to dryness in vacuo. The residue was purified by prep-HPLC to give the title compound (400 mg, 25%). LCMS m/z=542.1 [MH]$^+$ Preparation 4: N'-(7-(1-(1-(2-fluorophenyl)-1H-pyrazol-4-yl)propyl)-5-(2-(trifluoromethyl)pyrimidin-5-yl)-7H-pyrrolo[2,3-d]pyrimidin-4-yl)-N,N-dimethyl formimidamide

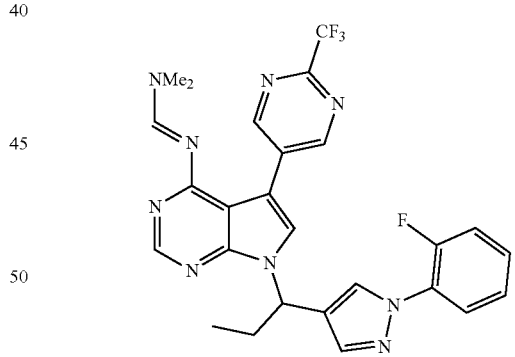

To a solution of 4-(1-chloropropyl)-1-(2-fluorophenyl)-1H-pyrazole (preparation 100, 0.58 g, 2.42 mmol) in DMF (30 mL) was added N,N-dimethyl-N'-(5-(2-(trifluoromethyl)pyrimidin-5-yl)-7H-pyrrolo[2,3-d]pyrimidin-4-yl) formimidamide (Preparation 17, 0.54 g, 1.61 mmol) and $Cs_2CO_3$ (2.62 g, 8.05 mmol) and the reaction stirred at 90° C. under $N_2$ overnight. The reaction was quenched with $H_2O$, extracted with EtOAc (100 mL×2) and the combined organics washed with brine, dried and evaporated to dryness in vacuo. The residue was purified by column chromatography over silica gel (DCM:MeOH=9:1) to give the title compound (0.3 g, 35%). $^1$HNMR (400 MHz, DMSO-$d_6$): 0.80 (t, 3H), 2.31 (m, 2H), 2.95 (s, 3H), 3.17 (s, 3H), 5.97

(t, 1H), 7.30-7.50 (m, 3H), 7.74 (t, 1H), 7.90 (s, 1H), 8.21 (s, 1H), 8.31 (s, 1H), 8.47 (s, 1H), 8.87 (s, 1H), 9.52 (s, 2H). LCMS m/z=538.1 [MH]+

Preparation 5: N'-(7-(1-(1-(2,4-difluorophenyl)-1H-pyrazol-4-yl)propyl)-5-(2-(trifluoromethyl)pyrimidin-5-yl)-7H-pyrrolo[2,3-d]pyrimidin-4-yl)-N,N-dimethylformimidamide

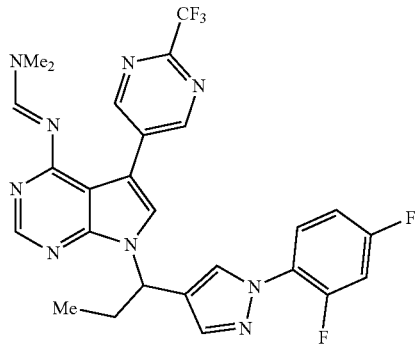 [SMILES: CCC(c1cnn(-c2ccc(F)cc2F)c1)n1cc(-c2cnc(C(F)(F)F)nc2)c2c(/N=C/N(C)C)ncnc21]

Step 1: SOCl₂ (976 mg, 8.4 mmol) was added drop wise to a solution of 1-(1-(2,4-difluorophenyl)-1H-pyrazol-4-yl)propan-1-ol (Preparation 104, 1.0 g, 4.2 mmol) in DCM (40 mL) at 0° C. The reaction was stirred at rt for 3 hrs and evaporated to dryness to afford 4-(1-chloropropyl)-1-(2,4-difluorophenyl)-1H-pyrazole (1.1 g, crude) as a brown oil, which was used directly in next step without further purification. LCMS m/z=253.2 [MH]+

Step 2: To a mixture of N,N-dimethyl-N'-(5-(2-(trifluoromethyl)pyrimidin-5-yl)-7H-pyrrolo[2,3-d]pyrimidin-4-yl)formimidamide (Preparation 17, 1.44 g, 4.28 mmol) in DMF (30 mL) was added Cs₂CO₃ (6.95 g, 21.4 mmol) and 4-(1-chloropropyl)-1-(2,4-difluorophenyl)-1H-pyrazole (1.1 g, 4.28 mmol) and the mixture was stirred at 80° C. for 16 h. The solvent was evaporated under reduced pressure and the residue was partitioned between water (50 mL) and EtOAc (30 mL). The layers were separated and the aqueous phase extracted with additional EtOAc (30 mL×3). The combined organic extracts were dried (Na₂SO₄) and evaporated to dryness under reduced pressure. The residue was purified by silica gel chromatography eluting with methanol in dichloromethane from 0 to 10% in 20 minutes to give the title compound as a brown solid (650 mg, 27% for 2 steps). ¹HNMR (400 MHz, DMSO-d₆): 0.83 (t, 3H), 2.33 (q, 2H), 2.95 (s, 3H), 3.17 (s, 3H), 5.96 (q, 1H), 7.22 (t, 1H), 7.52 (m, 1H), 7.75 (m, 1H), 7.80 (s, 1H), 8.20 (s, 1H), 8.28 (s, 1H), 8.46 (s, 1H), 8.87 (s, 1H), 9.52 (s, 2H). LCMS m/z=556.2 [MH]+

Preparation 6: N'-{5-(4-Methoxypyrimidin-5-yl)-7-[1-(1-phenyl-1H-1,2,3-triazol-4-yl)propyl]-7H-pyrrolo[2,3-d]pyrimidin-4-yl}-N,N-dimethylformimidamide

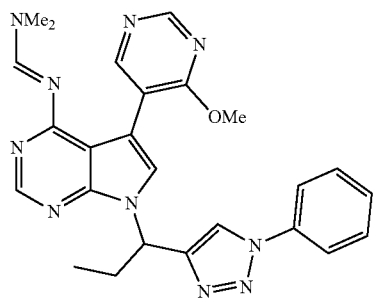 [SMILES: CCC(c1cn(-c2ccccc2)nn1)n1cc(-c2cncnc2OC)c2c(/N=C/N(C)C)ncnc21]

To a stirred solution of N'-[5-(4-methoxypyrimidin-5-yl)-7H-pyrrolo[2,3-d] pyrimidin-4-yl]-N,N-dimethylimidoformamide (Preparation 19, 1 g, 3.36 mmol) and 4-(1-chloropropyl)-1-phenyl-1H-1,2,3-triazole (Preparation 119, 895 mg, 4.06 mmol) in DMF (20 mL) was added Cs₂CO₃ (2.74 g, 8.41 mmol) and the reaction stirred at 60° C. for 5 hr. The cooled reaction mixture was diluted with EtOAc and washed with water followed by brine. The organic phase was dried (Na₂SO₄) and concentrated in vacuo. The crude product was purified by column chromatography on silica gel eluting with MeOH:DCM (3:97) to afford the title compound as an off white solid (1 g, 61.7%). ¹HNMR (400 MHz, DMSO-d₆): 0.85 (t, 3H), 2.38 (m, 2H), 2.75 (s, 3H), 3.10 (s, 3H), 3.87 (s, 3H), 6.11 (m, 1H), 7.48 (m, 1H), 7.59 (m, 2H), 7.71 (s, 1H), 7.88 (d, 1H), 8.41 (s, 1H), 8.67 (s 1H), 8.72 (d, 2H), 8.95 (s, 1H). LCMS m/z=482.8 [MH]+

Preparation 7: N'-(7-(1-(2-(2,4-difluorophenyl)-2H-imidazol-4-yl)propyl)-5-(2-(trifluoromethyl) pyrimidin-5-yl)-7H-pyrrolo[2,3-d]pyrimidin-4-yl)-N,N-dimethyl formimidamide

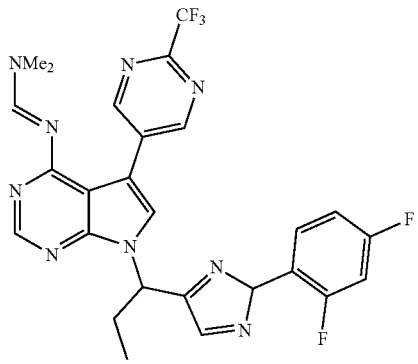 [SMILES: CCC(C1=NC(c2ccc(F)cc2F)N=C1)n1cc(-c2cnc(C(F)(F)F)nc2)c2c(/N=C/N(C)C)ncnc21]

Step 1: SOCl₂ (5 mL) was added drop wise to a solution of 1-(2-(2,4-difluorophenyl)-1H-imidazol-4-yl)propan-1-ol (Preparation 137, 1.4 g, 5.88 mmol) in DCM (50 mL). The reaction was stirred at rt for 2 hrs and evaporated to dryness in vacuo to give 4-(1-chloropropyl)-2-(2,4-difluorophenyl)-1H-imidazole which used directly in Step 2 (1.4 g, 92%).

Step 2: To a solution of N,N-dimethyl-N'-(5-(2-(trifluoromethyl)pyrimidin-5-yl)-7H-pyrrolo[2,3-d]pyrimidin-4-yl)formimidamide (Preparation 17, 1.22 g, 3.64 mmol) in DMF (50 mL) was added 4-(1-chloropropyl)-2-(2,4-difluorophenyl)-1H-imidazole (Step 1, 1.4 g, 5.45 mmol) and Cs₂CO₃ (5.93 g, 18.2 mmol). The reaction was stirred at 90° C. overnight, cooled and extracted with EtOAc. The organic layer was washed with brine, dried and evaporated. The residue was purified by column chromatography over silica gel (DCM:MeOH=9:1) to afford the title compound (450 mg, 22%). LCMS m/z=556.1 [MH]+

Preparation 8: N'-(7-(1-(1-(2-fluorophenyl)-5-methyl-1H-1,2,3-triazol-4-yl)ethyl)-5-(2-(trifluoromethyl) pyrimidin-5-yl)-7H-pyrrolo[2,3-d]pyrimidin-4-yl)-N,N-dimethyl formimidamide

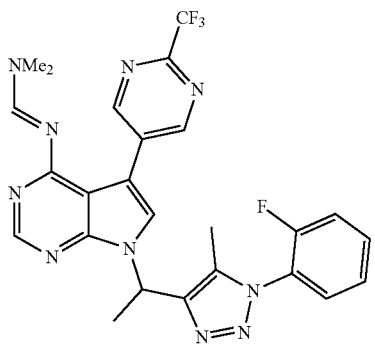 [SMILES: Cc1c(C(C)n2cc(-c3cnc(C(F)(F)F)nc3)c3c(/N=C/N(C)C)ncnc32)nnn1-c1ccccc1F]

To a solution of N,N-dimethyl-N'-(5-(2-(trifluoromethyl)pyrimidin-5-yl)-7H-pyrrolo[2,3-d]pyrimidin-4-yl)formimidamide (Preparation 17, 839 mg, 2.5 mmol) in DMF (30 mL) was added $Cs_2CO_3$ (3.25 g, 10 mmol) and 4-(1-chloroethyl)-1-(2-fluorophenyl)-5-methyl-1H-1,2,3-triazole (Preparation 114, 600 mg, 2.5 mmol). The mixture was stirred at 80° C. for 16 hr and the cooled reaction mixture then poured into water (20 mL) and extracted with EtOAc (15 mL×3). The combined extracts were washed with brine (10 mL), dried ($Na_2SO_4$) and evaporated to dryness in vacuo. The residue triturated with pet. ether to afford the title compound as a brown solid (900 mg, 66%). LCMS m/z=539.1 [MH+]

Preparation 9: N'-(7-(1-(1-(2,4-difluorophenyl)-5-methyl-1H-1,2,3-triazol-4-yl)propyl)-5-(2-(trifluoromethyl)pyrimidin-5-yl)-7H-pyrrolo[2,3-d]pyrimidin-4-yl)-N,N-dimethylformimidamide

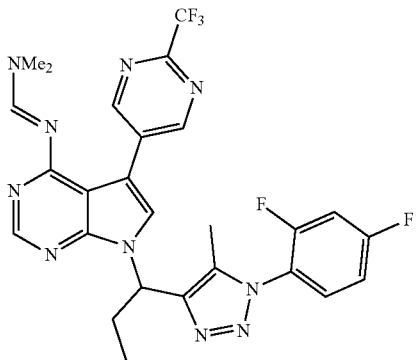 [SMILES: CCC(c1nnn(-c2ccc(F)cc2F)c1C)n1cc(-c2cnc(C(F)(F)F)nc2)c2c(/N=C/N(C)C)ncnc21]

To a solution of 4-(1-chloropropyl)-1-(2,4-difluorophenyl)-5-methyl-1H-1,2,3-triazole (Preparation 111, 2.2 g, 8.83 mmol) in DMF (80 mL) was added N,N-dimethyl-N'-(5-(2-(trifluoromethyl)pyrimidin-5-yl)-7H-pyrrolo[2,3-d]pyrimidin-4-yl) formimidamide (Preparation 17, 2.96 g, 8.83 mmol) and $Cs_2CO_3$ (11.5 g, 35.32 mmol). The reaction mixture was stirred at 80° C. for 5 hr, poured into water (100 mL) and extracted with EtOAc (50 mL×3). The organic extracts were washed (brine, 100 mL), dried ($Na_2SO_4$) and evaporated to dryness in vacuo. The residue was purified by combi-flash eluting with EtOAc in pet. ether (20-80%) to give the title compound as an off-white solid (2.8 g, 55%). $^1$HNMR (400 MHz, MeOD-$d_4$): 0.87 (t, 3H), 2.44 (m, 2H), 2.76 (s, 3H), 2.89 (s, 6H), 6.04 (t, 1H), 7.11 (m, 1H), 7.24 (m, 1H), 7.52 (m, 1H), 7.88 (s, 1H), 8.34 (s, 1H), 8.58 (s, 1H), 9.29 (s, 2H). LCMS m/z=571 [MH]+

Preparation 10: N'-(7-((1-(2,4-difluorophenyl)-1H-1,2,3-triazol-4-yl)methyl)-5-(6-methoxypyridin-3-yl)-6-methyl-7H-pyrrolo[2,3-d]pyrimidin-4-yl)-N,N-dimethylformimidamide

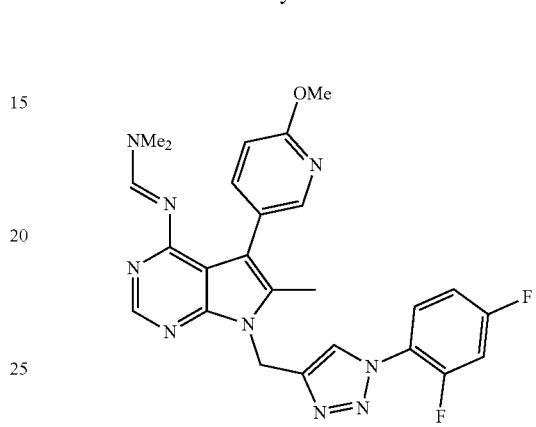

To a solution of N'-(5-(6-methoxypyridin-3-yl)-6-methyl-7-(prop-2-ynyl)-7H-pyrrolo[2,3-d]pyrimidin-4-yl)-N,N-dimethylformimidamide (Preparation 11, 0.23 g, 0.66 mmol) in toluene (20 mL) was added under $N_2$ t-BuOH (5 mL), DIPEA (2 mL), 1-azido-2,4-difluorobenzene (0.26 g, 1.65 mmol) and CuI (76 mg, 0.40 mmol). The reaction was stirred at rt overnight, water added and the mixture was extracted with EtOAc. The organic layer was collected, washed with brine, dried and evaporated to dryness in vacuo. The residue was purified by column chromatography over silica gel (DCM/MeOH=9/1) to afford the title compound as a solid, (0.22 g, 66.2%). $^1$HNMR (400 MHz, DMSO-$d_6$): 2.50 (s, 3H), 2.79 (s, 3H), 3.06 (s, 3H), 3.87 (s, 3H), 5.67 (s, 2H), 6.83 (d, 1H), 7.33 (m, 1H), 7.65 (m, 1H), 7.75-7.90 (m, 2H), 8.19 (s, 1H), 8.61 (s, 1H), 8.68 (s, 2H).

Preparation 11: N'-(5-(6-methoxypyridin-3-yl)-6-methyl-7-(prop-2-yn-1-yl)-7H-pyrrolo[2,3-d]pyrimidin-4-yl)-N,N-dimethylformimidamide

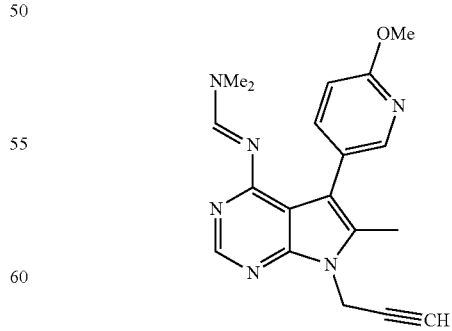

To a solution of N'-(5-(6-methoxypyridin-3-yl)-6-methyl-7H-pyrrolo[2,3-d]pyrimidin-4-yl)-N,N-dimethylformimidamide (Preparation 12, 0.42 g, 1.35 mmol) in DMF (25 mL) was added NaH (60%, 81 mg, 2.03 mmol) portion wise and stirred for 10 mins. 3-Bromoprop-1-yne (0.24 g, 2.03 mmol) was added and the reaction stirred at rt overnight. The reaction was carefully quenched with water and extracted with EtOAc. The combined organics were washed with brine, dried and evaporated to dryness in vacuo. The residue was purified by column chromatography over silica gel (EtOAc/MeOH=10/1) to afford the title compound (0.23 g, 48.9%) as a grey solid.
LCMS m/z=349.2 [MH]$^+$ Preparation 12: N'-(5-(6-methoxypyridin-3-yl)-6-methyl-7H-pyrrolo[2,3-d]pyrimidin-4-yl)-N, N-dimethylformimidamide

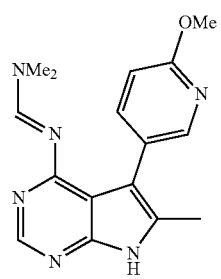 [SMILES: COc1ccc(-c2c(C)[nH]c3ncnc(/N=C/N(C)C)c23)cn1]

A solution of 5-(6-methoxypyridin-3-yl)-6-methyl-7H-pyrrolo[2,3-d]pyrimidin-4-amine (Preparation 23, 0.45 g, 1.7 mmol) in DMF-DMA (30 mL) was stirred at 100° C. for 2 hrs. The mixture was evaporated to dryness in vacuo and the residue diluted with EtOAc and NaHCO$_3$ solution. The organic layer was washed with brine, dried and evaporated to dryness to give the title compound (0.42 g, 79.6%) as a solid. LCMS m/z=311.2 [MH]$^+$; RT [HPLC method A]=1.183 min.

Preparation 13: N'-[7-(But-3-yn-2-yl)-5-(4-chlorophenyl)-2-methyl-7H-pyrrolo[2,3-d]pyrimidin-4-yl]-N,N-dimethylimidoformamide

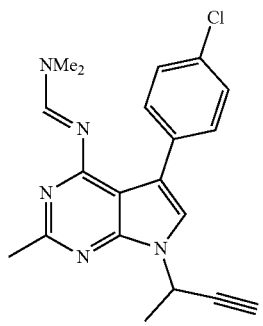 [SMILES: C#CC(C)n1cc(-c2ccc(Cl)cc2)c2c(/N=C/N(C)C)nc(C)nc21]

Sodium ethoxide (66.4 mg, 0.96 mmol) was added to an ice cooled solution of N'-[7-(but-3-yn-2-yl)-5-(4-chlorophenyl)-2-methyl-7H-pyrrolo[2,3-d]pyrimidin-4-yl]-N,N-dimethylimidoformamide (Preparation 14, 200 mg, 0.637 mmol) in anhydrous DMF (4 mL) and the mixture stirred for 30 mins. 3-Bromo-1-butyne (0.134 mL, 1.27 mmol) was added drop wise and the reaction stirred at rt for 18 hrs. The mixture was diluted with water and extracted with EtOAc, the combined organic layers washed with brine, dried (MgSO$_4$) and evaporated under reduced pressure. The crude product was purified by column chromatography on silica gel eluting with EtOAc:heptane (20:80 to 100:0) to afford the title compound as an oil. LCMS m/z=366.1 [MH]$^+$ Preparation 14: N'-(5-(4-chlorophenyl)-2-methyl-7H-pyrrolo[2,3-d]pyrimidin-4-yl)-N,N-dimethylformimidamide

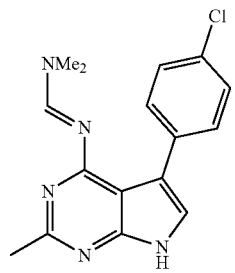 [SMILES: Cc1nc(/N=C/N(C)C)c2c(-c3ccc(Cl)cc3)c[nH]c2n1]

A solution of 5-(4-chlorophenyl)-2-methyl-7H-pyrrolo[2,3-d]pyrimidin-4-amine (Preparation 79, 300 mg, 1.16 mmol) in N,N-dimethylformamide dimethyl acetal (4.8 mL) was stirred at rt for an hour, and then a further 16 hrs at 50° C. The cooled mixture was diluted with water and extracted with EtOAc. The combined organic layers were washed with brine, dried (MgSO$_4$), filtered and evaporated under reduced pressure to afford the title compound as an off white solid (350 mg, 96.2%). LCMS m/z=314.1 [MH]$^+$ Preparation 15: N'-(7-(but-3-yn-2-yl)-5-(4-chlorophenyl)-6-methyl-7H-pyrrolo[2,3-d]pyrimidin-4-yl)-N,N-dimethylformimidamide

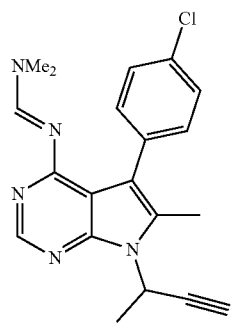 [SMILES: C#CC(C)n1c(C)c(-c2ccc(Cl)cc2)c2c(/N=C/N(C)C)ncnc21]

To a stirred solution of N'-(5-(4-chlorophenyl)-6-methyl-7H-pyrrolo[2,3-d]pyrimidin-4-yl)-N,N-dimethylformimidamide (Preparation 16, 50 mg, 0.16 mmol) in DMF (1.5 mL) was added NaH (9.56 mg, 0.24 mmol) at 0° C. After 15 mins, 3-bromo-but-1-yne (0.022 mL, 0.24 mmol) was added and the reaction stirred to rt for 16 hrs. The reaction mixture was diluted with EtOAc, washed with water, brine, dried (Na$_2$SO$_4$) and evaporated to dryness in vacuo. The residue was purified by prep-TLC using 50% EtOAc:Hexane to afford the title compound as an off-white solid (30 mg, 51.5%). $^1$HNMR (400 MHz, CDCl$_3$): 1.79 (d, 3H), 2.43 (s, 3H), 2.77 (s, 3H), 3.00 (s, 3H), 6.14 (m, 2H), 7.32 (d, 2H), 7.39 (d, 2H), 8.45 (s, 1H), 8.50 (br s, 1H).

Preparation 16: N'-(5-(4-chlorophenyl)-6-methyl-7H-pyrrolo[2,3-d]pyrimidin-4-yl)-N,N-dimethylformimidamide

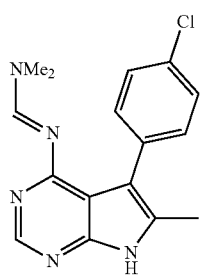 [SMILES: Cc1[nH]c2ncnc(/N=C/N(C)C)c2c1-c1ccc(Cl)cc1]

N,N-dimethylformamidedimethylacetal (2.0 mL) was added to a 5-(4-chlorophenyl)-6-methyl-7H-pyrrolo[2,3-d]pyrimidin-4-amine (Preparation 24, 100.0 mg, 0.4 mmol) at 0° C. and stirred at rt for 16 hrs. The reaction mixture was evaporated to dryness and diluted with EtOAc, washed with water, brine, dried (Na$_2$SO$_4$) and evaporated in vacuo to afford the title compound as a light brown solid (80.0 mg, 66%). LCMS m/z=314.2 [MH]$^+$

Preparation 17: N,N-dimethyl-N'-5-[2-(trifluoromethyl)pyrimidin-5-yl]-7H-pyrrolo[2,3-d]pyrimidin-4-yl)formimidamide

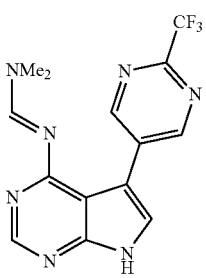 [SMILES: CN(C)/C=N/c1ncnc2[nH]cc(-c3cnc(C(F)(F)F)nc3)c12]

A solution of 5-[2-(trifluoromethyl)pyrimidin-5-yl]-7H-pyrrolo[2,3-d]pyrimidin-4-amine (Preparation 18, 24 g, 85.7 mmol) in DMF-DMA (300 mL) was heated to 100° C. for 3 hr. The cooled mixture was concentrated in vacuo and the crude product purified by silica gel column chromatography eluting with DCM:MeOH=20:1 to afford the title compound (25 g, 87%) as a yellow solid. $^1$HNMR (400 MHz, DMSO-d$_6$): 2.96 (s, 3H), 3.16 (s, 3H), 7.92 (s, 1H), 8.39 (s, 1H), 8.86 (s, 1H), 9.52 (s, 2H). LCMS m/z=336.1 [MH]$^+$

Preparation 18: 5-[2-(trifluoromethyl)pyrimidin-5-yl]-7H-pyrrolo[2,3-d]pyrimidin-4-amine

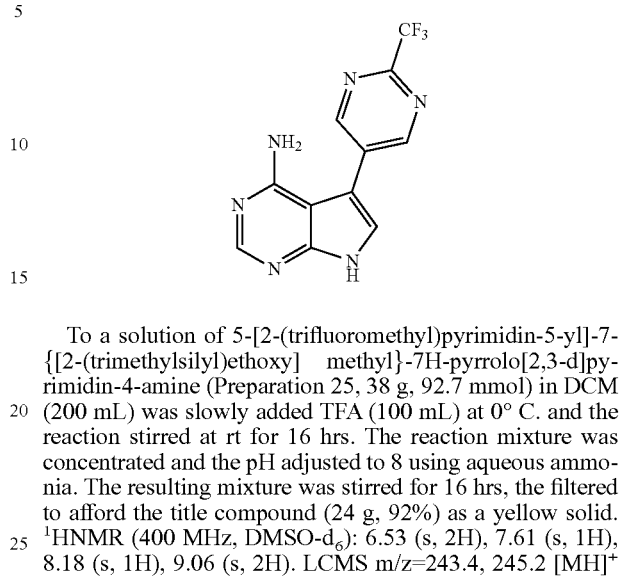

To a solution of 5-[2-(trifluoromethyl)pyrimidin-5-yl]-7-{[2-(trimethylsilyl)ethoxy] methyl}-7H-pyrrolo[2,3-d]pyrimidin-4-amine (Preparation 25, 38 g, 92.7 mmol) in DCM (200 mL) was slowly added TFA (100 mL) at 0° C. and the reaction stirred at rt for 16 hrs. The reaction mixture was concentrated and the pH adjusted to 8 using aqueous ammonia. The resulting mixture was stirred for 16 hrs, the filtered to afford the title compound (24 g, 92%) as a yellow solid. $^1$HNMR (400 MHz, DMSO-d$_6$): 6.53 (s, 2H), 7.61 (s, 1H), 8.18 (s, 1H), 9.06 (s, 2H). LCMS m/z=243.4, 245.2 [MH]$^+$

Preparation 19: N'-[5-(4-Methoxypyrimidin-5-yl)-7H-pyrrolo[2,3-d]pyrimidin-4-yl]-N,N-dimethylimidoformamide

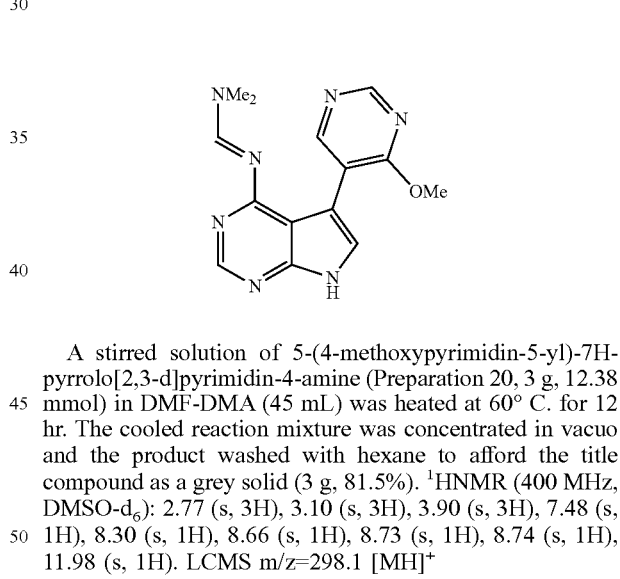

A stirred solution of 5-(4-methoxypyrimidin-5-yl)-7H-pyrrolo[2,3-d]pyrimidin-4-amine (Preparation 20, 3 g, 12.38 mmol) in DMF-DMA (45 mL) was heated at 60° C. for 12 hr. The cooled reaction mixture was concentrated in vacuo and the product washed with hexane to afford the title compound as a grey solid (3 g, 81.5%). $^1$HNMR (400 MHz, DMSO-d$_6$): 2.77 (s, 3H), 3.10 (s, 3H), 3.90 (s, 3H), 7.48 (s, 1H), 8.30 (s, 1H), 8.66 (s, 1H), 8.73 (s, 1H), 8.74 (s, 1H), 11.98 (s, 1H). LCMS m/z=298.1 [MH]$^+$

Preparation 20: 5-(4-Methoxypyrimidin-5-yll)-7H-pyrrolo[2,3-d]pyrimidin-4-amine

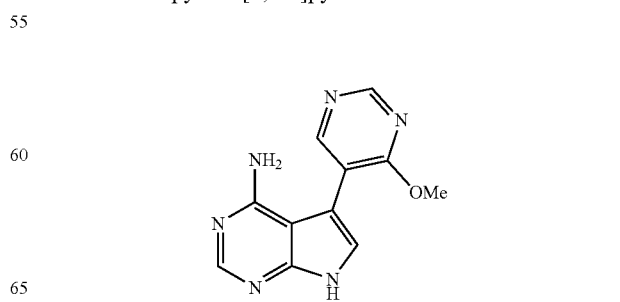

To a stirred solution of 5-(4-methoxypyrimidin-5-yl)-7-{[2-(trimethylsilyl)ethoxy]methyl}-7H-pyrrolo[2,3-d]pyrimidin-4-amine (Preparation 27, 32 g, 85.90 mmol) in DCM (300 mL) was added TFA (131.5 mL, 1718.1 mmol) at 0° C. and the reaction stirred at rt for 16 hrs. The reaction mixture was concentrated in vacuo, the residue diluted with MeOH and aqueous ammonia (150 mL) added. The resulting solution was stirred at rt for 12 hrs and the reaction mixture then concentrated and filtered. The resulting solid was washed with water, followed by 10% MeOH:DCM and dried under vacuum to afford the title compound as a gray solid (18.2 g, 87.5%). $^1$HNMR (400 MHz, DMSO-$d_6$): 3.94 (s, 3H), 6.14 (br s, 2H), 7.26 (s, 1H), 8.08 (s, 1H), 8.41 (s, 1H), 8.75 (s, 1H), 11.82 (s, 1H). LCMS m/z=243.2 [MH]$^+$ Preparation 21: N'-(5-(2-methoxypyridin-3-yl)-7H-pyrrolo[2,3-d]pyrimidin-4-yl)-N,N-dimethylformimidamide

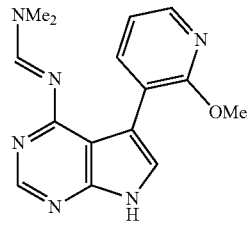 [SMILES: COc1ncccc1-c1c[nH]c2ncnc(/N=C/N(C)C)c12]

A solution of 5-(2-methoxypyridin-3-yl)-7H-pyrrolo[2,3-d]pyrimidin-4-amine (Preparation 22, 1 g, 4.145 mmol) in DMF-DMA (20 mL) was stirred at 60° C. for 6 h. The reaction mixture was evaporated under reduced pressure and the resulting solid was triturated with Et$_2$O to afford the title compound as a light brown solid (900 mg, 73%). $^1$HNMR (400 MHz, DMSO-$d_6$): 2.74 (s, 3H), 3.09 (s, 3H), 3.80 (s, 3H), 6.98 (dd, 1H), 7.39 (s, 1H), 7.92 (d, 1H), 8.05 (d, 1H), 8.31 (s, 1H), 8.67 (s, 1H), 11.83 (s, 1H). LCMS m/z=297.4 [MH]$^+$ Preparation 22: 5-(2-methoxypyridin-3-yl)-7H-pyrrolo[2,3-d]pyrimidin-4-amine

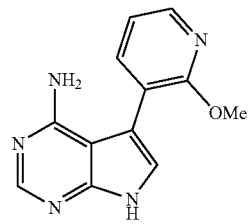 [SMILES: COc1ncccc1-c1c[nH]c2ncnc(N)c12]

The title compound was obtained as a white solid (11 g, 84.5%) from 5-(2-methoxypyridin-3-yl)-7-{[2-(trimethylsilyl)ethoxy]methyl}-7H-pyrrolo[2,3-d]pyrimidin-4-amine (Preparation 26, 20 g, 53.77 mmol) following a similar procedure to that described in Preparation 190. $^1$HNMR (400 MHz, DMSO-$d_6$): 3.87 (s, 3H), 5.91 (br s, 2H), 7.07 (m, 1H), 7.20 (s, 1H), 7.63 (m, 1H), 8.08 (s, 1H), 8.16 (m, 1H), 11.79 (s, 1H). LCMS m/z=242.0 [MH]$^+$ Preparation 23: 5-(6-methoxypyridin-3-yl)-6-methyl-7H-pyrrolo[2,3-d]pyrimidin-4-amine

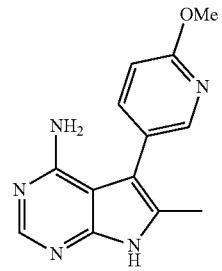 [SMILES: COc1ccc(-c2c(C)[nH]c3ncnc(N)c23)cn1]

A solution of 5-(6-methoxypyridin-3-yl)-6-methyl-7-((2-(trimethylsilyl)ethoxy) methyl)-7H-pyrrolo[2,3-d]pyrimidin-4-amine (Preparation 28, 0.8 g, 2.1 mmol) in 25% TFA in DCM (30 mL) was stirred at rt overnight. The mixture was concentrated and excess NaHCO$_3$ solution was added. The mixture was extracted with DCM and the combined organics washed with brine, dried and evaporated to dryness. The residue was washed with TBME to give the title compound (0.45 g, 83.9%) as a grey solid. LCMS m/z=256.2 [MH]$^+$ Preparation 24: 5-(4-chlorophenyl)-6-methyl-7H-pyrrolo[2,3-d]pyrimidin-4-amine

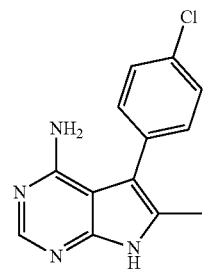 [SMILES: Cc1[nH]c2ncnc(N)c2c1-c1ccc(Cl)cc1]

TFA (2.4 mL, 30.7 mmol) was added to a stirred solution of 5-(4-chlorophenyl)-6-methyl-7-((2-(trimethylsilyl)ethoxy)methyl)-7H-pyrrolo[2,3-d]pyrimidin-4-amine (Preparation 29, 400 mg, 1.023 mmol) in DCM (10.0 mL) at 0° C. and stirred at rt for 16 hrs. The reaction mixture was evaporated to dryness under reduced pressure and the residue dissolved in methanol (3 mL) and treated with NH$_4$OH (6 mL) and the mixture was stirred at rt for 16 hrs. The reaction mixture was evaporated to dryness in vacuo to afford the title compound as a brown solid (200 mg, 75%). LCMS m/z=259.0 [MH]$^+$

Preparation 25: 5-[2-(trifluoromethyl)pyrimidin-5-yl]-7-{[2-(trimethylsilyl)ethoxy] methyl}-7H-pyrrolo[2,3-d]pyrimidin-4-amine

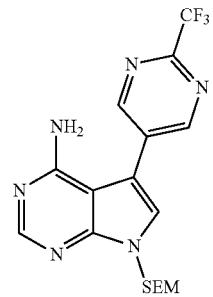 [SMILES: C[Si](C)(C)CCOCn1cc(-c2cnc(C(F)(F)F)nc2)c2c(N)ncnc21]

To a solution of 5-iodo-7-{[2-(trimethylsilyl)ethoxy]methyl}-7H-pyrrolo[2,3-d]pyrimidin-4-amine (Preparation 33, 43 g, 110 mmol), 2-(trifluoromethyl)pyrimidin-5-yl boronic acid (36.2 g, 132 mmol) in 1,4-dioxane (220 mL) at rt was added $K_2CO_3$ (30 g, 217 mmol) in $H_2O$ (40 mL) and $PdCl_2(dppf)$ (8.1 g, 11.1 mmol) under $N_2$ and the reaction stirred at 100° C. for 4 hrs. The cooled reaction was filtered and the filtrate concentrated under reduced pressure. The crude product was purified by column chromatography on silica gel eluting with pet. ether:EtOAc (50:50) to afford the title compound (38 g, 84%) as a yellow solid. $^1$HNMR (400 MHz, DMSO-$d_6$): 0.00 (s, 9H), 0.93 (t, 2H), 3.64 (t, 2H), 5.64 (s, 2H), 6.73 (br s, 2H), 7.88 (s, 1H), 8.31 (s, 1H), 9.13 (s, 2H). LCMS m/z=411.1 [MH]$^+$

Preparation 26: 5-(2-methoxypyridin-3-yl)-7-{[2-(trimethylsilyl)ethoxy]methyl}-7H-pyrrolo[2,3-d]pyrimidin-4-amine

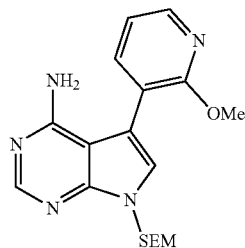

To a stirred solution of 5-iodo-7-{[2-(trimethylsilyl)ethoxy]methyl}-7H-pyrrolo[2,3-d]pyrimidin-4-amine (Preparation 33, 25 g, 64.05 mmol) in EtOH: water (4:1, 750 mL) was added 2-methoxypyridin-3-yl boronic acid (14.69 g, 96.08 mmol) followed by $Na_2CO_3$ (27.15 g, 256.21 mmol) and the mixture degassed with Ar for 15 min. $Pd(PPh_3)_4$ (7.39 g, 6.4 mmol) was added and the reaction was heated at 100° C. for 3 hrs. The cooled mixture was diluted with water and the solution extracted with EtOAc. The combined organic extracts were dried ($Na_2SO_4$) and concentrated under reduced pressure. The crude product was purified by column chromatography on silica gel to afford the title compound (40 g, 79% for composite batch) as a white solid. $^1$HNMR (400 MHz, DMSO-$d_6$): −0.08 (s, 9H), 0.84 (t, 2H), 3.56 (t, 2H), 3.87 (s, 3H), 5.52 (s, 2H), 6.06 (br s, 2H), 7.10 (m, 1H), 7.39 (s, 1H), 7.55-7.64 (m, 2H), 8.15 (s, 1H). LCMS m/z=372.4 [MH]$^+$

Preparation 27: 5-(4-Methoxypyrimidin-5-yl)-7-{[2-(trimethylsilyl)ethoxy]methyl}-7H-pyrrolo[2,3-d]pyrimidin-4-amine

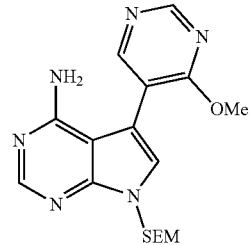 [SMILES: COc1ncncc1-c1cn(COCC[Si](C)(C)C)c2ncnc(N)c12]

To a stirred solution of 5-iodo-7-{[2-(trimethylsilyl)ethoxy]methyl}-7H-pyrrolo[2,3-d]pyrimidin-4-amine (Preparation 33, 35 g, 89.68 mmol) in EtOH: water (1.4 L, 4:1) was added 4-methoxy-5-(4,4,5,5-tetramethyl-1,3,2-dioxaborolan-2-yl)pyrimidine (25.4 g, 107.61 mmol) followed by $Na_2CO_3$ (28.51 g, 269.0 mmol) and the reaction mixture was degassed with Ar for 15 mins. $Pd(PPh_3)_4$ (10.36 g, 8.97 mmol) was added and the reaction stirred at 100° C. for 5 hrs. The cooled mixture was diluted with water and extracted with DCM. The combined organic extracts were dried ($Na_2SO_4$) and concentrated in vacuo. The crude product was purified by column chromatography on silica gel eluting with acetone-DCM (30:70) to afford the title compound as an off white solid (17.81 g, 53.4%). $^1$HNMR (400 MHz, DMSO-$d_6$): 0.07 (s, 9H), 0.84 (t, 2H), 3.58 (t, 2H), 3.94 (s, 3H), 5.52 (s, 2H), 6.34 (br s, 2H), 7.46 (s, 1H), 8.15 (s, 1H), 8.40 (s, 1H), 8.77 (s, 1H). LCMS m/z=373.0 [MH]$^+$

Preparation 28: 5-(6-methoxypyridin-3-yl)-6-methyl-7-((2-(trimethylsilyl)ethoxy) methyl)-7H-pyrrolo[2,3-d]pyrimidin-4-amine

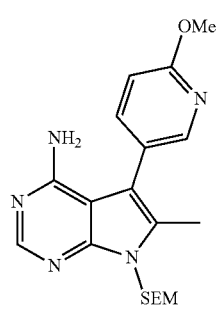 [SMILES: COc1ccc(-c2c(C)n(COCC[Si](C)(C)C)c3ncnc(N)c23)cn1]

To a solution of 5-iodo-6-methyl-7-((2-(trimethylsilyl)ethoxy)methyl)-7H-pyrrolo[2,3-d]pyrimidin-4-amine (Preparation 34, 1.5 g, 3.7 mmol) in dioxane (60 mL) was added 6-methoxypyridin-3-ylboronic acid (0.85 g, 5.6 mmol), $NaHCO_3$ solution (15 mL) and $Pd(PPh_3)_4$ (0.21 g, 0.185 mmol) and the reaction stirred at 100° C. overnight under $N_2$. The cooled reaction mixture was diluted with water and extracted with EtOAc. The combined organics were washed with brine, dried and evaporated to dryness. The residue was purified by column chromatography over silica gel (pet. ether:EtOAc=3:1) to give the title compound as a yellow solid (0.8 g, 56.1%). $^1$HNMR (400 MHz, CDCl$_3$): 0.00 (s, 9H), 0.98 (t, 2H), 2.42 (s, 3H), 3.64 (t, 2H), 4.05 (s, 3H), 5.68 (s, 2H), 6.92 (d, 1H), 7.45-7.75 (m, 3H), 8.26 (s, 1H), 8.33 (s, 1H). LCMS m/z=256.2 [MH]+

Preparation 29: 5-(4-chlorophenyl)-6-methyl-7-((2-(trimethylsilyl)ethoxy)methyl)-7H-pyrrolo[2,3-d]pyrimidin-4-amine

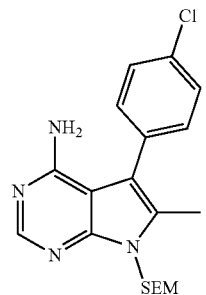 [SMILES: Cc1c(-c2ccc(Cl)cc2)c2c(N)ncnc2n1COCC[Si](C)(C)C]

To a degassed solution of 5-iodo-6-methyl-7-((2-(trimethylsilyl)ethoxy)methyl)-7H-pyrrolo[2,3-d]pyrimidin-4-amine (Preparation 34, 800 mg, 1.97 mmol), 4-chloro phenyl boronic acid (433.2 mg, 2.77 mmol) and Na$_2$CO$_3$ (838.8 mg, 7.92 mmol) in EtOH-water (4:1, 20 mL) under N$_2$ was added Pd(PPh$_3$)$_4$ (71.5 mg, 0.062 mmol) and the reaction degassed with Ar for 15 min. The reaction was heated at 90° C. for 5 hrs, filtered through a plug of Celite® and washed with EtOAc (2×30 mL). The combined filtrates were washed with water, dried (Na$_2$SO$_4$), and evaporated to dryness in vacuo. The residue was purified by column chromatography on silica gel (20-25% EtOAc in hexane) to afford the title compound as a light yellow solid (400 mg, 51.98%). $^1$HNMR (400 MHz, DMSO-d$_6$): −0.09 (s, 9H), 0.84 (t, 2H), 2.31 (s, 3H), 3.52 (t, 2H), 5.58 (s, 2H), 5.80 (br s, 2H), 7.36 (d, 2H), 7.54 (d, 2H), 8.13 (s, 1H). LCMS m/z=389.0 [MH]+

Preparation 30: N'-(7-((5-(2-fluorophenyl)-4-((2-(trimethylsilyl)ethoxy)methyl)-4H-1,2,4-triazol-3-yl)methyl)-5-(2-methoxypyridin-3-yl)-7H-pyrrolo[2,3-d]pyrimidin-4-yl)-N,N-dimethylformimidamide

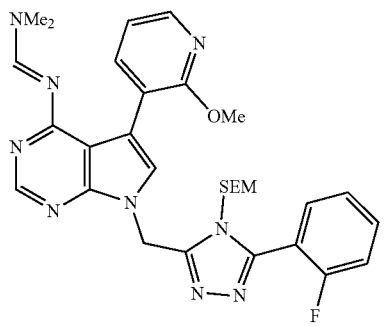 [SMILES: COc1ncccc1-c1cn(Cc2nnc(-c3ccccc3F)n2COCC[Si](C)(C)C)c2ncnc(/N=C/N(C)C)c12]

To a stirred solution of N'-(5-(2-methoxypyridin-3-yl)-7H-pyrrolo[2,3-d] pyrimidin-4-yl)-N,N-dimethylformimidamide (Preparation 21, 100 mg, 0.337 mmol) in DMF was added Cs$_2$CO$_3$ (220.02 mg, 0.675 mmol) followed by 3-(chloromethyl)-5-(2-fluorophenyl)-4-((2-(trimethylsilyl)ethoxy)methyl)-4H-1,2,4-triazole (Preparation 121, 172.6 mg, 0.506 mmol, as mixture of isomers) and the mixture stirred at rt for 16 hr. The reaction was diluted with ice water and extracted with EtOAc (30 mL×2). The combined extracts were washed with water, brine, dried (Na$_2$SO$_4$) and evaporated to dryness in vacuo. The residue was purified by column chromatography on silica gel to afford the title compound as a sticky yellow solid (160 mg, 78%, mixture of two isomers). The mixture of isomers was used without further purification. LCMS m/z=602 [MH]+

Preparation 31: N'-(5-(2-methoxypyridin-3-yl)-7-((5-phenyl-4-((2-(trimethylsilyl) ethoxy)methyl)-4H-1,2,4-triazol-3-yl)methyl)-7H-pyrrolo[2,3-d]pyrimidin-4-yl)-N,N-dimethylformimidamide

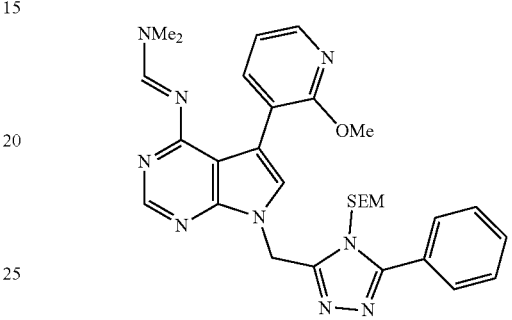

The title compound was prepared (140 mg, 71%) as a mixture of isomers in an analogous way to Preparation 30 using 3-(chloromethyl)-5-phenyl-4-((2-(trimethylsilyl)ethoxy)methyl)-4H-1,2,4-triazole (Preparation 122, 163.5 mg, 0.506 mmol) and N'-(5-(2-methoxypyridin-3-yl)-7H-pyrrolo[2,3-d]pyrimidin-4-yl)-N,N-dimethylformimidamide (Preparation 21, 100 mg, 0.337 mmol). $^1$HNMR (400 MHz, DMSO-d$_6$): −0.09 (s, 6H), 0.79 (t, 2H), 3.08 (s, 3H), 3.57 (t, 2H), 3.80 (s, 3H), 5.75 (s, 2H), 6.98 (m, 1H), 7.41-7.46 (m, 3H), 7.60 (s, 1H), 7.95 (m, 3H), 8.05 (m, 1H), 8.37 (s, 1H), 8.71 (s, 1H). LCMS m/z=584.2 [MH]+

Preparation 32: N'-(7-((1-(2-fluorophenyl)-1H-pyrazol-4-yl)methyl)-5-(2-(trifluoromethyl)pyrimidin-5-yl)-7H-pyrrolo[2,3-d]pyrimidin-4-yl)-N,N-dimethylformimidamide

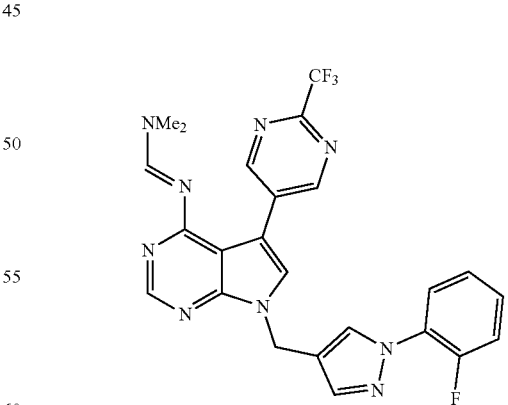

A mixture of 7-((1-(2-fluorophenyl)-1H-pyrazol-4-yl)methyl)-5-(2-(trifluoromethyl)pyrimidin-5-yl)-7H-pyrrolo[2,3-d]pyrimidin-4-amine (Example 57, 160 mg, 0.352 mmol) in DMF-DMA (8 mL) was stirred at 90° C. for 0.5 hr. The mixture was concentrated to give the crude product which was purified by combi-flash on a silica column eluting with MeOH in DCM (0%-5%) to give the title compound as an orange solid (110 mg, 61%). ¹HNMR (400 MHz, DMSO-$d_6$): −0.09 (s, 9H), 0.84 (t, 2H), 2.31 (s, 3H), 3.52 (t, 2H), 5.58 (s, 2H), 5.80 (br s, 2H), 7.36 (d, 2H), 7.54 (d, 2H), 8.13 (s, 1H). LCMS m/z=510.1 [MH]⁺

Preparation 33: 5-Iodo-7-{[2-(trimethylsilyl)ethoxy]methyl}-7H-pyrrolo[2,3-d] pyrimidin-4-amine

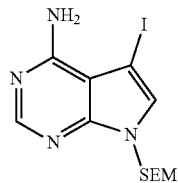

To a stirred solution of 4-chloro-5-iodo-7-{[2-(trimethylsilyl)ethoxy]methyl}-7H-pyrrolo[2,3-d]pyrimidine (Preparation 72, 40 g, 97.8 mmol) in dioxane: MeOH (110 mL, 5:1) was added NH₄OH$_{(aq)}$ (570 mL) and the resulting suspension stirred in an autoclave at 70° C. for 2 hr then at 90° C. for 16 hr. The cooled reaction mixture was diluted with DCM, the layers separated and the organic layer washed with brine, dried (Na₂SO₄) and concentrated in vacuo. The crude product was triturated with diethyl ether and dried under reduced pressure to afford the title compound as an off-white solid (32 g, 83.84%). ¹HNMR (400 MHz, DMSO-$d_6$): 0.09 (s, 9H), 0.82 (t, 2H), 3.48 (t, 2H), 5.44 (s, 2H), 6.66 (br s, 2H), 7.56 (s, 1H), 8.12 (s, 1H). LCMS m/z=391.0 [MH]⁺

Preparation 34: 5-iodo-6-methyl-7-((2-(trimethylsilyl)ethoxy)methyl)-7H-pyrrolo[2,3-d]pyrimidin-4-amine

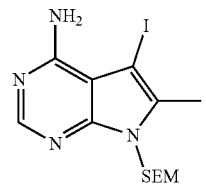 [SMILES: Cc1c(I)c2c(N)ncnc2n1COCC[Si](C)(C)C]

NH₄OH was added to a stirred solution of 4-chloro-5-iodo-6-methyl-7-((2-(trimethylsilyl)ethoxy)methyl)-7H-pyrrolo[2,3-d]pyrimidine (Preparation 73, 1 g, 2.36 mmol) in dioxane (25.0 mL) (75 mL) and heated to 120° C. for 16 hrs. The reaction was evaporated to dryness in vacuo and extracted with EtOAc (3×25 mL), washed with water, brine, dried (Na₂SO₄) and evaporated to dryness. The residue was purified by column chromatography to afford the title compound as an off white solid (400 mg, 42.11%). ¹HNMR (400 MHz, DMSO-$d_6$): −0.10 (s, 9H), 0.82 (t, 2H), 2.38 (s, 3H), 3.45 (t, 2H), 5.54 (s, 2H), 6.58 (br s, 2H), 8.09 (s, 1H). LCMS m/z=405.2 [MH]⁺

Preparation 35: 4-Chloro-7-{1-[1-(2-fluorophenyl)-1H-1,2,3-triazol-4-yl]ethyl}-5-(oxetan-3-yl)-7H-pyrrolo[2,3-d]pyrimidine

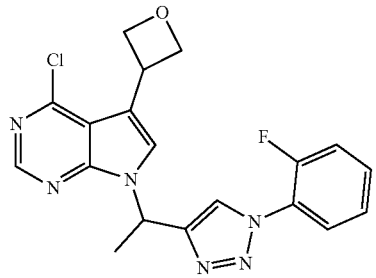 [SMILES: CC(c1cn(-c2ccccc2F)nn1)n1cc(C2COC2)c2c(Cl)ncnc21]

(4-Chloro-7-{1-[1-(2-fluorophenyl)-1H-1,2,3-triazol-4-yl]ethyl}-7H-pyrrolo[2,3-d]pyrimidin-5-yl)boronic acid (Preparation 61, 340 mg, 0.88 mmol), powdered NiI (40 mg, 0.12 mmol) and trans-2-aminocyclohexanol (20 mg, 0.12 mmol) were suspended in anhydrous iPrOH (1.25 mL) and DMSO (1.75 mL). NaHMDS (1M in THF, 0.97 mL, 0.97 mmol) was added, the suspension degassed under N₂, iodo-oxetane (70 μL, 0.79 mmol) in anhydrous iPrOH (0.5 mL) added and the reaction heated at 80° C. for 30 mins under microwave irradiation. The mixture was partitioned between water and EtOAc, the layers separated, the aqueous extracted with EtOAC and the combined organics dried (MgSO₄), filtered, and concentrated in vacuo. The crude yellow oil was purified by column chromatography on silica gel eluting with EtOAc:heptane (50:50 to 100:0) to afford the title compound as a yellow oil (77.4 mg, 14)%. ¹HNMR (400 MHz, DMSO-$d_6$): 1.98 (d, 3H), 4.50-4.60 (m, 3H), 5.04 (m, 2H), 6.38 (q, 1H), 7.45 (m, 1H), 7.54-7.62 (m, 2H), 7.73 (m, 1H), 8.17 (s, 1H), 8.70 (s, 2H). LCMS m/z=399.0 [MH]⁺

Preparation 36: 4-Chloro-7-{1-[1-(2-fluorophenyl)-1H-1,2,3-triazol-4-yl]ethyl}-5-[4-methoxy-2-(trifluoromethyl)pyrimidin-5-yl]-7H-pyrrolo[2,3-d]pyrimidine

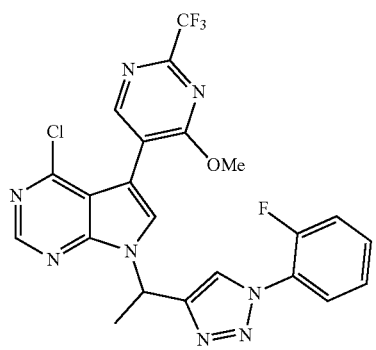 [SMILES: COc1nc(C(F)(F)F)ncc1-c1cn(C(C)c2cn(-c3ccccc3F)nn2)c2ncnc(Cl)c12]

A suspension of (4-chloro-7-{1-[1-(2-fluorophenyl)-1H-1,2,3-triazol-4-yl]ethyl}-7H-pyrrolo[2,3-d]pyrimidin-5-yl) boronic acid (Preparation 61, 35 mg, 0.074 mmol), 5-bromo-4-methoxy-2-(trifluoromethyl)pyrimidine (Preparation 141, 19 mg, 0.074 mmol) and Na₂CO₃ (32 mg, 0.3 mmol) in EtOH (4.5 mL) and H₂O (0.5 mL) was degassed with N₂. Pd(PPh₃)₄ (8 mg) was added and the reaction stirred at ~90°

C. for 2 hrs. The solvents were blown off under a stream of N₂, the residue partitioned between water and EtOAc, the layers separated and the aqueous extracted with EtOAc. The combined organic extracts were dried (MgSO₄) filtered, and concentrated in vacuo to afford the title compound in quantitative yield. The product was used without further purification. LCMS m/z=519.0 [MH]⁺

Preparation 37: 4-Chloro-7-{1-[1-(2-fluorophenyl)-1H-1,2,3-triazol-4-yl]propyl}-5-(3-methoxypyrazin-2-yl)-7H-pyrrolo[2,3-d]pyrimidine

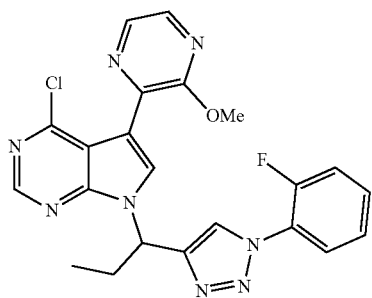 [SMILES: CCC(c1cn(-c2ccccc2F)nn1)n1cc(-c2nccnc2OC)c2c(Cl)ncnc21]

A suspension of 4-chloro-7-(1-(1-(2-fluorophenyl)-1H-1,2,3-triazol-4-yl)propyl)-5-(4,4,5,5-tetramethyl-1,3,2-dioxaborolan-2-yl)-7H-pyrrolo[2,3-d]pyrimidine (Preparation 63, 827 mg, 1.71 mmol), 2-chloro-3-methoxypyrazine (521 mg, 3.61 mmol), and Na₂CO₃ (726 mg, 6.85 mmol) in EtOH (9 mL) and H₂O (1.5 mL) was degassed under N₂. Pd(PPh₃)₄ (198 mg, 0.17 mmol) was added and the reaction stirred at 90° C. The cooled reaction was partitioned between, water and EtOAc, the layers separated and the aqueous phase extracted with EtOAc. The combined organic layers were dried (MgSO₄), filtered, and concentrated to give a yellow oil. This was purified by column chromatography on silica gel eluting with EtOAc:DCM (40:60 to 100:0) to afford the title compound as an off-white foam (370 mg, 46.6%). ¹HNMR (400 MHz, DMSO-d₆): 0.86 (t, 3H), 2.48 (m, 2H), 3.90 (s, 3H), 6.25 (m, 1H), 7.45 (m, 1H), 7.52-7.62 (m, 2H), 7.84 (m, 1H), 8.22-8.30 (m, 3H), 8.78 (s, 1H), 8.82 (d, 1H). LCMS m/z=465.1 [MH]⁺

Preparation 38: 5-(4-Chlorophenyl)-7-(1H-pyrazol-4-ylmethyl)-7H-pyrrolo[2,3-d]pyrimidin-4-amine

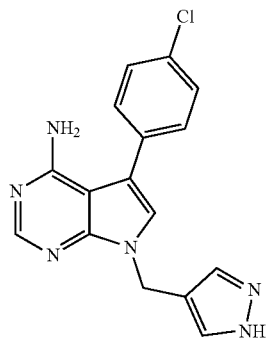 [SMILES: Nc1ncnc2c1c(-c1ccc(Cl)cc1)cn2Cc1cn[nH]c1]

To a solution of 5-(4-chlorophenyl)-7H-pyrrolo[2,3-d]pyrimidin-4-amine (Preparation 80, 5.43 g, 22.2 mmol) in DMF (120 mL) was added Cs₂CO₃ (14.5 g, 44.4 mmol) and 4-(chloromethyl)-1H-pyrazole hydrochloride (5.1 g, 33.3 mmol) and the reaction heated at 60° C. for 12 hrs. The cooled mixture was diluted with water, extracted with EtOAc, the organic phase washed with brine and dried (Na₂SO₄). The residue was purified by column chromatography on silica gel eluting with DCM:MeOH (15:1) to afford the title compound as a white solid (1.1 g, 15% yield). ¹HNMR (400 MHz, DMSO-d₆): 5.24 (s, 2H), 6.17 (br s, 2H), 7.40-7.76 (m, 7H), 8.19 (s, 1H), 12.81 (s, 1H). LCMS m/z=325.2 [MH]⁺

Preparation 39: 5-(2-methoxypyridin-3-yl)-7-(1H-pyrazol-4-ylmethyl)-7H-pyrrolo[2,3-d]pyrimidin-4-amine

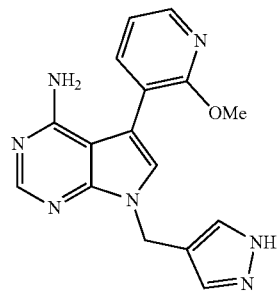 [SMILES: COc1ncccc1-c1cn(Cc2cn[nH]c2)c2ncnc(N)c12]

To a stirred solution of 5-(2-methoxypyridin-3-yl)-7-((1-((2-(trimethylsilyl)ethoxy)methyl)-1H-pyrazol-4-yl)methyl)-7H-pyrrolo[2,3-d]pyrimidin-4-amine (Preparation 40, 22 g, 48.78 mmol) in DCM (300 mL) was added TFA (37.35 mL, 487.8 mmol) at 0° C. and the reaction stirred at rt for 16 hr. The reaction mixture was concentrated and diluted with cold water. Aqueous ammonia was added and the solution stirred at rt for 24 hr. The resulting mixture was filtered, the solid washed with water, then diethyl ether and dried under vacuum. The solid was suspended in DCM/MeOH and purified by passing through a neutral alumina bed to afford the title compound as a white sold (10 g, 67.7%). ¹HNMR (400 MHz, DMSO-d₆): 3.85 (s, 3H), 5.21 (s, 2H), 5.98 (br s, 2H), 7.06 (m, 1H), 7.32 (s, 1H), 7.43-7.77 (m, 3H), 8.16 (s, 2H), 12.76 (s, 1H). LCMS m/z=323 [MH]⁺

Preparation 40: 5-(2-methoxypyridin-3-yl)-7-((1-((2-(trimethylsilyl)ethoxy)methyl)-1H-pyrazol-4-yl)methyl)-7H-pyrrolo[2,3-d]pyrimidin-4-amine

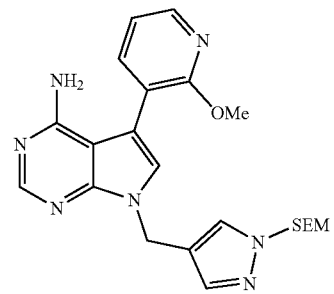 [SMILES: COc1ncccc1-c1cn(Cc2cnn(COCC[Si](C)(C)C)c2)c2ncnc(N)c12]

To a stirred solution of 5-iodo-7-((1-((2-(trimethylsilyl)ethoxy)methyl)-1H-pyrazol-4-yl)methyl)-7H-pyrrolo[2,3- d]pyrimidin-4-amine (Preparation 74, 35 g, 74.4 mmol) in EtOH: water (4:1, 875 mL) was added 2-methoxypyridin-3-yl boronic acid (17.07 g, 111.61 mmol) followed by $Na_2CO_3$ (31.54 g, 297.62 mmol) and the mixture degassed with Ar for 15 mins. $Pd(PPh_3)_4$ (8.59 g, 7.44 mmol) was added and the reaction was heated at 100° C. for 3 hrs. The cooled reaction mixture was diluted with water, the solution extracted with EtOAc, the combined organic extracts dried ($Na_2SO_4$) and concentrated under reduced pressure. The crude product was purified by column chromatography on silica gel to afford the title compound (22 g, 65.5%) as an off white solid. $^1$HNMR (400 MHz, DMSO-$d_6$): −0.12 (s, 9H), 0.78 (t, 2H), 3.47 (t, 2H), 3.85 (s, 3H), 5.23 (s, 2H), 5.33 (s, 2H), 6.00 (br s, 2H), 7.06 (m, 1H), 7.32 (s, 1H), 7.56 (s, 1H), 7.61 (m, 1H), 7.89 (s, 1H), 8.16 (s, 2H). LCMS m/z=452.0 [MH]$^+$ Preparation 41: 7-{[1-(2-Fluorophenyl)-1H-1,2,3-triazol-4-yl]methyl}-5-iodo-7H-pyrrolo[2,3-d]pyrimidin-4-amine

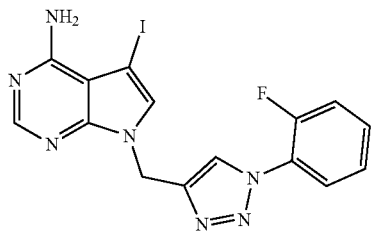 [SMILES: Nc1ncnc2c1c(I)cn2Cc1cn(-c2ccccc2F)nn1]

A mixture of 5-iodo-7-(prop-2-yn-1-yl)-7H-pyrrolo[2,3-d]pyrimidin-4-amine (Preparation 85, 60 g, 0.201 mol), CuI (21.08 g, 0.11 mol), DIPEA (347.4 mL, 2.01 mol) and 1-azido-2-fluorobenzene (56.92 g, 0.362 mol) in toluene (1.9 L) and t-BuOH (480 mL) was stirred at rt for 16 hr. The reaction was diluted with hexane (500 mL) and the mixture filtered under reduced pressure. The resulting solid was suspended in saturated methanolic $NH_3$: DCM (1:5, 2 L) and filtered through Celite® washing through with saturated methanolic $NH_3$: DCM (1:5, 5×500 mL). The filtrate was concentrated under reduced pressure the residue triturated with diethyl ether (200 mL), filtered and dried to afford the title compound as a light yellow solid (40 g, 45.9%). $^1$HNMR (400 MHz, DMSO-$d_6$): 5.50 (s, 2H), 6.64 (br s, 2H), 7.41 (m, 1H), 7.53-7.63 (m, 3H), 7.79 (m, 1H), 8.14 (s, 1H), 8.57 (s, 1H). LCMS m/z=436.0 [MH]$^+$ Preparation 42: 7-{1-[1-(2-Fluorophenyl)-1H-1,2,3-triazol-4-yl]ethyl}-5-iodo-7H-pyrrolo[2,3-d] pyrimidin-4-amine

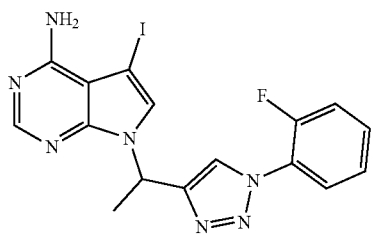 [SMILES: CC(c1cn(-c2ccccc2F)nn1)n1cc(I)c2c(N)ncnc21]

To a stirred solution of 7-(but-3-yn-2-yl)-5-iodo-7H-pyrrolo[2,3-d]pyrimidin-4-amine (Preparation 86, 19 g, 60.88 mmol) in toluene (37.5 mL) was added t-BuOH (12.5 mL), CuI (5.80 g, 30.44 mmol) and DIPEA (99.75 mL, 547.88 mmol) at rt. The mixture was cooled to 0° C., 1-azido-2-fluoro-benzene (14.39 g, 103.49 mmol) added and the reaction stirred for 16 hrs at rt. The mixture was filtered, the resulting solid suspended in hot THF and the mixture filtered to afforded the crude material. This material was washed with $Et_2O$ and dried in vacuo to afford the title compound as a brown solid (22.2 g, 81.17%). $^1$HNMR (400 MHz, DMSO-$d_6$): 1.87 (d, 3H), 6.21-6.26 (m, 1H), 6.62-6.76 (br s, 2H), 7.43 (m, 1H), 7.54-7.63 (m, 3H), 7.80-7.84 (m, 1H), 8.17-8.29 (m, 1H), 8.64 (s, 1H). LCMS m/z=450.0 [MH]$^+$ Preparation 43: 7-{1-[1-(3-Fluoropyridin-2-yl)-1H-1,2,3-triazol-4-yl]ethyl}-5-iodo-7H-pyrrolo[2,3-d]pyrimidin-4-amine

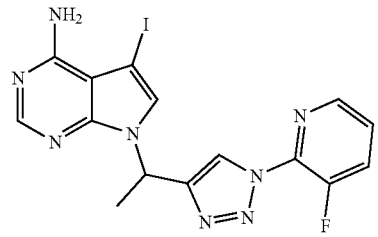 [SMILES: CC(c1cn(-c2ncccc2F)nn1)n1cc(I)c2c(N)ncnc21]

To a stirred solution of 7-(but-3-yn-2-yl)-5-iodo-7H-pyrrolo[2,3-d]pyrimidin-4-amine (Preparation 86, 700 mg, 2.24 mmol) in a mixture of toluene:tBuOH (3:1) (70 mL) was added 2-azido-3-fluoropyridine (Preparation 144, 624.16 mg, 4.49 mmol), DIPEA (4.02 mL, 22.44 mmol) and CuI (235 mg, 1.23 mmol) successively at 0° C. under $N_2$ and the reaction stirred at rt for 24 hrs. The mixture was diluted with EtOAc and washed with water followed by brine. The organic layer was dried ($Na_2SO_4$) and concentrated in vacuo. The crude product was purified by column chromatography on silica gel eluting with MeOH:DCM (4:96) to afford the title compound as an off-white solid (250 mg, 24.75%). $^1$HNMR (400 MHz, DMSO-$d_6$): 1.88 (d, 3H), 6.22-6.27 (m, 1H), 6.63 (br s, 2H), 7.60 (s, 1H), 7.69-7.73 (m, 1H), 8.13-8.17 (m, 2H), 8.48 (m, 1H), 8.72 (s, 1H). LCMS m/z=450.8 [MH]$^+$ Preparation 44: 7-{1-[1-(2,4-Difluorophenyl)-1H-1,2,3-triazol-4-yl]ethyl}-5-iodo-7H-pyrrolo[2,3-d]pyrimidin-4-amine

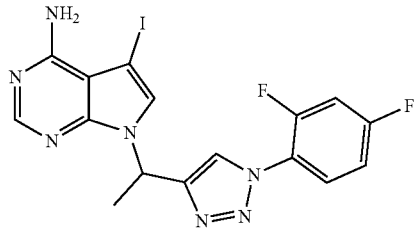 [SMILES: CC(c1cn(-c2ccc(F)cc2F)nn1)n1cc(I)c2c(N)ncnc21]

The title compound was obtained as a white solid (2.7 g, 72%) from 7-(but-3-yn-2-yl)-5-iodo-7H-pyrrolo[2,3-d]pyrimidin-4-amine (Preparation 86) and 1-azido-2,4-difluorobenzene following an analogous procedure to that described in preparation 43. ¹HNMR (400 MHz, DMSO-d₆): 1.89 (d, 3H), 6.24 (m, 1H), 6.70-6.90 (br s, 2H), 7.33 (m, 1H), 7.59 (s, 1H), 7.68 (m, 1H), 7.88 (m, 1H), 8.40 (s, 1H), 8.64 (s, 1H). LCMS m/z=468.0 [MH]⁺

Preparation 45: 7-{1-[1-(2-Fluorophenyl)-1H-1,2,3-triazol-4-yl]propyl}-5-iodo-7H-pyrrolo[2,3-d]pyrimidin-4-amine

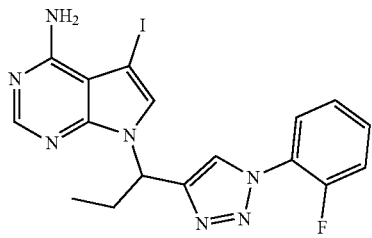 [SMILES: CCC(c1cn(-c2ccccc2F)nn1)n1cc(I)c2c(N)ncnc21]

DIPEA (15 mL, 82.8 mmol) and CuI (876 mg, 4.6 mmol) were added to a solution of 5-iodo-7-(pent-1-yn-3-yl)-7H-pyrrolo[2,3-d]pyrimidin-4-amine (Preparation 87, 3 g, 9.2 mmol) in toluene:t-BuOH (100 mL, 4:1) at 0° C., followed by 1-azido-2-fluorobenzene (2.2 g, 16.06 mmol) and the reaction stirred at rt or 16 hrs. The mixture was filtered, washing through with ether: hexane (1:4) and the filtrate evaporated under reduced pressure to afford the title compound as a light brown solid (3 g, 96.15%). ¹HNMR (400 MHz, DMSO-d₆): 0.80 (t, 3H), 2.32 (m, 2H), 6.04 (m, 1H), 6.64 (br s, 2H), 7.44 (m, 1H), 7.55-7.67 (m, 4H), 7.85 (m, 1H), 8.15 (s, 1H), 8.48 (s, 1H). LCMS m/z=463.9 [MH]⁺

Preparation 46: 7-{1-[1-(2,4-Difluorophenyl)-1H-1,2,3-triazol-4-yl]propyl}-5-iodo-7H-pyrrolo[2,3-d]pyrimidin-4-amine

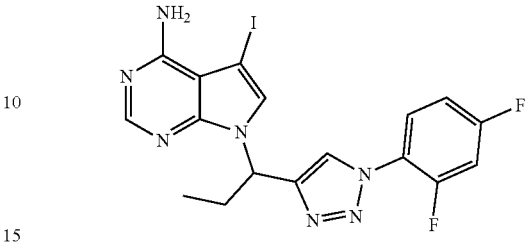

To a solution of 5-iodo-7-(pent-1-yn-3-yl)-7H-pyrrolo[2,3-d]pyrimidin-4-amine (Preparation 87, 70 g, 214.85 mmol) in toluene (200 ml) was added 1-azido-2,4-difluorobenzene (50 g, 322.25 mmol), CuI (24.55 g, 128.9 mmol), DIPEA (177.5 ml, 1.07 mol) and t-BuOH (750 ml) added under N₂ and the reaction stirred at rt for 16 hrs. The mixture was filtered, concentrated in vacuo and the residue purified by flash chromatography (eluting with DCM:MeOH=20:1) to afford the title compound as a white solid (70 g, 67.8%). ¹HNMR (400 MHz, DMSO-d₆): 0.79 (t, 3H), 2.31 (m, 2H), 6.00 (m, 1H), 6.65 (br s, 2H), 7.35 (m, 1H), 7.61 (s, 1H), 7.69 (m, 1H), 7.90 (m, 1H), 8.14 (s, 1H), 8.67 (d, 1H). LCMS m/z=482.0 [MH]⁺

Preparations 47 to 53

The following compounds were prepared from 5-iodo-7-(pent-1-yn-3-yl)-7H-pyrrolo[2,3-d]pyrimidin-4-amine (Preparation 87) and the appropriate commercial azide, following the procedure described in Preparation 46.

| Preparation No | Structure/Name | Analytical Data |
| --- | --- | --- |
| 47 | ![structure] 7-{1-[1-(4-fluorophenyl)-1H-1,2,3-triazol-4-yl]propyl}-5-iodo-7H-pyrrolo[2,3-d]pyrimidin-4-amine | ¹HNMR (400 MHz, DMSO-d₆): 0.78 (t, 3H), 2.25-2.33 (m, 2H), 5.98 (m, 1H), 6.64 (br s, 2H), 7.42-7.58 (m, 3H), 7.97 (m, 2H), 8.17 (s, 1H), 8.88 (s, 1H). LCMS m/z = 463.9 [MH]⁺ |
| 48 | ![structure] 7-{1-[1-(3,4-difluorophenyl)-1H-1,2,3-triazol-4-yl]propyl}-5-iodo-7H-pyrrolo[2,3-d]pyrimidin-4-amine | ¹HNMR (400 MHz, DMSO-d₆): 0.79 (t, 3H), 2.31 (m, 2H), 5.97 (m, 1H), 6.65 (br s, 2H), 7.54 (s, 1H), 7.69 (m, 1H), 7.79 (m, 1H), 8.08-8.14 (m, 2H), 8.90 (s, 1H). LCMS m/z = 482.0 [MH]⁺ |

-continued

| Preparation No | Structure/Name | Analytical Data |
|---|---|---|
| 49 | 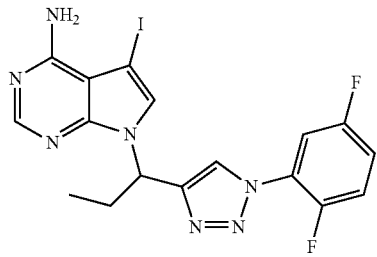<br>7-{1-[1-(2,5-difluorophenyl)-1H-1,2,3-triazol-4-yl]propyl}-5-iodo-7H-pyrrolo[2,3-d]pyrimidin-4-amine | $^1$HNMR (400 MHz, DMSO-d$_6$): 0.79 (t, 3H), 2.31 (m, 2H), 6.01 (m, 1H), 6.66 (br s, 2H), 7.50 (m, 1H), 7.63-7.68 (m, 2H), 7.84 (m, 1H), 8.14 (s, 1H), 8.72 (s, 1H).<br>LCMS m/z = 482.1 [MH]$^+$ |
| 50 | 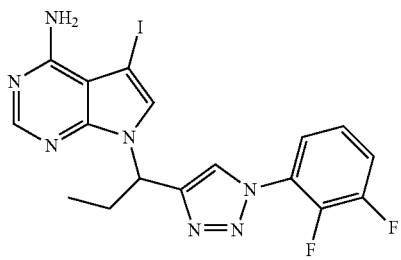<br>7-{1-[1-(2,3-difluorophenyl)-1H-1,2,3-triazol-4-yl]propyl}-5-iodo-7H-pyrrolo[2,3-d]pyrimidin-4-amine | $^1$HNMR (400 MHz, DMSO-d$_6$): 0.79 (t, 3H), 2.31 (m, 2H), 6.02 (m, 1H), 6.68 (br s, 2H), 7.44 (m, 1H), 7.63-7.71 (m, 3H), 8.18 (s, 1H), 8.74 (s, 1H).<br>LCMS m/z = 482.1 [MH]$^+$ |
| 51 | 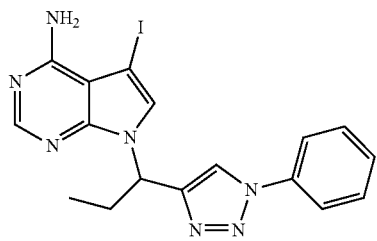<br>5-iodo-7-[1-(1-phenyl-1H-1,2,3-triazol-4-yl)propyl]-7H-pyrrolo[2,3-d]pyrimidin-4-amine | LCMS m/z = 446.1 [MH]$^+$ |
| 52 | 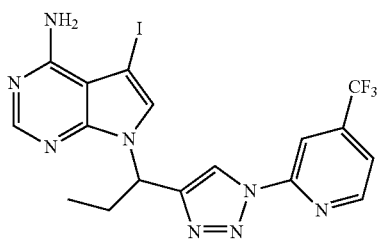<br>5-iodo-7-(1-{1-[4-(trifluoromethyl)pyridine-2-yl]-1H-1,2,3-triazol-4-yl}propyl)-7H-pyrrolo[2,3-d]pyrimidin-4-amine | $^1$HNMR (400 MHz, DMSO-d$_6$): 0.81 (t, 3H), 2.34 (m, 2H), 6.03 (m, 1H), 6.63 (br s, 2H), 7.67 (s, 1H), 7.95 (d, 1H), 8.14 (s, 1H), 8.34 (s, 1H), 8.89 (s, 1H), 9.03 (s, 1H). LCMS m/z = 514.8 [MH]$^+$ |

| Preparation No | Structure/Name | Analytical Data |
|---|---|---|
| 53 | 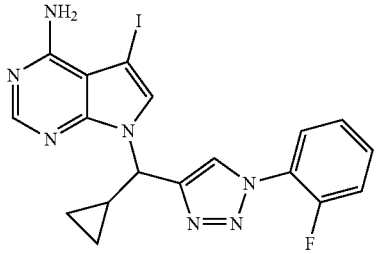<br>7-{Cyclopropyl[1-(2-fluorophenyl)-1H-1,2,3-triazol-4-yl)methyl]-5-iodo-7H-pyrrolo[2,3-d]pyrimidin-4-amine | $^1$HNMR (400 MHz, DMSO-d$_6$): 0.38 (m, 1H), 0.53-0.60 (m, 2H), 0.71 (m, 1H), 1.92 (m, 1H), 5.35 (d, 1H), 6.03 (m, 1H), 6.64 (br s, 2H), 7.45 (m, 1H), 7.58-7.68 (m, 2H), 7.70 (s, 1H), 7.84 (m, 1H), 8.10 (s, 1H), 8.73 (s, 1H). LCMS m/z = 475.8 [MH]$^+$ |

Preparation 54: 7-((1-(2-fluorophenyl)-1H-1,2,3-triazol-4-yl)methyl)-5-iodo-2-methyl-7H-pyrrolo[2,3-d]pyrimidin-4-amine

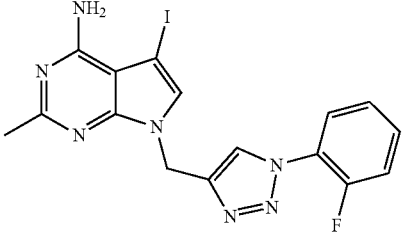 [SMILES: Cc1nc(N)c2c(I)cn(Cc3cn(-c4ccccc4F)nn3)c2n1]

To a solution of 5-iodo-2-methyl-7-prop-2-ynyl-7H-pyrrolo[2,3-d]pyrimidin-4-ylamine (Preparation 89, 3.8 g, 12.18 mmol) in toluene: t-BuOH (60 mL, 4:1) was added DIPEA (16.84 mL, 97.45 mmol), copper iodide (1.16 g, 6.09 mmol) and 1-azido-2-fluorobenzene (Preparation 145, 2.87 g, 20.71 mmol) at 0° C. The reaction mixture was stirred at room temperature for 16 hr. The reaction was evaporated to dryness in vacuo and water was added followed by ammonium hydroxide solution and the resulting mixture stirred for 30 min and filtered (the process was repeated until the filtrate was colorless). Solid was washed with 5% EtOAc in hexane and dried. The residue was purified by column chromatography (0.5% MeOH in DCM) to afford the title compound as an off-white solid (3.35 g, 61.4%). $^1$HNMR (400 MHz, DMSO-d$_6$): 2.56 (s, 3H), 5.51 (s, 4H), 7.19 (s, 1H), 7.25-7.44 (m, 3H), 7.93 (t, 1H), 8.08 (d, 1H). LCMS m/z=450.0 [MH]$^+$ Preparation 55: 7-((1-(2-fluorophenyl)-1H-pyrazol-4-yl)methyl)-5-iodo-7H-pyrrolo[2,3-d]pyrimidin-4-amine

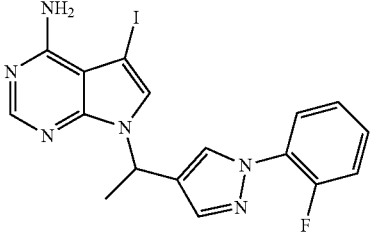 [SMILES: CC(c1cnn(-c2ccccc2F)c1)n1cc(I)c2c(N)ncnc21]

A mixture of 4-chloro-7-((1-(2-fluorophenyl)-1H-pyrazol-4-yl)methyl)-5-iodo-7H-pyrrolo[2,3-d]pyrimidine (Preparation 67, 20 g, 44.2 mmol) and NH$_4$OH (100 mL) in 1,4-dioxane (50 mL) was stirred at 100° C. in an autoclave for 8 hrs. The reaction mixture was cooled to rt, solids removed by filtration which were washed with water to afford the title compound as a white solid (17 g, 89%). $^1$HNMR (400 MHz, DMSO-d$_6$): 5.27 (s, 2H), 6.63 (br s, 2H), 7.31-7.48 (m, 3H), 7.56 (s, 1H), 7.74-7.79 (m, 2H), 8.16 (s, 1H), 8.25 (d, 1H). LCMS m/z=434.9 [MH]$^+$ Preparation 56: 7-(1-(1-(2-fluorophenyl)-1H-pyrazol-4-yl)ethyl)-5-iodo-7H-pyrrolo[2,3-d]pyrimidin-4-amine

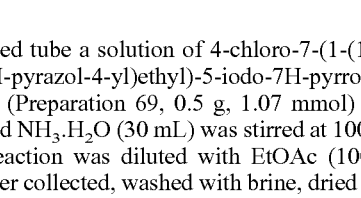

In a sealed tube a solution of 4-chloro-7-(1-(1-(2-fluorophenyl)-1H-pyrazol-4-yl)ethyl)-5-iodo-7H-pyrrolo[2,3-d]pyrimidine (Preparation 69, 0.5 g, 1.07 mmol) in dioxane (10 mL) and NH$_3$.H$_2$O (30 mL) was stirred at 100° C. for 18 hrs. The reaction was diluted with EtOAc (100 mL) and organic layer collected, washed with brine, dried and evaporated in vacuo to give the title compound (360 mg, 75%). $^1$HNMR (400 MHz, DMSO-d$_6$): 1.81 (d, 3H), 6.04 (q, 1H), 6.50-6.75 (br s, 2H), 7.30-7.48 (m, 3H), 7.60 (s, 1H), 7.75 (m, 2H), 8.18 (s, 1H), 8.22 (s, 1H). LCMS m/z=449.1 [MH]$^+$ Preparation 57: 7-(1-(2-(2-fluorophenyl)-1H-imidazol-5-yl)ethyl)-5-iodo-7H-pyrrolo[2,3-d]pyrimidin-4-amine

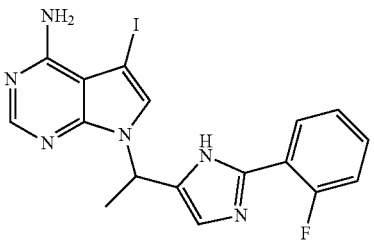 [SMILES: CC(c1cnc(-c2ccccc2F)[nH]1)n1cc(I)c2c(N)ncnc21]

The following reaction was carried out 4 times in parallel. To a stirred solution of 4-chloro-7-(1-(2-(2-fluorophenyl)-1H-imidazol-5-yl)ethyl)-5-iodo-7H-pyrrolo[2,3-d]pyrimidine (Preparation 70, 2 g, 4.277 mmol) in 1,4-dioxane (35 mL) was added aq. NH$_3$ (75 mL) in a sealed tube and resulting suspension was heated to 130° C. for 16 hrs. The reaction was evaporated to dryness in vacuo and the residue dissolved in H$_2$O and extracted with EtOAc. The combined organics were washed with water, brine, dried (Na$_2$SO$_4$) and concentrated under reduced pressure to afford an impure sample of the title compound as a brown solid (2.02 g). The products of all four reactions were combined and purified by flash chromatography to afford the title compound as an off white solid (4.8 g, 62.6%). $^1$HNMR (400 MHz, DMSO-d$_6$): 1.74 9d, 3H), 5.98 (q, 1H), 6.59 (br s, 2H), 7.20-7.43 (m, 5H), 7.94 (t, 1H), 8.13 (s, 1H), 12.19 (s, 1H). LCMS m/z=449 [MH]$^+$ Preparation 58: 7-((2-(2-fluorophenyl)-1H-imidazol-5-yl)methyl)-5-iodo-7H-pyrrolo[2,3-d]pyrimidin-4-amine

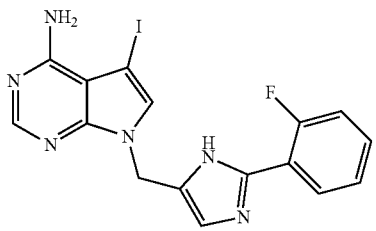 [SMILES: Nc1ncnc2c1c(I)cn2Cc1cnc(-c2ccccc2F)[nH]1]

NH$_4$OH (75.0 mL) was added to a stirred solution of 4-chloro-7-[2-(2-fluoro-phenyl)-3H-imidazol-4-ylmethyl]-5-iodo-7H-pyrrolo[2,3-d]pyrimidine (Preparation 68, 8 g, 17.63 mmol) in dioxane (25.0 mL) and the reaction heated for 16 hr at 120° C. The reaction mixture was evaporated to dryness in vacuo and the residue extracted with EtOAc (3×100 mL). The combined organics were washed with water, then brine, dried (Na$_2$SO$_4$) and evaporated to dryness in vacuo. The residue was purified by column chromatography on silica gel to afford the title compound as an off-white solid (4 g, 52%). $^1$HNMR (400 MHz, DMSO-d$_6$): 2.14 (s, 2H), 6.60 (br s, 2H), 7.15 (s, 1H), 7.26-7.35 (m, 2H), 7.40 (m, 1H), 7.50 (s, 1H), 7.94 (t, 1H), 8.14 (s, 1H). LCMS m/z=435 [MH]$^+$ Preparation 59: 7-(1-(3-(2-fluorophenyl)isoxazol-5-yl)ethyl)-5-iodo-7H-pyrrolo[2,3-d]pyrimidin-4-amine

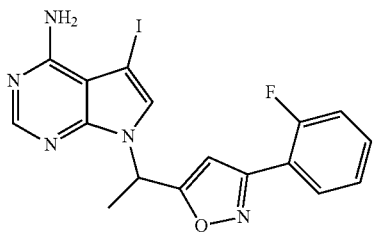 [SMILES: CC(c1cc(-c2ccccc2F)no1)n1cc(I)c2c(N)ncnc21]

To a stirred solution of 7-(but-3-yn-2-yl)-5-iodo-7H-pyrrolo[2,3-d]pyrimidin-4-amine (Preparation 85, 15 g, 48.06 mmol) and 2-fluoro-N-hydroxybenzimidoyl chloride (Preparation 130, 12.51 g, 72.09 mmol) in toluene (600 mL) was added Et$_3$N (11.32 mL, 81.70 mmol) at 0° C. The reaction was stirred at 60° C. for 16 hr. The solids were removed by filtration and the filtrate was evaporated to dryness and the residue purified by column chromatography on silica gel eluting with 50% EtOAc:hexane to afford the title compound as an off white solid (11 g, 51%). $^1$HNMR (400 MHz, DMSO-d$_6$): 1.90 (d, 3H), 6.24 (q, 1H), 6.69 (br s, 2H), 6.89 (s, 1H), 7.33-7.42 (m, 2H), 7.55 (m, 1H), 7.66 (s, 1H), 7.86 (t, 1H), 8.13 (s, 1H). LCMS m/z=450 [MH]$^+$ Preparation 60: N'-(7-((1-(2-fluorophenyl)-1H-1,2,3-triazol-4-yl)methyl)-5-iodo-7H-pyrrolo[2,3-d]pyrimidin-4-yl)-N,N-dimethylformimidamide

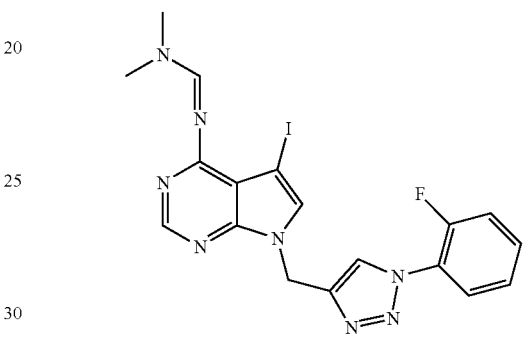

A solution of 7-((1-(2-fluorophenyl)-1H-1,2,3-triazol-4-yl)methyl)-5-iodo-7H-pyrrolo[2,3-d]pyrimidin-4-amine (Preparation 41, 1.0 g, 2.99 mmol) in DMF-DMA (15 mL) was stirred at 80° C. overnight. The reaction mixture was evaporated to dryness in vacuo to afford the title compound (1.1 g, 98%) as a yellow solid. $^1$HNMR (400 MHz, DMSO-d$_6$): 3.20 (s, 3H), 3.25 (s, 3H), 5.58 (s, 2H), 7.43 (m, 1H), 7.54-7.62 (m, 3H), 7.83 (m, 1H), 8.36 (s, 1H), 8.59 (s, 1H), 8.87 (s, 1H). LCMS m/z=491 [MH]$^+$ Preparation 61: (4-Chloro-7-{1-[1-(2-fluorophenyl)-1H-1,2,3-triazol-4-yl]ethyl}-7H-pyrrolo[2,3-d]pyrimidin-5-yl)boronic Acid

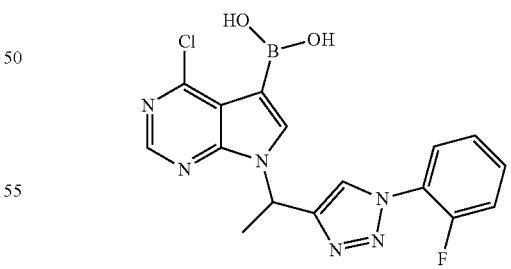

Sodium periodate (2.24 g, 10.5 mmol) was added to 4-chloro-7-{1-[1[(2-fluoro phenyl)-1H-1,2,3-triazol-4-yl]ethyl}-5-(4,4,5,5-tetramethyl-1,3,2-dioxaborolan-2-yl)-7H-pyrrolo[2,3-d]pyrimidine (Preparation 62, 2.46 g, 5.25 mmol) in THF (30 mL) and water (40 mL) and the reaction stirred at rt for 18 hrs. The mixture was acidified to pH 2 using 1N HCl, then poured into water and extracted with DCM (3×). The combined organics were dried (MgSO$_4$)

filtered, and concentrated. The crude product was purified by column chromatography on silica gel eluting with MeOH:EtOAc (0:100 to 5:95) to afford the title compound as an off-white foam (741 mg, 36.6%). ¹HNMR (400 MHz, DMSO-d₆): 1.98 (d, 3H), 4.08 (br s, 1H), 6.38 (m, 1H), 6.73 (d, 1H), 7.43 (m, 1H), 7.54-7.65 (m, 2H), 7.82 (m, 1H), 7.92 (s, 1H), 8.67 (s, 1H). LCMS m/z=386.9 [MH]⁺

Preparation 62: 4-Chloro-7-{1-[1[(2-fluorophenyl)-1H-1,2,3-triazol-4-yl]ethyl}-5-(4,4,5,5-tetramethyl-1,3,2-dioxaborolan-2-yl)-7H-pyrrolo[2,3-d]pyrimidine

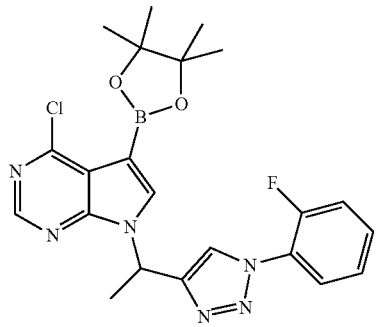 [SMILES: CC(c1cn(-c2ccccc2F)nn1)n1cc(B2OC(C)(C)C(C)(C)O2)c2c(Cl)ncnc21]

4,4,5,5-Tetramethyl-1,3,2-dioxaborolane solution in THF (9.2 mL, 1 M, 9.2 mmol) was added to a suspension of 4-chloro-7-{1-[1-(2-fluorophenyl)-1H-1,2,3-triazol-4-yl]ethyl}-5-iodo-7H-pyrrolo[2,3-d]pyrimidine (Preparation 65, 3.44 g, 7.3 mmol), Et₃N (1.3 mL, 9.2 mmol), Pd₂(dba)₃ (400 mg, 0.37 mmol), and XPhos (361 mg, 0.73 mmol) in dioxane (37 mL) and the reaction stirred at 75° C. for 18 hrs. The cooled reaction was diluted with EtOAc, filtered through Celite® and the filtrate evaporated under reduced pressure. The crude dark orange oil was purified by column chromatography on silica gel eluting with EtOAc:heptane (20:80 to 80:20) to afford the title compound as a yellow foam (2.46 g, 72%). ¹HNMR (400 MHz, CDCl₃): 1.26 (s, 3H), 1.29 (s, 1H), 1.39 (2×s, 6H), 2.10 (d, 3H), 6.43 (m, 1H), 7.26-7.37 (m, 2H), 7.45 (m, 1H), 7.92-8.01 (m, 3H), 8.76 (s, 1H). LCMS m/z=469.1 [MH]⁺

Preparation 63: 4-chloro-7-(1-(1-(2-fluorophenyl)-1H-1,2,3-triazol-4-yl)propyl)-5-(4,4,5,5-tetramethyl-1,3,2-dioxaborolan-2-yl)-7H-pyrrolo[2,3-d]pyrimidine

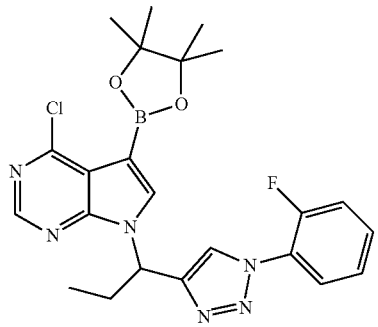 [SMILES: CCC(c1cn(-c2ccccc2F)nn1)n1cc(B2OC(C)(C)C(C)(C)O2)c2c(Cl)ncnc21]

The title compound was obtained (827 mg, 69%) from 4-chloro-7-{1-[1-(2-fluorophenyl)-1H-1,2,3-triazol-4-yl]propyl}-5-iodo-7H-pyrrolo[2,3-d]pyrimidine (Preparation 66) following an analogous procedure to that described in preparation 62. ¹HNMR (400 MHz, DMSO-d₆): 0.86 (t, 3H), 1.32 (s, 12H), 2.48 (m, 2H), 6.15 (m, 1H), 7.45 (m, 1H), 7.52-7.62 (m, 2H), 7.84 (m, 1H), 8.15 (s, 1H), 8.70 (s, 1H), 8.82 (d, 1H). LCMS m/z=483.1 [MH]⁺

Preparation 64: 4-Chloro-7-[1-(2-fluoro-phenyl)-1H-[1,2,3]triazol-4-ylmethyl]-5-(4,4,5,5-tetramethyl-1,3,2-dioxaborolan-2-yl)-7H-pyrrolo[2,3-d]pyrimidine

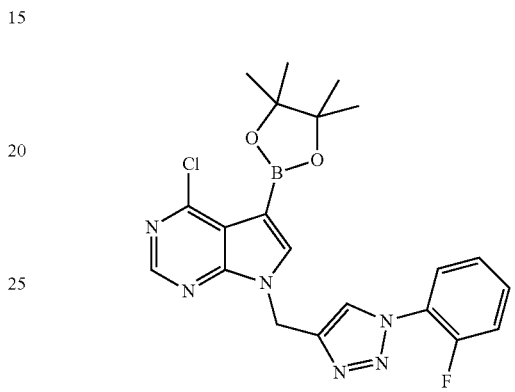

To a stirred solution 4-chloro-7-[1-(2-fluoro-phenyl)-1H-[1,2,3]triazol-4-ylmethyl]-5-iodo-7H-pyrrolo[2,3-d]pyrimidine (Preparation 95, 2.5 g, 5.507 mmol) in degassed dioxane (50 mL) was added X-Phos (449 mg, 0.551 mmol), Pd₂(dba)₃ (226 mg, 0.275 mmol) and 4,4,5,5-tetramethyl-1,3,2-dioxaborolane (22.03 mL, 22.03 mmol, 1M sol in THF) and the mixture stirred at room temperature for 10 min. Et₃N (3.07 mL, 22.026 mmol) was added and stirred at 75° C. for 2 hr. The reaction mixture was filtered through Celite® and evaporated to dryness in vacuo. The residue was purified by flash column chromatography (100% DCM) to afford the title compound as a pale yellow solid (2.2 g, 88%). ¹HNMR (400 MHz, CDCl₃): 1.35 (s, 12H), 5.65 (s, 2H), 7.25-7.32 (m, 2H), 7.42 (m, 1H), 7.87-7.90 (m, 2H), 8.07 (d, 1H), 8.66 (s, 1H). LCMS m/z=455.0 [MH]⁺

Preparation 65: 4-Chloro-7-{1-[1-(2-fluorophenyl)-1H-1,2,3-triazol-4-yl]ethyl}-5-iodo-7H-pyrrolo[2,3-d]pyrimidine

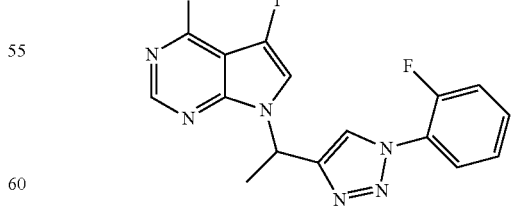

7-(But-3-yn-2-yl)-4-chloro-5-iodo-7H-pyrrolo[2,3-d]pyrimidine (Preparation 91, 3.0 g, 9.0 mmol) was suspended in toluene (40 mL) and tBuOH (10 mL) under N₂, 1-azido-2-fluorobenzene (1.96 g, 13.6 mmol), CuI (0.95 mg, 5.0 mmol), and Hünig's base (16 mL, 90 mmol) added and the reaction stirred at rt for 18 hrs. The reaction was partitioned between EtOAc and water, the mixture filtered through Celite® and the layers separated. The aqueous phase was extracted with EtOAc and the combined organic extracts were dried (MgSO₄), filtered, and concentrated in vacuo. The light brown solid was triturated with Et₂O to remove residual azide. The crude product was purified by column chromatography on silica gel eluting with EtOAc:DCM (0:100 to 10:90) to afford the title compound as a pale yellow solid (3.44 g, 81.7%). $^1$HNMR (400 MHz, DMSO-$d_6$): 1.98 (d, 3H), 6.35 (q, 1H), 7.45 (m, 1H), 7.54-7.61 (m, 2H), 7.84 (m, 1H), 8.18 (s, 1H), 8.70 (m, 2H). LCMS m/z=469.1 [MH]⁺

Preparation 66: 4-Chloro-7-{1-[1-(2-fluorophenyl)-1H-1,2,3-triazol-4-yl]propyl}-5-iodo-7H-pyrrolo[2,3-d]pyrimidine

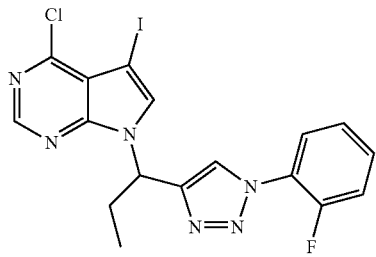 [SMILES: CCC(c1cn(-c2ccccc2F)nn1)n1cc(I)c2c(Cl)ncnc21]

Step 1: 2-Fluorophenyl azide (2.26 g, 16.5 mmol), copper iodide (1.25 g, 6.5 mmol), and Hunig's base (10 eq, 118 mmol, 21 mL) were added to a solution of 1-pentyn-3-ol (1 g, 12 mmol) in toluene (40 mL) and tBuOH (10 mL) under N₂. The suspension was stirred overnight at rt. The reaction was concentrated in vacuo and partitioned between EtOAc and 15% NH₄OH. The aqueous layer was extracted with EtOAc (2×) and the combined organics vigorously shaken with 15% NH₄OH (2×) until the solution was essentially colourless. The organics were dried (MgSO₄) and evaporated to dryness in vacuo. The residue was purified using Biotage 50 g snap cartridge, eluting with 50-80-100% EtOAc/heptane gradient to afford 1-(1-(2-fluorophenyl)-1H-1,2,3-triazol-4-yl)propan-1-ol (2.29 g, 86.3%). $^1$HNMR (400 MHz, CDCl₃): 1.05 (t, 3H), 1.90-2.20 (m, 3H), 4.95 (m, 1H), 7.30-7.50 (m, 2H), 8.00 (m, 2H), 8.10 (s, 1H). LCMS m/z=222.2 [MH]⁺

Step 2: 1-(1-(2-Fluorophenyl)-1H-1,2,3-triazol-4-yl)propan-1-ol (Step 1, 1 g, 4.5 mmol) was dissolved in DCM (24 mL). SOCl₂ (5.0 mL, 67.8 mmol) was added slowly and the reaction stirred at rt for 2.5 hr. The reaction mixture was evaporated to dryness in vacuo and the resulting brown oil azeotroped a few times with toluene to remove the last traces of SOCl₂ to afford 4-(1-chloropropyl)-1-(2-fluorophenyl)-1H-1,2,3-triazole (1.1 g, 100%) which was used without further purification. LCMS m/z=242.1[MH]⁺

Step 3: 4-Chloro-5-iodo-7H-pyrrolo[2,3-d]pyrimidine (Preparation 71, 898 mg, 3.21 mmol) was dissolved in DMF (20 mL), Cs₂CO₃ (2.09 g, 6.43 mmol) added and the reaction stirred for 30 min at rt then cooled in an ice/water bath. 4-(1-chloropropyl)-1-(2-fluorophenyl)-1H-1,2,3-triazole (Step 2, 1.54 g, 6.43 mmol) in DMF (7 mL) was added drop wise, the reaction allowed to warm to rt and then stirred at 50° C. for 24 hrs. The mixture was partitioned between water and EtOAc and the layers separated. The organic layer was evaporated under reduced pressure and the residual oil purified by column chromatography on silica gel eluting with EtOAc: heptane (10:90 to 50:50) to afford the title compound (1.24 g, 44%). $^1$HNMR (400 MHz, CDCl₃): 0.95 (t, 3H), 2.42-2.60 (m, 2H), 6.15 (m, 1H), 7.24-7.39 (m, 2H), 7.45 (m, 1H), 7.82 (s, 1H), 7.94 (m, 1H), 8.10 (s, 1H), 8.64 (s, 1H). LCMS m/z=483.0 [MH]⁺

Preparation 67: 4-chloro-7-((1-(2-fluorophenyl)-1H-pyrazol-4-yl)methyl)-5-iodo-7H-pyrrolo[2,3-d]pyrimidine

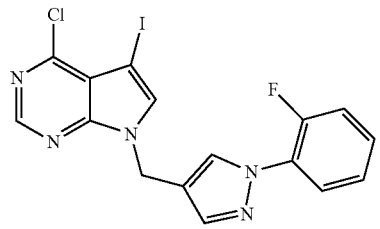 [SMILES: Fc1ccccc1-n1cc(Cn2cc(I)c3c(Cl)ncnc32)cn1]

To a mixture of 4-chloro-5-iodo-7H-pyrrolo[2,3-d]pyrimidine (Preparation 71, 20 g, 71.7 mmol) in DMF (200 mL) was added K₂CO₃ (49.5 g, 358.5 mmol) and the mixture stirred for 10 min at rt before 4-(chloromethyl)-1-(2-fluorophenyl)-1H-pyrazole (Preparation 98, 20 g, 95.2 mmol) was added. The resulting mixture was stirred at 60° C. for 6 hr, filtered and concentrated under reduced pressure to give a crude product which was washed with EtOAc and water to afford the title compound (20 g, 62.5%) as a yellow solid. $^1$HNMR (400 MHz, CDCl₃): 5.41 (s, 2H), 7.20-7.32 (m, 3H), 7.42 (s, 1H), 7.72 (s, 1H), 7.84-7.87 (m, 1H), 8.05 (d, 1H), 8.68 (s, 1H). LCMS m/z=453.9 [MH]⁺

Preparation 68: 4-chloro-7-((2-(2-fluorophenyl)-1H-imidazol-5-yl)methyl)-5-iodo-7H-pyrrolo[2,3-d]pyrimidine

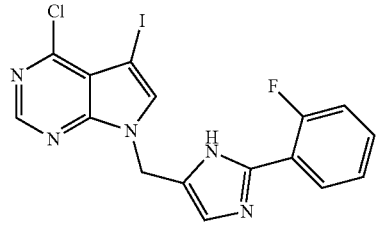 [SMILES: Fc1ccccc1-c1ncc(Cn2cc(I)c3c(Cl)ncnc32)[nH]1]

Cesium carbonate (42.43 g, 130.55 mmol) was added to a stirred solution of 5-chloromethyl-2-(2-fluoro-phenyl)-1H-imidazole (Preparation 108, 11 g, 52.22 mmol) in DMF (100 mL) at 0° C., followed by 4-chloro-5-iodo-7H-pyrrolo[2,3-d] pyrimidine (Preparation 71, 14.6 g, 52.22 mmol) in DMF (50 mL) at the same temperature. The reaction mixture was stirred at rt for 16 hr, diluted with EtOAc. The combined organics were washed with H₂O, brine and dried (Na₂SO₄) and evaporated to dryness in vacuo. The residue was purified by column chromatography on silica gel to afford the title compound as a yellow solid (8 g, 33.77%). $^1$HNMR (400 MHz, MeOD-$d_4$): 5.48 (s, 2H), 7.20-7.26 (m, 3H), 7.41 (m, 1H), 7.79 (s, 1H), 7.92 (t, 1H), 8.60 (s, 1H). LCMS m/z=453.8 [MH]⁺

Preparation 69: 4-chloro-7-(1-(1-(2-fluorophenyl)-1H-pyrazol-4-yl)ethyl)-5-iodo-7H-pyrrolo[2,3-d]pyrimidine

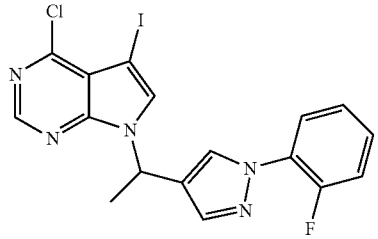 [SMILES: CC(c1cnn(-c2ccccc2F)c1)n1cc(I)c2c(Cl)ncnc21]

To a solution of 4-(1-chloroethyl)-1-(2-fluorophenyl)-1H-pyrazole (WO2013/071232 compound 32, 2.17 g, 9.7 mmol) in DMF (50 mL) was added 4-chloro-5-iodo-7H-pyrrolo[2,3-d]pyrimidine (Preparation 71, 2.46 g, 8.8 mmol) and $Cs_2CO_3$ (14.3 g, 44.0 mmol) and the reaction stirred at 60° C. for 18 hrs. After cooling, water was added and the mixture extracted with EtOAc (60 mL×2). The organic extracts were collected, washed with brine, dried and evaporated to give a residue which was purified by column chromatography on silica gel (pet. ether/EtOAc=1/9) to afford the title compound (0.5 g, 12%). $^1$HNMR (400 MHz, DMSO-$d_6$): 1.89 (d, 3H), 6.20 (q, 1H), 7.30-7.50 (m, 3H), 7.72 (t, 1H), 7.76 (s, 1H), 8.16 (s, 1H), 8.27 (s, 1H), 8.69 (s, 1H). LCMS m/z=468.0 [MH]$^+$ Preparation 70: 4-chloro-7-(1-(2-(2-fluorophenyl)-1H-imidazol-5-yl)ethyl)-5-iodo-7H-pyrrolo[2,3-d]pyrimidine

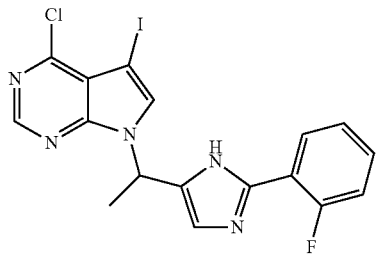 [SMILES: CC(c1cnc(-c2ccccc2F)[nH]1)n1cc(I)c2c(Cl)ncnc21]

To a stirred solution of 4-chloro-5-iodo-7H-pyrrolo[2,3-d]pyrimidine (Preparation 71, 5 g, 17.89 mmol) in THF (150 mL) was added DIAD (3.90 mL, 19.68 mmol) followed by $PPh_3$ (5.25 g, 20.038 mmol) at 0° C. and was stirred at 0° C. for 10 mins. To this mixture was added a solution of 1-(2-(2-fluorophenyl)-1H-imidazol-5-yl)ethan-1-ol (Preparation 135, 3.68 mg, 17.89 mmol) in THF (100 mL) at 0° C. and the reaction mixture was stirred at rt for 16 hr. The reaction was quenched with $H_2O$ and extracted with EtOAc. The combined extracts were washed with water, brine, dried ($Na_2SO_4$) and evaporated to dryness in vacuo. The residue was purified by flash chromatography in 20% EtOAc:Hexane to afford the title compound as an off white solid (4 g, 48%). LCMS m/z=468.8 [MH]$^+$ Preparation 71: 4-Chloro-5-iodo-7H-pyrrolo[2,3-d]pyrimidine

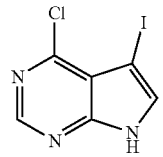 [SMILES: Clc1ncnc2[nH]cc(I)c12]

A mixture of 4-chloro-7H-pyrrolo[2,3-d]pyrimidine (500 g, 3255.84 mmol) and NIS (805.74 g, 3581.43 mmol) in DMF (3.3 L) was stirred at rt for 3 hrs. The mixture was poured into ice water (20 L) and resulting solid was filtered, washed with saturated sodium thiosulphate solution (4×2.5 L), water (4×2.5 L) and dried under vacuum to afford the title compound as an off white solid (780 g, 85.8%). $^1$HNMR (400 MHz, DMSO-$d_6$): 7.94 (s, 1H), 8.59 (s, 1H). LCMS m/z=279.6 [MH]$^+$ Preparation 72: 4-Chloro-5-iodo-7-{[2-(trimethylsilyl)ethoxy]methyl}-7H-pyrrolo[2,3-d]pyrimidine

NaH (60%, 15.74 g, 393.60 mmol) was added portion wise to an ice-cooled solution of 4-chloro-5-iodo-7H-pyrrolo[2,3-d]pyrimidine (Preparation 71, 100 g, 357.82 mmol) in THF (2.5 L) and the resulting suspension stirred at 0° C. for 1 hr. SEM-Cl (69.81 mL, 393.60 mmol) was added drop wise and the reaction stirred at rt for 16 hrs. The reaction was cooled to 0° C. and quenched with brine solution and the mixture extracted with EtOAc. The combined organic extracts were washed with brine, dried ($Na_2SO_4$) and concentrated under reduced pressure. The crude product was purified by column chromatography on silica gel eluting with EtOAc:Hexane (7:93) to afford the title compound as a white solid (85 g, 58.0%). $^1$HNMR (400 MHz, DMSO-$d_6$): 0.10 (s, 9H), 0.82 (t, 2H), 3.51 (t, 2H), 5.60 (s, 2H), 8.13 (s, 1H), 8.69 (s, 1H). LCMS m/z=410.0 [MH]$^+$ Preparation 73: 4-Chloro-5-iodo-6-methyl-7-{[2-(trimethylsilyl)ethoxy]methyl}-7H-pyrrolo[2,3-d]pyrimidine

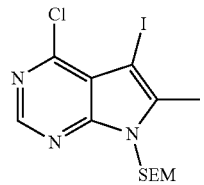 [SMILES: Cc1c(I)c2c(Cl)ncnc2n1COCC[Si](C)(C)C]

To a solution of 4-chloro-5-iodo-7-((2-(trimethylsilyl)ethoxy)methyl)-7H-pyrrolo[2,3-d]pyrimidine (Preparation 72, 43 g, 105.68 mmol) in THF (500 mL) was added LDA (79.26 mL, 158.52 mmol) at −78° C. under N$_2$. The mixture was stirred at −20° C. for 2 hr re-cooled to −78° C. and MeI (8 mL, 126.82 mmol) added. The reaction mixture was stirred at −20° C. for 2 hr. The reaction was quenched with saturated NH$_4$Cl solution and extracted with EtOAc (3×500 mL). The combined organics were washed with water (100 mL), brine (100 mL), dried (Na$_2$SO$_4$) and evaporated to dryness in vacuo. The residue was purified by column chromatography (pet. ether/EtOAc 10:1) to give the title compound as a yellow solid (10 g, 65%). $^1$HNMR (400 MHz, DMSO-d$_6$): 0.11 (s, 9H), 0.83 (t, 2H), 2.54 (s, 3H), 3.47 (t, 2H), 5.70 (s, 2H), 8.62 (s, 1H). LCMS m/z=424, 426 [MH]$^+$ Preparation 74: 5-iodo-7-((1-((2-(trimethylsilyl)ethoxy)methyl)-1H-pyrazol-4-yl)methyl)-7H-pyrrolo[2,3-d]pyrimidin-4-amine

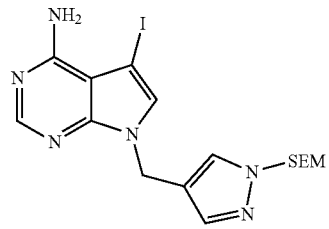 [SMILES: C[Si](C)(C)CCOCn1cc(Cn2cc(I)c3c(N)ncnc32)cn1]

To a stirred solution of 4-chloro-5-iodo-7-((1-((2-(trimethylsilyl)ethoxy)methyl)-1H-pyrazol-4-yl)methyl)-7H-pyrrolo[2,3-d]pyrimidine (Preparation 75, 5 g, 10.2 mmol) in dioxane (30 mL) was added NH$_4$OH (100 mL) and the reaction was stirred at 120° C. in a sealed tube for 16 hr. The cooled reaction was diluted with ice cold water, the resulting solid filtered off, washed with water, then hexane and dried under reduced pressure to afford the title compound (12 g, 83.3% for composite batch) as a white solid. $^1$HNMR (400 MHz, DMSO-d$_6$): 0.10 (s, 9H), 0.76 (m, 2H), 3.46 (t, 2H), 5.17 (s, 2H), 5.34 (s, 2H), 6.58 (br s, 2H), 7.45 (s, 1H), 7.52 (s, 1H), 7.84 (s, 1H), 8.13 (s, 1H).

Preparation 75: 4-chloro-5-iodo-7-((1-((2-(trimethylsilyl)ethoxy)methyl)-1H-pyrazol-4-yl)methyl)-7H-pyrrolo[2,3-d]pyrimidine

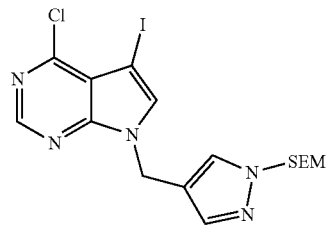 [SMILES: C[Si](C)(C)CCOCn1cc(Cn2cc(I)c3c(Cl)ncnc32)cn1]

NaH (60% in oil, 3.4 g, 85.87 mmol) was added to a stirred solution of 4-chloro-5-iodo-7H-pyrrolo[2,3-d]pyrimidine (Preparation 71, 20 g, 71.56 mmol) in DMF (400 mL), followed by 4-(chloromethyl)-1-((2-(trimethylsilyl)ethoxy)methyl)-1H-pyrazole (26.49 g, 107.34 mmol) and the reaction stirred at rt for 12 hrs. The reaction mixture was diluted with water and EtOAc (250 mL each), the layers separated and the organic layer was washed with water followed by brine solution, dried (Na$_2$SO$_4$) and concentrated in vacuo. The crude product was purified by column chromatography on silica gel to afford the title compound (15.2 g, 43.3%) as a colorless gum. $^1$HNMR (400 MHz, DMSO-d$_6$): 0.11 (s, 9H), 0.73 (m, 2H), 3.43 (t, 2H), 5.32 (m, 4H), 7.57 (s, 1H), 7.89 (s, 1H), 8.03 (s, 1H), 8.67 (s, 1H). LCMS m/z=489.6 [MH]$^+$ Preparation 76: 6-Bromo-5-(4-chlorophenyl)-7-(prop-2-yn-1-yl)-7H-pyrrolo[2,3-d]pyrimidin-4-amine

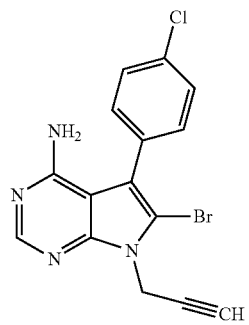 [SMILES: C#CCn1c(Br)c(-c2ccc(Cl)cc2)c2c(N)ncnc21]

Propargyl bromide (73.8 mg, 0.5 mmol) was added to a solution of 6-bromo-5-(4-chlorophenyl)-7H-pyrrolo[2,3-d]pyrimidin-4-amine (Preparation 78, 107 mg, 0.331 mmol) in DMF (6 mL) and the mixture cooled to 0° C. NaOEt (27 mg, 0.4 mmol) was added and the reaction stirred at rt for 18 hrs. The reaction was diluted with aq. NH$_4$Cl and extracted with EtOAc (3×50 mL). The combined organic extracts were washed with 20% LiCl soln., dried (Na$_2$SO$_4$) and concentrated in vacuo. The crude product was purified by column chromatography on silica gel eluting with EtOAc:heptane (0:100 to 100:0) to afford the title compound as a beige solid (67 mg, 55.9%). $^1$HNMR (400 MHz, CDCl$_3$): 2.98 (s, 1H), 5.04 (br s, 2H), 5.15 (s, 2H), 7.45-7.53 (m, 4H), 8.36 (s, 1H). LCMS m/z=363.0 [MH]$^+$ Preparation 77: 7-(But-3-yn-2-yl)-5-(4-chlorophenyl)-7H-pyrrolo[2,3-d]pyrimidine-4-amine

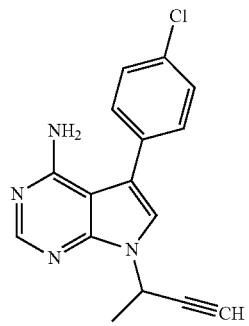 [SMILES: C#CC(C)n1cc(-c2ccc(Cl)cc2)c2c(N)ncnc21]

To a stirred solution of 7-(but-3-yn-2-yl)-5-iodo-7H-pyrrolo[2,3-d]pyrimidine-4-amine (Preparation 86, 5 g, 16.02 mmol) in EtOH: water (125 mL, 9:1) was added 4-chlorophenylboronic acid (3.50 g, 22.43 mmol) followed by Na₂CO₃ (6.79 g, 64.08 mmol) and the resulting reaction mixture was degassed with Ar$_{(g)}$ for 15 mins. Pd(PPh₃)₄ (1.11 g, 0.96 mmol) was added and the reaction was stirred at 90° C. for 5 hrs. The cooled mixture was filtered and the filtrate concentrated in vacuo. The residue was diluted with water, extracted with DCM, the combined organic extracts dried (Na₂SO₄) and concentrated in vacuo. The crude product was purified by column chromatography on silica gel eluting with EtOAc:hexane (50:50) to afford the title compound as an off white solid (2.7 g, 56.84%). ¹HNMR (400 MHz, DMSO-d₆): 1.70 (d, 3H), 3.62 (s, 1H), 5.70 (m, 1H), 6.22 (br s, 2H), 7.48-7.53 (m, 5H), 8.17 (s, 1H). LCMS m/z=297.0 [MH]⁺

Preparation 78: 6-Bromo-5-(4-chlorophenyl)-7H-pyrrolo[2,3-d]pyrimidin-4-amine

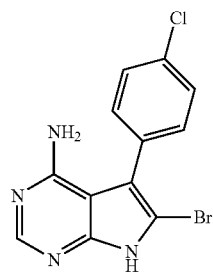 [SMILES: Nc1ncnc2[nH]c(Br)c(-c3ccc(Cl)cc3)c12]

A mixture of 6-bromo-5-(4-chlorophenyl)-7-{[2-(trimethylsilyl)ethoxy]methyl}-7H-pyrrolo[2,3-d]pyrimidin-4-amine (Preparation 82, 150 mg, 0.331 mmol) and TBAF (343 mg, 1.24 mmol) in THF (3.3 mL) was heated at 70° C. for 18 hrs. 1M HCl (2 mL) and water (2 mL) were added and the cooled mixture was then basified by the addition of sat. NaHCO₃. The mixture was extracted with DCM (3×50 mL) and the combined organic extracts dried (Na₂SO₄) and concentrated under reduced pressure to afford the title compound, which was used without further purification. LCMS m/z=324.9 [MH]⁺

Preparation 79: 5-(4-Chlorophenyl)-2-methyl-7H-pyrrolo[2,3-d]pyrimidin-4-amine

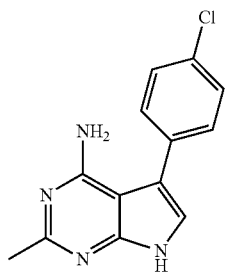 [SMILES: Cc1nc(N)c2c(-c3ccc(Cl)cc3)c[nH]c2n1]

A solution of 5-(4-chlorophenyl)-2-methyl-7-{[2-(trimethylsilyl)ethoxy}methyl]-7H-pyrrolo[2,3-d]pyrimidin-4-amine (Preparation 81, 500 mg, 1.28 mmol) in TFA (3 mL) was stirred at rt for 30 min. The solution was diluted with heptane and concentrated in vacuo to remove TFA. The residue was dissolved in MeCN (12 mL), 35% aqueous NH₄OH (6 mL) added to adjust pH to 10, the mixture diluted with additional MeCN and water and the resulting solid filtered off and dried under vacuum, to afford the title compound as an off white solid, which was used without further purification. LCMS m/z=289.0 [MNa]⁺

Preparation 80: 5-(4-Chlorophenyl)-7H-pyrrolo[2,3-d]pyrimidin-4-amine

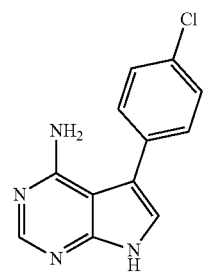 [SMILES: Nc1ncnc2[nH]cc(-c3ccc(Cl)cc3)c12]

TFA (73.52 mL, 960.13 mmol) was added to an ice cooled stirred solution of 5-(4-chlorophenyl)-7-{[2-(trimethylsilyl)ethoxy]methyl}-7H-pyrrolo[2,3-d]pyrimidin-4-amine (Preparation 83, 18 g, 48.0 mmol) in DCM (180 mL) and the resulting suspension stirred at rt for 16 hr. The reaction mixture was concentrated in vacuo, diluted with MeOH (80 mL) and treated with EDA (57.75 mL, 480.06 mmol) and the solution stirred for 16 hrs. The reaction mixture was concentrated and filtered, the resulting solid washed with water and dried under vacuum to afford the title compound as a white solid (10 g, 85.11%). ¹HNMR (400 MHz, DMSO-d₆): 6.06 (br s, 2H), 7.28 (s, 1H), 7.46-7.51 (m, 4H), 8.11 (s, 1H), 11.84 (br s, 1H). LCMS m/z=245.0 [MH]⁺

Preparation 81: 5-(4-Chlorophenyl)-2-methyl-7-{[2-(trimethylsilyl)ethoxy}methyl]-7H-pyrrolo[2,3-d]pyrimidin-4-amine

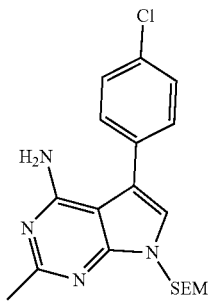 [SMILES: Cc1nc(N)c2c(-c3ccc(Cl)cc3)cn(COCC[Si](C)(C)C)c2n1]

4-Chloro-5-iodo-2-methyl-7-{[2-(trimethylsilyl)ethoxy]methyl}-7H-pyrrolo[2,3-d]pyrimidine (Preparation 84, 1.1 g, 2.60 mmol) was suspended in NH₄OH (3 mL) and dioxane (1 mL) and the reaction heated at 130° C. under microwave irradiation for 60 mins. The cooled mixture was concentrated and the residue suspended in water and stirred for 1 hr. The mixture was filtered and dried to give a brown solid. A mixture of this solid, (680 mg, 1.68 mmol), 4-chlorophenylboronic acid (312 mg, 1.93 mmol) and Na₂CO₃ (713 mg, 6.73 mmol) was suspended in EtOH (9 mL) and water (1 mL) and degassed for 5 mins. Pd(PPh₃)₄ (97.1 mg, 0.084 mmol) was added and the reaction heated to 90° C. for 18 hrs. The cooled reaction was diluted with water, extracted with EtOAc and the organic phase washed with brine and dried (MgSO$_4$), filtered and concentrated in vacuo. The crude product was purified by column chromatography on silica gel eluting with 50-100% EtOAc: heptane to afford the title compound as a solid (500 mg, 49.4%). LCMS m/z=390.1 [MH]$^+$ Preparation 82: 6-Bromo-5-(4-chlorophenyl)-7-{[2-(trimethylsilyl)ethoxy]methyl}-7H-pyrrolo[2,3-d]pyrimidin-4-amine

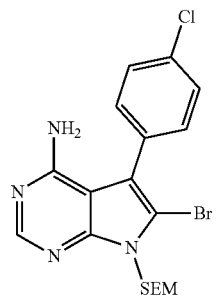 [SMILES: C[Si](C)(C)CCOCn1c(Br)c(-c2ccc(Cl)cc2)c2c(N)ncnc21]

To the stirred solution of 5-(4-chlorophenyl)-7-{[2-(trimethylsilyl)ethoxy]methyl}-7H-pyrrolo[2,3-d]pyrimidin-4-amine (Preparation 83, 500 mg, 1.334 mmol) in DMF (20 mL) was added NBS (284.8 mg, 1.6 mmol) and the reaction stirred at rt for 5 hrs. The reaction was diluted with water, extracted with EtOAc and the combined organic extracts washed with water followed by brine, dried (Na$_2$SO$_4$) and concentrated under reduced pressure to afford the title compound as an off white solid (500 mg, 82.62%). $^1$HNMR (400 MHz, DMSO-d$_6$): 0.08 (s, 9H), 0.85 (t, 2H), 3.58 (t, 2H), 5.60 (s, 2H), 6.09 (br s, 2H), 7.42 (d, 2H), 7.58 (d, 2H), 8.18 (s, 1H). LCMS m/z=454.8 [MH]$^+$ Preparation 83: 5-(4-Chlorophenyl)-7-{[2-(trimethylsilyl)ethoxy]methyl}-7H-pyrrolo[2,3-d]pyrimidin-4-amine

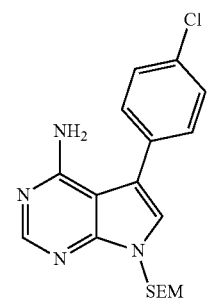 [SMILES: C[Si](C)(C)CCOCn1cc(-c2ccc(Cl)cc2)c2c(N)ncnc21]

To a stirred solution of 5-iodo-7-{[2-(trimethylsilyl)ethoxy]methyl}-7H-pyrrolo[2,3-d]pyrimidin-4-amine (Preparation 33, 25 g, 64.05 mmol) in EtOH:water (620 mL, 9:1) was added 4-chlorophenylboronic acid (14.02 g, 89.68 mmol) followed by Na$_2$CO$_3$ (27.15 g, 256.21 mmol) and the mixture degassed with Ar for 15 mins. Pd(PPh$_3$)$_4$ (4.44 g, 3.84 mmol) was added and the reaction stirred at 90° C. for 5 hrs. The cooled mixture was filtered, the filtrate concentrated and the residue diluted with water and extracted with DCM. The combined organic layers were dried (Na$_2$SO$_4$) and concentrated in vacuo. The crude product was purified by column chromatography on silica gel eluting with EtOAc:hexane (40:60) to afford the title compound as an off white solid (18 g, 74.94%). $^1$HNMR (400 MHz, DMSO-d$_6$) 0.08 (s, 9H), 0.84 (t, 2H), 3.55 (t, 2H), 5.53 (s, 2H), 6.21 (br s, 2H), 7.46-7.53 (m, 5H), 8.18 (s, 1H). LCMS m/z=451.0 [MH]$^+$ Preparation 84: 4-Chloro-5-iodo-2-methyl-7-{[2-(trimethylsilyl)ethoxy]methyl}-7H-pyrrolo[2,3-d]pyrimidine

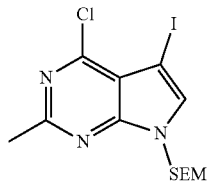 [SMILES: Cc1nc(Cl)c2c(I)cn(COCC[Si](C)(C)C)c2n1]

To a mixture of 4-chloro-5-iodo-2-methyl-7H-pyrrolo[2,3-d]pyrimidine (1.7 g, 5.79 mmol) in DMF (25 mL) was slowly added 60% NaH dispersion (0.290 g, 7.24 mmol) and the mixture stirred for 15 mins under Ar. SEM-Cl (1.28 mL, 7.24 mmol) was added in portions over 5 mins and the reaction stirred at rt for 18 hrs. Sat. aq. sodium bicarbonate (25 mL) was added and the mixture extracted with EtOAc. The organic extracts were dried (MgSO$_4$) and concentrated under reduced pressure to afford the title compound as an oil (1.1 g, 44.9%), which was used without further purification. $^1$HNMR (400 MHz, MeOD-d$_4$): −0.05 (s, 9H), 0.89 (t, 2H), 2.71 (s, 3H), 3.59 (t, 2H), 5.63 (s, 2H), 7.78 (s, 1H). LCMS m/z=423.9 [MH]$^+$ Preparation 85: 5-Iodo-7-(prop-2-yn-1-yl)-7H-pyrrolo[2,3-d]pyrimidin-4-amine

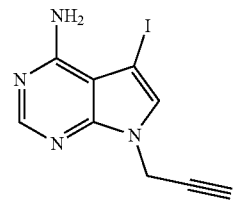

A mixture of 4-chloro-5-iodo-7-(prop-2-yn-1-yl)-7H-pyrrolo[2,3-d]pyrimidine (Preparation 90, 8 g, 0.025 mol) and aqueous NH$_4$OH solution (30%, 100 mL) in 1,4-dioxane (45 mL) was heated to 90° C. for 4 hr followed by a further 16 hr at rt. The reaction mixture was filtered and washed with EtOAc (15 mL) to afford the title compound (6.8 g, 90%). $^1$HNMR (400 MHz, DMSO-d$_6$) 3.57 (s, 1H), 4.95 (s, 2H), 6.66 (br s, 2H), 7.52 (s, 1H), 8.13 (s, 1H). LCMS m/z=299.0 [MH]$^+$

Preparation 86: 7-(But-3-yn-2-yl)-5-iodo-7H-pyrrolo[2,3-d]pyrimidine-4-amine

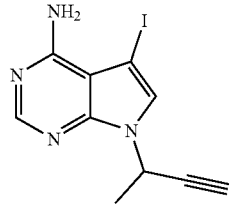

To a stirred solution of 7-(but-3-yn-2-yl)-4-chloro-5-iodo-7H-pyrrolo[2,3-d]pyrimidine (Preparation 91, 28 g, 84.45 mmol) in dioxane (120 mL) was added NH$_4$OH (400 mL) and the reaction stirred at 120° C. in a sealed tube for 16 hr. The cooled mixture was filtered, the solid washed with water followed by 50% EtOAc-Hexane and dried in vacuo to afford the title compound as an off-white solid (20 g, 75.87%). $^1$HNMR (400 MHz, DMSO-d$_6$) 1.63 (d, 3H), 3.51 (d, 1H), 5.61 (m, 1H), 6.67 (br s, 2H), 7.60 (s, 1H), 8.12 (s, 1H). LCMS m/z=312.8 [MH]$^+$

Preparation 87: 5-Iodo-7-(pent-1-yn-3-yl)-7H-pyrrolo[2,3-d]pyrimidin-4-amine

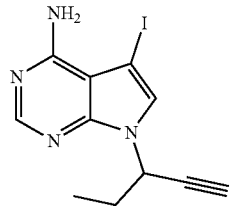 [SMILES: C#CC(CC)n1cc(I)c2c(N)ncnc21]

A mixture of 4-chloro-5-iodo-7-(pent-1-yn-3-yl)-7H-pyrrolo[2,3-d]pyrimidine (Preparation 92, 350.0 g, 1.012 mol) in dioxane (1.75 L) was added NH$_3$—H$_2$O (5.0 L) and the reaction stirred at 80° C. in an autoclave (10 L) for 10 hrs. The cooled reaction mixture was filtered and dissolved in EtOAc (7.0 L). The solution was washed with brine (2×5.0 L), dried (Na$_2$SO$_4$), and concentrated in vacuo. The crude solid was triturated (pet. ether:EtOAc=3.0 L:300.0 mL) for 24 hrs, filtered and dried to afford the title compound as a brown solid (200.0 g, 60.61%). $^1$HNMR (400 MHz, CDCl$_3$): 0.97 (t, 3H), 1.96-2.02 (m, 2H), 2.50 (d, 1H), 5.55 (m, 1H), 5.76 (br s, 2H), 7.33 (s, 1H), 8.26 (s, 1H).

Preparation 88: 5-Iodo-7-(1-cyclopropylprop-2-yn-1-yl)-7H-pyrrolo[2,3-d]pyrimidin-4-amine

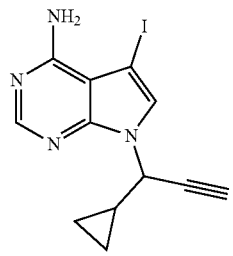 [SMILES: C#CC(C1CC1)n1cc(I)c2c(N)ncnc21]

The title compound was obtained as a light yellow solid (1.8 g 65%) from 4-chloro-7-(1-cyclopropylprop-2-yn-1-yl)-5-iodo-7H-pyrrolo[2,3-d]pyrimidine (Preparation 93), following the procedure described in preparation 85. $^1$HNMR (400 MHz, DMSO-d$_6$) 0.38 (m, 1H), 0.48 (m, 1H), 0.61-0.66 (m, 2H), 1.54 (m, 1H), 3.53 (s, 1H), 5.17 (m, 1H), 7.60 (s, 1H), 8.10 (s, 1H). LCMS m/z=338.8 [MH]$^+$

Preparation 89: 5-Iodo-2-methyl-7-(prop-2-yn-1-yl)-7H-pyrrolo[2,3-d]pyrimidin-4-amine

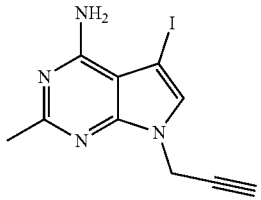

To a solution of 4-chloro-5-iodo-2-methyl-7-prop-2-ynyl-7H-pyrrolo[2,3-d]pyrimidine (Preparation 94, 10 g, 30.21 mmol) in 1,4-dioxane (40 mL) was added ammonium hydroxide solution (75 mL) in a sealed tube and the reaction stirred at 110° C. for 10 hr. The reaction volume was reduced to half of its original volume and cooled. A solid precipitated and was collected by filtration, washed with Et$_2$O and dried to afford the title compound as an off-white solid (4.8 g, 50.9%). $^1$HNMR (400 MHz, DMSO-d$_6$) 2.39 (s, 3H), 3.38 (s, 1H), 4.92 (s, 2H), 6.57 (br s, 2H), 7.39 (s, 1H). LCMS m/z=312.9 [MH]$^+$

Preparation 90: 4-Chloro-5-iodo-7-(prop-2-yn-1-yl)-7H-pyrrolo[2,3-d]pyrimidine

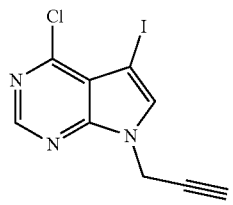

To a stirred solution of 4-chloro-5-iodo-7H-pyrrolo[2,3-d]pyrimidine (155 g, 0.554 mol) in DMF (750 mL) was added NaOEt (21% in EtOH, 215.7 g, 0.665 mol) solution at rt the mixture stirred for 10 min, then cooled to 0° C. Propargyl bromide (80% solution in toluene, 123.7 g, 0.831 mol) was added drop wise and the reaction stirred at rt for 16 hr. The mixture was diluted with cold water (1 L), the resulting suspension filtered and washed with water followed by hexane (2×200 mL) and dried under reduced pressure to afford the title compound as a light yellow solid (162 g, 92.5%). $^1$HNMR (400 MHz, DMSO-d$_6$) 3.49 (s, 1H), 5.14 (s, 2H), 8.05 (s, 1H), 8.69 (s, 1H). LCMS m/z=318.0 [MH]$^+$

Preparation 91: 7-(But-3-yn-2-yl)-4-chloro-5-iodo-7H-pyrrolo[2,3-d]pyrimidine

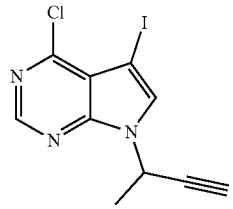

To a stirred solution of 4-chloro-5-iodo-7H-pyrrolo[2,3-d]pyrimidine (80 g, 286.26 mmol) in DMF (1 L) was added K$_2$CO$_3$ (79.12 g, 572.51 mmol) followed by but-3-yn-2-yl methanesulfonate (63.62 g, 429.38 mmol) and the reaction stirred at 80° C. for 16 hrs. The reaction was cooled to 0° C. and diluted with water. The resulting solid was filtered off, washed with ether and dried in vacuo to afford the title compound, as a yellow solid (49 g, 51.63%). $^1$HNMR (400 MHz, CDCl$_3$) 1.70 (d, 3H), 2.54 (d, 1H), 5.78 (m, 1H), 7.69 (s, 1H), 8.61 (s, 1H). LCMS m/z=331.6 [MH]$^+$

Preparation 92: 4-Chloro-5-iodo-7-(pent-1-yn-3-yl)-7H-pyrrolo[2,3-d]pyrimidine

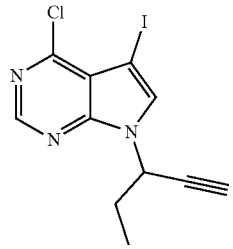 [SMILES: C#CC(CC)n1cc(I)c2c(Cl)ncnc21]

K$_2$CO$_3$ (296.72 g, 2146.92 mmol) and pent-1-yn-3-yl methansulfonate (Preparation 138, 313.4 g, 1932.22 mmol) were added to a solution of 4-chloro-5-iodo-7H-pyrrolo[2,3-d]pyrimidine (Preparation 71, 300 g, 1073.46 mmol) in DMF (2500 mL) cooled to 5° C., and the reaction mixture stirred at 80° C. for 5 hrs. Water (4 L) was added to the cooled mixture and stirred at rt for 2 hrs. The resulting solid material was filtered off, washed with water (3 L), 10% EtOAc:hexane, diethyl ether (500 mL) and dried to afford the title compound as an off white solid (190 g, 57.2%). $^1$HNMR (400 MHz, CDCl$_3$) 0.97 (t, 3H), 1.96-2.09 (m, 2H), 2.55 (s, 1H), 5.61 (m, 1H), 7.66 (s, 1H), 8.60 (s, 1H). LCMS m/z=345.9 [MH]$^+$

Preparation 93: 4-Chloro-7-(1-cyclopropylprop-2-yn-1-yl)-5-iodo-7H-pyrrolo[2,3-d]pyrimidine

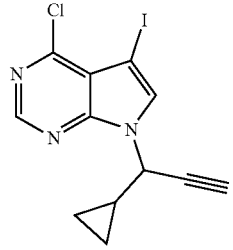 [SMILES: C#CC(C1CC1)n1cc(I)c2c(Cl)ncnc21]

To a stirred solution of 4-chloro-5-iodo-7H-pyrrolo[2,3-d]pyrimidine (9.0 g, 34.61 mmol) in DMF (75 mL) at 0-5° C. was added Cs$_2$CO$_3$ (33.75 g, 103.8 mmol) followed by (1-chloroprop-2-yn-1-yl)cyclopropane (9.91 g, 86.53 mmol and the reaction stirred at rt for 16 hrs. The reaction mixture was diluted with water and extracted with EtOAc, the combined organic phases washed with water, dried (Na$_2$SO$_4$) and concentrated under reduced pressure. The crude product was purified by column chromatography on silica gel to afford the title compound as an off white solid (6.5 g, 38%). $^1$HNMR (400 MHz, DMSO-d$_6$) 0.38 (m, 1H), 0.53 (m, 1H), 0.65-0.76 (m, 2H), 1.62-1.69 (m, 1H), 3.62 (s, 1H), 5.31 (m, 1H), 8.18 (s, 1H), 8.67 (s, 1H). LCMS m/z=357.8 [MH]$^+$

Preparation 94: 4-chloro-5-iodo-2-methyl-7-(prop-2-yn-1-yl)-7H-pyrrolo[2,3-d]pyrimidine

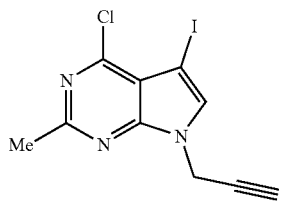

To a solution of 4-chloro-5-iodo-2-methyl-7H-pyrrolo[2,3-d]pyrimidine (10 g, 34.13 mmol) in DMF (55 mL) was added sodium ethoxide solution (19.177 mL, 51.195 mmol. 2.67M in ethanol) followed by, propargyl bromide (4.56 mL, 51.19 mmol) at 0° C. and the resulting mixture stirred at room temperature for 16 hr. The reaction mixture was diluted with EtOAc, washed with water, brine, dried (Na$_2$SO$_4$) and evaporated to dryness in vacuo. The residue was purified by column chromatography (2% EtOAc in hexane) to afford the title compound as an off-white solid (4 g, 35.34%). $^1$HNMR (400 MHz, CDCl$_3$) 2.73 9s, 3H), 5.00 (s, 2H), 7.50 (s, 1H). LCMS m/z=332 [MH]$^+$

Preparation 95: 4-chloro-7-((1-(2-fluorophenyl)-1H-1,2,3-triazol-4-yl)methyl)-5-iodo-7H-pyrrolo[2,3-d]pyrimidine

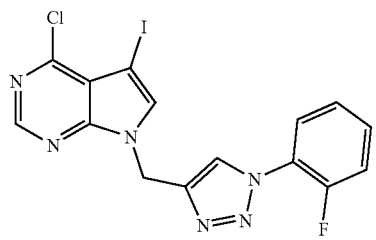 [SMILES: Fc1ccccc1-n1cc(Cn2cc(I)c3c(Cl)ncnc32)nn1]

To a stirred solution of 4-chloro-5-iodo-7-(prop-2-yn-1-yl)-7H-pyrrolo[2,3-d]pyrimidine (Preparation 90, 48 g, 151.17 mmol) in toluene: t-BuOH (1000 mL, 4:1) was added CuI (15.83 g, 83.14 mmol) and DIPEA (263.3 mL, 1511.72 mmol) and the reaction mixture stirred for 10 min at rt. 1-Azido-2-fluorobenzene (Preparation 145, 31.09 g, 226.76 mmol) was added at 0° C. and the resulting mixture stirred at rt for 48 hrs. The reaction mixture was diluted with water and aqueous ammonia and extracted with EtOAc. The combined extracts were washed with water, brine, dried (Na$_2$SO$_4$) and evaporated to dryness in vacuo. The residue was triturated with 20% EtOAc-Hexane to afford the title compound as an off white solid (38 g, 55.3%). $^1$HNMR (400 MHz, DMSO-d$_6$) 5.68 (s, 2H), 7.42 (t, 1H), 7.57 (m, 2H), 7.80 (t, 1H), 8.11 (s, 1H), 8.63 (s, 1H), 8.69 (s, 1H). LCMS m/z=455 [MH]$^+$ Preparation 96: 2-Amino-4-(4-chlorophenyl)-1-{2-[1-(2-fluorophenyl)-1H-1,2,3-triazol-4-yl]propan-2-yl}-1H-pyrrole-3-carbonitrile

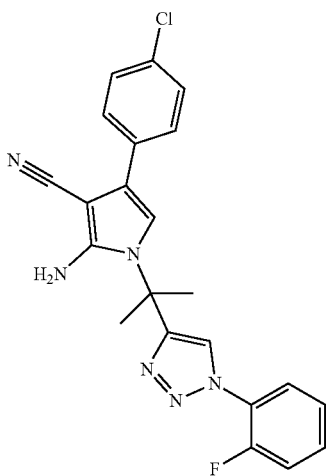 [SMILES: CC(C)(c1cn(-c2ccccc2F)nn1)n1cc(-c2ccc(Cl)cc2)c(C#N)c1N]

1-Azido-2-fluorobenzene (Preparation 145, 38 mg, 0.26 mmol), CuI (19 mg, 0.10 mmol) and Hünig's base (0.31 mL, 1.8 mmol) were added to 2-amino-4-(4-chlorophenyl)-1-[2-methylbut-3-yn-2-yl]-1H-pyrrole-3-carbonitrile (Preparation 97, 50 mg, 0.18 mmol) in toluene (2.5 mL) and tBuOH (0.6 mL) under N$_2$ and the reaction stirred at rt for 4 hrs. The mixture was poured into water, extracted twice with EtOAc, the combined organic extracts dried (MgSO$_4$), filtered, and evaporated under reduced pressure. The crude product was purified by column chromatography on silica gel eluting with EtOAc:heptane (20:80 to 80:20) to afford the title compound as a dark green oil (78.4 mg, 71.7%). LCMS m/z=421.4 [MH]$^+$ Preparation 97: 2-Amino-4-(4-chlorophenyl)-1-[2-methylbut-3-yn-2-yl]-1H-pyrrole-3-carbonitrile

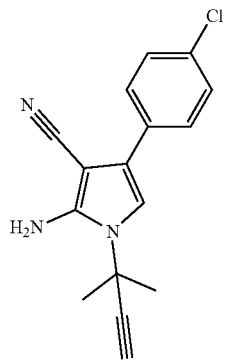 [SMILES: C#CC(C)(C)n1cc(-c2ccc(Cl)cc2)c(C#N)c1N]

Malononitrile (187 mg, 2.8 mmol) was added to 4-chloro-N-(2-methylbut-3-yn-2-yl)benzamide (587 mg, 2.1 mmol) in MeOH (10 mL) and the solution degassed under N$_2$ while cooling in an ice/water bath. KOH (336 mg, 5.93 mmol) in water (1.5 mL) was added drop wise and the reaction then stirred at 65° C. for 1 hr. The cooled mixture was poured into water, extracted with EtOAc (3×), the combined organic extracts dried (MgSO$_4$), filtered and concentrated in vacuo. The resulting brown oil was purified by column chromatography on silica gel eluting with EtOAc:heptane (20:80 to 80:20) to afford the title compound as a dark yellow oil (288 mg, 48.4%). $^1$HNMR (400 MHz, CDCl$_3$) 1.85 (s, 6H), 2.68 (s, 1H), 4.72 (s, 2H), 6.46 (s, 1H), 7.32 (d, 2H), 7.52 (d, 2H). LCMS m/z=284.3 [MH]$^+$ Preparation 98: 4-(chloromethyl)-1-(2-fluorophenyl)-1H-pyrazole

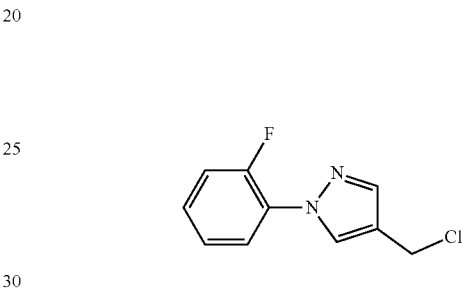

To a solution of (1-(2-fluorophenyl)-1H-pyrazol-4-yl)methanol (Preparation 99, 20 g, 130.2 mmol) in DCM (200 mL) was added SOCl$_2$ (45.3 mL, 625 mmol) drop wise at 0° C. After the addition was complete, the reaction was stirred at rt for 4 hr. The mixture was concentrated in vacuo to afford the title product (20 g, 99%) as a dark brown oil which was used directly in the next step without further purification. $^1$HNMR (400 MHz, CDCl$_3$) 4.62 (s, 2H), 7.22-7.36 (m, 3H), 7.83 (s, 1H), 7.88-7.92 (m, 1H), 8.05 (d, 1H).

Preparation 99: (1-(2-fluorophenyl)-1H-pyrazol-4-yl)methanol

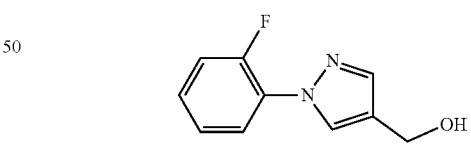

To a mixture of 1-(2-fluorophenyl)-1H-pyrazole-4-carbaldehyde (20.0 g, 131.6 mmol) and MeOH (200 mL) was added NaBH$_4$ (12 g, 315.6 mmol) in several portions at 0° C. After the addition was completed, the mixture was stirred at rt for 2 hrs. The reaction was carefully quenched with water (100 mL) at 0° C. The mixture was extracted with EtOAc (200 mL×3), dried (Na$_2$SO$_4$), and concentrated in vacuo to give the title compound (20 g, 99%) as a brown solid. $^1$HNMR (400 MHz, CDCl$_3$) 2.02 (br s, 1H), 4.68 (s, 2H), 7.20-7.31 (m, 3H), 7.75 (s, 1H), 7.87 (m, 1H), 8.00 (d, 1H). LCMS m/z=193.1 [MH]$^+$

Preparation 100: 4-(1-chloropropyl)-1-(2-fluorophenyl)-1H-pyrazole

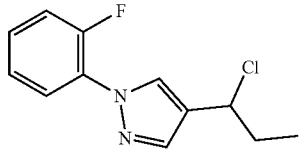 [SMILES: CCC(Cl)c1cnn(-c2ccccc2F)c1]

SOCl$_2$ (2 mL) was added slowly to a solution of 1-(1-(2-fluorophenyl)-1H-pyrazol-4-yl)propan-1-ol (Preparation 101, 0.5 g, 2.42 mmol) in DCM (20 mL) and stirred at rt for 3 hrs. The reaction was evaporated to dryness in vacuo to afford the title compound (0.58 g, 100%). $^1$HNMR (400 MHz, CDCl$_3$) 1.09 (t, 3H), 2.15 (m, 2H), 4.95 (t, 1H), 7.20-7.30 (m, 3H), 7.74 (s, 1H), 7.87 (m, 1H), 8.00 (s, 1H). LCMS m/z=235.1 [MH]$^+$

Preparation 101: 1-[1-(2-Fluorophenyl)-1H-pyrazol-4-yl]propan-1-ol

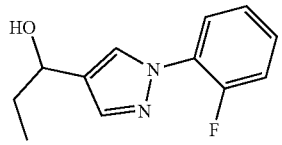 [SMILES: CCC(O)c1cnn(-c2ccccc2F)c1]

To a solution of 1-(2-fluorophenyl)-1H-pyrazole-4-carbaldehyde (3 g, 15.8 mmol) in THF (50 mL) was added EtMgBr (31.6 mL, 31.6 mmol) drop wise at 0° C. and the reaction stirred at rt for 2 hrs. Water was added to quench the reaction and the mixture extracted with EtOAc. The organic layer was collected, washed with brine, dried and evaporated. The crude product was purified by column chromatography on silica gel eluting with DCM:MeOH (95:5) to afford the title compound (3 g, 86%). $^1$HNMR (400 MHz, CDCl$_3$) 1.00 (t, 3H), 1.88 (m, 2H), 4.71 (m, 1H), 7.19-7.27 (m, 3H), 7.71 (s, 1H), 7.87 (m, 1H), 7.95 (s, 1H). LCMS m/z=221.2 [MH]$^+$

Preparation 102: (1-(2,4-difluorophenyl)-1H-pyrazol-4-yl)methanol

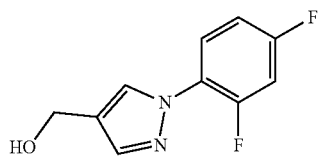 [SMILES: OCc1cnn(-c2ccc(F)cc2F)c1]

To a solution of 1-(2,4-difluorophenyl)-1H-pyrazole-4-carbaldehyde (0.7 g, 3.365 mmol) in MeOH (20 mL) was added NaBH$_4$ (0.32 g, 8.43 mmol) drop wise at 0° C. Cooling was removed and the reaction mixture stirred for 30 min at rt. The mixture was quenched with water, extracted with EtOAc (150 mL×2). The combined extracts were washed with brine (2×100 mL), dried (Na$_2$SO$_4$) and evaporated in vacuo to give the title compound (0.70 g, 99%) as an oil. $^1$HNMR (400 MHz, DMSO-d$_6$) 4.45 (d, 2H), 5.02 (t, 1H), 7.24 (t, 1H), 7.53 (t, 1H), 7.72 (s, 1H), 7.80 (m, 1H), 8.04 (s, 1H). LCMS m/z=211.1 [MH]$^+$

Preparation 103: 1-(1-(2,4-difluorophenyl)-1H-pyrazol-4-yl)propan-1-ol

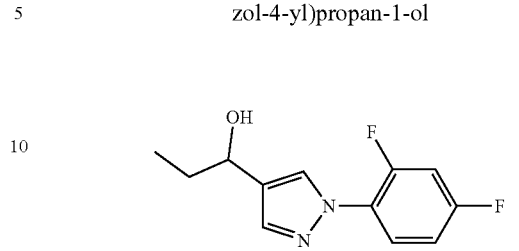

To a solution of 1-(1-(2,4-difluorophenyl)-1H-pyrazol-4-yl)propan-1-one (1.5 g, 6.35 mmol) in MeOH (60 mL) was added NaBH$_4$ (360 mg, 9.52 mmol) at 0° C. and the reaction mixture was stirred at rt for 2 hr. The reaction was quenched with 1N HCl (2 mL), the solvent evaporated under reduced pressure and the residue partitioned between EtOAc (20 mL) and water (30 mL). The aqueous phase was extracted with EtOAc (20 mL×2) and the combined extracts dried (Na$_2$SO$_4$) and evaporated to dryness in vacuo. The residue was purified by silica gel chromatography eluting with MeOH in DCM from 0 to 15% in 20 mins to give the title compound (1.0 g, 66%) as a red oil. $^1$HNMR (400 MHz, DMSO-d$_6$) 0.88 (t, 3H), 1.67 (q, 2H), 4.50 (q, 1H), 5.04 (d, 1H), 7.24 (m, 1H), 7.53 (m, 1H), 7.58 (s, 1H), 7.80 (m, 1H), 7.99 (s, 1H). LCMS m/z=239.2 [MH]$^+$

Preparation 104: 1-(1-(2,4-difluorophenyl)-1H-pyrazol-4-yl)propan-1-one

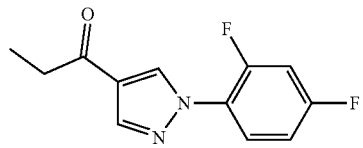 [SMILES: CCC(=O)c1cnn(-c2ccc(F)cc2F)c1]

Step 1: A degassed mixture of (E)-2-(ethoxymethylene)-3-oxopentanenitrile (Australian. J. Chem. 44(9) 1263-73; 1991; 6 g, 39.17 mmol), Et$_3$N (11.89 g, 117.5 mmol) and (2,4-difluorophenyl)hydrazine hydrochloride (10.61 g, 58.75 mmol) in EtOH (200 mL) was heated at reflux for 2 hrs under an atmosphere of N$_2$. The reaction was cooled to rt and the solvent was removed under reduced pressure to give a residue. The crude product was purified by column chromatography on silica gel eluting with pet. ether:EtOAc (10:1 to 1:1) to afford the 1-(5-amino-1-(2,4-difluorophenyl)-1H-pyrazol-4-yl)propan-1-one as a yellow oil (5 g, 50.8%). LCMS m/z=252.1 [MH]$^+$ Step 2: To a mixture of 1-(5-amino-1-(2,4-difluorophenyl)-1H-pyrazol-4-yl)propan-1-one (5 g, 19.9 mmol) in THF (150 mL) was added drop wise tert-butyl nitrite (4.1 g, 39.8 mmol) at rt and the reaction stirred at 65° C. for 4 hours. The solvent was evaporated under reduced pressure and the residue was purified by column chromatography on silica gel eluting with pet. ether:EtOAc (10:1 to 1:1) to afford the title compound as a yellow oil (2 g, 42.54%). $^1$HNMR (400 MHz, MeOD-d$_4$) 1.19 (t, 3H), 2.92 (q, 2H), 7.18 (m, 1H), 7.27 (m, 1H), 7.84 (m, 1H), 8.20 (s, 1H), 8.65 (s, 1H). LCMS m/z=237.1 [MH]$^+$

Preparation 105: 5-(chloromethyl)-2-(2-fluorophenyl)-1H-imidazole

(2-(2-Fluorophenyl)-1H-imidazol-5-yl)methanol (Preparation 110, 100 mg, 0.52 mmol) was heated with SOCl$_2$ (0.075 mL, 1.041 mmol) at 80° C. for 3 hrs. The reaction mixture was evaporated to dryness in vacuo and the residue dissolved in CHCl$_3$ and evaporated to dryness to afford the title compound as a brown solid (80 mg, 73%). $^1$HNMR (400 MHz, DMSO-d$_6$) 4.90 (s, 2H), 7.42-7.57 (m, 2H), 7.68 (m, 1H), 7.80 (s, 1H), 8.02 (m, 1H). LCMS m/z=175 [M-Cl]$^+$

Preparation 106: 5-(chloromethyl)-2-phenyl-1H-imidazole

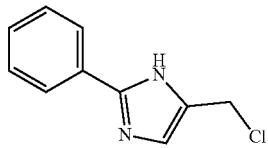 [SMILES: ClCc1cnc(-c2ccccc2)[nH]1]

The title compound was prepared as an off-white solid (312 mg, 93%), in an analogous way to Preparation 105 from (2-phenyl-1H-imidazol-5-yl)methanol (Preparation 107). $^1$HNMR (400 MHz, DMSO-d$_6$) 4.93 (s, 2H), 7.64-7.66 (m, 3H), 7.86 (s, 1H), 8.18-8.21 (m, 2H).

Preparation 107: (2-phenyl-1H-imidazol-5-yl)methanol

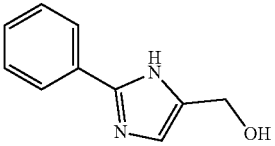 [SMILES: OCc1cnc(-c2ccccc2)[nH]1]

The title compound was prepared an off white solid (3.6 g, 43%) in an analogous way to Preparation 110 from benzamidine hydrochloride. The compound was used without purification in Preparation 106. $^1$HNMR (400 MHz, DMSO-d$_6$) 4.43 (s, 2H), 4.87-5.06 (m, 1H), 6.91-7.04 (m, 1H), 7.32 (m, 1H), 7.40 (m, 2H), 7.91 (m, 2H), 12.31-12.44 (m, 1H).

LCMS m/z=175.0 [MH]$^+$

Preparation 108: 4-(chloromethyl)-1-(2-fluorophenyl)-1H-imidazole

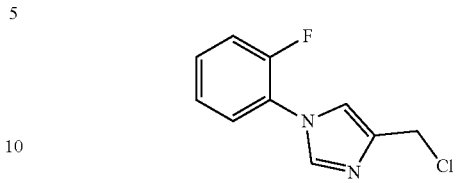

To a stirred solution of (1-(2-fluorophenyl)-1H-imidazol-4-yl)methanol (Preparation 109, 80 mg, 0.416 mmols) in DCM (1 mL) was added SOCl$_2$ (0.06 mL, 0.833 mmol) at 0° C. The resulting solution was heated to reflux for 16 hrs. The reaction mixture was concentrated under reduced pressure to afford the title compound (80 mg, 91.24%) as an off white solid. $^1$HNMR (400 MHz, DMSO-d$_6$) 4.83 (s, 2H), 7.40-7.78 (m, 5H), 7.93 (s, 1H).

Preparation 109: (1-(2-fluorophenyl)-1H-imidazol-4-yl)methanol

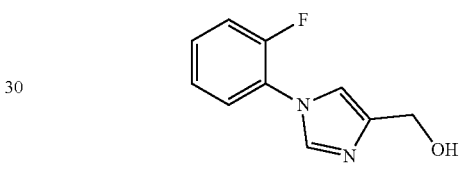

Borane-THF complex (1M solution) was added drop wise to a stirred solution of 1-(2-fluorophenyl)-1H-imidazole-4-carboxylic acid (300 mg, 1.46 mmol) in THF (2 mL) at rt and heated to reflux for 2 hrs followed by stirring at rt for 16 hrs. The reaction mixture was cooled to 0° C. and MeOH (1.5 mL) was added drop wise and the mixture was evaporated to dryness. The residue was dissolved in 1.5 mL 2N HCl solution and refluxed for 2 hr, cooled to 0° C. and treated drop wise with 2 mL 2N NaOH solution. The solid was removed by filtration and dried to afford the title compound as an off white solid (250 mg, 89%). $^1$HNMR (400 MHz, DMSO-d$_6$) 4.21 (d, 2H), 4.99 (t, 1H), 7.32-7.52 (m, 4H), 7.63 (t, 1H), 7.96 (s, 1H).

LCMS m/z=193 [MH]$^+$

Preparation 110: (2-(2-fluorophenyl)-1H-imidazol-5-yl)methanol

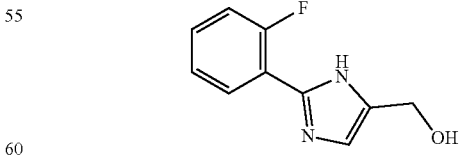

A suspension of 2-fluoro-benzamidine hydrochloride (3 g, 17.18 mmol), 1,3-dihydroxy-propan-2-one (3.17 g, 35.22 mmol), and NH$_4$Cl (4.2 g) in NH$_4$Cl (30 mL) was heated at 80° C. for 1 hr. The reaction mixture was extracted with EtOAc (50 mL×3), washed with brine, dried (Na$_2$SO$_4$) and evaporated in vacuo to give a solid that was purified by column chromatography on silica gel eluting with 2% methanol in DCM to afford the title compound as an off-white solid (2.2 g, 66.6%). ¹HNMR (400 MHz, DMSO-d₆, 100° C.) 4.50 (s, 2H), 7.01 (s, 1H), 7.25 (m, 2H), 7.38 (m, 1H), 7.99 (m, 1H). LCMS m/z=175 [M-Cl]⁺

Preparation 111: 4-(1-chloropropyl)-1-(2,4-difluorophenyl)-5-methyl-1H-1,2,3-triazole

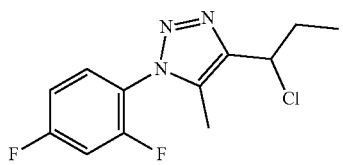 [SMILES: CCC(Cl)c1nnn(-c2ccc(F)cc2F)c1C]

To a solution of 1-(1-(2,4-difluorophenyl)-5-methyl-1H-1,2,3-triazol-4-yl)propan-1-ol (Preparation 112, 2.8 g, 11.1 mmol) in DCM (80 mL) was added SOCl₂ (2.64 g, 22.2 mmol) at 0° C. and the reaction mixture stirred at 40° C. for 5 hr. The reaction mixture was evaporated to dryness to give the title compound as a yellow solid (2.4 g, 80%). ¹HNMR (400 MHz, CDCl₃) 1.11 (t, 3H), 2.30 (s, 3H), 2.38 (m, 2H), 5.07 (t, 1H), 7.08 (m, 2H), 7.53 (m, 1H). LCMS m/z=272.1 [MH]⁺

Preparation 112: 1-(1-(2,4-difluorophenyl)-5-methyl-1H-1,2,3-triazol-4-yl)propan-1-ol

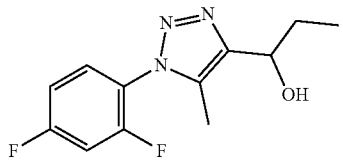 [SMILES: CCC(O)c1nnn(-c2ccc(F)cc2F)c1C]

To a solution of 1-(1-(2,4-difluorophenyl)-5-methyl-1H-1,2,3-triazol-4-yl)propan-1-one (Preparation 113, 1.24 g, 4.94 mmol) in MeOH (25 mL) was added NaBH₄ (374 mg, 9.88 mmol) at 0° C. and the reaction mixture stirred at rt for 3 hr. The mixture was quenched with 1N HCl and concentrated in vacuo. The residue was diluted with EtOAc (50 mL), washed with brine (30 mL), dried (Na₂SO₄) and evaporated to dryness in vacuo. The residue was purified by combi-flash eluting with EtOAc in pet. ether (10-70%) to afford the title compound as a white solid (1.1 g, 88%). ¹HNMR (400 MHz, MeOD-d₄) 1.01 (t, 3H), 2.02 (m, 2H), 2.31 (s, 3H), 4.81 (t, 1H), 7.29 (m, 1H), 7.40 (m, 1H), 7.65 (m, 1H). LCMS m/z=254.1 [MH]⁺

Preparation 113: 1-(1-(2,4-difluorophenyl)-5-methyl-1H-1,2,3-triazol-4-yl)propan-1-one

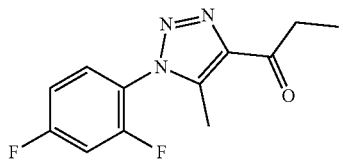 [SMILES: CCC(=O)c1nnn(-c2ccc(F)cc2F)c1C]

Step 1: To a stirred solution of 1-(2,4-difluorophenyl)-5-methyl-1H-1,2,3-triazole-4-carboxylic acid (7 g, 29.3 mmol) in DCM (150 mL) was added HATU (22.3 g, 58.6 mmol) and DIPEA (11.34 g, 87.9 mmol) simultaneously at 0-5° C. under N₂ and the solution stirred for 15 min. N,O-Dimethylhydroxylamine (3.7 g, 38 mmol) was added and the reaction stirred at rt for 16 hr. The reaction mixture was diluted with water (150 mL) and extracted with DCM (150 mL×2). The combined organic layers were washed with brine (100 mL), dried (Na₂SO₄) and concentrated under reduced pressure. The residue was purified by column chromatography on silica gel chromatography eluting with EtOAc in pet. ether (20-70%) to afford 1-(2,4-difluorophenyl)-N-methoxy-N,5-dimethyl-1H-1,2,3-triazole-4-carboxamide (7.6 g) as a light solid.

Step 2: To a solution of 1-(2,4-difluorophenyl)-N-methoxy-N,5-dimethyl-1H-1,2,3-triazole-4-carboxamide (Step 1, 2 g, 7.09 mmol) in THF (25 mL) was added EtMgBr (1.42 mL, 14.2 mmol, 1M) at 0° C. under N₂ and stirred at rt for 3 hr. The reaction was quenched with NH₄Cl solution (20 mL) and extracted with EtOAc (100 mL×2). The combined organics were washed with brine (50 mL), dried (Na₂SO₄) and evaporated to dryness in vacuo. The residue was purified by column chromatography on silica gel eluting with EtOAc in pet. ether (10-70%) to give the title compound as a white solid (1.24 g, 69%). ¹HNMR (400 MHz, CDCl₃) 1.19 (t, 3H), 2.44 (s, 3H), 3.16 (q, 2H), 7.06 (m, 2H), 7.42 (m, 1H). LCMS m/z=252.2 [MH]⁺

Preparation 114: 4-(1-chloroethyl)-1-(2-fluorophenyl)-5-methyl-1H-1,2,3-triazole

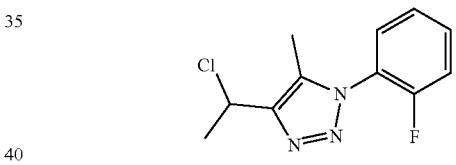

To a solution of 1-(1-(2-fluorophenyl)-5-methyl-1H-1,2,3-triazol-4-yl)ethanol (Preparation 115, 650 mg, 2.94 mmol) in DCM (10 mL) was added SOCl₂ (699 mg, 5.88 mmol) at 0° C. Then the reaction mixture was stirred at rt for 3 hr. and evaporated to dryness to afford the title compound as a yellow solid (600 mg, 85%). LCMS m/z=240.1 [MH]⁺

Preparation 115: 1-(1-(2-fluorophenyl)-5-methyl-1H-1,2,3-triazol-4-yl)ethan-1-ol

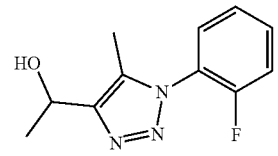 [SMILES: Cc1c(C(C)O)nnn1-c1ccccc1F]

Step 1: To a solution of 1-(2-fluorophenyl)-N-methoxy-N,5-dimethyl-1H-1,2,3-triazole-4-carboxamide (Preparation 116, 900 mg, 3.4 mmol) in THF (30 mL) was added CH₃MgBr (2.3 mL, 6.8 mmol) at 0° C. and the reaction stirred at rt for 2 hrs. The reaction mixture was quenched with ammonium chloride solution (20 mL) and extracted with EtOAc (30 mL×2). The combined organics were washed with brine (50 mL), dried (Na$_2$SO$_4$) and evaporated to dryness in vacuo to afford 1-(1-(2-fluorophenyl)-5-methyl-1H-1,2,3-triazol-4-yl)ethan-1-one (700 mg, 94%) which was used in Step 2 without further purification. LCMS m/z=220.1 [MH]$^+$ Step 2: To a solution of 1-(1-(2-fluorophenyl)-5-methyl-1H-1,2,3-triazol-4-yl)ethanone (700 mg, 3.2 mmol) in MeOH (20 mL) was added NaBH$_4$ (182 mg, 4.8 mmol) at 0° C. and the reaction mixture stirred at rt for 2 hr. The reaction mixture was quenched with 1N HCl and the solvent removed in vacuo. The residue was extracted with EtOAc (20 mL), washed with brine (10 mL), dried (Na$_2$SO$_4$) and evaporated to dryness in vacuo. The residue was purified by combi-flash eluting with 10-50% EtOAc in pet. ether to afford the title compound as an off-white solid (650 mg, 91%). LCMS m/z=222.1 [MH]$^+$ Preparation 116: 1-(2-fluorophenyl)-N-methoxy-N,5-dimethyl-1H-1,2,3-triazole-4-carboxamide

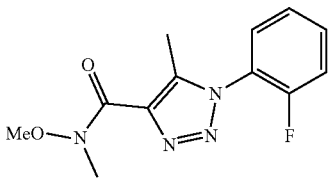 [SMILES: CON(C)C(=O)c1nnn(-c2ccccc2F)c1C]

To a solution of 1-(2-fluorophenyl)-5-methyl-1H-1,2,3-triazole-4-carboxylic acid (Preparation 117, 5 g, 22.6 mmol) in DCM (80 mL) was added HATU (12.88 g, 33.9 mmol) and DIPEA (12 mL, 67.8 mmol) simultaneously at 0-5° C. under N$_2$ and stirred for 20 min. N,O-dimethylhydroxylamine (3.3 g, 33.9 mmol) was added and the reaction stirred at rt for 14 hr. The reaction mixture was diluted with water (50 mL) and extracted with DCM (100 mL×2). The combined organic extracts were washed by brine (100 mL), dried (Na$_2$SO$_4$) and concentrated under reduced pressure. The residue was purified by silica gel chromatography eluting with EtOAc in pet. ether (20-60%) to afford the title compound as a white solid (4.8 g, 80%). LCMS m/z=265.1 [MH]$^+$ Preparation 117: 1-(2-fluorophenyl)-5-methyl-1H-1,2,3-triazole-4-carboxylic acid

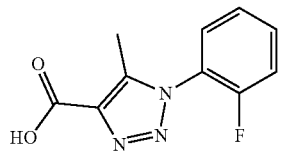 [SMILES: Cc1c(C(=O)O)nnn1-c1ccccc1F]

LiOH (1.68 g, 70.2 mmol) was added to a solution of methyl 1-(2-fluorophenyl)-5-methyl-1H-1,2,3-triazole-4-carboxylate (Preparation 118, 5.5 g, 23.4 mmol) in MeOH/H$_2$O (30 mL/10 mL) and the reaction stirred at rt for 3 hr. The solvent was removed in vacuo and the residue treated with 1N HCl. The resulting solid was collected by filtration, washed with water (20 mL) and dried to give the title compound as a white solid (5 g, 96%). $^1$HNMR (400 MHz, DMSO-d$_6$) 2.41 (s, 3H), 7.50 (m, 1H), 7.61 (m, 1H), 7.71-7.76 (m, 2H), 13.25 (br s, 1H). LCMS m/z=222.1 [MH]$^+$ Preparation 118: methyl 1-(2-fluorophenyl)-5-methyl-1H-1,2,3-triazole-4-carboxylate

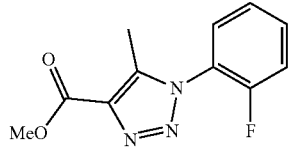 [SMILES: COC(=O)c1nnn(-c2ccccc2F)c1C]

1-Azido-2-fluorobenzene (Preparation 145, 7.13 g, 52 mmol) and methyl 3-oxobutanoate (6 g, 52 mmol) were added to a suspension of milled K$_2$CO$_3$ (14.35 g, 104 mmol) in DMSO (100 mL) and the reaction stirred at rt for 14 hr. The reaction mixture was poured into water (50 mL) and the solid collected, washed with water (50 mL) and diethyl ether (20 mL) to give the title compound as an off-white solid (5.5 g, 44.7%). $^1$HNMR (400 MHz, DMSO-d$_6$) 2.42 (s, 3H), 3.89 (s, 3H), 7.50 (m, 1H), 7.61 (m, 1H), 7.71-7.77 (m, 2H). LCMS m/z=236.1 [MH]$^+$ Preparation 119: 4-(1-chloropropyl)-1-phenyl-1H-1,2,3-triazole

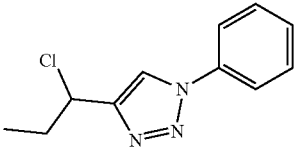

SOCl$_2$ (0.23 mL, 3.171 mmol) was added to solution of 1-(1-phenyl-1H-1,2,3-triazol-4-yl)propan-1-ol (Preparation 120, 200 mg, 1.057 mmol) in DCM (10 mL) at 0° C. and the reaction mixture heated under reflux for 3 hr. The reaction mixture was evaporated to dryness to afford the title compound (200 mg, 85.4%) which was used without further purification. $^1$HNMR (400 MHz, DMSO-d$_6$) 1.03 (t, 3H), 2.15-2.30 (m, 2H), 5.31 (t, 1H), 7.50 (t, 1H), 7.61 (t, 2H), 7.91 (d, 2H).

Preparation 120: 1-(1-phenyl-1H-1,2,3-triazol-4-yl)propan-1-ol

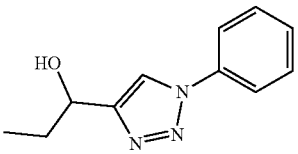

To a stirred solution of 1-pentyn-3-ol (1 g, 11.89 mmol) in toluene: t-BuOH (4:1, 28 mL) was added CuI (1.24 g, 6.538 mmol) and DIPEA (20.7 mL, 118.88 mmol). The reaction mixture was stirred for 10 min at room temperature followed by phenylazide (Preparation 143, 2.61 g, 21.40 mmol) at 0° C. and the resulting reaction mixture stirred at room temperature for 18 hrs. The reaction mixture was diluted with aq NH$_4$OH and extracted with EtOAc. The combined organics were washed with water, brine, dried (Na$_2$SO$_4$) and evaporated to dryness under reduced pressure. The residue was purified by flash chromatography to afford the title compound as an off-white solid (1.3 g, 53.7%). $^1$HNMR (400 MHz, DMSO-d$_6$) 0.91 (t, 3H), 1.73-1.89 (m, 2H), 4.67 (m, 1H), 5.34 (d, 1H), 7.47 (t, 1H), 7.58 (t, 2H), 7.91 (d, 2H), 8.63 (s, 1H). LCMS m/z=204.4 [MH]$^+$ Preparation 121: 3-(chloromethyl)-5-(2-fluorophenyl)-4-((2-(trimethylsilyl)ethoxy) methyl)-4H-1,2,4-triazole

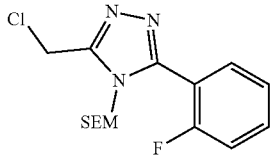 [SMILES: C[Si](C)(C)CCOCn1c(CCl)nnc1-c1ccccc1F]

To a stirred solution of 3-(chloromethyl)-5-(2-fluorophenyl)-4H-1,2,4-triazole (Preparation 123, 400 mg, 1.896 mmol) in DCM (40 mL) was added SEM-Cl (1.009 mL, 5.687 mmol) drop wise at 0° C. The reaction was stirred for 10 min and Et$_3$N (1.056 mL, 7.583 mmol) added drop wise at 0° C. and stirred at rt for 8 hr. The reaction was quenched with ice-cold water and basified with aq.NaHCO$_3$ solution. The two layers were separated and the aqueous layer extracted with DCM (40 mL). The combined organics were dried (Na$_2$SO$_4$) and evaporated under reduced pressure. The residue was purified by flash chromatography using 10-15% EtOAc in hexane to afford the title compound as a colorless oily liquid (180 mg, 27.77%, mixture of two isomers). LCMS m/z=342 [MH]$^+$ Preparation 122: 3-(chloromethyl)-5-phenyl-4-((2-(trimethylsilyl)ethoxy)methyl)-4H-1,2,4-triazole

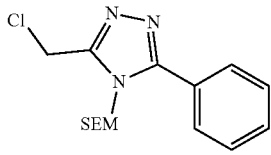 [SMILES: C[Si](C)(C)CCOCn1c(CCl)nnc1-c1ccccc1]

The title compound was prepared in an analogous method to Preparation 121 using 3-(chloromethyl)-5-phenyl-4H-1,2,4-triazole (300 mg, 1.554 mmol) to afford the title compound (160 mg, 31.78%, mixture of two isomers). LCMS m/z=324 [MH]$^+$ Preparation 123: 3-(chloromethyl)-5-(2-fluorophenyl)-4H-1,2,4-triazole hydrochloride

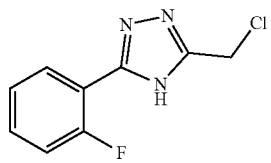 [SMILES: Fc1ccccc1-c1nnc(CCl)[nH]1]

Step 1: A solution of ethyl (Z)-2-amino-2-(2-(2-fluorobenzoyl)hydrazono) acetate (Preparation 143, 6.2 g, 24.484 mmol) in n-butanol (50 mL) was stirred at 180° C. for 24 hr. The reaction was evaporated to dryness in vacuo and the residue purified by flash chromatography (silica gel, 10-20% EtOAc in Hexane) to afford mixture of ethyl 5-(2-fluorophenyl)-4H-1,2,4-triazole-3-carboxylate and butyl 5-(2-fluorophenyl)-4H-1,2,4-triazole-3-carboxylate as an off-white solid (2.5 g, 43%) which was used in Step 2. LCMS m/z=236.0, 264.0 [MH]$^+$ Step 2: To a stirred suspension of LAH (1.297 g, 34.185 mmol) in dry THF (140 mL) was added drop wise a solution of the compound of Step 1 (6 g, 22.79 mmol) in dry THF (20 mL) at 0° C. The reaction mixture was stirred at 0° C. for 1 hr and at rt for 1 hr. The reaction mixture was cooled to 0° C. and quenched by Fischer workup (1.3 mL H$_2$O+1.3 mL 15% NaOH+2.6 mL H$_2$O), and the solids filtered through a Celite® bed. The combined filtrates were concentrated under reduced pressure and the residue purified by column chromatography on silica gel using 3-5% MeOH in DCM to afford (5-(2-fluorophenyl)-4H-1,2,4-triazol-3-yl)methanol as a yellow solid (1.07 g, 24%). $^1$HNMR (400 MHz, DMSO-d$_6$, 100° C.) 4.64 (s, 2H), 5.20 (br s, 1H), 7.29 (br s, 2H), 7.45 (br s, 1H), 7.97 (t, 1H), 13.70 (br s, 1H). LCMS m/z=194 [MH]$^+$ Step 3: (5-(2-Fluorophenyl)-4H-1,2,4-triazol-3-yl)methanol (Step 2, 350 mg, 1.81 mmol) was dissolved in SOCl$_2$ (48 mmol, 3 mL) and heated to 80° C. for 1.5 hrs. The cooled reaction mixture was evaporated to dryness in vacuo and the residue azeotroped several times with toluene to afford the title compound as a light yellow solid (450 mg, 100%). $^1$HNMR (400 MHz, DMSO-d$_6$) 4.82 (s, 2H), 7.33-7.43 (m, 2H), 7.54 (m, 1H), 7.99 (m, 1H). LCMS m/z=212.2 [MH]$^+$ Preparation 124: 5-(1-chloroethyl)-3-(2-methoxyphenyl)isoxazole

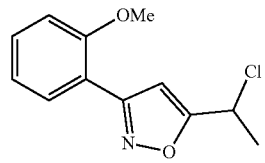 [SMILES: COc1ccccc1-c1cc(C(C)Cl)on1]

SOCl$_2$ (0.11 mL, 1.60 mmol) was added to a stirred solution of 1-(3-(2-methoxyphenyl)isoxazol-5-yl)ethan-1-ol (Preparation 125, 100 mg, 0.46 mmol) in DCM (3 mL) and heated under reflux for 4 hrs. The reaction mixture was evaporated to dryness in vacuo under N$_2$ to afford the title compound (107 mg) which was used without further purification. $^1$HNMR (400 MHz, MeOD-d$_4$) 1.87 (d, 3H), 3.88 (s, 3H), 5.59 (m, 1H), 6.96-7.75 (m, 5H). LCMS m/z=237.6 [MH]$^+$ Preparation 125: 1-(3-(2-methoxyphenyl)isoxazol-5-yl)ethan-1-ol

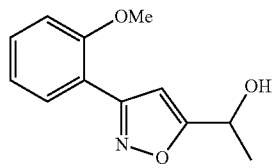 [SMILES: COc1ccccc1-c1cc(C(C)O)on1]

Step 1: NH$_2$OH.HCl (612 mg, 8.814 mmol) was added to a stirred solution of 2-methoxybenzaldehyde (1 g, 7.35 mmol) and KOH (989 mg, 17.63 mmol) in water (5 mL) and the reaction heated to 70° C. for 2 hr. The reaction mixture was acidified to pH 3 with 2N HCl at 0 C, and extracted with EtOAc (50 mL×3). The combined organics were washed with water (20 mL×2), brine, dried (Na$_2$SO$_4$) and evaporated to dryness in vacuo to afford 2-methoxybenzaldehyde oxime as an off white solid (1.1 g) which was used in Part 2 without further purification. $^1$HNMR (400 MHz, DMSO-d$_6$) 2.50 (s, 3H), 3.82 (s, 3H), 6.95 (t, 1H), 7.06 (d, 1H), 7.37 (t, 1H), 7.65 (d, 1H), 8.28 (s, 1H), 11.20 (s, 1H).

Step 2: To a stirred solution of 2-methoxybenzaldehyde oxime (Step 1, 500 mg, 3.311 mmols) in DMF (5 mL) was added NCS (530 mg, 3.974 mmol) and stirred at rt for 2 hrs. The reaction was diluted with water and extracted with MTBE (2×). The combined extracts were washed with water, brine, dried (Na$_2$SO$_4$) and evaporated to dryness in vacuo to afford (Z)—N-hydroxy-2-methoxybenzimidoyl chloride (400 mg, 65.08%) as an off white solid which was used without further purification.

Step 3: Et$_3$N (0.51 mL, 3.696 mmol) was added to a stirred solution of (Z)—N-hydroxy-2-methoxybenzimidoyl chloride (300 mg, 21.17 mmol) in toluene (7 mL) and methylpropargyl alcohol (167 mg, 2.39 mmol) in toluene (3 mL) at 0° C. The reaction mixture was heated to 80° C. for 3 hrs. The reaction was filtered and filtrate concentrated under reduced pressure and the residue purified by combi flash using 10-20% EtOAc in hexane to afford the title compound as a light brown liquid (325 mg, 68.19%). $^1$HNMR (400 MHz, DMSO-d$_6$) 1.44 (d, 3H), 3.87 (d, 3H), 4.89 (m, 1H), 5.75 (m, 1H), 6.67-6.74 (m, 1H), 7.01-7.25 (m, 2H), 7.45-7.54 (m, 1H), 7.71-7.75 (m, 1H).

Preparation 126:
5-(1-chloroethyl)-3-(3-methoxyphenyl)isoxazole

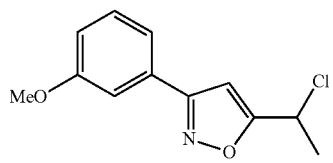 [SMILES: COc1cccc(-c2cc(C(C)Cl)on2)c1]

The title compound was prepared in an analogous way to Preparation 124, from 1-(3-(3-methoxyphenyl)isoxazol-5-yl)ethan-1-ol (Preparation 127). $^1$HNMR (400 MHz, DMSO-d$_6$) 1.88 (d, 3H), 3.81 (s, 3H), 5.57 (m, 1H), 7.08 (m, 1H), 7.25 (s, 1H), 7.38-7.48 (m, 3H).

Preparation 127: 1-(3-(3-methoxyphenyl)isoxazol-5-yl)ethan-1-ol

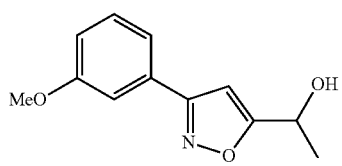 [SMILES: COc1cccc(-c2cc(C(C)O)on2)c1]

The title compound was prepared as a pale yellow solid in 44% yield (210 mg), in an analogous way to Preparation 124 starting with 3-methoxybenzaldehyde. $^1$HNMR (400 MHz, DMSO-d$_6$) 1.45 (d, 3H), 3.81 (s, 3H), 4.88 (m, 1H), 5.78 (d, 1H), 7.06 (m, 1H), 7.38-7.47 (m, 3H). LCMS m/z=220.4 [MH]$^+$ Preparation 128:
5-(1-chloroethyl)-3-(2-fluorophenyl)isoxazole

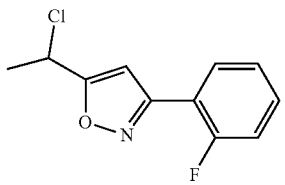

SOCl$_2$ (1.225 mL, 16.891 mmol) was added to a stirred solution of 1-(3-(2-fluorophenyl)isoxazol-5-yl)ethan-1-ol (Preparation 129, 1.0 g, 4.826 mmol) in DCM at 0-5° C. The reaction was heated under reflux for 5 hr, evaporated to dryness in vacuo and the residue diluted with EtOAc, washed with water, brine, dried (Na$_2$SO$_4$), and evaporated to dryness in vacuo. The residue was purified by column chromatography on silica gel eluting with 13% EtOAc/Hexane to afford the title compound as a brown liquid (600 mg, 55%). $^1$HNMR (400 MHz, DMSO-d$_6$) 1.89 (d, 3H), 5.61 (q, 1H), 7.04 (s, 1H), 7.32-7.46 (m, 2H), 7.58 (m, 1H), 7.90 (m, 1H). LCMS m/z=225 [M]$^+$ Preparation 129: 1-(3-(2-fluorophenyl)isoxazol-5-yl)ethan-1-ol

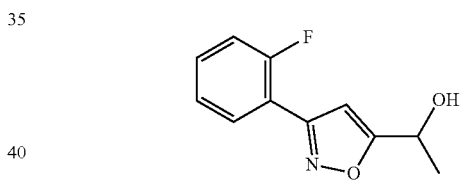

Et$_3$N (38.202 mL, 274.225 mmol) was added to a stirred solution of 2-fluoro-N-hydroxybenzimidoyl chloride (Preparation 130, 28 g, 161.3 mmol) and but-3-yn-2-ol (13.53 mL, 177.4 mmol) in toluene at 0-5° C. The reaction was stirred at 60° C. for 4 hr whereby it was cooled and the solids removed by filtration. The filtrate was concentrated under reduced pressure. The resulting residue was purified by column chromatography using 15% EtOAc/Hexane to afford the title compound as a brown liquid (15 g. 45%). $^1$HNMR (400 MHz, DMSO-d$_6$) 1.46 (d, 3H), 4.92 (m, 1H), 5.83 (d, 1H), 6.73 (d, 1H), 7.32-7.42 (m, 2H), 7.58 (m, 1H), 7.89 (m, 1H). LCMS m/z=208.2 [MH]$^+$ Preparation 130: 2-fluoro-N-hydroxybenzimidoyl Chloride

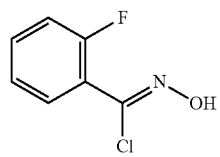 [SMILES: O/N=C(\Cl)c1ccccc1F]

NCS (26.39 g, 197.66 mmol) was added portion wise to a stirred solution of (E)-2-fluorobenzaldehyde oxime (Preparation 131, 25.0 g, 179.69 mmol) in DMF (50 mL) at 10-20° C. The reaction mixture was stirred at rt for 4 hrs, diluted with water and extracted with Et$_2$O. The combined organic extracts were washed with water, then brine, dried (Na$_2$SO$_4$) and evaporated to dryness in vacuo to afford the title compound (28 g, 90%) as a white gummy liquid. $^1$HNMR (400 MHz, DMSO-d$_6$) 7.32 (m, 2H), 7.54 (m, 1H), 7.64 (m, 1H), 12.61 (s, 1H).

Preparation 131: (E)-2-fluorobenzaldehyde Oxime

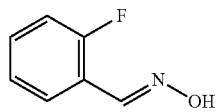

To a suspension of 2-fluorobenzaldehyde (48 g, 386.75 mmol) and hydroxylamine hydrochloride (29.56 g, 425.42 mmol) in EtOH was added water below 10° C. An aqueous solution of NaOH was added drop wise at 10° C. and the reaction stirred at rt for 12 hr. The reaction was acidified to pH 4 with HCl (5N) and extracted with DCM. The combined organics were washed with brine, dried (Na$_2$SO$_4$) and concentrated under reduced pressure. The residue was purified by column chromatography on silica gel using 4% EtOAc/Hexane to afford the title compound as a white solid (32 g, 59.47%). $^1$HNMR (400 MHz, DMSO-d$_6$) 7.21-7.28 (m, 2H), 7.44 (m, 1H), 7.74 (m, 1H), 8.23 (s, 1H). LCMS m/z=139 [M]+

Preparation 132: 5-(1-chloroethyl)-3-(o-tolyl)isoxazole

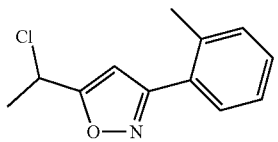

To a stirred solution of 1-[3-(o-tolyl)isoxazol-5-yl]ethan-1-ol (Preparation 133, 100 mg, 0.49 mmol) in DCM (5 mL) was added SOCl$_2$ (0.1 mL, 1.476 mmol) and the reaction mixture was heated at reflux for 6 hr. The cooled reaction mixture was concentrated under reduced pressure and co-evaporated with DCM to afford the title compound (104 mg, crude) as a brown oil. $^1$HNMR (400 MHz, DMSO-d$_6$) 1.88 (d, 3H), 2.43 (s, 3H), 5.59 (q, 1H), 7.02 (s, 1H), 7.30-7.43 (m, 3H), 7.55 (d, 1H). LCMS m/z=222.0 [MH]$^+$ Preparation 133: 1-[3-(o-tolyl)isoxazol-5-yl]ethan-1-ol

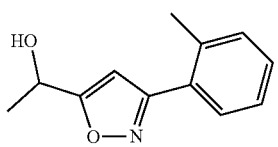

To a stirred solution of N-hydroxy-2-methylbenzenecarboximidoyl chloride (400 mg, 2.358 mmol) in toluene (10 mL) was added but-3-yn-2-ol (181 mg, 2.594 mmol) followed by Et$_3$N (0.55 mL, 4.01 mmol) and the reaction stirred at 80° C. for 3 hrs. The cooled reaction mixture was filtered and the filtrate concentrated under reduced pressure to afford a brown liquid. This was purified by column chromatography on silica gel to afford the title compound (250 mg, 52.16%) as a light yellow liquid. $^1$HNMR (400 MHz, DMSO-d$_6$) 2.43 (s, 3H), 2.50 (s, 3H), 4.90 (m, 1H), 5.77 (d, 1H), 6.67 (s, 1H), 7.29-7.40 (m, 3H), 7.51 (d, 1H). LCMS m/z=204.2 [MH]$^+$ Preparation 134: 5-(1-chloroethyl)-3-(3-fluorophenyl)isoxazole

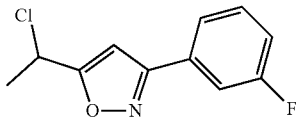

To a stirred solution of 1-[3-(3-fluorophenyl)isoxazol-5-yl]ethanol (100 mg, 0.483 mmols) in DCM (5 mL) was added SOCl$_2$ (0.12 mL, 1.69 mmol) and the reaction stirred at reflux for 5 hr. The cooled reaction mixture was concentrated under reduced pressure; the resulting crude was triturated with hexane, filtered and dried under reduced pressure to afford the title compound (108 mg, quantitative) as a light yellow solid. $^1$HNMR (400 MHz, CDCl$_3$) 1.93 (d, 3H), 5.15 (m, 1H), 6.57 (s, 1H), 7.13 (m, 1H), 7.40-7.57 (m, 3H).

Preparation 135: 1-(2-(2-fluorophenyl)-1H-imidazol-5-yl)ethan-1-ol

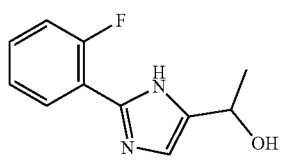

CH$_3$MgBr (90.2 mL, 126.32 mmol, 1.4 M) was added slowly to a stirred solution of 2-(2-fluorophenyl)-1H-imidazole-5-carbaldehyde (Preparation 136, 8 g, 42.105 mmol) in dry THF (250 mL) at 0° C. The resulting mixture was stirred for 30 mins at 0° C. followed by 3 hr at rt. The reaction mixture was cooled to 0° C. and quenched with saturated ammonium chloride solution and extracted with EtOAc. The combined organics were washed with water, brine, dried (Na$_2$SO$_4$) and concentrated under reduced pressure to afford the title compound as a pale yellow solid (6.3 g, 72.6%). LCMS m/z=207.2 [MH]$^+$

Preparation 136: 2-(2-fluorophenyl)-1H-imidazole-5-carbaldehyde

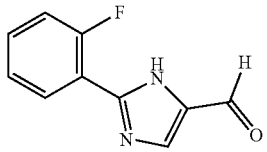 [SMILES: O=Cc1cnc(-c2ccccc2F)[nH]1]

MnO₂ (45.28 g, 520.83 mmol) was added to a stirred solution of (2-(2-fluorophenyl)-1H-imidazol-5-yl)methanol (Preparation 110, 10 g, 52.08 mmol) in DCM (320 mL) at 0° C. and the reaction mixture stirred at rt for 8 hrs. The reaction mixture was filtered through Celite® and the bed washed with DCM. The combined filtrate was evaporated to dryness in vacuo and the residue purified by trituration with hexane to afford the title compound as an off white solid (7.8 g, 79%). $^1$HNMR (400 MHz, DMSO-d₆) 7.36 (m, 2H), 7.52 (m, 1H), 8.00 (m, 1H), 8.13 (s, 1H), 9.80 (s, 1H), 13.2 (br s, 1H). LCMS m/z=191 [MH]⁺

Preparation 137: 1-(2-(2,4-difluorophenyl)-1H-imidazol-4-yl)propan-1-ol

Step 1: To a 0° C. solution of LiHMDS (360 mL, 359.5 mmol) in THF (200 mL) was added drop wise, 2,4-difluorobenzonitrile (20 g, 143.8 mmol) in THF (100 mL). The reaction was warmed to rt and stirred for 4 hrs and c.HCl (100 mL) was added drop wise to keep the temperature below 30° C. EtOAc was added and the aqueous layer was collected. The pH was adjusted to 10 by the careful addition of 6N NaOH and the organic layer collected, dried and evaporated to dryness to give 2,4-difluoro benzimidamide (10 g, 44%) which was used without further purification in Step 2.

Step 2: To a solution of 2,4-difluorobenzimidamide (10 g, 64.0 mmol) in NH₃.H₂O (250 mL) was added 1,3-dihydroxypropan-2-one (11.5 g, 128.0 mmol) and NH₄Cl (13.7 g). The reaction was stirred at 80° C. for 2 hrs, cooled, diluted with water extracted with EtOAc, dried and evaporated to dryness. The residue was purified by column chromatography on silica gel (DCM/MeOH=9/1) to give (2-(2,4-difluorophenyl)-1H-imidazol-4-yl)methanol (2 g, 15%) which was used without further purification in Step 3.

Step 3: To a solution of (2-(2,4-difluorophenyl)-1H-imidazol-4-yl)methanol (Step 2, 2 g, 8.09 mmol) in DCM (100 mL) was added MnO₂ (22.6 g, 66.6 mmol). The reaction was stirred at rt for 4 hrs and the mixture filtered. The filtrate was collected and evaporated in vacuo to give 2-(2,4-difluorophenyl)-1H-imidazole-4-carbaldehyde (1.5 g, 75%) which was used without further purification in Step 4.

Step 4: To a solution of 2-(2,4-difluorophenyl)-1H-imidazole-4-carbaldehyde (Step 3, 1.5 g, 7.2 mmol) in THF (50 mL) was added EtMgBr (21.6 mL, 21.6 mmol) dropwise at 0° C. After addition was complete the reaction was warmed to rt and stirred for 2 hrs. The reaction was quenched (c. NH₄Cl solution) and extracted with EtOAc. The combined extracts were washed (brine), dried and evaporated to give the title compound (1 g, 58%).

LCMS m/z=239.2 [MH]⁺

Preparation 138: Pent-1-yn-3-yl methansulfonate

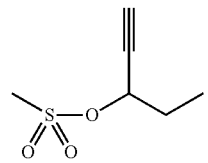

Et₃N (745.6 mL, 5349.48 mmol) and DMAP (43.56 g, 356.61 mmol) were added to an ice-cooled solution of pent-1-yn-3-ol (300 g, 3566.33 mmol) in DCM (2400 ml) and the solution stirred for 15 mins. Methane sulfonyl chloride (333.48 ml, 4279.59 mmol) was added and the reaction stirred at rt for 3 hrs. The reaction mixture was quenched with water (1200 mL) at 0° C. and organic layer was separated, washed with water (1200 mL), dried (Na₂SO₄) and concentrated in vacuo to afford the title compound as a brown liquid (580 gm, quant.). $^1$HNMR (400 MHz, DMSO-d₆) 0.98 (t, 3H), 1.82 (m, 2H), 3.23 (s, 3H), 3.86 (d, 1H), 5.21 (m, 1H).

Preparation 139: 2-(Difluoromethyl)-5-(4,4,5,5-tetramethyl-1,3,2-dioxaborolan-2-yl)pyrimidine

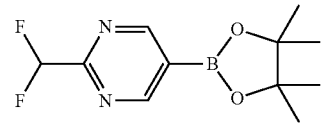 [SMILES: CC1(C)OB(c2cnc(C(F)F)nc2)OC1(C)C]

A mixture of 2-(difluoromethyl)-5-bromopyrimidine (500 mg, 2.23 mmol), bis(pinacolato)diboron (623 mg, 2.5 mmol) and KOAc (657 mg, 6.7 mmol) in DMF (11 mL) of DMF was degassed under N₂. Pd(dppf)Cl₂.DCM (82 mg, 0.11 mmol) was added and the reaction stirred at 90° C. for 2.5 hrs. The cooled reaction was poured into water and extracted with EtOAc (2×), the combined organic extracts were washed with brine, dried (MgSO₄), filtered, and concentrated in vacuo. The crude material was purified by column chromatography on silica gel eluting with EtOAc:Heptane (0:100 to 20:80) to afford the title compound (388.8 mg, 68%). $^1$HNMR (400 MHz, CDCl₃) 1.38 (s, 12H), 6.86-7.13 (dd, 1H), 8.52 (s, 2H). LCMS m/z=175.0 [M-C₆H₁₀]⁺

Preparation 140: 5-fluoro-2-methoxy-3-(4,4,5,5-tetramethyl-1,3,2-dioxaborolan-2-yl)pyridine

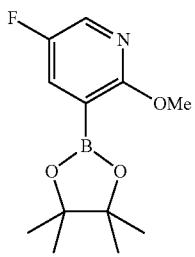 [SMILES: COc1ncc(F)cc1B1OC(C)(C)C(C)(C)O1]

3-Bromo-5-fluoro-2-methoxypyridine (250 mg, 1.21 mmol) was added to a stirred solution of KOAc (238.2 mg, 2.42 mmol) in dioxane (10 mL) followed by the addition of bispinacolatodiborane (308.1 mg, 1.21 mmol). The reaction mixture was degassed with $N_2$ for 10 mins and $PdCl_2$(dppf).DCM (99.02 mg, 0.12 mmol) added and degassed for another 10 min. The reaction mixture was heated at 100° C. for 45 mins and evaporated to dryness under reduced pressure. The residue was dissolved in 50% EtOAc in hexane, filtered through Celite® and evaporated to dryness in vacuo afford the title compound (250 mg, 81.4%) which was used without further purification. LCMS m/z=254 [MH]+

Preparation 141: 5-bromo-4-methoxy-2-(trifluoromethyl)pyrimidine

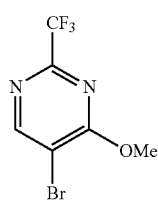

5-Bromo-4-chloro-2-(trifluoromethyl)pyrimidine (740 mg 2.83 mmol,) was dissolved in MeOH (5.5 mL) and cooled in an ice/water bath. NaOMe (156 mg 2.83 mmol) was dissolved in 2.5 mL of MeOH and added drop wise to the cooled solution. The reaction was allowed to warm to rt and stirred overnight. Additional NaOMe (60 mg) was added to the cooled reaction and stirred for another hour at rt. The reaction was quenched with water and extracted with DCM (2×). The combined organics were dried (MgSO$_4$), and evaporated to dryness to afford the title compound as an orange oil (638.7 mg, 98%) which was used without further purification. $^1$HNMR (400 MHz, CDCl$_3$) 4.08 (s, 3H), 8.62 (s, 1H).

Preparation 142: ethyl (Z)-2-amino-2-(2-(2-fluorobenzoyl)hydrazono)acetate

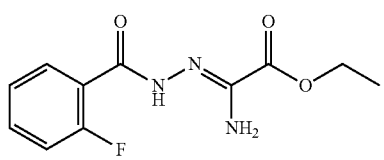 [SMILES: CCOC(=O)/C(N)=N/NC(=O)c1ccccc1F]

A solution of ethyl 2-ethoxy-2-iminoacetate (19 g, 123.26 mmol) and 2-fluorobenzoic hydrazide (19.68 g, 135.59 mmol) in DCM (350 mL) was stirred at reflux for 12 h. The resulting solid was collected by filtration and washed with DCM (200 mL) to afford the title compound as an off-white solid (24.5 g, 80%). $^1$HNMR (400 MHz, DMSO-d$_6$) 1.28 (t, 3H), 4.25 (q, 2H), 6.66 (s, 2H), 7.29 (m, 2H), 7.57 (m, 2H), 10.18 (s, 1H). LCMS m/z=254 [MH]+

Preparation 143: Phenylazide

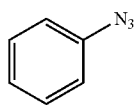

To a stirred solution of aniline (2 g, 21.475 mmol) in water (20 mL) was added HCl (10 mL) followed by a solution of NaNO$_2$ (1.92 g, 27.918 mmol) in water (10 mL) drop-wise at 0° C. The reaction mixture was stirred at 0° C. for 30 min and to this was added solution of NaN$_3$ (1.67 g, 25.77 mmol) in water (10 mL) at the same temperature and the resulting reaction mixture stirred at 0° C. for 1 h. The reaction mixture was extracted with MTBE and the combined organics washed with water, NaHCO$_3$, brine, dried (Na$_2$SO$_4$) and concentrated under reduced pressure (keeping bath temperature at 10° C.) to afford the title compound as a yellow liquid (2.61 g) as yellow liquid. $^1$HNMR (400 MHz, DMSO-d$_6$) 7.11 (d, 2H), 7.19 (t, 1H), 7.42 (t, 2H).

Preparation 144: 2-Azido-3-fluoropyridine

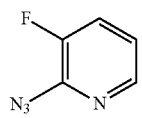

To a stirred solution of 2-bromo-3-fluoro-pyridine (500 mg, 2.84 mmol) in EtOH:H$_2$O (20 mL) was added ethylenediamine (0.056 mL, 0.57 mmol), ascorbic acid (Na-salt) (112.6 mg, 0.57 mmol), CuI (54.11 mg, 0.3 mmol) and NaN$_3$ (277.0 mg, 4.3 mmol) at 0° C. and the reaction stirred at 80° C. for 16 hrs. The cooled mixture was concentrated in vacuo, the residue diluted with EtOAc, washed with water followed by brine and dried (Na$_2$SO$_4$). The organic layer was then filtered and evaporated under reduced pressure to afford the title compound as a yellow solid (300 mg, 75.91%). $^1$HNMR (400 MHz, DMSO-d$_6$) 7.47 (m, 1H), 7.81 (dd, 1H), 9.44 (d, 1H). LCMS m/z=138 [MH]+, 110 [M-N$_2$]+

Preparation 145: 1-azido-2-fluorobenzene

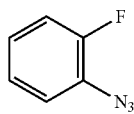

A solution of NaNO$_2$ (6.52 g, 94.5 mmol) in H$_2$O (10 mL) was added dropwise to a solution of 2-fluorobenzenamine (10 g, 90 mmol) in TFA (50 mL) and H$_2$SO$_4$ (20 mL) while keeping internal temperature between 0-10° C. After addition was complete the mixture was kept at 0-10° C. for 1 hr and a solution of NaN$_3$ (6.44 g, 99 mmol) in H$_2$O (10 mL) added drop wise whilst keeping the internal temperature between 0-10° C. and stirring for a further hour. The reaction mixture was extracted with DCM (50 mL) and the combined extracts washed with sat aq. NaHCO$_3$ (20 mL×2), brine (20 mL) and dried (Na$_2$SO$_4$). The solvent was removed in vacuo to afford the title compound (10 g, 81%) as a yellow oil. $^1$HNMR (400 MHz, CDCl$_3$) 7.05-7.12 (m, 5H).

Preparation 146: 4-(1-chloroethyl)-1-(2,4-difluorophenyl)-1H-pyrazole

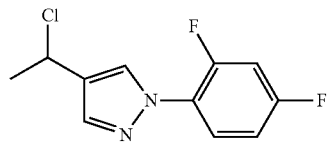

To a solution of 1-(1-(2,4-difluorophenyl)-1H-pyrazol-4-yl)ethanol (Preparation 147, 6.0 g, 26.67 mmol) in DCM (15 mL) was added SOCl$_2$ (4.83 mL, 66.67 mmol) at 0° C. under N$_2$ and the reaction stirred at rt for 1 hr. The mixture was concentrated under reduced pressure to afford the title compound as a brown oil (6.46 g, 99%). $^1$HNMR (400 MHz, CDCl$_3$) 1.90 (d, 3H), 5.21 (q, 1H), 7.01 (m, 2H), 7.78-7.85 (m, 2H), 7.93 (s, 1H).

Preparation 147: 1-(1-(2,4-difluorophenyl)-1H-pyrazol-4-yl)ethan-1-ol

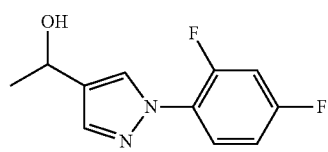 [SMILES: CC(O)c1cnn(-c2ccc(F)cc2F)c1]

To a solution of 1-(2,4-difluorophenyl)-1H-pyrazole-4-carbaldehyde (8 g, 38.462 mmol) in THF (50 mL) was added CH$_3$MgBr (32 mL, 96.154 mmol) drop wise quickly at 0° C. After addition, the mixture was allowed to warm to rt and stirred for another 30 min. The mixture was quenched with NH$_4$Cl solution then diluted with EtOAc (50 mL) and washed with brine (150 mL×2). The organic solution was dried (Na$_2$SO$_4$) and concentrated to give the desired product as an orange oil (6 g, 65%). $^1$HNMR (400 MHz, DMSO-d$_6$) 1.38 (d, 3H), 4.77 (m, 1H), 5.08 (d, 1H), 7.24 (m, 1H), 7.52 (m, 1H), 7.70 (s, 1H), 7.80 (m, 1H), 7.98 (d, 1H). LCMS m/z=225.1 [MH]$^+$ Examples 1 and 2: 4-Amino-5-[2-(difluoromethyl)pyrimidin-5-yl]-7-{1-[1-(2-fluorophenyl)-1H-pyrazol-4-yl] ethyl}-7H-pyrrolo[2,3-d]pyrimidine-6-carbonitrile, Enantiomers 1 and 2

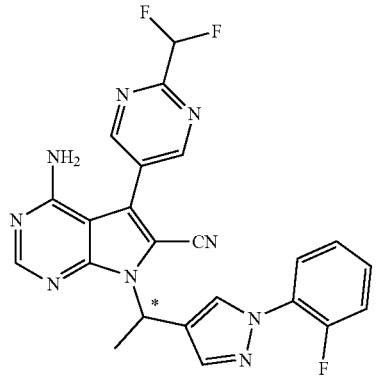

To a solution of 6-bromo-5-[2-(difluoromethyl)pyrimidin-5-yl]-7-{1-[1-(2-fluorophenyl)-1H-pyrazol-4-yl]ethyl}-7H-pyrrolo[2,3-d]pyrimidin-4-amine (Example 46, 160 mg, 0.30 mmol) in NMP (5 mL) was added Zn(CN)$_2$ (106 mg, 0.91 mmol), Pd$_2$(dba)$_3$ (27 mg, 0.03 mmol) and dppf (33 mg, 0.06 mmol) and the reaction stirred at 155° C. for 3 hrs under microwave irradiation. The cooled reaction was diluted with water and the mixture extracted with EtOAc (30 mL×2). The organic layer was collected, washed with brine, dried and evaporated under reduced pressure. The crude was purified by column chromatography on silica gel eluting with pet. Ether: EtOAc (20:80) to afford 4-amino-5-[2-(difluoromethyl)pyrimidin-5-yl]-7-{1-[1-(2-fluorophenyl)-1H-pyrazol-4-yl]ethyl}-7H-pyrrolo[2,3-d]pyrimidine-6-carbonitrile (80 mg, 56%). The product was further purified by prep HPLC method E6 to afford Example 1, enantiomer 1. $^1$HNMR (400 MHz, DMSO-d$_6$): 2.01 (d, 3H), 6.36 (m, 1H), 7.00-7.25 (br s, 2H), 7.10 (t, 1H), 7.33 (m, 1H), 7.42 (m, 2H), 7.74 (t, 2H), 8.25 (d, 1H), 8.38 (s, 1H), 9.09 (s, 2H). LCMS m/z=476.2 [MH]$^+$; RT [HPLC Method E7]=9.845 min.

Further elution provided Example 2, enantiomer 2. $^1$HNMR (400 MHz, DMSO-d$_6$): 2.01 (d, 3H), 6.36 (m, 1H), 7.00-7.25 (br s, 2H), 7.10 (t, 1H), 7.33 (m, 1H), 7.42 (m, 2H), 7.74 (t, 2H), 8.25 (d, 1H), 8.38 (s, 1H), 9.09 (s, 2H). LCMS m/z=476.2 [MH]$^+$; RT [HPLC Method E7]=10.941 min.

Examples 3 and 4: 4-Amino-7-{1-[1-(2-fluorophenyl)-1H-pyrazol-4-yl]propyl}-5-[2-(trifluoromethyl)pyrimidin-5-yl]-7H-pyrrolo[2,3-d] pyrimidine-6-carbonitrile, Enantiomers 1 and 2

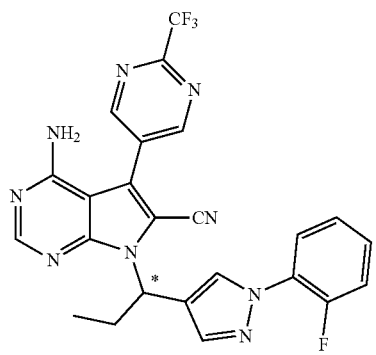 [SMILES: CCC(c1cnn(-c2ccccc2F)c1)n1c(C#N)c(-c2cnc(C(F)(F)F)nc2)c2c(N)ncnc21]

4-Amino-7-{1-[1-(2-fluorophenyl)-1H-pyrazol-4-yl]propyl}-5-[2-(trifluoromethyl) pyrimidin-5-yl]-7H-pyrrolo[2,3-d]pyrimidine-6-carbonitrile was prepared in 66% yield from 6-bromo-7-{1-[1-(2-fluorophenyl)-1H-pyrazol-4-yl]propyl}-5-[2-(trifluoromethyl) pyrimidin-5-yl]-7H-pyrrolo[2,3-d]pyrimidin-4-amine (Example 50), following the procedure described in Example 1/2. This was further purified by prep HPLC method H3 to afford Example 3, enantiomer 1. $^1$HNMR (400 MHz, DMSO-d$_6$): 0.86 (t, 3H), 2.50 (d, 2H), 6.10 (t, 1H), 7.19 (br s, 2H), 7.30-7.48 (m, 3H), 7.75-7.80 (m, 2H), 8.26 (s, 1H), 8.39 (s, 1H), 9.21 (s, 2H). LCMS m/z=508.2 [MH]$^+$; RT [HPLC method C16]=4.128 min.

Further elution provided Example 4, enantiomer 2. $^1$HNMR (400 MHz, DMSO-d$_6$): 0.86 (t, 3H), 2.53 (m, 2H), 6.10 (m, 1H), 7.18 (br s, 2H), 7.35-7.46 (m, 3H), 7.74-7.79 (m, 2H), 8.26 (s, 1H), 8.39 (s, 1H), 9.21 (s, 2H). LCMS m/z=508.1 [MH]$^+$; RT [HPLC method C16]=7.540 min.

Examples 5 to 19

The following examples were obtained from the appropriate racemic compound using appropriate chiral HPLC or SFC conditions.

| Ex. No. | Structure | Separation Method Starting Material | Analytical Data |
|---|---|---|---|
| 5 | enantiomer 1 | HPLC Method C34; 4-Amino-7-(1-(1-(2-fluorophenyl)-1 H-pyrazol-4-yl)ethyl)-5-(2-(trifluoromethyl) pyrimidin-5-yl)-7H-pyrrolo[2,3-d] pyrimidine-6-carbonitrile (Example 31). | $^1$HNMR (400 MHz, DMSO-d$_6$) 2.01 (d, 3H), 6.38 (q, 1H), 7.00-7.25 (br s, 2H), 7.33 (m, 1H), 7.44 (m, 2H), 7.74 (m, 2H), 8.26 (s, 1H), 8.39 (s, 1H), 9.19 (s, 2H). LCMS m/z = 494.2 [MH]$^+$; RT [HPLC Method C11] = 4.324 min. |
| 6 | enantiomer 2 | HPLC Method C34; 4-Amino-7-(1-(1-(2-fluoro phenyl)-1H-pyrazol-4-yl)ethyl)-5-(2-(trifluoro methyl) pyrimidin-5-yl)-7H-pyrrolo[2,3-d] pyrimidine-6-carbonitrile (Example 31). | $^1$HNMR (400 MHz, DMSO-d$_6$) 2.01 (d, 3H), 6.38 (q, 1H), 7.00-7.25 (br s, 2H), 7.33 (m, 1H), 7.44 (m, 2H), 7.74 (m, 2H), 8.26 (s, 1H), 8.39 (s, 1H), 9.19 (s, 2H). LCMS m/z = 494.2 [MH]$^+$; RT [HPLC Method C11] = 7.111 min. |
| 7 | enantiomer 1 | HPLC Method C25B; 4-Amino-7-{1-[1-(2,4-difluoro phenyl)-1H-pyrazol-4-yl]ethyl}-5-[2-(trifluoromethyl) pyrimidin-5-yl]-7H-pyrrolo[2,3-d] pyrimidine-6-carbonitrile (Example 32) | $^1$HNMR (400 MHz, DMSO-d$_6$) 2.00 (d, 3H), 6.37 (q, 1H), 7.00-7.25 (br s, 2H), 7.25 (m, 1H), 7.57 (m, 1H), 7.70-7.80 (m, 2H), 8.23 (s, 1H), 8.39 (s, 1H), 9.19 (s, 2H). LCMS m/z = 512.2 [MH]$^+$; RT [HPLC Method C8] = 2.672 min. |

| Ex. No. | Structure | Separation Method Starting Material | Analytical Data |
|---|---|---|---|
| 8 | 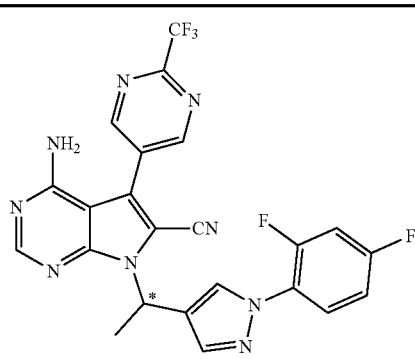<br>enantiomer 2 | HPLC Method C25B; 4-Amino-7-{1-[1-(2,4-difluoro phenyl)-1H-pyrazol-4-yl]ethyl}-5-[2-(trifluoromethyl) pyrimidin-5-yl]-7H-pyrrolo[2,3-d]pyrimidine-6-carbonitrile (Example 32) | $^1$HNMR (400 MHz, DMSO-$d_6$) 2.00 (d, 3H), 6.37 (q, 1H), 7.00-7.25 (br s, 2H), 7.25 (m, 1H), 7.57 (m, 1H), 7.70-7.80 (m, 2H), 8.24 (s, 1H), 8.39 (s, 1H), 9.19 (s, 2H). LCMS m/z = 512.2 [MH]$^+$; RT [HPLC Method C8] = 3.283 min. |
| 9 | 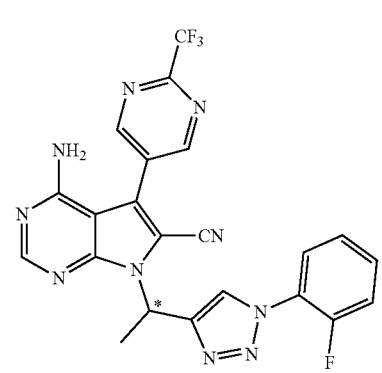<br>enantiomer 1 | HPLC Method C23A; 4-amino-7-{1-[1-(2-fluorophenyl)-1H-1,2,3-triazol-4-yl]ethyl}-5-[2-(trifluoromethyl) pyrimidin-5-yl]-7H-pyrrolo[2,3-d]pyrimidine-6-carbonitrile (Example 28) | $^1$HNMR (400 MHz, DMSO-$d_6$): 2.06 (d, 3H), 6.53 (q, 1H), 7.20 (br s, 2H), 7.43 (m, 1H), 7.55-7.63 (m, 2H), 7.79 (m, 1H), 8.38 (s, 1H), 8.79 (s, 1H), 9.20 (s, 1H). LCMS m/z = 495.1 [MH]$^+$; RT [HPLC Method C6] = 2.270 min. |
| 10 | 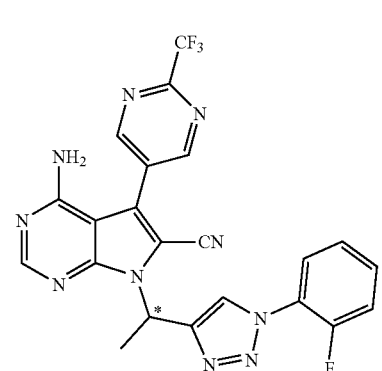<br>enantiomer 2 | HPLC Method C23A; 4-Amino-7-{1-[1-(2-fluoro phenyl)-1H-1,2,3-triazol-4-yl]ethyl}-5-[2-(trifluoro methyl)pyrimidin-5-yl]-7H-pyrrolo[2,3-d]pyrimidine-6-carbonitrile (Example 28) | $^1$HNMR (400 MHz, DMSO-$d_6$) 2.06 (d, 3H), 6.52 (q, 1H), 7.21 (br s, 2H), 7.43 (m, 1H), 7.55-7.63 (m, 2H), 7.77 (m, 1H), 8.38 (s, 1H), 8.79 (s, 1H), 9.20 (s, 1H). LCMS m/z = 495.1 [MH]$^+$; RT [HPLC Method C6] = 4.536 min. |
| 11 | 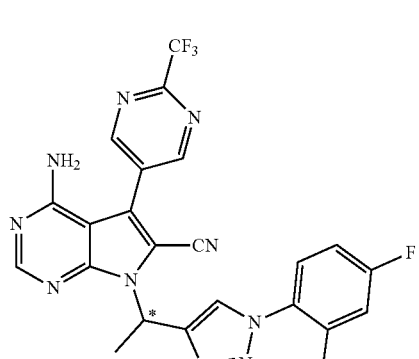<br>enantiomer 1 | HPLC Method C21; 4-Amino-7-{1-[1-(2,4-difluoro phenyl)-1H-1,2,3-triazol-4-yl]ethyl}-5-[2-(trifluoromethyl) pyrimidin-5-yl]-7H-pyrrolo[2,3-d]pyrimidine-6-carbonitrile (Example 33) | $^1$HNMR (400 MHz, DMSO-$d_6$) 2.07 (d, 3H), 6.53 (q, 1H), 7.25-7.38 (m, 3H), 7.68 (m, 1H), 7.83 (m, 1H), 8.40 (s, 1H), 8.78 (s, 1H), 9.20 (s, 2H). LCMS m/z = 513.1 [MH]$^+$; RT [HPLC Method C5] = 2.393 min |

| Ex. No. | Structure | Separation Method Starting Material | Analytical Data |
|---|---|---|---|
| 12 | enantiomer 1 | HPLC Method C32 4-amino-7-(1-(1-(2-fluorophenyl)-5-methyl-1H-1,2,3-triazol-4-yl)ethyl)-5-(2-(trifluoromethyl) pyrimidin-5-yl)-7H-pyrrolo[2,3-d]pyrimidine-6-carbonitrile (Example 34) | $^1$HNMR (400 MHz, DMSO-$d_6$) 2.07 (s, 3H), 2.12 (d, 3H), 6.58 (m, 1H), 7.18 (br s, 2H), 7.45 (m, 1H), 7.55 (m, 2H), 7.67 (m, 1H), 8.40 (s, 1H), 9.20 (s, 2H). LCMS m/z = 509.2 [MH]$^+$; RT [HPLC Method C16A] = 5.733 min |
| 13 | enantiomer 2 | HPLC Method C32 4-amino-7-(1-(1-(2-fluorophenyl)-5-methyl-1H-1,2,3-triazol-4-yl)ethyl)-5-(2-(trifluoromethyl) pyrimidin-5-yl)-7H-pyrrolo[2,3-d] pyrimidine-6-carbonitrile (Example 34) | $^1$HNMR (400 MHz, DMSO-$d_6$) 2.06 (s, 3H), 2.12 (d, 3H), 6.58 (m, 1H), 7.19 (br s, 2H), 7.47 (m, 1H), 7.59 (m, 2H), 7.67 (m, 1H), 8.40 (s, 1H), 9.20 (s, 2H). LCMS m/z = 509.2 [MH]$^+$; RT [HPLC Method C16A] = 6.505 min |
| 14 | enantiomer 1 | HPLC Method F7 4-amino-7-{1-[3-(2-fluorophenyl)-1,2-oxazol-5-yl]ethyl}-5-(2-methoxy pyrimidin-5-yl)-7H-pyrrolo[2,3-d]pyrimidine-6-carbonitrile (Example 39) | $^1$HNMR (400 MHz, MeOD-$d_4$) 2.18 (d, 3H), 4.12 (s, 3H), 6.58 (m, 1H), 6.99 (s, 1H), 7.27 (m, 2H), 7.55 (br s, 1H), 7.92 (m, 1H), 8.36 (s, 1H), 8.78 (s, 2H). LCMS m/z = 457.2 [MH]$^+$; RT [HPLC Method F4] = 9.189 min |

-continued

| Ex. No. | Structure | Separation Method Starting Material | Analytical Data |
|---|---|---|---|
| 15 | 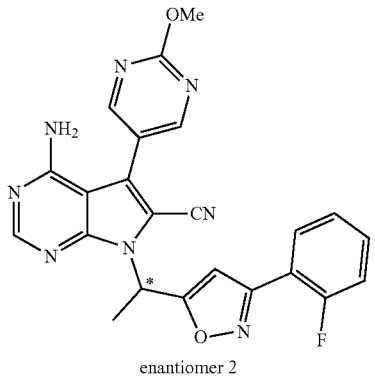 [SMILES: COc1ncc(-c2c(C#N)n(C(C)c3cc(-c4ccccc4F)no3)c3ncnc(N)c23)cn1]<br>enantiomer 2 | HPLC Method F7<br>4-amino-7-{1-[3-(2-fluorophenyl)-1,2-oxazol-5-yl]ethyl}-5-(2-methoxy pyrimidin-5-yl)-7H-pyrrolo[2,3-d]pyrimidine-6-carbonitrile (Example 39) | $^1$HNMR (400 MHz, MeOD-$d_4$) 2.18 (d, 3H), 4.11 (s, 3H), 6.58 (m, 1H), 6.99 (s, 1H), 7.26 (m, 2H), 7.51 (br s, 1H), 7.92 (m, 1H), 8.35 (s, 1H), 8.78 (s, 2H). LCMS m/z = 457.2 [MH]$^+$; RT [HPLC Method F4] = 13.190 min |
| 16 | 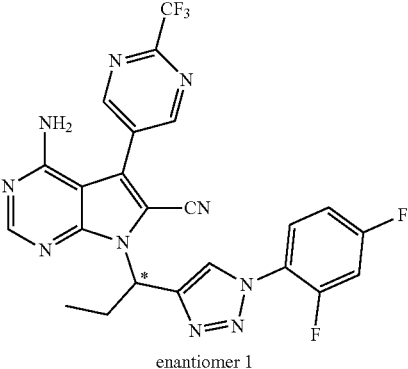 [SMILES: CCC(c1cn(-c2ccc(F)cc2F)nn1)n1c(C#N)c(-c2cnc(C(F)(F)F)nc2)c2c(N)ncnc21]<br>enantiomer 1 | HPLC Method H1<br>4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile (Example 38) | $^1$HNMR (400 MHz, CDCl$_3$) 1.04 (t, 3H), 2.60-2.65 (m, 1H), 2.67-2.76 (m, 1H), 5.36 (br s, 2H), 6.40 (t, 1H), 7.06 (m, 2H), 7.91 (m, 1H), 8.25 (s, 1H), 8.49 (s, 1H), 9.15 (s, 2H). LCMS m/z = 527.1 [MH]$^+$; RT [HPLC Method H2] = 3.613 min |
| 17 | 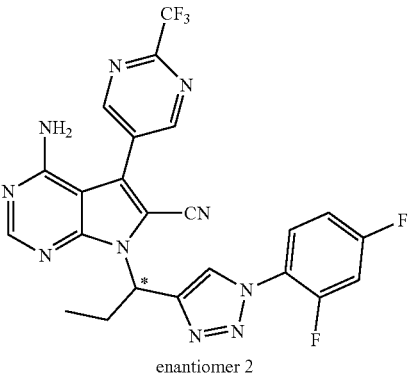 [SMILES: CCC(c1cn(-c2ccc(F)cc2F)nn1)n1c(C#N)c(-c2cnc(C(F)(F)F)nc2)c2c(N)ncnc21]<br>enantiomer 2 | HPLC Method H1;<br>4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile (Example 38) | $^1$HNMR (400 MHz, CDCl$_3$) 1.04 (t, 3H), 2.60-2.65 (m, 1H), 2.67-2.76 (m, 1H), 5.36 (br s, 2H), 6.40 (t, 1H), 7.06 (m, 2H), 7.87 (m, 1H), 8.25 (s, 1H), 8.49 (s, 1H), 9.15 (s, 2H). LCMS m/z = 527.1 [MH]$^+$; RT [HPLC Method H2] = 5.132 min |
| 18 | 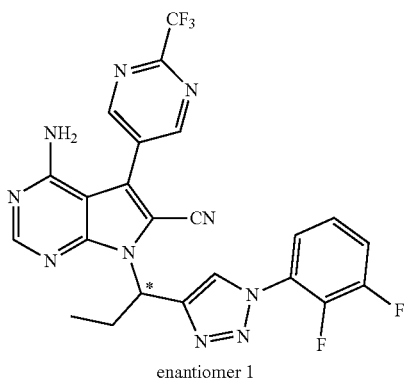 [SMILES: CCC(c1cn(-c2cccc(F)c2F)nn1)n1c(C#N)c(-c2cnc(C(F)(F)F)nc2)c2c(N)ncnc21]<br>enantiomer 1 | HPLC Method C21;<br>4-amino-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile (Example 36) | $^1$HNMR (400 MHz, DMSO-$d_6$) 0.92 (t, 3H), 2.56-2.62 (m, 2H), 6.29 (t, 1H), 7.20 (br s, 2H), 7.45 (m, 1H), 7.67 (m, 2H), 8.38 (s, 1H), 8.83 (s, 1H), 9.22 (s, 2H). LCMS m/z = 527.0 [MH]$^+$; RT [HPLC Method C9] = 2.133 min |

| Ex. No. | Structure | Separation Method Starting Material | Analytical Data |
|---|---|---|---|
| 19 |  enantiomer 2 | HPLC Method C21; 4-amino-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile (Example 36) | $^1$HNMR (400 MHz, DMSO-$d_6$) 0.92 (t, 3H), 2.56-2.62 (m, 2H), 6.30 (t, 1H), 7.20 (br s, 2H), 7.45 (m, 1H), 7.67 (m, 2H), 8.38 (s, 1H), 8.83 (s, 1H), 9.22 (s, 2H). LCMS m/z = 527.0 [MH]$^+$; RT [HPLC Method C9] = 2.558 min |

Examples 20 and 21: 4-Amino-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile, Enantiomers 1 and

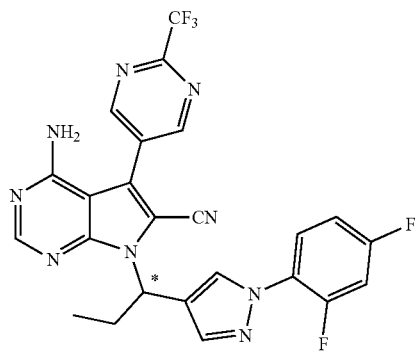

A mixture of 6-bromo-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidin-4-amine (Example 51, 150 mg, 0.25 mmol) in NMP (2 mL) was added Zn(CN)$_2$ (59 mg, 0.5 mmol), dppf (14 mg, 0.025 mmol) and Pd$_2$(dba)$_3$ (23 mg, 0.025 mmol) under N$_2$ and the reaction heated under microwave irradiation for 1.5 hrs at 155° C. The cooled mixture was diluted with water (25 mL) and the mixture extracted with DCM (15 mL×4). The combined organic layer was dried (Na$_2$SO$_4$), filtered and the filtrate was evaporated under reduced pressure. The residue was purified by prep-HPLC eluting with MeCN in water (0.1% TFA) from 55% to 65% to give 4-amino-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile (90 mg, 68%) as a yellow solid. This solid was further purified by chiral HPLC Method E8, to afford Example 20, enantiomer 1. $^1$HNMR (400 MHz, DMSO-$d_6$): 0.86 (t, 3H), 2.53 (m, 2H), 6.10 (m, 1H), 7.17 (br s, 2H), 7.24 (t, 1H), 7.53 (t, 1H), 7.76 (m, 2H), 8.24 (s, 1H), 8.38 (s, 1H), 9.21 (s, 2H). LCMS m/z=526.2 [MH]$^+$; RT [HPLC method C17]=3.301 min.

Further elution provided Example 21, enantiomer 2. $^1$HNMR (400 MHz, DMSO-$d_6$): 0.86 (t, 3H), 2.53 (m, 2H), 6.10 (m, 1H), 7.17 (br s, 2H), 7.24 (t, 1H), 7.53 (t, 1H), 7.76 (m, 2H), 8.24 (s, 1H), 8.38 (s, 1H), 9.21 (s, 2H). LCMS m/z=526.2 [MH]$^+$; RT [HPLC method C17]=7.568 min.

Example 22 and 23: 4-Amino-7-{1-[1-(2-fluorophenyl)-1H-1,2,3-triazol-4-yl]propyl}-5-[2-(trifluoromethyl) pyrimidin-5-yl]-7H-pyrrolo[2,3-d]pyrimidine-6-carbonitrile, Enantiomers 1 and 2

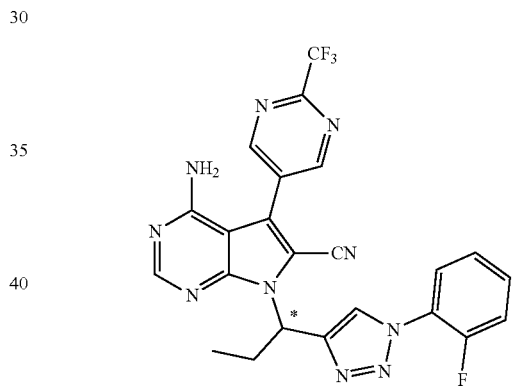

To a solution of 6-bromo-7-{1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine (Example 52, 3.3 g, 6.238 mmol) in DMF (30 mL) was added Zn(CN)$_2$ (1.04 g, 8.82 mmol), dppf (0.65 g, 1.176 mmol) and Pd$_2$(dba)$_3$ (0.57 g, 0.624 mmol) and the reaction stirred in a microwave reactor at 140° C. for 2 hr under N$_2$. The cooled mixture was concentrated and diluted with EtOAc (150 mL). The organic solution was washed with brine (2×100 ml), dried (Na$_2$SO$_4$) and concentrated in vacuo. The crude product was purified by prep-HPLC to give 4-amino-7-{1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile (1.7 g, 56%) as a white solid. The compound was further purified by chiral HPLC Method C20B to afford, Example 23, enantiomer 1. $^1$HNMR (400 MHz, DMSO-$d_6$): 0.92 (t, 3H), 2.57-2.62 (m, 2H), 6.30 (t, 1H), 7.20 (br s, 2H), 7.42 (m, 1H), 7.52-7.60 (m, 2H), 7.80 (m, 1H), 8.38 (s, 1H), 8.78 (s, 1H), 9.22 (s, 2H). LCMS m/z=509.2 [MH]$^+$; RT [HPLC Method C5]=2.143 min.

Further elution provided Example 23, enantiomer 2. $^1$HNMR (400 MHz, DMSO-$d_6$): 0.92 (t, 3H), 2.57-2.62 (m, 2H), 6.30 (t, 1H), 7.22 (br s, 2H), 7.42 (m, 1H), 7.52-7.60 (m, 2H), 7.80 (m, 1H), 8.38 (s, 1H), 8.78 (s, 1H), 9.22 (s, 2H). LCMS m/z=509.2 [MH]$^+$; RT [HPLC Method C5]=2.585 min.

Example 24: 4-Amino-5-[6-(difluoromethoxy)pyridin-3-yl]-7-{1-[1-(2-fluorophenyl)-1H-1,2,3-triazol-4-yl]propyl}-7H-pyrrolo[2,3-d]pyrimidine-6-carbonitrile, Single Enantiomer

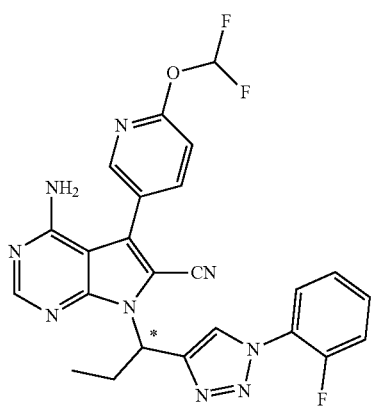 [SMILES: CCC(c1cn(-c2ccccc2F)nn1)n1c(C#N)c(-c2ccc(OC(F)F)nc2)c2c(N)ncnc21]

Copper cyanide (32 mg, 0.35 mmol) was added to a solution of 6-bromo-5-[6-(difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine, single enantiomer (Example 55, 66 mg, 0.12 mmol) in DMF (1 mL) the reaction degassed with N$_2$ and heated at 165° C. for 1 hr under microwave irradiation. The cooled reaction was diluted with DCM (30 mL), 30% NH$_4$OH added and the mixture stirred vigorously for 45 min. The phases were separated, the aqueous extracted with DCM and the combined organic extracts washed with 30% NH$_4$OH (30 mL), then dried (MgSO$_4$), filtered, and concentrated in vacuo. The orange oil was suspended in DCM/heptane and evaporated under reduced pressure to provide an orange solid. This was purified by HPLC to yield the title compound (27 mg, 44%). $^1$HNMR (400 MHz, DMSO-d$_6$): 0.92 (t, 3H), 2.56-2.62 (m, 2H), 6.25 (m, 1H), 7.26 (m, 2H), 7.42-7.47 (m, 1H), 7.55-7.65 (m, 2H), 7.80 (m, 1H), 8.18 (m, 1H), 8.34 (s, 1H), 8.42 (s, 1H), 8.75 (s, 1H). LCMS m/z=506.3 [MH]$^+$ Example 25: 4-Amino-5-(4-chlorophenyl)-7-{[1-(propan-2-yl)-1H-pyrazol-4-yl]methyl}-7H-pyrrolo[2,3-d]pyrimidine-6-carbonitrile

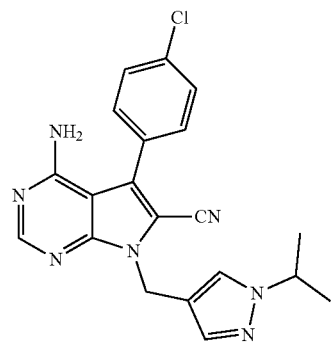

To a solution of 6-bromo-5-(4-chlorophenyl)-7-{[1-(propan-2-yl)-1H-pyrazol-4-yl]methyl}-7H-pyrrolo[2,3-d]pyrimidin-4-amine (Example 43, 0.15 g, 0.34 mmol) in DMF (3 mL) was added Zn(CN)$_2$ (40 mg, 0.50 mmol), Pd$_2$(dba)$_3$ (31 mg, 0.034 mmol) and dppf (38 mg, 0.068 mmol) and the reaction stirred at 140° C. for 3 hrs. The cooled mixture was diluted with water then extracted with EtOAc, the organic phase washed with brine, dried and evaporated. The crude product was purified by prep-HPLC to give the title compound (25.6 mg, 19%). $^1$HNMR (400 MHz, DMSO-d$_6$): 1.35 (d, 6H), 4.46 (m, 1H), 5.34 (s, 2H), 7.42 (s, 1H), 7.54 (d, 2H), 7.62 (d, 2H), 7.76 (s, 1H), 8.35 (s, 1H). LCMS m/z=392.2 [MH]$^+$ Example 26: 4-Amino-5-(4-chlorophenyl)-7-{[1-(2-fluorophenyl)-1H-1,2,3-triazol-4-yl]methyl}-7H-pyrrolo[2,3-d]pyrimidine-6-carbonitrile

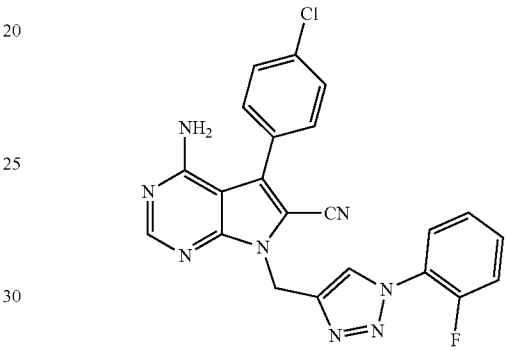

A mixture of 6-bromo-5-(4-chlorophenyl)-7-{[1-(2-fluorophenyl)-1H-1,2,3-triazol-4-yl]methyl}-7H-pyrrolo[2,3-d]pyrimidin-4-amine (Example 56, 20 mg, 0.04 mmol), Zn(CN)$_2$ (4.71 mg, 0.04 mmol), Pd$_2$(dba)$_3$ (1.84 mg, 0.002 mmol) and TFP (1.40 mg, 0.006 mmol) in DMF (0.4 mL) in a microwave vial was purged under Ar. The reaction was then heated at 90° C. for 18 hrs under microwave irradiation. The cooled mixture was filtered through Celite® and the filtrate purified by column chromatography on silica gel eluting with MeOH:DCM (0:100 to 5:95) to afford the title compound (4.6 mg, 26%). $^1$HNMR (400 MHz, CDCl$_3$): 5.10 (s, 2H), 5.45 (br s, 2H), 7.28-7.58 (m, 7H), 7.92 (m, 1H), 8.28 (s, 1H), 8.50 (s, 1H). LCMS m/z=445.1 [MH]$^+$ Example 27: 4-Amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile

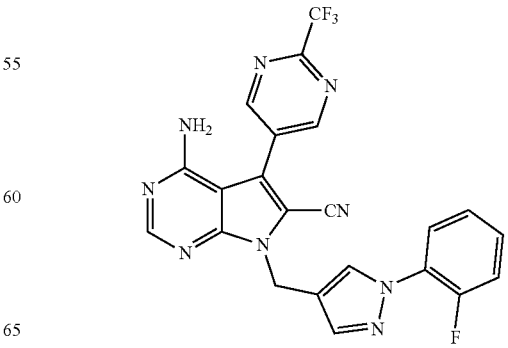

A mixture of 6-bromo-7-{[1-(2-fluorophenyl)-1H-pyrazol-4-yl]methyl}-5-[2-(trifluoromethyl)pyrimidin-5-yl]-7H-pyrrolo[2,3-d]pyrimidin-4-amine (Example 40, 1.5 g, 2.81 mmol), Zn(CN)$_2$ (660 mg, 5.63 mmol), Pd$_2$(dba)$_3$ (258 mg, 0.281 mmol), dppf (306 mg, 0.563 mmol) and DMF (15 mL) was stirred at 140° C. for 1 hr under N$_2$ under microwave irradiation. The cooled mixture was concentrated under reduced pressure to give a residue which was purified by silica gel column (eluting with DCM:MeOH=10:1) to afford the title compound (500 mg, yield: 37.1%) as a brown solid. $^1$HNMR (400 MHz, DMSO-d$_6$): 5.54 (s, 2H), 7.18 (br s, 2H), 7.32-7.47 (m, 3H), 7.76 (m, 1H), 7.79 (s, 1H), 8.26 (d, 1H), 8.41 (s, 1H), 9.21 (s, 2H). LCMS m/z=480.0 [MH]$^+$ The solid material was further purified by silica gel column (eluting with 50-100% EtOAc/CH$_2$Cl$_2$ gradient) to provide the desired product as a light yellow solid which was slurried in ethanol. The slurry was chilled for 1 hour and collected by vacuum filtration, washing with minimal chilled ethanol. The title compound was obtained as a crystalline solid (415 mg, 30.8%) after drying under high vacuum overnight. $^1$HNMR (400 MHz, DMSO-d$_6$): 5.55 (s, 2H), 7.19 (br s, 2H), 7.34-7.38 (m, 1H), 7.41-7.50 (m, 2H), 7.78 (m, 1H), 7.80 (s, 1H), 8.27 (s, 1H), 8.43 (s, 1H), 9.22 (s, 2H). LCMS m/z=480.0 [MH]$^+$ Example 28: 4-Amino-7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-6-carbonitrile

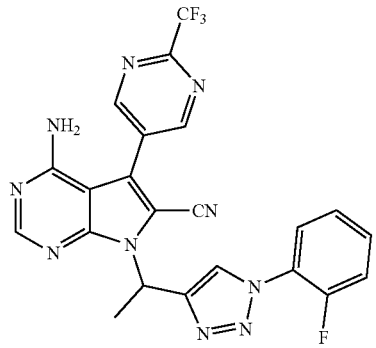 [SMILES: CC(c1cn(-c2ccccc2F)nn1)n1c(C#N)c(-c2cnc(C(F)(F)F)nc2)c2c(N)ncnc21]

To a solution of 6-bromo-7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-4-amine (Example 44, 0.2 g, 0.36 mmol) in DMF (6 mL) was added Zn(CN)$_2$ (64 mg, 0.55 mmol), Pd$_2$(dba)$_3$ (33 mg, 0.036 mmol) and dppf (40 mg, 0.072 mmol) under N$_2$ and the reaction stirred at 140° C. for 1.5 hr under microwave irradiation. The cooled mixture was partitioned between water and EtOAc, the layers separated and the organic phase washed with brine, dried and evaporated under reduced pressure. The crude product was purified by prep-HPLC to afford the title compound (110 mg, 61.8%). LCMS m/z=495.1 [MH]$^+$ Examples 29 to 36

The following examples were prepared according to an analogous procedure to that described in Example 28, from the appropriate bromo starting material.

| Ex. No. | Structure | Starting Material | Analytical Data |
|---|---|---|---|
| 29$^a$ | ![structure] | 6-Bromo-7-{[1-(2,4-difluorophenyl)-1H-pyrazol-4-yl]methyl}-5-[2-(trifluoromethyl) pyrimidin-5-yl]-7H-pyrrolo[2,3-d]pyrimidin-4-amine (Example 41) | $^1$HNMR (400 MHz, DMSO-d$_6$) 5.53 (s, 2H), 7.00-7.30 (m, 3H), 7.53 (t, 1H), 7.70-7.85 (m, 2H), 8.23 (s, 1H), 8.41 (s, 1H), 9.21 (s, 2H). LCMS m/z = 498.2 [MH]$^+$ |
| 30$^a$ | ![structure] | 6-Bromo-5-[2-(difluoromethyl)pyrimidin-5-yl]-7-{[1-(2-fluoro phenyl)-1H-pyrazol-4-yl]methyl}-7H-pyrrolo [2,3-d]pyrimidin-4-amine (Example 42) | $^1$HNMR (400 MHz, DMSO-d$_6$) 5.52 (s, 2H), 6.94-7.50 (m, 6H), 7.74-7.78 (m, 2H), 8.25 (s, 1H), 8.40 (s, 1H), 9.11 (s, 2H). LCMS m/z = 462.2 [MH]$^+$ |

-continued

| Ex. No. | Structure | Starting Material | Analytical Data |
|---|---|---|---|
| 31 | 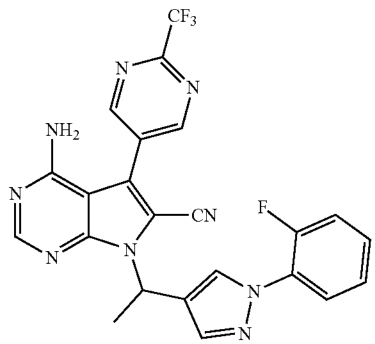 | 6-Bromo-7-{1-[1-(2-fluorophenyl)-1H-pyrazol-4-yl]ethyl}-5-[2-(trifluoromethyl)pyrimidin-5-yl]-7H-pyrrolo[2,3-d]pyrimidin-4-amine (Example 47) | LCMS m/z = 512.2 [MH]+ |
| 32 | 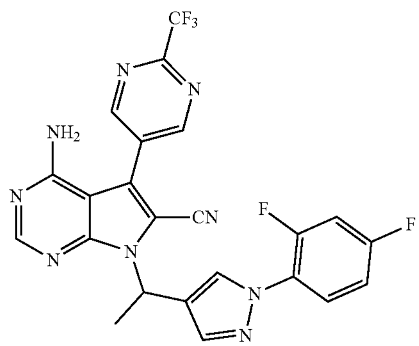 [SMILES: CC(c1cnn(-c2ccc(F)cc2F)c1)n1c(C#N)c(-c2cnc(C(F)(F)F)nc2)c2c(N)ncnc21] | 6-Bromo-7-{1-[1-(2,4-difluorophenyl)-1H-pyrazol-4-yl]ethyl}-5-[2-(trifluoromethyl)pyrimidin-5-yl]-7H-pyrrolo[2,3-d]pyrimidin-4-amine (Example 48) | LCMS m/z = 512.0 [MH]+ |
| 33 | 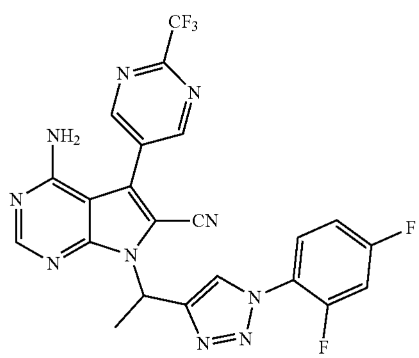 [SMILES: CC(c1cn(-c2ccc(F)cc2F)nn1)n1c(C#N)c(-c2cnc(C(F)(F)F)nc2)c2c(N)ncnc21] | 6-Bromo-7-{1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidin-4-amine (Example 45) | $^1$HNMR (400 MHz, DMSO-d$_6$) 2.06 (d, 3H), 6.53 (q, 1H), 7.32-7.40 (m, 3H), 7.69 (m, 1H), 7.84 (m, 1H), 8.41 (s, 1H), 8.79 (s, 1H), 9.21 (s, 2H). LCMS m/z = 513.1 [MH]+ |
| 34 | 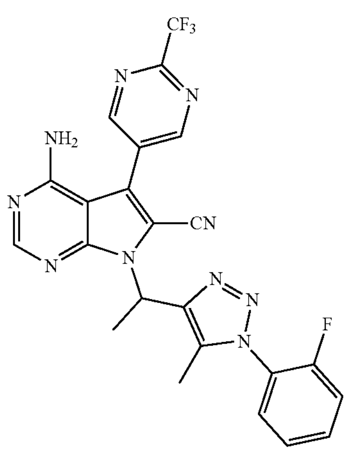 [SMILES: Cc1c(C(C)n2c(C#N)c(-c3cnc(C(F)(F)F)nc3)c3c(N)ncnc32)nnn1-c1ccccc1F] | 6-Bromo-7-{1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d] pyrimidin-4-amine (Example 49) | LCMS m/z = 509.1 [MH+] |

| Ex. No. | Structure | Starting Material | Analytical Data |
|---|---|---|---|
| 35 | 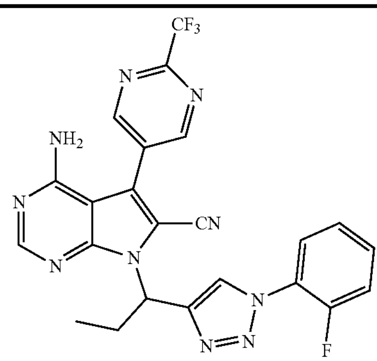 | 6-Bromo-7-{1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine (Example 52) | $^1$HNMR (400 MHz, MeOD-$d_4$) 0.93 (t, 3H), 2.60 (m, 2H), 6.31 (m, 1H), 7.30-7.65 (m, 5H), 7.80 (m, 1H), 8.42 (s, 1H), 8.80 (s, 1H), 9.24 (S, 2H). LCMS m/z = 509.1 [MH]$^+$ |
| 36$^a$ | | 6-Bromo-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine (Example 54) | LCMS m/z = 527.0 [MH]$^+$ |

$^a$NMP was used as the reaction solvent, instead of DMF.

Example 37: 4-Amino-7-{[1-(2-difluorophenyl)-1H-1,2,3-triazol-4-yl]methyl}-5-[2-(trifluoromethyl)pyrimidin-5-yl]-7H-pyrrolo[2,3-d]pyrimidin-6-carbonitrile

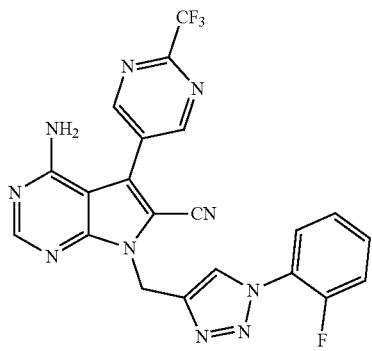 [SMILES: N#Cc1c(-c2cnc(C(F)(F)F)nc2)c2c(N)ncnc2n1Cc1cn(-c2ccccc2F)nn1]

Step 1: To a solution of N'-(7-((1-(2-fluorophenyl)-1H-1,2,3-triazol-4-yl)methyl)-5-iodo-7H-pyrrolo[2,3-d]pyrimidin-4-yl)-N,N-dimethylformimidamide (Preparation 60, 500 mg, 1.02 mmol) in dioxane (10 mL) was added H$_2$O (2 mL), 2-(trifluoromethyl) pyrimidin-5-ylboronic acid (391 mg, 2.04 mmol), PdCl$_2$(dppf) (75 mg, 0.102 mmol) and K$_2$CO$_3$ (282 mg, 2.04 mmol) and the reaction stirred at 100° C. for 5 hr under N$_2$. The cooled mixture was filtered and the filtrate concentrated. The residue was diluted with EtOAc (150 mL) the solution washed with brine (2×150 mL), dried (Na$_2$SO$_4$) and concentrated. The crude product was purified by column chromatography on silica gel eluting with MeOH:DCM (1:20) to give N'-(7-((1-(2-fluorophenyl)-1H-1,2,3-triazol-4-yl)methyl)-5-(2-(trifluoromethyl)pyrimidin-5-yl)-7H-pyrrolo[2,3-d]pyrimidin-4-yl)-N,N-dimethylformimidamide as a yellow solid (300 mg, 57%). LCMS m/z=511.2 [MH]$^+$ Step 2: To a solution of N'-(7-((1-(2-fluorophenyl)-1H-1,2,3-triazol-4-yl)methyl)-5-(2-(trifluoromethyl)pyrimidin-5-yl)-7H-pyrrolo[2,3-d]pyrimidin-4-yl)-N,N-dimethylformimidamide (Step 1, 300 mg, 0.588 mmol) in MeOH (5 mL) was added NH$_3$.H$_2$O (5 mL) and the reaction stirred at 70° C. for 18 hrs in a sealed tube. The cooled mixture was concentrated to give a brown solid (240 mg, 90%).

Step 3: To an ice-cooled solution of the solid from Step 2, in DMF (4 mL) was added NBS (103 mg, 0.578 mmol) portion wise over 1 min and the mixture then allowed to warm to rt and stirred for 18 hrs. The mixture was concentrated in vacuo and the crude product was purified by column chromatography on silica gel eluting with MeOH:DCM (1:20) to give the title compound as a yellow solid (140 mg, 50%).

LCMS m/z=511.2 [MH]$^+$

Step 4: To a solution of the compound from Step 3, (140 mg, 0.262 mmol) in DMF (4 mL) was added CuCN (71 mg, 0.787 mmol) in a microwave vial. The solution was degassed with N$_2$ for 2 min, then the reaction heated at 160° C. for 2 hr under microwave irradiation. The cooled reaction was filtered and concentrated in vacuo. The crude product was purified by prep-HPLC to afford the title compound as a white solid (9.4 mg, 7%). $^1$HNMR (400 MHz, MeOD-d$_4$): 5.83 (s, 2H), 7.33-7.49 (m, 2H), 7.52-7.62 (m, 1H), 7.82 (m, 1H), 8.38 (s, 1H), 8.51 (d, 1H), 9.19 (s, 2H). LCMS m/z=481.1 [MH]$^+$ Example 38: 4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile

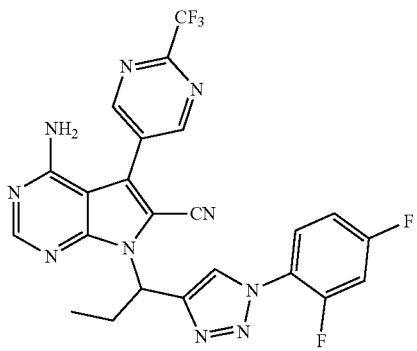 [SMILES: CCC(c1cn(-c2ccc(F)cc2F)nn1)n1c(C#N)c(-c2cnc(C(F)(F)F)nc2)c2c(N)ncnc21]

A solution of 6-bromo-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine (Example 53, 170 mg, 0.29 mmol), Zn(CN)$_2$ (137 mg, 1.17 mmol), Pd$_2$(dba)$_3$ (40 mg, 0.044 mmol) and dppf (48 mg, 0.087 mmol) in DMF (3 mL) was stirred at 145° C. for 2 hr under microwave irradiation. The cooled mixture was evaporated under reduced pressure to give a residue which was purified by column chromatography on silica gel eluting with MeOH:DCM (0:100 to 10:90) to afford the desired compound as a brown solid (80 mg, 52.44%). LCMS m/z=527.0 [MH]$^+$ Example 39: 4-Amino-7-{(1-[3-(2-fluorophenyl)-1,2-oxazol-5-yl]ethyl}-5-(2-methoxypyrimidin-5-yl)-7H-pyrrolo[2,3-d]pyrimidine-6-carbonitrile

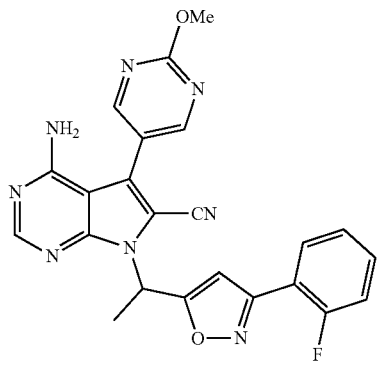 [SMILES: COc1ncc(-c2c(C#N)n(C(C)c3cc(-c4ccccc4F)no3)c3ncnc(N)c23)cn1]

Step 1: To a solution of 4-chloro-5-iodo-7H-pyrrolo[2,3-d]pyrimidine (Preparation 71, 1.2 g, 4.285 mmol) in DMF (8 mL) was added 18-Crown-6 (1.13 g, 4.285 mmol), K$_2$CO$_3$ (1.18 g, 8.571 mmol) and 5-(1-chloroethyl)-3-(2-fluorophenyl)isoxazole (Preparation 128, 1.34 g, 4.714 mmol). The mixture was stirred at 60° C. for 2 hr, evaporated to dryness in vacuo, diluted with EtOAc (80 mL) and washed with brine (2×100 mL), dried (Na$_2$SO$_4$) and concentrated. The residue was purified on a 20 g silica column eluting with MeOH:DCM (1:30) to give 5-[1-(4-chloro-5-iodo-7H-pyrrolo[2,3-d]pyrimidin-7-yl]ethyl)-3-(2-fluorophenyl)isoxazole (1.42 g, 71%) as an orange solid. LCMS m/z=468.9 [MH]$^+$ Step 2: To a solution of the compound from Step 1, (1.42 g, 3.04 mmol) in dioxane (15 mL) was added NH$_3$.H$_2$O (5 mL). The mixture was stirred at 90° C. overnight in a sealed tube and then evaporated to dryness to give 1-{1-[3-(2-fluorophenyl)isoxazol-5-yl]ethyl}-3-iodo-1H-pyrrolo[2,3-d]pyridin-4-amine as a white solid (1.3 g, 97.0%) which was used in Step 3. LCMS m/z=450.0 [MH]$^+$ Step 3: To a solution of the compound from Step 2, (1.3 g, 2.895 mmol) in dioxane (16 mL) was added H$_2$O (4 mL), 2-methoxypyrimidin-5-ylboronic acid (0.54 g, 3.474 mmol), PdCl$_2$(pddf).DCM (0.21 g, 0.289 mmol) and K$_2$CO$_3$ (0.8 g, 5.790 mmol) and the mixture stirred at 90° C. for 3 hr under N$_2$. The reaction mixture was filtered, and evaporated to dryness in vacuo. The residue was purified by column chromatography on silica gel eluting with MeOH:DCM (1:20) to give 7-{1-[3-(2-fluorophenyl)isoxazol-5-yl]ethyl}-5-(2-methoxypyrimidin-5-yl)-7H-pyrrolo[2,3-d]pyrimidin-4-amine as a brown solid (0.77 g, yield 61%) which was used in Step 4. LCMS m/z=432.1 [MH]$^+$ Step 4: To a solution of the compound from Step 3, (0.77 g, 1.786 mmol) in DMF (15 mL) was added NBS (0.35 g, 1.965 mmol) portion wise. The mixture was stirred at 0° C. overnight, concentrated and diluted with EtOAc (80 mL). The organic layer was washed with brine (2×70 mL), dried (Na$_2$SO$_4$) and evaporated to dryness in vacuo. The residue was purified by column chromatography on silica gel eluting with MeOH:DCM (1:20) to give 5-(4-amino-6-bromo-7-{1-[3-(2-fluorophenyl)isoxazol-5-yl]ethyl}-7H-pyrrolo[2,3-d]pyrimidin-5-yl)pyrimidin-2-ol as a brown solid (0.56 g, 62%) which was used in Step 5. LCMS m/z=510.0, 512.0 [MH]$^+$ Step 5: To a solution of the compound from Step 4, (560 mg, 1.1 mmol) in DMF (15 mL) in a microwave vial was added Zn(CN)$_2$ (193 mg, 1.65 mmol), dppf (123 mg, 0.22 mmol) and Pd$_2$(dba)$_3$ (100 mg, 0.11 mmol). The mixture was stirred in a microwave reactor at 140° C. for 2 hr under N$_2$ atmosphere. The mixture was concentrated and diluted with EtOAc (100 mL), washed with brine (2×100 mL), dried (Na$_2$SO$_4$) and concentrated. The residue was purified by prep-HPLC to give the title compound (92.9 mg, 18%) as a yellow solid. $^1$HNMR (400 MHz, DMSO-d$_6$): 2.06 (s, 3H), 4.00 (s, 3H), 6.51 (m, 1H), 6.98-7.17 (m, 3H), 7.32-7.45 (m, 2H), 7.60 (m, 1H), 7.89 (m, 1H), 8.34 (s, 1H), 8.74 (s, 2H). LCMS m/z=457.2 [MH]$^+$

Example 40: 6-Bromo-7-{[1-(2-fluorophenyl)-1H-pyrazol-4-yl]methyl}-5-[2-(trifluoromethyl) pyrimidin-5-yl]-7H-pyrrolo[2,3-d]pyrimidin-4-amine

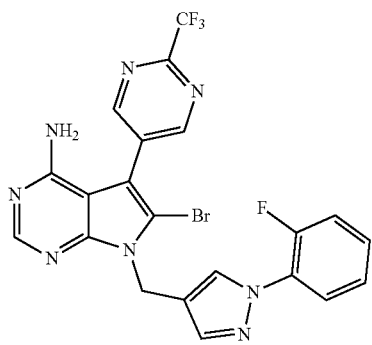 [SMILES: Nc1ncnc2c1c(-c1cnc(C(F)(F)F)nc1)c(Br)n2Cc1cnn(-c2ccccc2F)c1]

To a mixture of 7-{[1-(2-fluorophenyl)-1H-pyrazol-4-yl]methyl}-5-[2-(trifluoromethyl)pyrimidin-5-yl]-7H-pyrrolo[2,3-d]pyrimidin-4-amine (Example 57, 13 g, 28.6 mmol) and DCM (130 mL) was added NBS (5.09 g, 28.6 mmol) in several portions at 0° C. and the mixture stirred at 0° C. for 60 min. The reaction was quenched (5% NaHCO$_3$ solution), extracted with DCM (150 mL×3), washed (brine, 100 mL x 1), dried (Na$_2$SO$_4$) and the solvent removed in vacuo. The residue was purified by silica gel column (eluting with DCM:MeOH=20:1) to afford the title compound (13 g, 86%) as a yellow solid. $^1$HNMR (400 MHz, CDCl$_3$): 5.54 (s, 2H), 5.65 (br s, 2H), 7.19-7.29 (m, 3H), 7.81-7.82 (m, 2H), 8.16 (m, 1H), 8.44 (s, 1H), 9.06 (s, 2H). LCMS m/z=532.9 [MH]$^+$ Examples 41 to 55

The following examples were prepared following an analogous procedure to that described in Example 40, from the appropriate pyrrolo[2,3-d]pyrimidin-4-amine starting material.

| Ex. No. | Structure | Starting Material | Analytical Data |
|---|---|---|---|
| 41 | (structure shown) | 7-{[1-(2,4-Difluorophenyl)-1H-pyrazol-4-yl]methyl}-5-(2-(trifluoromethyl) pyrimidin-5-yl)-7H-pyrrolo[2,3-d]pyrimidin-4-amine (Example 279) | $^1$HNMR (400 MHz, DMSO-d$_6$) 5.46 (s, 2H), 6.66 (br s, 2H), 7.23 (t, 1H), 7.51 (t, 1H), 7.70-7.85 (m, 2H), 8.18 (s, 1H), 8.27 (s, 1H), 9.06 (s, 2H). LCMS m/z = 550.9 and 552.9 [MH]$^+$ |
| 42 | (structure shown) | 5-[2-(Difluoromethyl) pyrimidin-5-yl]-7-{[1-(2-fluorophenyl)-1H-pyrazol-4-yl]methyl}-7H-pyrrolo[2,3-d]pyrimidin-4-amine (Example 204) | $^1$HNMR (400 MHz, DMSO-d$_6$) 5.46 (s, 2H), 6.61 (br s, 2H), 7.05 (t, 1H), 7.30-7.50 (m, 3H), 7.75 (m, 2H), 8.34 (s, 2H), 8.98 (s, 2H). LCMS m/z = 515.1 and 517.1 [MH]$^+$ |

| Ex. No. | Structure | Starting Material | Analytical Data |
|---|---|---|---|
| 43 | 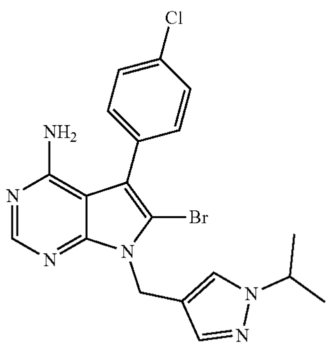 [SMILES: CC(C)n1cc(Cn2c(Br)c(-c3ccc(Cl)cc3)c3c(N)ncnc32)cn1] | 5-(4-Chlorophenyl)-7-{[1-(propan-2-yl)-1H-pyrazol-4-yl]methyl}-7H-pyrrolo[2,3-d]pyrimidin-4-amine (Example 254) | LCMS m/z = 447.1 [MH]+ |
| 44 | 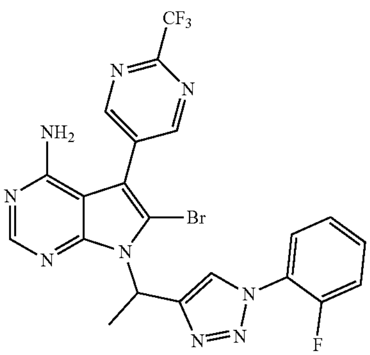 [SMILES: CC(c1cn(-c2ccccc2F)nn1)n1c(Br)c(-c2cnc(C(F)(F)F)nc2)c2c(N)ncnc21] | 7-{1-[1-(2-Fluorophenyl)-1H-1,2,3-triazol-4-yl]ethyl}-5-[2-(trifluoromethyl)pyrimidin-5-yl]-7H-pyrrolo[2,3-d]pyrimidin-4-amine (Example 216) | LCMS m/z = 548.1 and 550.0 [MH]+ |
| 45 | 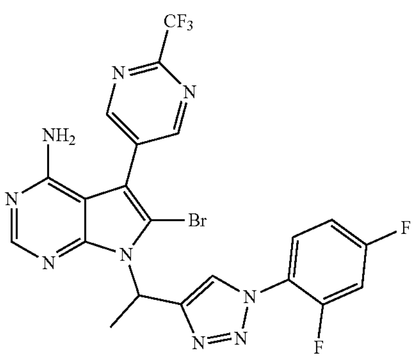 [SMILES: CC(c1cn(-c2ccc(F)cc2F)nn1)n1c(Br)c(-c2cnc(C(F)(F)F)nc2)c2c(N)ncnc21] | 7-{1-[1-(2,4-Difluorophenyl)-1H-1,2,3-triazol-4-yl]ethyl}-5-[2-(trifluoromethyl)pyrimidin-5-yl]-7H-pyrrolo[2,3-d]pyrimidin-4-amine (Example 217) | LCMS m/z = 566.0 and 568.0 [MH]+ |
| 46 | 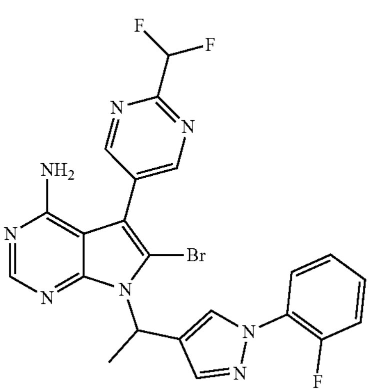 [SMILES: CC(c1cnn(-c2ccccc2F)c1)n1c(Br)c(-c2cnc(C(F)F)nc2)c2c(N)ncnc21] | 5-[2-(Difluoromethyl)pyrimidin-5-yl]-7-{1-[1-(2-fluorophenyl)-1H-pyrazol-4-yl]ethyl}-7H-pyrrolo[2,3-d]pyrimidin-4-amine (Example 205) | 1HNMR (400 MHz, DMSO-d6) 2.08 (d, 3H), 6.26 (br s, 1H), 6.54 (br s, 2H), 7.10 (t, 1H), 7.25-7.50 (m, 3H), 7.75 (m, 2H), 8.20 (m, 2H), 8.98 (s, 2H). LCMS m/z = 529.1 and 531.1 [MH]+ |

| Ex. No. | Structure | Starting Material | Analytical Data |
|---|---|---|---|
| 47 | 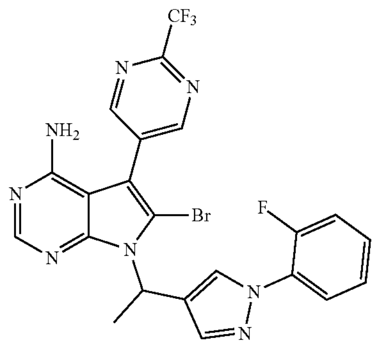 [SMILES: CC(c1cnn(-c2ccccc2F)c1)n1c(Br)c(-c2cnc(C(F)(F)F)nc2)c2c(N)ncnc21] | 7-{1-[1-(2-Fluorophenyl)-1H-pyrazol-4-yl]ethyl}-5-[2-(trifluoromethyl)pyrimidin-5-yl]-7H-pyrrolo[2,3-d]pyrimidin-4-amine (Example 277) | LCMS m/z = 547.0 and 549.0 [MH]+ |
| 48 | 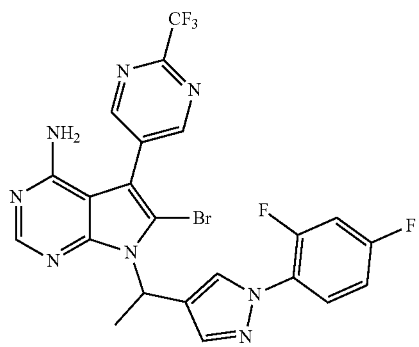 [SMILES: CC(c1cnn(-c2ccc(F)cc2F)c1)n1c(Br)c(-c2cnc(C(F)(F)F)nc2)c2c(N)ncnc21] | 7-{1-[1-(2,4-Difluorophenyl)-1H-pyrazol-4-yl]ethyl}-5-[2-(trifluoromethyl)pyrimidin-5-yl]-7H-pyrrolo[2,3-d]pyrimidin-4-amine (Example 275) | LCMS m/z = 564.9 and 566.9 [MH]+ |
| 49 | 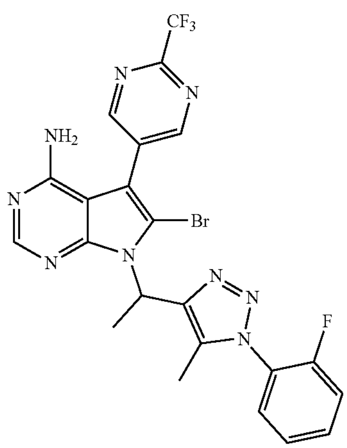 [SMILES: Cc1c(C(C)n2c(Br)c(-c3cnc(C(F)(F)F)nc3)c3c(N)ncnc32)nnn1-c1ccccc1F] | 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine (Example 273) | LCMS m/z = 562.0 [MH+] |
| 50 | 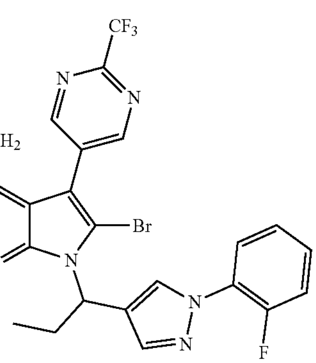 | 7-{1-[1-(2-Fluorophenyl)-1H-pyrazol-4-yl]propyl}-5-[2-(trifluoromethyl)pyrimidin-5-yl]-7H-pyrrolo[2,3-d]pyrimidin-4-amine (Example 271) | LCMS m/z = 561.0 and 563.0 [MH]+ |

-continued

| Ex. No. | Structure | Starting Material | Analytical Data |
|---|---|---|---|
| 51 | 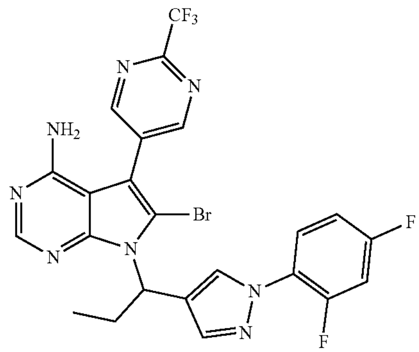 [SMILES: CCC(c1cnn(-c2ccc(F)cc2F)c1)n1c(Br)c(-c2cnc(C(F)(F)F)nc2)c2c(N)ncnc21] | 7-{1-[1-(2,4-Difluoro phenyl)-1H-pyrazol-4-yl]propyl}-5-[2-(trifluoro methyl)pyrimidin-5-yl]-7H-pyrrolo[2,3-d] pyrimidin-4-amine (Example 274) | $^1$HNMR (400 MHz, DMSO-$d_6$) 0.84 (t, 3H), 2.48 (m, 2H), 5.98 (br s, 1H), 7.23 (t, 1H), 7.25-7.40 (br s, 2H), 7.58 (t, 1H), 7.70-7.80 (m, 2H), 8.22 (s, 1H), 8.36 (s, 1H), 9.11 (s, 2H). LCMS m/z = 579.0 and 581.1 [MH]$^+$ |
| 52 | 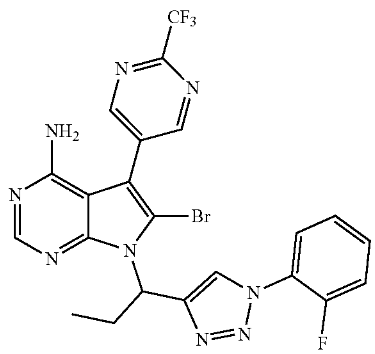 [SMILES: CCC(c1cn(-c2ccccc2F)nn1)n1c(Br)c(-c2cnc(C(F)(F)F)nc2)c2c(N)ncnc21] | 7-{1-[1-(2-Fluorophenyl)-1H-1,2,3-triazol-4-yl]propyl}-5-[2-(trifluoro methyl)pyrimidin-5-yl]-7H-pyrrolo[2,3-d] pyrimidin-4-amine (Example 224) | $^1$HNMR (400 MHz, CDCl$_3$) 1.03 (t, 3H), 2.65 (m, 2H), 5.19 (br s, 2H), 6.27 (m, 1H), 7.35 (m, 1H), 7.46 (m, 1H), 7.95 (m, 1H), 8.05 (s, 1H), 8.38 (s, 1H), 8.41 (m, 1H), 9.11 (s, 2H). LCMS m/z = 562.0 [MH]$^+$ |
| 53 | 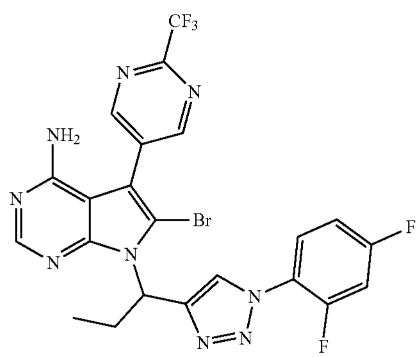 [SMILES: CCC(c1cn(-c2ccc(F)cc2F)nn1)n1c(Br)c(-c2cnc(C(F)(F)F)nc2)c2c(N)ncnc21] | 7-{1-[1-(2,4-Difluoro phenyl)-1H-1,2,3-triazol-4-yl]propyl}-5-[2-(trifluoro methyl)pyrimidin-5-yl]-7H-pyrrolo[2,3-d] pyrimidin-4-amine (Example 235) | LCMS m/z = 580.1 [MH]$^+$ |
| 54 | 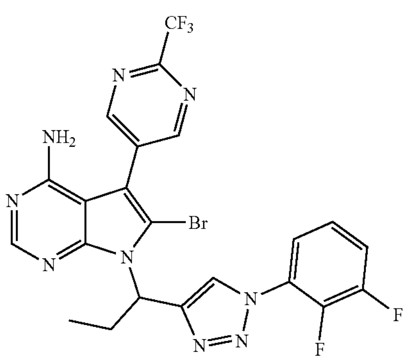 [SMILES: CCC(c1cn(-c2cccc(F)c2F)nn1)n1c(Br)c(-c2cnc(C(F)(F)F)nc2)c2c(N)ncnc21] | 7-{1-[1-(2,3-Difluoro phenyl)-1H-1,2,3-triazol-4-yl]propyl}-5-(2-(trifluoro methyl)pyrimidin-5-yl]-7H-pyrrolo[2,3-d] pyrimidin-4-amine (Example 187/188, Step 1) | LCMS m/z = 580.0 [MH]$^+$ |

| Ex. No. | Structure | Starting Material | Analytical Data |
|---|---|---|---|
| 55 | 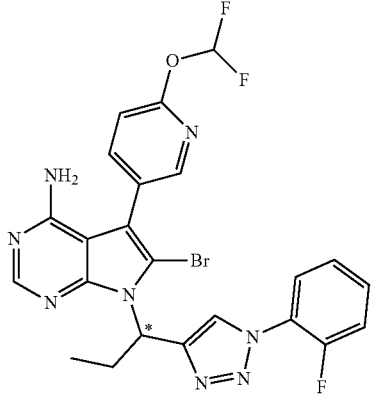<br>Single enantiomer | (+) 5-[6-(Difluoro methoxy)pyridin-3-yl]-7-(1-[1-(2-fluorophenyl)-1H-1,2,3-triazol-4-yl] propyl}-7H-pyrrolo[2,3-d] pyrimidin-4-amine, enantiomer 2 (Example 142) | $^1$HNMR (400 MHz, DMSO-$d_6$) 0.86 (t, 3H), 2.48-2.55 (m, 2H), 6.14 (m, 1H), 7.24 (m, 1H), 7.45 (m, 1H), 7.52-7.66 (m, 2H), 7.80 (m, 2H), 7.90 (m, 1H), 8.14 (s, 1H), 8.30 (s, 1H), 8.67 (s, 1H). LCMS m/z = 561.1 [MH]$^+$ |

Example 56: 6-Bromo-5-(4-chlorophenyl)-7-{[1-(2-fluorophenyl)-1H-1,2,3-triazol-4-yl]methyl}-7H-pyrrolo[2,3-d]pyrimidin-4-amine

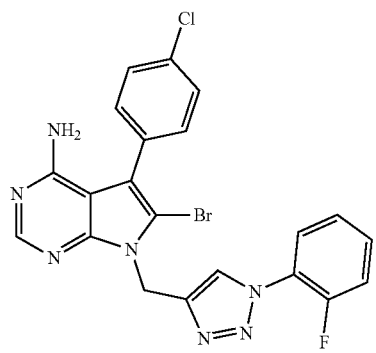 [SMILES: Nc1ncnc2c1c(-c1ccc(Cl)cc1)c(Br)n2Cc1cn(-c2ccccc2F)nn1]

CuI (19.6 mg, 0.102 mmol), Hünig's base (0.33 mL, 1.85 mmol) and 2-fluorophenyl azide (35.6 mg, 0.259 mmol) were added to a suspension of 6-bromo-5-(4-chlorophenyl)-7-(prop-2-yn-1-yl)-7H-pyrrolo[2,3-d]pyrimidin-4-amine (Preparation 76, 67 mg, 0.19 mmol) in t-BuOH (0.5 mL) and toluene (2 mL) and the reaction stirred at rt for 18 hrs. NH$_4$OH (20 mL) was added and the mixture extracted with EtOAc (3×50 mL). The combined organic extracts were dried (Na$_2$SO$_4$), filtered and evaporated under reduced pressure. The crude product was purified by column chromatography on silica gel to afford the title compound (26 mg, 28%). $^1$HNMR (400 MHz, CDCl$_3$): 5.20 (br s, 2H), 5.78 (s, 2H), 7.28-7.34 (m, 2H), 7.44-7.51 (m, 5H), 7.94 (m, 1H), 8.13 (s, 1H), 8.36 (m, 1H). LCMS m/z=499.9 [MH]$^+$

Example 57: 7-{[1-(2-fluorophenyl)-1H-pyrazol-4-yl]methyl}-5-[2-(trifluoromethyl) pyrimidin-5-yl]-7H-pyrrolo[2,3-d]pyrimidin-4-amine

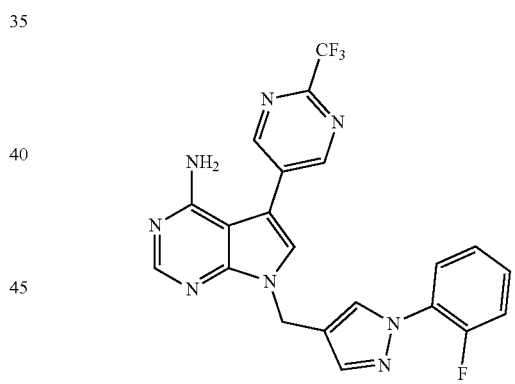

A mixture of 7-((1-(2-fluorophenyl)-1H-pyrazol-4-yl) methyl)-5-iodo-7H-pyrrolo[2,3-d]pyrimidin-4-amine (Preparation 55, 17 g, 39.2 mmol), 5-(4,4,5,5-tetramethyl-1,3,2-dioxaborolan-2-yl)-2-(trifluoromethyl)pyrimidine (16 g, 58.8 mmol), Pd(dppf)Cl$_2$ (1.43 g, 1.96 mmol) and K$_2$CO$_3$ (13.5 g, 98 mmol) in DMF (170 mL) and water (17 mL) was stirred at 85° C. for 6 h under N$_2$. The resulting mixture was filtered and concentrated to give a black solid which was purified by silica gel column eluting with pet. ether:EtOAc (2:1) to afford the title compound (13 g, 73%) as a pale yellow solid. $^1$HNMR (400 MHz, CDCl$_3$): 5.25 (br s, 2H), 5.45 (s, 2H), 7.20-7.30 (m, 3H), 7.76 (s, 1H), 7.86 (m, 1H), 8.00 (s, 1H), 8.10 (d, 1H); 8.48 (s, 1H), 9.03 (s, 2H). LCMS m/z=455.1 [MH]$^+$

Example 58: 5-(4-Chlorophenyl)-7-{1-[1-(2-fluorophenyl)-1H-1,2,3-triazol-4-yl]ethyl}-7H-pyrrolo[2,3-d]pyrimidin-4-amine

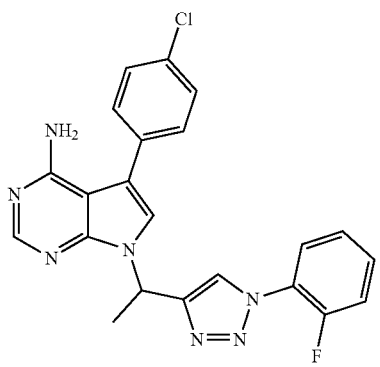 [SMILES: CC(c1cn(-c2ccccc2F)nn1)n1cc(-c2ccc(Cl)cc2)c2c(N)ncnc21]

To a stirred solution of 7-(but-3-yn-2-yl)-5-(4-chlorophenyl)-7H-pyrrolo[2,3-d]pyrimidine-4-amine (Preparation 77, 800 mg, 2.70 mmol) in toluene (24 mL) and tBuOH (8 mL) were added CuI (283 mg, 1.49 mmol), DIPEA (0.29 mL, 1.69 mmol) and the mixture then cooled in ice. 1-Azido-2-fluorobenzene (676 mg, 4.87 mmol) was added and the reaction stirred for 16 hrs at rt. The mixture was filtered through Celite®, washing through with EtOAc and the filtrate concentrated in vacuo. The solid was diluted with water, extracted with EtOAc, the combined organic extracts washed with water, then brine, dried (Na$_2$SO$_4$) and concentrated under reduced pressure. The crude compound was purified by column chromatography on silica gel eluting with EtOAc:Hexane (60:40) to afford the title compound, as a pale yellow solid (550 mg, 46.9%). $^1$HNMR (400 MHz, DMSO-d$_6$): 1.91 (d, 3H), 6.12-6.22 (br s, 2H), 6.31 (m, 1H), 7.42-7.59 (m, 8H), 7.80 (m, 1H), 8.19 (s, 1H), 8.66 (s, 1H). LCMS m/z=434.0 [MH]$^+$

Examples 59 to 71

Examples 59-71 were prepared via a palladium catalysed boronic acid cross-coupling of 7-{1-[2-(2-fluorophenyl)-1H-imidazol-5-yl]ethyl}-5-iodo-7H-pyrrolo[2,3-d]pyrimidin-4-amine (Preparation 57) and 13 different boronic acids or esters using the nine step reaction protocol described below.

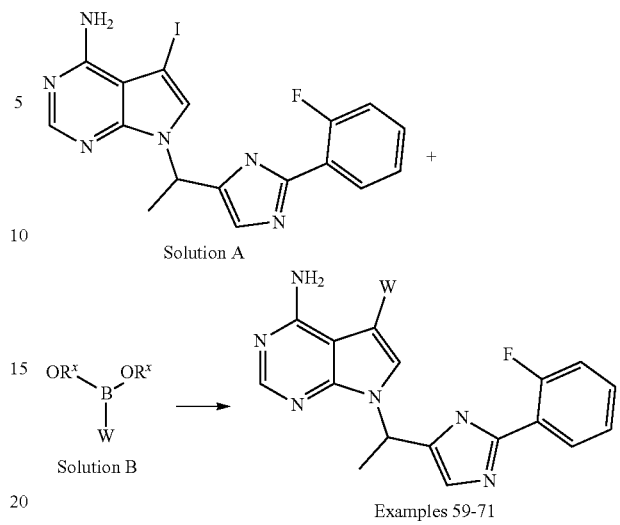

Examples 59-71

1. A 0.3 M solution of boronic acid or ester monomers in degassed mixture of Dioxane:EtOH:H$_2$O (7:3:2) was prepared (solution B).
2. A 0.2 M solution of 7-{1-[2-(2-fluorophenyl)-1H-imidazol-5-yl]ethyl}-5-iodo-7H-pyrrolo[2,3-d]pyrimidin-4-amine (Preparation 57) in degassed mixture of Dioxane:EtOH:H$_2$O (7:3:2) was prepared (solution A).
3. 10 mL 2M solution of Na$_2$CO$_3$ was prepared in degassed distilled water (solution C).
4. 500 μL of solution A (1.5 eq, 150 μmol) was added followed by 500 μL of solution B (1 eq, 100 μmol) to each reaction vial under argon purging condition.
5. 150 μL (3 eq, 300 μmol) of solution C was added to each vial.
6. Pd(PPh$_3$)$_4$ (0.1 eq, 10 μmol, 12 mg) was dispensed as solid under argon flow.
7. Each reaction vial was stirred at 10° C. for 16 hrs.
8. Reactions were filtered and solvent was evaporated in thermo explorer (1 hr, 5 torr, and 45° C.).
9. 1 mL DMSO was added to the crude products. 10 μL of the DMSO solution was diluted to 200 μL with DMSO for QC analysis and remaining amount was submitted for prep-HPLC to afford the title compounds.

| Ex. No. | Structure | Purification Method | Analytical Data |
|---|---|---|---|
| 59 | OMe (structure) | HPLC Method N1 | RT [HPLC Method M1] = 1.43 minutes<br>LCMS m/z = 447.25 [MH]$^+$ |

-continued
| Ex. No. | Structure | Purification Method | Analytical Data |
|---|---|---|---|
| 60 | 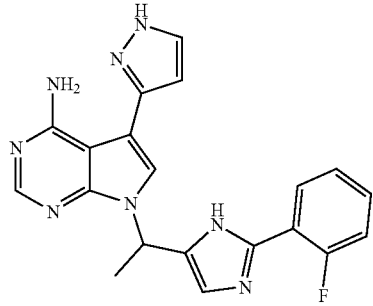 [SMILES: CC(c1cnc(-c2ccccc2F)[nH]1)n1cc(-c2cc[nH]n2)c2c(N)ncnc21] | HPLC Method L2 | RT [HPLC Method M1] = 1.29 minutes<br>LCMS m/z = 389.25 [MH]+ |
| 61 | 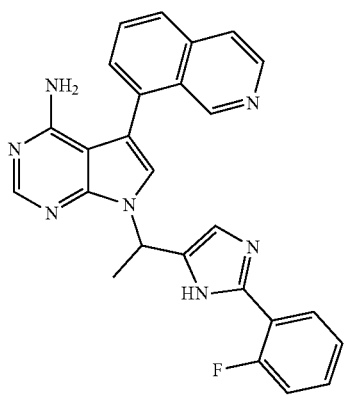 [SMILES: CC(c1cnc(-c2ccccc2F)[nH]1)n1cc(-c2cccc3ccncc23)c2c(N)ncnc21] | HPLC Method P1 | RT [HPLC Method M1] = 1.32 minutes<br>LCMS m/z = 450.27 [MH]+ |
| 62 | 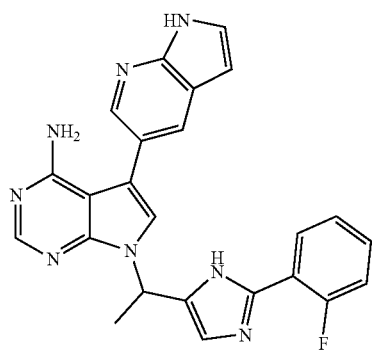 | HPLC Method P1 | RT [HPLC Method M1] = 1.35 minutes<br>LCMS m/z = 439.29 [MH]+ |
| 63 | 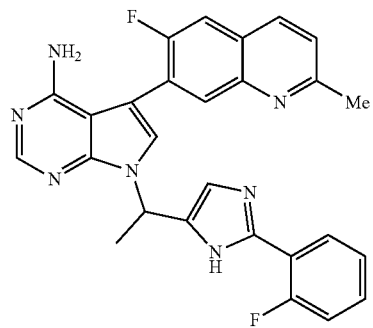 [SMILES: Cc1ccc2cc(F)c(-c3cn(C(C)c4cnc(-c5ccccc5F)[nH]4)c4ncnc(N)c34)cc2n1] | HPLC Method P1 | RT [HPLC Method M1] = 1.38 minutes<br>LCMS m/z = 482.29 [MH]+ |

-continued

| Ex. No. | Structure | Purification Method | Analytical Data |
|---|---|---|---|
| 64 | 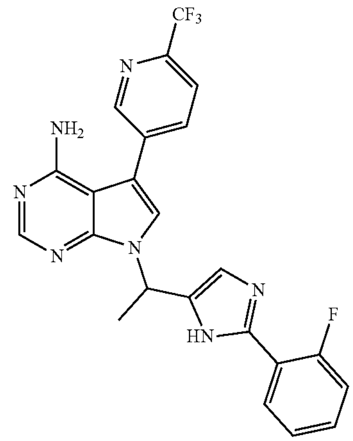 [SMILES: CC(c1cnc(-c2ccccc2F)[nH]1)n1cc(-c2ccc(C(F)(F)F)nc2)c2c(N)ncnc21] | HPLC Method N1 | RT [HPLC Method M1] = 1.44 minutes<br>LCMS m/z = 468.27 [MH]⁺ |
| 65 | 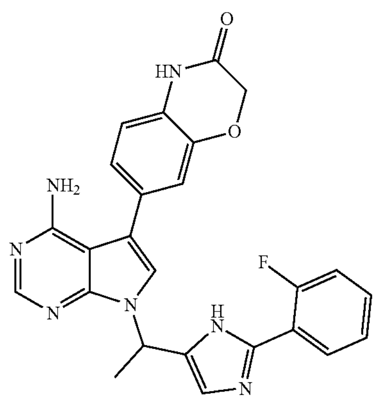 [SMILES: CC(c1cnc(-c2ccccc2F)[nH]1)n1cc(-c2ccc3c(c2)OCC(=O)N3)c2c(N)ncnc21] | HPLC Method N1 | RT [HPLC Method M1] = 1.34 minutes<br>LCMS m/z = 470.3 [MH]⁺ |
| 66 | 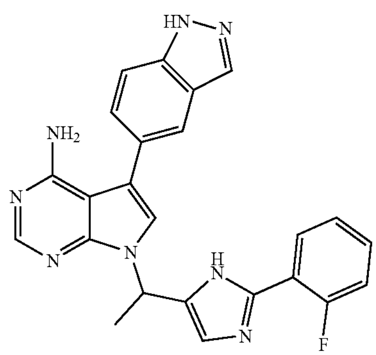 [SMILES: CC(c1cnc(-c2ccccc2F)[nH]1)n1cc(-c2ccc3[nH]ncc3c2)c2c(N)ncnc21] | HPLC Method L2 | RT [HPLC Method M1] = 1.34 minutes<br>LCMS m/z = 439.29 [MH]⁺ |
| 67 | 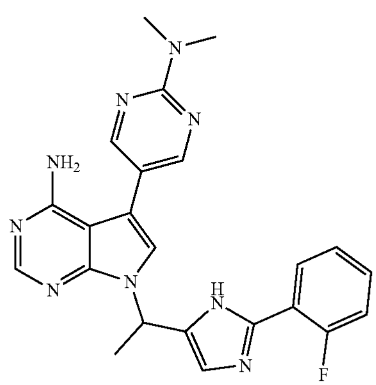 [SMILES: CC(c1cnc(-c2ccccc2F)[nH]1)n1cc(-c2cnc(N(C)C)nc2)c2c(N)ncnc21] | HPLC Method N1 | RT [HPLC Method M1] = 1.36 minutes<br>LCMS m/z = 444.32 [MH]⁺ |

-continued

| Ex. No. | Structure | Purification Method | Analytical Data |
|---|---|---|---|
| 68 | 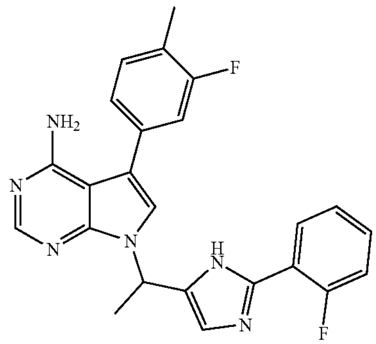 [SMILES: Cc1ccc(-c2cn(C(C)c3cnc(-c4ccccc4F)[nH]3)c3ncnc(N)c23)cc1F] | HPLC Method P1 | RT [HPLC Method M1] = 1.49 minutes<br>LCMS m/z = 431.3 [MH]$^+$ |
| 69 | 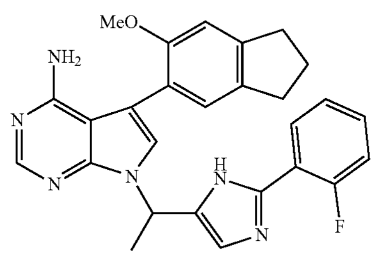 | HPLC Method L2 | RT [HPLC Method M1] = 1.46 minutes<br>LCMS m/z = 466.27 [MH]$^+$ |
| 70 | 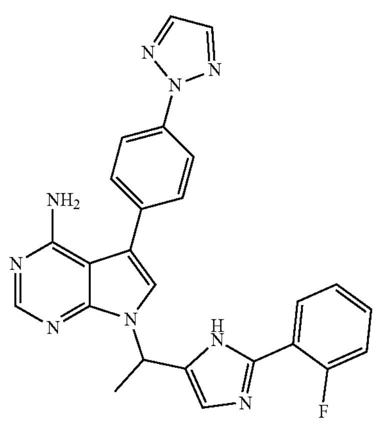 [SMILES: CC(c1cnc(-c2ccccc2F)[nH]1)n1cc(-c2ccc(-n3nccn3)cc2)c2c(N)ncnc21] | HPLC Method P1 | RT [HPLC Method M1] = 1.46 minutes<br>LCMS m/z = 466.27 [MH]$^+$ |
| 71 | 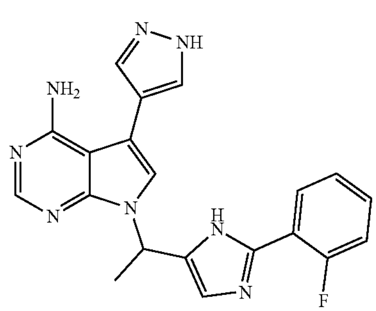 [SMILES: CC(c1cnc(-c2ccccc2F)[nH]1)n1cc(-c2cn[nH]c2)c2c(N)ncnc21] | HPLC Method L2 | RT [HPLC M1] = 1.24 minutes<br>LCMS m/z = 389.26 [MH]$^+$ |

Examples 72 to 86

Examples 72 to 86 were prepared via a palladium catalysed boronic acid cross-coupling of 7-{[1-(2-fluorophenyl)-1H-1,2,3-triazol-4-yl]methyl}-5-iodo-7H-pyrrolo[2,3-d]pyrimidin-4-amine (Preparation 41) and 15 different boronic acids or esters using the eight step reaction protocol described below.

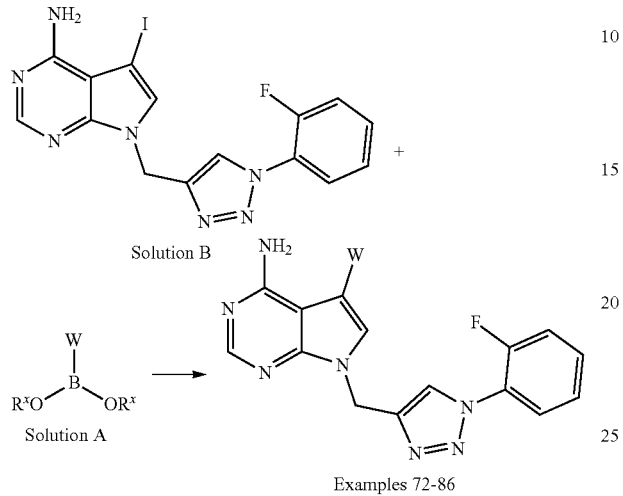

1. A 0.2 M solution of boronic acid or ester monomers in degassed mixture of DMF:H₂O (4:1) was prepared (solution A).
2. A 0.2 M solution of 7-{[1-(2-fluorophenyl)-1H-1,2,3-triazol-4-yl]methyl}-5-iodo-7H-pyrrolo[2,3-d]pyrimidin-4-amine (Preparation 41) in degassed mixture of DMF:H₂O (4:1) was prepared (solution B).
3. 500 µL of solution A (1 eq, 100 µmol) was added followed by 500 µL of solution B (1 eq, 100 µmol) to each reaction vial under argon purging condition.
4. 98 mg (3 eq, 300 µmol) of anhydrous $Cs_2CO_3$ was added to each vial.
5. $PdCl_2$ (dppf).DCM (0.17 eq, 17 µmol, ~15 mg) was dispensed under argon flow.
6. Each reaction vial was stirred at 100° C. for 16 hrs.
7. Reactions were filtered and solvent was evaporated in thermo explorer (1 hr, 5t torr, 45° C.).
8. 1 mL DMSO was added to the crude products. 10 µL of the DMSO solution was diluted to 200 µL with DMSO for QC analysis and remaining amount was purified by prep-HPLC to afford the title compounds.

| Ex. No. | Structure | Purification Method | Analytical Data |
|---|---|---|---|
| 72 | 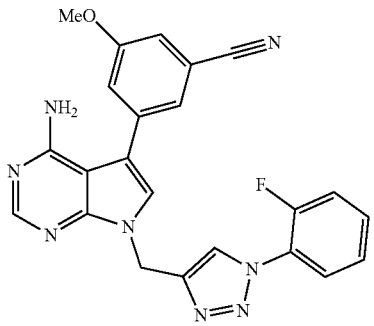 [SMILES: COc1cc(C#N)cc(-c2cn(Cc3cn(-c4ccccc4F)nn3)c3ncnc(N)c23)c1] | HPLC Method N2 | RT [HPLC Method M1] = 1.48 min<br>LCMS m/z = 441.3[MH]⁺ |
| 73 | 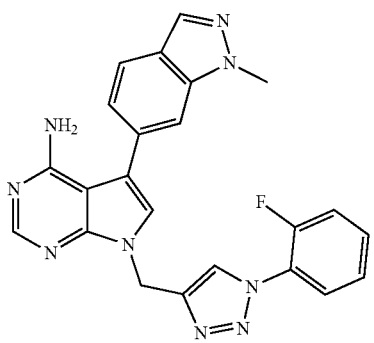 [SMILES: Cn1ncc2ccc(-c3cn(Cc4cn(-c5ccccc5F)nn4)c4ncnc(N)c34)cc21] | HPLC Method N2 | RT [HPLC Method M1] = 1.45 min<br>LCMS m/z = 440.32 [MH]⁺ |

| Ex. No. | Structure | Purification Method | Analytical Data |
|---|---|---|---|
| 74 | 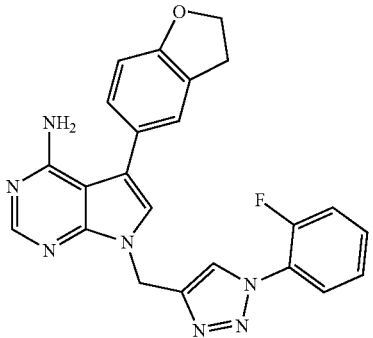 [SMILES: Nc1ncnc2c1c(-c1ccc3c(c1)CCO3)cn2Cc1cn(-c2ccccc2F)nn1] | HPLC Method N2 | RT [HPLC Method M1] = 1.46 min<br>LCMS m/z = 428.27 [MH]+ |
| 75 | 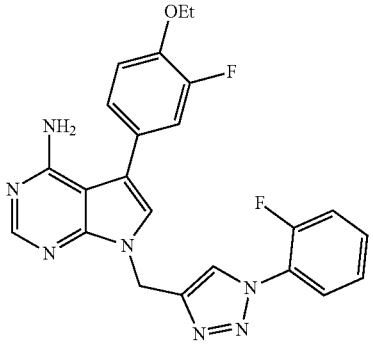 [SMILES: CCOc1ccc(-c2cn(Cc3cn(-c4ccccc4F)nn3)c3ncnc(N)c23)cc1F] | HPLC Method N2 | RT [HPLC Method M1] = 1.52 min<br>LCMS m/z = 448.27 [MH]+ |
| 76 | 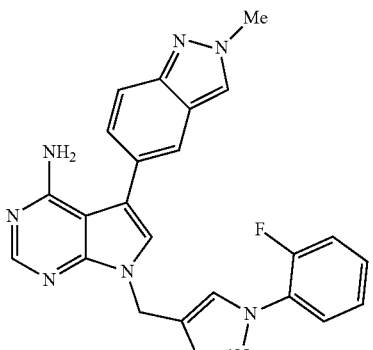 | HPLC Method N2 | RT [HPLC Method M1] = 1.41 min<br>LCMS m/z = 440.32 [MH]+ |
| 77 | 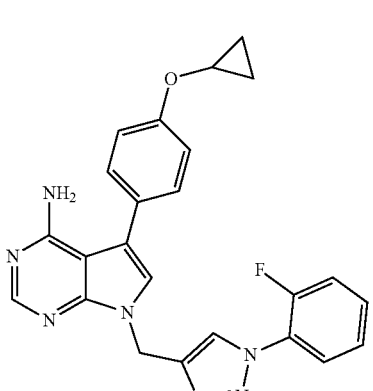 | HPLC Method P1 | RT [HPLC Method M1] = 1.53 min<br>LCMS m/z = 442.27 [MH]+ |

| Ex. No. | Structure | Purification Method | Analytical Data |
|---|---|---|---|
| 78 | 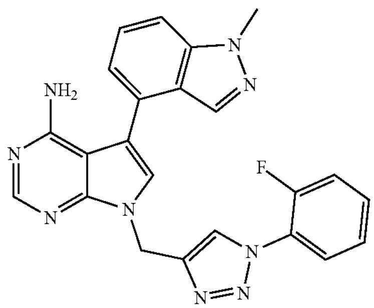 [SMILES: Cn1ncc2c(-c3cn(Cc4cn(-c5ccccc5F)nn4)c4ncnc(N)c34)cccc21] | HPLC Method P1 | RT [HPLC Method M1] = 1.44 minutes<br>LCMS m/z = 440.28 [MH]⁺ |
| 79 | 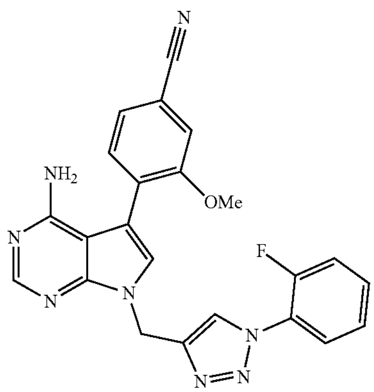 [SMILES: COc1cc(C#N)ccc1-c1cn(Cc2cn(-c3ccccc3F)nn2)c2ncnc(N)c12] | HPLC Method P1 | RT [HPLC Method M1] = 1.45 min<br>LCMS m/z = 441.3 [MH]⁺ |
| 80 | 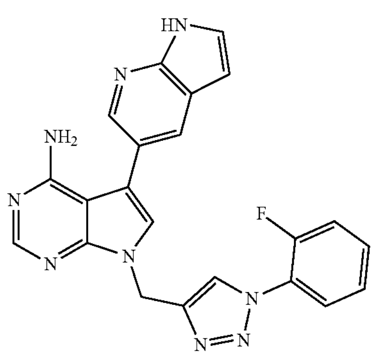 [SMILES: Nc1ncnc2c1c(-c1cnc3[nH]ccc3c1)cn2Cc1cn(-c2ccccc2F)nn1] | HPLC Method N1 | RT [HPLC Method M1] = 1.39 min<br>LCMS m/z = 426.28 [MH]⁺ |
| 81 | 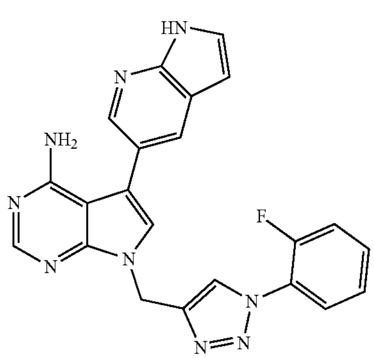 [SMILES: Nc1ncnc2c1c(-c1cnc3[nH]ccc3c1)cn2Cc1cn(-c2ccccc2F)nn1] | HPLC Method N1 | RT [HPLC Method M1] = 1.44 min<br>LCMS m/z = 425.3 [MH]⁺ |

| Ex. No. | Structure | Purification Method | Analytical Data |
|---|---|---|---|
| 82 | 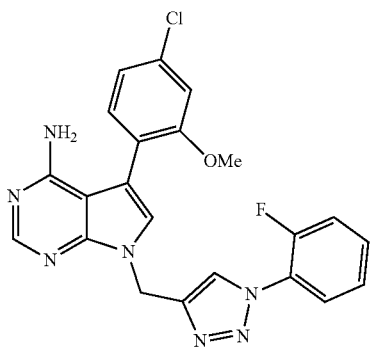 [SMILES: COc1cc(Cl)ccc1-c1cn(Cc2cn(-c3ccccc3F)nn2)c2ncnc(N)c12] | HPLC Method N1 | RT [HPLC Method M1] = 1.51 min<br>LCMS m/z = 450.23 [MH]+ |
| 83 | 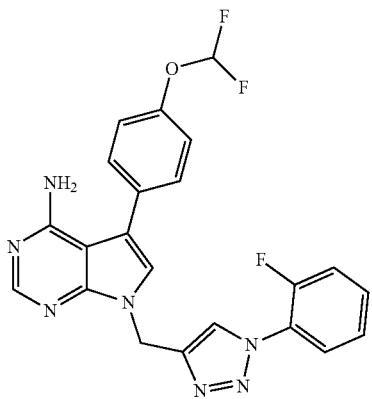 [SMILES: Nc1ncnc2c1c(-c1ccc(OC(F)F)cc1)cn2Cc1cn(-c2ccccc2F)nn1] | HPLC Method N2 | RT [HPLC Method M1] = 1.75 min<br>LCMS m/z = 452.27 [MH]+ |
| 84 | 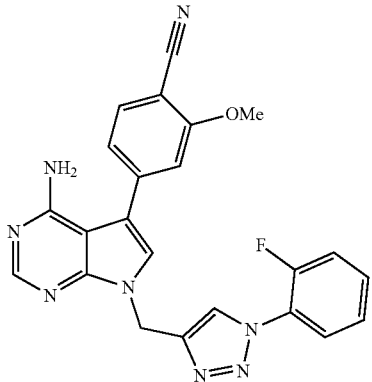 [SMILES: COc1cc(-c2cn(Cc3cn(-c4ccccc4F)nn3)c3ncnc(N)c23)ccc1C#N] | HPLC Method N2 | RT [HPLC Method M1] = 1.48 min<br>LCMS m/z = 441.25 [MH]+ |
| 85 | 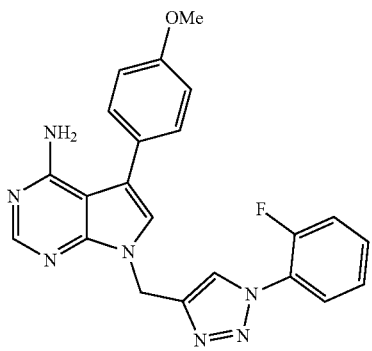 [SMILES: COc1ccc(-c2cn(Cc3cn(-c4ccccc4F)nn3)c3ncnc(N)c23)cc1] | HPLC Method N1 | RT [HPLC Method M1] = 1.46 min<br>LCMS m/z = 416.28 [MH]+ |

| Ex. No. | Structure | Purification Method | Analytical Data |
|---|---|---|---|
| 86 | (structure shown) | HPLC Method N2 | RT [HPLC Method M1] = 1.44 min<br>LCMS m/z = 440.28 [MH]+ |

Examples 87 to 100

The following compounds of generic structure:

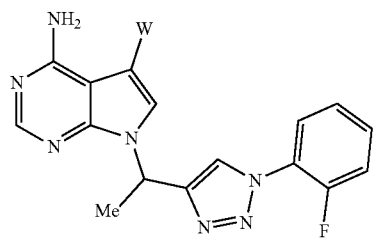

were prepared according to the following procedure.
1. 0.2 M solution of appropriate boronic acid in a degassed mixture of DMF:H$_2$O (4:1) was prepared (solution A).
2. 0.2 M solution of 7-{1-[1-(2-fluorophenyl)-1H-1,2,3-triazol-4-yl]ethyl}-5-iodo-7H-pyrrolo[2,3-d]pyrimidin-4-amine (Preparation 42) in degassed mixture of DMF:H$_2$O (4:1) was prepared (solution B).
3. 500 μL of solution A (1 eq, 100 μmol) followed by 500 μL of solution B (1 eq, 100 μmol) was added to each reaction vial under Ar.
4. 98 mg (3 eq, 300 μmol) of anhydrous Cs$_2$CO$_3$ was added to each vial.
5. PdCl$_2$ (dppf).DCM (0.17 eq, 17 μmol, 15 mg) was dispensed under Ar.
6. Each reaction vial was stirred at 100° C. for 16 hrs.
7. The reactions were filtered and solvent evaporated in vacuo.
8. DMSO (1 mL) was added to the crude products and the solutions purified by preparative HPLC to afford the desired compounds.

| Example Number | Structure of Group W | Purification Method | Analytical Data |
|---|---|---|---|
| 87 | OMe (structure with two OMe) | HPLC Method L1 | LCMS m/z = 460.22 [MH]+; RT [HPLC Method M1] = 1.47 min |
| 88 | SMe | HPLC Method K1 | LCMS m/z = 446.31 [MH]+; RT [HPLC Method M1] = 1.56 min |
| 89 | F$_2$CHO-phenyl | HPLC Method K1 | LCMS m/z = 466.27 [MH]+; RT [HPLC Method M1] = 1.55 min |
| 90 | SMe (with F) | HPLC Method L1 | LCMS m/z = 464.18 [MH]+; RT [HPLC Method M1] = 1.57 min |
| 91 | thiophene acetyl | HPLC Method L1 | LCMS m/z = 448.18 [MH]+; RT [HPLC Method M1] = 1.51 min |
| 92 | N-methyl indole | HPLC Method L1 | LCMS m/z = 454.23 [MH]+; RT [HPLC Method M1] = 1.47 min |

161
-continued

| Example Number | Structure of Group W | Purification Method | Analytical Data |
|---|---|---|---|
| 93 | (6-methoxy-5,6,7,8-tetrahydronaphthalene) | HPLC Method L1 | LCMS m/z = 484.26 [MH]+; RT [HPLC Method M1] = 1.61 min |
| 94 | (phenyl) | HPLC Method J1 | LCMS m/z = 400.29 [MH]+; RT [HPLC Method M1] = 1.49 min |
| 95 | (1-methyl-1H-indazol-5-yl) | HPLC Method L1 | LCMS m/z = 454.36 [MH]+; RT [HPLC Method M1] = 1.46 min |
| 96 | (4-acetylphenyl) | HPLC Method K1 | LCMS m/z = 442.24 [MH]+; RT [HPLC Method M1] = 1.48 min |
| 97 | (3-trifluoromethylphenyl) | HPLC Method K1 | LCMS m/z = 468.18 [MH]+; RT [HPLC Method M1] = 1.61 min |
| 98 | (4-chloro-3-fluorophenyl) | HPLC Method K1 | LCMS m/z = 452.15 [MH]+; RT [HPLC Method M1] = 1.61 min |
| 99 | (3-chloro-5-fluorophenyl) | HPLC Method J1 | LCMS m/z = 452.24 [MH]+; RT [HPLC Method M1] = 1.62 min |
| 100 | (5,6,7,8-tetrahydroquinolin-3-yl) | HPLC Method J1 | LCMS m/z = 451.3 [MH]+; RT [HPLC Method M1] = 1.51 min |

*a* Boronate ester used instead of boronic acid. The bond with the arrow indicates the point of attachment of Group W.

Examples 101 to 107

The following examples were prepared via a palladium catalysed boronic acid cross-coupling of 7-{1-[3-(2-fluorophenyl)isoxazol-5-yl]ethyl}-5-iodo-7H-pyrrolo[2,3-d]pyrimidin-4-amine (Preparation 59) and 7 different boronic acids or boronate esters using the reaction protocol described below.

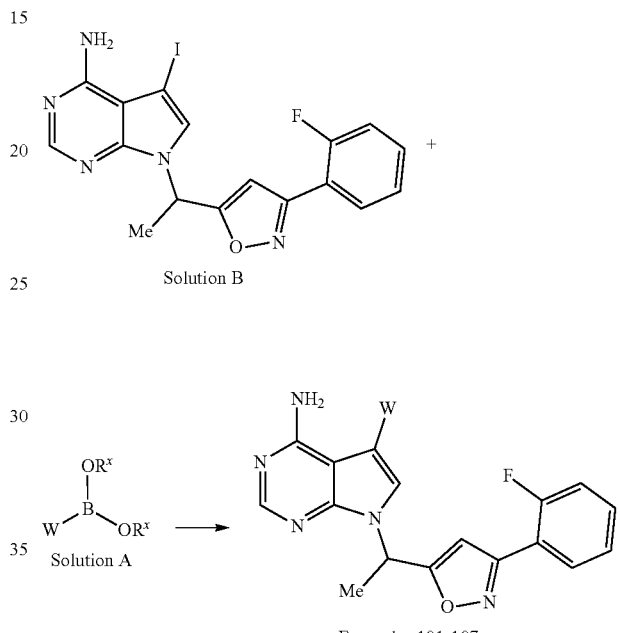

Examples 101-107

1. A 0.2 M solution of boronic acid or ester monomers in degassed mixture of DMF:H$_2$O (4:1) was prepared (solution A).
2. A 0.2 M solution of 7-{1-[3-(2-fluorophenyl)isoxazol-5-yl]ethyl}-5-iodo-7H-pyrrolo[2,3-d]pyrimidin-4-amine (Preparation 59) in degassed mixture of DMF:H$_2$O (4:1) was prepared (solution B).
3. 500 μL of solution A (1 eq, 100 μmol) was added followed by 500 μL of solution B (1 eq, 100 μmol) to each reaction vial under argon purging condition.
4. 98 mg (3 eq, 300 μmol) of anhydrous Cs$_2$CO$_3$ was added to each vial.
5. PdCl$_2$(dppf).DCM (0.17 eq, 17 μmol, 15 mg) was dispensed under argon flow.
6. Each reaction vial was stirred at 100° C. for 16 hrs.
7. Reactions were filtered and solvent was evaporated in thermo explorer (1 h, 5t torr, 45° C.).
8. 1 mL DMSO was added to the crude products. 10 μL of the DMSO solution was diluted to 200 μL with DMSO for QC analysis and remaining amount was purified by prep-HPLC to afford the title compounds.

| Ex. No. | Structure | Purification Method | Analytical Data |
|---|---|---|---|
| 101 | 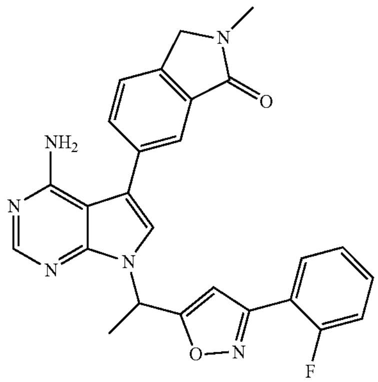 [SMILES: CC(c1cc(-c2ccccc2F)no1)n1cc(-c2ccc3c(c2)C(=O)N(C)C3)c2c(N)ncnc21] | HPLC Method L2 | RT [HPLC Method M1] = 1.52 min<br>LCMS m/z = 469.22 [MH]⁺ |
| 102 | 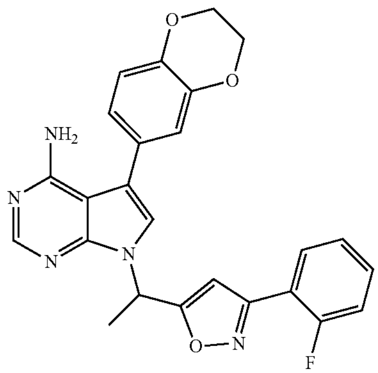 [SMILES: CC(c1cc(-c2ccccc2F)no1)n1cc(-c2ccc3c(c2)OCCO3)c2c(N)ncnc21] | HPLC Method K1 | RT [HPLC Method M1] = 1.58 min<br>LCMS m/z = 458.2 [MH]⁺ |
| 103 | 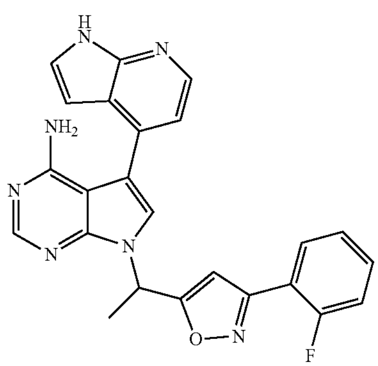 [SMILES: CC(c1cc(-c2ccccc2F)no1)n1cc(-c2ccnc3[nH]ccc23)c2c(N)ncnc21] | HPLC Method L2 | RT [HPLC Method M1] = 1.49 min<br>LCMS m/z = 440.28 [MH]⁺ |
| 104 | 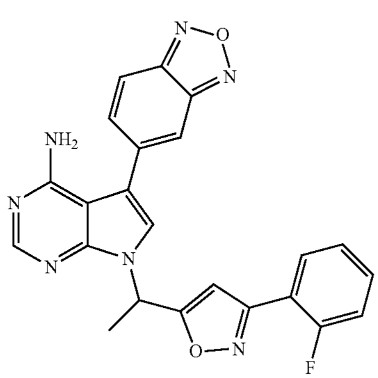 [SMILES: CC(c1cc(-c2ccccc2F)no1)n1cc(-c2ccc3nonc3c2)c2c(N)ncnc21] | HPLC Method K1 | RT [HPLC Method M1] = 1.65 min<br>LCMS m/z = 442.18 [MH]⁺ |

| Ex. No. | Structure | Purification Method | Analytical Data |
|---|---|---|---|
| 105 | 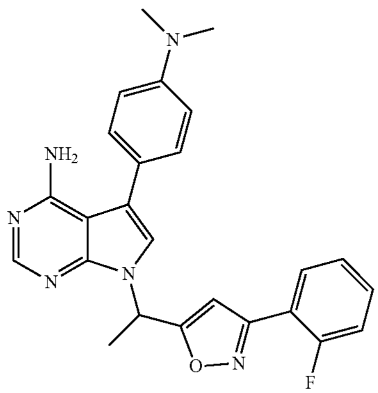 [SMILES: CC(c1cc(-c2ccccc2F)no1)n1cc(-c2ccc(N(C)C)cc2)c2c(N)ncnc21] | HPLC Method K1 | RT [HPLC Method M1] = 1.6 min<br>LCMS m/z = 443.2 [MH]$^+$ |
| 106 | 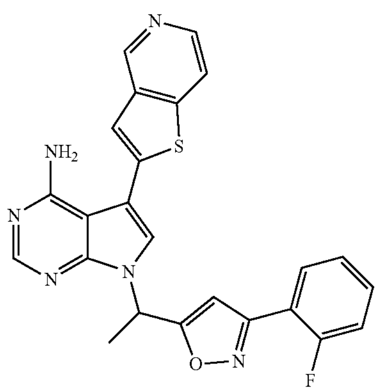 [SMILES: CC(c1cc(-c2ccccc2F)no1)n1cc(-c2cc3cnccc3s2)c2c(N)ncnc21] | HPLC Method K1 | RT [HPLC Method M1] = 1.49 min<br>LCMS m/z = 457.12 [MH]$^+$ |
| 107 | 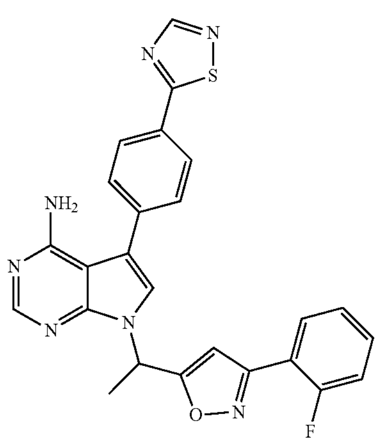 [SMILES: CC(c1cc(-c2ccccc2F)no1)n1cc(-c2ccc(-c3ncns3)cc2)c2c(N)ncnc21] | HPLC Method L2 | RT [HPLC Method M1] = 1.68 min<br>LCMS m/z = 484.13 [MH]$^+$ |

Examples 108 to 182

The following examples were obtained from the appropriate racemic compound using the chiral HPLC or SFC conditions described.

| Ex. No. | Structure | Separation Method Starting Material | Analytical Data |
|---|---|---|---|
| 108 | Enantiomer 1 | SFC Method A7; 5-Cyclopropyl-7-{1-[1-(2-fluorophenyl)-1H-1,2,3-triazol-4-yl]ethyl}-7H-pyrrolo[2,3-d]pyrimidin-4-amine (Example 238) | $^1$HNMR (400 MHz, DMSO-$d_6$) 0.52-0.58 (m, 2H), 0.84-0.89 (m, 2H), 1.82 (d, 3H), 2.04 (m, 1H), 6.18 (m, 1H), 6.58 (br s, 2H), 6.97 (d, 1H), 7.44 (m, 1H), 7.55-7.62 (m, 2H), 7.82 (m, 1H), 8.16 (s, 1H), 8.55 (s, 1H). LCMS m/z = 364.4 [MH]$^+$; RT [SFC Method A8] = 4.338 min |
| 109 | Enantiomer 2 | SFC Method A7; 5-Cyclopropyl-7-{1-[1-(2-fluorophenyl)-1H-1,2,3-triazol-4-yl]ethyl}-7H-pyrrolo[2,3-d]pyrimidin-4-amine (Example 238) | $^1$HNMR (400 MHz, DMSO-$d_6$) 0.52-0.58 (m, 2H), 0.84-0.89 (m, 2H), 1.82 (d, 3H), 2.04 (m, 1H), 6.18 (m, 1H), 6.58 (br s, 2H), 6.97 (d, 1H), 7.44 (m, 1H), 7.55-7.62 (m, 2H), 7.82 (m, 1H), 8.16 (s, 1H), 8.55 (s, 1H). LCMS m/z = 364.4 [MH]$^+$; RT [SFC Method A8] = 4.645 min |
| 110 | Enantiomer 2 | SFC Method A9; 5-Cyclobutyl-7-{1-[1-(2-fluorophenyl)-1H-1,2,3-triazol-4-yl]ethyl}-7H-pyrrolo[2,3-d]pyrimidin-4-amine (Example 247) | $^1$HNMR (400 MHz, DMSO-$d_6$) 1.91-1.95 (m, 1H), 2.00-2.20 (m, 8H), 2.33-2.42 (m, 2H), 5.07 (s, 2H), 6.31 (m, 1H), 7.23-7.31 (m, 2H), 7.41 (m, 1H), 7.92 (m, 2H), 8.26 (s, 1H). LCMS m/z = 378.2 [MH]$^+$; RT [SFC Method A8] = 5.199 min |
| 111 | Enantiomer 1 | SFC Method A1; 5-(4-Chlorophenyl)-7-{1-[1-(2-fluorophenyl)-1H-1,2,3-triazol-4-yl]ethyl}-7H-pyrrolo[2,3-d]pyrimidin-4-amine (Example 58) | $^1$HNMR (400 MHz, CDCl$_3$) 2.12 (d, 3H), 5.48 (br s, 2H), 6.48 (m, 1H), 7.35-7.60 (m, 8H), 7.98 (m, 1H), 8.10 (s, 1H), 8.38 (s, 1H). LCMS m/z = 434.1 [MH]$^+$; [α]$_D$ MeOH = −51.12°; RT [SFC Method A2] = 6.350 min |

-continued

| Ex. No. | Structure | Separation Method Starting Material | Analytical Data |
|---|---|---|---|
| 112 | 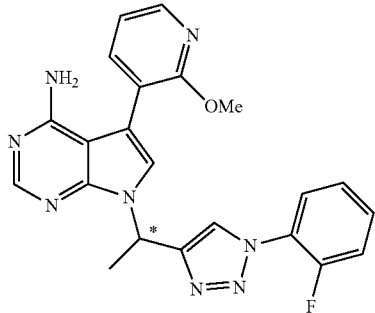<br>Enantiomer 2 | SFC Method A1; 5-(4-Chlorophenyl)-7-{1-[1-(2-fluorophenyl)-1H-1,2,3-triazol-4-yl]ethyl}-7H-pyrrolo[2,3-d]pyrimidin-4-amine (Example 58) | $^1$HNMR (400 MHz, CDCl$_3$) 2.12 (d, 3H), 5.49 (m, 2H), 6.45 (m, 1H), 7.32-7.60 (m, 8H), 7.98 (m, 1H), 8.10 (s, 1H), 8.38 (m, 1H). LCMS m/z = 434.1 [MH]$^+$; [α]$_D$ MeOH = +48.3°; RT [SFC Method A2] = 6.884 min |
| 113 | 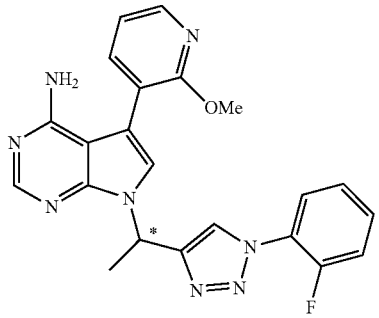<br>Enantiomer 1 | SFC Method B1; 7-{1-[1-(2-Fluorophenyl)-1H-1,2,3-triazol-4-yl]ethyl}-5-(2-methoxy pyridin-3-yl)-7H-pyrrolo[2,3-d]pyrimidin-4-amine (Example 215) | $^1$HNMR (400 MHz, DMSO-d$_6$) 1.90 (d, 3H), 3.86 (s, 3H), 6.04 (br s, 2H), 6.31 (m, 1H), 7.06 (m, 1H), 7.42 (m, 2H), 7.53-7.65 (m, 3H), 7.82 (m, 1H), 8.17 (m, 2H), 8.65 (s, 1H). LCMS m/z = 431.2 [MH]$^+$; [α]$_D$ MeOH = −27.9°; RT [SFC Method B2] = 5.598 min |
| 114 | 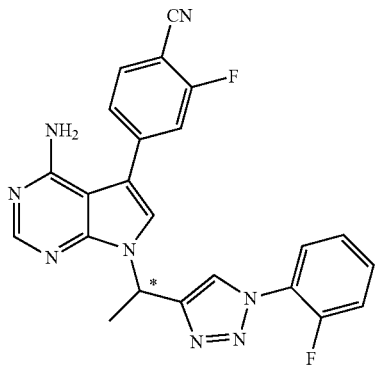<br>Enantiomer 2 | SFC Method B1; 7-{1-[1-(2-Fluorophenyl)-1H-1,2,3-triazol-4-yl]ethyl}-5-(2-methoxy pyridin-3-yl)-7H-pyrrolo[2,3-d]pyrimidin-4-amine (Example 215) | $^1$HNMR (400 MHz, DMSO-d$_6$) 1.90 (d, 3H), 3.86 (s, 3H), 6.04 (br s, 2H), 6.31 (m, 1H), 7.06 (m, 1H), 7.42 (m, 2H), 7.53-7.65 (m, 3H), 7.82 (m, 1H), 8.17 (m, 2H), 8.65 (s, 1H). LCMS m/z = 431.2 [MH]$^+$; [α]$_D$ MeOH = +32.6°; RT [SFC Method B2] = 5.775 min |
| 115 | Enantiomer 1 | SFC Method A1; 4-(4-Amino-7-{1-[1-(2-fluorophenyl)-1H-1,2,3-triazol-4-yl]ethyl]-7H-pyrrolo[2,3-d]pyrimidin-5-yl}-2-fluorobenzonitrile (Example 239) | $^1$HNMR (400 MHz, DMSO-d$_6$) 1.95 (d, 3H), 6.34 (m, 1H), 6.48 (br s, 2H), 7.44 (m, 2H), 7.48 (m, 2H), 7.52-7.60 (m, 2H), 7.82 (m, 1H), 7.96 (m, 1H), 8.25 (s, 1H), 8.68 (s, 1H). LCMS m/z = 443.0 [MH]$^+$; RT [SFC Method A2] = 6.451 min |

| Ex. No. | Structure | Separation Method Starting Material | Analytical Data |
|---|---|---|---|
| 116 | 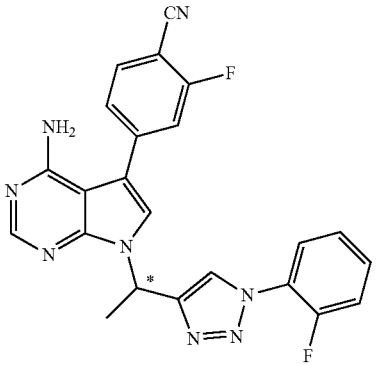  Enantiomer 2 | SFC Method A1; 4-(4-Amino-7-{1-[1-(2-fluorophenyl)-1H-1,2,3-triazol-4-yl)ethyl]-7H-pyrrolo[2,3-d]pyrimidin-5-yl}-2-fluorobenzonitrile (Example 239) | $^1$HNMR (400 MHz, DMSO-$d_6$) 1.95 (d, 3H), 6.34 (m, 1H), 6.48 (br s, 2H), 7.44 (m, 2H), 7.48 (m, 2H), 7.52-7.60 (m, 2H), 7.82 (m, 1H), 7.96 (m, 1H), 8.25 (s, 1H), 8.68 (s, 1H). LCMS m/z = 443.0 [MH]$^+$; RT [SFC Method A2] = 7.408 min |
| 117 | 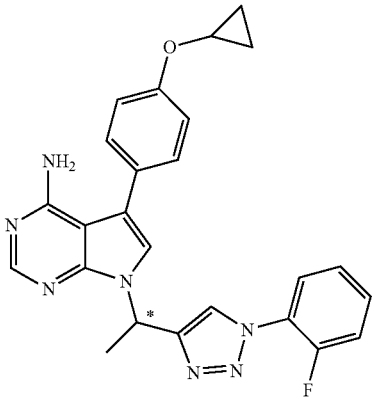  Enantiomer 1 | SFC Method C1 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine (Example 212) | $^1$HNMR (400 MHz, DMSO-$d_6$): 0.68 (m, 2H), 0.78 (m, 2H), 1.90 (d, 3H), 3.87 (m, 1H), 6.32 (q, 1H), 7.14 (m, 2H), 7.37-7.44 (m 4H), 7.55-7.61 (m, 2H), 7.81 (m, 1H), 8.18 (s, 1H), 8.65 (s, 1H) LCMS m/z = 456.5 [MH]$^+$; [α]$_D$ MeOH = +48.8°; RT [SFC Method C2] = 6.871 min |
| 118 | 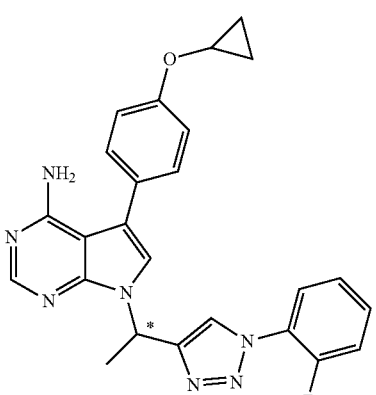  Enantiomer 2 | SFC Method C1 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine (Example 212) | $^1$HNMR (400 MHz, DMSO-$d_6$): 0.68 (m, 2H), 0.78 (m, 2H), 1.90 (d, 3H), 3.87 (m, 1H), 6.32 (q, 1H), 7.14 (m, 2H), 7.37-7.44 (m, 4H), 7.55-7.61 (m, 2H), 7.81 (m, 1H), 8.18 (s, 1H), 8.65 (s, 1H) LCMS m/z = 456.5 [MH]$^+$; [α]$_D$ MeOH = −42.9°; RT [SFC-method C2] = 7.555 min |

| Ex. No. | Structure | Separation Method Starting Material | Analytical Data |
|---|---|---|---|
| 119 | Enantiomer 1 | SFC Method A3; 5-[4-(Cyclopropyloxy) pyridin-3-yl]-7-{1-[1-(2-fluorophenyl)-1H-1,2,3-triazol-4-yl]ethyl}-7H-pyrrolo[2,3-d]pyrimidin-4-amine (Example 213) | $^1$HNMR (400 MHz, DMSO-$d_6$) 0.69 (m, 2H), 0.78 (m, 2H), 1.91 (d, 3H), 4.22 (m, 1H), 6.18 (br s, 2H), 6.32 (q, 1H), 6.93 (d, 1H), 7.43 (m, 1H), 7.47 (s, 1H), 7.53-7.61 (m, 2H), 7.77-7.84 (m, 2H), 8.18 (s, 1H), 8.26 (d, 1H), 8.65 (s, 1H). LCMS m/z = 457.1 [MH]$^+$; [α]$_D$ MeOH = −48.8°; RT [SFC Method A5] = 5.808 min |
| 120 | Enantiomer 2 | SFC Method A3; 5-[4-(Cyclopropyloxy) pyridin-3-yl]-7-{1-[1-(2-fluorophenyl)-1H-1,2,3-triazol-4-yl]ethyl}-7H-pyrrolo[2,3-d]pyrimidin-4-amine (Example 213) | $^1$HNMR (400 MHz, DMSO-$d_6$) 0.69 (m, 2H), 0.78 (m, 2H), 1.91 (d, 3H), 4.22 (m, 1H), 6.18 (br s, 2H), 6.32 (q, 1H), 6.93 (d, 1H), 7.43 (m, 1H), 7.47 (s, 1H), 7.53-7.61 (m, 2H), 7.77-7.84 (m, 2H), 8.18 (s, 1H), 8.26 (d, 1H), 8.65 (s, 1H). LCMS m/z = 457.1 [MH]$^+$; [α]$_D$ MeOH = +50.1°; RT [SFC Method A5] = 6.269 min |
| 121 | Enantiomer 1 | HPLC Method F1; 7-{1-[1-(2-Fluorophenyl)-1H-1,2,3-triazol-4-yl]ethyl}-5-(1H-pyrazol-3-yl)-7H-pyrrolo[2,3-d]pyrimidin-4-amine (Example 218) | $^1$HNMR (400 MHz, MeOD-$d_4$) 1.96 (d, 3H), 6.30 (m, 1H), 6.59 (m, 1H), 7.28-7.33 (m, 2H), 7.46 (m, 1H), 7.67 (s, 1H), 7.74 (m, 1H), 7.82 (s, 1H), 8.12 (s, 1H), 8.37 (s, 1H). LCMS m/z = 390.1 [MH]$^+$; RT [HPLC Method F3] = 6.657 min |

| Ex. No. | Structure | Separation Method Starting Material | Analytical Data |
|---|---|---|---|
| 122 | Enantiomer 2 | HPLC Method F1; 7-{1-[1-(2-Fluorophenyl)-1H-1,2,3-triazol-4-yl]ethyl}-5-(1H-pyrazol-3-yl)-7H-pyrrolo[2,3-d]pyrimidin-4-amine (Example 218) | $^1$HNMR (400 MHz, MeOD-d$_4$) 1.96 (d, 3H), 6.30 (m, 1H), 6.59 (m, 1H), 7.28-7.33 (m, 2H), 7.46 (m, 1H), 7.67 (s, 1H), 7.74 (m, 1H), 7.82 (s, 1H), 8.12 (s, 1H), 8.37 (s, 1H). LCMS m/z = 390.1 [MH]$^+$; RT [HPLC Method F3] = 11.212 min |
| 123 | Enantiomer 1 | HPLC method C20B; 7-{1-[1-(2,4-Difluorophenyl)-1H-1,2,3-triazol-4-yl]ethyl}-5-[2-(trifluoromethyl) pyrimidin-5-yl]-7H-pyrrolo[2,3-d]pyrimidin-4-amine (Example 217) | $^1$HNMR (400 MHz, DMSO-d$_6$) 1.97 (d, 3H), 6.37 (q, 1H), 7.33 (m, 1H), 7.54-7.70 (m, 3H), 7.87 (m, 1H), 8.00 (s, 1H), 8.42 (s, 1H), 8.69 (s, 1H), 9.09 (s, 2H). LCMS m/z = 488.1 [MH]$^+$; RT [HPLC Method C5] = 2.711 min |
| 124 | Enantiomer 2 | HPLC method C20B; 7-{1-[1-(2,4-Difluorophenyl)-1H-1,2,3-triazol-4-yl]ethyl}-5-[2-(trifluoromethyl) pyrimidin-5-yl]-7H-pyrrolo[2,3-d]pyrimidin-4-amine (Example 217) | $^1$HNMR (400 MHz, DMSO-d$_6$) 1.97 (d, 3H), 6.36 (q, 1H), 7.33-7.45 (m, 3H), 7.67 (m, 1H), 7.87 (m, 1H), 8.00 (s, 1H), 8.40 (s, 1H), 8.69 (s, 1H), 9.08 (s, 2H). LCMS m/z = 488.1 [MH]$^+$; RT [HPLC Method C5] = 3.982 min |
| 125 | Enantiomer 1 | HPLC method B4; 5-(6-methoxypyridin-3-yl)-7-[1-(1-phenyl-1H-1,2,3-triazol-4-yl)propyl]-7H-pyrrolo[2,3-d] pyrimidin-4-amine (Example 220) | $^1$HNMR (400 MHz, DMSO-d$_6$) 0.84 (t, 3H), 2.35 (m, 2H), 3.15 (s, 3H), 6.06 (t, 1H), 6.18 (br s, 2H), 6.90 (d, 1H), 7.49 (m, 2H), 7.60 (m, 2H), 7.78 (m, 1H), 7.89 (m, 2H), 8.19 (s, 1H), 8.25 (s, 1H), 8.93 (s, 1H). LCMS m/z = 427.2 [MH]$^+$; RT [HPLC Method B2] = 4.530 min |

| Ex. No. | Structure | Separation Method Starting Material | Analytical Data |
|---|---|---|---|
| 126 | Enantiomer 2 | HPLC method B4; 5-(6-methoxypyridin-3-yl)-7-[1-(1-phenyl-1H-1,2,3-triazol-4-yl)propyl]-7H-pyrrolo[2,3-d] pyrimidin-4-amine (Example 220) | $^1$HNMR (400 MHz, DMSO-$d_6$) 0.84 (t, 3H), 2.35 (m, 2H), 3.15 (s, 3H), 6.08 (t, 1H), 6.18 (br s, 2H), 6.90 (d, 1H), 7.49 (m, 2H), 7.60 (m, 2H), 7.78 (m, 1H), 7.89 (m, 2H), 8.19 (s, 1H), 8.25 (s, 1H), 8.93 (s, 1H). LCMS m/z = 427.2 [MH]$^+$; RT [HPLC Method B2] = 9.460 min |
| 127 | Enantiomer 1 | SFC Method C4; 5-(4-Methoxypyrimidin-5-yl)-7-{1-[1-phenyl-1H-1,2,3-triazol-4-yl]propyl}-7H-pyrrolo[2,3-d]pyrimidin-4-amine (Example 248) | $^1$HNMR (400 MHz, DMSO-$d_6$) 0.86 (t, 3H), 2.38 (m, 2H), 3.94 (s, 3H), 6.18 (m, 1H), 6.30 (s, 2H), 7.50 (m, 2H), 7.60 (m, 2H), 7.88 (m, 2H), 8.18 (s, 1H), 8.42 (s, 1H), 8.70 (s, 1H), 8.94 (s, 1H). LCMS m/z = 428.3 [MH]$^+$; $[\alpha]_D$ MeOH = −21.8°; RT [SFC Method C2] = 6.113 min |
| 128 | Enantiomer 2 | SFC Method C4; 5-(4-Methoxypyrimidin-5-yl)-7-{1-[1-phenyl-1H-1,2,3-triazol-4-yl]propyl}-7H-pyrrolo[2,3-d]pyrimidin-4-amine (Example 248) | $^1$HNMR (400 MHz, DMSO-$d_6$) 0.86 (t, 3H), 2.38 (m, 2H), 3.96 (s, 3H), 6.10 (m, 1H), 6.30 (s, 2H), 7.50 (m, 2H), 7.60 (m, 2H), 7.88 (m, 2H), 8.18 (s, 1H), 8.42 (s, 1H), 8.70 (s, 1H), 8.94 (s, 1H). LCMS m/z = 428.3 [MH]$^+$; $[\alpha]_D$ MeOH = +23.6°; RT [SFC Method C2] = 6.382 min |
| 129 | Enantiomer 1 | HPLC Method B4; 7-[1-(1-phenyl-1H-1,2,3-triazol-4-yl)propyl]-5-[2-(trifluoromethyl)pyrimidin-5-yl]-7H-pyrrolo[2,3-d]pyrimidin-4-amine (Example 219) | $^1$HNMR (400 MHz, DMSO-$d_6$): 0.87 (t, 3H), 2.34-2.44 (m, 2H), 6.12 (t, 1H), 7.12 (s, 2H), 7.47 (m, 1H), 7.60 (m, 2H), 7.89 (m, 3H), 8.34 (s, 1H), 8.95 (s, 1H), 9.08 (s, 2H). LCMS m/z = 466.1 [MH]$^+$; RT [HPLC Method E2] = 10.002 min |

| Ex. No. | Structure | Separation Method Starting Material | Analytical Data |
|---|---|---|---|
| 130 | Enantiomer 2 | HPLC Method B4; 7-[1-(1-phenyl-1H-1,2,3-triazol-4-yl)propyl]-5-[2-(trifluoromethyl)pyrimidin-5-yl]-7H-pyrrolo[2,3-d]pyrimidin-4-amine (Example 219) | $^1$HNMR (400 MHz, DMSO-$d_6$): 0.86 (t, 3H), 2.33-2.43 (m, 2H), 6.11 (t, 1H), 6.80 (s, 2H), 7.49 (m, 1H), 7.59 (m, 2H), 7.88 (m, 3H), 8.29 (m, 1H), 8.94 (s, 1H), 9.07 (s, 2H). LCMS m/z = 466.1 [MH]$^+$; RT [HPLC Method E2] = 12.342 min |
| 131 | Enantiomer 1 | SFC Method A7; 5-(4-Chlorophenyl)-7-{1-[1-(2-fluorophenyl)-1H-1,2,3-triazol-4-yl]propyl}-7H-pyrrolo[2,3-d]pyrimidin-4-amine (Example 211) | $^1$HNMR (400 MHz, DMSO-$d_6$) 0.85 (t, 3H), 2.38 (m, 2H), 6.12 (m, 1H), 6.18 (br s, 2H), 7.42 (m, 1H), 7.48-7.63 (m, 7H), 7.83 (m, 1H), 8.18 (s, 1H), 8.72 (s, 1H). LCMS m/z = 448.2 [MH]$^+$; RT [SFC Method A8] = 6.274 min |
| 132 | Enantiomer 2 | SFC Method A7; 5-(4-Chlorophenyl)-7-{1-[1-(2-fluorophenyl)-1H-1,2,3-triazol-4-yl]propyl}-7H-pyrrolo[2,3-d]pyrimidin-4-amine (Example 211) | $^1$HNMR (400 MHz, DMSO-$d_6$) 0.85 (t, 3H), 2.38 (m, 2H), 6.12 (m, 1H), 6.18 (br s, 2H), 7.42 (m, 1H), 7.48-7.63 (m, 7H), 7.83 (m, 1H), 8.18 (s, 1H), 8.72 (s, 1H). LCMS m/z = 448.2 [MH]$^+$; [α]$_D$ MeOH = +53.2°; RT [SFC Method A8] = 7.088 min |
| 133 | Enantiomer 1 | SFC Method B4; 7-{1-[1-(2-Fluorophenyl)-1H-1,2,3-triazol-4-yl]propyl}-5-[4-methoxypyrimidin-5-yl]-7H-pyrrolo[2,3-d]pyrimidin-4-amine (Example 244) | $^1$HNMR (400 MHz, DMSO-$d_6$) 0.85 (t, 3H), 2.35 (m, 2H), 3.94 (s, 3H), 6.12 (t, 1H), 6.32 (br s, 2H), 7.42 (m, 1H), 7.53-7.62 (m, 2H), 7.82 (m, 2H), 8.18 (d, 1H), 8.42 (s, 1H), 8.72 (d, 1H), 8.76 (s, 1H). LCMS m/z = 446.2 [MH]$^+$; [α]$_D$ MeOH = −18.2°; RT [SFC Method B2] = 5.194 min |

| Ex. No. | Structure | Separation Method Starting Material | Analytical Data |
|---|---|---|---|
| 134 | Enantiomer 2 | SFC Method B4; 7-{1-[1-(2-Fluorophenyl)-1H-1,2,3-triazol-4-yl]propyl}-5-[4-methoxy pyrimidin-5-yl]-7H-pyrrolo[2,3-d]pyrimidin-4-amine (Example 244) | $^1$HNMR (400 MHz, DMSO-$d_6$) 0.85 (t, 3H), 2.35 (m, 2H), 3.94 (s, 3H), 6.12 (t, 1H), 6.32 (br s, 2H), 7.42 (m, 1H), 7.53-7.62 (m, 2H), 7.82 (m, 2H), 8.18 (s, 1H), 8.42 (s, 1H), 8.72 (d, 1H), 8.76 (s, 1H). LCMS m/z = 446.2 [MH]$^+$; [α]$_D$ MeOH = +20.6°; RT [SFC Method B2] = 5.597 min |
| 135 | Enantiomer 1 | SFC Method D1; 7-{1-[1-(2-Fluorophenyl)-1H-1,2,3-triazol-4-yl]propyl}-5-(3-methoxy pyrazin-2-yl)-7H-pyrrolo[2,3-d]pyrimidin-4-amine (Example 251) | $^1$HNMR (400 MHz, DMSO-$d_6$) 0.86 (t, 3H), 2.48 (m, 2H), 3.90 (s, 3H), 6.25 (m, 1H), 7.45 (m, 1H), 7.52-7.62 (m, 2H), 7.84 (m, 1H), 8.22-8.30 (m, 3H), 8.78 (s, 1H), 8.82 (d, 1H). LCMS m/z = 446.2 [MH]$^+$; [α]$_D$ MeOH = −98.9°; RT [SFC Method D2] = 8.390 minutes |
| 136 | Enantiomer 2 | SFC Method D1; 7-{1-[1-(2-Fluorophenyl)-1H-1,2,3-triazol-4-yl]propyl}-5-(3-methoxy pyrazin-2-yl)-7H-pyrrolo[2,3-d]pyrimidin-4-amine (Example 251) | $^1$HNMR (400 MHz, DMSO-$d_6$) 0.86 (t, 3H), 2.48 (m, 2H), 3.90 (s, 3H), 6.25 (m, 1H), 7.45 (m, 1H), 7.52-7.62 (m, 2H), 7.84 (m, 1H), 8.22-8.30 (m, 3H), 8.78 (s, 1H), 8.82 (d, 1H). LCMS m/z = 446.2 [MH]$^+$; [α]$_D$ MeOH = +87.6°; RT [SFC Method D2] = 9.059 mins |
| 137 | Enantiomer 1 | SFC Method C29; 7-{1-[1-(2-Fluorophenyl)-1H-1,2,3-triazol-4-yl]propyl}-5-[2-(trifluoro methyl)pyrimidin-5-yl]-7H-pyrrolo[2,3-d]pyrimidin-4-amine (Example 224) | $^1$HNMR (400 MHz, DMSO-$d_6$) 0.86 (t, 3H), 2.39 (m, 2H), 6.13 (m, 1H), 6.66 (br s, 2H), 7.43 (m, 1H), 7.52-7.70 (m, 2H), 7.80 (m, 1H), 7.95 (s, 1H), 8.25 (s, 1H), 8.72 (s, 1H), 9.06 (s, 2H). LCMS m/z = 484.2 [MH]$^+$; RT [HPLC Method C6] = 3.893 min |

-continued

| Ex. No. | Structure | Separation Method Starting Material | Analytical Data |
|---|---|---|---|
| 138 | 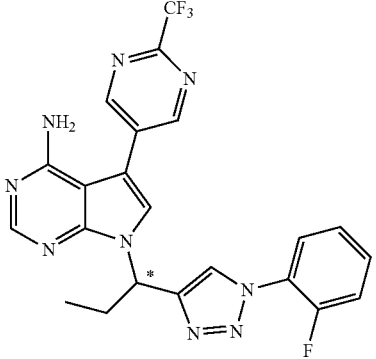<br>Enantiomer 2 | SFC Method C29; 7-{1-[1-(2-Fluorophenyl)-1H-1,2,3-triazol-4-yl]propyl}-5-[2-(trifluoromethyl)pyrimidin-5-yl]-7H-pyrrolo[2,3-d]pyrimidin-4-amine (Example 224) | $^1$HNMR (400 MHz, DMSO-$d_6$): 0.86 (t, 3H), 2.39 (m, 2H), 6.13 (m, 1H), 6.66 (br s, 2H), 7.43 (m, 1H), 7.52-7.70 (m, 2H), 7.80 (m, 1H), 7.95 (s, 1H), 8.25 (s, 1H), 8.72 (s, 1H), 9.06 (s, 2H). LCMS m/z = 484.2 [MH]$^+$; RT [HPLC Method C6] = 5.176 min |
| 139 | 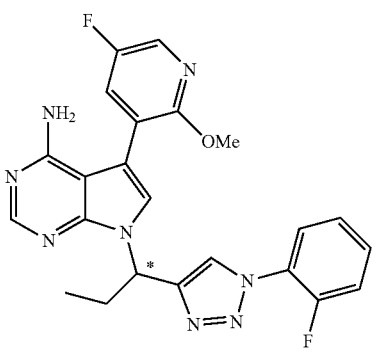<br>Enantiomer 1 | SFC Method C5; 7-{1-[1-(2-Fluorophenyl)-1H-1,2,3-triazol-4-yl]propyl}-5-(5-fluoro-2-methoxypyridin-3-yl)-7H-pyrrolo[2,3-d]pyrimidin-4-amine (Example 223) | $^1$HNMR (400 MHz, DMSO-$d_6$) 0.86 (t, 3H), 2.39 (m, 2H), 3.86 (s, 3H), 6.09 (m, 1H), 6.24 (br s, 2H), 7.45 (m, 1H), 7.57-7.65 (m, 4H), 7.85 (m, 1H), 8.12 (d, 1H), 8.18 (s, 1H), 8.72 (s, 1H). LCMS m/z = 463.1 [MH]$^+$; [α]$_D$ MeOH = +37.1°; RT [SFC Method C2] = 2.90 min |
| 140 | 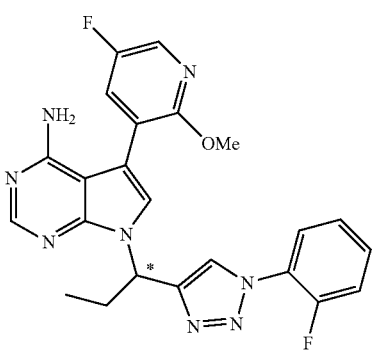<br>Enantiomer 2 | SFC Method C5; 7-{1-[1-(2-Fluorophenyl)-1H-1,2,3-triazol-4-yl]propyl}-5-(5-fluoro-2-methoxypyridin-3-yl)-7H-pyrrolo[2,3-d]pyrimidin-4-amine (Example 223) | $^1$HNMR (400 MHz, DMSO-$d_6$) 0.86 (t, 3H), 2.39 (m, 2H), 3.86 (s, 3H), 6.09 (m, 1H), 6.24 (br s, 2H), 7.45 (m, 1H), 7.57-7.65 (m, 4H), 7.85 (m, 1H), 8.12 (d, 1H), 8.18 (s, 1H), 8.72 (s, 1H). LCMS m/z = 463.1 [MH]$^+$; [α]$_D$ MeOH = −33.7°; RT [SFC Method C2] = 3.19 min |

| Ex. No. | Structure | Separation Method; Starting Material | Analytical Data |
|---|---|---|---|
| 141 | 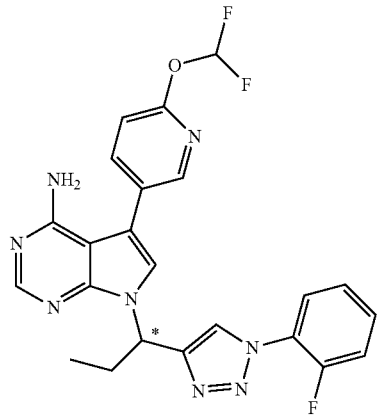<br>Enantiomer 1 | SFC Method B4; 5-[6-(Difluoromethoxy) pyridin-3-yl]-7-{1-[1-(2-fluorophenyl)-1H-1,2,3-triazol-4-yl]propyl}-7H-pyrrolo[2,3-d]pyrimidin-4-amine (Example 240) | $^1$HNMR (400 MHz, DMSO-$d_6$) 0.86 (t, 3H), 2.39 (m, 2H), 6.10 (m, 1H), 7.17 (d, 1H), 7.43 (m, 1H), 7.52-7.62 (m, 2H), 7.74 (s, 1H), 7.82 (m, 1H), 7.89 (s, 1H), 7.95 (d, 1H), 8.25 (s, 1H), 8.33 (s, 1H), 8.72 (s, 1H). LCMS m/z = 481.3 [MH]$^+$; [α]$_D$ MeOH = −31.7°; RT [SFC Method B2] = 6.160 min |
| 142 | 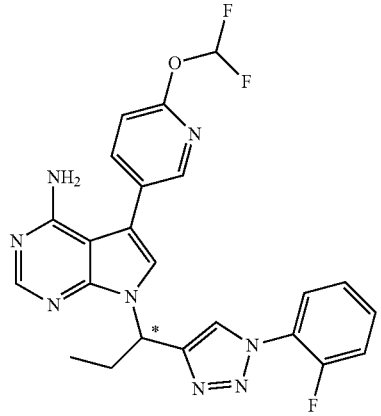<br>Enantiomer 2 | SFC Method B4; 5-[6-(Difluoromethoxy) pyridin-3-yl]-7-{1-[1-(2-fluorophenyl)-1H-1,2,3-triazol-4-yl]propyl}-7H-pyrrolo[2,3-d]pyrimidin-4-amine (Example 240) | $^1$HNMR (400 MHz, DMSO-$d_6$) 0.86 (t, 3H), 2.39 (m, 2H), 6.10 (m, 1H), 7.17 (d, 1H), 7.43 (m, 1H), 7.52-7.62 (m, 2H), 7.74 (s, 1H), 7.82 (m, 1H), 7.89 (s, 1H), 7.95 (d, 1H), 8.25 (s, 1H), 8.33 (s, 1H), 8.72 (s, 1H). LCMS m/z = 481.3 [MH]$^+$; [α]$_D$ MeOH = +37.1°; RT [SFC Method B2] = 7.065 min |
| 143 | 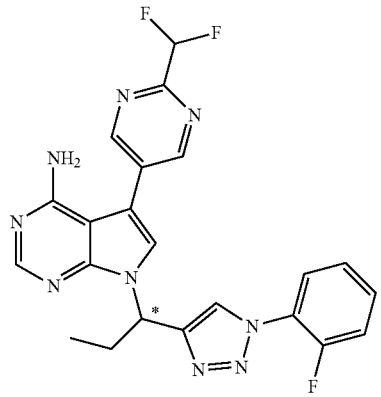<br>Enantiomer 1 | HPLC Method C22A; 5-[2-(Difluoromethyl) pyrimidin-5-yl]-7-{1-[1-(2-fluorophenyl)-1H-1,2,3-triazol-4-yl]propyl}-7H-pyrrolo[2,3-d] pyrimidin-4-amine (Example 221) | $^1$HNMR (400 MHz, DMSO-$d_6$) 0.85 (t, 3H), 2.39 (m, 2H), 6.12 (m, 1H), 6.60 (br s, 2H), 6.88-7.14 (dd, 1H), 7.41 (m, 1H), 7.52-7.62 (m, 2H), 7.82-7.80 (m, 2H), 8.24 (s, 1H), 8.71 (s, 1H), 9.00 (s, 2H). LCMS m/z = 466.1 [MH]$^+$; RT [HPLC Method C7] = 2.873 min |

| Ex. No. | Structure | Separation Method; Starting Material | Analytical Data |
|---|---|---|---|
| 144 | Enantiomer 2 | HPLC Method C22A; 5-[2-(Difluoromethyl) pyrimidin-5-yl]-7-{1-[1-(2-fluorophenyl)-1H-1,2,3-triazol-4-yl]propyl}-7H-pyrrolo[2,3-d] pyrimidin-4-amine (Example 221) | $^1$HNMR (400 MHz, DMSO-$d_6$) 0.85 (t, 3H), 2.39 (m, 2H), 6.12 (m, 1H), 6.60 (br s, 2H), 6.88-7.14 (dd, 1H), 7.41 (m, 1H), 7.52-7.62 (m, 2H), 7.82-7.80 (m, 2H), 8.24 (s, 1H), 8.71 (s, 1H), 9.00 (s, 2H). LCMS m/z = 466.1 [MH]$^+$; RT [HPLC Method C7]= 3.931 min |
| 145 | Enantiomer 1 | HPLC Method C24A; 5-[2-(Dimethylamino) pyrimidin-5-yl]-7-{1-[1-(2-fluorophenyl)-1H-1,2,3-triazol-4-yl]propyl}-7H-pyrrolo[2,3-d]pyrimidin-4-amine (Example 222) | $^1$HNMR (400 MHz, DMSO-$d_6$) 0.84 (t, 3H), 2.33 (m, 2H), 3.16 (s, 6H), 6.08 (m, 1H), 6.24 (br s, 2H), 7.41 (m, 1H), 7.53 (s, 1H), 7.56-7.63 (m, 2H), 7.84 (m, 1H), 8.17 (s, 1H), 8.41 (s, 2H), 8.69 (s, 1H). LCMS m/z = 459.2 [MH]$^+$; RT [HPLC Method A] = 1.278 min |
| 146 | Enantiomer 2 | HPLC Method C24A; 5-[2-(Dimethylamino) pyrimidin-5-yl]-7-{1-[1-(2-fluorophenyl)-1H-1,2,3-triazol-4-yl]propyl}-7H-pyrrolo[2,3-d]pyrimidin-4-amine (Example 222) | $^1$HNMR (400 MHz, DMSO-$d_6$) 0.84 (t, 3H), 2.33 (m, 2H), 3.16 (s, 6H), 6.08 (m, 1H), 6.24 (br s, 2H), 7.41 (m, 1H), 7.53 (s, 1H), 7.56-7.63 (m, 2H), 7.84 (m, 1H), 8.17 (s, 1H), 8.41 (s, 2H), 8.69 (s, 1H). LCMS m/z = 459.2 [MH]$^+$; RT [HPLC method A] = 1.278 min |

-continued

| Ex. No. | Structure | Separation Method Starting Material | Analytical Data |
|---|---|---|---|
| 147 | Enantiomer 1 | HPLC Method F2; 7-{1-[1-(2-Fluorophenyl)-1H-1,2,3-triazol-4-yl]propyl}-5-(1H-pyrazol-3-yl)-7H-pyrrolo[2,3-d]pyrimidin-4-amine (Example 226) | $^1$HNMR (400 MHz, MeOD-d$_4$) 0.96 (t, 3H), 2.43-2.51 (m, 2H), 6.09 (m, 1H), 6.64 (s, 1H), 7.35-7.45 (m, 2H), 7.56 (m, 1H), 7.66 (s, 1H), 7.76 (s, 1H), 7.85 (m, 1H), 8.12 (s, 1H), 8.43 (s, 1H). LCMS m/z = 404.1 [MH]$^+$; RT [HPLC Method D3] = 4.538 min |
| 148 | Enantiomer 2 | HPLC Method F2; 7-{1-[1-(2-Fluorophenyl)-1H-1,2,3-triazol-4-yl]propyl}-5-(1H-pyrazol-3-yl)-7H-pyrrolo[2,3-d]pyrimidin-4-amine (Example 226) | $^1$HNMR (400 MHz, MeOD-d$_4$) 0.96 (t, 3H), 2.43-2.51 (m, 2H), 6.09 (m, 1H), 6.65 (s, 1H), 7.35-7.45 (m, 2H), 7.56 (m, 1H), 7.66 (s, 1H), 7.76 (s, 1H), 7.83 (m, 1H), 8.13 (s, 1H), 8.43 (s, 1H). LCMS m/z = 404.1 [MH]$^+$; RT [HPLC Method D3] = 5.961 min |
| 149 | Enantiomer 1 | SFC Method A4; 7-{1-[1-(4-Fluorophenyl)-1H-1,2,3-triazol-4-yl] propyl}-5-[4-methoxy pyrimidin-5-yl]-7H-pyrrolo[2,3-d]pyrimidin-4-amine (Example 241) | $^1$HNMR (400 MHz, DMSO-d$_6$) 0.84 (t, 3H), 2.33 (m, 2H), 3.92 (s, 3H), 6.08 (m, 1H), 6.29 (br s, 2H), 7.42-7.48 (m, 3H), 7.95 (m, 2H), 8.16 (s, 1H), 8.41 (s, 1H), 8.69 (s, 1H), 8.92 (s, 1H). LCMS m/z = 446.01 [MH]$^+$; [α]$_D$ MeOH = +24.1°; RT [SFC Method A5] = 6.959 min |
| 150 | Enantiomer 2 | SFC Method A4; 7-{1-[1-(4-Fluorophenyl)-1H-1,2,3-triazol-4-yl] propyl}-5-[4-methoxy pyrimidin-5-yl]-7H-pyrrolo[2,3-d]pyrimidin-4-amine (Example 241) | $^1$HNMR (400 MHz, DMSO-d$_6$) 0.84 (t, 3H), 2.33 (m, 2H), 3.92 (s, 3H), 6.08 (m, 1H), 6.32 (br s, 2H), 7.42-7.50 (m, 3H), 7.95 (m, 2H), 8.18 (s, 1H), 8.41 (s, 1H), 8.69 (s, 1H), 8.92 (s, 1H). LCMS m/z = 446.01 [MH]$^+$; [α]$_D$ MeOH = −23.8°; RT [SFC Method A5] = 7.770 min |

| Ex. No. | Structure | Separation Method; Starting Material | Analytical Data |
|---|---|---|---|
| 151 | Enantiomer 1 | SFC Method A3; 7-{1-[1-(3,4-Difluoro phenyl)-1H-1,2,3-triazol-4-yl]propyl}-5-[4-methoxypyrimidin-5-yl]-7H-pyrrolo[2,3-d]pyrimidin-4-amine (Example 245) | $^1$HNMR (400 MHz, DMSO-$d_6$): 0.84 (t, 3H), 2.33 (m, 2H), 3.92 (s, 3H), 6.08 (m, 1H), 6.32 (br s, 2H), 7.35 (m, 1H), 7.54 (s, 1H), 7.72 (m, 1H), 7.90 (m, 1H), 8.18 (m, 1H), 8.42 (s, 1H), 8.70 (s, 1H), 8.77 (s, 1H). LCMS m/z = 465.3 [MH]$^+$; [α]$_D$ MeOH = +28.5° |
| 152 | Enantiomer 2 | SFC Method A3; 7-{1-[1-(3,4-Difluoro phenyl)-1H-1,2,3-triazol-4-yl]propyl}-5-[4-methoxypyrimidin-5-yl]-7H-pyrrolo[2,3-d]pyrimidin-4-amine (Example 245) | $^1$HNMR (400 MHz, DMSO-$d_6$): 0.84 (t, 3H), 2.33 (m, 2H), 3.92 (s, 3H), 6.08 (m, 1H), 6.32 (br s, 2H), 7.35 (m, 1H), 7.54 (s, 1H), 7.72 (m, 1H), 7.90 (m, 1H), 8.18 (m, 1H), 8.42 (s, 1H), 8.70 (s, 1H), 8.77 (s, 1H). LCMS m/z = 465.3 [MH]$^+$; [α]$_D$ MeOH = −22.5° |
| 153 | Enantiomer 1 | HPLC Method G2; 7-{1-[1-(3,4-Difluoro phenyl)-1H-1,2,3-triazol-4-yl]propyl}-5-[2-(trifluoro methyl)pyrimidin-5-yl]-7H-pyrrolo[2,3-d] pyrimidin-4-amine (Example 227) | $^1$HNMR (400 MHz, DMSO-$d_6$) 0.85 (t, 3H), 2.31-2.43 (m, 2H), 6.10 (t, 1H), 6.70 (s, 2H), 7.72 (m, 2H), 7.82 (m, 1H), 8.08 (m, 1H), 8.26 (s, 1H), 8.94 (s, 1H), 9.06 (s, 2H). LCMS m/z = 502.2 [MH]$^+$; RT [HPLC Method G1] = 6.820 min |
| 154 | Enantiomer 2 | HPLC Method G2; 7-{1-[1-(3,4-Difluoro phenyl)-1H-1,2,3-triazol-4-yl]propyl}-5-[2-(trifluoro methyl)pyrimidin-5-yl]-7H-pyrrolo[2,3-d] pyrimidin-4-amine (Example 227) | $^1$HNMR (400 MHz, DMSO-$d_6$) 0.87 (t, 3H), 2.34-2.43 (m, 2H), 6.12 (t, 1H), 7.27 (s, 2H), 7.68 (m, 2H), 7.75 (m, 1H), 7.93 (s, 1H), 8.37 (s, 1H), 8.96 (s, 1H), 9.09 (s, 2H). LCMS m/z = 502.1 [MH]$^+$; RT [HPLC Method G1] = 9.739 min |

| Ex. No. | Structure | Separation Method Starting Material | Analytical Data |
|---|---|---|---|
| 155 | Enantiomer 1 | HPLC Method B6; 7-{1-[1-(3,4-Difluoro phenyl)-1H-1,2,3-triazol-4-yl]propyl}-5-(5-fluoro-2-methoxypyridin-3-yl)-7H-pyrrolo[2,3-d] pyrimidin-4-amine (Example 228) | $^1$HNMR (400 MHz, DMSO-$d_6$) 0.85 (t, 3H), 2.31 (m, 2H), 3.84 (s, 3H), 6.07 (m, 1H), 6.61 (br s, 2H), 7.55 (s, 1H), 7.64 (m, 1H), 7.70 (m, 1H), 7.82 (m, 1H), 8.08 (m, 2H), 8.23 (s, 1H), 8.96 (s, 1H). LCMS m/z = 481.2 [MH]$^+$; RT [HPLC Method B2] = 3.866 min |
| 156 | Enantiomer 2 | HPLC Method B6; 7-{1-[1-(3,4-Difluoro phenyl)-1H-1,2,3-triazol-4-yl]propyl}-5-(5-fluoro-2-methoxypyridin-3-yl)-7H-pyrrolo[2,3-d]pyrimidin-4-amine (Example 228) | $^1$HNMR (400 MHz, DMSO-$d_6$) 0.84 (t, 3H), 2.31 (m, 2H), 3.84 (s, 3H), 6.06 (m, 1H), 6.25 (br s, 2H), 7.49 (s, 1H), 7.62 (m, 1H), 7.72 (m, 1H), 7.82 (m, 1H), 8.10 (m, 2H), 8.16 (s, 1H), 8.95 (s, 1H). LCMS m/z = 481.2 [MH]$^+$; RT [HPLC Method B2] = 5.840 min |
| 157 | Enantiomer 1 | HPLC Method B5; 7-{1-[1-(3,4-Difluoro phenyl)-1H-1,2,3-triazol-4-yl]propyl}-5-(5-fluoro-6-methoxypyridin-3-yl)-7H-pyrrolo[2,3-d] pyrimidin-4-amine (Example 229) | $^1$HNMR (400 MHz, MeOD-$d_4$) 0.85 (t, 3H), 2.31-2.39 (m, 2H), 3.94 (s, 3H), 5.99 (m, 1H), 7.34 (s, 1H), 7.40 (m, 1H), 7.53 (d, 1H), 7.63 (m, 1H), 7.75 (m, 1H), 7.96 (s, 1H), 8.10 (s, 1H), 8.50 (s, 1H). LCMS m/z = 481.2 [MH]$^+$; RT [HPLC Method B2] = 4.327 min |
| 158 | Enantiomer 2 | HPLC Method B5; 7-{1-[1-(3,4-Difluoro phenyl)-1H-1,2,3-triazol-4-yl]propyl}-5-(5-fluoro-6-methoxypyridin-3-yl)-7H-pyrrolo[2,3-d] pyrimidin-4-amine (Example 229) | $^1$HNMR (400 MHz, MeOD-$d_4$) 0.84 (t, 3H), 2.33-2.38 (m, 2H), 3.93 (s, 3H), 5.99 (m, 1H), 7.33 (s, 1H), 7.39 (m, 1H), 7.51 (d, 1H), 7.61 (m, 1H), 7.75 (m, 1H), 7.96 (s, 1H), 8.10 (s, 1H), 8.50 (s, 1H). LCMS m/z = 481.2 [MH]$^+$; RT [HPLC Method B2] = 5.926 min |

-continued

| Ex. No. | Structure | Separation Method Starting Material | Analytical Data |
|---|---|---|---|
| 159 | Enantiomer 1 | SFC Method A6; 7-{1-[1-(2,4-Difluoro phenyl)-1H-1,2,3-triazol-4-yl]propyl}-5-[4-methoxypyrimidin-5-yl]-7H-pyrrolo[2,3-d] pyrimidin-4-amine (Example 246) | $^1$HNMR (400 MHz, DMSO-$d_6$) 0.86 (t, 3H), 2.32-2.40 (m, 2H), 3.97 (s, 3H), 6.08 (m, 1H), 6.32 (br s, 2H), 7.35 (m, 1H), 7.54 (m, 1H), 7.62-7.70 (m, 1H), 7.87 (m, 1H), 8.18 (s, 1H), 8.45 (s, 1H), 8.68 (s, 1H), 8.76 (s, 1H). LCMS m/z = 464.2 [MH]$^+$; [α]$_D$ MeOH = +23.2°; RT [SFC Method A5] = 6.709 min |
| 160 | Enantiomer 2 | SFC Method A6; 7-{1-[1-(2,4-Difluoro phenyl)-1H-1,2,3-triazol-4-yl]propyl}-5-[4-methoxypyrimidin-5-yl]-7H-pyrrolo[2,3-d] pyrimidin-4-amine (Example 246) | $^1$HNMR (400 MHz, DMSO-$d_6$) 0.86 (t, 3H), 2.32-2.40 (m, 2H), 3.97 (s, 3H), 6.08 (m, 1H), 6.32 (br s, 2H), 7.35 (m, 1H), 7.54 (m, 1H), 7.62-7.70 (m, 1H), 7.87 (m, 1H), 8.18 (s, 1H), 8.45 (s, 1H), 8.68 (s, 1H), 8.76 (s, 1H). LCMS m/z = 464.2 [MH]$^+$; [α]$_D$ MeOH = −23.5°; RT [SFC Method A5] = 7.063 min |
| 161 | Enantiomer 1 | HPLC Method C21; 7-{1-[1-(2,4-Difluoro phenyl)-1H-1,2,3-triazol-4-yl]propyl}-5-[2-(trifluoro methyl)pyrimidin-5-yl]-7H-pyrrolo[2,3-d] pyrimidin-4-amine (Example 235) | $^1$HNMR (400 MHz, DMSO-$d_6$) 0.86 (t, 3H), 2.39 (m, 2H), 6.12 (m, 1H), 6.65 (br s, 2H), 7.34 (m, 1H), 7.68 (m, 1H), 7.85-7.91 (m, 2H), 8.25 (s, 1H), 8.69 (d, 1H), 9.06 (s, 2H). LCMS m/z = 502.0 [MH]$^+$; RT [HPLC Method C9] = 4.472 min (+) optical rotation |
| 162 | Enantiomer 2 | HPLC Method C21; 7-{1-[1-(2,4-Difluoro phenyl)-1H-1,2,3-triazol-4-yl]propyl}-5-[2-(trifluoro methyl)pyrimidin-5-yl]-7H-pyrrolo[2,3-d] pyrimidin-4-amine (Example 235) | $^1$HNMR (400 MHz, DMSO-$d_6$) 0.86 (t, 3H), 2.39 (m, 2H), 6.12 (m, 1H), 6.65 (br s, 2H), 7.34 (m, 1H), 7.68 (m, 1H), 7.85-7.91 (m, 2H), 8.25 (s, 1H), 8.69 (d, 1H), 9.06 (s, 2H). LCMS m/z = 502.0 [MH]$^+$; RT [HPLC Method C9] = 4.841 min (−) optical rotation |

| Ex. No. | Structure | Separation Method Starting Material | Analytical Data |
|---|---|---|---|
| 163 | Enantiomer 1 | HPLC Method B6; 7-{1-[1-(2,4-Difluoro phenyl)-1H-1,2,3-triazol-4-yl]propyl}-5-(5-fluoro-2-methoxypyridin-3-yl)-7H-pyrrolo[2,3-d] pyrimidin-4-amine (Example 231) | $^1$HNMR (400 MHz, DMSO-$d_6$) 0.84 (t, 3H), 2.32-2.38 (m, 2H), 3.84 (s, 3H), 6.09 (t, 1H), 6.38 (br s, 2H), 7.35 (m, 1H), 7.59-7.75 (m, 3H), 7.85 (m, 1H), 8.13 (s, 1H), 8.19 (s, 1H), 8.71 (s, 1H). LCMS m/z = 481.2 [MH]$^+$; RT [HPLC Method B3] = 7.019 min |
| 164 | Enantiomer 2 | HPLC Method B6; 7-{1-[1-(2,4-Difluoro phenyl)-1H-1,2,3-triazol-4-yl]propyl}-5-(5-fluoro-2-methoxypyridin-3-yl)-7H-pyrrolo[2,3-d] pyrimidin-4-amine (Example 231) | $^1$HNMR (400 MHz, DMSO-$d_6$) 0.84 (t, 3H), 2.32-2.36 (m, 2H), 3.84 (s, 3H), 6.09 (t, 1H), 6.40 (br s, 2H), 7.35 (m, 1H), 7.59-7.75 (m, 3H), 7.85 (m, 1H), 8.13 (s, 1H), 8.19 (s, 1H), 8.71 (s, 1H). LCMS m/z = 481.2 [MH]$^+$; RT [HPLC Method B3] = 9.528 min |
| 165 | Enantiomer 1 | HPLC Method B5; 7-{1-[1-(2,4-Difluoro phenyl)-1H-1,2,3-triazol-4-yl]propyl}-5-(5-fluoro-6-methoxypyridin-3-yl)-7H-pyrrolo[2,3-d] pyrimidin-4-amine (Example 232) | $^1$HNMR (400 MHz, DMSO-$d_6$) 0.84 (t, 3H), 2.37 (m, 2H), 3.98 (s, 3H), 6.09 (m, 1H), 6.51 (br s, 2H), 7.35 (m, 1H), 7.61 (s, 1H), 7.73 (m, 2H), 7.96 (m, 1H), 8.03 (s, 1H), 8.22 (s, 1H), 8.69 (d, 1H). LCMS m/z = 481.2 [MH]$^+$; RT [HPLC Method B2] = 4.230 min |
| 166 | Enantiomer 2 | HPLC Method B5; 7-{1-[1-(2,4-Difluoro phenyl)-1H-1,2,3-triazol-4-yl]propyl}-5-(5-fluoro-6-methoxypyridin-3-yl)-7H-pyrrolo[2,3-d] pyrimidin-4-amine (Example 232) | $^1$HNMR (400 MHz, DMSO-$d_6$) 0.84 (t, 3H), 2.37 (m, 2H), 3.98 (s, 3H), 6.09 (m, 1H), 6.51 (br s, 2H), 7.35 (m, 1H), 7.61 (s, 1H), 7.73 (m, 2H), 7.96 (m, 1H), 8.03 (s, 1H), 8.22 (s, 1H), 8.69 (d, 1H). LCMS m/z = 481.2 [MH]$^+$; RT [HPLC Method B2] = 10.052 min |

| Ex. No. | Structure | Separation Method Starting Material | Analytical Data |
|---|---|---|---|
| 167 | 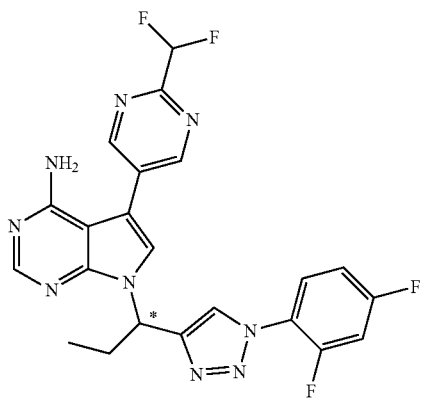

Enantiomer 1 | HPLC Method F8; 5-[2-(Difluoromethyl) pyrimidin-5-yl]-7-{1-[1-(2,4-difluorophenyl)-1H-1,2,3-triazol-4-yl]propyl}-7H-pyrrolo[2,3-d] pyrimidin-4-amine (Example 230) | $^1$HNMR (400 MHz, DMSO-$d_6$) 0.87 (t, 3H), 2.38-2.42 (m, 2H), 6.15 (t, 1H), 7.05 (dd, 1H), 7.35 (m, 1H), 7.65-7.71 (m, 3H), 7.90 (m, 1H), 8.03 (s, 1H), 8.44 (s, 1H), 8.74 (s, 1H), 9.03 (s, 2H). LCMS m/z = 484.2 [MH]$^+$; RT [HPLC Method C5] = 3.056 min |
| 168 |

Enantiomer 2 | HPLC Method F8; 5-[2-(Difluoromethyl) pyrimidin-5-yl]-7-{1-[1-(2,4-difluorophenyl)-1H-1,2,3-triazol-4-yl]propyl}-7H-pyrrolo[2,3-d] pyrimidin-4-amine (Example 230) | $^1$HNMR (400 MHz, DMSO-$d_6$) 0.85 (t, 3H), 2.37-2.42 (m, 2H), 6.12 (t, 1H), 6.79 (br s, 2H), 7.02 (dd, 1H), 7.34 (m, 1H), 7.65 (m, 1H), 7.85 (m, 2H), 8.27 (s, 1H), 8.70 (s, 1H), 9.00 (s, 2H). LCMS m/z = 484.1 [MH]$^+$; RT [HPLC Method C5] = 4.166 min |
| 169 | 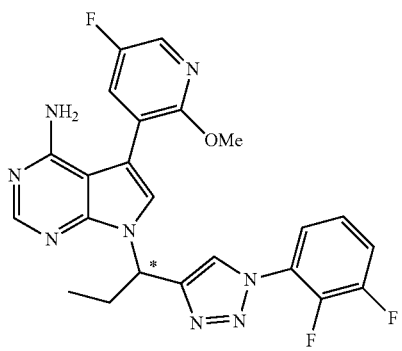

Enantiomer 1 | HPLC Method C30; 7-{1-[1-(2,3-Difluoro phenyl)-1H-1,2,3-triazol-4-yl]propyl}-5-(5-fluoro-2-methoxypyridin-3-yl)-7H-pyrrolo[2,3-d] pyrimidin-4-amine (Example 233) | $^1$HNMR (400 MHz, DMSO-$d_6$) 0.84 (t, 3H), 2.35 (m, 2H), 3.84 (s, 3H), 6.10 (m, 1H), 6.40 (br s, 2H), 7.44 (m, 1H), 7.58-7.63 (m, 2H), 7.68 (m, 2H), 8.14 (s, 1H), 8.19 (s, 1H), 8.78 (s, 1H). LCMS m/z = 481.1 [MH]$^+$; RT [HPLC Method C10] = 2.190 min |

| Ex. No. | Structure | Separation Method Starting Material | Analytical Data |
|---|---|---|---|
| 170 | Enantiomer 2 | HPLC Method C30; 7-{1-[1-(2,3-Difluoro phenyl)-1H-1,2,3-triazol-4-yl]propyl}-5-(5-fluoro-2-methoxypyridin-3-yl)-7H-pyrrolo[2,3-d] pyrimidin-4-amine (Example 233) | $^1$HNMR (400 MHz, DMSO-d$_6$) 0.84 (t, 3H), 2.35 (m, 2H), 3.84 (s, 3H), 6.10 (m, 1H), 6.30 (br s, 2H), 7.44 (m, 1H), 7.58-7.63 (m, 2H), 7.68 (m, 2H), 8.14 (s, 1H), 8.18 (s, 1H), 8.78 (s, 1H). LCMS m/z = 481.1 [MH]$^+$; RT [HPLC Method C10] = 2.511 min |
| 171 | Enantiomer 1 | HPLC Method C30; 7-{1-[1-(2,5-Difluoro phenyl)-1H-1,2,3-triazol-4-yl]propyl}-5-(5-fluoro-2-methoxypyridin-3-yl)-7H-pyrrolo[2,3-d]pyrimidin-4-amine (Example 234) | $^1$HNMR (400 MHz, DMSO-d$_6$) 0.84 (t, 3H), 2.34 (m, 2H), 3.84 (s, 3H), 6.09 (m, 1H), 6.30 (br s, 2H), 7.50 (m, 1H), 7.57 (s, 1H), 7.60-7.65 (m, 2H), 7.84 (m, 1H), 8.14 (d, 1H), 8.18 (s, 1H), 8.75 (d, 1H). LCMS m/z = 481.1 [MH]$^+$; RT [HPLC Method C10] = 2.214 min |
| 172 | Enantiomer 2 | HPLC Method C30; 7-{1-[1-(2,5-Difluoro phenyl)-1H-1,2,3-triazol-4-yl]propyl}-5-(5-fluoro-2-methoxypyridin-3-yl)-7H-pyrrolo[2,3-d]pyrimidin-4-amine (Example 234) | $^1$HNMR (400 MHz, DMSO-d$_6$) 0.84 (t, 3H), 2.34 (m, 2H), 3.84 (s, 3H), 6.09 (m, 1H), 6.30 (br s, 2H), 7.50 (m, 1H), 7.57 (s, 1H), 7.60-7.65 (m, 2H), 7.84 (m, 1H), 8.14 (d, 1H), 8.18 (s, 1H), 8.75 (d, 1H). LCMS m/z = 481.1 [MH]$^+$; RT [HPLC Method C10] = 2.570 min |
| 173 | Enantiomer 1 | SFC Method C3; 5-Cyclopropyl-7-{1-[1-(2-fluorophenyl)-1H-1,2,3-triazol-4-yl]propyl}-7H-pyrrolo[2,3-d]pyrimidin-4-amine (Example 236) | $^1$HNMR (400 MHz, DMSO-d$_6$) 0.54 (m, 2H), 0.76-0.85 (m, 6H), 2.20-2.33 (m, 2H), 5.95 (m, 1H), 6.60 (br s, 2H), 7.02 (s, 1H), 7.42 (m, 1H), 7.52-7.62 (m, 2H), 7.81 (m, 1H), 8.05 (s, 1H), 8.61 (s, 1H). LCMS m/z = 378.4 [MH]$^+$; [α]$_D$ MeOH = −26.0°; RT [SFC Method C2] = 5.618 min |

| Ex. No. | Structure | Separation Method Starting Material | Analytical Data |
|---|---|---|---|
| 174 | 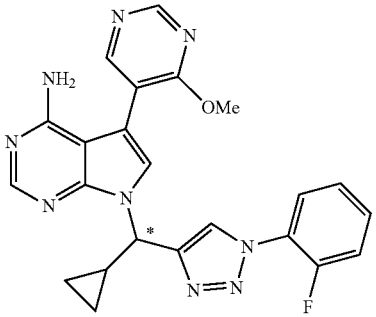<br>Enantiomer 1 | SFC Method D4; 7-{Cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine (Example 243) | $^1$HNMR (400 MHz, DMSO-$d_6$) 0.45 (m, 1H), 0.58 (m, 2H), 0.71 (m, 1H), 1.96 (m, 1H), 3.94 (s, 3H), 5.46 (d, 1H), 6.29 (s, 2H), 7.43 (m, 1H), 7.56-7.63 (m, 3H), 7.84 (m, 1H), 8.13 (s, 1H), 8.43 (s, 1H), 8.76 (s, 2H). LCMS m/z = 458.1 [MH]$^+$; [α]$_D$ MeOH = +29.5°; RT [SFC Method D2] = 8.319 min |
| 175 | 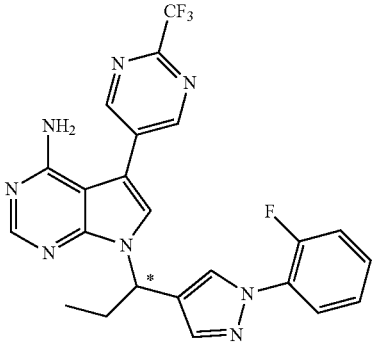<br>Enantiomer 1 | HPLC Method C33; 7-{1-[1-(2-Fluorophenyl)-1H-pyrazol-4-yl]propyl}-5-[2-(trifluoromethyl)pyrimidin-5-yl]-7H-pyrrolo[2,3-d]pyrimidin-4-amine (Example 271) | $^1$HNMR (400 MHz, DMSO-$d_6$) 0.83 (t, 3H), 2.31 (m, 2H), 5.92 (t, 1H), 6.63 (br s, 2H), 7.31 (m, 1H), 7.43 (m, 2H), 7.74 (t, 1H), 7.78 (s, 1H), 7.90 (s, 1H), 8.25 (s, 1H), 8.29 (s, 1H), 9.06 (s, 2H). LCMS m/z = 483.2 [MH]$^+$; RT [HPLC Method C12] = 3.70 min |
| 176 | 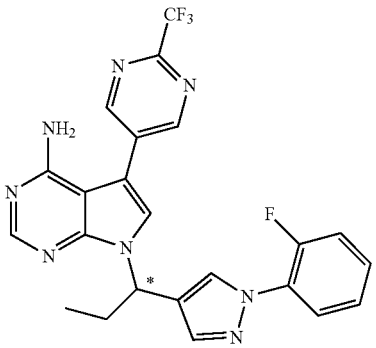<br>Enantiomer 2 | HPLC Method C33; 7-{1-[1-(2-Fluorophenyl)-1H-pyrazol-4-yl]propyl}-5-[2-(trifluoromethyl)pyrimidin-5-yl]-7H-pyrrolo[2,3-d]pyrimidin-4-amine (Example 271) | $^1$HNMR (400 MHz, DMSO-$d_6$) 0.83 (t, 3H), 2.31 (m, 2H), 5.92 (t, 1H), 6.63 (br s, 2H), 7.31 (m, 1H), 7.43 (m, 2H), 7.74 (t, 1H), 7.78 (s, 1H), 7.90 (s, 1H), 8.25 (s, 1H), 8.29 (s, 1H), 9.06 (s, 2H). LCMS m/z = 483.2 [MH]$^+$; RT [HPLC Method C12] = 4.460 min |
| 177 | 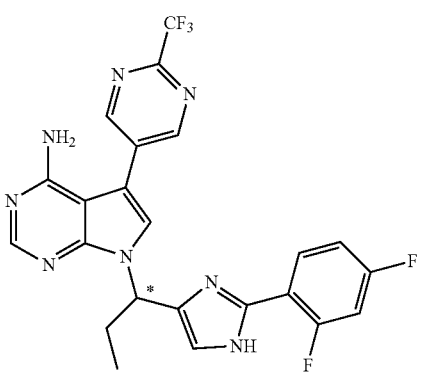<br>Enantiomer 1 | HPLC Method C20B; 7-{1-[2-(2,4-Difluorophenyl)-2H-imidazol-4-yl]propyl}-5-[2-(trifluoromethyl)pyrimidin-5-yl]-7H-pyrrolo[2,3-d] pyrimidin-4-amine (Example 276) | $^1$HNMR (400 MHz, DMSO-$d_6$) 0.82 (t, 3H), 2.26 (m, 1H), 2.34 (m, 1H), 5.88 (t, 1H), 6.59 (s, 2H), 7.13 (t, 1H), 7.27 (s, 1H), 7.40 (t, 1H), 7.82 (s, 1H), 7.98 (t, 1H), 8.24 (s, 1H), 9.05 (s, 2H), 12.22 (s, 1H). LCMS m/z = 501.2 [MH]$^+$; RT [HPLC Method C2] = 2.994 min |

| Ex. No. | Structure | Separation Method Starting Material | Analytical Data |
|---|---|---|---|
| 178 | 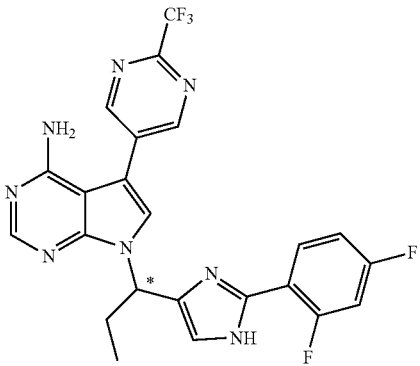<br>Enantiomer 2 | HPLC Method C20B; 7-{1-[2-(2,4-Difluoro phenyl)-2H-imidazol-4-yl]propyl}-5-[2-(trifluoro methyl)pyrimidin-5-yl]-7H-pyrrolo[2,3-d] pyrimidin-4-amine (Example 276) | $^1$HNMR (400 MHz, DMSO-d$_6$) 0.82 (t, 3H), 2.26 (m, 1H), 2.34 (m, 1H), 5.88 (t, 1H), 6.59 (s, 2H), 7.13 (t, 1H), 7.27 (s, 1H), 7.40 (t, 1H), 7.82 (s, 1H), 7.98 (t, 1H), 8.24 (s, 1H), 9.05 (s, 2H), 12.22 (s, 1H). LCMS m/z = 501.2 [MH]$^+$; RT [HPLC Method C2] = 3.524 min |
| 179 | 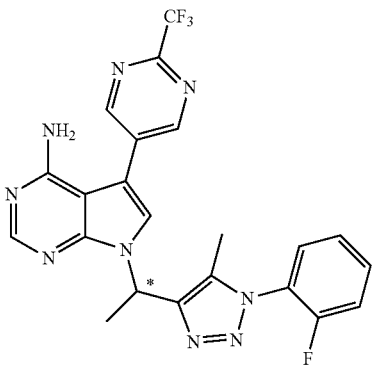<br>Enantiomer 1 | HPLC Method C34; 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine (Example 273) | $^1$HNMR (400 MHz, DMSO-d$_6$) 1.98 (d, 3H), 2.17 (s, 3H), 6.31 (m, 1H), 6.65 (br s, 2H), 7.41 (m, 1H), 7.54-7.65 (m, 3H), 7.93 (s, 1H), 8.26 (s, 1H), 9.07 (s, 2H). LCMS m/z = 484.2 [MH]$^+$; RT [HPLC Method F5] = 3.796 min |
| 180 | 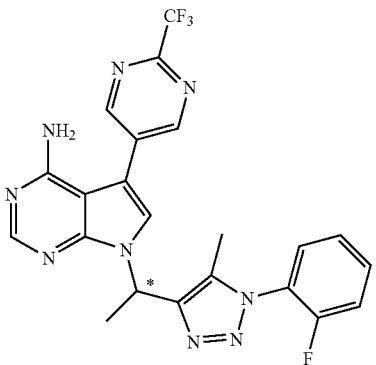<br>Enantiomer 2 | HPLC Method C34 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine (Example 273) | $^1$HNMR (400 MHz, DMSO-d$_6$) 1.98 (d, 3H), 2.17 (s, 3H), 6.31 (m, 1H), 6.65 (br s, 2H), 7.41 (m, 1H), 7.54-7.65 (m, 3H), 7.93 (s, 1H), 8.26 (s, 1H), 9.07 (s, 2H). LCMS m/z = 484.2 [MH]$^+$; RT [HPLC Method F5] = 4.868 min |

| Ex. No. | Structure | Separation Method Starting Material | Analytical Data |
|---|---|---|---|
| 181 | (Enantiomer 1) | SFC Method C1; 5-(4-Chlorophenyl)-7-{1-[3-(2-fluorophenyl)-1,2-oxazol-5-yl]ethyl}-7H-pyrrolo[2,3-d]pyrimidin-4-amine (Example 258) | $^1$HNMR (400 MHz, CDCl$_3$): 2.01 (d, 3H), 5.18 (br s, 2H), 6.46 (q, 1H), 6.65 (d, 1H), 7.12-7.30 (m, 4H), 7.48 (s, 4H), 7.95 (t, 1H), 8.38 (s, 1H). LCMS m/z = 434.3 [MH]$^+$; [□]$_D$ MeOH = +23.3°; RT [SFC Method C2] = 2.90 min |
| 182 | (Enantiomer 2) | SFC Method C1; 5-(4-Chlorophenyl)-7-{1-[3-(2-fluorophenyl)-1,2-oxazol-5-yl]ethyl}-7H-pyrrolo[2,3-d]pyrimidin-4-amine (Example 258) | $^1$HNMR (400 MHz, CDCl$_3$): 2.01 (d, 3H), 5.18 (br s, 2H), 6.46 (q, 1H), 6.65 (d, 1H), 7.12-7.30 (m, 4H), 7.48 (s, 4H), 7.95 (t, 1H), 8.38 (s, 1H). LCMS m/z = 434.3 [MH]$^+$; [□]$_D$ MeOH = −22.3° |

Examples 183 and 184: 7-{1-[3-(2-fluorophenyl) isoxazol-5-yl]ethyl}-5-(2-methoxypyrimidin-5-yl)-7H-pyrrolo [2,3-d]pyrimidin-4-amine, Enantiomers 1 and 2

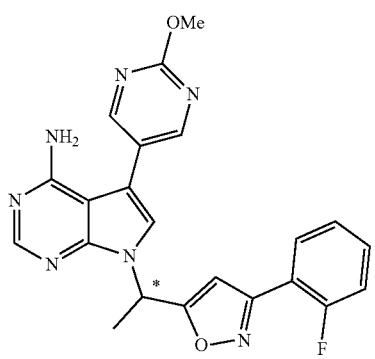 [SMILES: COc1ncc(-c2cn(C(C)c3cc(-c4ccccc4F)no3)c3ncnc(N)c23)cn1]

To a stirred solution of 7-{1-[3-(2-fluorophenyl)isoxazol-5-yl]ethyl}-5-iodo-7H-pyrrolo[2,3-d]pyrimidin-4-amine (Preparation 59, 1 g, 2.226 mmol) in EtOH:H$_2$O (30 mL, 4:1) was added 2-methoxypyrimidin-5-ylboronic acid (0.514 g, 3.34 mmol) and Na$_2$CO$_3$ (0.944 g, 8.904 mmol). The reaction mixture was degassed with Ar for 15 minutes and Pd(PPh$_3$)$_4$ (0.154 g, 0.134 mmol) added and the reaction heated at 90° C. for 6 hrs. The cooled mixture was concentrated to dryness in vacuo, diluted with H$_2$O and extracted with EtOAc. The combined extracts were dried (Na$_2$SO$_4$), evaporated to dryness and the residue purified by flash chromatography to afford the title compound (530 mg, 55%) as off white solid. This was combined with the product of a parallel reaction (210 mg).

The product was purified by chiral SFC method A7, to afford Example 183, enantiomer 1, (−) 7-{1-[3-(2-fluorophenyl)-1,2-oxazol-5-yl]ethyl}-5-(2-methoxypyrimidin-5-yl)-7H-pyrrolo[2,3-d]pyrimidin-4-amine (238.5 mg). $^1$HNMR (400 MHz, DMSO-d$_6$): 1.95 (d, 3H), 3.96 (s, 3H), 6.32 (q, 1H), 6.46 (br s, 2H), 6.92 (s, 1H), 7.35 (m, 1H), 7.41 (m, 1H), 7.57 (m, 1H), 7.64 (s, 1H), 7.85 (m, 1H), 8.22 (s, 1H), 8.63 (s, 2H). LCMS m/z=432.3 [MH]$^+$; RT [SFC method A8]=7.434 min; [α]$_D$ MeOH=−11.7°.

Further elution provided Example 184, enantiomer 2, (+) 7-{1-[3-(2-fluorophenyl)-1,2-oxazol-5-yl]ethyl}-5-(2-methoxypyrimidin-5-yl)-7H-pyrrolo[2,3-d]pyrimidin-4-amine (323.8 mg). $^1$HNMR (400 MHz, DMSO-d$_6$): 1.95 (d, 3H), 3.96 (s, 3H), 6.32 (q, 1H), 6.46 (br s, 2H), 6.92 (s, 1H), 7.35 (m, 1H), 7.41 (m, 1H), 7.57 (m, 1H), 7.64 (s, 1H), 7.85 (m, 1H), 8.22 (s, 1H), 8.63 (s, 2H). LCMS m/z=432.3 [MH]$^+$; RT [SFC method A8]=8.212 min; [α]$_D$ MeOH=+12.6°.

Examples 185 and 186: 7-{1-[1-(2,5-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, Enantiomers 1 and 2

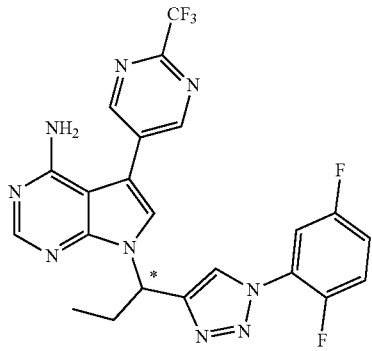 [SMILES: CCC(c1cn(-c2cc(F)ccc2F)nn1)n1cc(-c2cnc(C(F)(F)F)nc2)c2c(N)ncnc21]

Step 1: To a solution of 7-{1-[1-(2,5-difluorophenyl)-1H-1,2,3-triazol-4-yl]propyl}-5-iodo-7H-pyrrolo[2,3-d]pyrimidin-4-amine (Preparation 49, 400 mg, 0.83 mmol) in dioxane (20 mL) and water (5 mL) under $N_2$, was added 5-(4,4,5,5-tetramethyl-1,3,2-dioxaborolan-2-yl)-2-(trifluoromethyl)pyrimidine (250 mg, 0.91 mmol), Pd(dppf)Cl$_2$ (61 mg, 0.08 mmol), K$_2$CO$_3$ (344 mg, 2.49 mmol) and the reaction heated at 85° C. for 6 hrs. The cooled mixture was evaporated under reduced pressure and the residue purified by HPLC to afford 7-{1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine (125 mg, 30%).

Step 2: The racemic product was further purified by chiral HPLC using Method C31 to afford 7-{1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 1, Example 185, as a white solid (77 mg). $^1$HNMR (400 MHz, DMSO-d$_6$): 0.86 (t, 3H), 2.39 (m, 2H), 6.13 (m, 1H), 6.78 (br s, 2H), 7.49 (m, 1H), 7.65 (m, 1H), 7.79 (m, 1H), 7.92 (s, 1H), 8.27 (s, 1H), 8.68 (s, 1H), 9.07 (s, 2H). LCMS m/z=502.1 [MH]$^+$ RT [HPLC Method C10]=2.318 min.

Further elution provided enantiomer 2, Example 186, as a white solid, (46 mg). $^1$HNMR (400 MHz, DMSO-d$_6$): 0.86 (t, 3H), 2.39 (m, 2H), 6.13 (m, 1H), 6.84 (br s, 2H), 7.49 (m, 1H), 7.65 (m, 1H), 7.80 (m, 1H), 7.91 (s, 1H), 8.26 (s, 1H), 8.75 (s, 1H), 9.07 (s, 2H). LCMS m/z=502.1 [MH]$^+$ RT [HPLC Method C10]=2.871 min.

Examples 187 and 188: 7-{1-[1-(2,3-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, Enantiomers 1 and 2

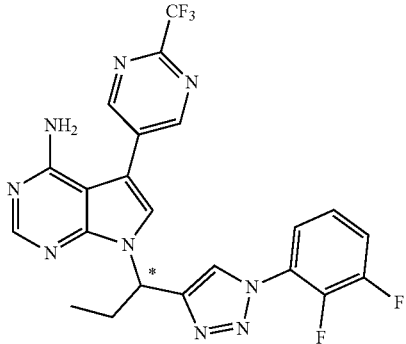 [SMILES: CCC(c1cn(-c2cccc(F)c2F)nn1)n1cc(-c2cnc(C(F)(F)F)nc2)c2c(N)ncnc21]

Step 1: 7-{1-[1-(2,3-Difluorophenyl)-1H-1,2,3-triazol-4-yl]propyl}-5-[2-(trifluoromethyl)pyrimidin-5-yl]-7H-pyrrolo[2,3-d]pyrimidin-4-amine was prepared from 7-{1-[1-(2,3-difluorophenyl)-1H-1,2,3-triazol-4-yl]propyl}-5-iodo-7H-pyrrolo[2,3-d]pyrimidin-4-amine (Preparation 50) and 5-(4,4,5,5-tetramethyl-1,3,2-dioxaborolan-2-yl)-2-(trifluoromethyl)pyrimidine, following a similar procedure to that described in Step 1 of Example 185/186.

Step 2: The compound from Step 1 was purified by chiral HPLC method F9, to afford 7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 1 $^1$HNMR (400 MHz, DMSO-d$_6$): 0.86 (t, 3H), 2.39 (m, 2H), 6.14 (m, 1H), 6.72 (br s, 2H), 7.46 (m, 1H), 7.64 (m, 2H), 7.92 (s, 1H), 8.26 (s, 1H), 8.77 (s, 1H), 9.07 (s, 2H). LCMS m/z=502.1 [MH]$^+$; RT [HPLC Method C10]=2.311 min.

and enantiomer 2; $^1$HNMR (400 MHz, DMSO-d$_6$): 0.86 (t, 3H), 2.39 (m, 2H), 6.14 (m, 1H), 6.72 (br s, 2H), 7.46 (m, 1H), 7.64 (m, 2H), 7.92 (s, 1H), 8.26 (s, 1H), 8.77 (s, 1H), 9.07 (s, 2H). LCMS m/z=502.1 [MH]$^+$; RT [HPLC Method C10]=2.843 min

Examples 189 and 190: 7-{1-[1-(2,4-Difluorophenyl)-5-methyl-1H-1,2,3-triazol-4-yl]propyl}-7H-pyrrolo[2,3-d] pyrimidin-4-amine, Enantiomer 1 and 2

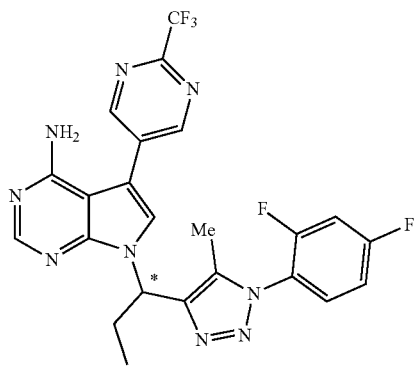 [SMILES: CCC(c1nnn(-c2ccc(F)cc2F)c1C)n1cc(-c2cnc(C(F)(F)F)nc2)c2c(N)ncnc21]

To a solution of N'-(7-(1-(1-(2,4-difluorophenyl)-5-methyl-1H-1,2,3-triazol-4-yl)propyl)-5-(2-(trifluoromethyl)pyrimidin-5-yl)-7H-pyrrolo[2,3-d]pyrimidin-4-yl)-N,N-dimethylformimidamide (Preparation 9, 2.8 g, 4.92 mmol) in dioxane was added NH$_4$OH (25 mL) and the sealed tube was heated at 100° C. for 18 hrs. The solvent was evaporated and the residue was diluted with EtOAc (150 mL) and water. The organic extract was washed with brine, dried (Na$_2$SO$_4$) and evaporated to dryness in vacuo. The residue was purified by prep-HPLC to provide 7-{1-[1-(2,4-difluorophenyl)-5-methyl-1H-1,2,3-triazol-4-yl]propyl}-7H-pyrrolo[2,3-d]pyrimidin-4-amine as a white solid (1.9 g, 75%). The solid was separated by HPLC using a CHIRALPAK IC column to afford enantiomer 1 (700 mg, 36%). $^1$HNMR (400 MHz, MeOD-d$_4$): 0.87 (t, 3H), 2.15 (s, 3H), 2.42 (m, 2H), 6.01 (t, 1H), 7.11 (m, 1H), 7.26 (m, 1H), 7.48 (m, 1H), 7.72 (s, 1H), 8.17 (s, 1H), 8.98 (s, 2H). LCMS m/z=516.2 [MH]$^+$; RT [HPLC method C13]=2.297 min;

Further elution provided enantiomer 2 (725 mg, 38%). $^1$HNMR (400 MHz, MeOD-d$_4$): 0.87 (t, 3H), 2.15 (s, 3H), 2.42 (m, 2H), 6.01 (t, 1H), 7.11 (m, 1H), 7.26 (m, 1H), 7.48

(m, 1H), 7.72 (s, 1H), 8.17 (s, 1H), 8.98 (s, 2H). LCMS m/z=516.2 [MH]⁺; RT [HPLC method C13]=3.405 min.

Example 191: 7-{1-[3-(2-Fluorophenyl)-1,2-oxazol-5-yl]ethyl}-5-(5-methoxypyrazin-2-yl)-7H-pyrrolo[2,3-d]pyrimidin-4-amine

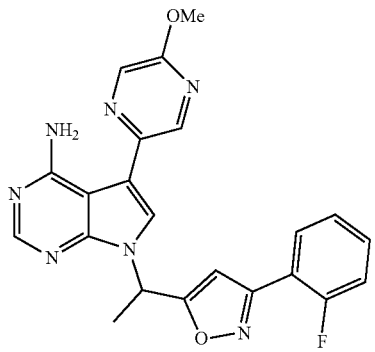 [SMILES: COc1cnc(-c2cn(C(C)c3cc(-c4ccccc4F)no3)c3ncnc(N)c23)cn1]

A stirred solution of 7-{1-[3-(2-Fluorophenyl)isoxazol-5-yl]ethyl}-5-iodo-7H-pyrrolo[2,3-d]pyrimidin-4-amine (Preparation 59, 100 mg, 0.226 mmol), 2-methoxy-5-(4,4,5,5-tetramethyl-1,3,2-dioxaborolan-2-yl)pyrazine (105 mg, 0.445 mmol) and K₃PO₄ (189 mg, 0.89 mmol) in dioxane:water (2.5 mL, 4:1) was degassed with N₂ for 30 mins. To this was added Pd₂(dba)₃ (20.38 mg, 0.022 mmol) followed by SPhos (18.25 mg, 0.045 mmol) and the mixture degassed for another 5 min and heated to 110° C. for 16 hr. The reaction mixture was partitioned between water and EtOAc, and the water further extracted with EtOAc. The combined organics were washed with water, brine, dried (Na₂SO₄) and evaporated to dryness in vacuo. The residue was purified by column chromatography on silica gel eluting with MeOH:DCM (0:100-1:10) followed by prep-TLC to afford the title compound as an off-white solid (18.5 mg, 19.3%). ¹HNMR (400 MHz, DMSO-d₆): 1.98 (d, 3H), 3.94 (s, 3H), 6.33 (q, 1H), 6.90 (m, 1H), 7.30-7.45 (m, 3H), 7.56 (q, 1H), 7.86 (m, 1H), 8.13 (br s, 1H), 8.27 (s, 1H), 8.33 (m, 1H), 8.89 (s, 1H). LCMS m/z=432.2 [MH]⁺

Example 192: 4-(4-Amino-7-{[2-(2-fluorophenyl)-1H-imidazol-5-yl]methyl}-7H-pyrrolo[2,3-d]pyrimidin-5-yl)-2-fluorobenzonitrile

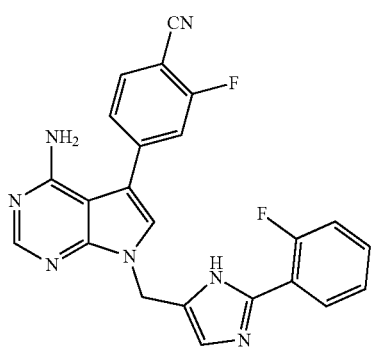 [SMILES: N#Cc1ccc(-c2cn(Cc3cnc(-c4ccccc4F)[nH]3)c3ncnc(N)c23)cc1F]

A stirred solution of 7-{[2-(2-fluorophenyl)-1H-imidazol-5-yl]methyl}-5-iodo-7H-pyrrolo[2,3-d]pyrimidin-4-amine (Preparation 58, 100 mg, 0.23 mmol), (4-cyano-3-fluorophenyl)boronic acid (76.76 mg, 0.46 mmol) and Na₂CO₃ (97.47 mg, 0.92 mmol) in EtOH:water (4:1, 5 mL) was degassed with N₂ for 30 mins. To this was added Pd(PPh₃)₄ (15.9 mg, 0.014 mmol) and the resulting brown suspension was heated to 110° C. for 6 hr. The reaction mixture was cooled to rt, diluted with water and extracted with EtOAc (2×). The combined extracts were washed with water, brine, dried (Na₂SO₄) and concentrated under reduced pressure. The residue was purified by column chromatography on silica gel eluting with MeOH:DCM (0:100-1:10) to afford the title compound as an off white solid (24 mg, 24.4%). ¹HNMR (400 MHz, MeOH-d₄): 5.58 (s, 2H), 7.32-7.44 (m, 3H), 7.56 (m, 1H), 7.60-7.67 (m, 3H), 7.93 (t, 1H), 8.09 (m, 1H), 8.40 (s, 1H). LCMS m/z=428 [MH]⁺

Example 193: 7-{[2-(2-Fluorophenyl)-1H-imidazol-5-yl]methyl}-5-(2-methoxypyridin-3-yl)-7H-pyrrolo[2,3-d]pyrimidin-4-amine

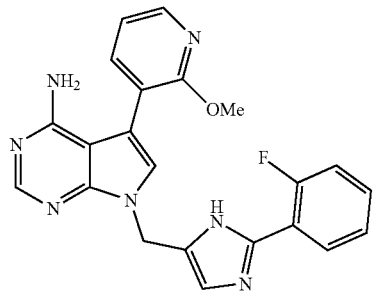 [SMILES: COc1ncccc1-c1cn(Cc2cnc(-c3ccccc3F)[nH]2)c2ncnc(N)c12]

The title compound was prepared as a white solid (235 mg, 41%) in an analogous manner to Example 192 using 7-{[2-(2-fluorophenyl)-1H-imidazol-5-yl]methyl}-5-iodo-7H-pyrrolo[2,3-d]pyrimidin-4-amine (Preparation 68, 500 mg, 1.15 mmol) and (2-methoxypyridin-3-yl)boronic acid (352 mg, 2.3 mmol). ¹HNMR (400 MHz, MeOD-d₄): 3.92 (s, 3H), 5.40 (s, 2H), 7.03 (dd, 1H), 7.12-7.30 (m, 4H), 7.40 (q, 1H), 7.67 (dd, 1H), 7.95 (t, 1H), 8.12-8.22 (m, 3H). LCMS m/z=416 [MH]⁺

Example 194: 7-{[1-(2-Fluorophenyl)-1H-1,2,3-triazol-4-yl]methyl}-5-(2-methoxy-6-methylpyridin-3-yl)-7H-pyrrolo[2,3-d]pyrimidin-4-amine

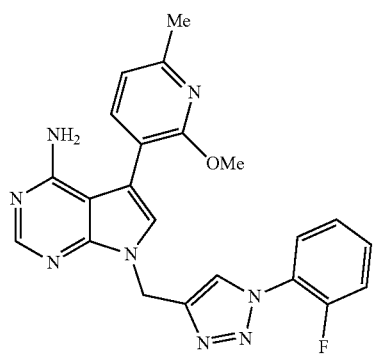 [SMILES: COc1nc(C)ccc1-c1cn(Cc2cn(-c3ccccc3F)nn2)c2ncnc(N)c12]

A stirred solution of 7-{[1-(2-fluorophenyl)-1H-1,2,3-triazol-4-yl]methyl}-5-iodo-7H-pyrrolo[2,3-d]pyrimidin-4- amine (Preparation 95, 150 mg, 0.345 mmol) in EtOH:water (4:1, 3 mL), (2-methoxy-6-methylpyridin-3-yl)boronic acid (86.32 mg, 0.517 mmol) and Na$_2$CO$_3$ (146.14 mg, 1.37 mmol) was degassed with Ar for 15 minutes and Pd(PPh$_3$)$_4$ (39.8 mg, 0.034 mmol) added and reaction mixture heated at 100° C. for 16 hours. The reaction was cooled to rt, diluted with water and extracted with EtOAc. The combined organics were dried (Na$_2$SO$_4$) and evaporated to dryness in vacuo. The residue was purified flash chromatography and prep-TLC to afford the title compound as an off-white solid (26 mg, 15%). $^1$HNMR (400 MHz, DMSO-d$_6$): 2.44 (s, 3H), 3.84 (s, 3H), 5.55 (s, 2H), 6.00 (br s, 2H), 6.92 (d, 1H), 7.36 (s, 1H), 7.42 (t, 1H), 7.51-7.61 (m, 3H), 7.82 (t, 1H), 8.16 (s, 1H), 8.61 (s, 1H). LCMS m/z=431 [MH]$^+$ Example 195: 5-(5-Fluoro-2-methoxypyridin-3-yl)-7-{[1-(2-fluorophenyl)-1H-1,2,3-triazol-4-yl]methyl}-7H-pyrrolo[2,3-d]pyrimidin-4-amine

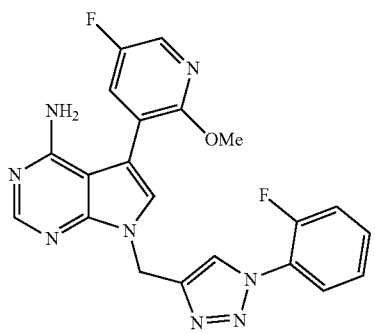 [SMILES: COc1ncc(F)cc1-c1cn(Cc2cn(-c3ccccc3F)nn2)c2ncnc(N)c12]

The title compound was prepared in an analogous manner to Example 194 using 7-{[1-(2-fluorophenyl)-1H-1,2,3-triazol-4-yl]methyl}-5-iodo-7H-pyrrolo[2,3-d]pyrimidin-4-amine (Preparation 95) and 5-fluoro-2-methoxy-3-(4,4,5,5-tetramethyl-1,3,2-dioxaborolan-2-yl)pyridine (Preparation 140) and obtained as a white solid (25 mg, 20.8%). $^1$HNMR (400 MHz, DMSO-d$_6$): 3.85 (s, 3H), 5.56 (s, 2H), 6.23 (br s, 2H), 7.42 (t, 1H), 7.47-7.63 (m, 4H), 7.81 (t, 1H), 8.11 (d, 1H), 8.17 (s, 1H), 8.62 (s, 1H). LCMS m/z=435 [MH]$^+$ Example 196: 5-[2-(Difluoromethoxy)pyridin-3-yl]-7-{[1-(2-fluorophenyl)-1H-1,2,3-triazol-4-yl]methyl}-7H-pyrrolo[2,3-d]pyrimidin-4-amine

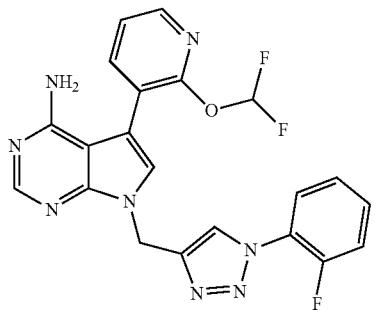 [SMILES: Nc1ncnc2c1c(-c1cccnc1OC(F)F)cn2Cc1cn(-c2ccccc2F)nn1]

A stirred solution of 7-{[1-(2-fluorophenyl)-1H-1,2,3-triazol-4-yl]methyl}-5-iodo-7H-pyrrolo[2,3-d]pyrimidin-4-amine (Preparation 95, 100 mg, 0.23 mmol), 2-(difluoromethoxy)-3-(4,4,5,5-tetramethyl-1,3,2-dioxaborolan-2-yl)pyridine (155 mg, 0.575 mmol) and Cs$_2$CO$_3$ (299.7 mg, 0.92 mmol) in DMF:water (4:1, 10 mL) was degassed with Ar for 15 mims. PdCl$_2$(dppf).DCM (37.5 mg, 0.046 mmol) was added and reaction mixture was heated at 100° C. for 6 hrs. The reaction was cooled to rt, diluted with water and extracted with EtOAc. The combined organics were dried (Na$_2$SO$_4$) and evaporated to dryness in vacuo. The residue was purified flash chromatography and prep-TLC to afford the title compound as an off-white solid (12.5 mg, 12.02%). $^1$HNMR (400 MHz, DMSO-d$_6$): 5.59 (s, 2H), 6.22 (br s, 2H), 7.32-7.90 (m, 8H), 8.19 (s, 1H), 8.22 (m, 1H), 8.61 (m, 1H). LCMS m/z=453 [MH]$^+$ Example 197: 7-{[1-(2-Fluorophenyl)-1H-1,2,3-triazol-4-yl]methyl}-5-(1,3-oxazol-5-yl)-7H-pyrrolo[2,3-d]pyrimidin-4-amine

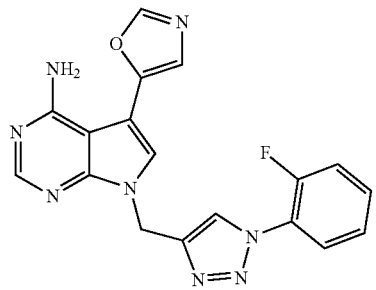 [SMILES: Nc1ncnc2c1c(-c1cnco1)cn2Cc1cn(-c2ccccc2F)nn1]

The title compound was prepared as a white solid (15 mg, 11.6%) in an analogous manner to Example 196 using 7-{[1-(2-fluorophenyl)-1H-1,2,3-triazol-4-yl]methyl}-5-iodo-7H-pyrrolo[2,3-d]pyrimidin-4-amine (Preparation 95, 150 mg, 0.345 mmol) and 5-(4,4,5,5-tetramethyl-1,3,2-dioxaborolan-2-yl)oxazole (168.1 mg, 0.862 mmol). $^1$HNMR (400 MHz, DMSO-d$_6$): 5.62 (s, 2H), 7.32-7.43 (m, 3H), 7.54 (m, 1H), 7.74 (s, 1H), 7.81 (t, 1H), 8.21 (s, 1H), 8.26 (s, 1H). 8.40 (d, 1H). LCMS m/z=377.0 [MH]$^+$ Example 198: 7-{[1-(2-Fluorophenyl)-1H-1,2,3-triazol-4-yl]methyl}-5-(tetrahydrofuran-2-yl)-7H-pyrrolo[2,3-d]pyrimidin-4-amine

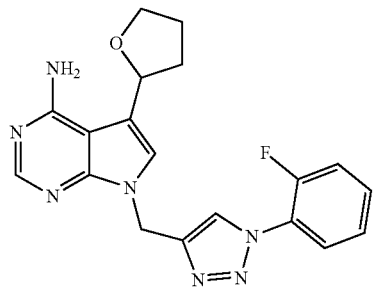 [SMILES: Nc1ncnc2c1c(C1CCCO1)cn2Cc1cn(-c2ccccc2F)nn1]

To a stirred solution of 5-(2,5-dihydrofuran-2-yl)-7-{[1-(2-fluorophenyl)-1H-1,2,3-triazol-4-yl]methyl}-7H-pyrrolo[2,3-d]pyrimidin-4-amine (Example 199, 40 mg, 0.106 mmol) in MeOH (2.0 mL) was added 50% moist Pd/C (20.0 mg) and the reaction mixture was stirred at rt under H$_2$ for 16 hr. The reaction mixture was filtered through Celite® and the solvent was evaporated to dryness in vacuo. The residue was purified by prep-TLC to afford the title compound as an off-white solid (10 mg, 32%). $^1$HNMR (400 MHz, DMSO-d$_6$): 1.24 (s, 1H), 1.87-2.23 (m, 3H), 3.83 (m, 1H), 3.94 (m, 1H), 4.96 (m, 1H), 5.47 (s, 2H), 6.79 (br s, 2H), 7.24 (s, 1H), 7.42 (t, 1H), 7.53-7.62 (m, 2H), 7.81 (t, 1H), 8.11 (s, 1H), 8.55 (s, 1H). LCMS m/z=380 [MH]$^+$ Example 199: 5-(2,5-Dihydrofuran-2-yl)-7-((1-(2-fluorophenyl)-1H-1,2,3-triazol-4-yl)methyl)-7H-pyrrolo[2,3-d]pyrimidin-4-amine

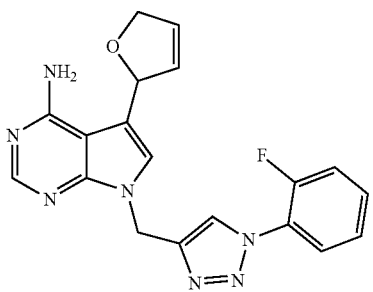 [SMILES: Nc1ncnc2c1c(C1C=CCO1)cn2Cc1cn(-c2ccccc2F)nn1]

To a degassed solution of 7-{[1-(2-fluorophenyl)-1H-1,2,3-triazol-4-yl]methyl}-5-iodo-7H-pyrrolo[2,3-d]pyrimidin-4-amine (Preparation 95, 2.0 g, 4.59 mmol) was added Bu$_4$NCl (1.59 g, 5.74 mmol), NaOAc (1.31 g, 13.78 mmol), 2,3-dihydrofuran (3.47 mL, 45.95 mmol) and Pd(OAc)$_2$ (1.03 g, 4.59 mmol). Degassing was discontinued for 15 min and the resulting reaction mixture was heated to 50° C. for 2 hrs. The reaction mixture was diluted with water and extracted with EtOAc. The combined organics were washed with water, brine, dried (Na$_2$SO$_4$) and evaporated to dryness in vacuo. The residue was purified by column chromatography on silica gel followed by prep-HPLC, to afford the title compound as an off white solid (80 mg, 4.6%). $^1$HNMR (400 MHz, DMSO-d$_6$) 4.67 (s, 2H), 5.47 (s, 2H), 6.02 (br s, 1H), 6.22 (m, 2H), 6.67 (br s, 2H), 7.42 (t, 1H), 7.51-7.64 (m, 2H), 7.81 (t, 1H), 8.12 (s, 1H), 8.56 (s, 1H). LCMS m/z=378 [MH]$^+$ Example 200: 7-{[1-(2-Fluorophenyl)-1H-1,2,3-triazol-4-yl]methyl}-5-(4-methoxypyrimidin-5-yl)-7H-pyrrolo[2,3-d]pyrimidin-4-amine

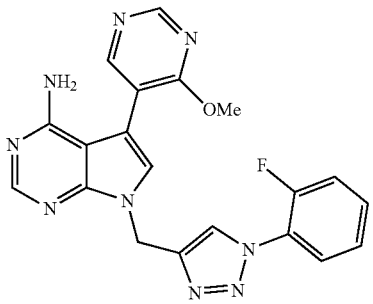 [SMILES: COc1ncncc1-c1cn(Cc2cn(-c3ccccc3F)nn2)c2ncnc(N)c12]

To a degassed solution of 7-{[1-(2-fluorophenyl)-1H-1,2,3-triazol-4-yl]methyl}-5-iodo-7H-pyrrolo[2,3-d]pyrimidin-4-amine (Preparation 95, 2 g, 4.56 mmol) in MeCN:H$_2$O (80 mL, 4:1) was added (4-methoxypyrimidin-5-yl)boronic acid (1.19 g, 5.055 mmol) followed by CsF (3.49 g, 23.0 mmol). The resulting mixture was degassed with Ar for 15 minutes and Pd(PPh$_3$)$_4$ (0.69 g, 0.597 mmol) was added and reaction mixture heated at 70° C. for 6 hours. The reaction mixture was diluted with water and extracted with DCM. The combined organics were dried (Na$_2$SO$_4$) and evaporated to dryness in vacuo. The residue was purified by column chromatography on silica gel, followed by trituration with DCM-ether to afford the title compound as off white solid (1.5 g, 78%). $^1$HNMR (400 MHz, DMSO-d$_6$) 3.93 (s, 3H), 5.57 (s, 2H), 6.33 (s, 2H), 7.42 (t, 1H), 7.48 (s, 1H), 7.52-7.62 (m, 2H), 7.81 (t, 1H), 8.17 (s, 1H), 8.41 (s, 1H), 8.62 (d, 1H), 8.75 (s, 1H). LCMS m/z=418 [MH]$^+$ Example 201

No Example 201 was Prepared

Example 202: 7-{[1-(2-Fluorophenyl)-1H-1,2,3-triazol-4-yl]methyl}-5-(2-methoxypyridin-3-yl)-2-methyl-7H-pyrrolo[2,3-d]pyrimidin-4-amine

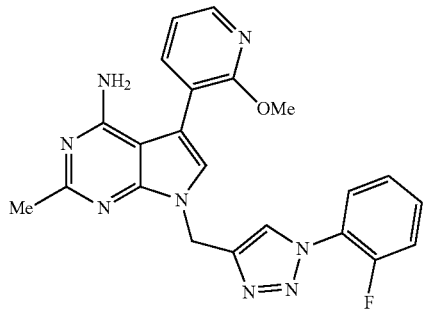 [SMILES: COc1ncccc1-c1cn(Cc2cn(-c3ccccc3F)nn2)c2nc(C)nc(N)c12]

To a stirred solution of 7-[1-(2-fluorophenyl)-1H-1,2,3-triazol-4-ylmethyl]-5-iodo-2-methyl-7H-pyrrolo[2,3-d]pyrimidin-4-amine (Preparation 54, 150.0 mg, 0.334 mmol) in EtOH-water (4:1) (8.0 mL) was added 2-methoxy-3-(4,4,5,5-tetramethyl-[1,3,2]dioxaborolan-2-yl)-pyridine (153.2 mg, 1.002 mmol) and Na$_2$CO$_3$ (106.16 mg, 1.002 mmol). The reaction mixture was degassed with Ar for 15 min and Pd(PPh$_3$)$_4$ (38.6 mg, 0.033 mmol) added and degassed with Ar for 5 min and heated to 90° C. for 6 h. The reaction mixture was filtered through Celite® washing through with 5% MeOH/DCM. The combined organics were evaporated to dryness under reduced pressure and the residue azeotroped with toluene. The solid was triturated with Et$_2$O and purified by prep TLC (3% MeOH:DCM) to afford the title compound as an off white solid (45.0 mg, 31.31%). $^1$HNMR (400 MHz, MeOD-d$_4$) 2.53 (s, 3H), 3.92 (s, 3H), 5.59 (s, 2H), 7.03 (dd, 1H), 7.24 (s, 1H), 7.38 (m, 2H), 7.54 (m, 1H), 7.67 (dd, 1H), 7.81 (t, 1H), 8.14 (dd, 1H), 8.37 (d, 1H). LCMS m/z=431 [MH]$^+$

Example 203: 7-{[1-(2-fluorophenyl)-1H-1,2,3-triazol-4-yl]methyl}-5-(4-methoxypyrimidin-5-yl)-2-methyl-7H-pyrrolo[2,3-d]pyrimidin-4-amine

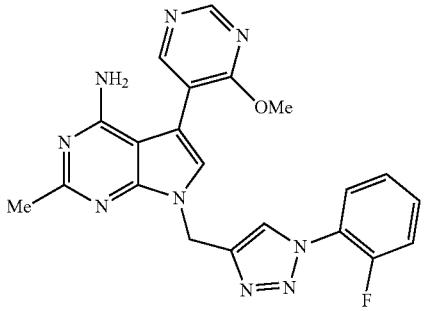 [SMILES: COc1ncncc1-c1cn(Cc2cn(-c3ccccc3F)nn2)c2nc(C)nc(N)c12]

The title compound was prepared as an off-white solid (32.19 mg, 16.8%) in an analogous manner to that described in Example 202 using 7-[1-(2-fluorophenyl)-1H-1,2,3-triazol-4-ylmethyl]-5-iodo-2-methyl-7H-pyrrolo[2,3-d]pyrimidin-4-amine (Preparation 54, 200.0 mg, 0.445 mmol) and 4-methoxy-5-(4,4,5,5-tetramethyl-[1,3,2]dioxaborolan-2-yl)-pyrimidine (94 mg, 0.49 mmol). $^1$HNMR (400 MHz, CDCl$_3$) 2.60 (s, 3H), 4.04 (s, 3H), 4.91 (s, 2H), 5.60 (s, 2H), 7.25-7.32 (m, 3H), 7.44 (m, 1H), 7.92 (m, 1H), 8.16 (d, 1H), 8.46 (s, 1H), 8.75 (s, 1H). LCMS m/z=432 [MH]$^+$

Example 204: 5-(2-(difluoromethyl)pyrimidin-5-yl)-7-{[1-(2-fluorophenyl)-1H-pyrazol-4-yl]methyl}-7H-pyrrolo[2,3-d]pyrimidin-4-amine

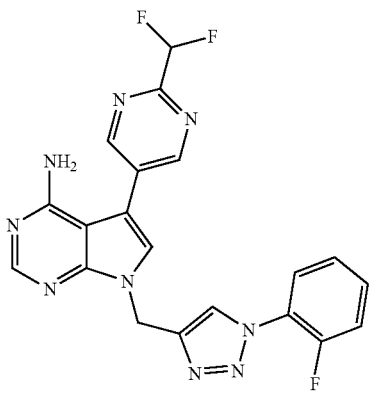 [SMILES: Nc1ncnc2c1c(-c1cnc(C(F)F)nc1)cn2Cc1cn(-c2ccccc2F)nn1]

To a solution of 7-{[1-(2-fluorophenyl)-1H-pyrazol-4-yl]methyl}-5-iodo-7H-pyrrolo[2,3-d]pyrimidin-4-amine (Preparation 55, 375 mg, 0.86 mmol) in DMF (20 mL) was added under N$_2$, 2-(difluoromethyl)pyrimidin-5-ylboronic acid (0.3 g, 1.73 mmol), Na$_2$CO$_3$ solution (5 mL) and Pd(dppf)Cl$_2$ (63 mg, 0.086 mmol). The reaction was stirred at 100° C. for 6 hours then was water added to the cooled mixture. The reaction mixture was extracted with EtOAc (40 mL×2) and the combined organics washed with brine, dried and evaporated to dryness in vacuo. The residue was purified by column chromatography over silica gel (DCM:MeOH=9:1) to give the title compound (200 mg, 58%). $^1$HNMR (400 MHz, DMSO-d$_6$) 5.38 (s, 2H), 6.59 (br s, 2H), 7.05 (t, 1H), 7.33-7.50 (m, 3H), 7.74 (m, 2H), 7.77 (s, 1H), 8.30 (s, 2H), 8.98 (s, 2H). LCMS m/z=437.1 [MH

Example 205: 5-[2-(difluoromethyl)pyrimidin-5-yl]-7-{1-[1-(2-fluorophenyl)-1H-pyrazol-4-yl]ethyl}-7H-pyrrolo[2,3-d]pyrimidin-4-amine

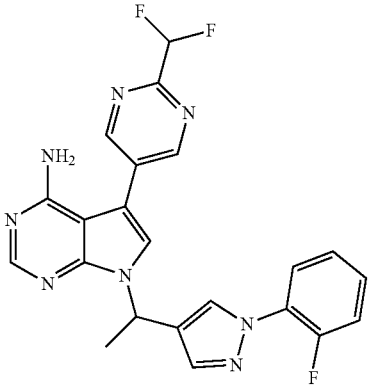 [SMILES: CC(c1cnn(-c2ccccc2F)c1)n1cc(-c2cnc(C(F)F)nc2)c2c(N)ncnc21]

To a solution of 7-{1-[1-(2-fluorophenyl)-1H-pyrazol-4-yl]ethyl}-5-iodo-7H-pyrrolo[2,3-d]pyrimidin-4-amine (Preparation 56, 360 mg, 0.80 mmol) in DMF (30 mL) was added 2-(difluoromethyl)pyrimidin-5-ylboronic acid (279 mg, 1.60 mmol), Na$_2$CO$_3$ solution (8 mL). Pd(dppf)Cl$_2$ (59 mg, 0.08 mmol) was added under N$_2$. The reaction was stirred at 100° C. overnight, cooled and water added. The mixture was extracted with EtOAc (50 mL×2) and the combined extracts washed with brine, dried and evaporated to dryness in vacuo. The residue was purified by column chromatography over silica gel (DCM:MeOH=10:1) to give the title compound (300 mg, 70%). $^1$HNMR (400 MHz, DMSO-d$_6$) 1.88 (d, 3H), 6.17 (q, 1H), 6.53 (br s, 2H), 7.00 (t, 1H), 7.30-7.45 (m, 3H), 7.74 (t, 1H), 7.80 (d, 2H), 8.26 (m, 2H), 8.99 (s, 2H). LCMS m/z=451.2 [MH]$^+$

Example 206: 7-{[1-(2-fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine

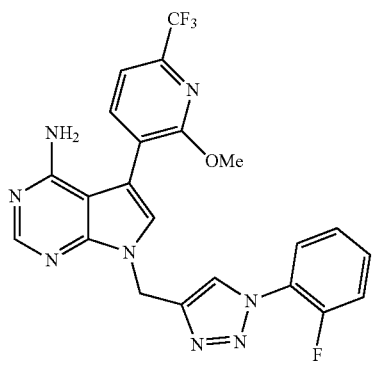 [SMILES: COc1nc(C(F)(F)F)ccc1-c1cn(Cc2cn(-c3ccccc3F)nn2)c2ncnc(N)c12]

To a stirred, degassed solution of 7-[1-(2-fluorophenyl)-1H-1,2,3-triazol-4-ylmethyl]-5-iodo-7H-pyrrolo[2,3-d]pyrimidin-4-amine (Preparation 95, 100.0 mg, 0.229 mmol) in MeCN/water (8.0 mL) was added 2-methoxy-6-trifluoromethylpyridine-3-boronic acid (65.6 mg, 0.298 mmol), CsF (138.5 mg, 0.917 mmol) and the mixture degassed with N$_2$ for 5 min. Pd(PPh$_3$)$_4$ (26.5 mg, 0.023 mmol) was added and the mixture degassed with N₂ for an additional 5 min. The reaction was heated to 90° C. for 16 hr, additional 2-methoxy-6-trifluoromethylpyridine-3-boronic acid (0.5 eq) was added and the reaction heated to 90° C. for a further 16 hr. The reaction mixture was filtered through Celite® and evaporated to dryness in vacuo. The residue was purified by repeated preparative TLC (70% EtOAc in hexane) to afford the title compound as a brown solid (13.0 mg, 11.7%). ¹HNMR (400 MHz, CDCl₃) 4.03 (s, 3H), 5.04 (s, 1H), 5.63 (s, 2H), 7.26-7.50 (m, 6H), 7.72 (d, 1H), 7.90 (t, 1H), 8.17 (d, 1H), 8.38 (s, 1H). LCMS m/z=485 [MH]⁺

Example 207: 7-{[1-(2-fluorophenyl)-1H-1,2,3-triazol-4-yl]methyl}-5-(3-methoxypyridin-2-yl)-7H-pyrrolo[2,3-d]pyrimidin-4-amine

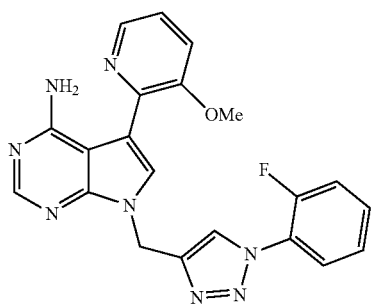 [SMILES: COc1cccnc1-c1cn(Cc2cn(-c3ccccc3F)nn2)c2ncnc(N)c12]

To a stirred solution of 7-{[1-(2-fluorophenyl)-1H-1,2,3-triazol-4-yl]methyl}-5-iodo-7H-pyrrolo[2,3-d]pyrimidin-4-amine (Preparation 95, 200 mg, 0.46 mmol) and 3-methoxy-2-(tributylstannyl)pyridine (845.8 mg, 2.298 mmol) in DMF (10 mL) was added dry LiCl (58.4 mg, 1.379 mmol) and the resulting mixture degassed with Ar for 15 minutes. Pd(PPh₃)₄ was added and reaction mixture was heated at 100° C. for 16 hours. The reaction was quenched with water, extracted with EtOAc, dried (Na₂SO₄) and concentrated in vacuo and the residue purified by flash chromatography followed by prep HPLC to afford the title compound as an off-white solid (11.5 mg, 6%). ¹HNMR (400 MHz, DMSO-d₆) 3.98 (s, 3H), 5.60 (s, 2H), 7.18 (br s, 1H), 7.27 (dd, 1H), 7.41 (t, 1H), 7.51-7.63 (m, 3H), 7.80 (t, 1H), 8.11 (s, 1H), 8.18 (d, 1H), 8.32 (s, 1H), 8.58 (s, 1H), 9.95 (br s, 1H). LCMS m/z=417 [MH]⁺

Example 208: 5-(4-Chlorophenyl)-7-{1-[1-(3-methylphenyl)-1H-1,2,3-triazol-4-yl]ethyl}-7H-pyrrolo[2,3-d]pyrimidin-4-amine

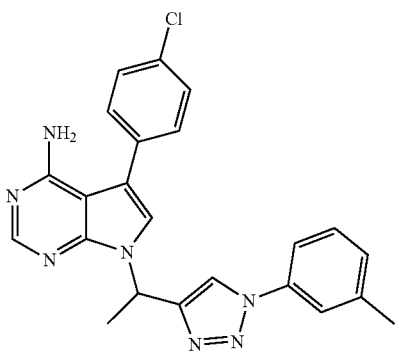 [SMILES: Cc1cccc(-n2cc(C(C)n3cc(-c4ccc(Cl)cc4)c4c(N)ncnc43)nn2)c1]

To a degassed solution of 7-(but-3-yn-2-yl)-5-(4-chlorophenyl)-7H-pyrrolo[2,3-d]pyrimidine-4-amine (Preparation 77, 50 mg, 0.30 mmol), was added 0.5(M) soln. of 3-methylphenylazide (0.58 mL, 0.286 mmol) in t-butyl ether, DIPEA (0.27 mL, 2.9 mmol) in t-BuOH:toluene (4:1, 5 mL) and CuI (16 mg, 0.145 mmol) and the reaction heated at 100° C. for 16 hr in a sealed tube. The cooled mixture was filtered through a pad of Celite®, the filtrate diluted with EtOAc (70 mL), washed with water (25 mL) and brine (25 mL). The organic solution was dried (Na₂SO₄), filtered and concentrated in vacuo. The residue was purified by prep TLC to afford the title compound as an off white solid (12.4 mg, 17%). ¹HNMR (400 MHz, MeOD-d₄) 2.00 (d, 3H), 2.42 (s, 3H), 6.29-6.35 (m, 1H), 7.30 (m, 1H), 7.34 (s, 1H), 7.39-7.48 (m, 5H), 7.60 (m, 1H), 7.65 (m, 1H), 8.20 (d, 1H), 8.51 (s, 1H). LCMS m/z=430.0 [MH]⁺

Example 209: 5-(4-Chlorophenyl)-7-{1-[1-(2-fluorophenyl)-1H-1,2,3-triazol-4-yl]ethyl}-2-methyl-7H-pyrrolo[2,3-d]pyrimidin-4-amine

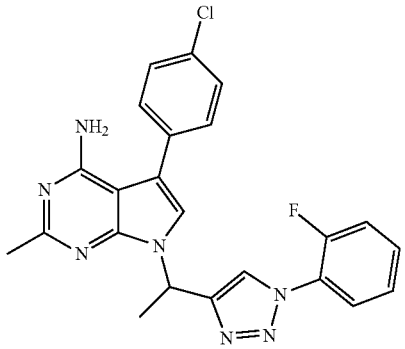 [SMILES: Cc1nc(N)c2c(-c3ccc(Cl)cc3)cn(C(C)c3cn(-c4ccccc4F)nn3)c2n1]

N'-[7-(but-3-yn-2-yl)-5-(4-chlorophenyl)-2-methyl-7H-pyrrolo[2,3-d]pyrimidin-4-yl]-N,N-dimethylimidoformamide (Preparation 13, 175 mg, 0.48 mmol), 2-fluorophenyl azide (104 mg, 0.72 mmol), CuI (50.6 mg, 0.263 mmol) and DIPEA (0.84 mL, 4.8 mmol) were suspended in t-BuOH (1 mL) and toluene (4 mL) and the reaction stirred at rt for 18 hrs. The mixture was partitioned between EtOAc and water, the organic layer washed with brine and dried (MgSO₄), filtered and concentrated in vacuo. The crude product was purified by column chromatography on silica gel eluting with EtOAc:Heptane (70:100 to 100:0). The product was treated with TFA followed by ammonia hydroxide, then the mixture diluted with water and extracted with EtOAc. The combined organic extracts were washed with brine, dried (MgSO₄) and concentrated under reduced pressure to afford the title compound, as a solid (130 mg, 60%). ¹HNMR (400 MHz, DMSO-d₆) 1.85 (d, 3H), 3.35 (s, 3H), 6.09 (br s, 2H), 6.33 (m, 1H), 7.38-7.48 (m, 6H), 7.54-7.62 (m, 2H), 7.80 (m, 1H), 8.64 (m, 1H). LCMS m/z=448.1 [MH]⁺

Example 210: 7-{[1-(2-Fluorophenyl)-1H-1,2,3-triazol-4-yl]methyl}-5-(2-methoxy-pyridin-3-yl)-7H-pyrrolo[2,3-d]pyrimidin-4-amine

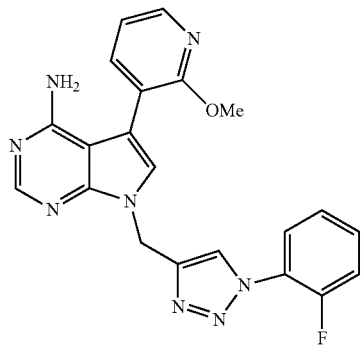 [SMILES: COc1ncccc1-c1cn(Cc2cn(-c3ccccc3F)nn2)c2ncnc(N)c12]

A stirred suspension of 7-{[1-(2-fluorophenyl)-1H-1,2,3-triazol-4-yl]methyl}-5-iodo-7H-pyrrolo[2,3-d]pyrimidin-4-amine (Preparation 41, 60 g, 0.137 mol), (2-methoxy-pyridin-3-yl) boronic acid (31.6 g, 0.206 mol) and $Na_2CO_3$ (58.4 g, 0.551 mol) in EtOH: Water (750 mL, 4:1) was degassed under $N_2$ for 30 minutes. $Pd(PPh_3)_4$ (15.97 g, 0.0137 mol) was added and the reaction heated at 90° C. for 16 hr under $N_2$. The cooled reaction was diluted with water (1 L) and EtOAc (500 mL), the layers separated and the aqueous extracted with EtOAc (2×1 L). The combined organic layers were washed with water (2×250 mL) followed by brine, dried ($Na_2SO_4$) and concentrated under reduced pressure. The crude product was purified by column chromatography on silica gel eluting with saturated ammonical MeOH: DCM, 0:100-10:100, to afford compound the title compound as a white solid (35 g, 61.4%). $^1$HNMR (400 MHz, DMSO-$d_6$) 3.86 (s, 3H), 5.56 (s, 2H), 6.05 (br s, 2H), 7.08 (m, 1H), 7.42 (m, 2H), 7.53-7.65 (m, 3H), 7.81 (m, 1H), 8.17 (s, 2H), 8.63 (s, 1H). LCMS m/z=417.1 [MH]$^+$

Example 211: 5-(4-Chlorophenyl)-7-{1-[1-(2-fluorophenyl)-1H-1,2,3-triazol-4-yl]propyl}-7H-pyrrolo[2,3-d]pyrimidin-4-amine

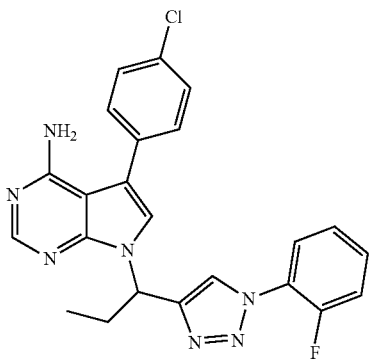 [SMILES: CCC(c1cn(-c2ccccc2F)nn1)n1cc(-c2ccc(Cl)cc2)c2c(N)ncnc21]

A suspension of 7-{1-[1-(2-fluorophenyl)-1H-1,2,3-triazol-4-yl]propyl}-5-iodo-7H-pyrrolo[2,3-d]pyrimidin-4-amine (Preparation 45, 3.0 g, 6.47 mmol), 4-chlorophenyl-boronic acid (2.02 g, 12.9 mmol), and $Na_2CO_3$ (2.7 g, 25.9 mmol) in EtOH (13.5 mL) and $H_2O$ (3.5 mL) was degassed with $N_2$. $Pd(PPh_3)_4$ (449 mg, 0.39 mmol) was added and the reaction stirred at 80° C. for 2 hrs. The cooled mixture was filtered through Celite®, washing through with 10% MeOH: DCM and the filtrate evaporated under reduced pressure. The crude product was purified by column chromatography on silica gel eluting with MeOH:DCM (1:99) to afford the title compound as a yellow sold (1.9 g, 65.5%). $^1$HNMR (400 MHz, DMSO-$d_6$) 0.83 (t, 3H), 2.36 (m, 2H), 6.10 (m, 1H), 6.22-6.35 (br s, 2H), 7.41 (m, 1H), 7.42-7.61 (m, 7H), 7.81 (m, 1H), 8.22 (s, 1H), 8.72 (s, 1H). LCMS m/z=447.9 [MH]$^+$

Example 212: 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine

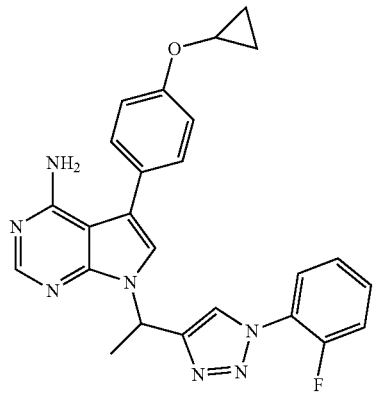 [SMILES: CC(c1cn(-c2ccccc2F)nn1)n1cc(-c2ccc(OC3CC3)cc2)c2c(N)ncnc21]

The title compound was obtained as an off white solid (550 mg, 34%), from 7-{1-[1-(2-fluorophenyl)-1H-1,2,3-triazol-4-yl]ethyl}-5-iodo-7H-pyrrolo[2,3-d]pyrimidin-4-amine (Preparation 42) and 4-cyclopropyloxyphenyl boronic acid, following the procedure described in Example 211. $^1$HNMR (400 MHz, DMSO-$d_6$) 0.68 (m, 2H), 0.78 (m, 2H), 1.90 (d, 3H), 3.87 (m, 1H), 6.10 (br s, 2H), 6.32 (q, 1H), 7.14 (m, 2H), 7.37-7.44 (m, 4H), 7.55-7.61 (m, 2H), 7.81 (m, 1H), 8.18 (s, 1H), 8.65 (s, 1H). LCMS m/z=456.0 [MH]$^+$

Example 213: 5-[6-(Cyclopropyloxy)pyridin-3-yl]-7-{1-[1-(2-fluorophenyl)-1H-1,2,3-triazol-4-yl]ethyl}-7H-pyrrolo[2,3-d]pyrimidin-4-amine

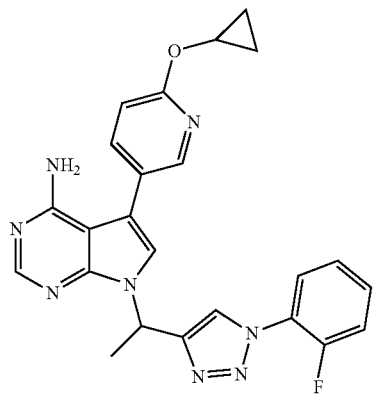 [SMILES: CC(c1cn(-c2ccccc2F)nn1)n1cc(-c2ccc(OC3CC3)nc2)c2c(N)ncnc21]

The title compound was obtained as an off white solid (590 mg, 25%) from 7-{1-[1-(2-fluorophenyl)-1H-1,2,3-triazol-4-yl]ethyl}-5-iodo-7H-pyrrolo[2,3-d]pyrimidin-4-amine (Preparation 42) and 6-cyclopropyloxy-3-pyridinyl boronic acid following a similar method to that described in Example 211, except 3 eq of boronic acid were used. $^1$HNMR (400 MHz, DMSO-$d_6$) 0.69 (m, 2H), 0.78 (m, 2H), 1.91 (d, 3H), 4.22 (m, 1H), 6.18 (br s, 2H), 6.32 (q, 1H), 6.93 (d, 1H), 7.43 (m, 1H), 7.47 (s, 1H), 7.53-7.61 (m, 2H), 7.77-7.84 (m, 2H), 8.18 (s, 1H), 8.26 (m, 1H), 8.65 (s, 1H). LCMS m/z=457.1 [MH]+

Example 214: 5-[4-(Cyclopropoxy)phenyl]-7-{1-[1-(3-fluoropyridin-2-yl)-1H-1,2,3-triazol-4-yl]ethyl}-7H-pyrrolo[2,3-d]pyrimidin-4-amine

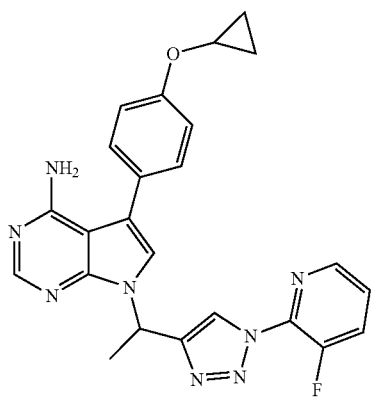 [SMILES: CC(c1cn(-c2ncccc2F)nn1)n1cc(-c2ccc(OC3CC3)cc2)c2c(N)ncnc21]

The title compound was obtained as a white solid (26 mg, 37%) from 7-{1-[1-(3-fluoropyridin-2-yl)-1H-1,2,3-triazol-4-yl]ethyl}-5-iodo-7H-pyrrolo[2,3-d]pyrimidin-4-amine (Preparation 42) and 4-cyclopropoxyphenyl boronic acid, following an analogous method to that described in Example 211. $^1$HNMR (400 MHz, DMSO-d$_6$) 0.67 (m, 2H), 0.79 (m, 2H), 1.95 (d, 3H), 3.87 (m, 1H), 6.35 (m, 1H), 7.13 (d, 2H), 7.37-7.42 (m, 3H), 7.69-7.73 (m, 1H), 8.12-8.19 (m, 2H), 8.48 (m, 1H), 8.74 (s, 1H). LCMS m/z=457.0 [MH]+

Examples 215 to 234

A mixture of the appropriate iodo starting material (1 eq), boronic acid or ester (1.5-2.0 eq), Pd(dppf)Cl$_2$ (0.1 eq) and K$_2$CO$_3$ (1-3 eq) in dioxane:H$_2$O (4:1 v/v) was degassed with N$_2$. The reaction mixture was stirred at 90° C. under N$_2$ for 2-4 hr. The cooled mixture was poured into water and extracted with DCM. The combined organic extracts were dried (Na$_2$SO$_4$), filtered and concentrated in vacuo. The crude product was purified by column chromatography on silica gel eluting with DCM:MeOH to afford the title compound.

| Ex. No. | Structure | Starting Materials | Analytical Data |
| --- | --- | --- | --- |
| 215[b,c] | 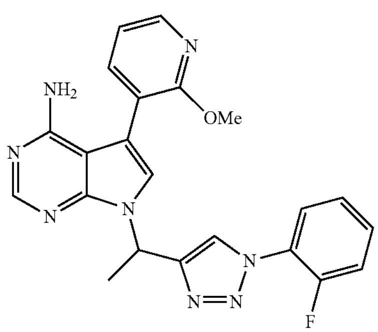 [SMILES: COc1ncccc1-c1cn(C(C)c2cn(-c3ccccc3F)nn2)c2ncnc(N)c12] | 7-{1-[1-(2-fluorophenyl)-1H-1,2,3-triazol-4-yl]ethyl}-5-iodo-7H-pyrrolo[2,3-d]pyrimidin-4-amine (Preparation 42) and 2-methoxy pyridine-3-boronic acid | $^1$HNMR (400 MHz, DMSO-d$_6$) 1.90 (d, 3H), 3.86 (s, 3H), 6.04 (br s, 2H), 6.31 (m, 1H), 7.06 (m, 1H), 7.42 (m, 2H), 7.53-7.65 (m, 3H), 7.82 (m, 1H), 8.17 (s, 2H), 8.65 (s, 1H). LCMS m/z = 431.2 [MH]+ |
| 216[d] | 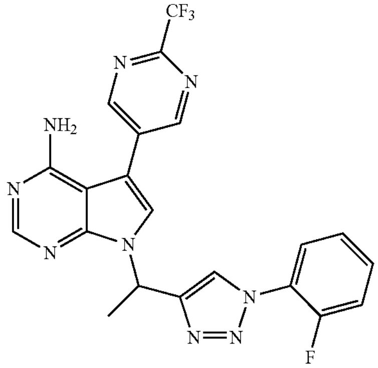 [SMILES: CC(c1cn(-c2ccccc2F)nn1)n1cc(-c2cnc(C(F)(F)F)nc2)c2c(N)ncnc21] | 7-{1-[1-(2-fluorophenyl)-1H-1,2,3-triazol-4-yl]ethyl}-5-iodo-7H-pyrrolo[2,3-d]pyrimidin-4-amine (Preparation 42) and 5-(4,4,5,5-tetramethyl-1,3,2-dioxaborolan-2-yl)-2-(trifluoromethyl)pyrimidine | $^1$HNMR (400 MHz, DMSO-d$_6$) 1.95 (d, 3H), 6.35 (m, 1H), 6.66 (br s, 2H), 7.43 (m, 1H), 7.55-7.61 (m, 2H), 7.80 (m, 1H), 7.86 (s, 1H), 8.25 (d, 1H), 8.67 (s, 1H), 9.05 (s, 2H). LCMS m/z = 470.1 [MH]+ |

| Ex. No. | Structure | Starting Materials | Analytical Data |
|---|---|---|---|
| 217 | 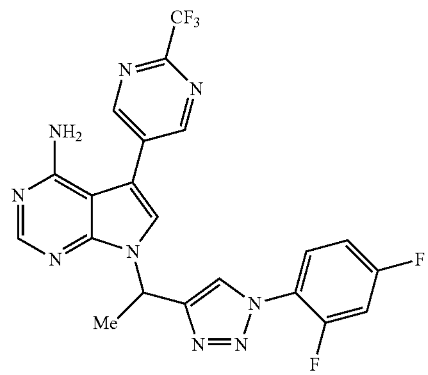 [SMILES: CC(c1cn(-c2ccc(F)cc2F)nn1)n1cc(-c2cnc(C(F)(F)F)nc2)c2c(N)ncnc21] | 7-{1-[1-(2,4-difluorophenyl)-1H-1,2,3-triazol-4-yl]ethyl}-5-iodo-7H-pyrrolo[2,3-d]pyrimidin-4-amine (Preparation 44) and 2-(trifluoromethyl)pyrimidin-5-ylboronic acid | $^1$HNMR (400 MHz, DMSO-$d_6$) 1.97 (d, 3H), 6.40 (m, 1H), 7.35 (m, 1H), 7.67 (m, 1H), 7.85-8.08 (m, 4H), 8.51 (m, 1H), 8.51 (s, 1H), 9.10 (s, 2H). LCMS m/z = 488.2 [MH]$^+$ |
| 218$^{d,e}$ | | 7-{1-[1-(2-fluorophenyl)-1H-1,2,3-triazol-4-yl]ethyl}-5-iodo-7H-pyrrolo[2,3-d]pyrimidin-4-amine (Preparation 42) and 3-(4,4,5,5-tetramethyl-1,3,2-dioxaborolan-2-yl)-1H-pyrazole | LCMS m/z = 390.1 [MH]$^+$ |
| 219 | 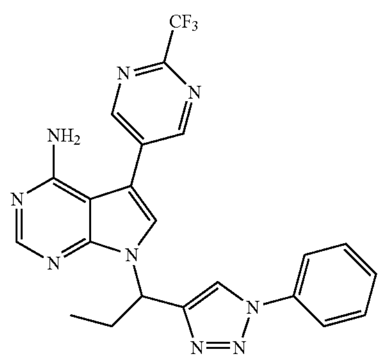 [SMILES: CCC(c1cn(-c2ccccc2)nn1)n1cc(-c2cnc(C(F)(F)F)nc2)c2c(N)ncnc21] | 5-iodo-7-[1-(1-phenyl-1H-1,2,3-triazol-4-yl)propyl]-7H-pyrrolo[2,3-d]pyrimidin-4-amine (Preparation 51) and 2-(trifluoromethyl)pyrimidin-5-ylboronic acid | $^1$HNMR (400 MHz, DMSO-$d_6$) 0.88 (t, 3H), 2.35-2.44 (m, 2H), 6.13 (t, 1H), 7.50 (m, 1H), 7.60 (m, 2H), 7.88 (d, 2H), 8.02 (m, 1H), 8.45 (m, 1H), 8.97 (s, 1H), 9.10 (s, 2H). |
| 220 | 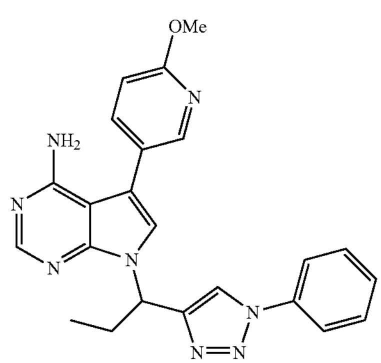 [SMILES: CCC(c1cn(-c2ccccc2)nn1)n1cc(-c2ccc(OC)nc2)c2c(N)ncnc21] | 5-iodo-7-[1-(1-phenyl-1H-1,2,3-triazol-4-yl)propyl]-7H-pyrrolo[2,3-d]pyrimidin-4-amine (Preparation 51) and 5-(4,4,5,5-tetramethyl-1,3,2-dioxaborolan-2-yl)-2-(trifluoromethyl)pyrimidine | $^1$HNMR (400 MHz, DMSO-$d_6$) 0.87 (t, 3H), 2.36-2.44 (m, 2H), 3.90 (s, 3H), 6.12 (t, 1H), 6.92 (d, 1H), 7.48 (m, 1H), 7.60 (m, 2H), 7.80 (m, 2H), 7.90 (m, 2H), 8.26 (s, 1H), 8.49 (s, 1H), 8.98 (s, 1H). |

| Ex. No. | Structure | Starting Materials | Analytical Data |
|---|---|---|---|
| 221[a] | 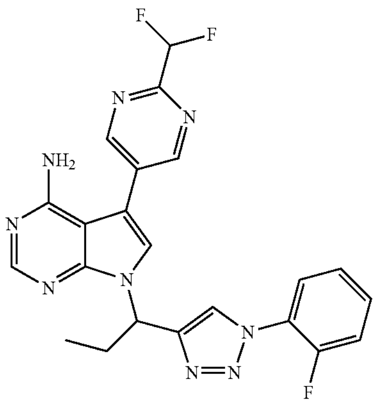 [SMILES: CCC(c1cn(-c2ccccc2F)nn1)n1cc(-c2cnc(C(F)F)nc2)c2c(N)ncnc21] | 7-{1-[1-(2-fluorophenyl)-1H-1,2,3-triazol-4-yl]propyl}-5-iodo-7H-pyrrolo[2,3-d]pyrimidin-4-amine (Preparation 45) and 2-(difluoromethyl)-5-(4,4,5,5-tetramethyl-1,3,2-dioxaborolan-2-yl)pyrimidine | $^1$HNMR (400 MHz, DMSO-$d_6$) 0.86 (t, 3H), 2.36 (m, 2H), 6.12 (m, 1H), 6.28 (m, 1H), 7.18 (d, 1H), 7.45 (m, 1H), 7.52-7.63 (m, 3H), 7.75 (d, 1H), 7.84 (m, 1H), 7.98 (m, 1H), 8.22 (s, 1H), 8.36 (s, 1H), 8.72 (s, 1H). LCMS m/z = 466.2 [MH]+ |
| 222 | 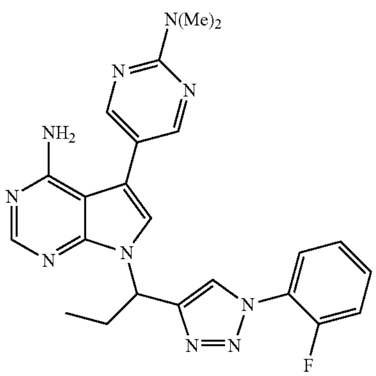 | 7-{1-[1-(2-fluorophenyl)-1H-1,2,3-triazol-4-yl]propyl}-5-iodo-7H-pyrrolo[2,3-d]pyrimidin-4-amine (Preparation 45) and 2-(dimethylamino)pyrimidin-5-ylboronic acid | $^1$HNMR (400 MHz, DMSO-$d_6$) 0.83 (t, 3H), 2.32 (m, 2H), 3.84 (s, 3H), 6.09 (t, 1H), 6.22 (br s, 2H), 7.42 (m, 1H), 7.54-7.62 (m, 4H), 7.82 (m, 1H), 8.12 (s, 1H), 8.16 (s, 1H), 8.70 (s, 1H). LCMS m/z = 463.2 [MH]+ |
| 223 | 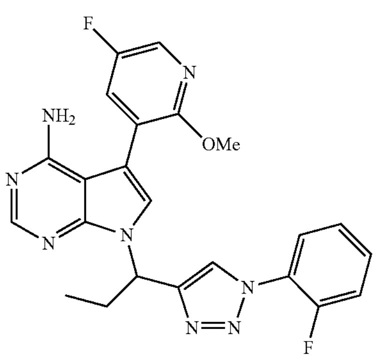 [SMILES: CCC(c1cn(-c2ccccc2F)nn1)n1cc(-c2cc(F)cnc2OC)c2c(N)ncnc21] | 7-{1-[1-(2-fluorophenyl)-1H-1,2,3-triazol-4-yl]propyl}-5-iodo-7H-pyrrolo[2,3-d]pyrimidin-4-amine (Preparation 45) and 5-fluoro-2-methoxy-3-(4,4,5,5-tetramethyl-1,3,2-dioxaborolan-2-yl)pyridine | $^1$HNMR (400 MHz, DMSO-$d_6$) 0.83 (t, 3H), 2.32 (m, 2H), 3.84 (s, 3H), 6.09 (t, 1H), 6.22 (br s, 2H), 7.42 (m, 1H), 7.54-7.62 (m, 4H), 7.82 (m, 1H), 8.12 (s, 1H), 8.16 (s, 1H), 8.70 (s, 1H). LCMS m/z = 463.2 [MH]+ |
| 224[d] | 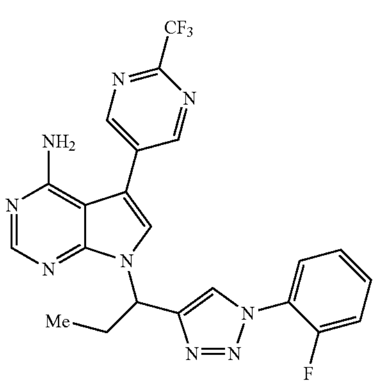 [SMILES: CCC(c1cn(-c2ccccc2F)nn1)n1cc(-c2cnc(C(F)(F)F)nc2)c2c(N)ncnc21] | 7-{1-[1-(2-fluorophenyl)-1H-1,2,3-triazol-4-yl]propyl}-5-iodo-7H-pyrrolo[2,3-d]pyrimidin-4-amine (Preparation 45) and 2-(trifluoromethyl)pyrimidin-5-ylboronic acid | $^1$HNMR (400 MHz, CDCl$_3$) 0.98 (t, 3H), 2.44-2.59 (m, 2H), 6.09 (t, 1H), 7.30 (m, 2H), 7.43 (m, 1H), 7.61 (s, 1H), 7.93 (m, 1H), 8.14 (s, 1H), 8.43 (s, 1H), 9.05 (s, 2H). LCMS m/z = 484.2 [MH]+ |

| Ex. No. | Structure | Starting Materials | Analytical Data |
|---|---|---|---|
| 225[a,c] | 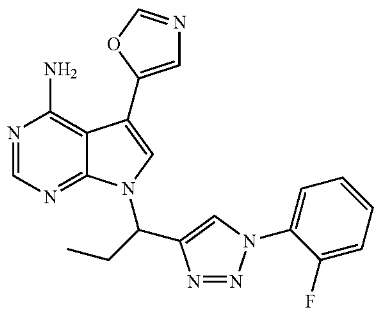 [SMILES: CCC(c1cn(-c2ccccc2F)nn1)n1cc(-c2cnco2)c2c(N)ncnc21] | 7-{1-[1-(2-fluorophenyl)-1H-1,2,3-triazol-4-yl]propyl}-5-iodo-7H-pyrrolo[2,3-d]pyrimidin-4-amine (Preparation 45) and 5-(4,4,5,5-tetramethyl-1,3,2-dioxaborolan-2-yl)oxazole | $^1$HNMR (400 MHz, CDCl$_3$) 0.94 (t, 3H), 2.40-2.57 (m, 2H), 5.75 (s, 2H), 6.12 (t, 1H), 7.22-7.32 (m, 3H), 7.41 (m, 1H), 7.66 (s, 1H), 7.93 (m, 2H), 8.07 (s, 1H), 8.34 (s, 1H). LCMS m/z = 405.2 [MH]$^+$ |
| 226[d,e] | 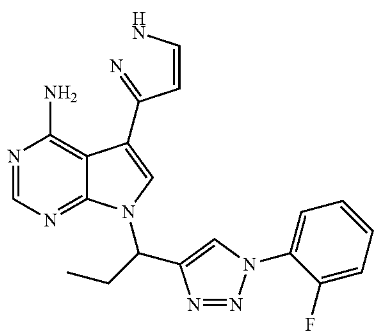 | 7-{1-[1-(2-fluorophenyl)-1H-1,2,3-triazol-4-yl]propyl}-5-iodo-7H-pyrrolo[2,3-d]pyrimidin-4-amine (Preparation 45) and 3-(4,4,5,5-tetramethyl-1,3,2-dioxaborolan-2-yl)-1H-pyrazole | $^1$HNMR (400 MHz, CDCl$_3$) 0.96 (t, 3H), 2.46-2.62 (m, 2H), 4.12 (m, 1H), 5.30 (s, 2H), 6.11 (m, 1H), 6.56 (d, 1H), 7.23-7.31 (m, 2H), 7.45 (m, 1H), 7.63 (m, 2H), 7.89 (m, 1H), 8.06 (s, 1H), 8.28 (s, 1H). LCMS m/z = 404.1 [MH]$^+$ |
| 227[c] | 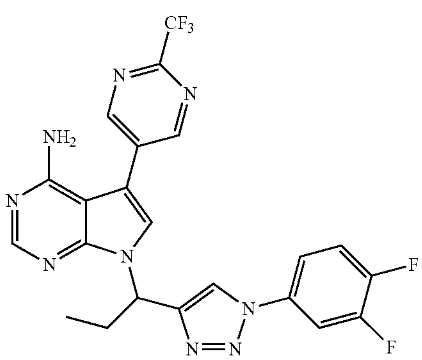 [SMILES: CCC(c1cn(-c2ccc(F)c(F)c2)nn1)n1cc(-c2cnc(C(F)(F)F)nc2)c2c(N)ncnc21] | 7-{1-[1-(3,4-difluorophenyl)-1H-1,2,3-triazol-4-yl]propyl}-5-iodo-7H-pyrrolo[2,3-d]pyrimidin-4-amine (Preparation 48) and 5-(4,4,5,5-tetramethyl-1,3,2-dioxaborolan-2-yl)-2-(trifluoromethyl)pyrimidine | $^1$HNMR (400 MHz, CDCl$_3$) 0.99 (t, 3H), 2.45-2.48 (m, 2H), 6.14 (t, 1H), 7.35 (m, 1H), 7.47 (m, 1H), 7.62 (m, 1H), 7.77 (s, 1H), 8.08 (s, 1H), 8.22 (s, 1H), 9.02 (s, 2H). LCMS m/z = 502.1 [MH]$^+$ |
| 228 | 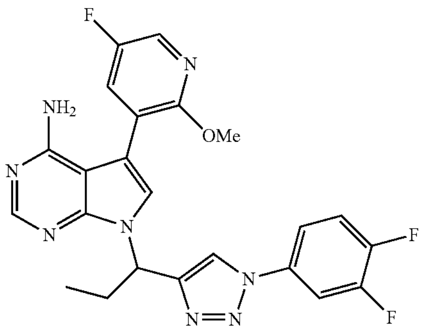 [SMILES: CCC(c1cn(-c2ccc(F)c(F)c2)nn1)n1cc(-c2cc(F)cnc2OC)c2c(N)ncnc21] | 7-{1-[1-(3,4-difluorophenyl)-1H-1,2,3-triazol-4-yl]propyl}-5-iodo-7H-pyrrolo[2,3-d]pyrimidin-4-amine (Preparation 48) and 5-fluoro-2-methoxy-3-pyridinylboronic acid | $^1$HNMR (400 MHz, MeOD-d$_4$) 0.99 (t, 3H), 2.45-2.56 (m, 2H), 3.94 (s, 3H), 6.24 (t, 1H), 7.48-7.56 (m, 1H), 7.64 (m, 1H), 7.72 (m, 2H), 7.90 (m, 1H), 8.12 (d, 1H), 8.37 (s, 1H), 8.73 (s, 1H). LCMS m/z = 481.1 [MH]$^+$ |

| Ex. No. | Structure | Starting Materials | Analytical Data |
|---|---|---|---|
| 229 | (structure) | 7-{1-[1-(3,4-difluorophenyl)-1H-1,2,3-triazol-4-yl]propyl}-5-iodo-7H-pyrrolo[2,3-d]pyrimidin-4-amine (Preparation 48) and 3-fluoro-2-methoxy-5-(4,4,5,5-tetramethyl-1,3,2-dioxaborolan-2-yl)pyridine | $^1$HNMR (400 MHz, DMSO-$d_6$) 0.80 (t, 3H), 2.45 (m, 2H), 6.15 (m, 1H), 7.65-7.80 (m, 6H), 8.15 (m, 2H), 8.45 (m, 1H), 9.00 (s, 1H). LCMS m/z = 481.2 [MH]$^+$ |
| 230 | (structure) | 7-{1-[1-(2,4-difluorophenyl)-1H-1,2,3-triazol-4-yl]propyl}-5-iodo-7H-pyrrolo[2,3-d]pyrimidin-4-amine (Preparation 46) and 2-(difluoromethyl)-5-(4,4,5,5-tetramethyl-1,3,2-dioxaborolan-2-yl)pyrimidine (Preparation 139) | $^1$HNMR (400 MHz, DMSO-$d_6$) 0.87 (t, 3H), 2.38-2.45 (m, 2H), 6.15 (m, 1H), 6.91-7.18 (dd, 1H), 7.35 (m, 1H), 7.67-7.88 (m, 4H), 8.03 (s, 1H), 8.45 (s, 1H), 8.74 (s, 1H), 9.03 (s, 2H). LCMS m/z = 484.2 [MH]$^+$ |
| 231 | (structure) | 7-{1-[1-(2,4-difluorophenyl)-1H-1,2,3-triazol-4-yl]propyl}-5-iodo-7H-pyrrolo[2,3-d]pyrimidin-4-amine (Preparation 46) and 5-fluoro-2-methoxy-3-pyridinyl boronic acid | $^1$HNMR (400 MHz, MeOD-$d_4$) 0.99 (t, 3H), 2.48-2.56 (m, 2H), 3.94 (s, 3H), 6.26 (t, 1H), 7.24 (m, 1H), 7.36 (m, 1H), 7.64 (d, 1H), 7.75 (s, 1H), 7.85 (m, 1H), 8.13 (s, 1H), 8.37 (s, 1H), 8.55 (s, 1H). LCMS m/z = 481.1 [MH]$^+$ |
| 232 | (structure) | 7-{1-[1-(2,4-difluorophenyl)-1H-1,2,3-triazol-4-yl]propyl}-5-iodo-7H-pyrrolo[2,3-d]pyrimidin-4-amine (Preparation 46) and 3-fluoro-2-methoxy-5-(4,4,5,5-tetramethyl-1,3,2-dioxaborolan-2-yl)pyridine | |

| Ex. No. | Structure | Starting Materials | Analytical Data |
|---|---|---|---|
| 233 | 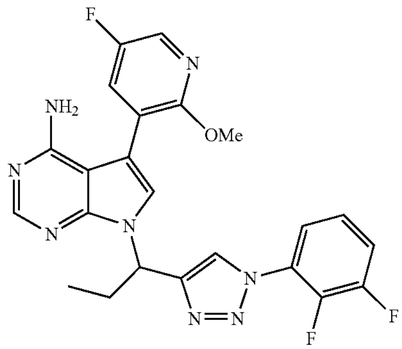 [SMILES: CCC(c1cn(-c2cccc(F)c2F)nn1)n1cc(-c2cc(F)cnc2OC)c2c(N)ncnc21] | 7-{1-[1-(2,3-difluorophenyl)-1H-1,2,3-triazol-4-yl]propyl}-5-iodo-7H-pyrrolo[2,3-d]pyrimidin-4-amine (Preparation 50) and 5-fluoro-2-methoxy-3-(4,4,5,5-tetramethyl-1,3,2-dioxaborolan-2-yl)pyridine | LCMS m/z = 481.2 [MH]+ |
| 234 | 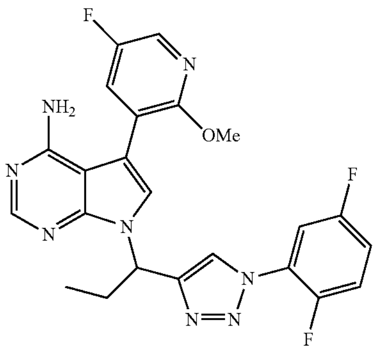 [SMILES: CCC(c1cn(-c2cc(F)ccc2F)nn1)n1cc(-c2cc(F)cnc2OC)c2c(N)ncnc21] | 7-{1-[1-(2,5-difluorophenyl)-1H-1,2,3-triazol-4-yl]propyl}-5-iodo-7H-pyrrolo[2,3-d]pyrimidin-4-amine (Preparation 49) and 5-fluoro-2-methoxy-3-(4,4,5,5-tetramethyl-1,3,2-dioxaborolan-2-yl)pyridine | LCMS m/z = 481.1 [MH]+ |

<sup>a</sup>DMF was used as the reaction solvent,
<sup>b</sup>Cs$_2$CO$_3$ was used instead of K$_2$CO$_3$,
<sup>c</sup>PdCl$_2$(dppf)•DCM was used instead of Pd(dppf)Cl$_2$,
<sup>d</sup>Na$_2$CO$_3$ was used as the base,
<sup>e</sup>DMF/Water (5:1 v/v) was used as the reaction solvent Example 235: 7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine

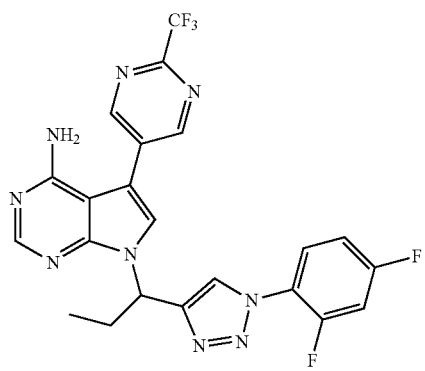 [SMILES: CCC(c1cn(-c2ccc(F)cc2F)nn1)n1cc(-c2cnc(C(F)(F)F)nc2)c2c(N)ncnc21]

To a solution of 7-(1-(1-(2,4-difluorophenyl)-1H-1,2,3-triazol-4-yl)propyl)-5-iodo-7H-pyrrolo[2,3-d]pyrimidin-4-amine (Preparation 46, 55 g, 114.33 mmol) in dioxane (1100 ml) and H$_2$O (275 ml) was added 5-(4,4,5,5-tetramethyl-1,3,2-dioxaborolan-2-yl)-2-(trifluoromethyl)pyrimidine (37.6 g, 137.2 mmol), Na$_2$CO$_3$ (36.3 g, 343 mmol) and Pd(PPh$_3$)$_4$ (13.2 g, 11.43 mmol) and the reaction stirred at 90° C. for 10 hrs under N$_2$. The cooled mixture was concentrated in vacuo and the residue diluted with EtOAc. The residue was purified by silica gel column (using pet. ether:EtOAc=1:10) to give the title compound as a white solid (32.8 g, 57%). $^1$HNMR (400 MHz, DMSO-d$_6$): 0.86 (t, 3H), 2.35-2.43 (m, 2H), 6.13 (t, 1H), 6.67 (br s, 2H), 7.34 (m, 1H), 7.68 (m, 1H), 7.90 (m, 2H), 8.25 (s, 1H), 8.70 (d, 1H), 9.07 (s, 2H). LCMS m/z=502.1 [MH]+

Example 236: 5-Cyclopropyl-7-{1-[1-(2-fluorophenyl)-1H-1,2,3-triazol-4-yl]propyl}-7H-pyrrolo[2,3-d]pyrimidin-4-amine

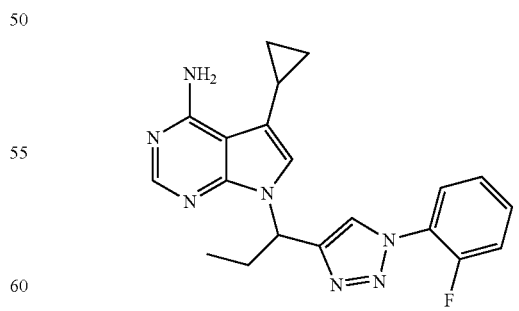

To a stirred solution of 7-{1-[1-(2-fluorophenyl)-1H-1,2,3-triazol-4-yl]propyl}-5-iodo-7H-pyrrolo[2,3-d]pyrimidin-4-amine (Preparation 45, 2.0 g, 4.32 mmol) and K$_3$PO$_4$ (4.58 g, 21.59 mmol) in dioxane:H$_2$O (2:1, 60 mL) was added cyclopropyl boronic acid (927 mg, 1.79 mmol) and the mixture degassed under Ar. PdCl₂(dppf)₂.DCM (705 mg, 0.86 mmol) was added and the reaction stirred at 80° C. for 16 hr N₂. The cooled mixture was concentrated under reduced pressure, the residue dissolved in EtOAc, washed with water followed by brine, dried (Na₂SO₄) and concentrated. The crude product was purified twice by prep-TLC eluting with MeOH:DCM to afford the title compound as a brown solid (250 mg, 15.34%). ¹HNMR (400 MHz, MeOD-d₄) 0.64 (m, 2H), 0.84-0.92 (m, 5H), 1.98 (m, 1H), 2.30-2.43 (m, 2H), 5.95 (m, 1H), 7.02 (s, 1H), 7.36-7.43 (m, 2H), 7.55 (m, 1H), 7.81 (m, 1H), 8.07 (s, 1H), 8.33 (s, 1H). LCMS m/z=378.4 [MH]⁺

Example 237: 5-(6-Cyclopropoxypyridin-3-yl)-7-{1-[1-(2,4-difluorophenyl)-1H-1,2,3-triazol-4-yl]ethyl}-7H-pyrrolo[2,3-d]pyrimidin-4-amine

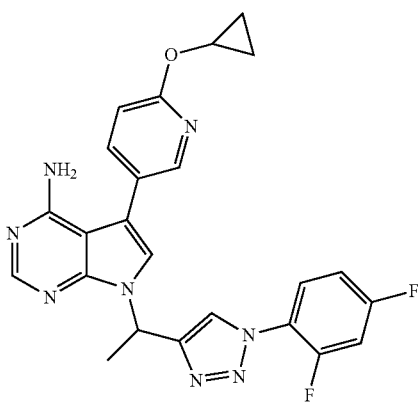 [SMILES: CC(c1cn(-c2ccc(F)cc2F)nn1)n1cc(-c2ccc(OC3CC3)nc2)c2c(N)ncnc21]

To a solution of 7-{1-[1-(2,4-difluorophenyl)-1H-1,2,3-triazol-4-yl]ethyl}-5-iodo-7H-pyrrolo[2,3-d]pyrimidin-4-amine (Preparation 44, 1 g, 2.14 mmol) in dioxane (20 mL) and H₂O (5 mL) was added 6-cyclopropoxypyridin-3-ylboronic acid (462 mg, 2.57 mmol), Pd(PPh₃)₄ (247 mg, 0.214 mmol) and Na₂CO₃ (680 mg, 6.42 mmol) under N₂ and the reaction heated to 90° C. for 5 hrs. The cooled mixture was evaporated under reduced pressure. The residue was purified by silica gel column chromatography eluting with DCM:MeOH (15:1) to afford the title compound as a white solid (500 mg 49%). LCMS m/z=475.1 [MH]⁺

Example 238: 5-Cyclopropyl-7-{1-[1-(2-fluorophenyl)-1H-1,2,3-triazol-4-yl)ethyl]-7H-pyrrolo[2,3-d]pyrimidin-4-amine

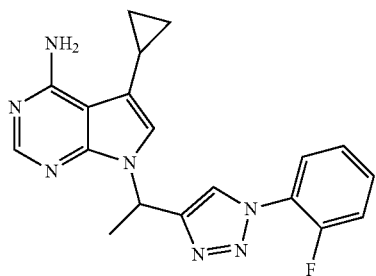 [SMILES: CC(c1cn(-c2ccccc2F)nn1)n1cc(C2CC2)c2c(N)ncnc21]

A suspension of 7-{1-[1-(2-fluorophenyl)-1H-1,2,3-triazol-4-yl]ethyl}-5-iodo-7H-pyrrolo[2,3-d]pyrimidin-4-amine (Preparation 42, 36.1 g, 80.4 mmol), cyclopropyl boronic acid (14.2 g, 161 mmol), S-Phos (13.5 g, 32.2 mmol), and K₃PO₄ (68.2 g, 321 mmol) in dioxane (220 mL) and H₂O (110 mL) was degassed with N₂ for 30 min. Pd₂(dba)₃ (14.7 mmol, 16.1 mmol) was added and the reaction heated at 100° C. for 18 hrs. The cooled mixture was partitioned between EtOAc (800 mL) and water (600 mL) the mixture filtered through Celite® and the layers separated. The aqueous phase was extracted with EtOAc, the combined organic extracts dried (MgSO₄) and concentrated in vacuo. The crude product was purified by column chromatography on silica gel eluting with acetone:DCM (30:70 to 0:100) to afford the title compound as a light orange solid (6.74 g, 23%). ¹HNMR (400 MHz, DMSO-d₆) 0.51-0.57 (m, 2H), 0.83 (m, 2H), 1.81 (d, 3H), 2.04 (m, 1H), 6.15 (q, 1H), 6.56 (s, 2H), 6.97 (s, 1H), 7.42 (m, 1H), 7.53-7.61 (m, 2H), 7.81 (m, 1H), 8.06 (s, 1H), 8.54 (s, 1H). LCMS m/z=364.24 [MH]⁺

Example 239: 4-(4-Amino-7-{1-[1-(2-fluorophenyl)-1H-1,2,3-triazol-4-yl)ethyl]-7H-pyrrolo[2,3-d]pyrimidin-5-yl}-2-fluorobenzonitrile

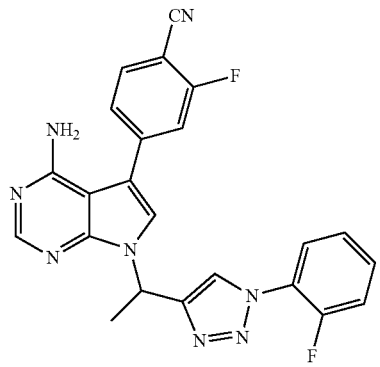 [SMILES: CC(c1cn(-c2ccccc2F)nn1)n1cc(-c2ccc(C#N)c(F)c2)c2c(N)ncnc21]

To stirred solution of 7-{1-[1-(2-fluorophenyl)-1H-1,2,3-triazol-4-yl]ethyl}-5-iodo-7H-pyrrolo[2,3-d]pyrimidin-4-amine (Preparation 42, 1.5 g, 3.34 mmol) in dioxane-water (15:7.5 mL) was added 4-cyano-3-fluorophenylboronic acid (1.1 g, 6.67 mmol), potassium phosphate (2.83 g, 13.35 mmol) and S-Phos (0.274 mg, 0.668 mmol). The mixture was degassed with N₂ for 15 min, Pd₂(dba)₃ (0.306 mg, 0.334 mmol) added, the reaction degassed with N₂ for 10 min then stirred at 100° C. for 1 hr. The cooled mixture was filtered through Celite® and the filtrate concentrated in vacuo. The crude product was purified by column chromatography on silica gel eluting with EtOAc:Hex (60:40) to afford the title compound as a brown solid (550 mg, 37.16%). ¹HNMR (400 MHz, MeOD-d₄) 2.02 (d, 3H), 6.36 (m, 1H), 7.36-7.43 (m, 2H), 7.48 (m, 2H), 7.52-7.58 (m, 2H), 7.76-7.82 (m, 2H), 8.25 (s, 1H), 8.42 (s, 1H). LCMS m/z=443.0 [MH]⁺

Example 240: 5-[6-(Difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine

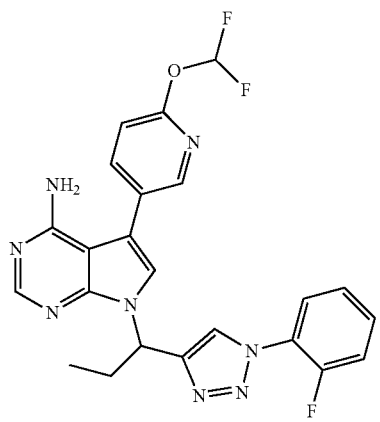 [SMILES: CCC(c1cn(-c2ccccc2F)nn1)n1cc(-c2ccc(OC(F)F)nc2)c2c(N)ncnc21]

A solution of 7-{1-[1-(2-fluorophenyl)-1H-1,2,3-triazol-4-yl]propyl}-5-iodo-7H-pyrrolo[2,3-d]pyrimidin-4-amine (Preparation 45, 470 mg, 1.0 mmol), (2-difluoro methoxy)-5-(4,4,5,5-tetramethyl-1,3-dioxaborolan-2-yl)pyridine (385 mg, 1.4 mmol), and CsF (623 mg, 4.1 mmol) in MeCN (8 mL) and H$_2$O (2 mL) was degassed under N$_2$. Pd(PPh$_3$)$_4$ (234 mg, 0.20 mmol) was added and the reaction stirred at 75° C. for 18 hrs. The cooled reaction was poured into water and extracted with EtOAc (2×). The combined organic extracts were dried (MgSO$_4$), filtered, and concentrated in vacuo. The crude product was purified by column chromatography on silica gel eluting with MeOH:DCM (0:100 to 10:90). The product was re-purified by column chromatography on silica gel eluting with EtOAc:heptane (50:50 to 100:0) to afford the title compound as a yellow foam (211 mg, 43.8%). $^1$HNMR (400 MHz, DMSO-d$_6$): 0.86 (t, 3H), 2.39 (m, 2H), 6.10 (m, 1H), 7.17 (d, 1H), 7.43 (m, 1H), 7.52-7.62 (m, 2H), 7.74 (s, 1H), 7.82 (m, 1H), 7.89 (s, 1H), 7.95 (d, 1H), 8.25 (s, 1H), 8.33 (s, 1H), 8.72 (s, 1H). LCMS m/z=481.3 [MH]$^+$

Example 241: 7-{1-[1-(4-Fluorophenyl)-1H-1,2,3-triazol-4-yl]propyl}-5-[4-methoxy pyrimidin-5-yl]-7H-pyrrolo[2,3-d]pyrimidin-4-amine

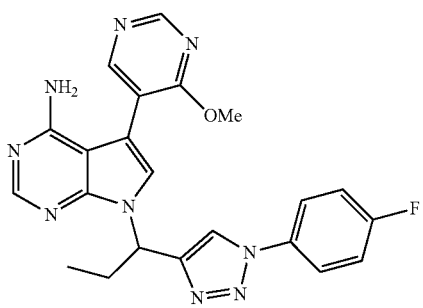 [SMILES: CCC(c1cn(-c2ccc(F)cc2)nn1)n1cc(-c2cncnc2OC)c2c(N)ncnc21]

The title compound was obtained as an orange foam in (240.5 mg, 54%) from 7-{1-[1-(4-fluorophenyl)-1H-1,2,3-triazol-4-yl]propyl}-5-iodo-7H-pyrrolo[2,3-d]pyrimidin-4-amine (Preparation 47, and 4-methoxy-5-(4,4,5,5-tetramethyl-[1,3,2]dioxaborolan-2-yl)-pyrimidine, following an analogous method to that described in Example 240. $^1$HNMR (400 MHz, DMSO-d$_6$) 0.84 (t, 3H), 2.33 (m, 2H), 3.92 (s, 3H), 6.08 (m, 1H), 6.32 (br s, 2H), 7.42-7.50 (m, 3H), 7.95 (m, 2H), 8.18 (s, 1H), 8.41 (s, 1H), 8.69 (s, 1H), 8.92 (s, 1H). LCMS m/z=446.2 [MH]$^+$

Example 242: 5-(4-Methoxypyrimidin-5-yl)-7-(1-{1-[4-(trifluoromethyl)pyridin-2-yl]-1H-1,2,3-triazol-4-yl]propyl}-7H-pyrrolo[2,3-d]pyrimidin-4-amine

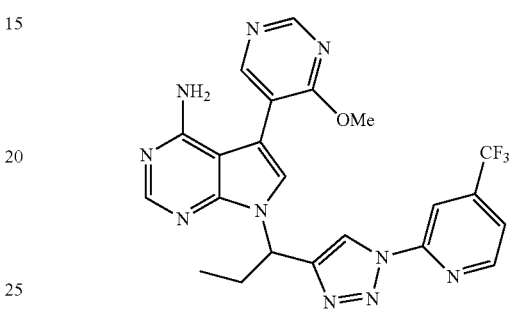

The title compound was obtained as an off-white solid in (18 mg, 11%) from 5-iodo-7-(1-{1-[4-(trifluoromethyl)pyridin-2-yl]-1H-1,2,3-triazol-4-yl]propyl}-7H-pyrrolo [2,3-d]pyrimidin-4-amine (Preparation 52), and 4-methoxy-5-(4,4,5,5-tetramethyl-[1,3,2]dioxaborolan-2-yl)-pyrimidine, following an analogous method to that described in Example 240. $^1$HNMR (400 MHz, DMSO-d$_6$) 0.85 (t, 3H), 2.39 (m, 2H), 3.92 (s, 3H), 6.11 (q, 1H), 6.32 (br s, 2H), 7.61 (s, 1H), 8.06 (m, 1H), 8.16 (s, 1H), 8.41 (m, 3H), 8.74 (s, 1H), 8.97 (s, 1H). LCMS m/z=496.8 [MH]$^+$

Example 243: 7-{Cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine

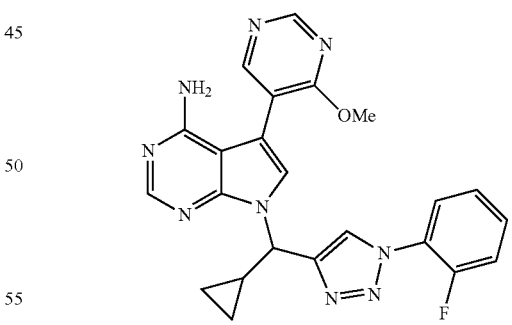

The title compound was obtained as a light brown solid (900 mg, 44%) from 7-{cyclopropyl[1-(2-fluorophenyl)-1H-1,2,3-triazol-4-yl)methyl]-5-iodo-7H-pyrolo[2,3-d]pyrimidin-4-amine (Preparation 53) and 4-methoxy-5-(4,4,5,5-tetramethyl-[1,3,2]dioxaborolan-2-yl)-pyrimidine, following the procedure described in Example 240. $^1$HNMR (400 MHz, DMSO-d$_6$) 0.45 (m, 1H), 0.58 (m, 2H), 0.71 (m, 1H), 1.96 (m, 1H), 3.94 (s, 3H), 5.46 (d, 1H), 6.29 (s, 2H), 7.43 (m, 1H), 7.56-7.63 (m, 3H), 7.84 (m, 1H), 8.13 (s, 1H), 8.43 (s, 1H), 8.76 (s, 2H). LCMS m/z=458.0 [MH]$^+$

Example 244: 7-{1-[1-(2-Fluorophenyl)-1H-1,2,3-triazol-4-yl]propyl}-5-[4-methoxypyrimidin-5-yl]-7H-pyrrolo[2,3-d]pyrimidin-4-amine

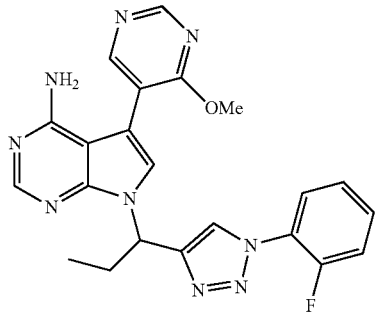 [SMILES: CCC(c1cn(-c2ccccc2F)nn1)n1cc(-c2cncnc2OC)c2c(N)ncnc21]

To a stirred suspension of 7-{1-[1-(2-fluorophenyl)-1H-[1,2,3]triazol-4-yl]-propyl}-5-iodo-7H-pyrrolo[2,3-d]pyrimidin-4-amine (Preparation 45, 100 g, 216.0 mmol) in MeCN:water (4 L, 4:1) was added 4-methoxy-5-(4,4,5,5-tetramethyl-[1,3,2]dioxaborolan-2-yl)-pyrimidine (71.36 g, 302.37 mmol) and the resulting reaction degassed with Ar for 15 mins. Pd(PPh$_3$)$_4$ (24.95 g, 21.6 mmol), followed by CsF (131.23 g, 863.9 mmol) were added and the reaction stirred at 70° C. for 1.5 hrs. The mixture was diluted with EtOAc, washed with water then brine and the organic phase dried (Na$_2$SO$_4$) and concentrated in vacuo. The crude product was purified by column chromatography on silica gel eluting with MeOH:EtOAc (3:97) to afford a yellow solid. This was treated with hot (60° C.) EtOAc and charcoal, the mixture filtered through Celite® and the filtrate evaporated under reduced pressure. The resulting solid was suspended in MeCN, stirred for an hour, filtered, washed with MTBE and dried to afford the title compound as an off-white solid (39 g, 45%). $^1$HNMR (400 MHz, DMSO-d$_6$) 0.84 (t, 3H), 2.33 (m, 2H), 4.01 (s, 3H), 6.08 (m, 1H), 6.32 (br s, 2H), 7.42 (m, 1H), 7.54-7.63 (m, 2H), 7.82 (m, 1H), 8.16 (s, 1H), 8.42 (s, 1H), 8.71 (s, 1H), 8.75 (s, 1H). LCMS m/z=445.8 [MH]$^+$

Example 245: 7-{1-[1-(3,4-Difluorophenyl)-1H-1,2,3-triazol-4-yl]propyl}-5-[4-methoxypyrimidin-5-yl]-7H-pyrrolo[2,3-d]pyrimidin-4-amine

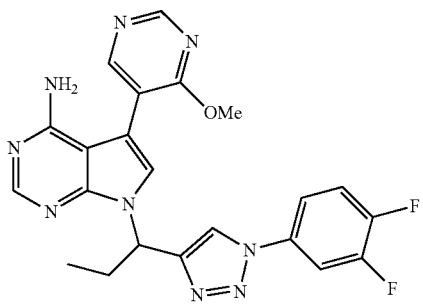 [SMILES: CCC(c1cn(-c2ccc(F)c(F)c2)nn1)n1cc(-c2cncnc2OC)c2c(N)ncnc21]

A suspension of 7-{1-[1-(3,4-difluorophenyl)-1H-1,2,3-triazol-4-yl]propyl}-5-iodo-7H-pyrrolo[2,3-d]pyrimidin-4-amine (Preparation 48, 400 mg, 0.86 mmol), 4-methoxy-5-(4,4,5,5-tetramethyl-[1,3,2]dioxaborolan-2-yl)-pyrimidine (275 mg, 1.16 mmol) and CsF (510 mg, 3.32 mmol) in MeCN (13 mL) and H$_2$O (4 mL) was degassed under N$_2$. Pd(PPh$_3$)$_4$ (100 mg, 0.09 mmol) was added and the reaction heated at 70° C. for 2 hrs. The cooled reaction was poured into water with a little brine and extracted twice with EtOAc. The combined organic layers were dried (MgSO$_4$) filtered and evaporated under reduced pressure. The resulting oil was purified by column chromatography on silica gel eluting with MeOH:EtOAc (0:100 to 10:90) to afford the title compound as an orange foam (235 mg, 58.7%). $^1$HNMR (400 MHz, DMSO-d$_6$) 0.84 (t, 3H), 2.33 (m, 2H), 3.94 (s, 3H), 6.08 (m, 1H), 6.32 (br s, 2H), 7.47 (s, 1H), 7.72 (m, 1H), 7.82 (m, 1H), 8.10 (m, 1H), 8.16 (s, 1H), 8.42 (s, 1H), 8.71 (s, 1H), 8.95 (s, 1H). LCMS m/z=465.3 [MH]$^+$

Example 246: 7-{1-[1-(2,4-Difluorophenyl)-1H-1,2,3-triazol-4-yl]propyl}-5-[4-methoxypyrimidin-5-yl]-7H-pyrrolo[2,3-d]pyrimidin-4-amine

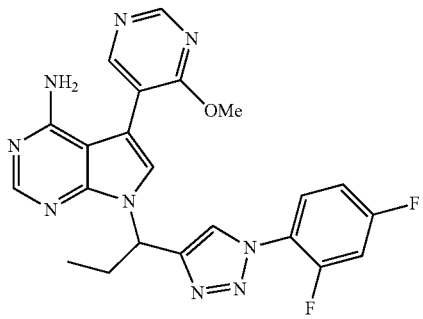 [SMILES: CCC(c1cn(-c2ccc(F)cc2F)nn1)n1cc(-c2cncnc2OC)c2c(N)ncnc21]

The title compound was obtained in 60% yield (241.4 mg), from 7-{1-[1-(2,4-difluorophenyl)-1H-1,2,3-triazol-4-yl]propyl}-5-iodo-7H-pyrrolo[2,3-d]pyrimidin-4-amine (Preparation 46) and 4-methoxy-5-(4,4,5,5-tetramethyl-[1,3,2]dioxaborolan-2-yl)-pyrimidine, following the procedure described in Example 245. $^1$HNMR (400 MHz, DMSO-d$_6$) 0.84 (t, 3H), 2.33 (m, 2H), 3.94 (s, 3H), 6.09 (m, 1H), 6.32 (br s, 2H), 7.36 (m, 1H), 7.54 (s, 1H), 7.68 (m, 1H), 7.90 (m, 1H), 8.16 (s, 1H), 8.46 (s, 1H), 8.71 (s, 1H), 8.75 (s, 1H). LCMS m/z=464.2 [MH]$^+$

Example 247: 5-Cyclobutyl-7-{1-[1-(2-fluorophenyl)-1H-1,2,3-triazol-4-yl]ethyl}-7H-pyrrolo[2,3-d]pyrimidin-4-amine

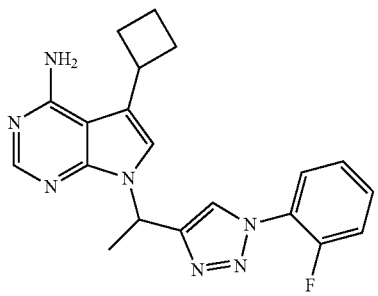 [SMILES: CC(c1cn(-c2ccccc2F)nn1)n1cc(C2CCC2)c2c(N)ncnc21]

A stirred solution of 7-{1-[1-(2-fluorophenyl)-1H-1,2,3-triazol-4-yl]ethyl}-5-iodo-7H-pyrrolo[2,3-d]pyrimidin-4-amine (Preparation 42, 3 g, 6.68 mmol) in THF (150 mL) was degassed with Ar for 30 min. Pd(OAc)$_2$ (300 mg, 1.34 mmol), s-Phos (1.1 g, 2.67 mmol) followed by cyclobutyl zinc bromide (67 mL, 33.39 mmol, 0.5M in THF) was added and the reaction stirred at rt for 6 hr under N₂. The mixture was diluted with EtOAc, washed with water followed by brine, dried (Na₂SO₄) and concentrated in vacuo. The crude product was purified twice by column chromatography on silica gel eluting with MeOH:DCM (2.5:97.5) to afford the title compound as an off white solid (800 mg, 31.75%). ¹HNMR (400 MHz, DMSO-d₆) 1.91-1.95 (m, 1H), 2.00-2.20 (m, 8H), 2.33-2.42 (m, 2H), 5.07 (s, 2H), 6.31 (m, 1H), 7.23-7.31 (m, 2H), 7.41 (m, 1H), 7.92 (m, 2H), 8.26 (s, 1H). LCMS m/z=378.2 [MH]⁺

Example 248: 5-(4-Methoxypyrimidin-5-yl)-7-{1-[1-phenyl-1H-1,2,3-triazol-4-yl]propyl}-7H-pyrrolo[2,3-d]pyrimidin-4-amine

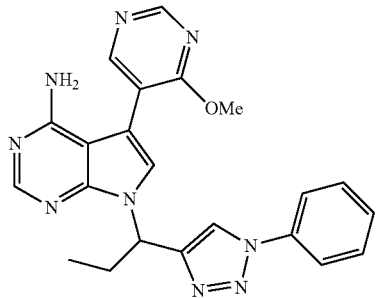 [SMILES: CCC(c1cn(-c2ccccc2)nn1)n1cc(-c2cncnc2OC)c2c(N)ncnc21]

Aq. NH₄OH (66 mL) was added to a stirred solution of N'-{5-(4-methoxypyrimidin-5-yl)-7-[1-(1-phenyl-1H-1,2,3-triazol-4-yl)propyl]-7H-pyrrolo[2,3-d]pyrimidin-4-yl}-N,N-dimethylformimidamide (Preparation 6, 1 g, 2.072 mmol) in MeOH (33 mL) and the reaction stirred at 80° C. for 12 hr in a sealed tube. The cooled reaction mixture was diluted with DCM and washed with water followed by brine. The organic layer was dried (Na₂SO₄) and concentrated in vacuo. The crude product was purified by column chromatography on silica gel eluting with MeOH:DCM (3:97) to afford the title compound as an off-white solid (530 mg, 59.55%). ¹HNMR (400 MHz, DMSO-d₆) 0.84 (t, 3H), 2.32 (m, 2H), 3.91 (s, 3H), 6.06 (m, 1H), 6.36 (br s, 2H), 7.48 (m, 3H), 7.59 (m, 2H), 7.88 (d, 1H), 8.17 (s, 1H), 8.43 (s, 1H), 8.75 (s, 1H), 8.93 (s, 1H). LCMS m/z=427.6 [MH]⁺

Example 249: 7-{1-[1-(2-Fluorophenyl)-1H-1,2,3-triazol-4-yl]ethyl}-5-[4-methoxy-2-(trifluoromethyl)pyrimidin-5-yl]-7H-pyrrolo[2,3-d]pyrimidin-4-amine

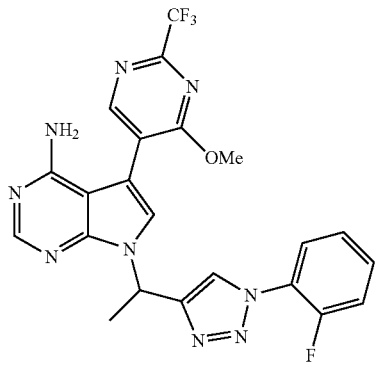 [SMILES: COc1nc(C(F)(F)F)ncc1-c1cn(C(C)c2cn(-c3ccccc3F)nn2)c2ncnc(N)c12]

37% aqueous NH₄OH (0.4 mL) was added to a solution of 4-chloro-7-{1-[1-(2-fluorophenyl)-1H-1,2,3-triazol-4-yl]ethyl}-5-[4-methoxy-2-(trifluoromethyl)pyrimidin-5-yl]-7H-pyrrolo[2,3-d]pyrimidine (Preparation 36, 38 mg, 0.07 mmol) in dioxane (0.2 mL) and the reaction heated at 130° C. for 45 min under microwave irradiation. The reaction was poured into ~10 mL of water and extracted with EtOAc. The combined organics were dried (MgSO₄), filtered, and concentrated in vacuo to provide 37 mg of crude product. The crude material was purified by prep HPLC column to afford the title compound (1.4 mg, 4%). LCMS m/z=500.0 [MH]⁺

Example 250: 7-{1-[1-(2-Fluorophenyl)-1H-1,2,3-triazol-4-yl]ethyl}-5-(oxetan-3-yl)-7H-pyrrolo[2,3-d]pyrimidin-4-amine

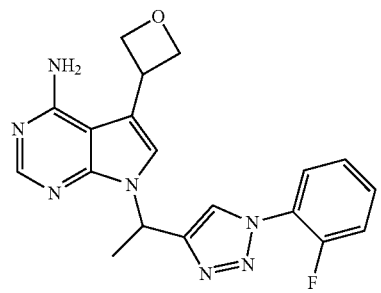 [SMILES: CC(c1cn(-c2ccccc2F)nn1)n1cc(C2COC2)c2c(N)ncnc21]

37% aq. NH₄OH (0.6 mL) was added to a solution of 4-chloro-7-{1-[1-(2-fluorophenyl)-1H-1,2,3-triazol-4-yl]ethyl}-5-(oxetan-3-yl)-7H-pyrrolo[2,3-d]pyrimidine (Preparation 35, 77 mg, 0.19 mmol) in dioxane (0.3 mL) and the reaction heated to 130° C. under microwave irradiation for 30 min. Additional 37% aq. NH₄OH (0.1 mL) was added and the reaction heated to 130° C. under microwave irradiation for a further 30 min. Water was added, the mixture extracted with DCM and the combined organic extracts dried (MgSO₄), filtered, and concentrated in vacuo. The resulting light orange oil was purified by column chromatography on silica gel eluting with MeOH:DCM (5:95 to 10:90) to afford the title compound (32.4 mg, 44.8%). ¹HNMR (400 MHz, DMSO-d₆) 1.88 (d, 3H), 4.50-4.60 (m, 3H), 5.04 (m, 2H), 6.24-6.28 (m, 1H), 6.77 (s, 2H), 7.32 (s, 1H), 7.42 (m, 1H), 7.54-7.63 (m, 2H), 7.84 (m, 1H), 8.12 (s, 1H), 8.61 (s, 1H). LCMS m/z=380.1 [MH]⁺

Example 251: 7-{1-[1-(2-Fluorophenyl)-1H-1,2,3-triazol-4-yl]propyl}-5-(3-methoxy pyrazin-2-yl)-7H-pyrrolo[2,3-d]pyrimidin-4-amine

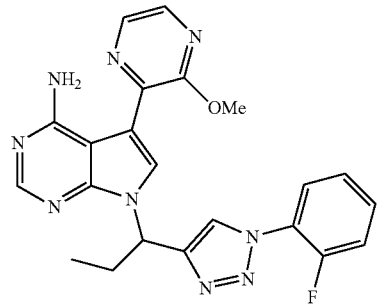 [SMILES: CCC(c1cn(-c2ccccc2F)nn1)n1cc(-c2nccnc2OC)c2c(N)ncnc21]

The title compound was obtained (252 mg, 73%) from 4-chloro-7-{1-[1-(2-fluorophenyl)-1H-1,2,3-triazol-4-yl]

propyl}-5-(3-methoxypyrazin-2-yl)-7H-pyrrolo[2,3-d]pyrimidine (Preparation 37), following an analogous procedure to that described in Example 250. $^1$HNMR (400 MHz, DMSO-$d_6$) 0.86 (t, 3H), 2.45 (m, 2H), 4.10 (s, 3H), 6.13 (t, 1H), 7.30 (br s, 2H), 7.48 (m, 1H), 7.55-7.62 (m, 2H), 7.82 (m, 1H), 8.10 (d, 1H), 8.15 (s, 1H), 8.24 (s, 1H), 8.42 (s, 1H), 8.76 (s, 1H). LCMS m/z=446.2 [MH]$^+$ Example 252: 7-{[1-(2-fluorophenyl)-1H-1,2,3-triazol-4-yl]methyl}-5-[4-methoxy-2-(trifluoromethyl) pyrimidin-5-yl]-7H-pyrrolo[2,3-d]pyrimidin-4-amine

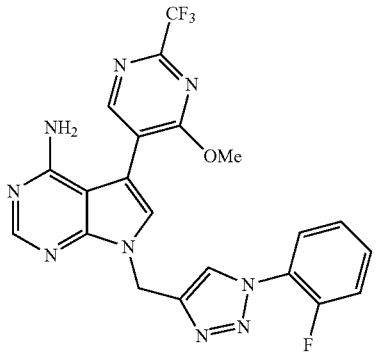 [SMILES: COc1nc(C(F)(F)F)ncc1-c1cn(Cc2cn(-c3ccccc3F)nn2)c2ncnc(N)c12]

Step 1: A suspension of 4-chloro-7-{[1-(2-fluorophenyl)-1H-1,2,3-triazol-4-yl]methyl}-5-(4,4,5,5-tetramethyl-1,3,2-dioxaborolan-2-yl)-7H-pyrrolo[2,3-d]pyrimidine (Preparation 64, 0.22 mmol, 100 mg), 5-bromo-4-methoxy-2-(trifluoromethyl) pyrimidine (Preparation 141, 0.29 mmol, 74 mg), and Na$_2$CO$_3$ (0.88 mmol, 93 mg) in EtOH (4.5 mL) and H$_2$O (0.5 mL) was degassed for a few min with N$_2$. Pd(PPh$_3$)$_4$ (0.022 mmol, 25 mg) was added and the reaction heated to 90° C. for 3 hrs. The reaction was quenched into water and washed with EtOAc (2×). The combined organics were dried (MgSO$_4$), and evaporated to dryness in vacuo to give a yellow solid which was purified using a 24 g Isco silica gel Gold column, 10-30-50% EtOAc/DCM gradient) to afford 4-chloro-7-{[1-(2-fluorophenyl)-1H-1,2,3-triazol-4-yl]methyl}-5-[4-methoxy-2-(trifluoromethyl)pyrimidin-5-yl]-7H-pyrrolo[2,3-d]pyrimidine as a white solid (62.4 mg). The compound was used without further purification in Step 2.

Step 2: Aqueous NH$_4$OH (0.4 mL of 37%) was added to the product from Step 1 (0.12 mmol, 62 mg) in dioxane (0.2 mL) in a microwave vial and the vial subjected to microwave irradiation at 130° C. for 30 min. An additional 0.3 mL of NH$_4$OH was added and the reaction re-subjected to the same conditions: The mixture was poured into H$_2$O (20 mL) of water and extracted with of EtOAc (30 mL×2). The combined organics were dried (MgSO$_4$) and evaporated to dryness to yield an off-white solid (47.9 mg). The resulting solid was purified by prep HPLC to afford the title compound (8 mg, 13.7%). LCMS m/z=486.0 [MH]$^+$ Example 253: 7-{[5-(2-fluorophenyl)-4H-1,2,4-triazol-3-yl]methyl}-5-(2-methoxypyridin-3-yl)-7H-pyrrolo[2,3-d]pyrimidin-4-amine

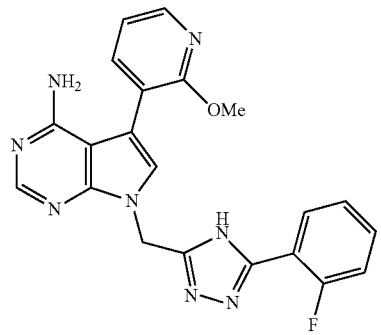 [SMILES: COc1ncccc1-c1cn(Cc2nnc(-c3ccccc3F)[nH]2)c2ncnc(N)c12]

Step 1: To a stirred solution of N'-(7-((5-(2-fluorophenyl)-4-((2-(trimethylsilyl)ethoxy)methyl)-4H-1,2,4-triazol-3-yl)methyl)-5-(2-methoxypyridin-3-yl)-7H-pyrrolo[2,3-d]pyrimidin-4-yl)-N,N-dimethylformimidamide (Preparation 30, 160 mg, 0.266 mmol) in DCM (16 mL) was added TFA (0.408 mL, 5.324 mmol) at rt. The reaction mixture was stirred and heated under reflux for 16 hr and evaporated to dryness under reduced pressure to afford N'-(7-((5-(2-fluorophenyl)-4H-1,2,4-triazol-3-yl)methyl)-5-(2-methoxypyridin-3-yl)-7H-pyrrolo[2,3-d]pyrimidin-4-yl)-N,N-dimethylformimidamide (150 mg, crude) as a sticky yellow liquid which was used without purification in Step 2.

Step 2: To a stirred solution of the compound from Step 1 (150 mg) in MeOH (5 mL) was added aq.NH$_4$OH (20 mL) at 0° C. and the reaction mixture stirred for 6 hr at 60° C. The mixture was extracted with 10% MeOH in DCM. The combined organics were dried (Na$_2$SO$_4$) and evaporated to dryness under reduced pressure. The residue was purified by prep-TLC to afford the title compound as an off-white solid (36 mg, 27%). $^1$HNMR (400 MHz, DMSO-$d_6$) 3.87 (s, 3H), 5.51 (br s, 2H), 6.05 (br s, 2H), 7.08 (m, 1H), 7.38-7.65 (m, 3H), 7.64 (d, 2H), 7.95 (t, 1H), 8.17 (m, 2H), 14.21 (br s, 1H). LCMS m/z=417 [MH]$^+$ Example 254: 5-(4-Chlorophenyl)-7-{[1-(propan-2-yl)-1H-pyrazol-4-yl]methyl}-7H-pyrrolo[2,3-d]pyrimidin-4-amine

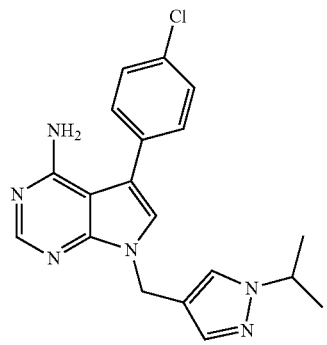 [SMILES: CC(C)n1cc(Cn2cc(-c3ccc(Cl)cc3)c3c(N)ncnc32)cn1]

To a solution of 5-(4-chlorophenyl)-7-(1H-pyrazol-4-ylmethyl)-7H-pyrrolo[2,3-d]pyrimidin-4-amine (Preparation 38, 0.7 g, 2.16 mmol) in DMF (20 mL) was added 2-bromopropane (0.32 g, 2.59 mmol) and Cs$_2$CO$_3$ (1.41 g, 4.32 mmol) and the reaction stirred at rt for 18 hrs. The reaction was diluted with water, extracted with EtOAc, the organic layer separated, washed with brine, dried and evaporated. The crude product was purified by prep-HPLC to afford the title compound (0.5 g, 63%). $^1$HNMR (400 MHz, DMSO-d$_6$) 1.35 (d, 6H), 4.42 (m, 1H), 5.20 (s, 2H), 6.13 (br s, 2H), 7.41 (s, 1H), 7.41-7.49 (m, 5H), 7.78 (s, 1H), 8.19 (s, 1H). LCMS m/z=367.2 [MH]$^+$ Example 255: 5-(4-Chlorophenyl)-7-{1-[1-(cyclobutylmethyl)-1H-1,2,3-triazol-4-yl]ethyl}-7H-pyrrolo[2,3-d]pyrimidin-4-amine

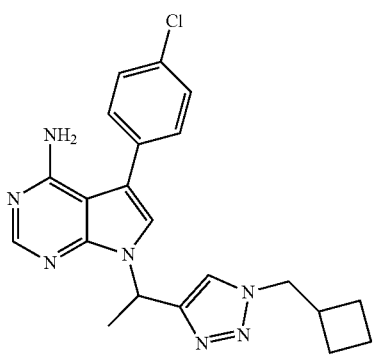 [SMILES: CC(c1cn(CC2CCC2)nn1)n1cc(-c2ccc(Cl)cc2)c2c(N)ncnc21]

Sodium azide (222 mg, 3.42 mmol) was added to a solution of cyclobutyl methyl bromide (102 mg, 0.68 mmol) in DMSO (5 mL) and the reaction stirred at 60° C. for 2 hrs. The cooled mixture was diluted with water (5 mL) and extracted with ether (3×3 mL). 7-(But-3-yn-2-yl)-5-(4-chlorophenyl)-7H-pyrrolo[2,3-d]pyrimidine-4-amine (Preparation 77, 100 mg, 0.34 mmol), CuI (10 mg, 0.052 mmol), DIPEA (500 µL, 2.86 mmol), toluene (2 mL) and t-BuOH (0.5 mL) were added and the reaction stirred at rt for 18 hrs. The mixture was evaporated under reduced pressure and the residue purified by column chromatography on silica gel eluting with DCM: DMA (0:100 to 90:10) to afford the title compound as a light brown solid (29.2 mg, 10.5%). $^1$HNMR (400 MHz, DMSO-d$_6$) 1.25 (m, 1H), 1.71-1.84 (m, 7H), 1.94-1.98 (m, 2H), 2.73 (m, 1H), 4.33 (d, 2H), 6.18 (m, 3H), 7.40 (s, 1H), 7.45 (d, 2H), 7.50 (d, 2H), 8.06 (s, 1H), 8.17 (s, 1H). LCMS m/z=408.18 [MH]$^+$ Example 256: 5-(4-Chlorophenyl)-7-{2-[1-(2-fluorophenyl)-1H-1,2,3-triazol-4-yl]propan-2-yl}-7H-pyrrolo[2,3-d]pyrimidin-4-amine

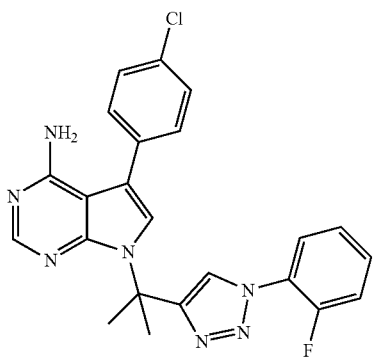 [SMILES: CC(C)(c1cn(-c2ccccc2F)nn1)n1cc(-c2ccc(Cl)cc2)c2c(N)ncnc21]

2-Amino-4-(4-chlorophenyl)-1-{2-[1-(2-fluorophenyl)-1H-1,2,3-triazol-4-yl]propan-2-yl}-1H-pyrrole-3-carbonitrile (Preparation 96, 23 mg, 0.05 mmol) was dissolved in formamide (0.2 mL, 5 mmol) and the reaction heated at 180° C. for 90 mins under microwave irradiation. The cooled mixture was diluted with water (10 mL), extracted with EtOAc (2×10 mL) and the combined organic phases dried (MgSO$_4$), filtered and evaporated under reduced pressure. The crude product was purified by column chromatography on silica gel eluting with MeOH:EtOAc to afford the title compound as a brown oil. $^1$HNMR (400 MHz, DMSO-d$_6$) 2.20 (s, 6H), 6.14 (br s, 2H), 7.38 (s, 1H), 7.45 (m, 1H), 7.50-7.60 (m, 6H), 7.84 (m, 1H), 8.04 (s, 1H), 8.56 (s, 1H). LCMS m/z=448.4 [MH]$^+$ Example 257: 5-(4-Chlorophenyl)-7-{1-[1-(2-fluorophenyl)-1H-1,2,3-triazol-4-yl]ethyl}-6-methyl-7H-pyrrolo[2,3-d]pyrimidin-4-amine

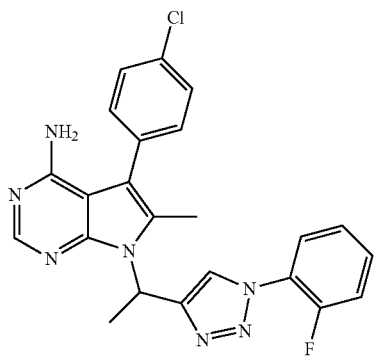 [SMILES: Cc1c(-c2ccc(Cl)cc2)c2c(N)ncnc2n1C(C)c1cn(-c2ccccc2F)nn1]

Step 1: To a stirred solution of N'-(7-(but-3-yn-2-yl)-5-(4-chlorophenyl)-6-methyl-7H-pyrrolo[2,3-d]pyrimidin-4-yl)-N,N-dimethylformimidamide (Preparation 15, 30 mg, 0.08 mmol) in toluene:t-BuOH (1.5 mL:0.4 mL) was added 1-azido-2-fluoro-benzene (32.21 mg, 0.21 mmol), DIPEA (0.15 mL) and CuI (8.6 mg) at 0° C. under N$_2$ atmosphere. The reaction was stirred at rt for 16 hr, diluted with EtOAc, washed with water, brine, dried (Na$_2$SO$_4$) and evaporated to dryness in vacuo to afford N'-5-(4-chlorophenyl)-7-(1-(1-(2-fluorophenyl)-1H-1,2,3-triazol-4-yl)ethyl)-6-methyl-7H-pyrrolo[2,3-d]pyrimidin-4-yl)-N,N-dimethylformimidamide as a brown gum (30 mg, 72.7%) which was used without any further purification.

Step 2: NH$_4$OH (2 mL) was added to a stirred solution of the compound from Step 1 (30 mg, 0.06 mmol) in MeOH (1.5 mL) in a sealed tube. The reaction was stirred at 60° C. for 16 hr and evaporated to dryness in vacuo. The residue was diluted with EtOAc, washed with water, brine, dried (Na$_2$SO$_4$) and evaporated to dryness in vacuo. The residue was purified by prep-TLC using 50% EtOAc in hexane to afford the title compound as an off-white solid (19.0 mg, 51.73%). $^1$HNMR (400 MHz, MeOH-d$_4$) 1.24 (m, 2H), 2.10 (d, 3H), 2.28 (s, 3H), 6.32 (q, 1H), 7.36-7.74 (m, 6H), 7.56 (m, 1H), 8.08 (s, 1H), 8.42 (d, 1H). LCMS m/z=448.0 [MH]$^+$

Example 258: 5-(4-Chlorophenyl)-7-{1-[3-(2-fluorophenyl)-1,2-oxazol-5-yl]ethyl}-7H-pyrrolo[2,3-d]pyrimidin-4-amine

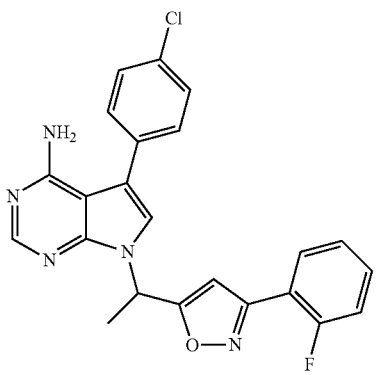 [SMILES: CC(c1cc(-c2ccccc2F)no1)n1cc(-c2ccc(Cl)cc2)c2c(N)ncnc21]

A stirred suspension of 5-(1-chloroethyl)-3-(2-fluorophenyl)isoxazole (Preparation 128, 50 mg, 0.204 mmol), 5-(4-chlorophenyl)-7H-pyrrolo[2,3-d]pyrimidin-4-amine (Preparation 80, 46.1 mg, 0.204) and $Cs_2CO_3$ (166.44 mg, 0.511 mmol) in DMF (0.5 mL) was heated at 70° C. under $N_2$ for 5 hr. The reaction mixture was evaporated to dryness in vacuo, diluted with EtOAc and washed with water. The residue was purified by column chromatography on silica gel eluting with 50% EtOAc in hexane to afford the title compound as a light yellow solid (25 mg, 28%). $^1$HNMR (400 MHz, MeOD-$d_4$) 2.01 (d, 3H), 6.33 (q, 1H), 6.77 (d, 1H), 7.20-7.30 (m, 2H), 7.39 (s, 1H), 7.46-7.52 (m, 5H), 7.88 (m, 1H), 8.20 (s, 1H). LCMS m/z=434 [MH]$^+$

Example 259: 5-(4-Chlorophenyl)-7-{1-[3-(2-fluorophenyl)-1,2-oxazol-5-yl]ethyl}-6-methyl-7H-pyrrolo[2,3-d]pyrimidin-4-amine

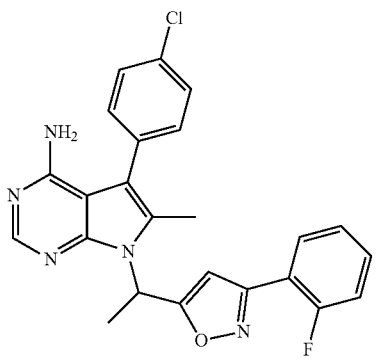 [SMILES: Cc1c(-c2ccc(Cl)cc2)c2c(N)ncnc2n1C(C)c1cc(-c2ccccc2F)no1]

To a stirred solution of 5-(4-chlorophenyl)-6-methyl-7H-pyrrolo[2,3-d] pyrimidin-4-amine (Preparation 24, 25.0 mg, 0.097 mmol) in DMF (1.0 mL) was added $Cs_2CO_3$ (78.71 mg, 0.11 mmol) at 0° C. 5-(1-Chloroethyl)-3-(2-fluorophenyl)isoxazole (Preparation 128, 23.9 mg, 0.242 mmol) was added and the reaction mixture heated at 60° C. for 16 hr. The reaction was diluted with EtOAc, washed with water, brine, dried ($Na_2SO_4$) and evaporated to dryness. The residue was purified by prep-HPLC to afford the title compound as a light brown solid (10 mg, 23%). $^1$HNMR (400 MHz, MeOH-$d_4$) 2.08 (d, 3H), 2.26 (s, 3H), 6.33 (q, 1H), 6.81 (d, 1H), 7.23-7.30 (m, 2H), 7.39 (d, 2H), 7.50 (d, 2H), 7.78-7.92 (m, 2H), 8.09 (s, 1H). LCMS m/z=448 [MH]$^+$

Example 260: 5-(4-Chlorophenyl)-7-{1-[3-(2-methoxyphenyl)-1,2-oxazol-5-yl]ethyl}-7H-pyrrolo[2,3-d] pyrimidin-4-amine

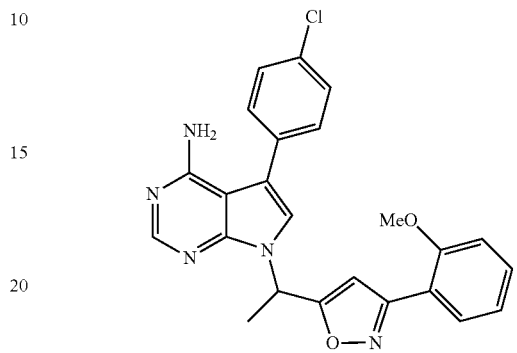

$Cs_2CO_3$ (267 mg, 0.82 mmol) was added to a stirred solution of 5-(4-chlorophenyl)-7H-pyrrolo[2,3-d]pyrimidin-4-amine (Preparation 80, 80 mg, 0.328 mmol) and 5-(1-chloroethyl)-3-(2-methoxyphenyl)isoxazole (Preparation 124, 93 mg, 0.393 mmol) in DMF (1 mL) at rt and the resulting mixture heated at 60° C. for 4 hr. The reaction mixture was diluted with water (20 mL) and extracted with EtOAc (2×20 mL). The combined extracts were washed with water, brine, dried ($Na_2SO_4$) and evaporated in vacuo. The residue was purified by column chromatography on silica gel to afford the title compound as an off white solid (12.5 mg, 8.55%). $^1$HNMR (400 MHz, MeOH-$d_4$) 1.99 (d, 3H), 3.87 (s, 3H), 6.32 (q, 1H), 6.80 (s, 1H), 7.00 (t, 1H), 7.11 (d, 1H), 7.36 (s, 1H), 7.40-7.51 9m, 5H), 7.73 (dd, 1H). LCMS m/z=446 [MH]$^+$

Example 261: 5-(4-Chlorophenyl)-7-{1-[3-(3-methoxyphenyl)-1,2-oxazol-5-yl]ethyl}-7H-pyrrolo[2,3-d] pyrimidin-4-amine

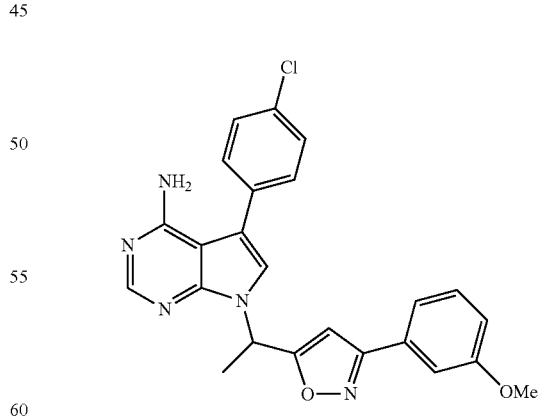

The title compound was prepared as an off white solid (28 mg, 17%) in an analogous manner to Example 260 using of 5-(4-chlorophenyl)-7H-pyrrolo[2,3-d]pyrimidin-4-amine (Preparation 80, 105 mg, 0.443 mmol) and 5-(1-chloroethyl)-3-(3-methoxyphenyl)isoxazole (Preparation 126, 90 mg, 0.369 mmol). $^1$HNMR (400 MHz, MeOH-$d_4$) 1.99 (s, 3H), 3.83 (s, 3H), 6.31 (q, 1H), 6.82 (s, 1H), 7.02 (m, 1H), 7.33-7.40 (m, 4H), 7.45-7.53 (m, 4H), 8.20 (s, 1H). LCMS m/z=446 [MH]+

Example 262: 5-(4-Chlorophenyl)-7-{[1-(2-fluorophenyl)-1H-pyrazol-4-yl]methyl}-7H-pyrrolo[2,3-d]pyrimidin-4-amine

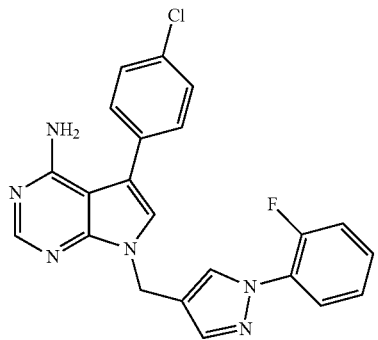 [SMILES: Nc1ncnc2c1c(-c1ccc(Cl)cc1)cn2Cc1cnn(-c2ccccc2F)c1]

The title compound was prepared as an off white solid (23 mg, 27%) in an analogous manner to Example 260 using 5-(4-chlorophenyl)-7H-pyrrolo[2,3-d]pyrimidin-4-amine (Preparation 80, 50 mg, 0.204 mmol) and 4-(chloromethyl)-1-(2-fluorophenyl)-1H-pyrazole (Preparation 98, 43 mg, 0.204 mmol). ¹HNMR (400 MHz, MeOH-d₄) 5.39 (s, 2H), 7.25-7.44 (m, 4H), 7.45 (m, 4H), 7.73 (t, 1H), 7.76 (s, 1H), 8.15 (d, 1H), 8.21 (s, 1H). LCMS m/z=419 [MH]+

Example 263: 5-(4-Chlorophenyl)-7-{[2-(2-fluorophenyl)-1H-imidazol-5-yl]methyl}-7H-pyrrolo[2,3-d] pyrimidin-4-amine

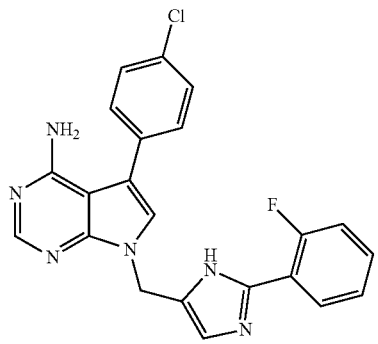 [SMILES: Nc1ncnc2c1c(-c1ccc(Cl)cc1)cn2Cc1cnc(-c2ccccc2F)[nH]1]

The title compound was prepared as an off white solid (13 mg, 13%) in an analogous manner to Example 260 using 5-(4-chlorophenyl)-7H-pyrrolo[2,3-d] pyrimidin-4-amine (Preparation 80, 58 mg, 0.24 mmol) and 5-chloromethyl-2-(2-fluorophenyl)-1H-imidazole (Preparation 105, 50 mg, 0.24 mmol). ¹HNMR (400 MHz, MeOD-d₄) 5.41 (m, 1H), 7.14-7.33 (m, 4H), 7.38-7.50 (m, 5H), 7.95 (m, 1H), 8.20 (s, 1H). LCMS m/z=419 [MH]+

Example 264: 5-(4-Chlorophenyl)-7-[(2-phenyl-1H-imidazol-5-yl)methyl]-7H-pyrrolo[2,3-d]pyrimidin-4-amine

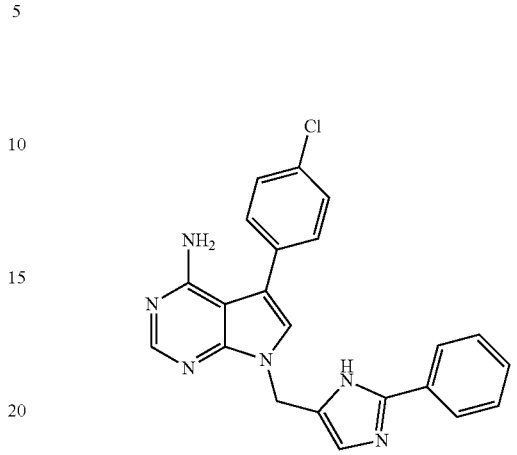

The title compound was prepared as a pale yellow solid (25 mg, 5.1%) in an analogous manner to Example 260 using 5-(4-chlorophenyl)-7H-pyrrolo[2,3-d] pyrimidin-4-amine (Preparation 80, 300 mg, 1.23 mmol) and 5-(chloromethyl)-2-phenyl-1H-imidazole (Preparation 106, 473 mg, 2.45 mmol). ¹HNMR (400 MHz, MeOH-d4) 5.39 (m, 2H), 7.13 (s, 1H), 7.28 (s, 1H), 7.34-7.49 (m, 7H), 7.82 (s, 1H), 7.84 (s, 1H), 8.20 (s, 1H). LCMS m/z=401 [MH]+

Example 265: 5-(4-Chlorophenyl)-7-{[1-(2-fluorophenyl)-1H-imidazol-4-yl]methyl}-7H-pyrrolo[2,3-d] pyrimidin-4-amine

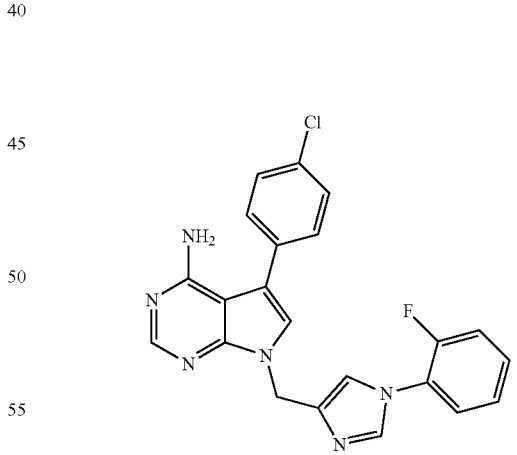

The title compound was prepared as an off-white solid (13.2 mg, 10%) in an analogous manner to Example 260 using 5-(4-chlorophenyl)-7H-pyrrolo[2,3-d]pyrimidin-4-amine (Preparation 80, 80 mg, 1.23 mmol) and 4-(chloromethyl)-1-(2-fluorophenyl)-1H-imidazole (Preparation 108, 76 mg, 0.36 mmol). ¹HNMR (400 MHz, DMSO-d₆) 5.32 (s, 2H), 6.13 (br s, 2H), 7.30-7.54 (m, 8H), 7.55 (s, 1H), 7.62 (t, 1H), 8.00 (s, 1H), 8.18 (s, 1H). LCMS m/z=419 [MH]+

Example 266: 5-(4-Chlorophenyl)-7-{1-[3-(2-methylphenyl)-1,2-oxazol-5-yl]ethyl}-7H-pyrrolo[2,3-d]pyrimidin-4-amine

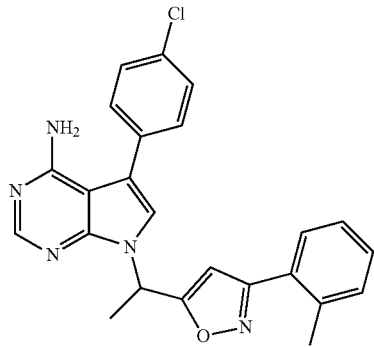 [SMILES: Cc1ccccc1-c1cc(C(C)n2cc(-c3ccc(Cl)cc3)c3c(N)ncnc32)on1]

The title compound was prepared as an off-white solid (40 mg, 23%) in an analogous manner to Example 260 using 5-(4-chlorophenyl)-7H-pyrrolo[2,3-d]pyrimidin-4-amine (Preparation 80, 100 mg, 0.41 mmol) and 5-(1-chloroethyl)-3-(o-tolyl)isoxazole (Preparation 132, 109 mg, 0.49 mmol). $^1$HNMR (400 MHz, MeOH-d$_4$) 2.00 (d, 3H), 2.41 (s, 3H), 6.34 (q, 1H), 6.62 (s, 1H), 7.22-7.36 (m, 3H), 7.39 (s, 1H), 7.44-7.52 (m, 5H), 8.20 (s, 1H). LCMS m/z=430 [MH]$^+$

Example 267: 5-(4-Chlorophenyl)-7-{1-[3-(3-fluorophenyl)-1,2-oxazol-5-yl]ethyl}-7H-pyrrolo[2,3-d]pyrimidin-4-amine

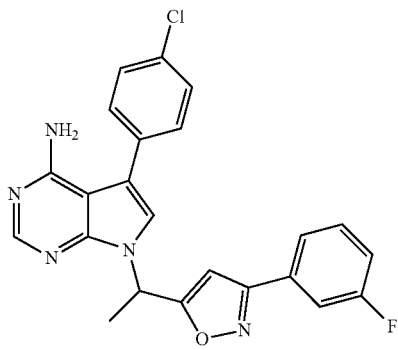 [SMILES: CC(c1cc(-c2cccc(F)c2)no1)n1cc(-c2ccc(Cl)cc2)c2c(N)ncnc21]

The title compound was prepared as an off-white solid (40 mg, 23%) in an analogous manner to Example 260 using of 5-(4-chlorophenyl)-7H-pyrrolo[2,3-d]pyrimidin-4-amine (Preparation 80, 100 mg, 0.41 mmol) and 5-(1-chloroethyl)-3-(3-fluorophenyl)isoxazole (Preparation 134, 110 mg, 0.49 mmol). $^1$HNMR (400 MHz, MeOD-d$_4$) 2.00 (d, 3H), 6.31 (q, 1H), 6.85 (s, 1H), 7.22 (m, 1H), 7.37 (s, 1H), 7.43-7.52 (m, 5H), 7.56 (m, 1H), 7.64 (m, 1H), 8.20 (s, 1H). LCMS m/z=434 [MH]$^+$

Example 268: 7-{[1-(2-Fluorophenyl)-1H-pyrazol-3-yl]methyl}-5-(2-methoxypyridin-3-yl)-7H-pyrrolo[2,3-d]pyrimidin-4-amine

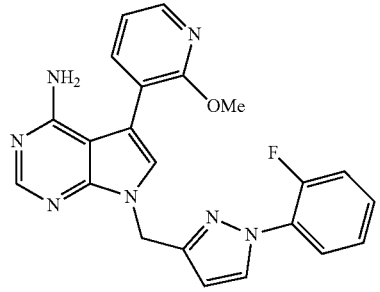 [SMILES: COc1ncccc1-c1cn(Cc2ccn(-c3ccccc3F)n2)c2ncnc(N)c12]

To a stirred solution of 5-(2-methoxypyridin-3-yl)-7H-pyrrolo[2,3-d]pyrimidin-4-amine (Preparation 22, 115 mg, 0.47 mmol) in DMF (8 mL) was added Cs$_2$CO$_3$ (387.3 mg, 1.2 mmol) and 3-chloromethyl-1-(2-fluorophenyl)-1H-pyrazole (110 mg, 0.52 mmol) at rt. The resulting mixture was stirred at rt for 16 hr, diluted with EtOAc, washed with water, brine, dried (Na$_2$SO$_4$) and evaporated to dryness in vacuo. The residue was purified by prep-TLC (50% EtOAc-Hexane) to afford the title compound as an off-white solid (12 mg, 6%). $^1$HNMR (400 MHz, CDCl$_3$) 3.91 (s, 3H), 5.45 (s, 2H), 6.37 (d, 1H), 6.94 (dd, 1H), 7.13 (s, 1H), 7.20-7.30 (m, 3H), 7.54 (m, 1H), 7.78 (m, 1H), 7.85 (t, 1H), 8.10 (m, 1H), 8.25 (s, 1H). LCMS m/z=416 [MH]$^+$

Example 269: 5-(4-Chlorophenyl)-7-[(3-cyclohexyl-1,2-oxazol-5-yl)methyl]-7H-pyrrolo[2,3-d]pyrimidin-4-amine

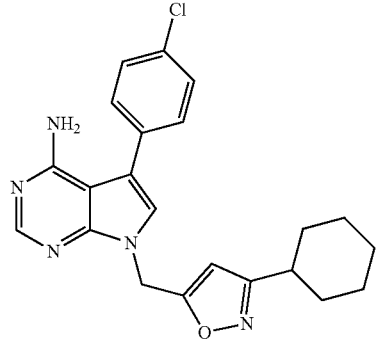 [SMILES: Nc1ncnc2c1c(-c1ccc(Cl)cc1)cn2Cc1cc(C2CCCCC2)no1]

NaH (60% dispersion in oil, 15 mg, 0.368 mmol) was added to 5-(4-chlorophenyl)-7H-pyrrolo[2,3-d]pyrimidin-4-amine (Preparation 80, 100 mg, 0.409 mmol) in DMF (1 mL) at 0° C., then 5-(chloromethyl)-3-cyclohexylisoxazole (82 mg, 0.409 mmol) was added and the reaction stirred at 60° C. in a sealed tube for 3 hr. The reaction was quenched with H$_2$O and extracted with EtOAc. The combined organics were washed (H$_2$O), dried (Na$_2$SO$_4$) and evaporated to dryness in vacuo. The residue was purified by column chromatography on silica gel eluting with 100% DCM to 95:5 DCM:MeOH to afford the title compound as a pale brown solid (96 mg, 57%). Mp: 173-175° C. $^1$HNMR (400 MHz, DMSO-d$_6$) 1.21-1.38 (m, 5H), 1.63-1.72 (m, 3H), 1.81-1.86 (m, 2H), 2.62-2.68 (m, 1H), 5.53 (s, 2H), 6.23 (br s, 2H), 6.32 (s, 1H), 7.46-7.54 (m, 5H), 8.19 (s, 1H). LCMS m/z=408.3 [MH+]

Example 270: 7-({1-[4-(Difluoromethyl)phenyl]-1H-pyrazol-4-yl}methyl)-5-(2-methoxypyridin-3-yl)-7H-pyrrolo[2,3-d]pyrimidin-4-amine

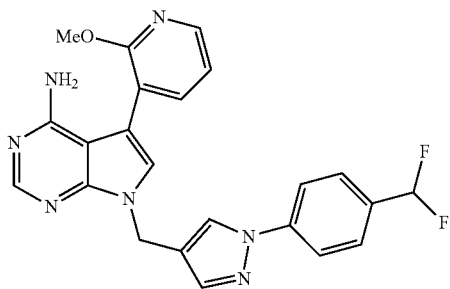 [SMILES: COc1ncccc1-c1cn(Cc2cnn(-c3ccc(C(F)F)cc3)c2)c2ncnc(N)c12]

1-Bromo-4-(difluoromethyl)benzene (625 μmol) was added to 5-(2-methoxypyridin-3-yl)-7H-pyrrolo[2,3-d]pyrimidin-4-amine (Preparation 22; 125 μmol, 40 mg) in a reaction vial. Anhydrous $Cs_2CO_3$ (312.5 μmol, 105 mg) was added followed by trans N,N'dimethylcyclohexane 1,2-diamine (62.5 μmol 10 μL) and CuI (25 μmol, 4.8 mg) under Ar. The reaction vial was heated with stirring at 110° C. for 30 hrs. The reaction mixture was diluted with DMSO (1 mL) and purified by prep-HPLC to afford the title compound. LCMS RT=1.48 minutes; LCMS m/z=448.37 [MH+]

Example 271: 7-{1-[1-(2-Fluorophenyl)-1H-pyrazol-4-yl]propyl}-5-[2-(trifluoromethyl) pyrimidin-5-yl]-7H-pyrrolo[2,3-d]pyrimidin-4-amine

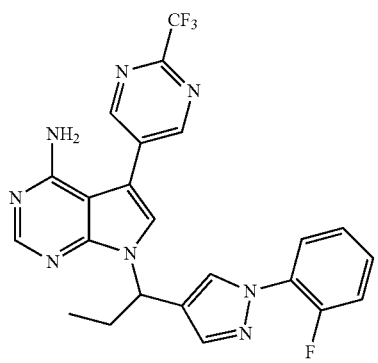 [SMILES: CCC(c1cnn(-c2ccccc2F)c1)n1cc(-c2cnc(C(F)(F)F)nc2)c2c(N)ncnc21]

A solution of N'-(7-(1-(1-(2-fluorophenyl)-1H-pyrazol-4-yl)propyl)-5-(2-(trifluoromethyl)pyrimidin-5-yl)-7H-pyrrolo[2,3-d]pyrimidin-4-yl)-N,N-dimethyl formimidamide (Preparation 4, 300 mg, 0.56 mmol), MeOH (10 mL) and added $NH_3.H_2O$ (20 mL) was stirred at 100° C. in a sealed tube overnight. The cooled mixture was diluted (EtOAc), washed with brine and the organic layer collected, dried and evaporated. The crude was purified by prep HPLC to afford the title compound (120 mg, 44%). $^1$HNMR (DMSO-$d_6$) 0.83 (t, 3H), 2.27-2.36 (m, 2H), 5.92 (m, 1H), 6.64 (s, 2H), 7.31 (m, 1H), 7.34-7.43 (m, 2H), 7.74 (m, 1H), 7.87 (s, 1H), 7.96 (s, 1H), 8.25 (s, 1H), 8.30 9s, 1H), 9.06 (s, 2H). LCMS m/z=483.1 [MH]+

Example 272: 5-(2-Methoxypyridin-3-yl)-7-[(5-phenyl-4H-1,2,4-triazol-3-yl)methyl]-7H-pyrrolo[2,3-d]pyrimidin-4-amine

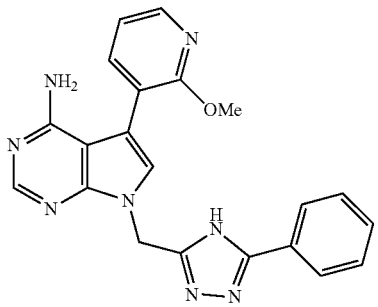 [SMILES: COc1ncccc1-c1cn(Cc2nnc(-c3ccccc3)[nH]2)c2ncnc(N)c12]

The title compound was prepared using an analogous method to Example 271 as an off-white solid (31 mg, 28%), using N'-(5-(2-methoxypyridin-3-yl)-7-((5-phenyl-4-((2-(trimethylsilyl)ethoxy)methyl)-4H-1,2,4-triazol-3-yl)methyl)-7H-pyrrolo [2,3-d]pyrimidin-4-yl)-N,N-dimethyl-formimidamide (Preparation 31). $^1$HNMR (400 MHz, DMSO-$d_6$) 3.90 (s, 3H), 5.52 (s, 2H), 5.73 (s, 2H), 7.06 (dd, 1H), 7.35 (s, 1H), 7.46 (m, 3H), 7.64 (d, 1H), 7.97 (m, 2H), 8.17 (s, 2H), 13.98 (br s, 1H). LCMS m/z=399 [MH]+

Example 273: 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine

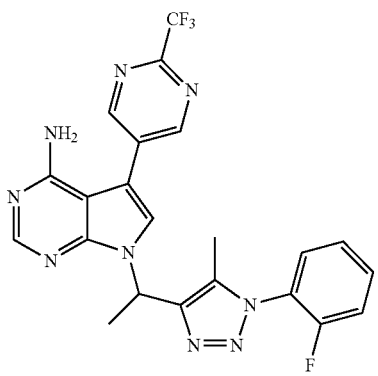 [SMILES: Cc1c(C(C)n2cc(-c3cnc(C(F)(F)F)nc3)c3c(N)ncnc32)nnn1-c1ccccc1F]

A mixture of N'-(7-(1-(1-(2-fluorophenyl)-5-methyl-1H-1,2,3-triazol-4-yl)ethyl)-5-(2-(trifluoromethyl)pyrimidin-5-yl)-7H-pyrrolo[2,3-d]pyrimidin-4-yl)-N,N-dimethyl-formimidamide (Preparation 8, 900 mg, 1.67 mmol) in dioxane (20 mL) and $NH_3.H_2O$ (30 mL) was stirred at 90° C. for 16 hrs. The solvent was removed in vacuo and the residue was purified by trituration with MeOH to afford the title compound (610 mg, 75%) as a brown solid. LCMS m/z=484.0 [MH]+

Example 274: 7-{1-[1-(2,4-Difluorophenyl)-1H-pyrazol-4-yl]propyl}-5-[2-(trifluoromethyl)pyrimidin-5-yl]-7H-pyrrolo[2,3-d]pyrimidin-4-amine

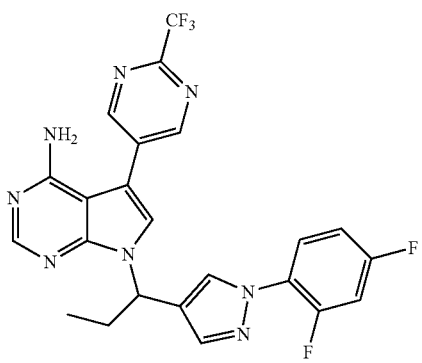 [SMILES: CCC(c1cnn(-c2ccc(F)cc2F)c1)n1cc(-c2cnc(C(F)(F)F)nc2)c2c(N)ncnc21]

A sealed tube was charged with N'-(7-(1-(1-(2,4-difluorophenyl)-1H-pyrazol-4-yl)propyl)-5-(2-(trifluoromethyl)pyrimidin-5-yl)-7H-pyrrolo[2,3-d]pyrimidin-4-yl)-N,N-dimethylformimidamide (Preparation 5, 650 mg, 1.17 mmol), dioxane (10 mL) and NH$_3$.H$_2$O (15 mL). The sealed tube was stirred at 90° C. for 16 hrs, cooled to rt and evaporated to dryness in vacuo. The residue was purified by prep-HPLC eluting with MeCN in water (0.1% TFA) from 40% to 50% in 8 minutes to give the title compound as a brown solid (420 mg, 71%). $^1$HNMR (400 MHz, DMSO-d$_6$): 0.86 (m, 3H), 2.35 (m, 2H), 5.96 (t, 1H), 7.25 (m, 1H), 7.53 (m, 1H), 7.75 (m, 1H), 7.80 (s, 1H), 8.10-8.40 (m, 4H), 8.54 (s, 1H), 9.13 (s, 2H). LCMS m/z=501.5 [MH]$^+$

Example 275: 7-{1-[1-(2,4-Difluorophenyl)-1H-pyrazol-4-yl]ethyl}-5-[2-(trifluoromethyl)pyrimidin-5-yl]-7H-pyrrolo[2,3-d]pyrimidin-4-amine

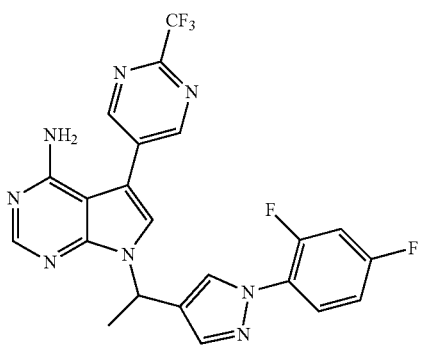 [SMILES: CC(c1cnn(-c2ccc(F)cc2F)c1)n1cc(-c2cnc(C(F)(F)F)nc2)c2c(N)ncnc21]

The title compound was prepared (300 mg, 83%) in an analogous manner to Example 274 using N'-(7-(1-(1-(2,4-difluorophenyl)-1H-pyrazol-4-yl)ethyl)-5-(2-(trifluoromethyl)pyrimidin-5-yl)-7H-pyrrolo[2,3-d]pyrimidin-4-yl)-N,N-dimethyl formimidamide (Preparation 3, 0.4 g, 0.74 mmol). LCMS m/z=487.0 [MH]$^+$

Example 276: 7-{1-[2-(2,4-Difluorophenyl)-2H-imidazol-4-yl]propyl}-5-[2-(trifluoromethyl)pyrimidin-5-yl]-7H-pyrrolo[2,3-d]pyrimidin-4-amine

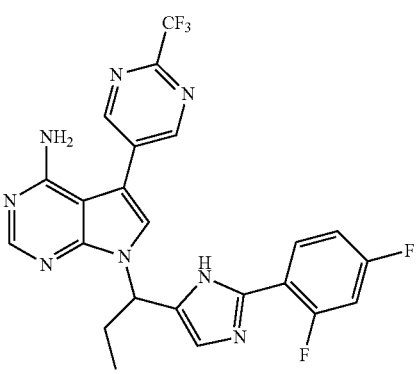 [SMILES: CCC(c1cnc(-c2ccc(F)cc2F)[nH]1)n1cc(-c2cnc(C(F)(F)F)nc2)c2c(N)ncnc21]

The title compound was prepared (220 mg, 54%) in an analogous manner to Example 274, using N'-(7-(1-(2-(2,4-difluorophenyl)-2H-imidazol-4-yl)propyl)-5-(2-(trifluoromethyl)pyrimidin-5-yl)-7H-pyrrolo[2,3-d]pyrimidin-4-yl)-N,N-dimethylformimidamide (Preparation 7, 0.45 g, 0.81 mmol). LCMS m/z=501.0 [MH$^+$]

Example 277: 7-(1-(1-(2-Fluorophenyl)-1H-pyrazol-4-yl)ethyl)-5-(2-(trifluoromethyl)pyrimidin-5-yl)-7H-pyrrolo[2,3-d]pyrimidin-4-amine

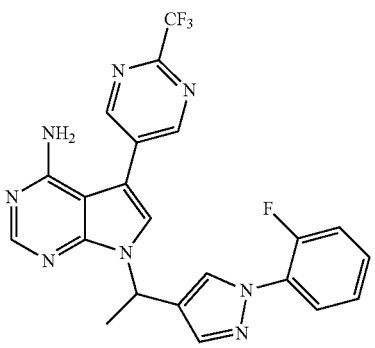 [SMILES: CC(c1cnn(-c2ccccc2F)c1)n1cc(-c2cnc(C(F)(F)F)nc2)c2c(N)ncnc21]

The title compound was prepared (400 mg, 67%) in an analogous manner to Example 274 using N'-(7-{1-[1-(2-fluorophenyl)-1H-pyrazol-4-yl]ethyl}-5-[2-(trifluoromethyl)pyrimidin-5-yl]-7H-pyrrolo[2,3-d]pyrimidin-4-yl)-N,N-dimethyl formimidamide (Preparation 2, 666 mg, 1.28 mmol). LCMS m/z=469.1 [MH]$^+$ Example 278: 7-{[1-(2,4-Difluorophenyl)-1H-1,2,3-triazol-4-yl]methyl}-5-(6-methoxypyridin-3-yl)-6-methyl-7H-pyrrolo[2,3-d]pyrimidin-4-amine

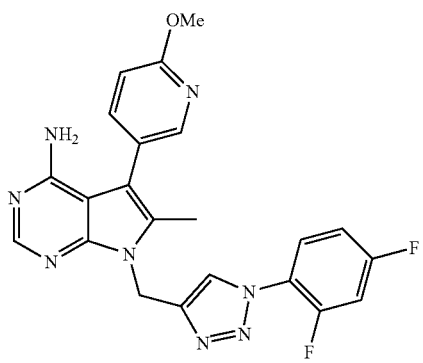 [SMILES: COc1ccc(-c2c(C)n(Cc3cn(-c4ccc(F)cc4F)nn3)c3ncnc(N)c23)cn1]

The title compound was prepared (54.5 mg, 28%) in an analogous manner to Example 274 using N'-(7-{[1-(2,4-difluorophenyl)-1H-1,2,3-triazol-4-yl]methyl}-5-(6-methoxypyridin-3-yl)-6-methyl-7H-pyrrolo[2,3-d]pyrimidin-4-yl)-N,N-dimethyl formimidamide (Preparation 10, 220 mg, 0.44 mmol). $^1$HNMR (400 MHz, DMSO-d$_6$): 2.39 (s, 3H), 3.91 (s, 3H), 5.59 (s, 2H), 5.86 (br s, 2H), 6.93 (d, 1H), 7.30 (t, 1H), 7.63 (m, 2H), 7.85 (t, 1H), 8.13 (m, 2H), 8.54 (s, 1H). LCMS m/z=449.2 [MH]$^+$ Example 279: 7-{[1-(2,4-Difluorophenyl)-1H-pyrazol-4-yl]methyl}-5-[2-(trifluoromethyl)pyrimidin-5-yl]-7H-pyrrolo[2,3-d]pyrimidin-4-amine

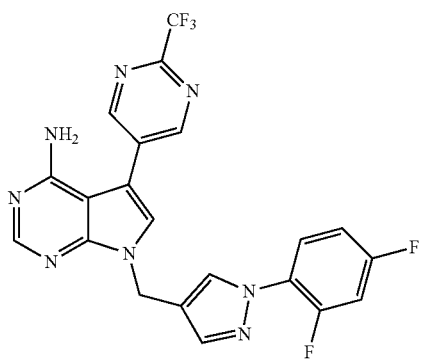 [SMILES: Nc1ncnc2c1c(-c1cnc(C(F)(F)F)nc1)cn2Cc1cnn(-c2ccc(F)cc2F)c1]

The title compound was prepared (600 mg, 89%) in an analogous manner to Example 274 using N'-(7-((1-(2,4-difluorophenyl)-1H-pyrazol-4-yl)methyl)-5-(2-(trifluoromethyl)pyrimidin-5-yl)-7H-pyrrolo[2,3-d]pyrimidin-4-yl)-N,N-dimethylformimidamide (Preparation 1, 750 mg, 1.422 mmol). $^1$HNMR (400 MHz, DMSO-d$_6$): 5.38 (s, 2H), 6.64 (br s, 2H), 7.23 (t, 1H), 7.52 (t, 1H), 7.70-7.80 (m, 3H), 8.26 (s, 2H), 9.04 (s, 1H). LCMS m/z=473.1 [MH]$^+$ The following compounds were prepared by analogy to the methods previously described:

Example 280: 5-(4-Chlorophenyl)-7-[(3-cyclopropyl-1,2-oxazol-5-yl)methyl]-7H-pyrrolo[2,3-d]pyrimidin-4-amine $^1$HNMR (400 MHz, DMSO-d$_6$) 0.71 (m, 2H), 0.96 (m, 2H), 1.94 (m, 1H), 5.50 (s, 2H), 6.15 (s, 1H), 6.22 (br s, 2H), 7.43 (s, 1H), 7.44 (d, 2H), 7.52 (d, 2H), 8.10 (s, 1H). LCMS m/z=366.0 [MH]$^+$ Example 281: 5-(4-Chlorophenyl)-7-[(1-cyclopentyl-1H-1,2,3-triazol-4-yl)methyl]-7H-pyrrolo[2,3-d]pyrimidin-4-amine $^1$HNMR (400 MHz, CDCl$_3$): 1.71-1.78 (m, 2H), 1.85-1.89 (m, 2H), 1.97-2.04 (m, 2H), 2.19-2.25 (m, 2H), 4.84-4.90 (m, 1H), 5.10 (br s, 2H), 5.11 (s, 2H), 7.18 (s, 1H), 7.38-7.43 (m, 4H), 7.58 (s, 1H), 8.37 (s, 1H). LCMS m/z=394.0 [MH]$^+$ Example 282: 5-(4-Chlorophenyl)-7-[(4-phenyl-1H-imidazol-2-yl)methyl]-7H-pyrrolo[2,3-d]pyrimidin-4-amine $^1$HNMR (400 MHz, DMSO-d$_6$): 2.36 (s, 3H), 5.54 (s, 2H), 6.17 (br s, 2H), 7.37 (s, 2H), 7.46-7.52 (m, 5H), 7.75 (s, 2H), 8.20 (s, 1H), 8.75 (s, 1H). LCMS m/z=416.0 [MH]$^+$ Example 283: 5-(4-Chlorophenyl)-7-{[3-(propan-2-yl)-1,2-oxazol-5-yl]methyl}-7H-pyrrolo[2,3-d]pyrimidin-4-amine $^1$HNMR (400 MHz, CDCl$_3$): 1.24 (d, 6H), 3.02 (m, 1H), 5.10 (m, 1H), 5.49 (s, 2H), 6.07 (s, 1H), 7.07 (s, 1H), 7.43 (m, 4H), 8.36 (s, 1H). LCMS m/z=366.1 [MH]$^+$ Example 284: 5-(4-Chlorophenyl)-7-[(5-phenyl-4H-1,2,4-triazol-3-yl)methyl]-7H-pyrrolo[2,3-d]pyrimidin-4-amine $^1$HNMR (400 MHz, DMSO-d$_6$) 0.85 (m, 2H), 0.97 (m, 2H), 1.98 (m, 1H), 5.31 (s, 2H), 6.16 (br s, 2H), 7.31 (s, 1H), 7.46 (d, 2H), 7.49 (d, 2H), 8.15 (s, 1H), 13.47 (s, 1H). LCMS m/z=366.0 [MH]$^+$ Example 285: 5-(4-Chlorophenyl)-7-{[5-(2-fluorophenyl)-1H-imidazol-2-yl]methyl}-7H-pyrrolo[2,3-d]pyrimidin-4-amine $^1$HNMR (400 MHz, MeOD-d$_4$) 5.70 (s, 2H), 7.10-7.24 (m, 4H), 7.34 (s, 1H), 7.44 (m, 4H), 7.88 (m, 1H), 8.42 (s, 1H). LCMS m/z=419.0 [MH]$^+$ Example 286: 7-{[1-(2,6-Difluorophenyl)-1H-pyrazol-4-yl]methyl}-5-(2-methoxypyridin-3-yl)-7H-pyrrolo[2,3-d]pyrimidin-4-amine $^1$HNMR (400 MHz, DMSO-d$_6$) 3.86 (s, 3H), 5.33 (s, 2H), 6.03 (br s, 2H), 7.07 (m, 1H), 7.34 (m, 2H), 7.42 (s, 1H), 7.54-7.60 (m, 1H), 7.64 (m, 1H), 7.84 (s, 1H), 8.16 (m, 3H). LCMS m/z=491.2 [MH]$^+$ Example 287: 5-(4-Chlorophenyl)-7-{1-[1-(3-fluoropyridin-2-yl)-1H-1,2,3-triazol-4-yl]ethyl}-7H-pyrrolo[2,3-d]pyrimidin-4-amine $^1$HNMR (400 MHz, MeOD-d$_4$): 2.03 (d, 3H), 6.36 (q, 1H), 7.38 (s, 1H), 7.44-7.49 (m, 4H), 7.60 (m, 1H), 7.92-7.97 (m, 1H), 8.20 (d, 1H), 8.41 (m, 1H), 8.58 (s, 1H). LCMS m/z=435.0 [MH]$^+$

Example 288: [4-(Cyclopropyloxy)phenyl]-7-{1-[1-(3-fluoropyridin-2-yl)-1H-1,2,3-triazol-4-yl]ethyl}-7H-pyrrolo[2,3-d]pyrimidin-4-amine $^1$HNMR (400 MHz, DMSO-d$_6$) 0.67 (m, 2H), 0.80 (m, 2H), 1.94 (d, 3H), 3.87 (m, 1H), 6.14 (br s, 2H), 6.32 (q, 1H), 7.14 (m, 2H), 7.40 (m, 3H), 7.71 (m, 1H), 8.15 (m, 1H), 8.19 (s, 1H), 8.48 (d, 1H), 8.74 (s, 1H). LCMS m/z=457.0 [MH]$^+$

Example 289: 5-Cyclopropyl-7-{[1-(2-fluorophenyl)-1H-1,2,3-triazol-4-yl]methyl}-7H-pyrrolo[2,3-d]pyrimidin-4-amine $^1$HNMR (400 MHz, DMSO-d$_6$) 0.63 (m, 2H), 0.91 (m, 2H), 2.00 (m, 1H), 5.46 (s, 2H), 6.96 (s, 1H), 7.35-7.42 (m, 2H), 7.54 (m, 1H), 7.78 (m, 1H), 8.09 (s, 1H), 8.30 (s, 1H). LCMS m/z=349.9 [MH]$^+$

Example 290: 7-{[1-(2-Fluorophenyl)-1H-1,2,3-triazol-4-yl]methyl}-5-[2-(methoxymethyl)cyclopropyl]-7H-pyrrolo[2,3-d]pyrimidin-4-amine $^1$HNMR (400 MHz, MeOD-d$_4$) 0.86 (m, 1H), 1.08 (m, 1H), 1.16-1.26 (m, 1H), 1.86 (m, 1H), 2.86 (dd, 1H), 3.30 (s, 3H), 3.88 (m, 1H), 5.48 (s, 2H), 6.96 (s, 1H), 7.35-7.42 (m, 2H), 7.53 (m, 1H), 7.78 (m, 1H), 8.06 (s, 1H), 8.30 (s, 1H). LCMS m/z=394.2 [MH]$^+$

Example 292: [3-(4-Amino-7-{[1-(2-fluorophenyl)-1H-1,2,3-triazol-4-yl]methyl}-7H-pyrrolo[2,3-d]pyrimidin-5-yl)azetidin-1-yl](cyclopropyl)methanone $^1$HNMR (400 MHz, DMSO-d$_6$) 0.72 (m, 4H), 1.58 (m, 1H), 3.86 (m, 1H), 4.21 (m, 1H), 4.27 (m, 2H), 4.78 (m, 1H), 5.49 (s, 2H), 6.55 (s, 2H), 7.40 (m, 2H), 7.54-7.63 (m, 2H), 7.72 (m, 1H), 8.12 (s, 1H), 8.55 (s, 1H). LCMS m/z=433.0 [MH]$^+$

Example 293: 5-{1-[(Cyclopropylmethyl)sulfonyl]azetidin-3-yl}-7-{[1-(2-fluorophenyl)-1H-1,2,3-triazol-4-yl]methyl}-7H-pyrrolo[2,3-d]pyrimidin-4-amine $^1$HNMR (400 MHz, DMSO-d$_6$) 0.38 (m, 2H), 0.62 (m, 2H), 1.08 (m, 1H), 1.32 (m, 1H), 3.17 (m, 1H), 3.98 (m, 2H), 4.30 (m, 3H), 5.54 (s, 2H), 6.66 (br s, 2H), 7.42-7.67 (m, 4H), 7.86 (m, 1H), 8.14 (s, 1H), 8.60 (s, 1H). LCMS m/z=483.1 [MH]$^+$

Example 294: 5-Cyclobutyl-7-{1-[1-(2-fluorophenyl)-1H-1,2,3-triazol-4-yl]ethyl}-7H-pyrrolo[2,3-d]pyrimidin-4-amine, Enantiomer 1

$^1$HNMR (400 MHz, DMSO-d$_6$) 1.91-1.95 (m, 1H), 2.00-2.20 (m, 8H), 2.33-2.42 (m, 2H), 5.07 (s, 2H), 6.31 (m, 1H), 7.23-7.31 (m, 2H), 7.41 (m, 1H), 7.92 (m, 2H), 8.26 (s, 1H). LCMS m/z=378.2 [MH]$^+$; RT [SFC Method A8]=4.963 mins

Example 295: 5-Cyclopropyl-7-{1-[1-(2-fluorophenyl)-1H-1,2,3-triazol-4-yl]cyclopropyl}-7H-pyrrolo[2,3-d]pyrimidin-4-amine $^1$HNMR (400 MHz, CDCl$_3$) 0.69 (m, 2H), 0.91 (m, 2H), 1.68 (m, 2H), 1.89-1.94 (m, 3H), 5.46 (s, 2H), 6.86 (s, 1H), 7.17-7.26 (m, 2H), 7.36 (m, 1H), 7.50 (s, 1H), 7.80 (m, 1H), 8.29 (s, 1H). LCMS m/z=376.0 [MH]$^+$

Example 296: 7-{[1-(2-Fluorophenyl)-1H-1,2,3-triazol-4-yl]methyl}-5-(3-methoxypyrazin-2-yl)-7H-pyrrolo[2,3-d]pyrimidin-4-amine $^1$HNMR (400 MHz, DMSO-d$_6$) 4.15 (s, 3H), 5.74 (s, 2H), 7.42 (m, 1H), 7.52-7.64 (m, 2H), 7.79 (m, 1H), 8.20 (d, 1H), 8.32 (d, 1H), 8.42 (s, 1H), 8.65 (d, 1H), 8.70 (d, 1H), 10.78 (br s, 1H). LCMS m/z=418.2 [MH]$^+$

Example 297: 7-{Cyclopropyl[1-(2-fluorophenyl)-1H-1,2,3-triazol-4-yl]methyl}-5-(2-methoxypyridin-3-yl)-7H-pyrrolo[2,3-d]pyrimidin-4-amine $^1$HNMR (400 MHz, DMSO-d$_6$) 0.45 (m, 1H), 0.58 (m, 2H), 0.73 (m, 1H), 1.97 (m, 1H), 3.87 (s, 3H), 5.45 (d, 1H), 6.06 (br s, 2H), 7.08 (m, 1H), 7.44 (m, 1H), 7.54-6.62 (m, 3H), 7.66 (m, 1H), 7.84 (m, 1H), 8.13 (s, 1H), 8.18 (m, 1H), 8.77 (s, 1H). LCMS m/z=457.0 [MH]$^+$

Example 298: 7-{1-[1-(2-Fluorophenyl)-1H-1,2,3-triazol-4-yl]cyclopropyl}-5-(2-methoxypyridin-3-yl)-7H-pyrrolo[2,3-d]pyrimidin-4-amine $^1$HNMR (400 MHz, CDCl$_3$) 1.80 (m, 2H), 1.96 (m, 2H), 3.98 (s, 3H), 5.04 (br s, 2H), 6.99 (m, 1H), 7.18-7.28 (m, 3H), 7.34-7.40 (m, 1H), 7.62 (m, 1H), 7.66 (d, 1H), 7.82 (m, 1H), 8.19 (m, 1H), 8.37 (s, 1H). LCMS m/z=443.0 [MH]$^+$

Example 299: 5-(1,3-Benzoxazol-7-yl)-7-{[1-(2-fluorophenyl)-1H-1,2,3-triazol-4-yl]methyl}-7H-pyrrolo[2,3-d]pyrimidin-4-amine $^1$HNMR (400 MHz, DMSO-d$_6$) 5.63 (s, 2H), 6.17 (br s, 2H), 7.39-7.61 (m, 5H), 7.67 (s, 1H), 7.76 (d, 1H), 7.81 (m, 1H), 8.23 (s, 1H), 8.63 (m, 1H), 8.78 (s, 1H). LCMS m/z=427.0 [MH]$^+$

Example 300: (−) 7-{Cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine, Enantiomer 2

Separated using SFC Method D4; $^1$HNMR (400 MHz, DMSO-d$_6$) 0.45 (m, 1H), 0.58 (m, 2H), 0.71 (m, 1H), 1.96 (m, 1H), 3.94 (s, 3H), 5.46 (d, 1H), 6.29 (s, 2H), 7.43 (m, 1H), 7.56-7.63 (m, 3H), 7.84 (m, 1H), 8.13 (s, 1H), 8.43 (s, 1H), 8.76 (s, 2H). LCMS m/z=458.1 [MH]$^+$; RT [SFC Method D2]=9.322 min; [α]$_D$ MeOH=−19.9°.

Example 301: 7-{[1-(2-Fluorophenyl)-1H-1,2,3-triazol-4-yl]methyl}-5-(1,3-oxazol-2-yl)-7H-pyrrolo[2,3-d]pyrimidin-4-amine $^1$HNMR (400 MHz, DMSO-d$_6$) 5.65 (s, 2H), 7.40-7.67 (m, 5H), 7.86 (m, 1H), 8.12 (d, 1H), 8.18 (s, 1H), 8.22 (s, 1H), 8.66 (s, 1H), 9.02 (br s, 1H). LCMS m/z=377.1 [MH]$^+$

Example 302: 7-{1-[1-(2-Fluorophenyl)-1H-1,2,3-triazol-4-yl]propyl}-5-(4-methoxypyrimidin-5-yl)-2-methyl-7H-pyrrolo[2,3-d]pyrimidin-4-amine $^1$HNMR (400 MHz, CDCl$_3$) 0.95 (t, 3H), 2.38-2.48 (m, 1H), 2.50-2.60 (m, 1H), 4.03 (s, 3H), 4.92 (s, 2H), 6.13 (m, 1H), 7.25-7.32 (m, 2H) 7.38-7.43 (m, 2H), 7.93 (m, 1H), 8.09 (s, 1H), 8.47 (s, 1H), 8.74 (s, 1H). LCMS m/z=460.2 [MH]⁺

Example 303: (+) 7-{1-[1-(2-Fluorophenyl)-1H-1,2,3-triazol-4-yl]propyl}-5-(4-methoxypyrimidin-5-yl)-2-methyl-7H-pyrrolo[2,3-d]pyrimidin-4-amine, Enantiomer 1

Separated using SFC Method B1; ¹HNMR (400 MHz, DMSO-d₆) 0.84 (t, 3H), 2.28-2.36 (m, 2H), 2.48 (s, 3H), 3.93 (s, 3H), 6.08 (m, 1H), 6.22 (br s, 2H), 7.45 (m, 2H), 7.68 (m, 2H), 7.83 (m, 1H), 8.40 (s, 1H), 8.74 (m, 2H). LCMS m/z=460.3 [MH]⁺; RT [SFC method B2]=5.064 min; [α]$_D$ MeOH=+4.4°

Example 304: (−) 7-{1-[1-(2-Fluorophenyl)-1H-1,2,3-triazol-4-yl]propyl}-5-(4-methoxypyrimidin-5-yl)-2-methyl-7H-pyrrolo[2,3-d]pyrimidin-4-amine, Enantiomer 2

Separated using SFC Method B1; ¹HNMR (400 MHz, DMSO-d₆) 0.84 (t, 3H), 2.28-2.36 (m, 2H), 2.48 (s, 3H), 3.93 (s, 3H), 6.08 (m, 1H), 6.22 (br s, 2H), 7.45 (m, 2H), 7.55-7.64 (m, 2H), 7.83 (m, 1H), 8.40 (s, 1H), 8.72 (s, 1H), 8.75 (s, 1H). LCMS m/z=460.3 [MH]⁺; RT [SFC method B2]=5.884 min

Example 305: (−) 7-{1-[1-(2,3-Difluorophenyl)-1H-1,2,3-triazol-4-yl]propyl}-5-(4-methoxypyrimidin-5-yl)-7H-pyrrolo[2,3-d]pyrimidin-4-amine, Enantiomer 1

Separated using SFC method A10; ¹HNMR (400 MHz, DMSO-d₆) 0.87 (t, 3H), 2.36 (m, 2H), 3.95 (s, 3H), 6.10 (t, 1H), 6.32 (br s, 2H), 7.45 (m, 1H), 7.53 (s, 1H), 7.65-7.73 (m, 2H), 8.18 (s, 1H), 8.43 (s, 1H), 8.76 (s, 2H). LCMS m/z=464.1 [MH]⁺; RT [SFC Method A2]=4.106 min; [α]$_D$ MeOH=−25.2°

Example 306: (+) 7-{1-[1-(2,3-Difluorophenyl)-1H-1,2,3-triazol-4-yl] propyl}-5-(4-methoxypyrimidin-5-yl)-7H-pyrrolo[2,3-d]pyrimidin-4-amine, Enantiomer 2

Separated using SFC Method A10; ¹HNMR (400 MHz, DMSO-d₆) 0.87 (t, 3H), 2.36 (m, 2H), 3.95 (s, 3H), 6.10 (t, 1H), 6.32 (br s, 2H), 7.45 (m, 1H), 7.55 (s, 1H), 7.65-7.73 (m, 2H), 8.18 (s, 1H), 8.43 (s, 1H), 8.76 (s, 2H). LCMS m/z=464.1 [MH]⁺; RT [SFC Method A2]=4.455 min; [α]$_D$ MeOH=+27.3°

Example 307: (+) 7-{1-[1-(2,5-Difluorophenyl)-1H-1,2,3-triazol-4-yl]propyl}-5-(4-methoxypyrimidin-5-yl)-7H-pyrrolo[2,3-d]pyrimidin-4-amine, Enantiomer 1

Separated using SFC Method F1; ¹HNMR (400 MHz, DMSO-d₆) 0.87 (t, 3H), 2.36 (m, 2H), 3.95 (s, 3H), 6.10 (t, 1H), 6.35 (br s, 2H), 7.50 (m, 1H), 7.56 (s, 1H), 7.67 (m, 1H), 7.84 (m, 1H), 8.18 (s, 1H), 8.43 (s, 1H), 8.76 (s, 2H). LCMS m/z=464.1 [MH]⁺; RT [SFC Method F2]=7.170 min; [α]$_D$ MeOH=+25.9°

Example 308: (−) 7-{1-[1-(2,5-Difluorophenyl)-1H-1,2,3-triazol-4-yl]propyl}-5-(4-methoxypyrimidin-5-yl)-7H-pyrrolo[2,3-d]pyrimidin-4-amine, Enantiomer 2

Separated using SFC Method F1; ¹HNMR (400 MHz, DMSO-d₆) 0.87 (t, 3H), 2.36 (m, 2H), 3.95 (s, 3H), 6.10 (t, 1H), 6.35 (br s, 2H), 7.50 (m, 1H), 7.56 (s, 1H), 7.67 (m, 1H), 7.84 (m, 1H), 8.18 (s, 1H), 8.43 (s, 1H), 8.76 (s, 2H). LCMS m/z=464.1 [MH]⁺; RT [SFC Method F2]=7.535 min; [α]$_D$ MeOH=−21.9°

Example 309: 7-{1-[1-(6-Methoxypyridin-3-yl)-1H-1,2,3-triazol-4-yl]propyl}-5-[2-(trifluoromethyl)pyrimidin-5-yl]-7H-pyrrolo[2,3-d]pyrimidin-4-amine, Enantiomer 1

Separated using method HPLC Method C30; ¹HNMR (400 MHz, DMSO-d₆) 0.87 (t, 3H), 2.34-2.40 (m, 2H), 3.92 (s, 3H), 6.11 (m, 1H), 7.00-7.06 (m, 3H), 7.90 (s, 1H), 8.20-8.35 (m, 2H), 8.67 (s, 1H), 8.88 (s, 1H), 9.08 (s, 2H). LCMS m/z=497.2 [MH]⁺; RT [HPLC method C10]=2.339 min

Example 310: 7-{1-[1-(6-Methoxypyridin-3-yl)-1H-1,2,3-triazol-4-yl]propyl}-5-[2-(trifluoromethyl)pyrimidin-5-yl]-7H-pyrrolo[2,3-d]pyrimidin-4-amine, Enantiomer 2

Separated using method HPLC Method C30; ¹HNMR (400 MHz, DMSO-d₆) 0.86 (t, 3H), 2.35-2.41 (m, 2H), 3.92 (s, 3H), 6.10 (m, 1H), 6.70 (br s, 2H), 7.05 (m, 1H), 7.86 (s, 1H), 8.18 (m, 1H), 8.26 (s, 1H), 8.67 (s, 1H), 8.90 (s, 1H), 9.07 (s, 2H). LCMS m/z=497.2 [MH]⁺; RT [HPLC Method C10]=2.882 min

Example 311: 7-{1-[1-(3,5-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, Enantiomer 1

Separated using method HPLC Method G3; ¹HNMR (400 MHz, DMSO-d₆) 0.86 (t, 3H), 2.37-2.41 (m, 2H), 6.10 (t, 1H), 6.67 (br s, 2H), 7.43 (m, 1H), 7.76 (m, 2H), 7.82 (s, 1H), 8.25 (s, 1H), 9.00 (s, 1H), 9.06 (s, 2H). LCMS m/z=502.1 [MH]⁺

Example 312: 7-{1-[1-(3,5-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, Enantiomer 2

Separated using HPLC Method G3; ¹HNMR (400 MHz, DMSO-d₆) 0.86 (t, 3H), 2.33-2.41 (m, 2H), 6.10 (t, 1H), 6.67 (br s, 2H), 7.43 (m, 1H), 7.76 (m, 2H), 7.82 (s, 1H), 8.25 (s, 1H), 9.00 (s, 1H), 9.06 (s, 2H). LCMS m/z=502.1 [MH]⁺

Example 313: 5-[2-(Difluoromethyl)pyrimidin-5-yl]-7-{1-[1-(3,4-difluorophenyl)-1H-1,2,3-triazol-4-yl]propyl}-7H-pyrrolo[2,3-d]pyrimidin-4-amine, Enantiomer 2

Separated using HPLC Method C22A; ¹HNMR (400 MHz, DMSO-d₆) 0.85 (t, 3H), 2.33-2.41 (m, 2H), 6.09 (t, 1H), 6.77 (br s, 2H), 6.88-7.15 (dd, 1H), 7.67 (m, 1H), 7.85

(m, 2H), 8.10 (m, 1H), 8.28 (s, 1H), 8.93 (s, 1H), 9.00 (s, 1H). LCMS m/z=484.1 [MH]$^+$; RT [HPLC Method C7]=4.154 min.

Example 314: 7-{1-[1-(2-Fluorophenyl)-1H-1,2,3-triazol-4-yl]-2-methoxyethyl}-5-(2-methoxypyridin-3-yl)-7H-pyrrolo[2,3-d]pyrimidin-4-amine $^1$HNMR (400 MHz, DMSO-d$_6$) 3.32 (s, 3H), 3.85 (s, 3H), 4.05 (m, 1H), 4.24 (m, 1H), 6.06 (br s, 2H), 6.42 (m, 1H), 7.08 (m, 1H), 7.42 (m, 1H), 7.50 (s, 1H), 7.54-7.66 (m, 3H), 7.83 (m, 1H), 8.16 (m, 2H), 8.74 (s, 1H). LCMS m/z=461.3 [MH]$^+$ Example 315: 7-{[1-(2-Fluorophenyl)-1H-1,2,3-triazol-4-yl](oxetan-3-yl)methyl}-5-(4-methoxypyrimidin-5-yl)-7H-pyrrolo[2,3-d]pyrimidin-4-amine $^1$HNMR (400 MHz, MeOD-d$_4$) 4.05 (s, 3H), 4.32 (m, 1H), 4.54 (m, 1H), 4.58 (m, 1H), 4.64 (m, 1H), 4.91 (m, 1H), 6.70 (d, 1H), 7.39-7.48 (m, 3H), 7.55 (m, 1H), 7.82 (m, 1H), 8.25 (s, 1H), 8.46 (s, 2H), 8.75 (s, 1H). LCMS m/z=474.2 [MH]$^+$ Example 316: (+) 5-Cyclopropyl-7-{1-[1-(2-fluorophenyl)-1H-1,2,3-triazol-4-yl]propyl}-7H-pyrrolo[2,3-d]pyrimidin-4-amine, Enantiomer 2

Separated using SFC method C3; $^1$HNMR (400 MHz, DMSO-d$_6$) 0.54 (m, 2H), 0.76-0.85 (m, 6H), 2.20-2.33 (m, 2H), 5.95 (m, 1H), 6.60 (br s, 2H), 7.02 (s, 1H), 7.42 (m, 1H), 7.52-7.62 (m, 2H), 7.81 (m, 1H), 8.05 (s, 1H), 8.61 (s, 1H). LCMS m/z=378.4 [MH]$^+$; RT [SFC Method C2]=6.081 min; [α]$_D$ MeOH=+29.5°

Example 317: 5-Cyclopropyl-7-{[1-(2-fluorophenyl)-1H-pyrazol-4-yl]methyl}-7H-pyrrolo[2,3-d]pyrimidin-4-amine $^1$HNMR (400 MHz, CDCl$_3$) 0.65 (m, 2H), 0.88 (m, 2H), 1.91 (m, 1H), 5.24 (s, 2H), 5.45 (s, 2H), 6.70 (s, 1H), 7.17-7.25 (m, 3H), 7.66 (s, 1H), 7.82 (m, 1H), 7.96 (s, 1H), 8.29 (s, 1H). LCMS m/z=349.2 [MH]$^+$ Example 318: 5-(4-Chlorophenyl)-7-{1-[1-(2-fluorophenyl)-1H-1,2,3-triazol-4-yl]ethyl}-N-methyl-7H-pyrrolo[2,3-d]pyrimidin-4-amine $^1$HNMR (400 MHz, MeOD-d$_4$) 2.00 (d, 3H), 2.98 (s, 3H), 6.34 (m, 1H), 7.30 (s, 1H), 7.36-7.47 (m, 6H), 7.54 (m, 1H), 7.81 (m, 1H), 8.23 (s, 1H), 8.38 (s, 1H). LCMS m/z=447.8 [MH]$^+$ Example 319: 6-Bromo-5-(4-chlorophenyl)-7-{[1-(3-fluorophenyl)-1H-1,2,3-triazol-4-yl]methyl}-7H-pyrrolo[2,3-d]pyrimidin-4-amine LCMS m/z=500.0 [MH]$^+$ Example 320: 4-Amino-5-[6-(cyclopropyloxy)pyridin-3-yl]-7-{1-[1-(2,4-difluorophenyl)-1H-1,2,3-triazol-4-yl]ethyl}-7H-pyrrolo[2,3-d]pyrimidine-6-carbonitrile, Enantiomer 1

Separated using HPLC method Q1; $^1$HNMR (400 MHz, CDCl$_3$): 0.77 (m, 4H), 2.12 (d, 3H), 4.20 (m, 1H), 5.31 (br s, 2H), 6.58 (m, 1H), 6.85 (d, 1H), 6.98 (m, 1H), 7.71 (d, 1H), 7.85 (m, 1H), 8.11 (s, 1H), 8.34 (s, 1H), 8.38 (s, 1H). LCMS m/z=500.1 [MH]$^+$ Example 321: 4-Amino-5-[6-(cyclopropyloxy)pyridin-3-yl]-7-{1-[1-(2,4-difluorophenyl)-1H-1,2,3-triazol-4-yl]ethyl}-7H-pyrrolo[2,3-d]pyrimidine-6-carbonitrile, Enantiomer 2

Separated using HPLC method Q1; $^1$HNMR (400 MHz, DMSO-d$_6$) 0.79 (m, 2H), 0.86 (m, 1H), 2.10 (d, 3H), 4.33 (m, 1H), 6.52 (q, 1H), 7.10 (d, 1H), 7.41 (m, 1H), 7.71 (m, 1H), 7.90 (m, 2H), 8.38 (s, 2H), 8.80 (s, 1H). LCMS m/z=500.1 [MH]$^+$ Example 322: 4-Amino-7-{1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, Enantiomer 1

Separated using method HPLC C34; $^1$HNMR (400 MHz, DMSO-d$_6$) 0.93 (m, 3H), 2.50-2.57 (m, 2H), 6.26 (t, 1H), 7.20 (br s, 2H), 7.68 (m, 1H), 7.84 (m, 1H), 8.09 (m, 1H), 8.38 (s, 1H), 9.02 (s, 1H), 9.22 (s, 2H). LCMS m/z=527.2 [MH]$^+$; RT [HPLC method C11]=5.864 min X-Ray Crystallography Methods The following methods were used to obtain X-Ray crystallography data for several compounds.

Single Crystal X-Ray Analysis for Example 27.

Data collection was performed on a Bruker APEX diffractometer at room temperature. Data collection consisted of omega and phi scans. The structure was solved by direct methods using SHELX software suite in the Monoclinic class space group C2/c. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. CF3 group is disordered and modeled with two occupancies. The final R-index was 3.8%. A final difference Fourier revealed no missing or misplaced electron density. Pertinent crystal, data collection and refinement are summarized in Table XRAY-EX27.

TABLE XRAY-EX27

Crystal data and structure refinement for Example 27.

| | |
|---|---|
| Empirical formula | C22 H13 N9 F4 |
| Formula weight | 479.41 |
| Temperature | 296(2) K. |
| Wavelength | 1.54178 Å |
| Crystal system | Monoclinic |
| Space group | C2/c |
| Unit cell dimensions | a = 40.9109(10) Å  ☐ = 90°. |
| | b = 6.1608(2) Å  ☐ = 116.502(3)°. |
| | c = 18.5613(5) Å  ☐ = 90°. |
| Volume | 4186.7(2) Å$^3$ |
| Z | 8 |
| Density (calculated) | 1.521 Mg/m$^3$ |
| Goodness-of-fit on F$^2$ | 1.034 |
| Final R indices [I > 2sigma(I)] | R1 = 0.0383, wR2 = 0.0996 |
| R indices (all data) | R1 = 0.0484, wR2 = 0.1062 |

Single Crystal X-Ray Analysis for Example 161.

The compound of Example 161 was found to be 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine.

Data collection was performed on a Bruker APEX diffractometer at room temperature. Data collection consisted of omega and phi scans. The structure was solved by direct methods using SHELX software suite in the space group $P2_1$. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. Molecules in asymmetric unit arranged in a pseudo-symmetry relationship. Both molecules in the asymmetric unit have the same chirality. Analysis of the absolute structure using likelihood methods (Hooft 2008) was performed using PLATON (Spek 2010). The sample was assumed to be enantiopure; the results indicate that the absolute structure has been correctly assigned. The final R-index was 4.9%. A final difference Fourier revealed no missing or misplaced electron density. Pertinent crystal, data collection and refinement are summarized in Table XRAY-EX161.

TABLE XRAY-EX161

Crystal data and structure refinement for Example 161.

| | |
|---|---|
| Empirical formula | C22 H16 F5 N9 |
| Formula weight | 501.44 |
| Temperature | 296(2) K. |
| Wavelength | 1.54178 Å |
| Crystal system | Monoclinic |
| Space group | $P2_1$ |
| Unit cell dimensions | a = 16.0097(8) Å  □ = 90°. |
| | b = 7.8827(5) Å  □ = 102.096(3)°. |
| | c = 17.6077(10) Å  □ = 90°. |
| Volume | 2172.8(2) Å$^3$ |
| Z | 4 |
| Density (calculated) | 1.533 Mg/m$^3$ |
| Goodness-of-fit on F$^2$ | 1.039 |
| Final R indices [I > 2sigma(I)] | R1 = 0.0491, wR2 = 0.1256 |
| R indices (all data) | R1 = 0.0657, wR2 = 0.1381 |

Single Crystal X-Ray Analysis for Example 162.

The compound of Example 162 was found to be 7-{(1R)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine.

Data collection was performed on a Bruker APEX diffractometer at room temperature. Data collection consisted of omega and phi scans. The structure was solved by direct methods using SHELX software suite in the Monoclinic class space group $P2_1$. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). Assuming the sample submitted is enantiopure, the results indicate that the absolute structure has been correctly assigned. Absolute configuration confirmed as opposite to other single enantiomer resolved. The final R-index was 5.8%. A final difference Fourier revealed no missing or misplaced electron density. Pertinent crystal, data collection and refinement are summarized in Table XRAY-EX162.

TABLE XRAY-EX162

Crystal data and structure refinement for Example 162.

| | |
|---|---|
| Empirical formula | C22 H16 F5 N9 |
| Formula weight | 501.44 |
| Temperature | 296(2) K. |
| Wavelength | 1.54178 Å |
| Crystal system | Monoclinic |
| Space group | $P2_1$ |
| Unit cell dimensions | a = 16.0163(6) Å  □ = 90°. |
| | b = 7.8766(3) Å  □ = 102.117(2)°. |
| | c = 17.6201(8) Å  □ = 90°. |
| Volume | 2173.32(15) Å$^3$ |
| Z | 4 |
| Density (calculated) | 1.533 Mg/m$^3$ |
| Goodness-of-fit on F$^2$ | 1.026 |
| Final R indices [I > 2sigma(I)] | R1 = 0.0576, wR2 = 0.1374 |
| R indices (all data) | R1 = 0.0758, wR2 = 0.1487 |

SOFTWARE AND REFERENCES

SHELXTL, Version 5.1, Bruker AXS, 1997.
PLATON, A. L. Spek, J. Appl. Cryst. 2003, 36, 7-13.
MERCURY, C. F. Macrae, P. R. Edington, P. McCabe, E. Pidcock, G. P. Shields, R. Taylor, M. Towler and J. van de Streek, *J. Appl. Cryst.* 39, 453-457, 2006.
OLEX2, Dolomanov, O. V.; Bourhis, L. J.; Gildea, R. J.; Howard, J. A. K.; Puschmann, H., (2009). J. Appl. Cryst., 42, 339-341.
R. W. W. Hooft et al. *J. Appl. Cryst.* (2008). 41. 96-103.
H. D. Flack, *Acta Cryst.* 1983, A39, 867-881.

Ussing Chamber Electrophysiology Assay of CFTR Potentiation in CF Bronchial Epithelial Cells Primary cystic fibrosis human bronchial epithelial (CF hBE) cells were expanded and cultured according to published methods (Neuberger et al., Ch. 4 of Cystic Fibrosis, Methods in Molecular Biology vol. 741, pp. 39-54 (2011)). Well-differentiated cells (>30 days at air/liquid interface) on Snapwell filters (Corning Costar, cat. no. 3801) were mounted in Ussing chambers (Physiologic Instruments, Inc., San Diego, Calif.). F508del/F508del cultures were assayed at 27° C. and G551D/F508del cells were assayed at 35° C. HEPES buffered physiological saline (composition (in mM): 137 NaCl, 4 KCl, 1 MgCl2, 1.8 CaCl2, 10 HEPES Na) was used in both apical and basolateral chambers. Chambers were bubbled with air to promote mixing and the voltage was clamped to zero. Amiloride (30 uM), forskolin (10 uM), test compound (4 increasing concentrations), and CFTRinh-172 (20 uM) were added sequentially with 20-25 minutes between additions. Short-circuit currents were acquired and analyzed using LabScribe2. Test compound responses were scaled relative to responses for DMSO (0%) and the maximal response of a positive control potentiator (100%).

FRT Ion Flux Assay of F508del CFTR Potentiation

Fischer rat thyroid (FRT) cell lines stably expressing recombinant F508del V470 CFTR and halide-sensitive yellow fluorescent protein (Pedemonte et al., J. Clin. Invest. 115(9) 2564-71 (2005)) were seeded at 25,000 cells/well in 50 uL/well of culture medium into black-walled, clear bottom tissue-culture-treated 384-well plates (Corning, cat.

no. 3712). After one day, the cells were pre-incubated at 27° C./5% $CO_2$ for 16-24 hours. The cells were then washed with dPBS and treated with forskolin (20 uM) and test compound for 30 min by addition of 20 uL of compound dilution buffer (dPBS containing forskolin and test compound). Plates were loaded into FLIPR384 fluorescence imaging plate reader (Molecular Devices). After an initial fluorescence reading, iodide buffer (25 uL) (composition (in mM): 137 NaI, 1.5 $K_2PO_4$, 8.1 $NaH_2PO_4$, 2.7 KCl, 0.5 $MgCl_2$, 1 $CaCl_2$) was added and a second fluorescence reading was made after approximately 21 seconds. Data treatment involved division of the second fluorescence reading by the initial fluorescence reading, then scaling of the resulting normalized endpoint fluorescence with respect to the responses for DMSO (0%) and a positive control potentiator (100%).

| Ex. No. | Compound Name | CF hBE Ussing $EC_{50}$ (nM) | FRT $EC_{50}$ (nM) |
|---|---|---|---|
| 1 | 4-Amino-5-[2-(difluoromethyl) pyrimidin-5-yl]-7-{1-[1(2-fluorophenyl)-1H-pyrazol-4-yl] ethyl}-7H-pyrrolo[2,3-d]pyrimidine-6-carbonitrile, enantiomer 1 | 1.66 | 0.55 |
| 2 | 4-Amino-5-[2-(difluoromethyl) pyrimidin-5-yl]-7-{1-[1(2-fluorophenyl)-1H-pyrazol-4-yl] ethyl}-7H-pyrrolo[2,3-d]pyrimidine-6-carbonitrile, enantiomer 2 | 8.77 | 7.51 |
| 3 | 4-Amino-7-{1-[1-(2-fluorophenyl)-1H-pyrazol-4-yl]propyl}-5-[2-(trifluoromethyl) pyrimidin-5-yl]-7H-pyrrolo[2,3-d] pyrimidine-6-carbonitrile, enantiomer 1 | 3.36 | 9.17 |
| 4 | 4-Amino-7-{1-[1-(2-fluorophenyl)-1H-pyrazol-4-yl]propyl}-5-[2-(trifluoromethyl) pyrimidin-5-yl]-7H-pyrrolo[2,3-d] pyrimidine-6-carbonitrile, enantiomer 2 | 0.56 | 0.61 |
| 5 | 4-Amino-7-(1-(1-(2-fluorophenyl)-1H-pyrazol-4-yl)ethyl)-5-(2-(trifluoromethyl) pyrimidin-5-yl)-7H-pyrrolo[2,3-d]pyrimidine-6-carbonitrile, enantiomer 1 | 7.73 | 7.69 |
| 6 | 4-Amino-7-(1-(1-(2-fluorophenyl)-1H-pyrazol-4-yl)ethyl)-5-(2-(trifluoromethyl) pyrimidin-5-yl)-7H-pyrrolo[2,3-d] pyrimidine-6-carbonitrile, enantiomer 2 | 1.19 | 1.01 |
| 7 | 4-Amino-7-{1-[1-(2,4-difluoro phenyl)-1H-pyrazol-4-yl]ethyl}-5-[2-(trifluoromethyl) pyrimidin-5-yl]-7H-pyrrolo[2,3-d] pyrimidine-6-carbonitrile, enantiomer 1 | 1.84 | 2.76 |
| 8 | 4-Amino-7-{1-[1-(2,4-difluorophenyl)-1H-pyrazol-4-yl]ethyl}-5-[2-(trifluoromethyl) pyrimidin-5-yl]-7H-pyrrolo[2,3-d] pyrimidine-6-carbonitrile, enantiomer 2 | 15.49 | 35.18 |
| 9 | 4-Amino-7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile, enantiomer 1 | 20.38 | 12.16 |
| 10 | 4-Amino-7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile, enantiomer 2 | 70.28 | 77.56 |
| 11 | 4-Amino-7-{1-[1-(2,4-difluorophenyl)-1H-1,2,3-triazol-4-yl]ethyl}-5-[2-(trifluoromethyl) pyrimidin-5-yl]-7H-pyrrolo[2,3-d]pyrimidine-6-carbonitrile, enantiomer 1 | 33.47 | 19.80 |
| 12 | 4-Amino-7-(1-(1-(2-fluorophenyl)-5-methyl-1H-1,2,3-triazol-4-yl)ethyl)-5-(2-(trifluoromethyl)pyrimidin-5-yl)-7H-pyrrolo[2,3-d] pyrimidine-6-carbonitrile, enantiomer 1 | 22.46 | 6.66 |
| 13 | 4-Amino-7-(1-(1-(2-fluorophenyl)-5-methyl-1H-1,2,3-triazol-4-yl)ethyl)-5-(2-(trifluoromethyl)pyrimidin-5-yl)-7H-pyrrolo[2,3-d] pyrimidine-6-carbonitrile, enantiomer 2 | 266.93 | 96.78 |
| 14 | 4-Amino-7-{1-[3-(2-fluorophenyl)-1,2-oxazol-5-yl]ethyl}-5-(2-methoxypyrimidin-5-yl)-7H-pyrrolo[2,3-d]pyrimidine-6-carbonitrile, enantiomer 1 | 12.96 | 23.61 |
| 15 | 4-Amino-7-{1-[3-(2-fluorophenyl)-1,2-oxazol-5-yl]ethyl}-5-(2-methoxypyrimidin-5-yl)-7H-pyrrolo[2,3-d]pyrimidine-6-carbonitrile, enantiomer 2 | 7.00 | 7.22 |
| 16 | 4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, enantiomer 1 | 9.0 | 6.39 |
| 17 | 4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, enantiomer 2 | 49.5 | 45.29 |
| 18 | 4-Amino-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, enantiomer 1 | 12.49 | 10.79 |
| 19 | 4-Amino-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, enantiomer 2 | 34.70 | 69.62 |
| 20 | 4-Amino-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile, enantiomer 1 | 5.48 | 14.15 |
| 21 | 4-Amino-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile, enantiomer 2 | 0.45 | 0.87 |

| Ex. No. | Compound Name | CF hBE Ussing EC$_{50}$ (nM) | FRT EC$_{50}$ (nM) |
|---|---|---|---|
| 22 | 4-Amino-7-{1-[1-(2-fluorophenyl)-1H-1,2,3-triazol-4-yl]propyl}-5-[2-(trifluoromethyl) pyrimidin-5-yl]-7H-pyrrolo[2,3-d]pyrimidine-6-carbonitrile, enantiomer 1 | 6.84 | 4.05 |
| 23 | 4-Amino-7-{1-[1-(2-fluorophenyl)-1H-1,2,3-triazol-4-yl]propyl}-5-[2-(trifluoromethyl) pyrimidin-5-yl]-7H-pyrrolo[2,3-d]pyrimidine-6-carbonitrile, enantiomer 2 | 32.50 | 41.79 |
| 24 | 4-Amino-5-[6-(difluoromethoxy)pyridin-3-yl]-7-{1-[1-(2-fluorophenyl)-1H-1,2,3-triazol-4-yl]propyl}-7H-pyrrolo[2,3-d]pyrimidine-6-carbonitrile, single enantiomer | 30.00 | 21.52 |
| 25 | 4-Amino-5-(4-chlorophenyl)-7-{[1-(propan-2-yl)-1H-pyrazol-4-yl]methyl}-7H-pyrrolo[2,3-d]pyrimidine-6-carbonitrile | 40.95 | 95.94 |
| 26 | 4-Amino-5-(4-chlorophenyl)-7-{[1-(2-fluorophenyl)-1H-1,2,3-triazol-4-yl]methyl}-7H-pyrrolo[2,3-d]pyrimidine-6-carbonitrile | 35.73 | 129.66 |
| 27 | 4-Amino-7-{[1-(2-fluorophenyl)-1H-pyrazol-4-yl]methyl}-5-[2-(trifluoromethyl) pyrimidin-5-yl]-7H-pyrrolo[2,3-d]pyrimidine-6-carbonitrile | 1.25 | 1.27 |
| 28 | 4-Amino-7-{1-[1-(2-fluorophenyl)-1H-1,2,3-triazol-4-yl]ethyl}-5-[2-(trifluoromethyl) pyrimidin-5-yl]-7H-pyrrolo[2,3-d]pyrimidin-6-carbonitrile | N.D. | N.D. |
| 29 | 4-Amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile | 2.24 | 2.33 |
| 30 | 4-Amino-5-[2-(difluoromethyl)pyrimidin-5-yl]-7-{[1-(2-fluorophenyl)-1H-pyrazol-4-yl]methyl}-7H-pyrrolo[2,3-d]pyrimidine-6-carbonitrile | 2.03 | 0.59 |
| 31 | 4-Amino-7-{1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile | N.D. | N.D. |
| 32 | 4-Amino-7-{1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile | N.D. | N.D. |
| 33 | 4-Amino-7-{1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile | N.D. | N.D. |
| 34 | 4-Amino-7-{1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidine-6-carbonitrile | N.D. | N.D. |
| 35 | 4-Amino-7-{1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile | N.D. | N.D. |
| 36 | 4-Amino-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile | N.D. | N.D. |
| 37 | 4-Amino-7-{[1-(2-difluorophenyl)-1H-1,2,3-triazol-4-yl]methyl}-5-[2-(trifluoromethyl) pyrimidin-5-yl]-7H-pyrrolo[2,3-d]pyrimidin-6-carbonitrile | 16.28 | 13.53 |
| 38 | 4-Amino-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-6-carbonitrile | N.D. | N.D. |
| 39 | 4-Amino-7-{(1-[3-(2-fluorophenyl)-1,2-oxazol-5-yl]ethyl}-5-(2-methoxypyrimidin-5-yl)-7H-pyrrolo[2,3-d]pyrimidine-6-carbonitrile | N.D. | N.D. |
| 40 | 6-Bromo-7-{[1-(2-fluorophenyl)-1H-pyrazol-4-yl]methyl}-5-[2-(trifluoromethyl) pyrimidin-5-yl]-7H-pyrrolo[2,3-d]pyrimidin-4-amine | 1.30 | 2.18 |
| 41 | 6-Bromo-7-{[1-(2,4-difluorophenyl)-1H-pyrazol-4-yl]methyl}-5-[2-(trifluoromethyl)pyrimidin-5-yl]-7H-pyrrolo[2,3-d]pyrimidin-4-amine | N.D. | N.D. |
| 42 | 6-Bromo-5-[2-(difluoromethyl)pyrimidin-5-yl]-7-{[1-(2-fluorophenyl)-1H-pyrazol-4-yl]methyl}-7H-pyrrolo[2,3-d]pyrimidin-4-amine | N.D. | N.D. |
| 43 | 6-Bromo-5-(4-chlorophenyl)-7-{[1-(propan-2-yl)-1H-pyrazol-4-yl] methyl}-7H-pyrrolo[2,3-d]pyrimidin-4-amine | N.D. | N.D. |
| 44 | 6-Bromo-7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-4-amine | N.D. | N.D. |
| 45 | 6-Bromo-7-{1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidin-4-amine | N.D. | N.D. |
| 46 | 6-Bromo-5[2-(difluoromethyl)pyrimidin-5-yl]-7-{1-[1-(2-fluorophenyl)-1H-pyrazol-4-yl]ethyl}-7H-pyrrolo[2,3-d]pyrimidin-4-amine | N.D. | N.D. |

| Ex. No. | Compound Name | CF hBE Ussing EC$_{50}$ (nM) | FRT EC$_{50}$ (nM) |
|---|---|---|---|
| 47 | 6-Bromo-7-{1-[1-(2-fluorophenyl)-1H-pyrazol-4-yl]ethyl}-5-[2-(trifluoromethyl) pyrimidin-5-yl]-7H-pyrrolo[2,3-d]pyrimidin-4-amine | N.D. | N.D. |
| 48 | 6-Bromo-7-{1-[1-(2,4-difluorophenyl)-1H-pyrazol-4-yl]ethyl}-5-[2-(trifluoromethyl)pyrimidin-5-yl]-7H-pyrrolo[2,3-d]pyrimidin-4-amine | N.D. | N.D. |
| 49 | 6-Bromo-7-{1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine | N.D. | N.D. |
| 50 | 6-Bromo-7-{1-[1-(2-fluorophenyl)-1H-pyrazol-4-yl]propyl}-5-[2-(trifluoromethyl)pyrimidin-5-yl]-7H-pyrrolo[2,3-d]pyrimidin-4-amine | N.D. | N.D. |
| 51 | 6-Bromo-7-{1-[1-(2,4-difluorophenyl)-1H-pyrazol-4-yl]propyl}-5-[2-(trifluoromethyl)pyrimidin-5-yl]-7H-pyrrolo[2,3-d]pyrimidin-4-amine | N.D. | N.D. |
| 52 | 6-Bromo-7-{1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine | N.D. | N.D. |
| 53 | 6-Bromo-7-{1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine | N.D. | N.D. |
| 54 | 6-Bromo-7-{1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine | N.D. | N.D. |
| 55 | 6-Bromo-5-[6-(difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine, single enantiomer | N.D. | N.D. |
| 56 | 6-Bromo-5-(4-chlorophenyl)-7-{[1-(2-fluorophenyl)-1H-1,2,3-triazol-4-yl]methyl}-7H-pyrrolo[2,3-d]pyrimidin-4-amine | N.D. | N.D. |
| 57 | 7-{[1-(2-Fluorophenyl)-1H-pyrazol-4-yl]methyl}-5-[2-(trifluoromethyl)pyrimidin-5-yl]-7H-pyrrolo[2,3-d]pyrimidin-4-amine | 65.88 | 28.80 |
| 58 | 5-(4-Chlorophenyl)-7-{1-[1-(2-fluorophenyl)-1H-1,2,3-triazol-4-yl]ethyl}-7H-pyrrolo[2,3-d]pyrimidin-4-amine | 28.89 | 231.93 |
| 59 | 5-(2-Fluoro-4-methoxyphenyl)-7-{1-[2-(2-fluorophenyl)-1H-imidazol-5-yl]ethyl}-7H-pyrrolo[2,3-d]pyrimidin-4-amine | 32.00 | 195.46 |
| 60 | 7-{1-[2-(2-Fluorophenyl)-1H-imidazol-5-yl]ethyl}-5-(1H-pyrazol-3-yl)-7H-pyrrolo[2,3-d]pyrimidin-4-amine | 80.00 | 45.26 |
| 61 | 7-{1-[2-(2-Fluorophenyl)-1H-imidazol-5-yl]ethyl}-5-(isoquinolin-8-yl)-7H-pyrrolo[2,3-d]pyrimidin-4-amine | N.D. | 1477.33 |
| 62 | 7-{1-[2-(2-Fluorophenyl)-1H-imidazol-5-yl]ethyl}-5-(7H-pyrrolo[2,3-b]pyridin-5-yl)-7H-pyrrolo[2,3-d]pyrimidin-4-amine | N.D. | 2223.78 |
| 63 | 5-(6-Fluoro-2-methylquinolin-7-yl)-7-{1-[2-(2-fluorophenyl)-1H-imidazol-5-yl]ethyl}-7H-pyrrolo[2,3-d]pyrimidin-4-amine | N.D. | 4536.99 |
| 64 | 7-{1-[2-(2-Fluorophenyl)-1H-imidazol-5-yl]ethyl}-5-[6-(trifluoromethyl)pyridin-3-yl]-7H-pyrrolo[2,3-d]pyrimidin-4-amine | 80.28 | 80.00 |
| 65 | 7-(4-Amino-7-{1-[2-(2-fluorophenyl)-1H-imidazol-5-yl]ethyl}-7H-pyrrolo[2,3-d]pyrimidin-5-yl)-2H-1,4-benzoxazin-3(4H)-one | N.D. | 1420.13 |
| 66 | 7-{1-[2-(2-Fluorophenyl)-1H-imidazol-5-yl]ethyl}-5-(1H-indazol-5-yl)-7H-pyrrolo[2,3-d]pyrimidin-4-amine | 1321.00 | 572.78 |
| 67 | 5-[2-(Dimethylamino)pyrimidin-5-yl]-7-{1-[2-(2-fluorophenyl)-1H-imidazol-5-yl]ethyl}-7H-pyrrolo[2,3-d]pyrimidin-4-amine | 142.00 | 54.59 |
| 68 | 5-(3-Fluoro-4-methylphenyl)-7-{1-[2-(2-fluorophenyl)-1H-imidazol-5-yl]ethyl}-7H-pyrrolo[2,3-d]pyrimidin-4-amine | 26.14 | 111.69 |
| 69 | 7-{1-[2-(2-Fluorophenyl)-1H-imidazol-5-yl]ethyl}-5-(6-methoxy-2,3-dihydro-1H-inden-5-yl)-7H-pyrrolo[2,3-d]pyrimidin-4-amine | N.D. | 915.49 |
| 70 | 7-{1-[2-(2-Fluorophenyl)-1H-imidazol-5-yl]ethyl}-5-[4-(2H-1,2,3-triazol-2-yl)phenyl]-7H-pyrrolo[2,3-d]pyrimidin-4-amine | 30.65 | 110.41 |
| 71 | 7-{1-[2-(2-Fluorophenyl)-1H-imidazol-5-yl]ethyl}-5-(1H-pyrazol-4-yl)-7H-pyrrolo[2,3-d]pyrimidin-4-amine | N.D. | 129.26 |
| 72 | 3-(4-Amino-7-{[1-(2-fluorophenyl)-1H-1,2,3-triazol-4-yl]methyl}-7H-pyrrolo[2,3-d]pyrimidin-5-yl)-5-methoxybenzonitrile | 57.00 | 186.40 |
| 73 | 7-{[1-(2-Fluorophenyl)-1H-1,2,3-triazol-4-yl]methyl}-5-(1-methyl-1H-indazol-6-yl)-7H-pyrrolo[2,3-d]pyrimidin-4-amine | N.D. | 320.24 |
| 74 | 5-(2,3-Dihydro-1-benzofuran-5-yl)-7-{[1-(2-fluorophenyl)-1H-1,2,3-triazol-4-yl]methyl}-7H-pyrrolo[2,3-d]pyrimidin-4-amine | 59.00 | 328.40 |
| 75 | 5-(4-Ethoxy-3-fluorophenyl)-7-{[1-(2-fluorophenyl)-1H-1,2,3-triazol-4-yl]methyl}-7H-pyrrolo[2,3-d]pyrimidin-4-amine | 38.02 | 99.58 |
| 76 | 7-{[1-(2-Fluorophenyl)-1H-1,2,3-triazol-4-yl]methyl}-5-(2-methyl-2H-indazol-5-yl)-7H-pyrrolo[2,3-d]pyrimidin-4-amine | N.D. | 2379.55 |
| 77 | 5-[4-(Cyclopropyloxy)phenyl]-7-{[1-(2-fluorophenyl)-1H-1,2,3-triazol-4-yl]methyl}-7H-pyrrolo[2,3-d]pyrimidin-4-amine | 17.40 | 62.46 |
| 78 | 7-{[1-(2-Fluorophenyl)-1H-1,2,3-triazol-4-yl]methyl}-5-(1-methyl-1H-indazol-4-yl)-7H-pyrrolo[2,3-d]pyrimidin-4-amine | N.D. | 1378.73 |

-continued

| Ex. No. | Compound Name | CF hBE Ussing EC$_{50}$ (nM) | FRT EC$_{50}$ (nM) |
|---|---|---|---|
| 79 | 4-(4-Amino-7-{[1-(2-fluorophenyl)-1H-1,2,3-triazol-4-yl]methyl}-7H-pyrrolo[2,3-d]pyrimidin-5-yl)-3-methoxybenzonitrile | 150.00 | 75.20 |
| 80 | 7-{[1-(2-Fluorophenyl)-1H-1,2,3-triazol-4-yl]methyl}-5-(7H-pyrrolo[2,3-b]pyridin-5-yl)-7H-pyrrolo[2,3-d]pyrimidin-4-amine | N.D. | 3780.33 |
| 81 | 7-{[1-(2-Fluorophenyl)-1H-1,2,3-triazol-4-yl]methyl}-5-(1H-indol-5-yl)-7H-pyrrolo[2,3-d]pyrimidin-4-amine | 338.00 | 378.76 |
| 82 | 5-(4-Chloro-2-methoxyphenyl)-7-{[1-(2-fluorophenyl)-1H-1,2,3-triazol-4-yl]methyl}-7H-pyrrolo[2,3-d]pyrimidin-4-amine | 25.00 | 77.38 |
| 83 | 5-[4-(Difluoromethoxy)phenyl]-7-{[1-(2-fluorophenyl)-1H-1,2,3-triazol-4-yl]methyl}-7H-pyrrolo[2,3-d]pyrimidin-4-amine | 39.76 | 71.88 |
| 84 | 4-(4-Amino-7-{[1-(2-fluorophenyl)-1H-1,2,3-triazol-4-yl]methyl}-7H-pyrrolo[2,3-d]pyrimidin-5-yl)-2-methoxybenzonitrile | N.D. | 1563.65 |
| 85 | 7-{[1-(2-Fluorophenyl)-1H-1,2,3-triazol-4-yl]methyl}-5-(4-methoxy phenyl)-7H-pyrrolo[2,3-d]pyrimidin-4-amine | 56.93 | 73.44 |
| 86 | 7-{[1-(2-Fluorophenyl)-1H-1,2,3-triazol-4-yl]methyl}-5-(1-methyl-1H-indazol-5-yl)-7H-pyrrolo[2,3-d]pyrimidin-4-amine | 659.00 | 539.38 |
| 87 | 5-(2,4-Dimethoxyphenyl)-7-{1-[1-(2-fluorophenyl)-1H-1,2,3-triazol-4-yl]ethyl}-7H-pyrrolo[2,3-d]pyrimidin-4-amine | 55.00 | 102.18 |
| 88 | 7-{1-[1-(2-Fluorophenyl)-1H-1,2,3-triazol-4-yl]ethyl}-5-[4-(methylsulfanyl)phenyl]-7H-pyrrolo[2,3-d]pyrimidin-4-amine | 38.17 | 41.28 |
| 89 | 5-[4-(Difluoromethoxy)phenyl]-7-{1-[1-(2-fluorophenyl)-1H-1,2,3-triazol-4-yl]ethyl}-7H-pyrrolo[2,3-d]pyrimidin-4-amine | 35.92 | 73.75 |
| 90 | 5-[2-Fluoro-4-(methylsulfanyl)phenyl]-7-{1-[1-(2-fluorophenyl)-1H-1,2,3-triazol-4-yl]ethyl}-7H-pyrrolo[2,3-d]pyrimidin-4-amine | 34.80 | 45.48 |
| 91 | 1-[5-(4-Amino-7-{1-[1-(2-fluorophenyl)-1H-1,2,3-triazol-4-yl]ethyl}-7H-pyrrolo[2,3-d]pyrimidin-5-yl)thiophen-2-yl]ethanone | N.D. | 111.23 |
| 92 | 7-{1-[1-(2-Fluorophenyl)-1H-1,2,3-triazol-4-yl]ethyl}-5-(1-methyl-1H-indazol-4-yl)-7H-pyrrolo[2,3-d]pyrimidin-4-amine | N.D. | 2418.75 |
| 93 | 7-{1-[1-(2-Fluorophenyl)-1H-1,2,3-triazol-4-yl]ethyl}-5-(3-methoxy-5,6,7,8-tetrahydronaphthalen-2-yl)-7H-pyrrolo[2,3-d]pyrimidin-4-amine | N.D. | 691.00 |
| 94 | 7-{1-[1-(2-Fluorophenyl)-1H-1,2,3-triazol-4-yl]ethyl}-5-phenyl-7H-pyrrolo[2,3-d]pyrimidin-4-amine | 140.00 | 361.46 |
| 95 | 7-{1-[1-(2-Fluorophenyl)-1H-1,2,3-triazol-4-yl]ethyl}-5-(1-methyl-1H-indazol-5-yl)-7H-pyrrolo[2,3-d]pyrimidin-4-amine | N.D. | 488.20 |
| 96 | 1-[4-(4-Amino-7-{1-[1-(2-fluorophenyl)-1H-1,2,3-triazol-4-yl]ethyl}-7H-pyrrolo[2,3-d]pyrimidin-5-yl)phenyl]ethanone | 133.00 | 98.61 |
| 97 | 7-{1-[1-(2-Fluorophenyl)-1H-1,2,3-triazol-4-yl]ethyl}-5-[3-(trifluoromethyl)phenyl]-7H-pyrrolo[2,3-d]pyrimidin-4-amine | 164.00 | 230.89 |
| 98 | 5-(4-Chloro-3-fluorophenyl)-7-{1-[1-(2-fluorophenyl)-1H-1,2,3-triazol-4-yl]ethyl}-7H-pyrrolo[2,3-d]pyrimidin-4-amine | 27.99 | 40.87 |
| 99 | 5-(3-Chloro-5-fluorophenyl)-7-{1-[1-(2-fluorophenyl)-1H-1,2,3-triazol-4-yl]ethyl}-7H-pyrrolo[2,3-d]pyrimidin-4-amine | 35.90 | 50.00 |
| 100 | 7-{1-[1-(2-Fluorophenyl)-1H-1,2,3-triazol-4-yl]ethyl}-5-(quinolin-3-yl)-7H-pyrrolo[2,3-d]pyrimidin-4-amine | N.D. | 277.25 |
| 101 | 6-(4-Amino-7-{1-[3-(2-fluorophenyl)-1,2-oxazol-5-yl]ethyl}-7H-pyrrolo[2,3-d]pyrimidin-5-yl)-2-methyl-2,3-dihydro-1H-isoindol-1-one | N.D. | 4063.27 |
| 102 | 5-(2,3-Dihydro-1,4-benzodioxin-6-yl)-7-{1-[3-(2-fluorophenyl)-1,2-oxazol-5-yl]ethyl}-7H-pyrrolo[2,3-d]pyrimidin-4-amine | N.D. | 321.59 |
| 103 | 7-{1-[3-(2-Fluorophenyl)-1,2-oxazol-5-yl]ethyl}-5-(1H-pyrrolo[2,3-b]pyridin-4-yl)-7H-pyrrolo[2,3-d]pyrimidin-4-amine | N.D. | 5149.07 |
| 104 | 5-(2,1,3-Benzoxadiazol-5-yl)-7-{1-[3-(2-fluorophenyl)-1,2-oxazol-5-yl]ethyl}-7H-pyrrolo[2,3-d]pyrimidin-4-amine | N.D. | 331.23 |
| 105 | 5-[4-(Dimethylamino)phenyl]-7-{1-[3-(2-fluorophenyl)-1,2-oxazol-5-yl]ethyl}-7H-pyrrolo[2,3-d]pyrimidin-4-amine | 75.00 | 374.14 |
| 106 | 7-{1-[3-(2-Fluorophenyl)-1,2-oxazol-5-yl]ethyl}-5-(thieno[3,2-c]pyridin-2-yl)-7H-pyrrolo[2,3-d]pyrimidin-4-amine | N.D. | 2084.01 |
| 107 | 7-{1-[3-(2-Fluorophenyl)-1,2-oxazol-5-yl]ethyl}-5-[4-(1,2,4-thiadiazol-5-yl)phenyl]-7H-pyrrolo[2,3-d]pyrimidin-4-amine | 122.00 | 172.41 |
| 108 | 5-Cyclopropyl-7-{1-[1-(2-fluorophenyl)-1H-1,2,3-triazol-4-yl]ethyl}-7H-pyrrolo[2,3-d]pyrimidin-4-amine, enantiomer 1 | 706.36 | 1198.68 |
| 109 | 5-Cyclopropyl-7-{1-[1-(2-fluorophenyl)-1H-1,2,3-triazol-4-yl]ethyl}-7H-pyrrolo[2,3-d]pyrimidin-4-amine, enantiomer 2 | 68.57 | 36.53 |
| 110 | 5-Cyclobutyl-7-{1-[1-(2-fluorophenyl)-1H-1,2,3-triazol-4-yl]ethyl}-7H-pyrrolo[2,3-d]pyrimidin-4-amine, enantiomer 2 | 6.21 | 2.65 |
| 111 | (−)-5-(4-Chlorophenyl)-7-{(1 R)-1-[1-(2-fluorophenyl)-1H-1,2,3-triazol-4-yl]ethyl}-7H-pyrrolo[2,3-d]pyrimidin-4-amine, enantiomer 1 | 135.93 | 533.25 |
| 112 | (+)-5-(4-Chlorophenyl)-7-{(1 S)-1-[1-(2-fluorophenyl)-1H-1,2,3-triazol-4-yl]ethyl}-7H-pyrrolo[2,3-d]pyrimidin-4-amine, enantiomer 2 | 17.50 | 68.57 |

-continued

| Ex. No. | Compound Name | CF hBE Ussing EC$_{50}$ (nM) | FRT EC$_{50}$ (nM) |
|---|---|---|---|
| 113 | (−) 7-{1-[1-(2-Fluorophenyl)-1H-1,2,3-triazol-4-yl]ethyl}-5-(2-methoxypyridin-3-yl)-7H-pyrrolo[2,3-d]pyrimidin-4-amine, enantiomer 1 | 818.00 | 826.09 |
| 114 | (+) 7-{1-[1-(2-Fluorophenyl)-1H-1,2,3-triazol-4-yl]ethyl}-5-(2-methoxypyridin-3-yl)-7H-pyrrolo[2,3-d]pyrimidin-4-amine, enantiomer 2 | 75.84 | 36.18 |
| 115 | 4-(4-Amino-7-{1-[1-(2-fluorophenyl)-1H-1,2,3-triazol-4-yl]ethyl}-7H-pyrrolo[2,3-d]pyrimidin-5-yl)-2-fluorobenzonitrile, enantiomer 1 | 614.00 | 566.01 |
| 116 | 4-(4-Amino-7-{1-[1-(2-fluorophenyl)-1H-1,2,3-triazol-4-yl-]ethyl}-7H-pyrrolo[2,3-d]pyrimidin-5-yl)-2-fluorobenzonitrile, enantiomer 2 | 26.00 | 36.04 |
| 117 | (+) 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine, enantiomer 1 | 49.27 | 58.82 |
| 118 | (−) 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine, enantiomer 2 | 162.50 | 378.28 |
| 119 | (−) 5-[6-(Cyclopropyloxy)pyridin-3-yl]-7-{1-[1-(2-fluorophenyl)-1H-1,2,3-triazol-4-yl]ethyl}-7H-pyrrolo[2,3-d]pyrimidin-4-amine, enantiomer 1 | 187.00 | 676.58 |
| 120 | (+) 5-[6-(Cyclopropyloxy)pyridin-3-yl]-7-{1-[1-(2-fluorophenyl)-1H-1,2,3-triazol-4-yl]ethyl}-7H-pyrrolo[2,3-d]pyrimidin-4-amine, enantiomer 2 | 5.48 | 33.40 |
| 121 | 7-{1-[1-(2-Fluorophenyl)-1H-1,2,3-triazol-4-yl]ethyl}-5-(1H-pyrazol-3-yl)-7H-pyrrolo[2,3-d]pyrimidin-4-amine, enantiomer 1 | 89.20 | 30.00 |
| 122 | 7-{1-[1-(2-Fluorophenyl)-1H-1,2,3-triazol-4-yl]ethyl}-5-(1H-pyrazol-3-yl)-7H-pyrrolo[2,3-d]pyrimidin-4-amine, enantiomer 2 | N.D. | 1045.61 |
| 123 | 7-{1-[1-(2,4-Difluorophenyl)-1H-1,2,3-triazol-4-yl]ethyl}-5-[2-(trifluoromethyl)pyrimidin-5-yl]-7H-pyrrolo[2,3-d]pyrimidin-4-amine, enantiomer 1 | 50.54 | 21.63 |
| 124 | 7-{1-[1-(2,4-Difluorophenyl)-1H-1,2,3-triazol-4-yl]ethyl}-5-[2-(trifluoromethyl)pyrimidin-5-yl]-7H-pyrrolo[2,3-d]pyrimidin-4-amine, enantiomer 2 | N.D. | 1236.99 |
| 125 | 5-(6-Methoxypyridin-3-yl)-7-[1-(1-phenyl-1H-1,2,3-triazol-4-yl)propyl]-7H-pyrrolo[2,3-d]pyrimidin-4-amine, enantiomer 1 | 199.00 | 395.01 |
| 126 | 5-(6-Methoxypyridin-3-yl)-7-[1-(1-phenyl-1H-1,2,3-triazol-4-yl)propyl]-7H-pyrrolo[2,3-d]pyrimidin-4-amine, enantiomer 2 | 11.96 | 21.55 |
| 127 | (−) 5-(4-Methoxypyrimidin-5-yl)-7-[1-(1-phenyl-1H-1,2,3-triazol-4-yl)propyl]-7H-pyrrolo[2,3-d]pyrimidin-4-amine, enantiomer 1 | 447.83 | 407.51 |
| 128 | (+) 5-(4-Methoxypyrimidin-5-yl)-7-[1-(1-phenyl-1H-1,2,3-triazol-4-yl)propyl]-7H-pyrrolo[2,3-d]pyrimidin-4-amine, enantiomer 2 | 42.64 | 19.08 |
| 129 | 7-[1-(1-Phenyl-1H-1,2,3-triazol-4-yl)propyl]-5-[2-(trifluoromethyl)pyrimidin-5-yl]-7H-pyrrolo[2,3-d]pyrimidin-4-amine, enantiomer 1 | 10.67 | 8.46 |
| 130 | 7-[1-(1-Phenyl-1H-1,2,3-triazol-4-yl)propyl]-5-[2-(trifluoromethyl)pyrimidin-5-yl]-7H-pyrrolo[2,3-d]pyrimidin-4-amine, enantiomer 2 | 187.00 | 234.04 |
| 131 | 5-(4-Chlorophenyl)-7-{1-[1-(2-fluorophenyl)-1H-1,2,3-triazol-4-yl] propyl}-7H-pyrrolo[2,3-d]pyrimidin-4-amine, enantiomer 1 | 282.00 | 623.43 |
| 132 | (+) 5-(4-Chlorophenyl)-7-{1-[1-(2-fluorophenyl)-1H-1,2,3-triazol-4-yl]propyl}-7H-pyrrolo[2,3-d]pyrimidin-4-amine, enantiomer 2 | 11.32 | 38.00 |
| 133 | (−) 7-{1-[1-(2-Fluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 721.00 | 918.45 |
| 134 | (+) 7-{1-[1-(2-Fluorophenyl)-1H-1,2,3-triazol-4-yl]propyl}-5-(4-methoxypyrimidin-5-yl)-7H-pyrrolo[2,3-d]pyrimidin-4-amine, enantiomer 2 | 28.90 | 13.41 |
| 135 | (−) 7-{1-[1-(2-Fluorophenyl)-1H-1,2,3-triazol-4-yl]propyl}-5-(3-methoxypyrazin-2-yl)-7H-pyrrolo[2,3-d]pyrimidin-4-amine, enantiomer 1 | 65.25 | 202.63 |
| 136 | (+) 7-{1-[1-(2-Fluorophenyl)-1H-1,2,3-triazol-4-yl]propyl}-5-(3-methoxypyrazin-2-yl)-7H-pyrrolo[2,3-d]pyrimidin-4-amine, enantiomer 2 | 3.46 | 15.35 |
| 137 | 7-{1-[1-(2-Fluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 1 | 10.26 | 5.86 |
| 138 | 7-{1-[1-(2-Fluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 2 | 260.71 | 265.51 |
| 139 | (+) 5-(5-Fluoro-2-methoxypyridin-3-yl)-7-{1-[1-(2-fluorophenyl)-1H-1,2,3-triazol-4-yl]propyl}-7H-pyrrolo[2,3-d]pyrimidin-4-amine, enantiomer 1 | 3.00 | 5.71 |

-continued

| Ex. No. | Compound Name | CF hBE Ussing EC$_{50}$ (nM) | FRT EC$_{50}$ (nM) |
|---|---|---|---|
| 140 | (−) 5-(5-Fluoro-2-methoxypyridin-3-yl)-7-{1-[1-(2-fluorophenyl)-1H-1,2,3-triazol-4-yl]propyl}-7H-pyrrolo[2,3-d]pyrimidin-4-amine, enantiomer 2 | 63.00 | 171.17 |
| 141 | (−) 5-[6-(Difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine, enantiomer 1 | 133.00 | 277.11 |
| 142 | (+) 5-[6-(Difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine, enantiomer 2 | 4.58 | 5.02 |
| 143 | 5-[2-(Difluoromethyl)pyrimidin-5-yl]-7-{1-[1-(2-fluorophenyl)-1H-1,2,3-triazol-4-yl]propyl}-7H-pyrrolo[2,3-d]pyrimidin-4-amine, enantiomer 1 | 25.98 | 10.50 |
| 144 | 5-[2-(Difluoromethyl)pyrimidin-5-yl]-7-{1-[1-(2-fluorophenyl)-1H-1,2,3-triazol-4-yl]propyl}-7H-pyrrolo[2,3-d]pyrimidin-4-amine, enantiomer 2 | N.D. | 731.90 |
| 145 | 5-[2-(Dimethylamino)pyrimidin-5-yl]-7-{1-[1-(2-fluorophenyl)-1H-1,2,3-triazol-4-yl]propyl}-7H-pyrrolo[2,3-d]pyrimidin-4-amine, enantiomer 1 | 29.73 | 26.03 |
| 146 | 5-[2-(Dimethylamino)pyrimidin-5-yl]-7-{1-[1-(2-fluorophenyl)-1H-1,2,3-triazol-4-yl]propyl}-7H-pyrrolo[2,3-d]pyrimidin-4-amine, enantiomer 2 | N.D. | 1187.28 |
| 147 | 7-{1-[1-(2-Fluorophenyl)-1H-1,2,3-triazol-4-yl]propyl}-5-(1H-pyrazol-3-yl)-7H-pyrrolo[2,3-d]pyrimidin-4-amine, enantiomer 1 | N.D. | 478.67 |
| 148 | 7-{1-[1-(2-Fluorophenyl)-1H-1,2,3-triazol-4-yl]propyl}-5-(1H-pyrazol-3-yl)-7H-pyrrolo[2,3-d]pyrimidin-4-amine, enantiomer 2 | 25.69 | 12.44 |
| 149 | (+) 7-{1-[1-(4-Fluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 45.28 | 28.89 |
| 150 | (−) 7-{1-[1-(4-Fluorophenyl)-1H-1,2,3-triazol-4yl]propyl}-5-(4-methoxypyrimidin-5-yl)-7H-pyrrolo[2,3-d]pyrimidin-4-amine, enantiomer 2 | 926.00 | 297.54 |
| 151 | (+) 7-{1-[1-(3,4-Difluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 35.50 | 34.08 |
| 152 | (−) 7-{1-[1-(3,4-Difluorophenyl)-1H-1,2,3-triazol-4-yl]propyl}-5-(4-methoxypyrimidin-5-yl)-7H-pyrrolo[2,3-d]pyrimidin-4-amine, enantiomer 2 | 445.00 | 182.50 |
| 153 | 7-{1-[1-(3,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 1 | 19.78 | 59.02 |
| 154 | 7-{[1-(3,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 2 | 326.70 | 630.35 |
| 155 | 7-{1-[1-(3,4-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 1 | 9.17 | 38.57 |
| 156 | 7-{1-[1-(3,4-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 2 | 57.57 | 229.77 |
| 157 | 7-{1-[1-(3,4-Difluorophenyl)-1H-1,2,3-triazol-4-yl]propyl}-5-(5-fluoro-6-methoxypyridin-3-yl)-7H-pyrrolo[2,3-d]pyrimidin-4-amine, enantiomer 1 | 239.00 | 432.94 |
| 158 | 7-{1-[1-(3,4-Difluorophenyl)-1H-1,2,3-triazol-4-yl]propyl}-5-(5-fluoro-6-methoxypyridin-3-yl)-7H-pyrrolo[2,3-d]pyrimidin-4-amine, enantiomer 2 | 19.50 | 112.01 |
| 159 | (+) 7-{1-[1-(2,4-Difluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 35.47 | 18.49 |
| 160 | (−) 7-{1-[1-(2,4-Difluorophenyl)-1H-1,2,3-triazol-4-yl]propyl}-5-(4-methoxypyrimidin-5-yl)-7H-pyrrolo[2,3-d]pyrimidin-4-amine, enantiomer 2 | 593.00 | 451.65 |
| 161 | 7-{(1 S)-1-[1-(2,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine | 10.88 | 8.60 |
| 162 | 7-{(1 R)-1-[1-(2,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine | 339.26 | 362.79 |
| 163 | 7-{1-[1-(2,4-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 1 | 97.15 | 295.97 |
| 164 | 7-{1-[1-(2,4-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 2 | 4.58 | 8.18 |

| Ex. No. | Compound Name | CF hBE Ussing EC$_{50}$ (nM) | FRT EC$_{50}$ (nM) |
|---|---|---|---|
| 165 | 7-{1-[1-(2,4-Difluorophenyl)-1H-1,2,3-triazol-4-yl]propyl}-5-(5-fluoro-6-methoxypyridin-3-yl)-7H-pyrrolo[2,3-d]pyrimidin-4-amine, enantiomer 1 | 247.00 | 727.74 |
| 166 | 7-{1-[1-(2,4-Difluorophenyl)-1H-1,2,3-triazol-4-yl]propyl}-5-(5-fluoro-6-methoxypyridin-3-yl)-7H-pyrrolo[2,3-d]pyrimidin-4-amine, enantiomer 2 | 9.00 | 24.58 |
| 167 | 5-[2-(Difluoromethyl)pyrimidin-5-yl]-7-{1-[1-(2,4-difluorophenyl)-1H-1,2,3-triazol-4-yl]propyl}-7H-pyrrolo[2,3-d]pyrimidin-4-amine, enantiomer 1 | 50.52 | 24.97 |
| 168 | 5-[2-(Difluoromethyl)pyrimidin-5-yl]-7-{1-[1-(2,4-difluorophenyl)-1H-1,2,3-triazol-4-yl]propyl}-7H-pyrrolo[2,3-d]pyrimidin-4-amine, enantiomer 2 | 2334.47 | 2951.43 |
| 169 | 7-{1-[1-(2,3-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 1 | 4.90 | 7.98 |
| 170 | 7-{1-[1-(2,3-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 2 | 48.76 | 214.23 |
| 171 | 7-{1-[1-(2,5-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 1 | 3.87 | 11.65 |
| 172 | 7-{1-[1-(2,5-Difluorophenyl)-1H-1,2,3-triazol-4-yl]propyl}-5-(5-fluoro-2-methoxypyridin-3-yl)-7H-pyrrolo[2,3-d]pyrimidin-4-amine, enantiomer 2 | 77.56 | 202.59 |
| 173 | (−) 5-Cyclopropyl-7-{1-[1-(2-fluorophenyl)-1H-1,2,3-triazol-4-yl]propyl}-7H-pyrrolo[2,3-d]pyrimidin-4-amine, enantiomer 1 | 26.66 | 29.26 |
| 174 | (+) 7-{Cyclopropyl]-(2-fluorophenyl)-1H-1,2,3-triazol-4-yl]methyl}-5-(4-methoxypyrimidin-5-yl)-7H-pyrrolo[2,3-d]pyrimidin-4-amine, enantiomer 1 | 31.55 | 19.63 |
| 175 | 7-{(1-[1-(2-Fluorophenyl)-1H-pyrazol-4-yl]propyl}-5-[2-(trifluoromethyl)pyrimidin-5-yl]-7H-pyrrolo[2,3-d]pyrimidin-4-amine, enantiomer 1 | 8.00 | 9.89 |
| 176 | 7-{(1-[1-(2-Fluorophenyl)-1H-pyrazol-4-yl]propyl}-5-[2-(trifluoromethyl)pyrimidin-5-yl]-7H-pyrrolo[2,3-d]pyrimidin-4-amine, enantiomer 2 | 106.00 | 203.77 |
| 177 | 7-{1-[2-(2,4-Difluorophenyl)-2H-imidazol-4-yl]propyl}-5-[2-(trifluoromethyl)pyrimidin-5-yl]-7H-pyrrolo[2,3-d]pyrimidin-4-amine, enantiomer 1 | 18.89 | 21.62 |
| 178 | 7-{1-[2-(2,4-Difluorophenyl)-2H-imidazol-4-yl]propyl}-5-[2-(trifluoromethyl)pyrimidin-5-yl]-7H-pyrrolo[2,3-d]pyrimidin-4-amine, enantiomer 2 | N.D. | 850.21 |
| 179 | 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine, enantiomer 1 | 23.07 | 9.97 |
| 180 | 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine, enantiomer 2 | N.D. | 1923.65 |
| 181 | (+)-5-(4-Chlorophenyl)-7-{1-[3-(2-fluorophenyl)-1,2-oxazol-5-yl]ethyl}-7H-pyrrolo[2,3-d]pyrimidin-4-amine, enantiomer 1 | 24.49 | 538.07 |
| 182 | (+)-5-(4-Chlorophenyl)-7-{1-[3-(2-fluorophenyl)-1,2-oxazol-5-yl]ethyl}-7H-pyrrolo[2,3-d]pyrimidin-4-amine, enantiomer 2 | 445.98 | 467.58 |
| 183 | 7-{1-[3-(2-Fluorophenyl)isoxazol-5-yl]ethyl}-5-(2-methoxypyrimidin-5-yl)-7H-pyrrolo[2,3-d]pyrimidin-4-amine, enantiomer 1 | 305.28 | 508.58 |
| 184 | 7-{1-[3-(2-Fluorophenyl)isoxazol-5-yl]ethyl}-5-(2-methoxypyrimidin-5-yl)-7H-pyrrolo [2,3-d]pyrimidin-4-amine, enantiomer 2 | 32.64 | 49.67 |
| 185 | 7-{1-[1-(2,5-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, enantiomer 1 | 14.36 | 34.73 |
| 186 | 7-{1-[1-(2,5-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, enantiomer 2 | 296.86 | 630.77 |
| 187 | 7-{1-[1-(2,3-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, enantiomer 1 | 12.97 | 13.18 |
| 188 | 7-{1-[1-(2,3-Difluorophenyl)-1H-1,2,3-triazol-4-yl]propyl}-5-[2-(trifluoromethyl) pyrimidin-5-yl]-7H-pyrrolo[2,3-d]pyrimidin-4-amine, enantiomer 2 | 243.00 | 551.27 |
| 189 | 7-{1-[1-(2,4-Difluorophenyl)-5-methyl-1H-1,2,3-triazol-4-yl]propyl}-7H-pyrrolo[2,3-d] pyrimidin-4-amine, enantiomer 1 | 10.18 | 6.72 |
| 190 | 7-{1-[1-(2,4-Difluorophenyl)-5-methyl-1H-1,2,3-triazol-4-yl]propyl}-7H-pyrrolo[2,3-d] pyrimidin-4-amine, enantiomer 2 | N.D. | 457.35 |

-continued

| Ex. No. | Compound Name | CF hBE Ussing EC$_{50}$ (nM) | FRT EC$_{50}$ (nM) |
|---|---|---|---|
| 191 | 7-{1-[3-(2-Fluorophenyl)-1,2-oxazol-5-yl]ethyl}-5-(5-methoxy pyrazin-2-yl)-7H-pyrrolo[2,3-d]pyrimidin-4-amine | 103.00 | 918.14 |
| 192 | 4-(4-Amino-7-{[2-(2-fluorophenyl)-1H-imidazol-5-yl]methyl}-7H-pyrrolo[2,3-d]pyrimidin-5-yl)-2-fluorobenzonitrile | 118.31 | 83.03 |
| 193 | 7-{[2-(2-Fluorophenyl)-1H-imidazol-5-yl]methyl}-5-(2-methoxy pyridin-3-yl)-7H-pyrrolo[2,3-d]pyrimidin-4-amine | 116.56 | 43.77 |
| 194 | 7-{[1-(2-Fluorophenyl)-1H-1,2,3-triazol-4-yl]methyl}-5-(2-methoxy-6-methylpyridin-3-yl)-7H-pyrrolo[2,3-d]pyrimidin-4-amine | 12.21 | 28.59 |
| 195 | 5-(5-Fluoro-2-methoxypyridin-3-yl)-7-{[1-(2-fluorophenyl)-1H-1,2,3-triazol-4-yl]methyl}-7H-pyrrolo[2,3-d]pyrimidin-4-amine | 25.29 | 63.62 |
| 196 | 5-[2-(Difluoromethoxy)pyridin-3-yl]-7-{[1-(2-fluorophenyl)-1H-1,2,3-triazol-4-yl]methyl}-7H-pyrrolo[2,3-d]pyrimidin-4-amine | 49.00 | 15.59 |
| 197 | 7-{[1-(2-Fluorophenyl)-1H-1,2,3-triazol-4-yl]methyl}-5-(1,3-oxazol-5-yl)-7H-pyrrolo[2,3-d]pyrimidin-4-amine | 811.00 | 254.38 |
| 198 | 7-{[1-(2-Fluorophenyl)-1H-1,2,3-triazol-4-yl]methyl}-5-(tetrahydrofuran-2-yl)-7H-pyrrolo[2,3-d]pyrimidin-4-amine | 2118.00 | >25000 |
| 199 | 5-(2,5-Dihydrofuran-2-yl)-7-((1-(2-fluorophenyl)-1H-1,2,3-triazol-4-yl)methyl)-7H-pyrrolo[2,3-d]pyrimidin-4-amine | N.D. | N.D. |
| 200 | 7-{[1-(2-Fluorophenyl)-1H-1,2,3-triazol-4-yl]methyl}-5-(4-methoxy pyrimidin-5-yl)-7H-pyrrolo[2,3-d]pyrimidin-4-amine | 477.59 | 100.23 |
| 201 | No example 201 was prepared | — | — |
| 202 | 7-{[1-(2-Fluorophenyl)-1H-1,2,3-triazol-4-yl]methyl}-5-(2-methoxy pyridin-3-yl)-2-methyl-7H-pyrrolo[2,3-d]pyrimidin-4-amine | 798.00 | 922.43 |
| 203 | 7-{[1-(2-Fluorophenyl)-1H-1,2,3-triazol-4-yl]methyl}-5-(4-methoxy pyrimidin-5-yl)-2-methyl-7H-pyrrolo[2,3-d]pyrimidin-4-amine | 2534.00 | 1606.59 |
| 204 | 5-(2-(Difluoromethyl)pyrimidin-5-yl)-7-{[1-(2-fluorophenyl)-1H-pyrazol-4-yl]methyl}-7H-pyrrolo[2,3-d]pyrimidin-4-amine | N.D. | N.D. |
| 205 | 5-[2-(Difluoromethyl)pyrimidin-5-yl]-7-{1-[1-(2-fluorophenyl)-1H-pyrazol-4-yl]ethyl}-7H-pyrrolo[2,3-d]pyrimidin-4-amine | N.D. | N.D. |
| 206 | 7-{[1-(2-Fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine | 10.80 | 22.85 |
| 207 | 7-{[1-(2-Fluorophenyl)-1H-1,2,3-triazol-4-yl]methyl}-5-(3-methoxy pyridin-2-yl)-7H-pyrrolo[2,3-d]pyrimidin-4-amine | 238.33 | 225.67 |
| 208 | 5-(4-Chlorophenyl)-7-{1-[1-(3-methylphenyl)-1H-1,2,3-triazol-4-yl] ethyl}-7H-pyrrolo[2,3-d]pyrimidin-4-amine | 55.00 | 404.18 |
| 209 | 5-(4-Chlorophenyl)-7-{1-[1-(2-fluorophenyl)-1H-1,2,3-triazol-4-yl]ethyl}-2-methyl-7H-pyrrolo[2,3-d]pyrimidin-4-amine | 295.00 | 343.12 |
| 210 | 7-{[1-(2-Fluorophenyl)-1H-1,2,3-triazol-4-yl]methyl}-5-(2-methoxy-pyridin-3-yl)-7H-pyrrolo[2,3-d]pyrimidin-4-amine | 158.22 | 123.09 |
| 211 | 5-(4-Chlorophenyl)-7-{1-[1-(2-fluorophenyl)-1H-1,2,3-triazol-4-yl] propyl}-7H-pyrrolo[2,3-d]pyrimidin-4-amine | 25.92 | 109.46 |
| 212 | 5-[4-(Cyclopropyloxy)phenyl]-7-{1-[1-(2-fluorophenyl)-1H-1,2,3-triazol-4-yl]ethyl}-7H-pyrrolo[2,3-d]pyrimidin-4-amine | 12.21 | 68.22 |
| 213 | 5-[6-(Cyclopropyloxy)pyridin-3-yl]-7-{1-[1-(2-fluorophenyl)-1H-1,2,3-triazol-4-yl]ethyl}-7H-pyrrolo[2,3-d]pyrimidin-4-amine | 23.11 | 58.63 |
| 214 | 5-[4-(Cyclopropoxy)phenyl]-7-{1-[1-(3-fluoropyridin-2-yl)-1H-1,2,3-triazol-4-yl]ethyl}-7H-pyrrolo[2,3-d]pyrimidin-4-amine | 39.64 | 90.62 |
| 215 | 7-{1-[1-(2-Fluorophenyl)-1H-1,2,3-triazol-4-yl]ethyl}-5-(2-methoxypyridin-3-yl)-7H-pyrrolo[2,3-d]pyrimidin-4-amine | 183.73 | 79.27 |
| 216 | 7-{1-[1-(2-Fluorophenyl)-1H-1,2,3-triazol-4-yl]ethyl}-5-[2-(trifluoromethyl) pyrimidin-5-yl]-7H-pyrrolo[2,3-d]pyrimidin-4-amine | 58.83 | 25.21 |
| 217 | 7-{1-[1-(2,4-Difluorophenyl)-1H-1,2,3-triazol-4-yl]ethyl}-5-[2-(trifluoromethyl)pyrimidin-5-yl]-7H-pyrrolo[2,3-d]pyrimidin-4-amine | N.D. | N.D. |
| 218 | 7-{1-[1-(2-Fluorophenyl)-1H-1,2,3-triazol-4-yl]ethyl}-5-(1H-pyrazol-3-yl)-7H-pyrrolo[2,3-d]pyrimidin-4-amine | N.D. | N.D. |
| 219 | 7-[1-(1-Phenyl-1H-1,2,3-triazol-4-yl)propyl]-5-[2-(trifluoromethyl)pyrimidin-5-yl]-7H-pyrrolo[2,3-d]pyrimidin-4-amine | N.D. | N.D. |
| 220 | 5-(6-methoxypyridin-3-yl)-7-[1-(1-phenyl-1H-1,2,3-triazol-4-yl)propyl]-7H-pyrrolo[2,3-d]pyrimidin-4-amine | N.D. | N.D. |
| 221 | 5-[2-(Difluoromethyl)pyrimidin-5-yl]-7-{1-[1-(2-fluorophenyl)-1H-1,2,3-triazol-4-yl]propyl}-7H-pyrrolo[2,3-d]pyrimidin-4-amine | N.D. | N.D. |
| 222 | 5-[2-(Dimethylamino)pyrimidin-5-yl]-7-{1-[1-(2-fluorophenyl)-1H-1,2,3-triazol-4-yl]propyl}-7H-pyrrolo[2,3-d]pyrimidin-4-amine | N.D. | N.D. |
| 223 | 7-{1-[1-(2-Fluorophenyl)-1H-1,2,3-triazol-4-yl]propyl}-5-(5-fluoro-2-methoxypyridin-3-yl)-7H-pyrrolo[2,3-d]pyrimidin-4-amine | 7.23 | 11.13 |

-continued

| Ex. No. | Compound Name | CF hBE Ussing EC$_{50}$ (nM) | FRT EC$_{50}$ (nM) |
|---|---|---|---|
| 224 | 7-{1-[1-(2-Fluorophenyl)-1H-1,2,3-triazol-4-yl]propyl}-5-[2-(trifluoromethyl)pyrimidin-5-yl]-7H-pyrrolo[2,3-d]pyrimidin-4-amine | 18.97 | 9.04 |
| 225 | 7-{1-[1-(2-Fluorophenyl)-1H-1,2,3-triazol-4-yl]propyl}-5-(1,3-oxazol-5-yl)-7H-pyrrolo[2,3-d]pyrimidin-4-amine | 93.22 | 37.31 |
| 226 | 7-{1-[1-(2-Fluorophenyl)-1H-1,2,3-triazol-4-yl]propyl}-5-(1H-pyrazol-3-yl)-7H-pyrrolo[2,3-d]pyrimidin-4-amine | N.D. | N.D. |
| 227 | 7-{1-[1-(3,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine | N.D. | N.D. |
| 228 | 7-{1-[1-(3,4-Difluorophenyl)-1H-1,2,3-triazol-4-yl]propyl}-5-(5-fluoro-2-methoxypyridin-3-yl)-7H-pyrrolo[2,3-d]pyrimidin-4-amine | N.D. | N.D. |
| 229 | 7-{1-[1-(3,4-Difluorophenyl)-1H-1,2,3-triazol-4-yl]propyl}-5-(5-fluoro-6-methoxypyridin-3-yl)-7H-pyrrolo[2,3-d]pyrimidin-4-amine | N.D. | N.D. |
| 230 | 5-[2-(Difluoromethyl)pyrimidin-5-yl]-7-{1-[1-(2,4-difluorophenyl)-1H-1,2,3-triazol-4-yl]propyl}-7H-pyrrolo[2,3-d]pyrimidin-4-amine | N.D. | N.D. |
| 231 | 7-{1-[1-(2,4-Difluorophenyl)-1H-1,2,3-triazol-4-yl]propyl}-5-(5-fluoro-2-methoxypyridin-3-yl)-7H-pyrrolo[2,3-d]pyrimidin-4-amine | N.D. | N.D. |
| 232 | 7-{1-[1-(2,4-Difluorophenyl)-1H-1,2,3-triazol-4-yl]propyl}-5-(5-fluoro-6-methoxypyridin-3-yl)-7H-pyrrolo[2,3-d]pyrimidin-4-amine | N.D. | N.D. |
| 233 | 7-{1-[1-(2,3-Difluorophenyl)-1H-1,2,3-triazol-4-yl]propyl}-5-(5-fluoro-2-methoxypyridin-3-yl)-7H-pyrrolo[2,3-d]pyrimidin-4-amine | N.D. | N.D. |
| 234 | 7-{1-[1-(2,5-Difluorophenyl)-1H-1,2,3-triazol-4-yl]propyl}-5-(5-fluoro-2-methoxypyridin-3-yl)-7H-pyrrolo[2,3-d]pyrimidin-4-amine | N.D. | N.D. |
| 235 | 7-{1-[1-(2,4-Difluorophenyl)-1H-1,2,3-triazol-4-yl]propyl}-5-[2-(trifluoromethyl)pyrimidin-5-yl]-7H-pyrrolo[2,3-d]pyrimidin-4-amine | N.D. | N.D. |
| 236 | 5-Cyclopropyl-7-{1-[1-(2-fluorophenyl)-1H-1,2,3-triazol-4-yl]propyl}-7H-pyrrolo[2,3-d]pyrimidin-4-amine | 38.78 | 56.00 |
| 237 | 5-(6-Cyclopropoxypyridin-3-yl)-7-{1-[1-(2,4-difluorophenyl)-1H-1,2,3-triazol-4-yl]ethyl}-7H-pyrrolo[2,3-d]pyrimidin-4-amine | N.D. | N.D. |
| 238 | 5-Cyclopropyl-7-{1-[1-(2-fluorophenyl)-1H-1,2,3-triazol-4-yl)ethyl]-7H-pyrrolo[2,3-d]pyrimidin-4-amine | 133.00 | 60.57 |
| 239 | 4-(4-Amino-7-{1-[1-(2-fluorophenyl)-1H-1,2,3-triazol-4-yl)ethyl]-7H-pyrrolo[2,3-d]pyrimidin-5-yl)-2-fluorobenzonitrile | 83.00 | 94.43 |
| 240 | 5-[6-(Difluoromethoxy)pyridin-3-yl]-7-{1-[1-(2-fluorophenyl)-1H-1,2,3-triazol-4-yl]propyl}-7H-pyrrolo[2,3-d]pyrimidin-4-amine | N.D. | N.D. |
| 241 | 7-{1-[1-(4-Fluorophenyl)-1H-1,2,3-triazol-4-yl]propyl}-5-[4-methoxy pyrimidin-5-yl]-7H-pyrrolo[2,3-d]pyrimidin-4-amine | N.D. | N.D. |
| 242 | 5-(4-Methoxypyrimidin-5-yl)-7-(1-{1-[4-(trifluoromethyl)pyridin-2-yl]-1H-1,2,3-triazol-4-yl}propyl)-7H-pyrrolo[2,3-d]pyrimidin-4-amine | 204.53 | 377.79 |
| 243 | 7-{Cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine | 95.27 | 56.23 |
| 244 | 7-{1-[1-(2-Fluorophenyl)-1H-1,2,3-triazol-4-yl]propyl}-5-[4-methoxypyrimidin-5-yl]-7H-pyrrolo[2,3-d]pyrimidin-4-amine | 61.55 | 34.12 |
| 245 | 7-{1-[1-(3,4-Difluorophenyl)-1H-1,2,3-triazol-4-yl]propyl}-5-[4-methoxypyrimidin-5-yl]-7H-pyrrolo[2,3-d]pyrimidin-4-amine | N.D. | 42.44 |
| 246 | 7-{1-[1-(2,4-Difluorophenyl)-1H-1,2,3-triazol-4-yl]propyl}-5-[4-methoxypyrimidin-5-yl]-7H-pyrrolo[2,3-d]pyrimidin-4-amine | N.D. | 17.24 |
| 247 | 5-Cyclobutyl-7-{1-[1-(2-fluorophenyl)-1H-1,2,3-triazol-4-yl]ethyl}-7H-pyrrolo[2,3-d]pyrimidin-4-amine | 12.43 | 16.20 |
| 248 | 5-(4-Methoxypyrimidin-5-yl)-7-{1-[1-phenyl-1H-1,2,3-triazol-4-yl]propyl}-7H-pyrrolo[2,3-d]pyrimidin-4-amine | 55.40 | 25.93 |
| 249 | 7-{1-[1-(2-Fluorophenyl)-1H-1,2,3-triazol-4-yl]ethyl}-5-[4-methoxy-2-(trifluoromethyl)pyrimidin-5-yl]-7H-pyrrolo[2,3-d]pyrimidin-4-amine | 27.72 | 12.15 |
| 250 | 7-{1-[1-(2-Fluorophenyl)-1H-1,2,3-triazol-4-yl]ethyl}-5-(oxetan-3-yl)-7H-pyrrolo[2,3-d] pyrimidin-4-amine | N.D. | 2197.25 |
| 251 | 7-{1-[1-(2-Fluorophenyl)-1H-1,2,3-triazol-4-yl]propyl}-5-(3-methoxy pyrazin-2-yl)-7H-pyrrolo[2,3-d]pyrimidin-4-amine | N.D. | 5.41 |
| 252 | 7-{[1-(2-Fluorophenyl)-1H-1,2,3-triazol-4-yl]methyl}-5-[4-methoxy-2-(trifluoromethyl)pyrimidin-5-yl]-7H-pyrrolo[2,3-d]pyrimidin-4-amine | 23.91 | 27.62 |
| 253 | 7-{[5-(2-Fluorophenyl)-4H-1,2,4-triazol-3-yl]methyl}-5-(2-methoxy pyridin-3-yl)-7H-pyrrolo[2,3-d]pyrimidin-4-amine | 1344.00 | 719.10 |
| 254 | 5-(4-Chlorophenyl)-7-{[1-(propan-2-yl)-1H-pyrazol-4-yl]methyl}-7H-pyrrolo[2,3-d]pyrimidin-4-amine | 140.00 | 422.22 |

-continued

| Ex. No. | Compound Name | CF hBE Ussing EC$_{50}$ (nM) | FRT EC$_{50}$ (nM) |
|---|---|---|---|
| 255 | 5-(4-Chlorophenyl)-7-{1-[1-(cyclobutylmethyl)-1H-1,2,3-triazol-4-yl]ethyl}-7H-pyrrolo[2,3-d]pyrimidin-4-amine | 64.70 | 259.42 |
| 256 | 5-(4-Chlorophenyl)-7-{2-[1-(2-fluorophenyl)-1H-1,2,3-triazol-4-yl]propan-2-yl}-7H-pyrrolo[2,3-d]pyrimidin-4-amine | 45.00 | 341.42 |
| 257 | 5-(4-Chlorophenyl)-7-{1-[1-(2-fluorophenyl)-1H-1,2,3-triazol-4-yl]ethyl}-6-methyl-7H-pyrrolo[2,3-d]pyrimidin-4-amine | 38.30 | 288.88 |
| 258 | 5-(4-Chlorophenyl)-7-{1-[3-(2-fluorophenyl)-1,2-oxazol-5-yl]ethyl}-7H-pyrrolo[2,3-d] pyrimidin-4-amine | 147.40 | 343.47 |
| 259 | 5-(4-Chlorophenyl)-7-{1-[3-(2-fluorophenyl)-1,2-oxazol-5-yl]ethyl}-6-methyl-7H-pyrrolo[2,3-d]pyrimidin-4-amine | 52.01 | 205.66 |
| 260 | 5-(4-Chlorophenyl)-7-{1-[3-(2-methoxyphenyl)-1,2-oxazol-5-yl]ethyl}-7H-pyrrolo[2,3-d]pyrimidin-4-amine | 110.00 | 197.37 |
| 261 | 5-(4-Chlorophenyl)-7-{1-[3-(3-methoxyphenyl)-1,2-oxazol-5-yl]ethyl}-7H-pyrrolo[2,3-d]pyrimidin-4-amine | 232.00 | 168.99 |
| 262 | 5-(4-Chlorophenyl)-7-{[1-(2-fluorophenyl)-1H-pyrazol-4-yl]methyl}-7H-pyrrolo[2,3-d]pyrimidin-4-amine | 60.22 | 313.23 |
| 263 | 5-(4-Chlorophenyl)-7-{[2-(2-fluorophenyl)-1H-imidazol-5-yl]methyl}-7H-pyrrolo[2,3-d]pyrimidin-4-amine | 21.63 | 199.36 |
| 264 | 5-(4-Chlorophenyl)-7-[(2-phenyl-1H-imidazol-5-yl)methyl]-7H-pyrrolo[2,3-d]pyrimidin-4-amine | 35.40 | 176.29 |
| 265 | 5-(4-Chlorophenyl)-7-{[1-(2-fluorophenyl)-1H-imidazol-4-yl]methyl}-7H-pyrrolo[2,3-d]pyrimidin-4-amine | N.D. | 3876.40 |
| 266 | 5-(4-Chlorophenyl)-7-{1-[3-(2-methylphenyl)-1,2-oxazol-5-yl]ethyl}-7H-pyrrolo[2,3-d]pyrimidin-4-amine | 252.72 | 138.20 |
| 267 | 5-(4-Chlorophenyl)-7-{1-[3-(3-fluorophenyl)-1,2-oxazol-5-yl]ethyl}-7H-pyrrolo[2,3-d]pyrimidin-4-amine | 136.00 | 1123.17 |
| 268 | 7-{[1-(2-Fluorophenyl)-1H-pyrazol-3-yl]methyl}-5-(2-methoxypyridin-3-yl)-7H-pyrrolo[2,3-d]pyrimidin-4-amine | 578.00 | 470.34 |
| 269 | 5-(4-Chlorophenyl)-7-[(3-cyclohexyl-1,2-oxazol-5-yl)methyl]-7H-pyrrolo[2,3-d]pyrimidin-4-amine | 22.70 | 478.17 |
| 270 | 7-({1-[4-(Difluoromethyl)phenyl]-1H-pyrazol-4-yl}methyl)-5-(2-methoxypyridin-3-yl)-7H-pyrrolo[2,3-d]pyrimidin-4-amine | 47.71 | 451.22 |
| 271 | 7-{1-[1-(2-fluorophenyl)-1H-pyrazol-4-yl]propyl}-5-[2-(trifluoro methyl)pyrimidin-5-yl]-7H-pyrrolo[2,3-d]pyrimidin-4-amine | N.D. | N.D. |
| 272 | 5-(2-Methoxypyridin-3-yl)-7-[(5-phenyl-4H-1,2,4-triazol-3-yl)methyl]-7H-pyrrolo[2,3-d]pyrimidin-4-amine | 833.00 | 397.95 |
| 273 | 7-{1-[1-(2-Fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine | N.D. | N.D. |
| 274 | 7-{1-[1-(2,4-Difluorophenyl)-1H-pyrazol-4-yl]propyl}-5-[2-(trifluoro methyl)pyrimidin-5-yl]-7H-pyrrolo[2,3-d]pyrimidin-4-amine | N.D. | N.D. |
| 275 | 7-{1-[1-(2,4-Difluorophenyl)-1H-pyrazol-4-yl]ethyl}-5[2-(trifluoro methyl)pyrimidin-5-yl]-7H-pyrrolo[2,3-d]pyrimidin-4-amine | N.D. | N.D. |
| 276 | 7-{1-[2-(2,4-Difluorophenyl)-2H-imidazol-4-yl]propyl}-5-[2-(trifluoromethyl)pyrimidin-5-yl]-7H-pyrrolo[2,3-d]pyrimidin-4-amine | N.D. | N.D. |
| 277 | 7-(1-(1-(2-Fluorophenyl)-1H-pyrazol-4-yl)ethyl)-5-(2-(trifluoro methyl)pyrimidin-5-yl)-7H-pyrrolo[2,3-d]pyrimidin-4-amine | N.D. | N.D. |
| 278 | 7-{[1-(2,4-Difluorophenyl)-1H-1,2,3-triazol-4-yl]methyl}-5-(6-methoxypyridin-3-yl)-6-methyl-7H-pyrrolo[2,3-d]pyrimidin-4-amine | 152.00 | 218.72 |
| 279 | 7-{[1-(2,4-Difluorophenyl)-1H-pyrazol-4-yl]methyl}-5-[2-(trifluoromethyl)pyrimidin-5-yl]-7H-pyrrolo[2,3-d]pyrimidin-4-amine | N.D. | N.D. |
| 280 | 5-(4-Chlorophenyl)-7-[(3-cyclopropyl-1,2-oxazol-5-yl)methyl]-7H-pyrrolo[2,3-d]pyrimidin-4-amine | 126.70 | 2667.23 |
| 281 | 5-(4-Chlorophenyl)-7-[(1-cyclopentyl-1H-1,2,3-triazol-4-yl)methyl]-7H-pyrrolo[2,3-d]pyrimidin-4-amine | N.D. | 170.33 |
| 282 | 5-(4-Chlorophenyl)-7-[(4-phenyl-1H-imidazol-2-yl)methyl]-7H-pyrrolo[2,3-d]pyrimidin-4-amine | 216.41 | 908.97 |
| 283 | 5-(4-Chlorophenyl)-7-{[3-(propan-2-yl)-1,2-oxazol-5-yl]methyl}-7H-pyrrolo[2,3-d]pyrimidin-4-amine | 111.00 | 659.26 |
| 284 | 5-(4-Chlorophenyl)-7-[(5-phenyl-4H-1,2,4-triazol-3-yl)methyl]-7H-pyrrolo[2,3-d]pyrimidin-4-amine | 551.50 | N.D. |
| 285 | 5-(4-Chlorophenyl)-7-{[5-(2-fluorophenyl)-1H-imidazol-2-yl]methyl}-7H-pyrrolo[2,3-d]pyrimidin-4-amine | 3504.00 | 3694.98 |
| 286 | 7-{[1-(2,6-Difluorophenyl)-1H-pyrazol-4-yl]methyl}-5-(2-methoxypyridin-3-yl)-7H-pyrrolo[2,3-d]pyrimidin-4-amine | 176.00 | 80.98 |
| 287 | 5-(4-Chlorophenyl)-7-{1-[1-(3-fluoropyridin-2-yl)-1H-1,2,3-triazol-4-yl]ethyl}-7H-pyrrolo[2,3-d]pyrimidin-4-amine | 254.00 | 112.12 |
| 288 | [4-(Cyclopropyloxy)phenyl]-7-{1-[1-(3-fluoropyridin-2-yl)-1H-1,2,3-triazol-4-yl]ethyl}-7H-pyrrolo[2,3-d]pyrimidin-4-amine | 39.64 | 90.62 |

-continued

| Ex. No. | Compound Name | CF hBE Ussing EC$_{50}$ (nM) | FRT EC$_{50}$ (nM) |
|---|---|---|---|
| 289 | 5-Cyclopropyl-7-{[1-(2-fluorophenyl)-1H-1,2,3-triazol-4-yl]methyl}-7H-pyrrolo[2,3-d]pyrimidin-4-amine | 342.00 | 141.76 |
| 290 | 7-{[1-(2-Fluorophenyl)-1H-1,2,3-triazol-4-yl]methyl}-5-[2-(methoxymethyl)cyclopropyl]-7H-pyrrolo[2,3-d]pyrimidin-4-amine | 997.00 | 668.58 |
| 291 | No example 291 was prepared | — | — |
| 292 | [3-(4-Amino-7-{[1-(2-fluorophenyl)-1H-1,2,3-triazol-4-yl]methyl}-7H-pyrrolo[2,3-d]pyrimidin-5-yl)azetidin-1-yl]cyclopropyl)methanone | N.D. | 3205.94 |
| 293 | 5-{1-[(Cyclopropylmethyl)sulfonyl]azetidin-3-yl}-7-{[1-(2-fluoro phenyl)-1H-1,2,3-triazol-4-yl]methyl}-7H-pyrrolo[2,3-d]pyrimidin-4-amine | N.D. | 1886.61 |
| 294 | 5-Cyclobutyl-7-{1-[1-(2-fluorophenyl)-1H-1,2,3-triazol-4-yl]ethyl}-7H-pyrrolo[2,3-d]pyrimidin-4-amine, enantiomer 1 | 189.00 | 167.01 |
| 295 | 5-Cyclopropyl-7-{1-[1-(2-fluorophenyl)-1H-1,2,3-triazol-4-yl]cyclopropyl}-7H-pyrrolo[2,3-d]pyrimidin-4-amine | 389.33 | 184.93 |
| 296 | 7-{[1-(2-Fluorophenyl)-1H-1,2,3-triazol-4-yl]methyl}-5-(3-methoxypyrazin-2-yl)-7H-pyrrolo[2,3-d]pyrimidin-4-amine | 50.29 | 123.84 |
| 297 | 7-{Cyclopropyl[1-(2-fluorophenyl)-1H-1,2,3-triazol-4-yl]methyl}-5-(2-methoxypyridin-3-yl)-7H-pyrrolo[2,3-d]pyrimidin-4-amine | 40.14 | 57.50 |
| 298 | 7-{1-[1-(2-Fluorophenyl)-1H-1,2,3-triazol-4-yl]cyclopropyl}-5-(2-methoxypyridin-3-yl)-7H-pyrrolo[2,3-d]pyrimidin-4-amine | 245.00 | 179.96 |
| 299 | 5-(1,3-Benzoxazol-7-yl)-7-{[1-(2-fluorophenyl)-1H-1,2,3-triazol-4-yl]methyl}-7H-pyrrolo[2,3-d]pyrimidin-4-amine | 273.00 | 235.15 |
| 300 | (−) 7-{Cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine, enantiomer 2 | 453.04 | 154.01 |
| 301 | 7-{[1-(2-Fluorophenyl)-1H-1,2,3-triazol-4-yl]methyl}-5-(1,3-oxazol-2-yl)-7H-pyrrolo[2,3-d]pyrimidin-4-amine | 461.00 | 359.89 |
| 302 | 7-{1-[1-(2-Fluorophenyl)-1H-1,2,3-triazol-4-yl]propyl}-5-(4-methoxypyrimidin-5-yl)-2-methyl-7H-pyrrolo[2,3-d]pyrimidin-4-amine | 297.00 | 232.22 |
| 303 | (+) 7-{1-[1-(2-Fluorophenyl)-1H-1,2,3-triazol-4-yl]propyl}-5-(4-methoxypyrimidin-5-yl)-2-methyl-7H-pyrrolo[2,3-d]pyrimidin-4-amine | 1636.00 | 2738.32 |
| 304 | (−) 7-{1-[1-(2-fluorophenyl)-1H-1,2,3-triazol-4-yl]propyl}-5-(4-methoxypyrimidin-5-yl)-2-methyl-7H-pyrrolo[2,3-d]pyrimidin-4-amine, enantiomer 2 | 134.86 | 190.32 |
| 305 | (−) 7-{1-[1-(2,3-Difluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 372.00 | 545.18 |
| 306 | (+) 7-{1-[1-(2,3-Difluorophenyl)-1H-1,2,3-triazol-4-yl] propyl}-5-(4-methoxypyrimidin-5-yl)-7H-pyrrolo[2,3-d]pyrimidin-4-amine, enantiomer 2 | 26.12 | 22.22 |
| 307 | (+) 7-{1-[1-(2-(2,5-Difluorophenyl)-1H-1,2,3-triazol-4-yl]propyl}-5-(4-methoxypyrimidin-5-yl)-7H-pyrrolo[2,3-d]pyrimidin-4-amine, enantiomer 1 | 55.39 | 45.80 |
| 308 | (−) 7-{1-[1-(2,5-Difluorophenyl)-1H-1,2,3-triazol-4-yl]propyl}-5-(4-methoxypyrimidin-5-yl)-7H-pyrrolo[2,3-d]pyrimidin-4-amine, enantiomer 2 | 430.00 | 361.69 |
| 309 | 7-{1-[1-(6-Methoxypyridin-3-yl)-1H-1,2,3-triazol-4-yl]propyl}-5-[2-(trifluoromethyl)pyrimidin-5-yl]-7H-pyrrolo[2,3-d]pyrimidin-4-amine, enantiomer 1 | 69.00 | 69.05 |
| 310 | 7-{1-[1-(6-Methoxypyridin-3-yl)-1H-1,2,3-triazol-4-yl]propyl}-5-[2-(trifluoromethyl)pyrimidin-5-yl]-7H-pyrrolo[2,3-d]pyrimidin-4-amine, enantiomer 2 | N.D. | 1296.62 |
| 311 | 7-{1-[1-(3,5-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 1 | 110.99 | 249.62 |
| 312 | 7-{1-[1-(3,5-Difluorophenyl)-1H-1,2,3-triazol-4-yl]propyl}-5-[2-(trifluoromethyl)pyrimidin-5-yl]-7H-pyrrolo[2,3-d]pyrimidin-4-amine, enantiomer 2 | 279.00 | 1019.89 |
| 313 | 5-[2-(Difluoromethyl)pyrimidin-5-yl]-7-{1-[1-(3,4-difluorophenyl)-1H-1,2,3-triazol-4-yl]propyl}-7H-pyrrolo[2,3-d]pyrimidin-4-amine, enantiomer 2 | 131.00 | 74.91 |
| 314 | 7-{1-[1-(2-Fluorophenyl)-1H-1,2,3-triazol-4-yl]-2-methoxy ethyl}-5-(2-methoxypyridin-3-yl)-7H-pyrrolo[2,3-d]pyrimidin-4-amine | 357.71 | 230.43 |
| 315 | 7-{[1-(2-Fluorophenyl)-1H-1,2,3-triazol-4-yl](oxetan-3-yl)methyl}-5-(4-methoxypyrimidin-5-yl)-7H-pyrrolo[2,3-d]pyrimidin-4-amine | 2934.00 | 933.26 |
| 316 | (+) 5-Cyclopropyl-7-{1-[1-(2-fluorophenyl)-1H-1,2,3-triazol-4-yl]propyl}-7H-pyrrolo[2,3-d]pyrimidin-4-amine, enantiomer 2 | 541.00 | 754.28 |

-continued

| Ex. No. | Compound Name | CF hBE Ussing EC$_{50}$ (nM) | FRT EC$_{50}$ (nM) |
|---|---|---|---|
| 317 | 5-Cyclopropyl-7-{[1-(2-fluorophenyl)-1H-pyrazol-4-yl]methyl}-7H-pyrrolo[2,3-d]pyrimidin-4-amine | 87.01 | 128.66 |
| 318 | 5-(4-Chlorophenyl)-7-{1-[1-(2-fluorophenyl)-1H-1,2,3-triazol-4-yl]ethyl}-N-methyl-7H-pyrrolo[2,3-d]pyrimidin-4-amine | 397.00 | 2992.44 |
| 319 | 6-Bromo-5-(4-chlorophenyl)-7-{[1-(3-fluorophenyl)-1H-1,2,3-triazol-4-yl]methyl}-7H-pyrrolo[2,3-d]pyrimidin-4-amine | N.D. | 193.70 |
| 320 | 4-Amino-5-[6-(cyclopropyloxy)pyridin-3-yl]-7-{1-[1-(2,4-difluorophenyl)-1H-1,2,3-triazol-4-yl]ethyl}-7H-pyrrolo[2,3-d]pyrimidine-6-carbonitrile, enantiomer 1 | 46.19 | 120.14 |
| 321 | 4-Amino-5-[6-(cyclopropyloxy)pyridin-3-yl]-7-{1-[1-(2,4-difluorophenyl)-1H-1,2,3-triazol-4-yl]ethyl}-7H-pyrrolo[2,3-d]pyrimidine-6-carbonitrile, enantiomer 2 | 140.59 | 359.50 |
| 322 | 4-Amino-7-{1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile, enantiomer 1 | 33.76 | 49.93 |

N.D. = not determined

The following data was obtained using the G551D/F508del Ussing chamber assay performed at 35 degrees Celsius.

| Example Number | CF hBE EC$_{50}$ (nM) |
|---|---|
| 27 | 17 |
| 134 | 826 |
| 161 | 303 |
| 162 | 8452 |

The invention claimed is:

1. A method for treating cystic fibrosis, asthma, bronchiectasis, chronic obstructive pulmonary disease (COPD), constipation, Diabetes mellitus, dry eye disease, pancreatitis, rhinosinusitis, or Sjogren's Syndrome in a patient in need of treatment thereof, the method comprising administering a therapeutically effective amount of a compound of Formula I

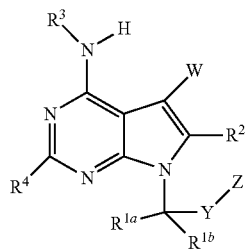

I or a pharmaceutically acceptable salt thereof, wherein
W is selected from the group consisting of phenyl, which is optionally fused with a five to six membered cycloalkyl or a five to six membered heterocycloalkyl comprising one, two, three, or four heteroatoms selected independently for each occurrence from the group consisting of N, O and $S(O)_n$;
a five to ten membered heteroaryl comprising one, two, three, or four heteroatoms selected independently for each occurrence from the group consisting of N, O and $S(O)_n$;
a four to seven membered heterocycloalkyl comprising one, two, three, or four heteroatoms selected independently for each occurrence from the group consisting of N, O and $S(O)_n$; and
$C_3$-$C_7$ cycloalkyl;
wherein the phenyl, heteroaryl, heterocycloalkyl, and cycloalkyl are optionally substituted with one, two, three, four, or five $R^5$;
Y is a five membered heteroaryl comprising one, two, three, or four heteroatoms selected independently for each occurrence from the group consisting of N, O and $S(O)_n$, wherein the heteroaryl is optionally substituted with one, two, or three substituents independently selected from the group consisting of halo, $C_1$-$C_6$alkyl, and $C_1$-$C_6$ haloalkyl;
Z is selected from the group consisting of phenyl, $C_1$-$C_6$ alkyl, $C_3$-$C_7$ cycloalkyl, a five or six membered heteroaryl comprising one, two or three heteroatoms selected independently for each occurrence from the group consisting of N, O and $S(O)_n$, and a four to seven membered heterocycloalkyl comprising one, two, or three heteroatoms selected independently for each occurrence from the group consisting of N, O and $S(O)_n$; wherein said phenyl, alkyl, cycloalkyl, heteroaryl, and heterocycloalkyl are each independently optionally substituted with one, two, three, four, or five $R^6$;
$R^{1a}$ and $R^{1b}$ are each independently selected from the group consisting of —H, —OH, halo, $C_1$-$C_6$ alkyl, $C_3$-$C_7$ cycloalkyl, and a four to seven membered heterocycloalkyl comprising one, two, or three heteroatoms each independently selected from the group consisting of N, O and $S(O)_n$, wherein the $C_1$-$C_6$ alkyl group is optionally substituted with one, two, or three substituents each independently selected from the group consisting of halo, —OH, $C_1$-$C_3$ alkyoxy, $C_3$-$C_7$ cycloalkyl, and a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents independently selected for each occurrence from the group consisting of —OH, halo, and $C_1$-$C_6$ alkyl;

or $R^{1a}$ and $R^{1b}$ taken together with the carbon to which they are attached form a $C_3$-$C_7$ cycloalkyl or a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents each independently selected from the group consisting of —OH, halo, and $C_1$-$C_6$ alkyl;

$R^2$ is selected from the group consisting of —H, halo, —CN, $C_1$-$C_6$ alkyl and $C_1$-$C_6$ haloalkyl;

$R^3$ and $R^4$ are independently selected for each occurrence from the group consisting of —H, $C_1$-$C_6$ alkyl and $C_1$-$C_6$ haloalkyl;

$R^5$ at each occurrence is independently selected from the group consisting of halo, —CN, $C_1$-$C_6$ alkyl, $C_1$-$C_6$haloalkyl, —$OR^7$, —$N(R^7)_2$, —$N(R^7)C(O)R^7$, —$SR^7$, oxo, $C_2$-$C_7$ alkoxyalkyl, —$S(O)_2$ $C_1$-$C_6$ alkyl, —$C(O)R^7$, and a five membered heteroaryl comprising one, two, three, or four heteroatoms selected independently for each occurrence from the group consisting of N, O and $S(O)_n$, wherein the heteroaryl is optionally substituted with one, two, or three substituents independently selected for each occurrence from the group consisting of halo, —CN, $C_1$-$C_6$ alkyl, $C_1$-$C_6$ haloalkyl, —$OR^7$, —$N(R^7)_2$ and —$SR^7$;

$R^6$ at each occurrence is independently selected from the group consisting of halo, $C_1$-$C_6$ alkyl and $C_1$-$C_6$ haloalkyl, —$OR^7$, —$N(R^7)_2$ and —$SR^7$;

$R^7$ is independently selected for each occurrence from the group consisting of —H, $C_1$-$C_6$ alkyl, $C_1$-$C_6$ haloalkyl, $C_3$-$C_7$ cycloalkyl, and $C_1$-$C_6$ alkyl$C_3$-$C_7$ cycloalkyl; and n at each occurrence is independently 0, 1, or 2, or a pharmaceutically acceptable salt of said compound, to the patient in need of treatment thereof.

2. The method of claim 1, wherein
$R^3$ and $R^4$ are both —H;
or a pharmaceutically acceptable salt thereof.

3. The method of claim 2, wherein
Y is selected from the group consisting of pyrazolyl, triazolyl, imidazolyl, and isoxazolyl, each of which is optionally substituted with a C1-C6 alkyl; or a pharmaceutically acceptable salt thereof.

4. The method of claim 2, wherein
the moiety Y—Z is selected from the group consisting of:

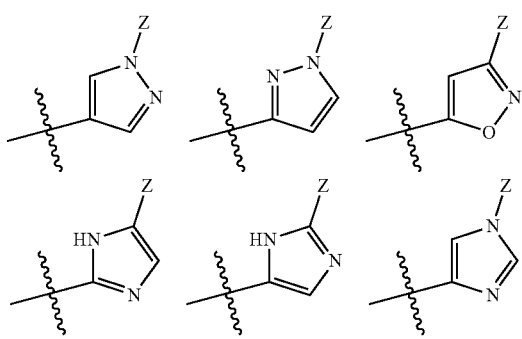
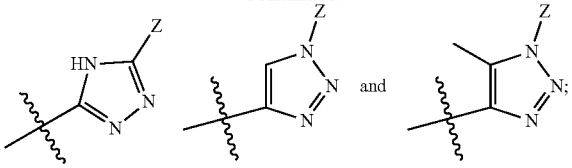

or a pharmaceutically acceptable salt thereof.

5. The method of claim 3, wherein
W is phenyl, optionally substituted with one, two, or three $R^5$;
or a pharmaceutically acceptable salt thereof.

6. The method of claim 3, wherein
W is selected from the group consisting of pyrimidinyl, pyridinyl, pyrazinyl, and pyrazolyl, each optionally substituted with one, two, or three $R^5$;
or a pharmaceutically acceptable salt thereof.

7. The method of claim 3, wherein
W is C3-C7cycloalkyl, optionally substituted with one, two, or three $R^5$; or a pharmaceutically acceptable salt thereof.

8. The method of claim 6, wherein W is

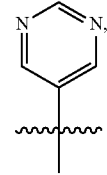 [SMILES: *c1cncnc1]

optionally substituted with one, two, or three $R^5$;
$R^5$ at each occurrence is independently selected from the group consisting of —$OCH_3$, —$CHF_2$, —$CF_3$, and —$N(CH_3)_2$; or a pharmaceutically acceptable salt thereof.

9. The method of claim 3, wherein
Z is selected from the group consisting of phenyl, $C_3$-$C_7$ cycloalkyl, and $C_1$-$C_6$ alkyl, each optionally substituted with one, two, or three $R^6$;
or a pharmaceutically acceptable salt thereof.

10. The method of claim 9, wherein
Z is phenyl, optionally substituted with one or two fluoro or chloro;
or a pharmaceutically acceptable salt thereof.

11. The method of claim 9, wherein
Z is $C_1$-$C_6$ alkyl or $C_3$-$C_7$ cycloalkyl;
or a pharmaceutically acceptable salt thereof.

12. The method of claim 2, wherein
$R^2$ is selected from the group consisting of: —H, —CN, and —Br;
or a pharmaceutically acceptable salt thereof.

13. The method of claim 1, wherein the compound is selected from the group consisting of
4-amino-5-[2-(difluoromethyl)pyrimidin-5-yl]-7-{(1S)-1-[1-(2-fluorophenyl)-1H-pyrazol-4-yl]ethyl}-7H-pyrrolo[2,3-d]pyrimidine-6-carbonitrile;
4-amino-5-[2-(difluoromethyl)pyrimidin-5-yl]-7-{(1R)-1-[1-(2-fluorophenyl)-1H-pyrazol-4-yl]ethyl}-7H-pyrrolo[2,3-d]pyrimidine-6-carbonitrile;
4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl] propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl] ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl] ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[3-(2-fluorophenyl)-1,2-oxazol-5-yl] ethyl}-5-[2-methoxypyrimidin-5-yl]-7H-pyrrolo[2,3-d]pyrimidine-6-carbonitrile;

4-amino-7-{(1S)-1-[3-(2-fluorophenyl)-1,2-oxazol-5-yl] ethyl}-5-[2-methoxypyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{[1-(2-fluorophenyl)-1H-pyrazol-4-yl] methyl}-5-[2-(trifluoromethyl)pyrimidin-5-yl]-7H-pyrrolo[2,3-d]pyrimidine-6-carbonitrile;

4-amino-7-{[1-(2,4-difluorophenyl)-1H-pyrazol-4-yl] methyl}-5-[2-(trifluoromethyl)pyrimidin-5-yl]-7H-pyrrolo[2,3-d]pyrimidine-6-carbonitrile;

4-amino-5-[2-(difluoromethyl)pyrimidin-5-yl]-7-{[1-(2-fluorophenyl)-1H-pyrazol-4-yl]methyl}-7H-pyrrolo[2,3-d]pyrimidine-6-carbonitrile;

4-amino-7-{[1-(2-fluorophenyl)-1H-1,2,3-triazol-4-yl] methyl}-5-[2-(trifluoromethyl)pyrimidin-5-yl]-7H-pyrrolo[2,3-d]pyrimidine-6-carbonitrile;

6-bromo-7-{[1-(2-fluorophenyl)-1H-pyrazol-4-yl] methyl}-5-[2-(trifluoromethyl)pyrimidin-5-yl]-7H-pyrrolo[2,3-d]pyrimidin-4-amine;

5-[4-(cyclopropyloxy)phenyl]-7-{[1-(2-fluorophenyl)-1H-1,2,3-triazol-4-yl]methyl}-7H-pyrrolo[2,3-d]pyrimidin-4-amine;

5-cyclobutyl-7-{(1S)-1-[1-(2-fluorophenyl)-1H-1,2,3-triazol-4-yl]ethyl}-7H-pyrrolo[2,3-d]pyrimidin-4-amine;

5-(4-chlorophenyl)-7-{(1S)-1-[1-(2-fluorophenyl)-1H-1,2,3-triazol-4-yl]ethyl}-7H-pyrrolo[2,3-d]pyrimidin-4-amine;

5-[6-(cyclopropyloxy)pyridin-3-yl]-7-{(1S)-1-[1-(2-fluorophenyl)-1H-1,2,3-triazol-4-yl]ethyl}-7H-pyrrolo[2,3-d]pyrimidin-4-amine;

5-(6-methoxypyridin-3-yl)-7-[(1S)-1-(1-phenyl-1H-1,2,3-triazol-4-yl)propyl]-7H-pyrrolo[2,3-d]pyrimidin-4-amine;

7-[(1S)-1-(1-phenyl-1H-1,2,3-triazol-4-yl)propyl]-5-[2-(trifluoromethyl)pyrimidin-5-yl]-7H-pyrrolo[2,3-d]pyrimidin-4-amine;

5-(4-chlorophenyl)-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(2-fluorophenyl)-1H-1,2,3-triazol-4-yl]propyl}-5-(3-methoxypyrazin-2-yl)-7H-pyrrolo[2,3-d]pyrimidin-4-amine;

7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine;

5-(5-fluoro-2-methoxypyridin-3-yl)-7-{(1S)-1-[1-(2-fluorophenyl)-1H-1,2,3-triazol-4-yl]propyl}-7H-pyrrolo[2,3-d]pyrimidin-4-amine;

5-[6-(difluoromethoxy)pyridin-3-yl]-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(3,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,5-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidin-4-amine;

7-{(1S)-1-[2-(2,4-difluorophenyl)-1H-imidazol-4-yl]propyl}-5-[2-(trifluoromethyl)pyrimidin-5-yl]-7H-pyrrolo[2,3-d]pyrimidin-4-amine;

7-{(1S)-1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-(2,4-difluorophenyl)-5-methyl-1H-1,2,3-triazol-4-yl]propyl}-5-[2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-(2-methoxy-6-methylpyridin-3-yl)-7H-pyrrolo[2,3-d]pyrimidin-4-amine;

7-{[1-(2-fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine;

4-amino-7-{(1S)-1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-5-methyl-1H-1,
2,3-triazol-4-yl]ethyl}-5-[2-(trifluoromethyl)pyrimi-
din-5-yl]-7H-pyrrolo[2,3-d]pyrimidine-6-carbonitrile;

4-amino-7-{(1R)-1-[1-(2,4-difluorophenyl)-1H-1,2,3-tri-
azol-4-yl]propyl}-5-[2-(trifluoromethyl)pyrimidin-5-
yl]-7H-pyrrolo[2,3-d]pyrimidine-6-carbonitrile;

4-amino-7-{(1R)-1-[1-(2,3-difluorophenyl)-1H-1,2,3-tri-
azol-4-yl]propyl}-5-[2-(trifluoromethyl)pyrimidin-5-
yl]-7H-pyrrolo[2,3-d]pyrimidine-6-carbonitrile;

4-amino-7-{(1R)-1-[1-(2-fluorophenyl)-1H-1,2,3-triazol-
4-yl]propyl}-5-[2-(trifluoromethyl)pyrimidin-5-yl]-
7H-pyrrolo[2,3-d]pyrimidine-6-carbonitrile;

4-amino-5-[2-(difluoromethoxy)pyrimidin-5-yl]-7-{(1S)-
1-[1-(2-fluorophenyl)-1H-1,2,3-triazol-4-yl]propyl}-
7H-pyrrolo[2,3-d]pyrimidine-6-carbonitrile;

4-amino-5-(4-chlorophenyl)-7-{[1-(propan-2-yl)-1H-
pyrazol-4-yl]methyl}-7H-pyrrolo[2,3-d]pyrimidine-6-
carbonitrile;

4-amino-5-(4-chlorophenyl)-7-{[1-(2-fluorophenyl)-1H-
1,2,3-triazol-4-yl]methyl}-7H-pyrrolo[2,3-d]pyrimi-
dine-6-carbonitrile;

5-(2-fluoro-4-methoxyphenyl)-7-{1-[2-(2-fluorophenyl)-
1H-imidazol-5-yl]ethyl}-7H-pyrrolo[2,3-d]pyrimidin-
4-amine;

5-(3-fluoro-4-methylphenyl)-7-{1-[2-(2-fluorophenyl)-
1H-imidazol-5-yl]ethyl}-7H-pyrrolo[2,3-d]pyrimidin-
4-amine;

7-{1-[2-(2-fluorophenyl)-1H-imidazol-5-yl]ethyl}-5-[4-
(2H-1,2,3-triazol-2-yl)phenyl]-7H-pyrrolo[2,3-d]py-
rimidin-4-amine;

5-(4-ethoxy-3-fluorophenyl)-7-{[1-(2-fluorophenyl)-1H-
1,2,3-triazol-4-yl]methyl}-7H-pyrrolo[2,3-d]pyrimi-
din-4-amine;

5-(4-chloro-2-methoxyphenyl)-7-{[1-(2-fluorophenyl)-
1H-1,2,3-triazol-4-yl]methyl}-7H-pyrrolo[2,3-d]py-
rimidin-4-amine;

5-[4-(difluoromethoxy)phenyl]-7{[1-(2-fluorophenyl)-
1H-1,2,3-triazol-4-yl]methyl}-7H-pyrrolo[2,3-d]py-
rimidin-4-amine;

7-{1-[1-(2-fluorophenyl)-1H-1,2,3-triazol-4-yl]ethyl}-5-
[4-(methylsulfanyl)phenyl]-7H-pyrrolo[2,3-d]pyrimi-
din-4-amine;

5-[4-(difluoromethoxy)phenyl]-7-{1-[1-(2-fluorophe-
nyl)-1H-1,2,3-triazol-4-yl]ethyl}-7H-pyrrolo[2,3-d]
pyrimidin-4-amine;

5-[2-fluoro-4-(methylsulfanyl)phenyl]-7-{1-[1-(2-fluoro-
phenyl)-1H-1,2,3-triazol-4-yl]ethyl}-7H-pyrrolo[2,3-
d]pyrimidin-4-amine;

5-(4-chloro-3-fluorophenyl)-7-{1-[1-(2-fluorophenyl)-
1H-1,2,3-triazol-4-yl]ethyl-7H-pyrrolo[2,3-d]pyrimi-
din-4-amine;

5-(3-chloro-5-fluorophenyl)-7-{1-[1-(2-fluorophenyl)-
1H-1,2,3-triazol-4-yl]ethyl}-7H-pyrrolo[2,3-d]pyrimi-
din-4-amine;

5-cyclopropyl-7-{(1S)-1-[1-(2-fluorophenyl)-1H-1,2,3-
triazol-4-yl]ethyl}-7H-pyrrolo[2,3-d]pyrimidin-4-
amine;

4-(4-amino-7-{(1S)-1-[1-(2-fluorophenyl)-1H-1,2,3-tri-
azol-4-yl]ethyl}-7H-pyrrolo[2,3-d]pyrimidin-5-yl)-2-
fluorobenzonitrile;

5[4-(cyclopropyloxy)phenyl]-7-{(1S)-1-[1-(2-fluorophe-
nyl)-1H-1,2,3-triazol-4-yl]ethyl}-7H-pyrrolo[2,3-d]
pyrimidin-4-amine;

5-(4-methoxypyrimidin-5-yl)-7-[(1S)-1-(1-phenyl-1H-1,
2,3-triazol-4-yl)propyl]-7H-pyrrolo[2,3-d]pyrimidin-
4-amine;

7-{(1S)-1-[1-(2-fluorophenyl)-1H-1,2,3-triazol-4-yl]pro-
pyl}-5-(4-methoxypyrimidin-5-yl)-7H-pyrrolo[2,3-d]
pyrimidin-4-amine;

5-[2-(difluoromethoxy)pyrimidin-5-yl]-7-{(1S)-1-[1-(2-
fluorophenyl)-1H-1,2,3-triazol-4-yl]propyl}-7H-pyr-
rolo[2,3-d]pyrimidin-4-amine;

5-[2-(dimethylamino)pyrimidin-5-yl]-7-{(1S)-1-[1-(2-
fluorophenyl)-1H-1,2,3-triazol-4-yl]propyl}-7H-pyr-
rolo[2,3-d]pyrimidin-4-amine;

7-{(1R)-1-[1-(2-fluorophenyl)-1H-1,2,3-triazol-4-yl]pro-
pyl}-5-(1H-pyrazol-3-yl)-7H-pyrrolo[2,3-d]pyrimidin-
4-amine;

7-{(1S)-1-[1-(4-fluorophenyl)-1H-1,2,3-triazol-4-yl]pro-
pyl}-5-(4-methoxypyrimidin-5-yl)-7H-pyrrolo[2,3-d]
pyrimidin-4-amine;

7-{(1S)-1-[1-(3,4-difluorophenyl)-1H-1,2,3-triazol-4-yl]
propyl}-5-(4-methoxypyrimidin-5-yl)-7H-pyrrolo[2,3-
d]pyrimidin-4-amine;

7-{(1R)-1-[1-(3,4-difluorophenyl)-1H-1,2,3-triazol-4-yl]
propyl}-5-(5-fluoro-6-methoxypyridin-3-yl)-7H-pyr-
rolo[2,3-d]pyrimidin-4-amine;

7-{(1S)-1-[1-(2,4-difluorophenyl)-1H-1,2,3-triazol-4-yl]
propyl}-5-(4-methoxypyrimidin-5-yl)-7H-pyrrolo[2,3-
d]pyrimidin-4-amine;

7-{(1R)-1-[1-(2,3-difluorophenyl)-1H-1,2,3-triazol-4-yl]
propyl}-5-(5-fluoro-2-methoxypyridin-3-yl)-7H-pyr-
rolo[2,3-d]pyrimidin-4-amine;

5-cyclopropyl-7-{(1S)-1-[1-(2-fluorophenyl)-1H-1,2,3-
triazol-4-yl]propyl}-7H-pyrrolo[2,3-d]pyrimidin-4-
amine;

7-{(S)-cyclopropyl[1-(2-fluorophenyl)-1H-1,2,3-triazol-
4-yl]methyl}-5-(4-methoxypyrimidin-5-yl)-7H-pyr-
rolo[2,3-d]pyrimidin-4-amine;

7-{(1S)-1-(2-fluorophenyl)-5-methyl-1H-1,2,3-triazol-4-
yl]ethyl}-5-[2-(trifluoromethyl)pyrimidin-5-yl]-7H-
pyrrolo[2,3-d]pyrimidin-4-amine;

5-(4-chlorophenyl)-7-{(1S)-1-[3-(2-fluorophenyl)-1,2-
oxazol-5-yl]ethyl}-7H-pyrrolo[2,3-d]pyrimidin-4-
amine;

7-{(1S)-1-[3-(2-fluorophenyl)-1,2-oxazol-5-yl]ethyl}-5-
(2-methoxypyrimidin-5-yl)-7H-pyrrolo[2,3-d]pyrimi-
din-4-amine;

5-(5-fluoro-2-methoxypyridin-3-yl)-7-{[1-(2-fluorophe-
nyl)-1H-1,2,3-triazol-4-yl]methyl}-7H-pyrrolo[2,3-d]
pyrimidin-4-amine;

5-[2-(difluoromethoxy)pyridin-3-yl]-7-{[1-(2-fluorophe-
nyl)-1H-1,2,3-triazol-4-yl]methyl}-7H-pyrrolo[2,3-d]
pyrimidin-4-amine;

7-{1-[1-(2-fluorophenyl)-1H-1,2,3-triazol-4-yl]ethyl}-5-
[2-(trifluoromethyl)pyrimidin-5-yl]-7H-pyrrolo[2,3-d]
pyrimidin-4-amine;

7-{1-[1-(2-fluorophenyl)-1H-1,2,3-triazol-4-yl]ethyl}-5-
[4-methoxy-2-(trifluoromethyl)pyrimidin-5-yl]-7H-
pyrrolo[2,3-d]pyrimidin-4-amine;

7-{[1-(2-fluorophenyl)-1H-1,2,3-triazol-4-yl]methyl}-5-
[4-methoxy-2-(trifluoromethyl)pyrimidin-5-yl]-7H-
pyrrolo[2,3-d]pyrimidin-4-amine;

5-(4-chlorophenyl)-7-{2-[1-(2-fluorophenyl)-1H-1,2,3-
triazol-4-yl]propan-2-yl}-7H-pyrrolo[2,3-d]pyrimidin-
4-amine;

5-(4-chlorophenyl)-7-{1 [1-(2-fluorophenyl)-1H-1,2,3-
triazol-4-yl]ethyl}-6-methyl-7H-pyrrolo[2,3-d]pyrimi-
din-4-amine;

5-(4-chlorophenyl)-7-{[2-(2-fluorophenyl)-1H-imidazol-
5-yl]methyl}-7H-pyrrolo[2,3-d]pyrimidin-4-amine;

5-(4-chlorophenyl)-7-[(2-phenyl-1H-imidazol-5-yl)
methyl]-7H-pyrrolo[2,3-d]pyrimidin-4-amine;

5-(4-chlorophenyl)-7-[(3-cyclohexyl-1,2-oxazol-5-yl)
   methyl]-7H-pyrrolo[2,3-d]pyrimidin-4-amine;
7-({1-[4-(difluoromethyl)phenyl]-1H-pyrazol-4-
   yl}methyl)-5-(2-methoxypyridin-3-yl)-7H-pyrrolo[2,
   3-d]pyrimidin-4-amine;
7-{(1S)-1-[1-(2,3-difluorophenyl)-1H-1,2,3-triazol-4-yl]
   propyl}-5-(4-methoxypyrimidin-5-yl)-7H-pyrrolo[2,3-
   d]pyrimidin-4-amine;
4-amino-5-[6-(cyclopropyloxy)pyridin-3-yl]-7-{(1S)-1-
   [1-(2,4-difluorophenyl)-1H-1,2,3-triazol-4-yl]ethyl}-
   7H-pyrrolo[2,3-d]pyrimidine-6-carbonitrile; and
4-amino-7-{(1S)-1-[1-(3,4-difluorophenyl)-1H-1,2,3-tri-
   azol-4-yl]propyl}-5-[2-(trifluoromethyl)pyrimidin-5-
   yl]-7H-pyrrolo[2,3-d]pyrimidine-6-carbonitrile;
or a pharmaceutically acceptable salt thereof.

14. The method of claim 1, wherein the compound is selected from the group consisting of
7-{(1S)-1-[1-(2,4-difluorophenyl)-1H-1,2,3-triazol-4-yl]
   propyl}-5-[2-(trifluoromethyl)pyrimidin-5-yl]-7H-pyr-
   rolo[2,3-d]pyrimidin-4-amine;
4-amino-7-{[1-(2-fluorophenyl)-1H-pyrazol-4-yl]
   methyl}-5-[2-(trifluoromethyl)pyrimidin-5-yl]-7H-
   pyrrolo[2,3-d]pyrimidine-6-carbonitrile;
4-amino-7-{(1S)-1-[1-(2-fluorophenyl)-1H-pyrazol-4-yl]
   ethyl}-5-[2-(trifluoromethyl)pyrimidin-5-yl]-7H-pyr-
   rolo[2,3-d]pyrimidine-6-carbonitrile;
4-amino-7-{(1S)-1-[1-(2-fluorophenyl)-1H-pyrazol-4-yl]
   propyl}-5-[2-(trifluoromethyl)pyrimidin-5-yl]-7H-pyr-
   rolo[2,3-d]pyrimidine-6-carbonitrile;
4-amino-7-{(1R)-1-[1-(2-fluorophenyl)-1H-pyrazol-4-yl]
   propyl}-5-[2-(trifluoromethyl)pyrimidin-5-yl]-7H-pyr-
   rolo[2,3-d]pyrimidine-6-carbonitrile;
4-amino-7-{(1S)-1-[1-(2,4-difluorophenyl)-1H-pyrazol-
   4-yl]ethyl}-5-[2-(trifluoromethyl)pyrimidin-5-yl]-7H-
   pyrrolo[2,3-d]pyrimidine-6-carbonitrile;
4-amino-7-{(1S)-1-[1-(2,4-difluorophenyl)-1H-1,2,3-tri-
   azol-4-yl]propyl}-5-[2-(trifluoromethyl)pyrimidin-5-
   yl]-7H-pyrrolo[2,3-d]pyrimidine-6-carbonitrile;
4-amino-7-{(1S)-1-[1-(2,4-difluorophenyl)-1H-pyrazol-
   4-yl]propyl}-5-[2-(trifluoromethyl)pyrimidin-5-yl]-
   7H-pyrrolo[2,3-d]pyrimidine-6-carbonitrile;
4-amino-7-{(1R)-1-[1-(2,4-difluorophenyl)-1H-pyrazol-
   4-yl]propyl}-5-[2-(trifluoromethyl)pyrimidin-5-yl]-
   7H-pyrrolo[2,3-d]pyrimidine-6-carbonitrile; and
4-amino-7-{[1-(2,4-difluorophenyl)-1H-pyrazol-4-yl]
   methyl}-5-[2-(trifluoromethyl)pyrimidin-5-yl]-7H-
   pyrrolo[2,3-d]pyrimidine-6-carbonitrile;
or a pharmaceutically acceptable salt thereof.

15. The method of claim 1, wherein the compound is 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine or a pharmaceutically acceptable salt thereof.

16. The method of claim 1, wherein the compound is 4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile or a pharmaceutically acceptable salt thereof.

17. The method of claim 1, wherein the compound is 4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile or a pharmaceutically acceptable salt thereof.

18. The method of claim 1, wherein the compound is 4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

19. The method of claim 1, wherein the compound is 4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

20. A method for treating cystic fibrosis in a patient in need of treatment thereof, the method comprising administering a therapeutically effective amount of a compound of Formula I

I or a pharmaceutically acceptable salt thereof, wherein
W is selected from the group consisting of phenyl, which is optionally fused with a five to six membered cycloalkyl or a five to six membered heterocycloalkyl comprising one, two, three, or four heteroatoms selected independently for each occurrence from the group consisting of N, O and $S(O)_n$;
a five to ten membered heteroaryl comprising one, two, three, or four heteroatoms selected independently for each occurrence from the group consisting of N, O and $S(O)_n$;
a four to seven membered heterocycloalkyl comprising one, two, three, or four heteroatoms selected independently for each occurrence from the group consisting of N, O and $S(O)_n$; and
$C_3$-$C_7$ cycloalkyl;
wherein the phenyl, heteroaryl, heterocycloalkyl, and cycloalkyl are optionally substituted with one, two, three, four, or five $R^5$;
Y is a five membered heteroaryl comprising one, two, three, or four heteroatoms selected independently for each occurrence from the group consisting of N, O and $S(O)_n$, wherein the heteroaryl is optionally substituted with one, two, or three substituents independently selected from the group consisting of halo, $C_1$-$C_6$alkyl, and $C_1$-$C_6$ haloalkyl;
Z is selected from the group consisting of phenyl, $C_1$-$C_6$ alkyl, $C_3$-$C_7$ cycloalkyl, a five or six membered heteroaryl comprising one, two or three heteroatoms selected independently for each occurrence from the group consisting of N, O and $S(O)_n$, and a four to seven membered heterocycloalkyl comprising one, two, or three heteroatoms selected independently for each occurrence from the group consisting of N, O and $S(O)_n$; wherein said phenyl, alkyl, cycloalkyl, heteroaryl, and heterocycloalkyl are each independently optionally substituted with one, two, three, four, or five $R^6$;
$R^{1a}$ and $R^{1b}$ are each independently selected from the group consisting of —H, —OH, halo, $C_1$-$C_6$ alkyl, $C_3$-$C_7$ cycloalkyl, and a four to seven membered heterocycloalkyl comprising one, two, or three heteroatoms each independently selected from the group consisting of N, O and $S(O)_n$, wherein the $C_1$-$C_6$ alkyl group is optionally substituted with one, two, or three substituents each independently selected from the group consisting of halo, —OH, $C_1$-$C_3$ alkyoxy, $C_3$-$C_7$ cycloalkyl, and a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents independently selected for each occurrence from the group consisting of —OH, halo, and $C_1$-$C_6$ alkyl;

or $R^{1a}$ and $R^{1b}$ taken together with the carbon to which they are attached form a $C_3$-$C_7$ cycloalkyl or a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents each independently selected from the group consisting of —OH, halo, and $C_1$-$C_6$ alkyl;

$R^2$ is selected from the group consisting of —H, halo, —CN, $C_1$-$C_6$ alkyl and $C_1$-$C_6$ haloalkyl;

$R^3$ and $R^4$ are independently selected for each occurrence from the group consisting of —H, $C_1$-$C_6$ alkyl and $C_1$-$C_6$ haloalkyl;

$R^5$ at each occurrence is independently selected from the group consisting of halo, —CN, $C_1$-$C_6$ alkyl, $C_1$-$C_6$haloalkyl, —$OR^7$, —$N(R^7)_2$, —$N(R^7)C(O)R^7$, —$SR^7$, oxo, $C_2$-$C_7$ alkoxyalkyl, —$S(O)_2$ $C_1$-$C_6$ alkyl, —$C(O)R^7$, and a five membered heteroaryl comprising one, two, three, or four heteroatoms selected independently for each occurrence from the group consisting of N, O and $S(O)_n$, wherein the heteroaryl is optionally substituted with one, two, or three substituents independently selected for each occurrence from the group consisting of halo, —CN, $C_1$-$C_6$ alkyl, $C_1$-$C_6$ haloalkyl, —$OR^7$, —$N(R^7)_2$ and —$SR^7$;

$R^6$ at each occurrence is independently selected from the group consisting of halo, $C_1$-$C_6$ alkyl and $C_1$-$C_6$ haloalkyl, —$OR^7$, —$N(R^7)_2$ and —$SR^7$;

$R^7$ is independently selected for each occurrence from the group consisting of —H, $C_1$-$C_6$ alkyl, $C_1$-$C_6$ haloalkyl, $C_3$-$C_7$ cycloalkyl, and $C_1$-$C_6$ alkyl$C_3$-$C_7$ cycloalkyl; and n at each occurrence is independently 0, 1, or 2, or a pharmaceutically acceptable salt of said compound, to the patient in need of treatment thereof.

21. The method of claim 20, wherein
$R^3$ and $R^4$ are both —H;
or a pharmaceutically acceptable salt thereof.

22. The method of claim 21, wherein
Y is selected from the group consisting of pyrazolyl, triazolyl, imidazolyl, and isoxazolyl, each of which is optionally substituted with a $C_1$-$C_6$ alkyl; or a pharmaceutically acceptable salt thereof.

23. The method of claim 21, wherein
the moiety Y—Z is selected from the group consisting of:

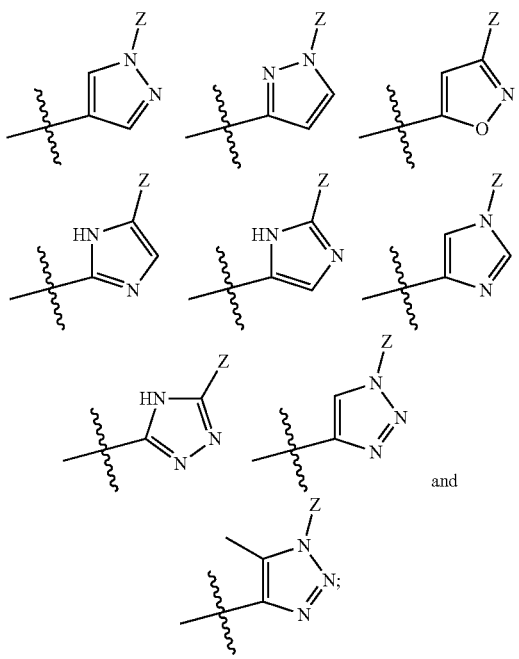

or a pharmaceutically acceptable salt thereof.

24. The method of claim 22, wherein
W is phenyl, optionally substituted with one, two, or three $R^5$;
or a pharmaceutically acceptable salt thereof.

25. The method of claim 22, wherein
W is selected from the group consisting of pyrimidinyl, pyridinyl, pyrazinyl, and pyrazolyl, each optionally substituted with one, two, or three $R^5$;
or a pharmaceutically acceptable salt thereof.

26. The method of claim 22, wherein
W is $C_3$-$C_7$cycloalkyl, optionally substituted with one, two, or three $R^5$; or a pharmaceutically acceptable salt thereof.

27. The method of claim 25, wherein W is

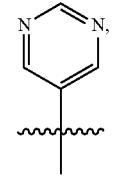 [SMILES: *c1cncnc1]

optionally substituted with one, two, or three $R^5$;
$R^5$ at each occurrence is independently selected from the group consisting of —$OCH_3$, —$CHF_2$, —$CF_3$, and —$N(CH_3)_2$; or a pharmaceutically acceptable salt thereof.

28. The method of claim 22, wherein
Z is selected from the group consisting of phenyl, C3-C7 cycloalkyl, and C1-C6 alkyl, each optionally substituted with one, two, or three $R^6$;
or a pharmaceutically acceptable salt thereof.

29. The method of claim 28, wherein
Z is phenyl, optionally substituted with one or two fluoro or chloro;
or a pharmaceutically acceptable salt thereof.

30. The method of claim 28, wherein
Z is $C_1$-$C_6$ alkyl or $C_3$-$C_7$ cycloalkyl;
or a pharmaceutically acceptable salt thereof.

31. The method of claim 21, wherein
$R^2$ is selected from the group consisting of: —H, —CN, and —Br;
or a pharmaceutically acceptable salt thereof.

32. The method of claim 20, wherein the compounds is selected from the group consisting of
4-amino-5-[2-(difluoromethyl)pyrimidin-5-yl]-7-{(1S)-1-[1-(2-fluorophenyl)-1H-pyrazol-4-yl]ethyl}-7H-pyrrolo[2,3-d]pyrimidine-6-carbonitrile;
4-amino-5-[2-(difluoromethyl)pyrimidin-5-yl]-7-{(1R)-1-[1-(2-fluorophenyl)-1H-pyrazol-4-yl]ethyl}-7H-pyrrolo[2,3-d]pyrimidine-6-carbonitrile;
4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1R)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1R)-1-[3-(2-fluorophenyl)-1,2-oxazol-5-yl]ethyl}-5-[2-methoxypyrimidin-5-yl)-7H-pyrrolo[2,3-d]pyrimidine-6-carbonitrile;
4-amino-7-{(1S)-1-[3-(2-fluorophenyl)-1,2-oxazol-5-yl]ethyl}-5-[2-methoxypyrimidin-5-yl)-7H-pyrrolo[2,3-d]pyrimidine-6-carbonitrile;
4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;
4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;
4-amino-5-[2-(difluoromethyl)pyrimidin-5-yl]-7-{[1-(2-fluorophenyl)-1H-pyrazol-4-yl]methyl}-7H-pyrrolo[2,3-d]pyrimidine-6-carbonitrile;
4-amino-7-{[1-(2-fluorophenyl)-1H-1,2,3-triazol-4-yl]methyl}-5-[2-(trifluoromethyl)pyrimidin-5-yl]-7H-pyrrolo[2,3-d]pyrimidine-6-carbonitrile;
6-bromo-7-{[1-(2-fluorophenyl)-1H-pyrazol-4-yl]methyl}-5-[2-(trifluoromethyl)pyrimidin-5-yl]-7H-pyrrolo[2,3-d]pyrimidin-4-amine;
5-[4-(cyclopropyloxy)phenyl]-7-{[1-(2-fluorophenyl)-1H-1,2,3-triazol-4-yl]methyl}-7H-pyrrolo[2,3-d]pyrimidin-4-amine;
5-cyclobutyl-7-{(1S)-1-[1-(2-fluorophenyl)-1H-1,2,3-triazol-4-yl]ethyl}-7H-pyrrolo[2,3-d]pyrimidin-4-amine;
5-(4-chlorophenyl)-7-{(1S)-1-[1-(2-fluorophenyl)-1H-1,2,3-triazol-4-yl]ethyl}-7H-pyrrolo[2,3-d]pyrimidin-4-amine;
5-[6-(cyclopropyloxy)pyridin-3-yl]-7-{(1S)-1-[1-(2-fluorophenyl)-1H-1,2,3-triazol-4-yl]ethyl}-7H-pyrrolo[2,3-d]pyrimidin-4-amine;
5-(6-methoxypyridin-3-yl)-7-[(1S)-1-(1-phenyl-1H-1,2,3-triazol-4-yl)propyl]-7H-pyrrolo[2,3-d]pyrimidin-4-amine;
7-[(1S)-1-(1-phenyl-1H-1,2,3-triazol-4-yl)propyl]-5-[2-(trifluoromethyl)pyrimidin-5-yl]-7H-pyrrolo[2,3-d]pyrimidin-4-amine;
5-(4-chlorophenyl)-7-{(1S)-1-[1-(2-fluorophenyl)-1H-1,2,3-triazol-4-yl]propyl}-7H-pyrrolo[2,3-d]pyrimidin-4-amine;
7-{(1S)-1-[1-(2-fluorophenyl)-1H-1,2,3-triazol-4-yl]propyl}-5-(3-methoxypyrazin-2-yl)-7H-pyrrolo[2,3-d]pyrimidin-4-amine;
7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine;
5-(5-fluoro-2-methoxypyridin-3-yl)-7-{(1S)-1-[1-(2-fluorophenyl)-1H-1,2,3-triazol-4-yl]propyl}-7H-pyrrolo[2,3-d]pyrimidin-4-amine;
5-[6-(difluoromethoxy)pyridin-3-yl]-7-{(1S)-1-[1-(2-fluorophenyl)-1H-1,2,3-triazol-4-yl]propyl}-7H-pyrrolo[2,3-d]pyrimidin-4-amine;
7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;
7-{(1S)-1-[1-(3,4-difluorophenyl)-1H-1,2,3-triazol-4-yl]propyl}-5-(5-fluoro-2-methoxypyridin-3-yl)-7H-pyrrolo[2,3-d]pyrimidin-4-amine;
7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;
7-{(1S)-1-[1-(2,4-difluorophenyl)-1H-1,2,3-triazol-4-yl]propyl}-5-(5-fluoro-2-methoxypyridin-3-yl)-7H-pyrrolo[2,3-d]pyrimidin-4-amine;
7-{(1S)-1-[1-(2,4-difluorophenyl)-1H-1,2,3-triazol-4-yl]propyl}-5-(5-fluoro-6-methoxypyridin-3-yl)-7H-pyrrolo[2,3-d]pyrimidin-4-amine;
7-{(1S)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;
7-{(1S)-1-[1-(2,5-difluorophenyl)-1H-1,2,3-triazol-4-yl]propyl}-5-(5-fluoro-2-methoxypyridin-3-yl)-7H-pyrrolo[2,3-d]pyrimidin-4-amine;
7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidin-4-amine;
7-{(1S)-1-[2-(2,4-difluorophenyl)-1H-imidazol-4-yl]propyl}-5-[2-(trifluoromethyl)pyrimidin-5-yl]-7H-pyrrolo[2,3-d]pyrimidin-4-amine;
7-{(1S)-1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-(2,4-difluorophenyl)-5-methyl-1H-1,2,3-triazol-4-yl]propyl}-5-[2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-(2-methoxy-6-methylpyridin-3-yl)-7H-pyrrolo[2,3-d]pyrimidin-4-amine;

7-{[1-(2-fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine;

4-amino-7-{(1S)-1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-5-[2-(difluoromethoxy)pyrimidin-5-yl]-7-{(1S)-1-[1-(2-fluorophenyl)-1H-1,2,3-triazol-4-yl]propyl}-7H-pyrrolo[2,3-d]pyrimidine-6-carbonitrile;

4-amino-5-(4-chlorophenyl)-7-{[1-(propan-2-yl)-1H-pyrazol-4-yl]methyl}-7H-pyrrolo[2,3-d]pyrimidine-6-carbonitrile;

4-amino-5-(4-chlorophenyl)-7-{[1-(2-fluorophenyl)-1H-1,2,3-triazol-4-yl]methyl}-7H-pyrrolo[2,3-d]pyrimidine-6-carbonitrile;

5-(2-fluoro-4-methoxyphenyl)-7-{1-[2-(2-fluorophenyl)-1H-imidazol-5-yl]ethyl}-7H-pyrrolo[2,3-d]pyrimidin-4-amine;

5-(3-fluoro-4-methylphenyl)-7-{1-[2-(2-fluorophenyl)-1H-imidazol-5-yl]ethyl}-7H-pyrrolo[2,3-d]pyrimidin-4-amine;

7-{1-[2-(2-fluorophenyl)-1H-imidazol-5-yl]ethyl}-5-[4-(2H-1,2,3-triazol-2-yl)phenyl]-7H-pyrrolo[2,3-d]pyrimidin-4-amine;

5-(4-ethoxy-3-fluorophenyl)-7-{[1-(2-fluorophenyl)-1H-1,2,3-triazol-4-yl]methyl}-7H-pyrrolo[2,3-d]pyrimidin-4-amine;

5-(4-chloro-2-methoxyphenyl)-7-{[1-(2-fluorophenyl)-1H-1,2,3-triazol-4-yl]methyl}-7H-pyrrolo[2,3-d]pyrimidin-4-amine;

5-[4-(difluoromethoxy)phenyl]-7-{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[4-(methylsulfanyl)phenyl]-7H-pyrrolo[2,3-d]pyrimidin-4-amine;

5-[4-(difluoromethoxy)phenyl]-7-{1-[1-(2-fluorophenyl)-1H-1,2,3-triazol-4-yl]ethyl}-7H-pyrrolo[2,3-d]pyrimidin-4-amine;

5-[2-fluoro-4-(methylsulfanyl)phenyl]-7-{1-[1-(2-fluorophenyl)-1H-1,2,3-triazol-4-yl]ethyl}-7H-pyrrolo[2,3-d]pyrimidin-4-amine;

5-(4-chloro-3-fluorophenyl)-7-{1-[1-(2-fluorophenyl)-1H-1,2,3-triazol-4-yl]ethyl-7H-pyrrolo[2,3-d]pyrimidin-4-amine;

5-(3-chloro-5-fluorophenyl)-7-{1-[1-(2-fluorophenyl)-1H-1,2,3-triazol-4-yl]ethyl}-7H-pyrrolo[2,3-d]pyrimidin-4-amine;

5-cyclopropyl-7-{(1S)-1-[1-(2-fluorophenyl)-1H-1,2,3-triazol-4-yl]ethyl}-7H-pyrrolo[2,3-d]pyrimidin-4-amine;

4-(4-amino-7-{(1S)-1-[1-(2-fluorophenyl)-1H-1,2,3-triazol-4-yl]ethyl}-7H-pyrrolo[2,3-d]pyrimidin-5-yl)-2-fluorobenzonitrile;

5[4-(cyclopropyloxy)phenyl]-7-{(1S)-1-[1-(2-fluorophenyl)-1H-1,2,3-triazol-4-yl]ethyl}-7H-pyrrolo[2,3-d]pyrimidin-4-amine;

5-(4-methoxypyrimidin-5-yl)-7-[(1S)-1-(1-phenyl-1H-1,2,3-triazol-4-yl)propyl]-7H-pyrrolo[2,3-d]pyrimidin-4-amine;

7-{(1S)-1-[1-(2-fluorophenyl)-1H-1,2,3-triazol-4-yl]propyl}-5-(4-methoxypyrimidin-5-yl)-7H-pyrrolo[2,3-d]pyrimidin-4-amine;

5-[2-(difluoromethyl)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

5-[2-(dimethylamino)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

7-{(1R)-1-[1-(2-fluorophenyl)-1H-1,2,3-triazol-4-yl]propyl}-5-(1H-pyrazol-3-yl)-7H-pyrrolo[2,3-d]pyrimidin-4-amine;

7-{(1S)-1-[1-(4-fluorophenyl)-1H-1,2,3-triazol-4-yl]propyl}-5-(4-methoxypyrimidin-5-yl)-7H-pyrrolo[2,3-d]pyrimidin-4-amine;

7-{(1S)-1-[1-(3,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(3,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

5-cyclopropyl-7-{(1S)-1-[1-(2-fluorophenyl)-1H-1,2,3-triazol-4-yl]propyl}-7H-pyrrolo[2,3-d]pyrimidin-4-amine;

7-{(S)-cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine;

7-{(1S)-1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine;

5-(4-chlorophenyl)-7-{(1S)-1-[3-(2-fluorophenyl)-1,2-oxazol-5-yl]ethyl}-7H-pyrrolo[2,3-d]pyrimidin-4-amine;

7-{(1S)-1-[3-(2-fluorophenyl)-1,2-oxazol-5-yl]ethyl}-5-(2-methoxypyrimidin-5-yl)-7H-pyrrolo[2,3-d]pyrimidin-4-amine;

5-(5-fluoro-2-methoxypyridin-3-yl)-7-{[1-(2-fluorophenyl)-1H-1,2,3-triazol-4-yl]methyl}-7H-pyrrolo[2,3-d]pyrimidin-4-amine;

5-[2-(difluoromethoxy)pyridin-3-yl]-7-{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-4-amine;

7-{1-[1-(2-fluorophenyl)-1H-1,2,3-triazol-4-yl]ethyl}-5-[4-methoxy-2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-[4-methoxy-2-(trifluoromethyl)pyrimidin-5-yl]-7H-pyrrolo[2,3-d]pyrimidin-4-amine;

5-(4-chlorophenyl)-7-{2-[1-(2-fluorophenyl)-1H-1,2,3-triazol-4-yl]propan-2-yl}-7H-pyrrolo[2,3-d]pyrimidin-4-amine;

5-(4-chlorophenyl)-7-{1 [1-(2-fluorophenyl)-1H-1,2,3-triazol-4-yl]ethyl}-6-methyl-7H-pyrrolo[2,3-d]pyrimidin-4-amine;

5-(4-chlorophenyl)-7-{[2-(2-fluorophenyl)-1H-imidazol-5-yl]methyl}-7H-pyrrolo[2,3-d]pyrimidin-4-amine;

5-(4-chlorophenyl)-7-[(2-phenyl-1H-imidazol-5-yl)methyl]-7H-pyrrolo[2,3-d]pyrimidin-4-amine;

5-(4-chlorophenyl)-7-[(3-cyclohexyl-1,2-oxazol-5-yl)methyl]-7H-pyrrolo[2,3-d]pyrimidin-4-amine;

7-({1-[4-(difluoromethyl)phenyl]-1H-pyrazol-4-yl}methyl)-5-(2-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(4-methoxypyrimidin-5-yl)-7H-pyrrolo[2,3-d]pyrimidin-4-amine;

4-amino-5-[6-(cyclopropyloxy)pyridin-3-yl]-7-{(1S)-1-[1-(2,4-difluorophenyl)-1H-1,2,3-triazol-4-yl]ethyl}-7H-pyrrolo[2,3-d]pyrimidine-6-carbonitrile; and 4-amino-7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

or a pharmaceutically acceptable salt thereof.

33. The method of claim 20, wherein the compound is selected from the group consisting of 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile; and 4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;

or a pharmaceutically acceptable salt thereof.

34. The method of claim 20, wherein the compound is 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine or a pharmaceutically acceptable salt thereof.

35. The method of claim 20, wherein the compound is 4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile or a pharmaceutically acceptable salt thereof.

36. The method of claim 20, wherein the compound is 4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile or a pharmaceutically acceptable salt thereof.

37. The method of claim 20, wherein the compound is 4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

38. The method of claim 20, wherein the compound is 4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

39. A method for treating cystic fibrosis in a patient in need of treatment thereof, the method comprising administering a pharmaceutical composition comprising a therapeutically effective amount of one or more of a compound of Formula I

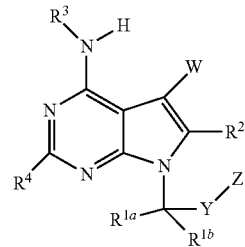

I or a pharmaceutically acceptable salt thereof, wherein

W is selected from the group consisting of phenyl, which is optionally fused with a five to six membered cycloalkyl or a five to six membered heterocycloalkyl comprising one, two, three, or four heteroatoms selected independently for each occurrence from the group consisting of N, O and $S(O)_n$;

a five to ten membered heteroaryl comprising one, two, three, or four heteroatoms selected independently for each occurrence from the group consisting of N, O and $S(O)_n$;

a four to seven membered heterocycloalkyl comprising one, two, three, or four heteroatoms selected independently for each occurrence from the group consisting of N, O and $S(O)_n$; and $C_3$-$C_7$ cycloalkyl;

wherein the phenyl, heteroaryl, heterocycloalkyl, and cycloalkyl are optionally substituted with one, two, three, four, or five $R^5$;

Y is a five membered heteroaryl comprising one, two, three, or four heteroatoms selected independently for each occurrence from the group consisting of N, O and $S(O)_n$, wherein the heteroaryl is optionally substituted with one, two, or three substituents independently selected from the group consisting of halo, $C_1$-$C_6$alkyl, and $C_1$-$C_6$ haloalkyl;

Z is selected from the group consisting of phenyl, $C_1$-$C_6$ alkyl, $C_3$-$C_7$ cycloalkyl, a five or six membered heteroaryl comprising one, two or three heteroatoms selected independently for each occurrence from the group consisting of N, O and $S(O)_n$, and a four to seven membered heterocycloalkyl comprising one, two, or three heteroatoms selected independently for each occurrence from the group consisting of N, O and $S(O)_n$; wherein said phenyl, alkyl, cycloalkyl, heteroaryl, and heterocycloalkyl are each independently optionally substituted with one, two, three, four, or five $R^6$;

$R^{1a}$ and $R^{1b}$ are each independently selected from the group consisting of —H, —OH, halo, $C_1$-$C_6$ alkyl, $C_3$-$C_7$ cycloalkyl, and a four to seven membered heterocycloalkyl comprising one, two, or three heteroatoms each independently selected from the group consisting of N, O and $S(O)_n$, wherein the $C_1$-$C_6$ alkyl group is optionally substituted with one, two, or three substituents each independently selected from the group consisting of halo, —OH, $C_1$-$C_3$ alkyoxy, $C_3$-$C_7$ cycloalkyl, and a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents independently selected for each occurrence from the group consisting of —OH, halo, and $C_1$-$C_6$ alkyl;

or $R^{1a}$ and $R^{1b}$ taken together with the carbon to which they are attached form a $C_3$-$C_7$ cycloalkyl or a four to seven membered heterocycloalkyl comprising one, two, or three heteroatoms each independently selected from the group consisting of N, O and $S(O)_n$; and wherein each $C_3$-$C_7$cycloalkyl and each four to seven membered heterocycloalkyl are optionally substituted with one, two or three substituents each independently selected from the group consisting of —OH, halo, and $C_1$-$C_6$ alkyl;

$R^2$ is selected from the group consisting of —H, halo, —CN, $C_1$-$C_6$ alkyl and $C_1$-$C_6$ haloalkyl;

$R^3$ and $R^4$ are independently selected for each occurrence from the group consisting of —H, $C_1$-$C_6$ alkyl and $C_1$-$C_6$ haloalkyl;

$R^5$ at each occurrence is independently selected from the group consisting of halo, —CN, $C_1$-$C_6$ alkyl, $C_1$-$C_6$haloalkyl, —$OR^7$, —$N(R^7)_2$, —$N(R^7)C(O)R^7$, —$SR^7$, oxo, $C_2$-$C_7$ alkoxyalkyl, —$S(O)_2$ $C_1$-$C_6$ alkyl, —$C(O)R^7$, and a five membered heteroaryl comprising one, two, three, or four heteroatoms selected independently for each occurrence from the group consisting of N, O and $S(O)_n$, wherein the heteroaryl is optionally substituted with one, two, or three substituents independently selected for each occurrence from the group consisting of halo, —CN, $C_1$-$C_6$ alkyl, $C_1$-$C_6$ haloalkyl, —$OR^7$, —$N(R^7)_2$ and —$SR^7$;

$R^6$ at each occurrence is independently selected from the group consisting of halo, $C_1$-$C_6$ alkyl and $C_1$-$C_6$ haloalkyl, —$OR^7$, —$N(R^7)_2$ and —$SR^7$;

$R^7$ is independently selected for each occurrence from the group consisting of —H, $C_1$-$C_6$ alkyl, $C_1$-$C_6$ haloalkyl, $C_3$-$C_7$ cycloalkyl, and $C_1$-$C_6$ alkyl$C_3$-$C_7$ cycloalkyl; and n at each occurrence is independently 0, 1, or 2, or a pharmaceutically acceptable salt thereof together with a pharmaceutically acceptable carrier, to the patient in need of treatment thereof.

40. The method of claim 39, further comprising one or more additional therapeutic agents.

41. The method of claim 40, wherein the one or more additional therapeutic agents are independently selected from the group consisting of a CFTR potentiator, a CFTR corrector, an epithelial sodium channel (ENaC) inhibitor, a CFTR amplifier, a CFTR stabilizer, a read-through agent, an oligonucleotide patch, an autophagy inducer, and a proteostasis modulator.

42. The method of claim 41, wherein the CFTR potentiator at each occurrence is selected from the group consisting of VX-770 (Ivacaftor), GLPG-1837, GLPG-2451, QBW-251, FDL-176, FDL-129, CTP-656, and PTI-P271.

43. The method of claim 41, wherein the CFTR corrector at each occurrence is selected from the group consisting of VX-809 (lumacaftor), VX-661 (tezacaftor), VX-983, VX-152, VX-440, VX-659, GLPG-2737, P247-A, GLPG-2222, GLPG-2665, GLPG-2851, FDL-169, and PTI-C1811.

44. The method of claim 41, wherein the epithelial sodium channel (ENaC) inhibitor at each occurrence is selected from the group consisting of SPX-101, QBW-276 and VX-371.

45. The method of claim 41, wherein the CFTR amplifier at each occurrence is selected from the group consisting of PTI-428 and PTI-130.

46. The method of claim 41, wherein the CFTR stabilizer is N-91115 (Cavosonstat).

47. The method of claim 41, wherein the read-through agent is ataluren.

48. The method of claim 41, wherein the oligonucleotide patch is QR-010.

49. The method of claim 41, wherein the autophagy inducer at each occurrence is selected from the group consisting of CX-4945 and the combination of cysteamine and epigallocatechin gallate (EGCG).

50. The method of claim 39, wherein
$R^3$ and $R^4$ are both —H;
or a pharmaceutically acceptable salt thereof.

51. The method of claim 50, wherein
Y is selected from the group consisting of pyrazolyl, triazolyl, imidazolyl, and isoxazolyl, each of which is optionally substituted with a $C_1$-$C_6$ alkyl; or a pharmaceutically acceptable salt thereof.

52. The method of claim 50, wherein
the moiety Y—Z is selected from the group consisting of:

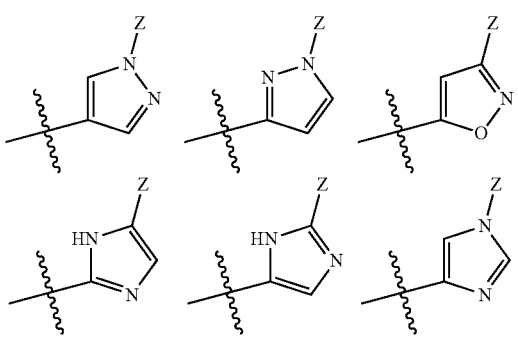

-continued

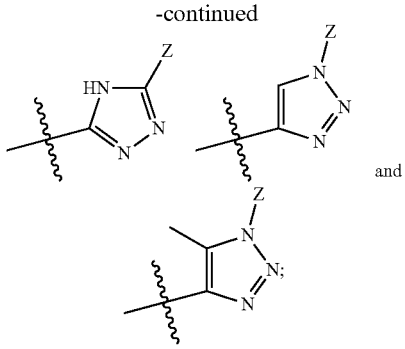

or a pharmaceutically acceptable salt thereof.

53. The method of claim 51, wherein
W is phenyl, optionally substituted with one, two, or three $R^5$;
or a pharmaceutically acceptable salt thereof.

54. The method of claim 51, wherein
W is selected from the group consisting of pyrimidinyl, pyridinyl, pyrazinyl, and pyrazolyl, each optionally substituted with one, two, or three $R^5$;
or a pharmaceutically acceptable salt thereof.

55. The method of claim 51, wherein
W is $C_3$-$C_7$cycloalkyl, optionally substituted with one, two, or three $R^5$; or a pharmaceutically acceptable salt thereof.

56. The method of claim 54, wherein W is

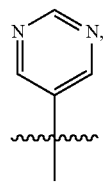

optionally substituted with one, two, or three $R^5$;
$R^5$ at each occurrence is independently selected from the group consisting of —$OCH_3$, —$CHF_2$, —$CF_3$, and —$N(CH_3)_2$; or a pharmaceutically acceptable salt thereof.

57. The method of claim 51, wherein
Z is selected from the group consisting of phenyl, $C_3$-$C_7$ cycloalkyl, and $C_1$-$C_6$ alkyl, each optionally substituted with one, two, or three $R^6$;
or a pharmaceutically acceptable salt thereof.

58. The method of claim 57, wherein
Z is phenyl, optionally substituted with one or two fluoro or chloro;
or a pharmaceutically acceptable salt thereof.

59. The method of claim 57, wherein
Z is $C_1$-$C_6$ alkyl or $C_3$-$C_7$ cycloalkyl;
or a pharmaceutically acceptable salt thereof.

60. The method of claim 50, wherein
$R^2$ is selected from the group consisting of: —H, —CN, and —Br;
or a pharmaceutically acceptable salt thereof.

61. The method of claim 39, wherein the compound is selected from the group consisting of
4-amino-5-[2-(difluoromethyl)pyrimidin-5-yl]-7-{(1S)-1-[1-(2-fluorophenyl)-1H-pyrazol-4-yl]ethyl}-7H-pyrrolo[2,3-d]pyrimidine-6-carbonitrile;
4-amino-5-[2-(difluoromethyl)pyrimidin-5-yl]-7-{(1R)-1-[1-(2-fluorophenyl)-1H-pyrazol-4-yl]ethyl}-7H-pyrrolo[2,3-d]pyrimidine-6-carbonitrile;
4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1R)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;
4-amino-7-{(1R)-1-[3-(2-fluorophenyl)-1,2-oxazol-5-yl]ethyl}-5-[2-methoxypyrimidin-5-yl)-7H-pyrrolo[2,3-d]pyrimidine-6-carbonitrile;
4-amino-7-{(1S)-1-[3-(2-fluorophenyl)-1,2-oxazol-5-yl]ethyl}-5-[2-methoxypyrimidin-5-yl)-7H-pyrrolo[2,3-d]pyrimidine-6-carbonitrile;
4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;
4-amino-7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;
4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;
4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;
4-amino-5-[2-(difluoromethyl)pyrimidin-5-yl]-7-{[1-(2-fluorophenyl)-1H-pyrazol-4-yl]methyl}-7H-pyrrolo[2,3-d]pyrimidine-6-carbonitrile;
4-amino-7-{[1-(2-fluorophenyl)-1H-1,2,3-triazol-4-yl]methyl}-5-[2-(trifluoromethyl)pyrimidin-5-yl]-7H-pyrrolo[2,3-d]pyrimidine-6-carbonitrile;
6-bromo-7-{[1-(2-fluorophenyl)-1H-pyrazol-4-yl]methyl}-5-[2-(trifluoromethyl)pyrimidin-5-yl]-7H-pyrrolo[2,3-d]pyrimidin-4-amine;
5-[4-(cyclopropyloxy)phenyl]-7-{[1-(2-fluorophenyl)-1H-1,2,3-triazol-4-yl]methyl}-7H-pyrrolo[2,3-d]pyrimidin-4-amine;
5-cyclobutyl-7-{(1S)-1-[1-(2-fluorophenyl)-1H-1,2,3-triazol-4-yl]ethyl}-7H-pyrrolo[2,3-d]pyrimidin-4-amine;
5-(4-chlorophenyl)-7-{(1S)-1-[1-(2-fluorophenyl)-1H-1,2,3-triazol-4-yl]ethyl}-7H-pyrrolo[2,3-d]pyrimidin-4-amine;

5-[6-(cyclopropyloxy)pyridin-3-yl]-7-{(1S)-1-[1-(2-fluorophenyl)-1H-1,2,3-triazol-4-yl]ethyl}-7H-pyrrolo[2,3-d]pyrimidin-4-amine;

5-(6-methoxypyridin-3-yl)-7-[(1S)-1-(1-phenyl-1H-1,2,3-triazol-4-yl)propyl]-7H-pyrrolo[2,3-d]pyrimidin-4-amine;

7-[(1S)-1-(1-phenyl-1H-1,2,3-triazol-4-yl)propyl]-5-[2-(trifluoromethyl)pyrimidin-5-yl]-7H-pyrrolo[2,3-d]pyrimidin-4-amine;

5-(4-chlorophenyl)-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(2-fluorophenyl)-1H-1,2,3-triazol-4-yl]propyl}-5-(3-methoxypyrazin-2-yl)-7H-pyrrolo[2,3-d]pyrimidin-4-amine;

7-{(1S)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidin-4-amine;

5-(5-fluoro-2-methoxypyridin-3-yl)-7-{(1S)-1-[1-(2-fluorophenyl)-1H-1,2,3-triazol-4-yl]propyl}-7H-pyrrolo[2,3-d]pyrimidin-4-amine;

5-[6-(difluoromethoxy)pyridin-3-yl]-7-{(1S)-1-[1-(2-fluorophenyl)-1H-1,2,3-triazol-4-yl]propyl}-7H-pyrrolo[2,3-d]pyrimidin-4-amine;

7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(3,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2,5-difluorophenyl)-1H-1,2,3-triazol-4-yl]propyl}-5-(5-fluoro-2-methoxypyridin-3-yl)-7H-pyrrolo[2,3-d]pyrimidin-4-amine;

7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidin-4-amine;

7-{(1S)-1-[2-(2,4-difluorophenyl)-1H-imidazol-4-yl]propyl}-5-[2-(trifluoromethyl)pyrimidin-5-yl]-7H-pyrrolo[2,3-d]pyrimidin-4-amine;

7-{(1S)-1-[1-(2,5-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

7-{(1S)-1-(2,4-difluorophenyl)-5-methyl-1H-1,2,3-triazol-4-yl]propyl}-5-[2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-(2-methoxy-6-methylpyridin-3-yl)-7H-pyrrolo[2,3-d]pyrimidin-4-amine;

7-{[1-(2-fluorophenyl)-1H-1,2,3-triazol-4-yl]methyl}-5-[2-methoxy-6-(trifluoromethyl)pyridin-3-yl]-7H-pyrrolo[2,3-d]pyrimidin-4-amine;

4-amino-7-{(1S)-1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,3-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-5-[2-(difluoromethoxy)pyrimidin-5-yl]-7-{(1S)-1-[1-(2-fluorophenyl)-1H-1,2,3-triazol-4-yl]propyl}-7H-pyrrolo[2,3-d]pyrimidine-6-carbonitrile;

4-amino-5-(4-chlorophenyl)-7-{[1-(propan-2-yl)-1H-pyrazol-4-yl]methyl}-7H-pyrrolo[2,3-d]pyrimidine-6-carbonitrile;

4-amino-5-(4-chlorophenyl)-7-{[1-(2-fluorophenyl)-1H-1,2,3-triazol-4-yl]methyl}-7H-pyrrolo[2,3-d]pyrimidine-6-carbonitrile;

5-(2-fluoro-4-methoxyphenyl)-7-{1-[2-(2-fluorophenyl)-1H-imidazol-5-yl]ethyl}-7H-pyrrolo[2,3-d]pyrimidin-4-amine;

5-(3-fluoro-4-methylphenyl)-7-{1-[2-(2-fluorophenyl)-1H-imidazol-5-yl]ethyl}-7H-pyrrolo[2,3-d]pyrimidin-4-amine;

7-{1-[2-(2-fluorophenyl)-1H-imidazol-5-yl]ethyl}-5-[4-(2H-1,2,3-triazol-2-yl)phenyl]-7H-pyrrolo[2,3-d]pyrimidin-4-amine;

5-(4-ethoxy-3-fluorophenyl)-7-{[1-(2-fluorophenyl)-1H-1,2,3-triazol-4-yl]methyl}-7H-pyrrolo[2,3-d]pyrimidin-4-amine;

5-(4-chloro-2-methoxyphenyl)-7-{[1-(2-fluorophenyl)-1H-1,2,3-triazol-4-yl]methyl}-7H-pyrrolo[2,3-d]pyrimidin-4-amine;

5-[4-(difluoromethoxy)phenyl]-7{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[4-(methylsulfanyl)phenyl]-7H-pyrrolo[2,3-d]pyrimidin-4-amine;

5-[4-(difluoromethoxy)phenyl]-7-{1-[1-(2-fluorophenyl)-1H-1,2,3-triazol-4-yl]ethyl}-7H-pyrrolo[2,3-d]pyrimidin-4-amine;

5-[2-fluoro-4-(methylsulfanyl)phenyl]-7-{1-[1-(2-fluorophenyl)-1H-1,2,3-triazol-4-yl]ethyl}-7H-pyrrolo[2,3-d]pyrimidin-4-amine;

5-(4-chloro-3-fluorophenyl)-7-{1-[1-(2-fluorophenyl)-1H-1,2,3-triazol-4-yl]ethyl-7H-pyrrolo[2,3-d]pyrimidin-4-amine;

5-(3-chloro-5-fluorophenyl)-7-{1-[1-(2-fluorophenyl)-1H-1,2,3-triazol-4-yl]ethyl}-7H-pyrrolo[2,3-d]pyrimidin-4-amine;

5-cyclopropyl-7-{(1S)-1-[1-(2-fluorophenyl)-1H-1,2,3-triazol-4-yl]ethyl}-7H-pyrrolo[2,3-d]pyrimidin-4-amine;

4-(4-amino-7-{(1S)-1-[1-(2-fluorophenyl)-1H-1,2,3-triazol-4-yl]ethyl}-7H-pyrrolo[2,3-d]pyrimidin-5-yl)-2-fluorobenzonitrile;

5[4-(cyclopropyloxy)phenyl]-7-{(1S)-1-[1-(2-fluorophenyl)-1H-1,2,3-triazol-4-yl]ethyl}-7H-pyrrolo[2,3-d]pyrimidin-4-amine;

5-(4-methoxypyrimidin-5-yl)-7-[(1S)-1-(1-phenyl-1H-1,2,3-triazol-4-yl)propyl]-7H-pyrrolo[2,3-d]pyrimidin-4-amine;

7-{(1S)-1-[1-(2-fluorophenyl)-1H-1,2,3-triazol-4-yl]propyl}-5-(4-methoxypyrimidin-5-yl)-7H-pyrrolo[2,3-d]pyrimidin-4-amine;

5-[2-(difluoromethyl)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

5-[2-(dimethylamino)pyrimidin-5-yl]-7-{(1S)-1-[1-(2-fluorophenyl)-1H-1,2,3-triazol-4-yl]propyl}-7H-pyrrolo[2,3-d]pyrimidin-4-amine;

7-{(1R)-1-[1-(2-fluorophenyl)-1H-1,2,3-triazol-4-yl]propyl}-5-(1H-pyrazol-3-yl)-7H-pyrrolo[2,3-d]pyrimidin-4-amine;

7-{(1S)-1-[1-(4-fluorophenyl)-1H-1,2,3-triazol-4-yl]propyl}-5-(4-methoxypyrimidin-5-yl)-7H-pyrrolo[2,3-d]pyrimidin-4-amine;

7-{(1S)-1-[1-(3,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(3,4-difluorophenyl)-1H-1,2,3-triazol-4-yl]propyl}-5-(5-fluoro-6-methoxypyridin-3-yl)-7H-pyrrolo[2,3-d]pyrimidin-4-amine;

7-{(1S)-1-[1-(2,4-difluorophenyl)-1H-1,2,3-triazol-4-yl]propyl}-5-(4-methoxypyrimidin-5-yl)-7H-pyrrolo[2,3-d]pyrimidin-4-amine;

7-{(1R)-1-[1-(2,3-difluorophenyl)-1H-1,2,3-triazol-4-yl]propyl}-5-(5-fluoro-2-methoxypyridin-3-yl)-7H-pyrrolo[2,3-d]pyrimidin-4-amine;

5-cyclopropyl-7-{(1S)-1-[1-(2-fluorophenyl)-1H-1,2,3-triazol-4-yl]propyl}-7H-pyrrolo[2,3-d]pyrimidin-4-amine;

7-{(S)-cyclopropyl[1-(2-fluorophenyl)-1H-1,2,3-triazol-4-yl]methyl}-5-(4-methoxypyrimidin-5-yl)-7H-pyrrolo[2,3-d]pyrimidin-4-amine;

7-{(1S)-1-(2-fluorophenyl)-5-methyl-1H-1,2,3-triazol-4-yl]ethyl}-5-[2-(trifluoromethyl)pyrimidin-5-yl]-7H-pyrrolo[2,3-d]pyrimidin-4-amine;

5-(4-chlorophenyl)-7-{(1S)-1-[3-(2-fluorophenyl)-1,2-oxazol-5-yl]ethyl}-7H-pyrrolo[2,3-d]pyrimidin-4-amine;

7-{(1S)-1-[3-(2-fluorophenyl)-1,2-oxazol-5-yl]ethyl}-5-(2-methoxypyrimidin-5-yl)-7H-pyrrolo[2,3-d]pyrimidin-4-amine;

5-(5-fluoro-2-methoxypyridin-3-yl)-7-{[1-(2-fluorophenyl)-1H-1,2,3-triazol-4-yl]methyl}-7H-pyrrolo[2,3-d]pyrimidin-4-amine;

5-[2-(difluoromethoxy)pyridin-3-yl]-7-{[1-(2-fluorophenyl)-1H-1,2,3-triazol-4-yl]methyl}-7H-pyrrolo[2,3-d]pyrimidin-4-amine;

7-{1-[1-(2-fluorophenyl)-1H-1,2,3-triazol-4-yl]ethyl}-5-[2-(trifluoromethyl)pyrimidin-5-yl]-7H-pyrrolo[2,3-d]pyrimidin-4-amine;

7-{1-[1-(2-fluorophenyl)-1H-1,2,3-triazol-4-yl]ethyl}-5-[4-methoxy-2-(trifluoromethyl)pyrimidin-5-yl]-7H-pyrrolo[2,3-d]pyrimidin-4-amine;

7-{[1-(2-fluorophenyl)-1H-1,2,3-triazol-4-yl]methyl}-5-[4-methoxy-2-(trifluoromethyl)pyrimidin-5-yl]-7H-pyrrolo[2,3-d]pyrimidin-4-amine;

5-(4-chlorophenyl)-7-{2-[1-(2-fluorophenyl)-1H-1,2,3-triazol-4-yl]propan-2-yl}-7H-pyrrolo[2,3-d]pyrimidin-4-amine;

5-(4-chlorophenyl)-7-{1 [1-(2-fluorophenyl)-1H-1,2,3-triazol-4-yl]ethyl}-6-methyl-7H-pyrrolo[2,3-d]pyrimidin-4-amine;

5-(4-chlorophenyl)-7-{[2-(2-fluorophenyl)-1H-imidazol-5-yl]methyl}-7H-pyrrolo[2,3-d]pyrimidin-4-amine;

5-(4-chlorophenyl)-7-[(2-phenyl-1H-imidazol-5-yl)methyl]-7H-pyrrolo[2,3-d]pyrimidin-4-amine;

5-(4-chlorophenyl)-7-[(3-cyclohexyl-1,2-oxazol-5-yl)methyl]-7H-pyrrolo[2,3-d]pyrimidin-4-amine;

7-({1-[4-(difluoromethyl)phenyl]-1H-pyrazol-4-yl}methyl)-5-(2-methoxypyridin-3-yl)-7H-pyrrolo[2,3-d]pyrimidin-4-amine;

7-{(1S)-1-[1-(2,3-difluorophenyl)-1H-1,2,3-triazol-4-yl]propyl}-5-(4-methoxypyrimidin-5-yl)-7H-pyrrolo[2,3-d]pyrimidin-4-amine;

4-amino-5-[6-(cyclopropyloxy)pyridin-3-yl]-7-{(1S)-1-[1-(2,4-difluorophenyl)-1H-1,2,3-triazol-4-yl]ethyl}-7H-pyrrolo[2,3-d]pyrimidine-6-carbonitrile; and 4-amino-7-{(1S)-1-[1-(3,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

or a pharmaceutically acceptable salt thereof.

62. The method of claim 39, wherein the compound is selected from the group consisting of 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine;

4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]ethyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidine-6-carbonitrile;

4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile;

4-amino-7-{(1R)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile; and 4-amino-7-{[1-(2,4-difluorophenyl)-1H-pyrazol-4-yl]methyl}-5-[2-(trifluoromethyl)pyrimidin-5-yl]-7H-pyrrolo[2,3-d]pyrimidine-6-carbonitrile;

or a pharmaceutically acceptable salt thereof.

63. The method of claim 39, wherein the compound is 7-{(1S)-1-[1-(2,4-difluorophenyl)-1H-1,2,3-triazol-4-yl]propyl}-5-[2-(trifluoromethyl)pyrimidin-5-yl]-7H-pyrrolo[2,3-d]pyrimidin-4-amine or a pharmaceutically acceptable salt thereof.

64. The method of claim 39, wherein the compound is 4-amino-7-{[1-(2-fluorophenyl)-1H-pyrazol-4-yl]methyl}-5-[2-(trifluoromethyl)pyrimidin-5-yl]-7H-pyrrolo[2,3-d]pyrimidine-6-carbonitrile or a pharmaceutically acceptable salt thereof.

65. The method of claim 39, wherein the compound is 4-amino-7-{(1S)-1-[1-(2-fluorophenyl)-1H-pyrazol-4-yl]

ethyl}-5-[2-(trifluoromethyl)pyrimidin-5-yl]-7H-pyrrolo[2,3-d]pyrimidine-6-carbonitrile or a pharmaceutically acceptable salt thereof.

66. The method of claim 39, wherein the compound is 4-amino-7-{(1S)-1-[1-(2-fluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

67. The method of claim 39, wherein the compound is 4-amino-7-{(1S)-1-[1-(2,4-difluorophenyl)-1H-pyrazol-4-yl]propyl}-5-[2-(trifluoromethyl)pyrimidin-5-yl]-7H-pyrrolo[2,3-d]pyrimidine-6-carbonitrile or a pharmaceutically acceptable salt thereof.

* * * * *